US012589078B2

(12) United States Patent
Navarro et al.

(10) Patent No.: US 12,589,078 B2

(45) Date of Patent: Mar. 31, 2026

(54) LIPID NANOPARTICLES FOR DELIVERY OF NUCLEIC ACIDS

(71) Applicant: CureVac SE, Tübingen (DE)

(72) Inventors: Gemma Navarro, Tübingen (DE); Patrick Baumhof, Tübingen (DE)

(73) Assignee: CureVac SE, Tübingen (DE)

(*) Notice: Subject to any disclaimer, the term of this patent is extended or adjusted under 35 U.S.C. 154(b) by 954 days.

(21) Appl. No.: 17/757,736

(22) PCT Filed: Dec. 18, 2020

(86) PCT No.: PCT/EP2020/087254

§ 371 (c)(1),
(2) Date: Jun. 20, 2022

(87) PCT Pub. No.: WO2021/123332

PCT Pub. Date: Jun. 24, 2021

(65) Prior Publication Data

US 2023/0090515 A1 Mar. 23, 2023

(30) Foreign Application Priority Data

Dec. 20, 2019 (WO) ................ PCT/EP2019/086825

(51) Int. Cl.

| | |
|---|---|
| ***A61K 9/51*** | (2006.01) |
| ***A61K 9/1271*** | (2025.01) |
| ***A61K 9/1272*** | (2025.01) |
| ***A61P 31/14*** | (2006.01) |
| ***A61P 31/16*** | (2006.01) |
| ***A61P 33/06*** | (2006.01) |
| ***C07D 211/22*** | (2006.01) |
| ***C07D 401/12*** | (2006.01) |
| ***C07D 405/12*** | (2006.01) |

(52) U.S. Cl.

CPC ............ *A61K 9/5123* (2013.01); *A61P 31/14* (2018.01); *A61P 31/16* (2018.01); *A61P 33/06* (2018.01); *C07D 211/22* (2013.01); *C07D 405/12* (2013.01)

(58) Field of Classification Search

None

See application file for complete search history.

(56) References Cited

U.S. PATENT DOCUMENTS

| | | | |
|---|---|---|---|
| 9,708,628 | B2 * | 7/2017 | Tange ................ C07D 311/72 |
| 2005/0032730 | A1 | 2/2005 | von der Mülbe et al. |
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2008/0025944 | A1 | 1/2008 | Hoerr et al. |
| 2008/0267873 | A1 | 10/2008 | Hoerr et al. |
| 2009/0324584 | A1 | 12/2009 | Hoerr et al. |
| 2010/0048883 | A1 | 2/2010 | Ketterer et al. |
| 2010/0189729 | A1 | 7/2010 | Hoerr et al. |
| 2010/0203076 | A1 | 8/2010 | Fotin-Mleczek et al. |
| 2010/0291156 | A1 | 11/2010 | Barner et al. |
| 2010/0305196 | A1 | 12/2010 | Probst et al. |
| 2011/0053829 | A1 | 3/2011 | Baumhof et al. |
| 2011/0250225 | A1 | 10/2011 | Fotin-Mleczek et al. |
| 2012/0021043 | A1 | 1/2012 | Kramps et al. |
| 2012/0258046 | A1 | 10/2012 | Mutzke |
| 2013/0129754 | A1 | 5/2013 | Thess et al. |
| 2013/0142818 | A1 | 6/2013 | Baumhof et al. |
| 2013/0259879 | A1 | 10/2013 | Baumhof et al. |
| 2013/0280283 | A1 | 10/2013 | Lorenz et al. |
| 2013/0295043 | A1 | 11/2013 | Kallen et al. |
| 2013/0336998 | A1 | 12/2013 | Kallen et al. |
| 2014/0335157 | A1 * | 11/2014 | Tange ................... C12N 15/88 546/196 |
| 2015/0037326 | A1 | 2/2015 | Butler-Ransohoff et al. |
| 2015/0050302 | A1 | 2/2015 | Thess |
| 2015/0057340 | A1 | 2/2015 | Thess et al. |
| 2015/0093413 | A1 | 4/2015 | Thess et al. |
| 2015/0118183 | A1 | 4/2015 | Baumhof |
| 2015/0118264 | A1 | 4/2015 | Baumhof et al. |
| 2015/0165006 | A1 | 6/2015 | Thess et al. |
| 2015/0184195 | A1 | 7/2015 | Thess et al. |
| 2015/0218554 | A1 | 8/2015 | Thess |
| 2015/0306249 | A1 | 10/2015 | Baumhof et al. |
| 2015/0320847 | A1 | 11/2015 | Thess et al. |
| 2016/0130345 | A1 | 5/2016 | Fotin-Mleczek et al. |
| 2016/0166668 | A1 | 6/2016 | Kallen et al. |
| 2016/0166678 | A1 | 6/2016 | Kallen et al. |
| 2016/0166710 | A1 | 6/2016 | Baumhof |
| 2016/0166711 | A1 | 6/2016 | Schnee et al. |
| 2016/0168207 | A1 | 6/2016 | Kramps et al. |
| 2016/0168227 | A1 | 6/2016 | Kallen et al. |
| 2016/0235864 | A1 | 8/2016 | Schlake et al. |
| 2016/0304883 | A1 | 10/2016 | Grund et al. |
| 2016/0304938 | A1 | 10/2016 | Wochner |
| 2016/0326575 | A1 | 11/2016 | von der Mülbe et al. |
| 2016/0331844 | A1 | 11/2016 | Fotin-Mleczek et al. |
| 2017/0014496 | A1 | 1/2017 | Fotin-Mleczek et al. |
| 2017/0029847 | A1 | 2/2017 | Thess |
| 2017/0114378 | A1 | 4/2017 | Wochner et al. |
| 2017/0252430 | A1 | 9/2017 | Fotin-Mleczek et al. |

(Continued)

FOREIGN PATENT DOCUMENTS

| | | |
|---|---|---|
| EP | 2781507 | 9/2014 |
| EP | 3252043 | 12/2017 |

(Continued)

OTHER PUBLICATIONS

Akita, Hidetaka, et al. "Molecular tuning of a vitamin E-scaffold pH-sensitive and reductive cleavable lipid-like material for accelerated in vivo hepatic siRNA delivery." ACS Biomaterials Science & Engineering 1.9 (2015): 834-844 and S1-S17. (Year: 2015).*

PCT International Search Report and Written Opinion issued in International Application No. PCT/EP2020/087254, mailed Mar. 11, 2021.

PCT International Search Report and Written Opinion issued in International Application No. PCT/EP2019/086825, mailed Jul. 6, 2020.

*Primary Examiner* — Bethany P Barham

*Assistant Examiner* — Peter Anthopolos

(74) *Attorney, Agent, or Firm* — pH IP Law

(57) ABSTRACT

The application relates to cationic lipids and to compositions comprising said cationic lipids useful for the delivery of nucleic acids into living cells.

20 Claims, 51 Drawing Sheets

Specification includes a Sequence Listing.

(56) References Cited

U.S. PATENT DOCUMENTS

| | | | |
|---|---|---|---|
| 2017/0326225 A1 | 11/2017 | Rauch et al. |
| 2018/0044687 A1 | 2/2018 | Thess et al. |
| 2018/0125952 A1 | 5/2018 | Fotin-Mleczek et al. |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund et al. |
| 2018/0201967 A1 | 7/2018 | Eber et al. |
| 2018/0208957 A1 | 7/2018 | Roos et al. |
| 2018/0214537 A1 | 8/2018 | Mutzke et al. |
| 2018/0237786 A1 | 8/2018 | Schlake et al. |
| 2018/0237817 A1 | 8/2018 | Roos et al. |
| 2018/0243219 A1 | 8/2018 | Ketterer et al. |
| 2018/0296663 A1 | 10/2018 | Hipp et al. |
| 2018/0298372 A1 | 10/2018 | Funkner et al. |
| 2018/0312545 A1 | 11/2018 | Baumhof et al. |
| 2018/0371392 A1 | 12/2018 | Mayer et al. |
| 2019/0010485 A1 | 1/2019 | Yazdan Panah et al. |
| 2019/0017100 A1 | 1/2019 | Wochner et al. |
| 2019/0024096 A1 | 1/2019 | Schmid et al. |
| 2019/0040378 A1 | 2/2019 | Fotin-Mleczek et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0125857 A1 | 5/2019 | Rauch et al. |
| 2019/0133950 A1 | 5/2019 | Eber et al. |
| 2019/0160164 A1 | 5/2019 | Rauch et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0241633 A1 | 8/2019 | Fotin-Mleczek et al. |
| 2019/0249219 A1 | 8/2019 | Reichert et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1 | 11/2019 | Fotin-Mleczek et al. |
| 2019/0351044 A1 | 11/2019 | Jasny et al. |
| 2019/0351047 A1 | 11/2019 | Jasny et al. |
| 2019/0351048 A1 | 11/2019 | Rauch |
| 2019/0381180 A1 | 12/2019 | Baumhof et al. |
| 2020/0023076 A1 | 1/2020 | Fotin-Mleczek et al. |
| 2020/0085852 A1 | 3/2020 | Fotin-Mleczek |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0179526 A1 | 6/2020 | Baumhof et al. |
| 2020/0318097 A1 | 10/2020 | Funkner et al. |
| 2020/0392572 A1 | 12/2020 | Yazdan Panah et al. |
| 2021/0030864 A1 | 2/2021 | Petsch et al. |
| 2021/0069315 A1 | 3/2021 | Baumhof et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0205434 A1 | 7/2021 | Petsch et al. |
| 2021/0260178 A1 | 8/2021 | Jasny et al. |
| 2021/0261897 A1 | 8/2021 | Yazdan Panah et al. |
| 2021/0361761 A1 | 11/2021 | Lutz et al. |
| 2021/0379181 A1 | 12/2021 | Rauch et al. |
| 2021/0403925 A1 | 12/2021 | Chevessier-Tünnesen et al. |
| 2022/0040281 A1 | 2/2022 | Schwendt et al. |
| 2022/0073962 A1 | 3/2022 | Schwenger et al. |
| 2022/0133908 A1 | 5/2022 | Rejman et al. |
| 2022/0144877 A1 | 5/2022 | Heinz et al. |
| 2022/0211838 A1 | 7/2022 | Oostvogels et al. |
| 2022/0233568 A1 | 7/2022 | Schlake et al. |
| 2022/0296628 A1 | 9/2022 | Thess et al. |
| 2022/0313813 A1 | 10/2022 | Rauch et al. |
| 2022/0340641 A1 | 10/2022 | Aggarwal et al. |

FOREIGN PATENT DOCUMENTS

| | | | |
|---|---|---|---|
| EP | 3360576 | 8/2018 | |
| EP | 3360576 A1 * | 8/2018 | .............. A61P 37/06 |
| WO | WO 2018/078053 | 5/2018 | |
| WO | WO 2018/081480 | 5/2018 | |
| WO | WO 2018/211038 | 11/2018 | |
| WO | WO 2018/237369 | 12/2018 | |
| WO | WO 2019/141814 | 7/2019 | |
| WO | WO 2019/188867 | 10/2019 | |
| WO | WO 2019/193183 | 10/2019 | |
| WO | WO 2019/202035 | 10/2019 | |
| WO | WO 2021/123332 | 6/2021 | |
| WO | WO 2021/254593 | 12/2021 | |
| WO | WO 2022/023559 | 2/2022 | |

* cited by examiner

A
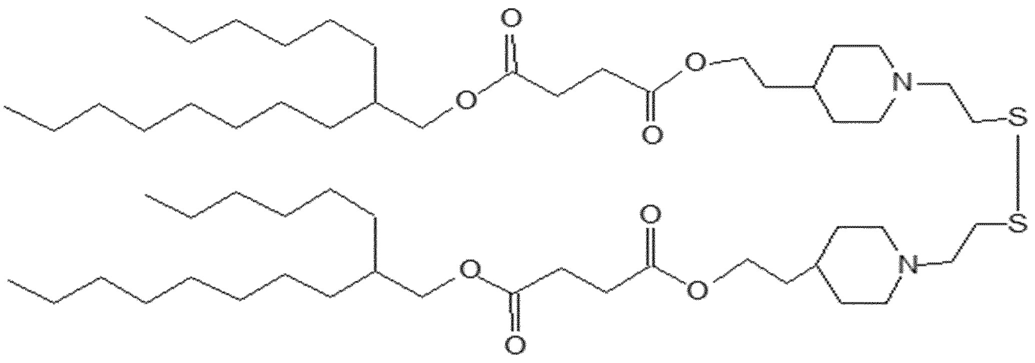
B
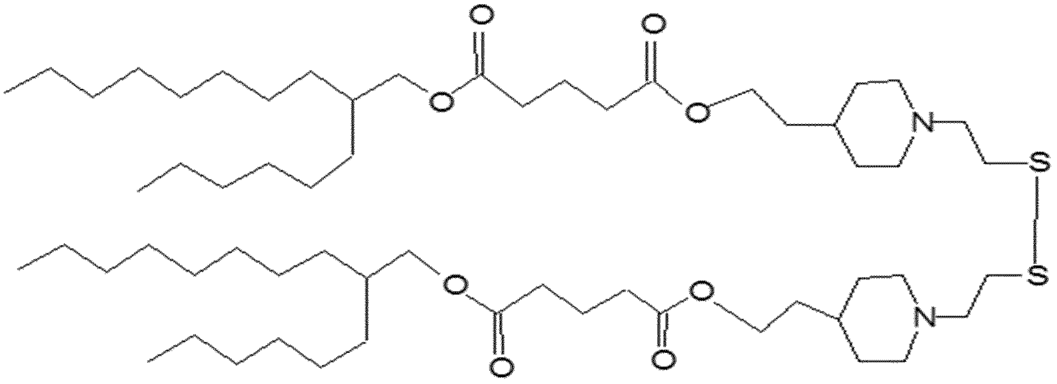
Figure 1

C
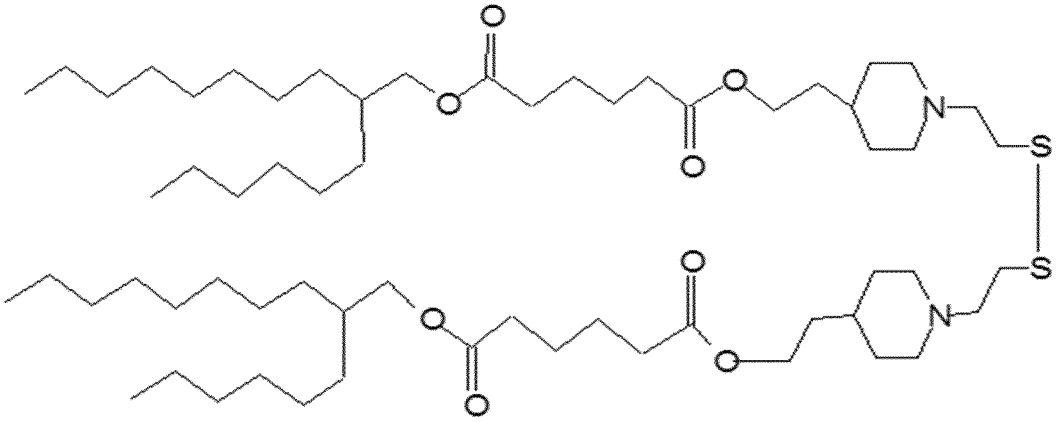
D
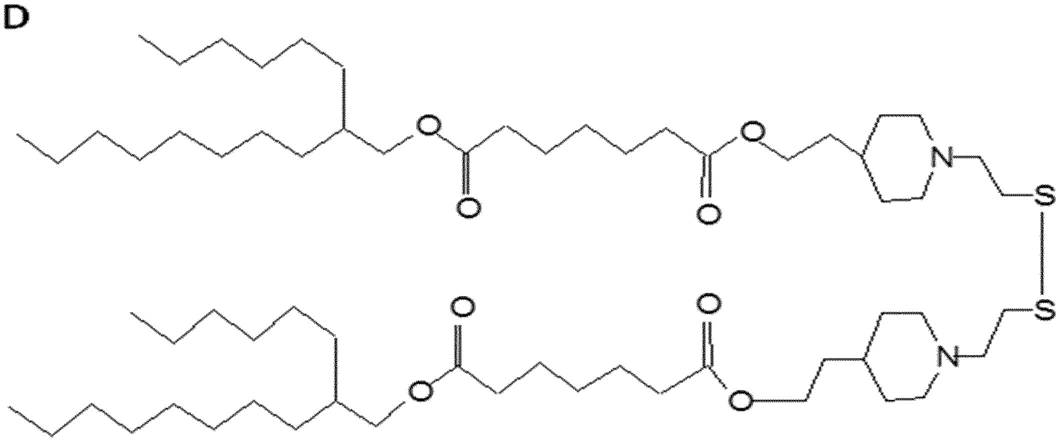
Figure 1 (cont.)

E
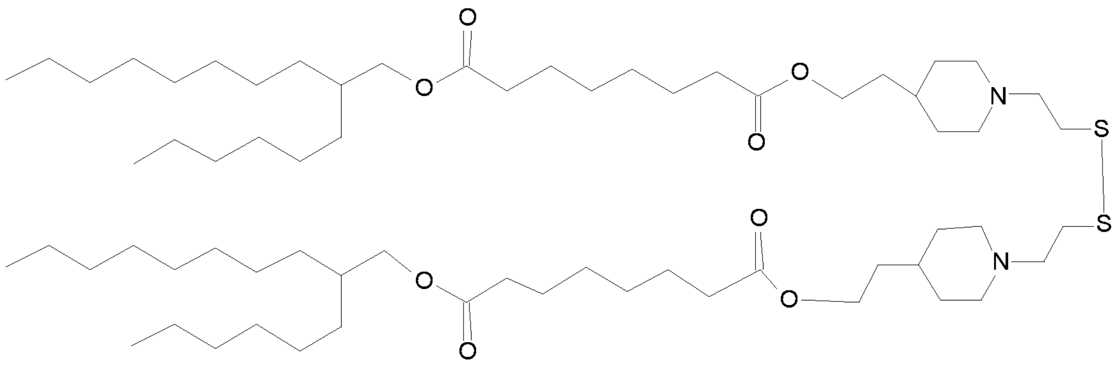
F
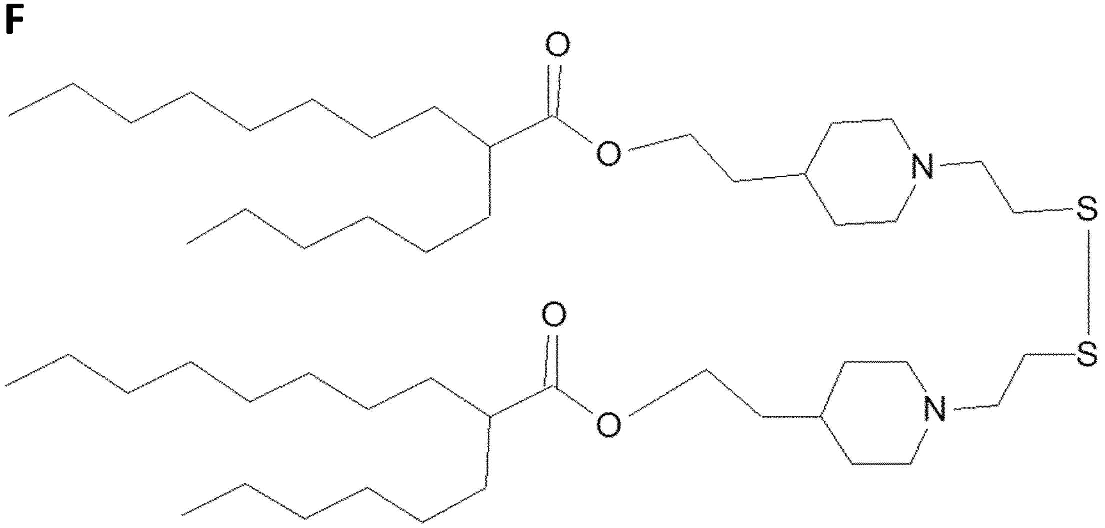
Figure 1 (cont.)

G
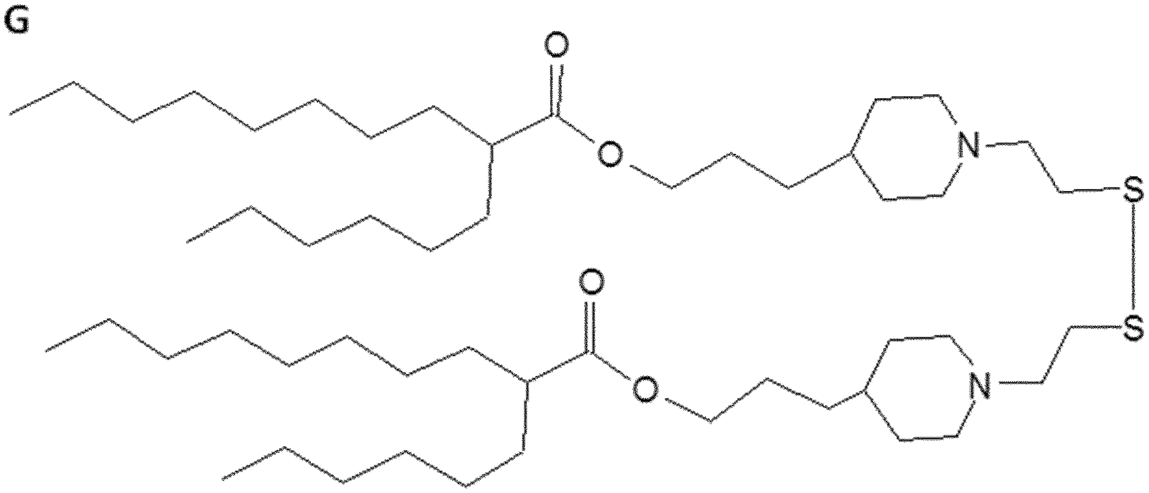
H
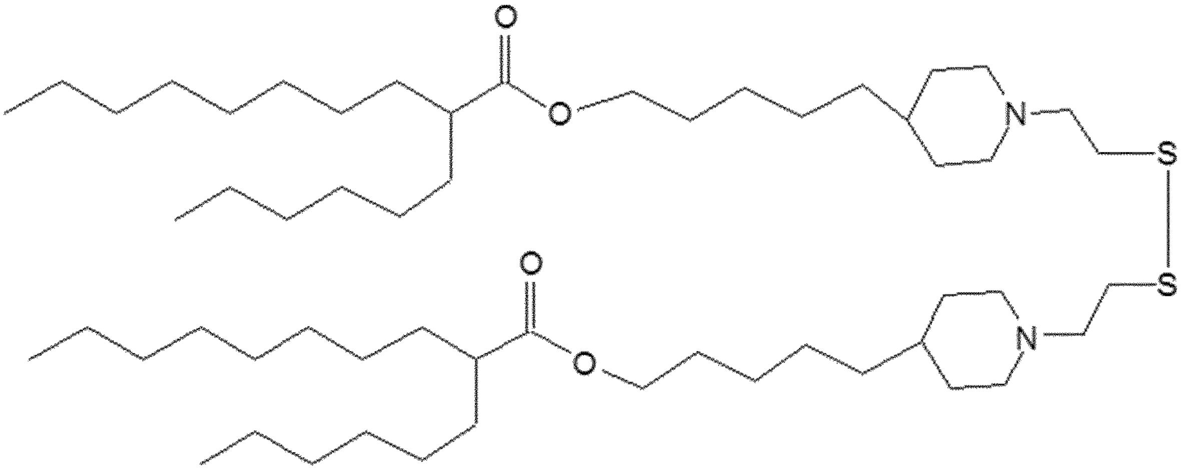
Figure 1 (cont.)

I

C
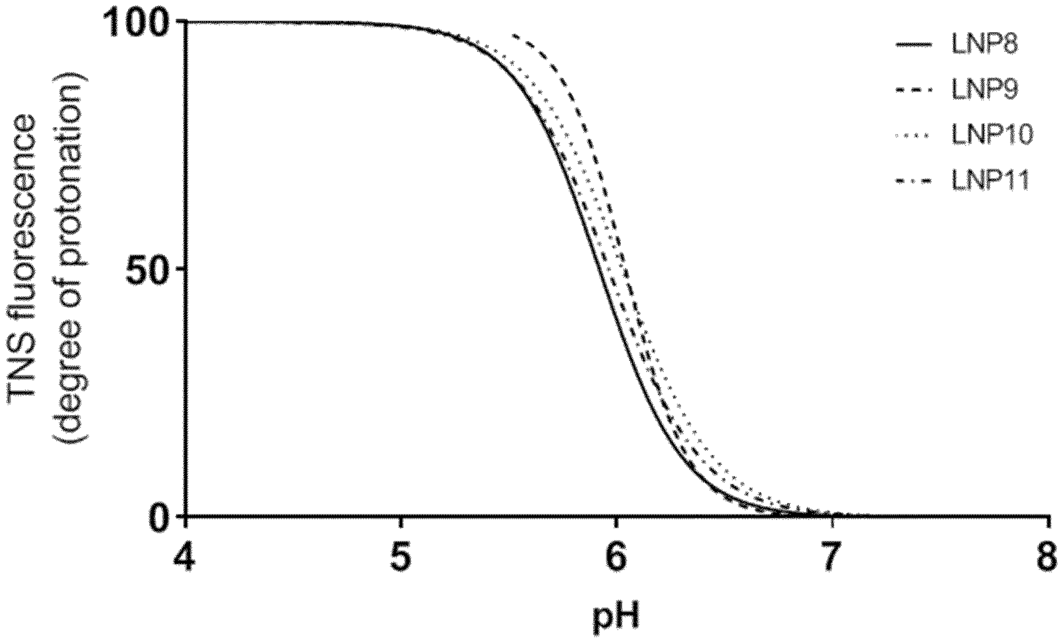
D
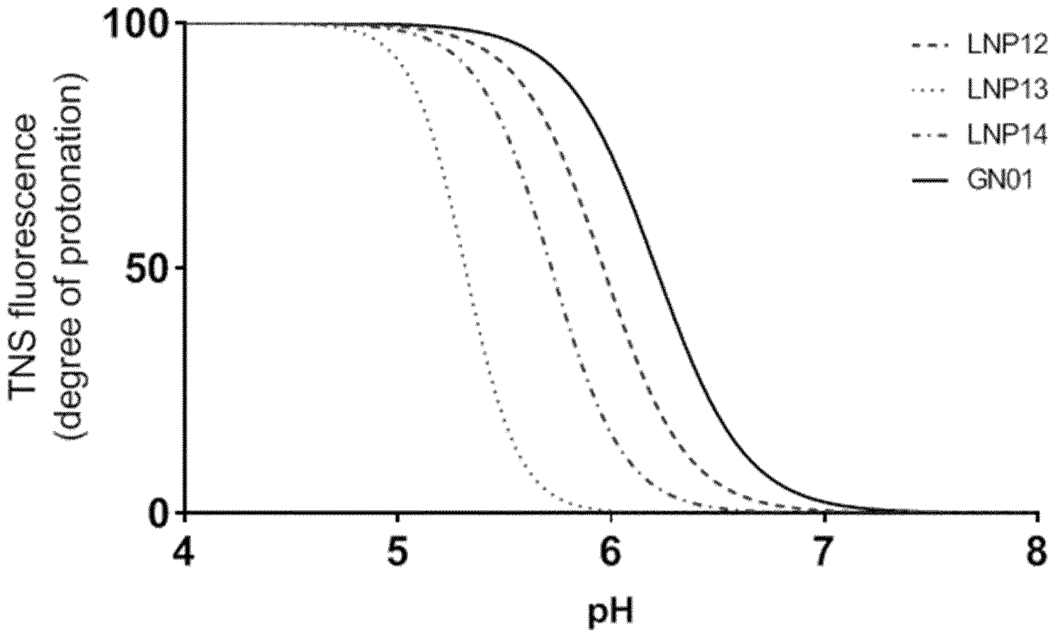
Figure 2 (cont.)

A

B

C

C

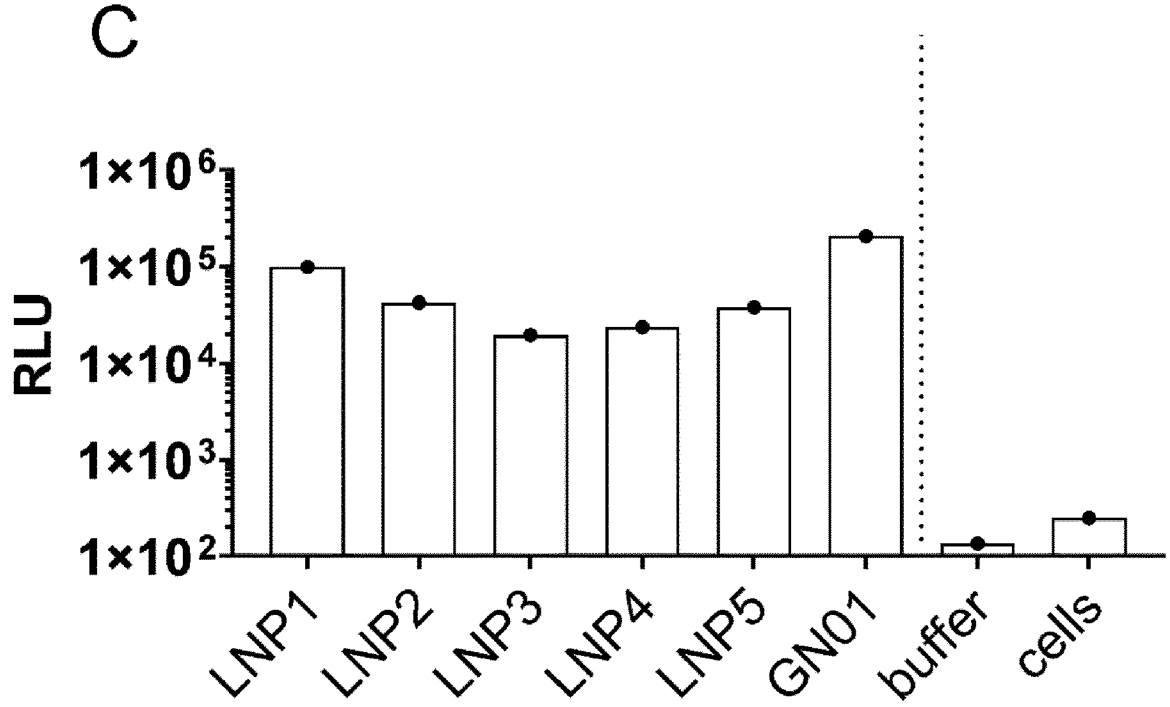
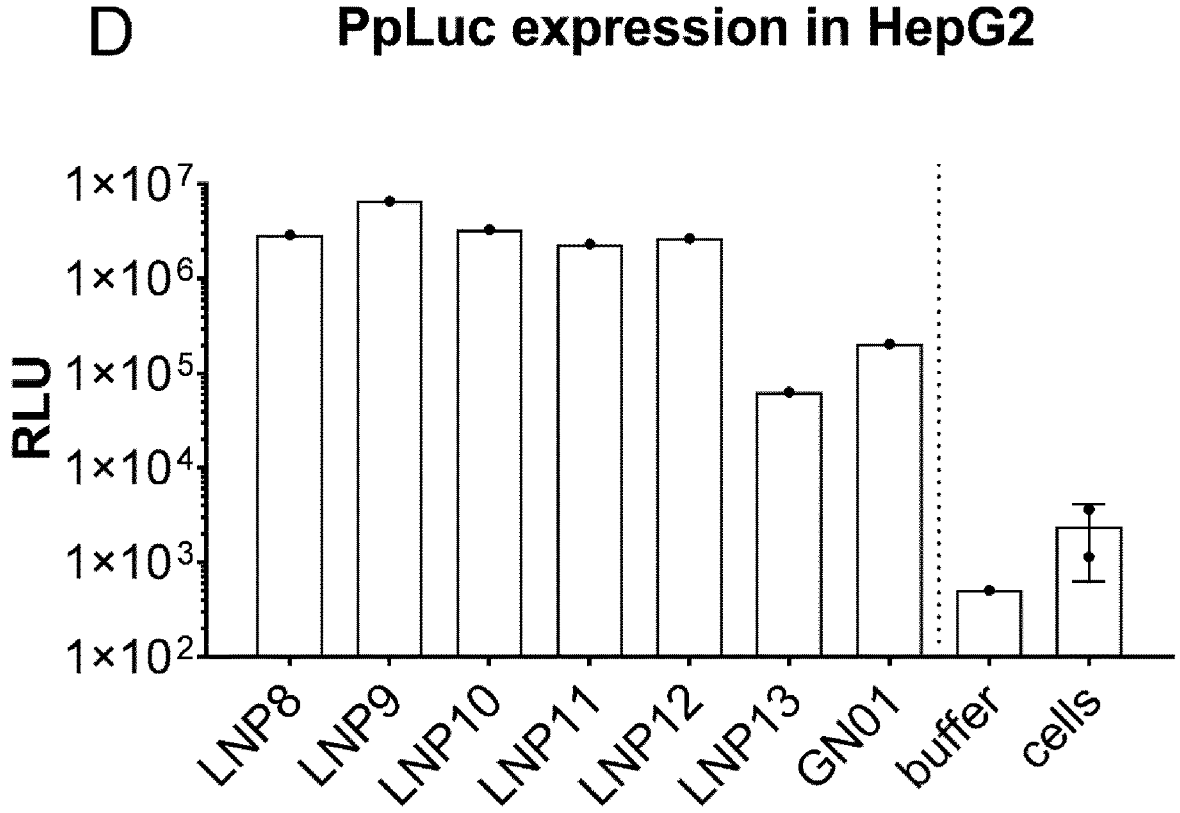
Figure 5 (cont.)

A
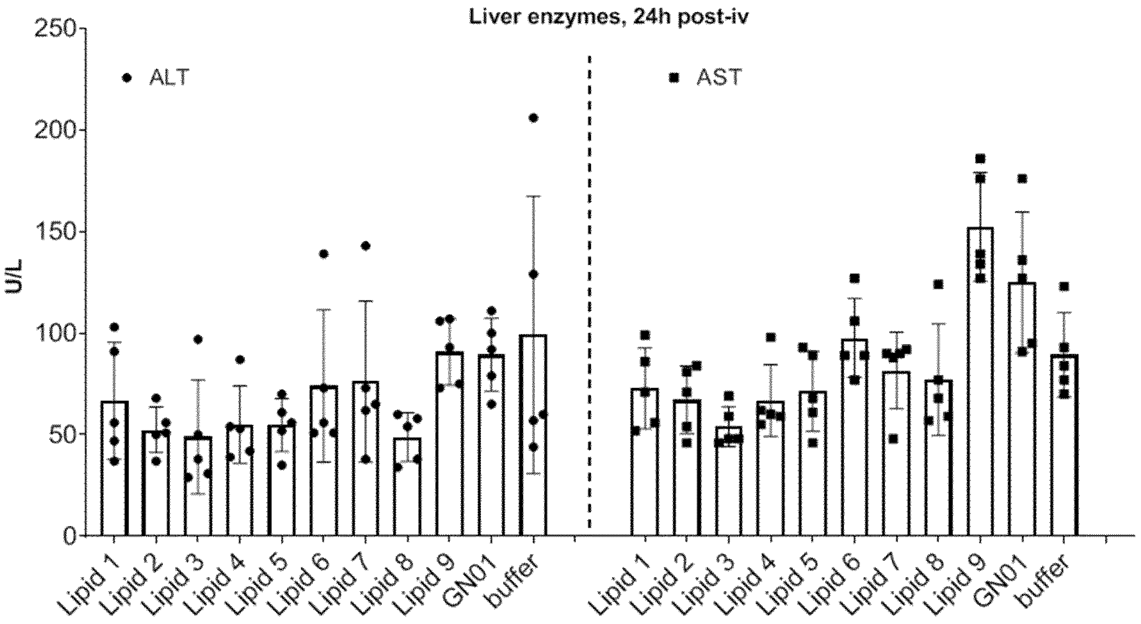
B
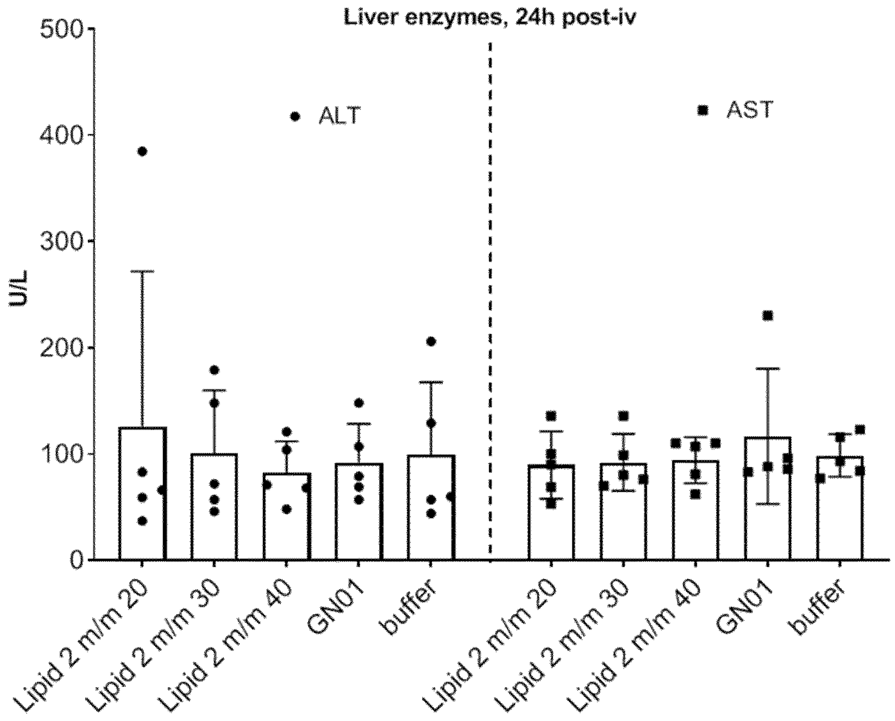
Figure 9

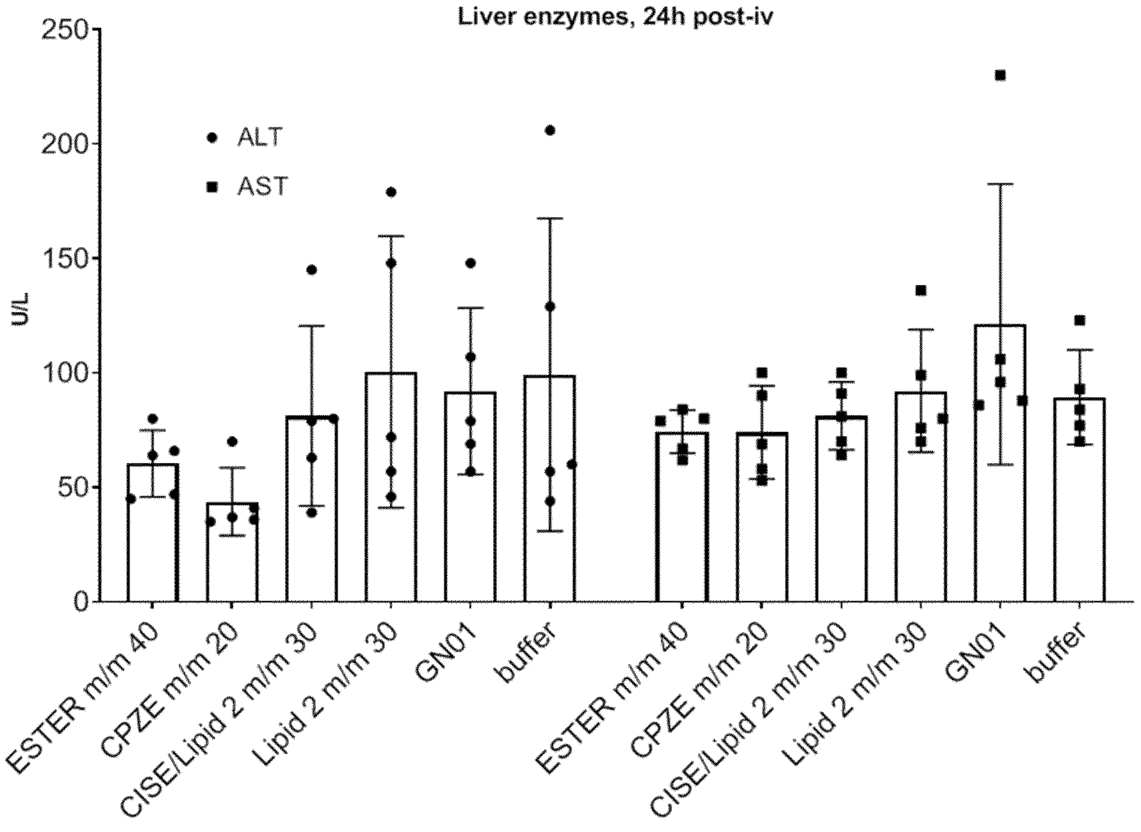
Figure 12.1

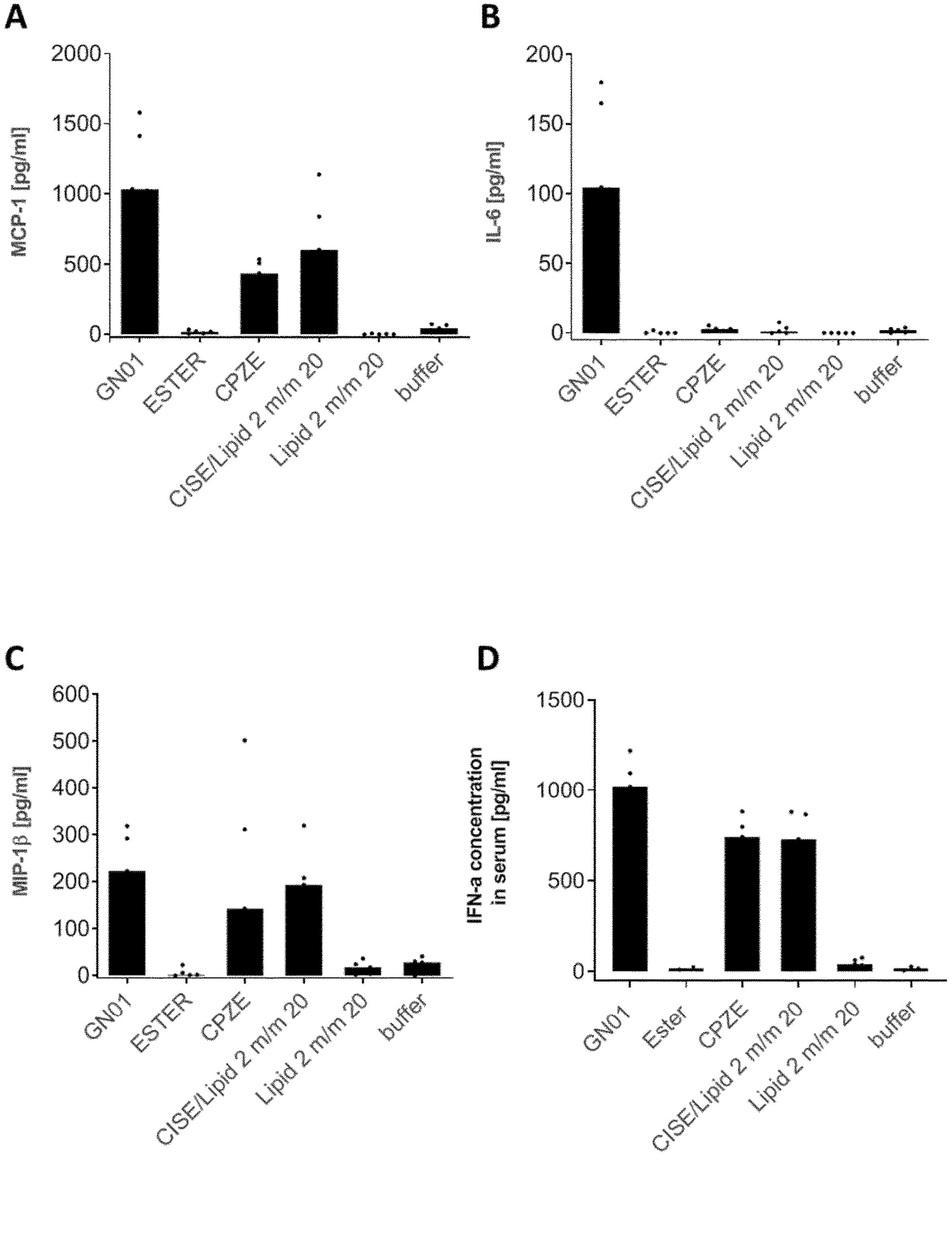
Figure 12.2

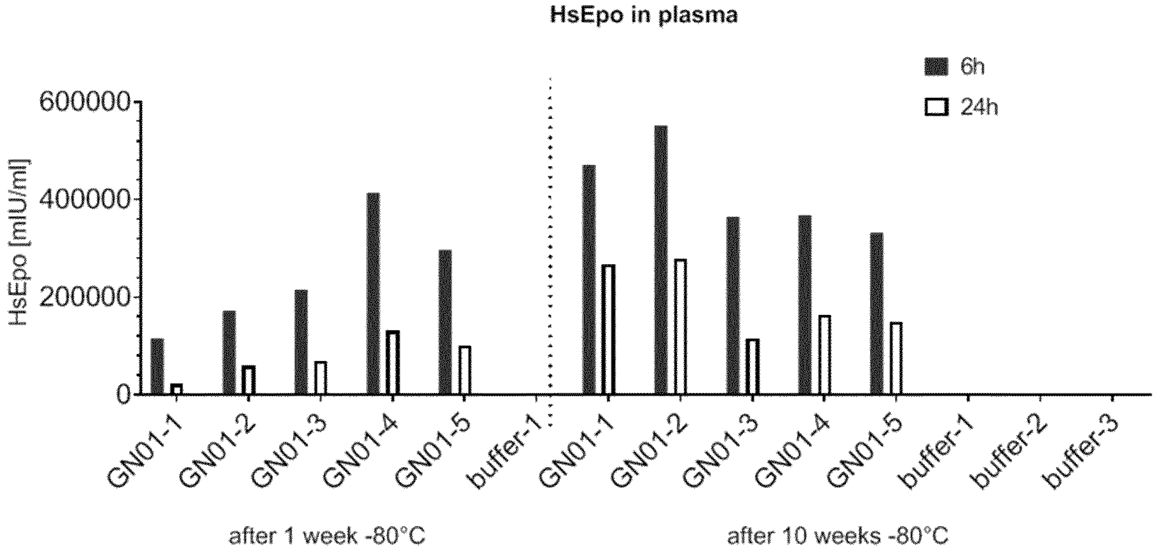
Figure 14.1

A
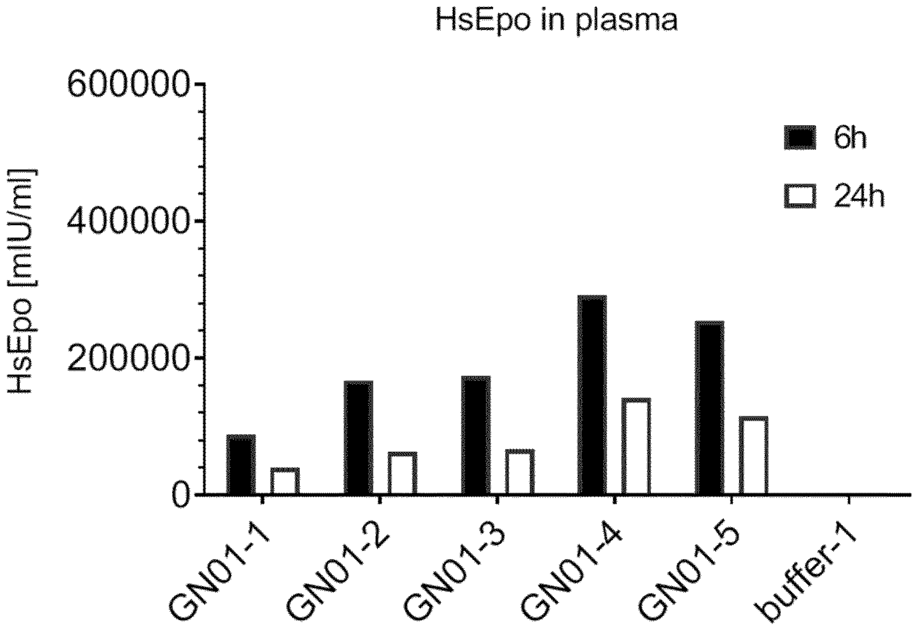
B
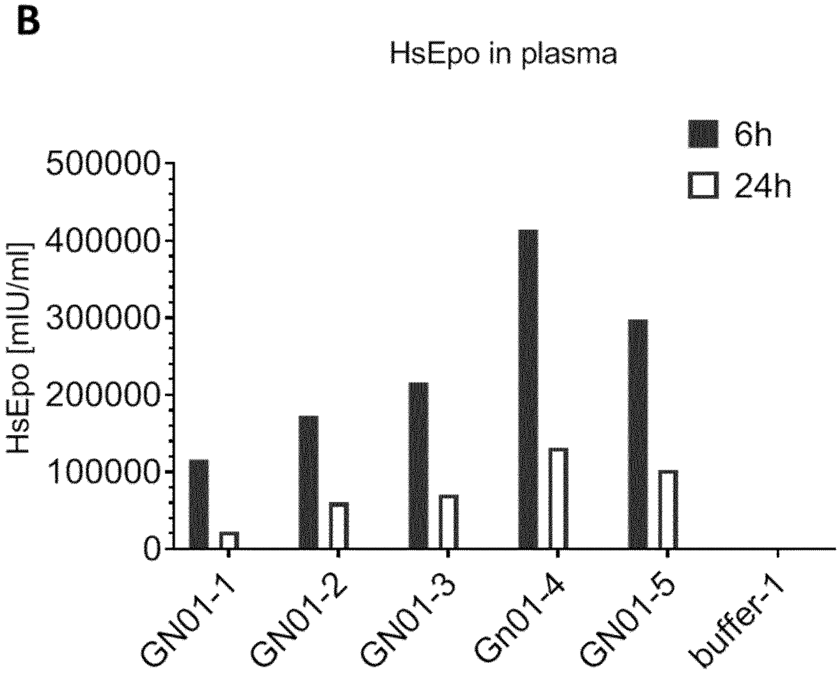
Figure 14.2

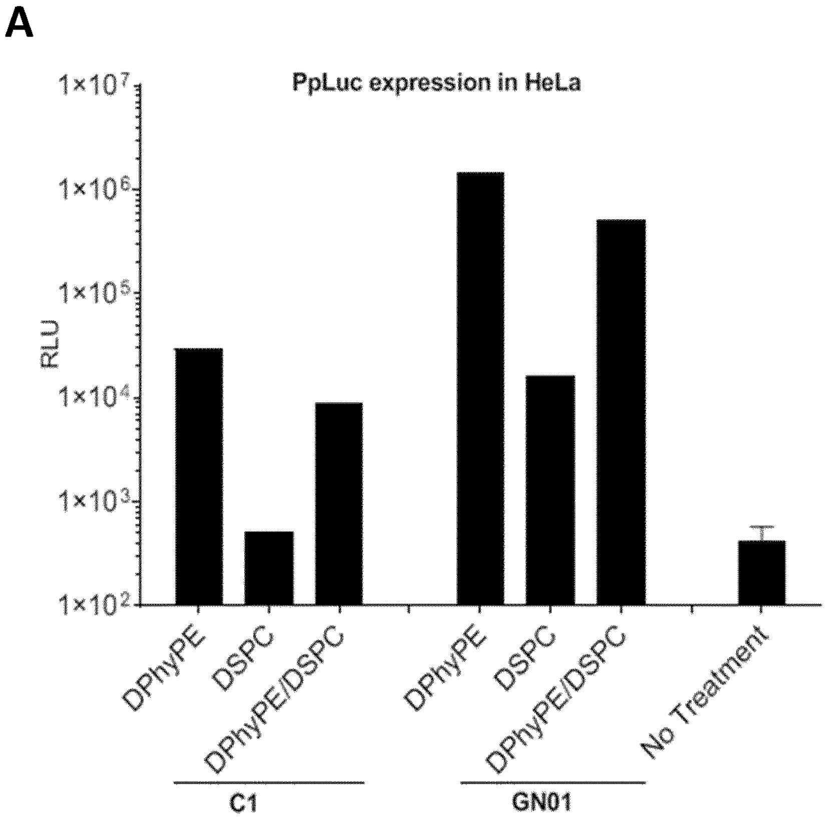
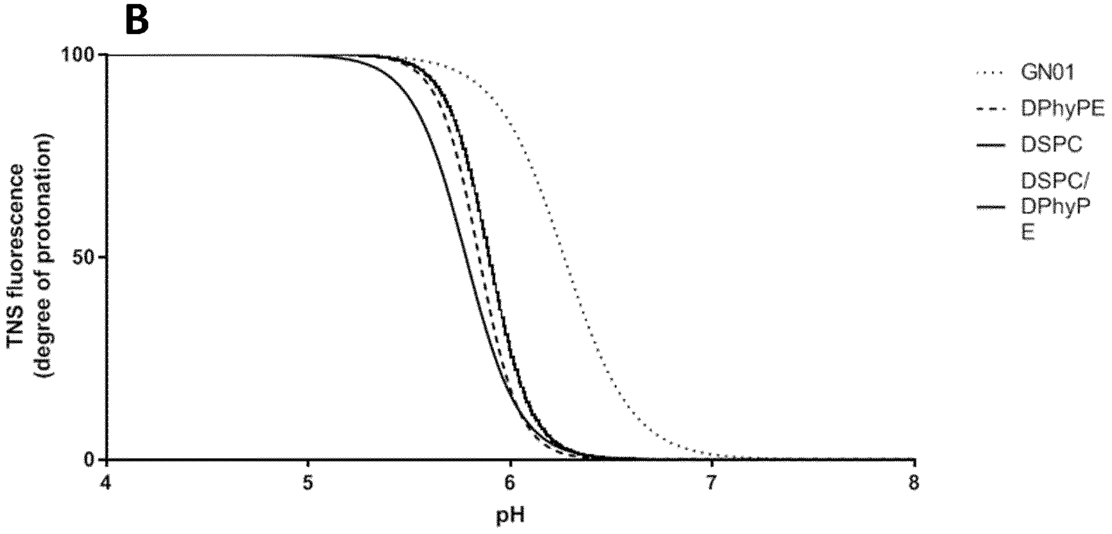
Figure 15.1

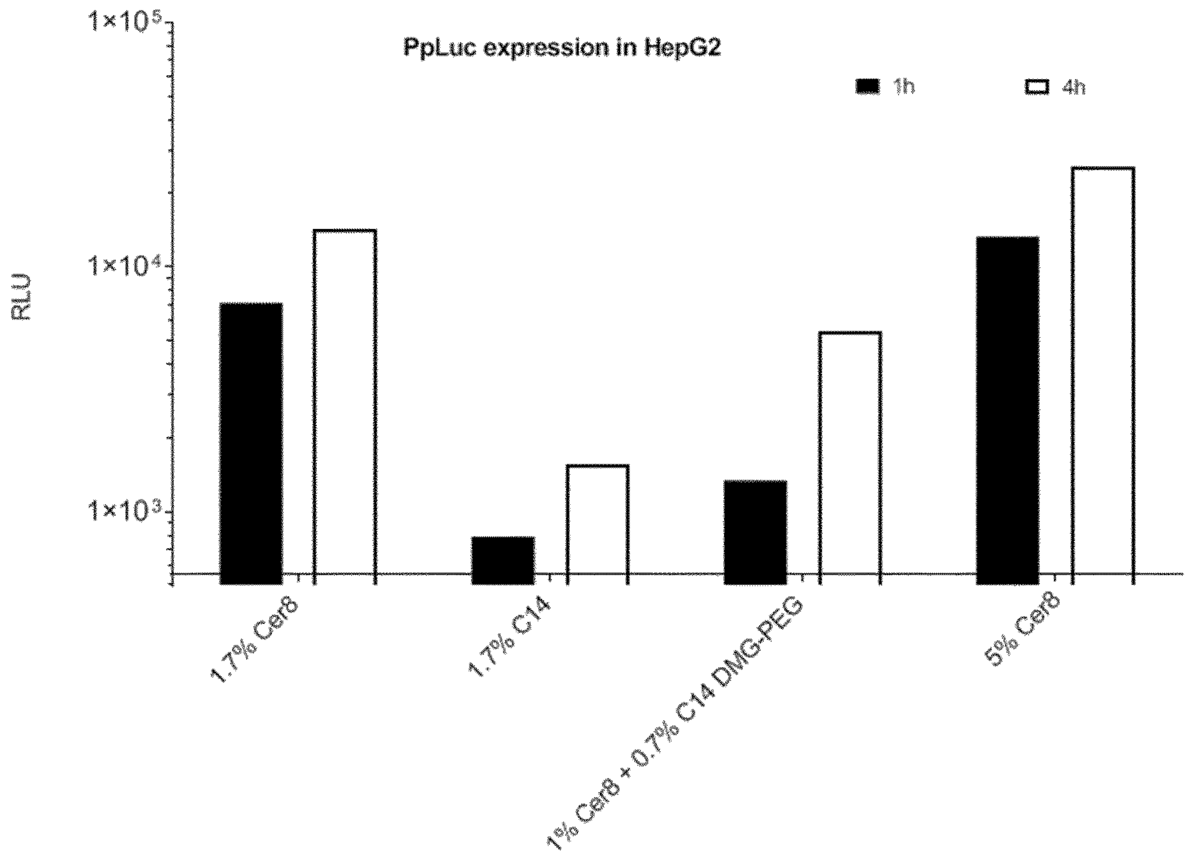
Figure 15.2

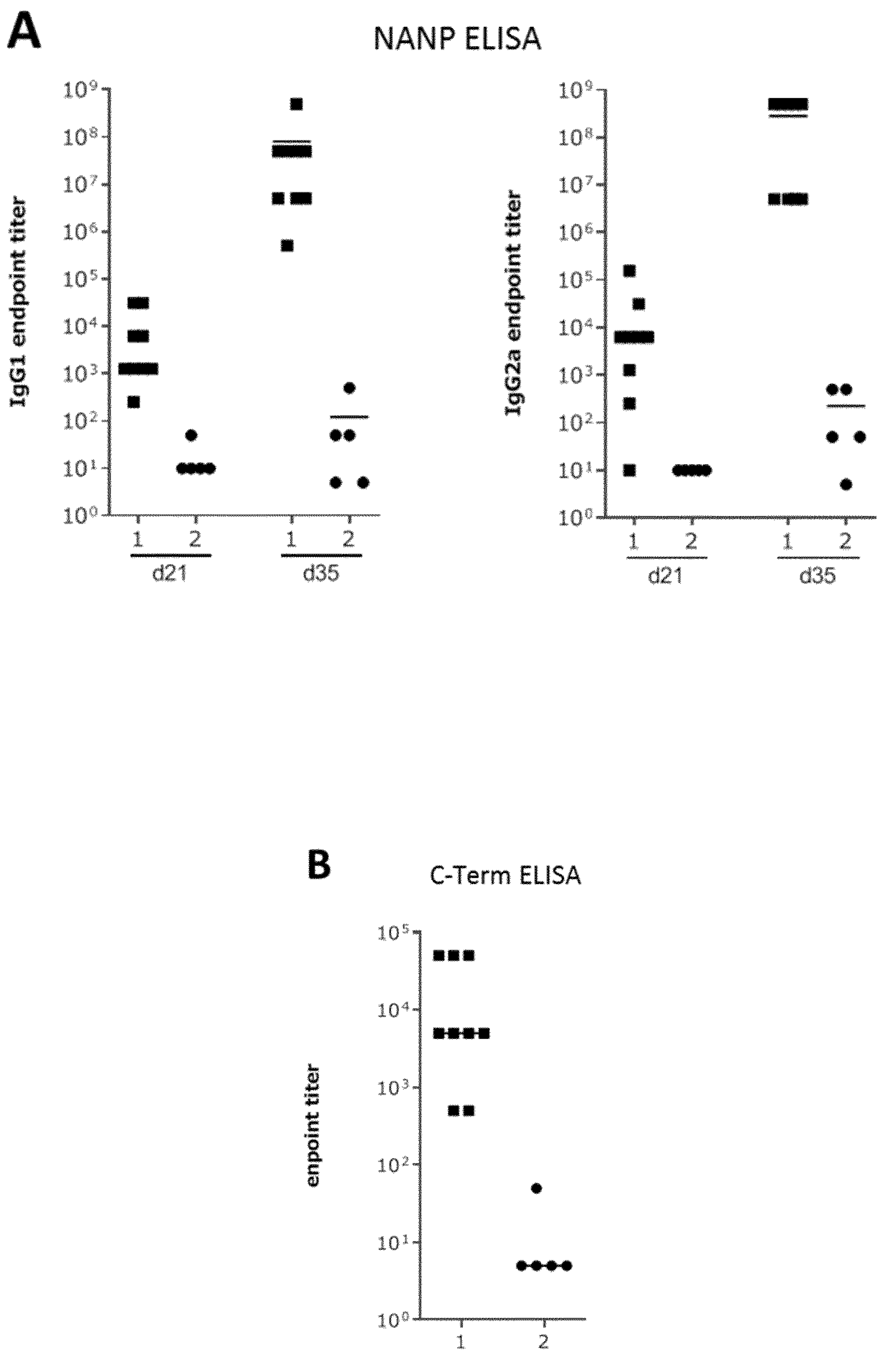
Figure 21.1

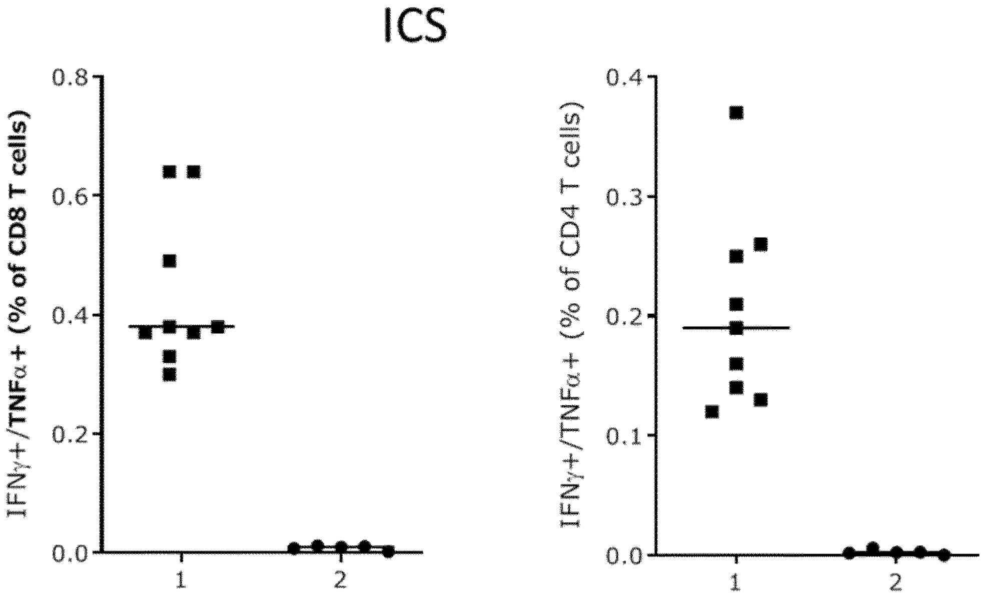
Figure 21.2

A
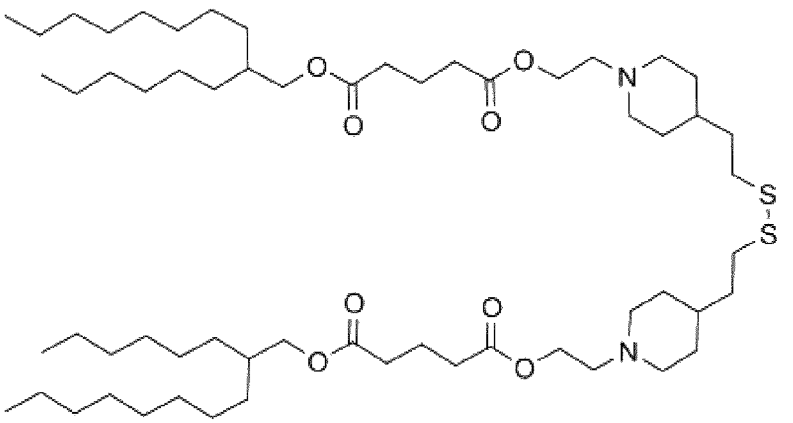
B
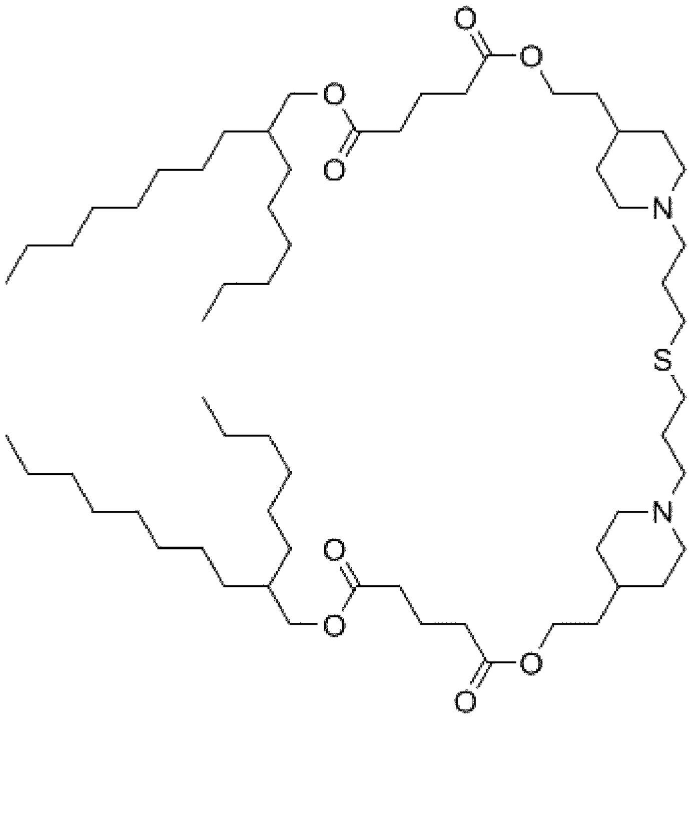
Figure 24

A
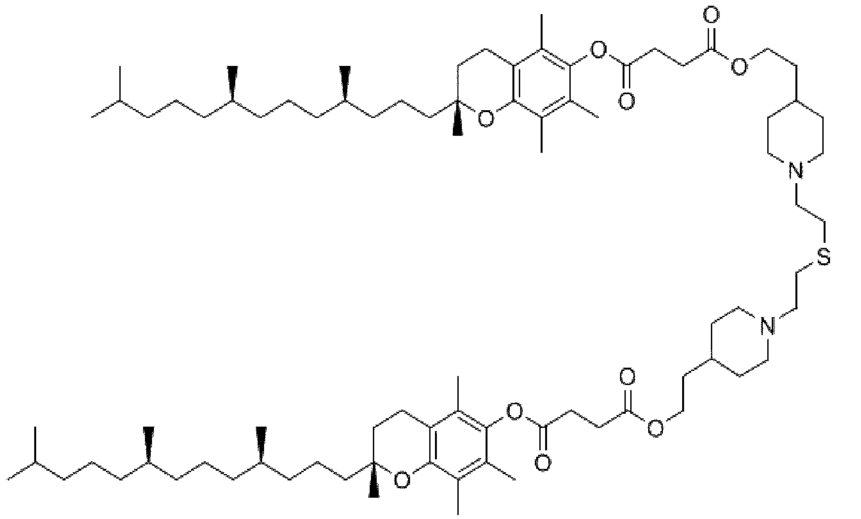
B
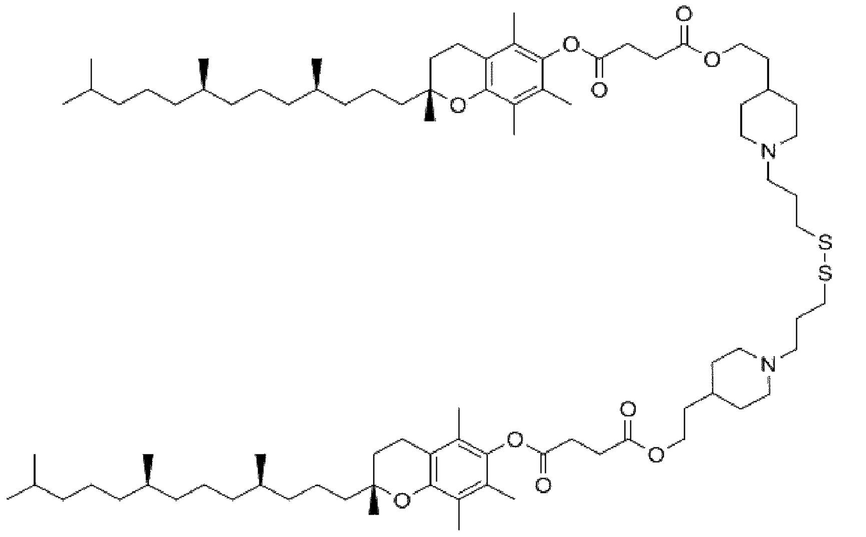
Figure 25

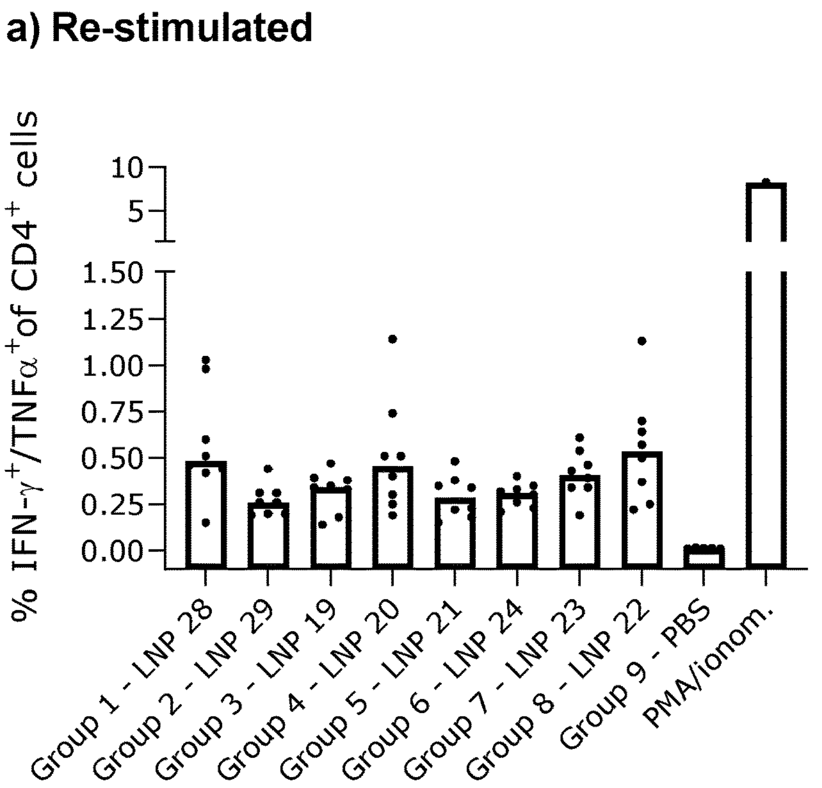
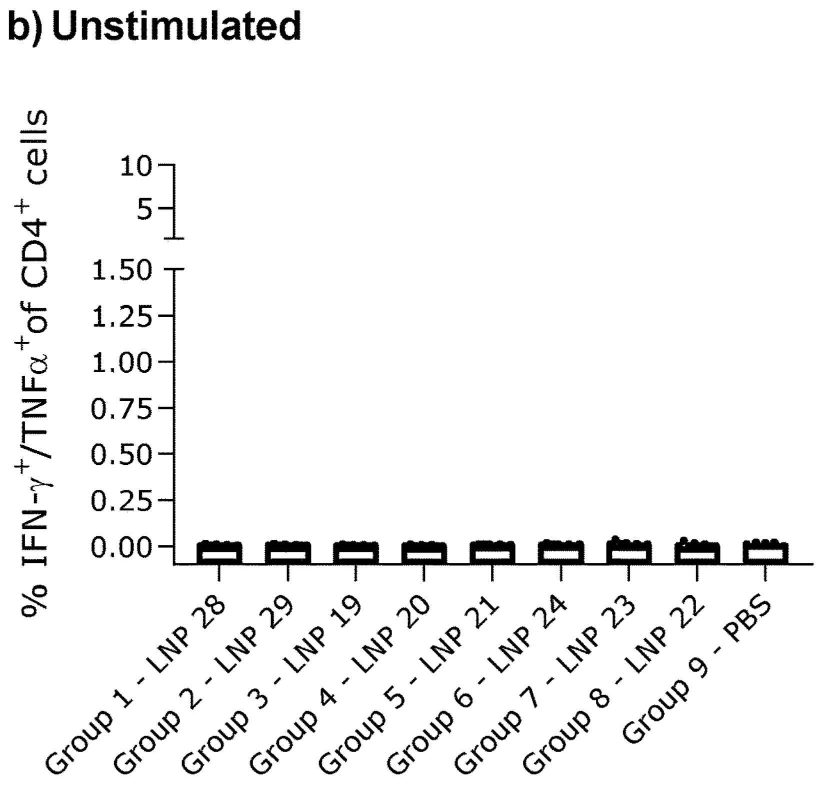
Figure 27B a) Re-stimulated
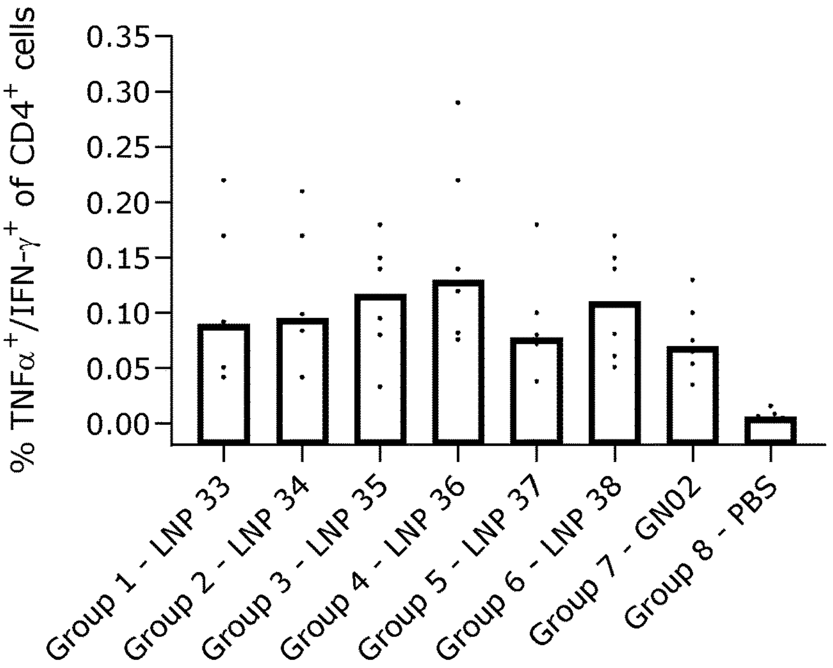
b) Unstimulated
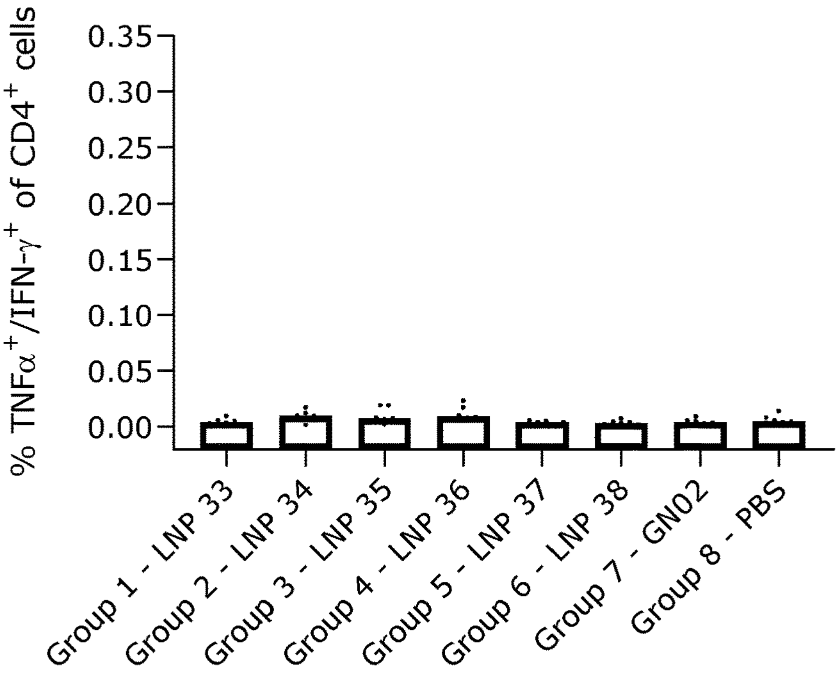
Figure 29

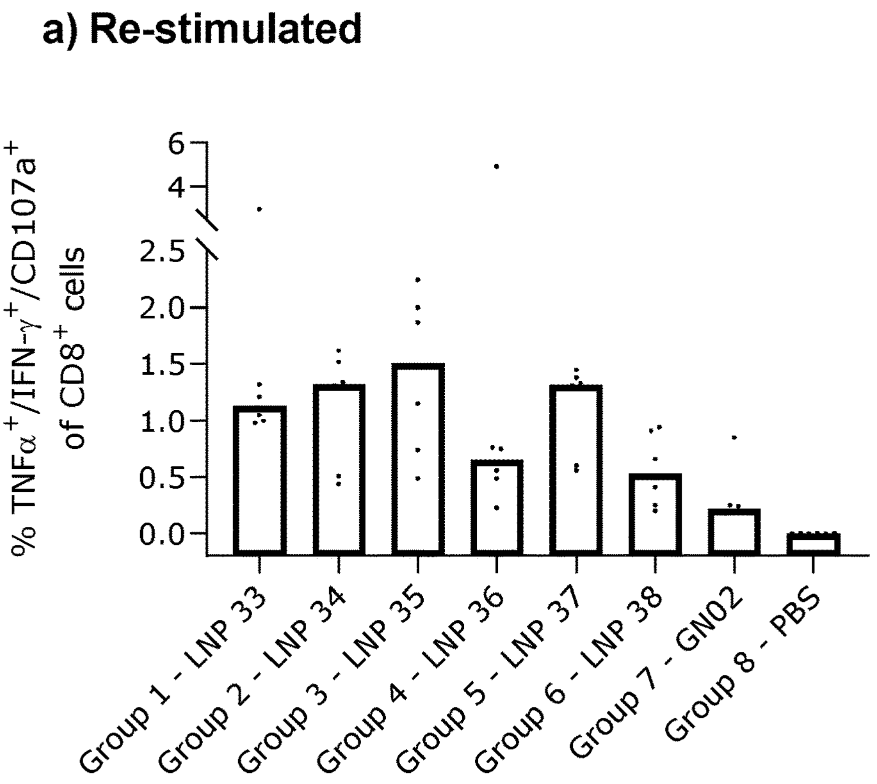
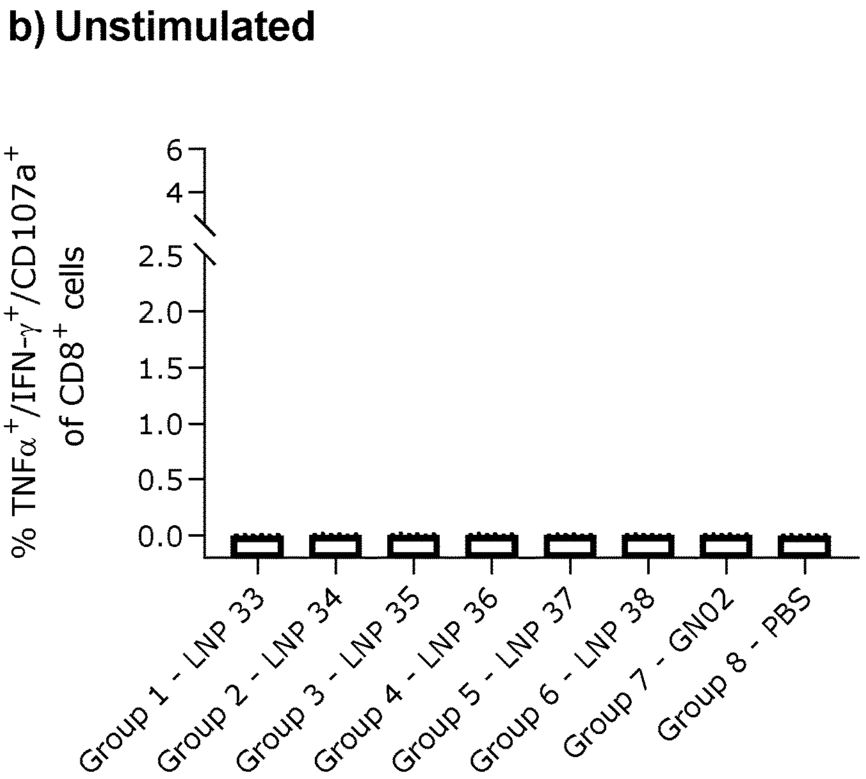
Figure 30

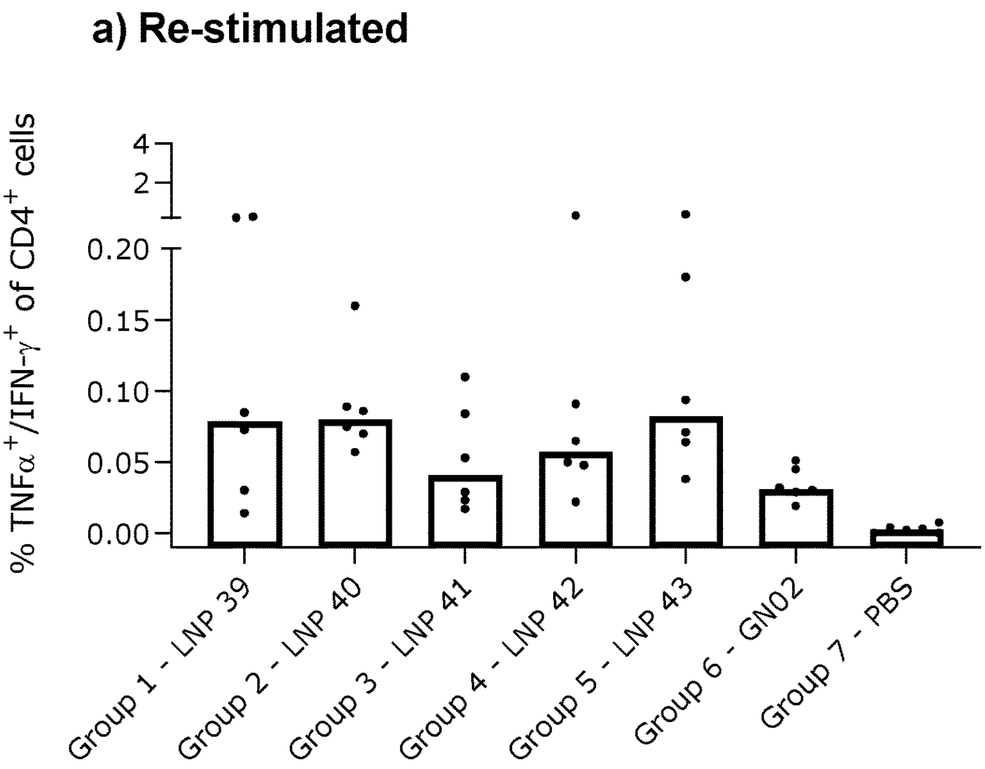
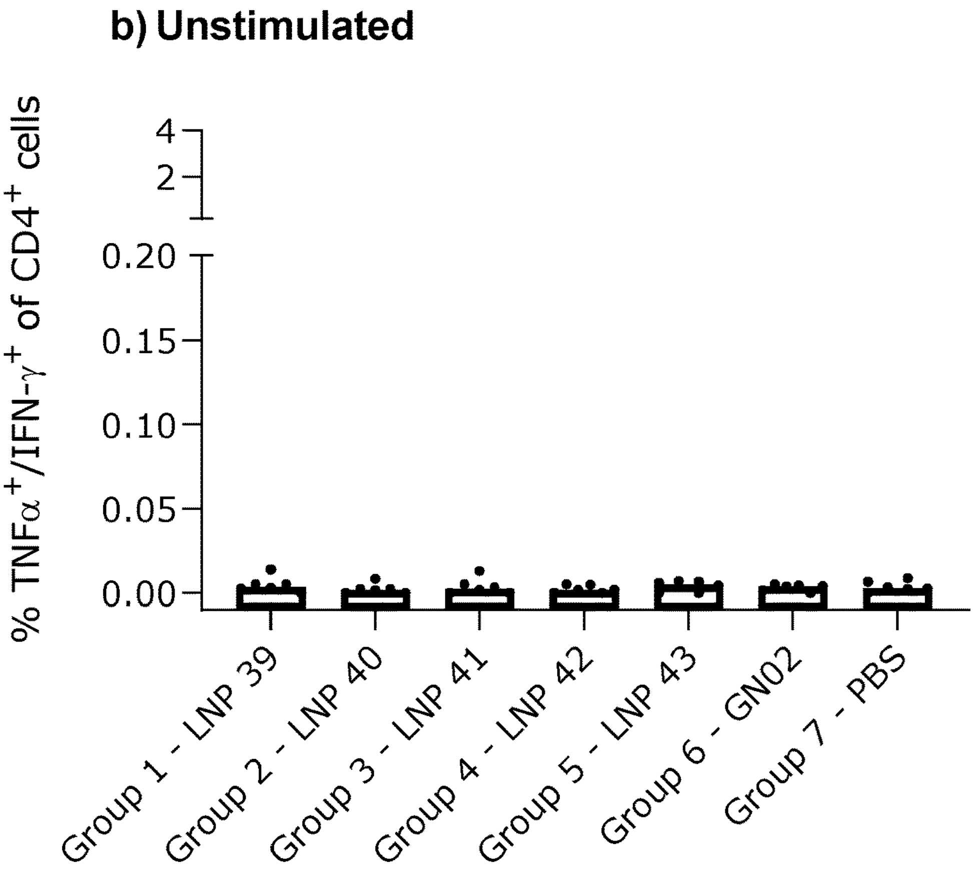
Figure 32

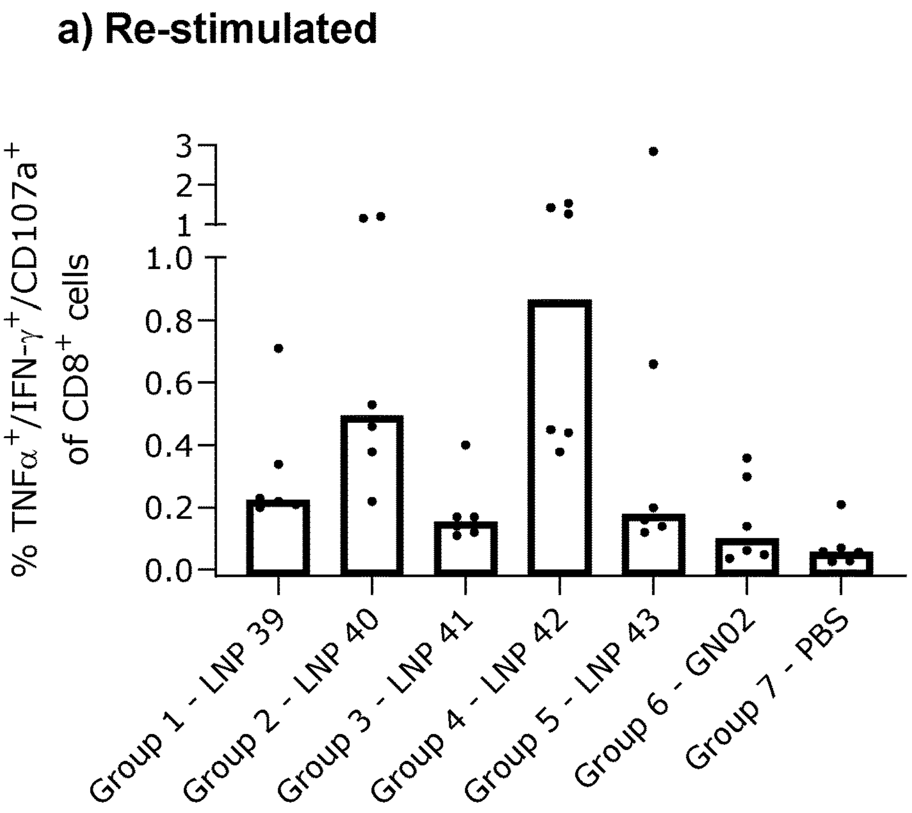
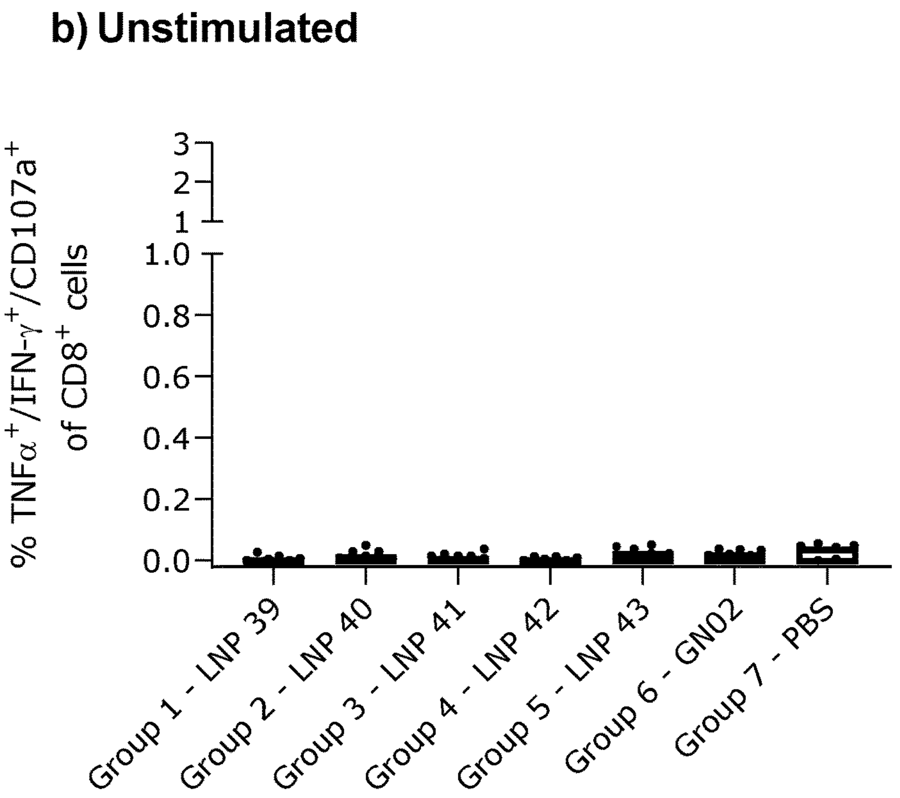
Figure 33

LIPID NANOPARTICLES FOR DELIVERY OF NUCLEIC ACIDS

The present application is a national phase application under 35 U.S.C. § 371 of International Application No. PCT/EP2020/087254, filed Dec. 18, 2020, the entire contents of which are hereby incorporated by reference. International Application No. PCT/EP2020/087254 claims the priority benefit of European Application No. PCT/EP2019/086825, filed Dec. 20, 2019.

BACKGROUND OF THE INVENTION

The present invention relates to mRNA comprising lipid nanoparticles useful as mRNA-based vaccines. Additionally, the present invention relates to a composition comprising the mRNA comprising lipid nanoparticles and the use of the mRNA comprising lipid nanoparticles or the composition for the preparation of a pharmaceutical composition, especially a vaccine, e.g. for use in the prophylaxis or treatment of infectious diseases, tumour or cancer diseases, allergies or autoimmune diseases. The present invention further describes a method of treatment or prophylaxis of the afore-mentioned diseases.

Gene therapy and genetic vaccination belong to the most promising and quickly developing methods of modern medicine. They may provide highly specific and individual options for therapy of a large variety of diseases. Genetic vaccination allows evoking a desired immune response to selected antigens, such as characteristic components of bacterial surfaces, viral particles, tumour antigens or the like. Generally, vaccination is one of the pivotal achievements of modern medicine. However, effective vaccines are currently available only for a limited number of diseases. Accordingly, infections that are not preventable by vaccination still affect millions of people every year.

Commonly, vaccines may be subdivided into "first", "second" and "third" generation vaccines. "First generation" vaccines are, typically, whole-organism vaccines. They are based on either live and attenuated or killed pathogens, e.g. viruses, bacteria or the like. The major drawback of live and attenuated vaccines is the risk for a reversion to life-threatening variants. Thus, although attenuated, such pathogens may still intrinsically bear unpredictable risks.

Killed pathogens may not be as effective as desired for generating a specific immune response. In order to minimize these risks, "second generation" vaccines were developed. These are, typically, subunit vaccines, consisting of defined antigens or recombinant protein components which are derived from pathogens.

Genetic vaccines, i.e. vaccines for genetic vaccination, are usually understood as "third generation" vaccines. They are typically composed of genetically engineered nucleic acid molecules which allow expression of peptide or protein (antigen) fragments characteristic for a pathogen or a tumour antigen in vivo. Genetic vaccines are expressed upon administration to a patient after uptake by target cells. Expression of the administered nucleic acids results in production of the encoded proteins. In the event these proteins are recognized as foreign by the patient's immune system, an immune response is triggered.

DNA as well as RNA may be used as nucleic acid molecules for administration in the context of genetic vaccination. DNA is known to be relatively stable and easy to handle. However, the use of DNA bears the risk of undesired insertion of the administered DNA-fragments into the patient's genome potentially resulting mutagenic events such as in loss of function of the impaired genes. As a further risk, the undesired generation of anti-DNA antibodies has emerged. Another drawback is the limited expression level of the encoded peptide or protein that is achievable upon DNA administration because the DNA must enter the nucleus in order to be transcribed before the resulting mRNA can be translated. Among other reasons, the expression level of the administered DNA will be dependent on the presence of specific transcription factors which regulate DNA transcription. In the absence of such factors, DNA transcription will not yield satisfying amounts of RNA. As a result, the level of translated peptide or protein obtained is limited.

By using RNA instead of DNA for genetic vaccination, the risk of undesired genomic integration and generation of anti-DNA antibodies is minimized or avoided. However, RNA is considered to be a rather unstable molecular species which may readily be degraded by ubiquitous RNAses.

mRNA vaccines comprising antigen-encoding mRNA complexed to protamine are already described in the prior art (e.g. PMID: 27336830, PMID: 23159882, EP1083232, WO2010/037539, WO2012/116811, WO2012/116810, and WO2015/024665). Also WO2016/176330 describes lipid nanoparticle compositions comprising nucleoside-modified RNA encoding different antigens.

Even if a lot of progress was made in the last years there is still a need in the art for providing an efficient method for mRNA vaccination, which allows eliciting an adaptive immune response, wherein the administration is not severely impaired by early degradation of the antigen or by an inefficient translation of the mRNA due to inefficient release of the mRNA in the cell. Furthermore, there is an urgent need to decrease the dose of mRNA vaccines to decrease potential safety concerns and to make the vaccines affordable for the third world.

There are many challenges associated with the delivery of nucleic acids to effect a desired response in a biological system. Nucleic acid based therapeutics, such as vaccines, have enormous potential but there remains a need for more effective delivery of nucleic acids to appropriate sites within a cell or organism in order to realize this potential.

However, two problems currently face the use of nucleic acids in therapeutic contexts. First, free RNAs are susceptible to nuclease digestion in plasma. Second, free RNAs have limited ability to gain access to the intracellular compartment where the relevant translation machinery resides. Lipid nanoparticles formed from cationic lipids with other lipid components, such as neutral lipids, cholesterol, PEG, PEGylated lipids, and oligonucleotides have been used to block degradation of the RNAs in plasma and facilitate the cellular uptake of the oligonucleotides.

There remains a need for improved cationic lipids and lipid nanoparticles for the delivery of oligonucleotides. Preferably, these lipid nanoparticles would provide optimal drug:lipid ratios, protect the nucleic acid from degradation and clearance in serum, be suitable for systemic or local delivery, and provide intracellular delivery of the nucleic acid. In addition, these lipid-nucleic acid particles should be well-tolerated and provide an adequate therapeutic index, such that patient treatment at an effective dose of the nucleic acid is not associated with unacceptable toxicity and/or risk to the patient. The present invention provides these and related advantages.

SUMMARY OF THE INVENTION

In one aspect, the present invention relates to novel cationic lipids which are useful for the delivery of nucleic acids into living cells. The cationic lipids are compounds according to formula (I):

$R^a$-A-$R^b$ formula (I)

wherein $R^a$ is selected from:

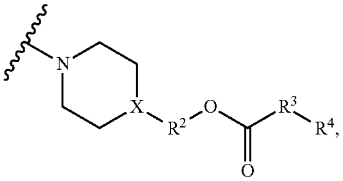

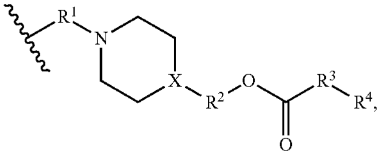

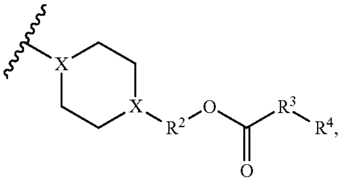

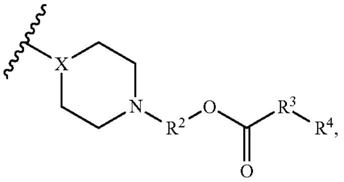

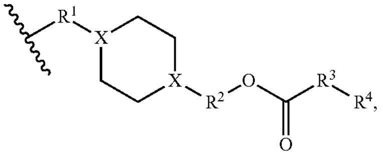

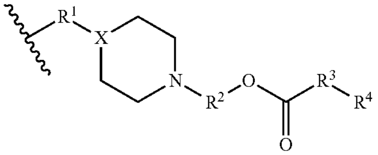 or

—$R^1$—N(H)—C(O)—$R^3$—$R^4$;

$R^b$ is selected from:

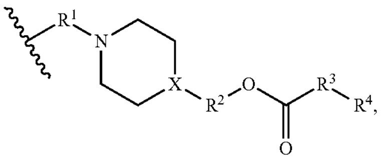

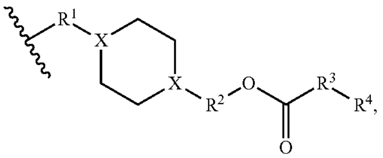

-continued

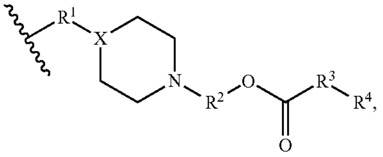

—$R^1$—N(H)—C(O)—$R^3$—$R^4$, or

—$R^1$—N($CH_3$)$_2$;

A is —S—, —S—S—, —S—C(O)—, —NH—C(O)—, —NH—C(O)O—, —NH—C(O)—NH—, —S—C(O)—N(H)—, —C(O)O—, or —O—P(O)(OH)—O—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is —$R^5$—C(O)—O—, or —$R^5$—O—C(O)—, —$R^5$—C(O)—NH—, —$R^5$—OC(O)—NH—, or $R^5$—NH—C(O)O—;

$R^4$ is a lipophilic substituent with 12 to 36 carbon atoms;

$R^5$ is an alkanediyl having 1 to 6 carbon atoms;

X is a carbon or nitrogen atom;

wherein all selections are independent of one another, optionally provided that if $R^1$, $R^2$ and $R^5$ are all ethanediyl, A is —S—S—, and $R^a$ and $R^b$ are identical, then $R^4$ is not

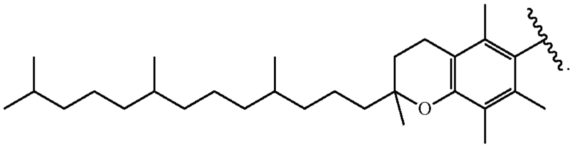 [SMILES: *c1c(C)c(C)c2c(c1C)CCC(C)(CCCC(C)CCCC(C)CCCC(C)C)O2]

In this regard, an alkanediyl is a term for a (—$C_nH_{2n}$—) group; f.e. an "alkanediyl having 2 to 8 carbon atoms" accordingly equals an alkanediyl group having the formula —$C_2H_4$—, —$C_3H_6$—, —$C_4H_6$—, —$C_5H_{10}$—, —$C_6H_{12}$—, —$C_7H_{14}$—, or respectively—$C_3H_{16}$—. In other words, an alkanediyl is a series of divalent radicals of the general formula $C_nH_{2n}$ derived from aliphatic hydrocarbons. Unless specified otherwise, such alkanediyls include substituted alkanediyls.

In another embodiment, in case $R^1$, $R^2$ and $R^5$ are all ethanediyl, A is —S—S—, and $R^a$ and $R^b$ are identical, then $R^4$ is not

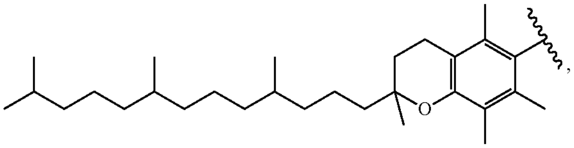 [SMILES: *c1c(C)c(C)c2c(c1C)CCC(C)(CCCC(C)CCCC(C)CCCC(C)C)O2]

or respectively in one embodiment, a lipid according to formula (I) is not lipid C23 as disclosed in Table 1 herein or respectively lipid SS-EC as described herein below (for the avoidance of doubt i.e. in some selected embodiments, cationic lipid COATSOME® SS-EC is disclaimed from embodiments which are related to cationic lipids according to formula (I)).

In another aspect, the invention provides novel compositions incorporating cationic lipids such as the novel cationic lipids defined above.

The cationic lipids and the compositions have been found to be particularly effective in introducing nucleic acids into living cells. For example, they enable improved RNA (e.g. mRNA) vaccines i.e. mRNA-based vaccines against certain infectious diseases or tumours.

In further aspects, the invention provides the use of the compositions incorporating a cationic lipid and a nucleic acid compound as medicines, and in particular as vaccines, as well as vaccination methods based on these vaccines.

In another aspect of the present invention, the present invention also provides a kit, in particular a kit of parts, comprising the mRNA compound comprising mRNA sequence as defined herein and at least one lipid according to formula (I) or formula (II) as defined herein.

Definitions

For the sake of clarity and readability, the following scientific background information and definitions are provided. Any technical features mentioned herein or disclosed thereby can be part of or may be read on each and every embodiment of the invention. Additional definitions and explanations can be provided in the context of this disclosure.

Unless defined otherwise, or unless the specific context requires otherwise, all technical terms used herein have the same meaning as is commonly understood by a person skilled in the relevant technical field.

Unless the context indicates or requires otherwise, the words “comprise”, “comprises” and “comprising” and similar expressions are to be construed in an open and inclusive sense, as “including, but not limited to” in this description and in the claims.

The expressions, “one embodiment”, “an embodiment”, “a specific embodiment” and the like mean that a particular feature, property or characteristic, or a particular group or combination of features, properties or characteristics, as referred to in combination with the respective expression, is present in at least one of the embodiments of the invention. The occurrence of these expressions in various places throughout this description do not necessarily refer to the same embodiment. Moreover, the particular features, properties or characteristics may be combined in any suitable manner in one or more embodiments.

The singular forms “a”, “an” and “the” should be understood as to include plural references unless the context clearly dictates otherwise.

Percentages in the context of numbers should be understood as relative to the total number of the respective items. In other cases, and unless the context dictates otherwise, percentages should be understood as percentages by weight (wt-%).

As used herein, a “compound” means a chemical substance, which is a material consisting of molecules having essentially the same chemical structure and properties. For a small molecular compound, the molecules are typically identical with respect to their atomic composition and structural configuration. For a macromolecular or polymeric compound, the molecules of a compound are highly similar but not all of them are necessarily identical. For example, a segment of a polymer that is designated to consist of 50 monomeric units may also contain individual molecules with e.g. 48 or 53 monomeric units.

The term “molecule” may either be used as a synonym for “compound” or for an individual (i.e. a single) molecule.

Any reference to a compound or moiety having a functional group which is ionizable under physiological conditions should be understood as including the ionized form of the respective compound or moiety. Vice versa, any reference to a compound or moiety having an ionized functional group which may also exist in the non-ionized form under physiological conditions should be understood as including the non-ionized form of the respective compound or moiety. For example, the disclosure of a compound having a carboxyl group should be interpreted as referring to the respective compound with non-ionized carboxyl group or with the ionized carboxylate group.

As used herein, “physiological conditions” refers to an aqueous environment having a pH that is within the pH range known from human physiology, including both extra- and intracellular conditions. An approximation of this pH range is from about pH 1 to about pH 9. Depending on the context, physiological conditions may also refer to approximately neutral conditions, such as from about pH 5 to about pH 8.5, or from about pH 5.5 to about pH 8.

A lipidoid compound, also simply referred to as lipidoid, is a lipid-like compound, i.e. an amphiphilic compound with lipid-like physical properties. In the context of the present invention, the term lipid is considered to encompass lipidoids.

In the context of the present invention, the term “selected from the group consisting of” followed by a certain group of elements (f.e. “A, B and C”) is meant within the context of the invention to be not limited to said group. In other words, such a term does not indicate that the disclosure is closed to unrecited elements, i.e. also alternative meanings are comprised within the group following this term. Therefore, in the context of the present invention, the term “selected from the group consisting of” followed by a certain group of elements (f.e. “A, B and C”) should be understood as “selected from A, B, and C” or alternatively “is A, B, or C” encompassing also other structurally and functionally related and unrelated but not mentioned elements.

The term “about” is used when parameters or values do not necessarily need to be identical, i.e. 100% the same. Accordingly, “about” means, that a parameter or values may diverge by 0.1% to 20%, preferably by 0.1% to 10%; in particular, by 0.5%, 1%, 2%, 3%, 4%, 5%, 6%, 7%, 8%, 9%, 10%, 11%, 12%, 13%, 14%, 15%, 16%, 17%, 18%, 19%, 20%. The skilled person will know that e.g. certain parameters or values may slightly vary based on the method how the parameter was determined. For example, if a certain parameter or value is defined herein to have e.g. a length of “about 1000 nucleotides”, the length may diverge by 0.1% to 20%, preferably by 0.1% to 10%; in particular, by 0.5%, 1%, 2%, 3%, 4%, 5%, 6%, 7%, 8%, 9%, 10%, 11%, 12%, 13%, 14%, 15%, 16%, 17%, 18%, 19%, 20%. Accordingly, the skilled person will know that in that specific example, the length may diverge by 1 to 200 nucleotides, preferably by 1 to 100 nucleotides; in particular, by 5, 10, 20, 30, 40, 50, 60, 70, 80, 90, 100, 110, 120, 130, 140, 150, 160, 170, 180, 190, 200 nucleotides.

The term “cationic” means, unless a different meaning is clear from the specific context, that the respective structure bears a positive charge, either permanently or not permanently but in response to certain conditions such as e.g. pH. Thus, the term “cationic” covers both “permanently cationic” and “cationisable”. The term “cationisable” as used herein means that a compound, or group or atom, is positively charged at a lower pH and uncharged at a higher pH of its environment. Also in non-aqueous environments where no pH value can be determined, a cationisable compound, group or atom is positively charged at a high hydrogen ion concentration and uncharged at a low concentration or activity of hydrogen ions. It depends on the individual properties of the cationisable or polycationisable compound, in particular the $pK_a$ of the respective cationisable group or atom, at which pH or hydrogen ion concentration it is charged or uncharged. In diluted aqueous environments, the fraction of cationisable compounds, groups or atoms bearing a positive charge may be estimated using the so-called Henderson-Hasselbalch equation which is well-known to a person skilled in the art. E.g., if a compound or moiety is cationisable, it is preferred that it is positively charged at a pH value of about 1 to 9, preferably 4 to 9, 5 to 8 or even 6 to 8, more preferably of a pH value of or below 9, of or below 8, of or below 7, most preferably at physiological pH values, e.g. about 7.3 to 7.4, i.e. under physiological conditions, particularly under physiological salt conditions of the cell in vivo. In embodiments, it is preferred that the cationisable compound or moiety is predominantly neutral at physiological pH values, e.g. about 7.0-7.4, but becomes positively charged at lower pH values. In some embodiments, the preferred range of $pK_a$ for the cationisable compound or moiety is about 5 to about 7. In some embodiments, the protonatable lipids have a $pK_a$ of the protonatable group in the range of about 4 to about 11, e.g., a $pK_a$ of about 5 to about 7.

Unless a different meaning is clear from the specific context, the term "cationic" means that the respective structure bears a positive charge, either permanently, or not permanently but in response to certain conditions such as pH. Thus, the term "cationic" covers both "permanently cationic" and "cationisable". For example, a compound or moiety with a primary, secondary or tertiary amino group is cationic, and more specifically, cationisable, as it may exist predominantly in the positively charged state under physiological conditions.

As used herein, "permanently cationic" means that the respective compound, or group or atom, is positively charged at any pH value or hydrogen ion activity of its environment. Very often, the positive charge results from the presence of a quaternary nitrogen atom. Where a compound carries a plurality of such positive charges, it may be referred to as permanently polycationic, which is a subcategory of permanently cationic.

Similarly, the terms "anionic", "anionizable" and "permanently anionic" are used to have the analog meaning as "cationic", "cationisable" and "permanently cationic", except that the charge of the respective compound, group or atom is negative rather than positive.

The expression "neutral", when applied to a compound such as a lipid or a steroid, or to a group or moiety, either means that it is neither cationic nor anionic, such as a compound having no functional groups that are ionizable under physiological conditions as, for example, like a hydrocarbon; or it is both cationic and anionic, i.e. zwitterionic, under typical physiological conditions, such as a typical native phosphatidylcholine.

A "lipid", as used herein, refers to a group of organic compounds that are derivatives of fatty acids (e.g., esters) and are generally characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids. Regarding glycolipids, in certain embodiments, the LNP comprises glycolipids (e.g., monosialoganglioside $GM_1$).

In this context, the prefix "poly-" refers to a plurality of atoms or groups having the respective property in a compound. If put in parenthesis, the presence of a plurality is optional. For example, (poly)cationic means cationic and/or polycationic. However, the absence of the prefix should not be interpreted such as to exclude a plurality. For example, a polycationic compound is also a cationic compound and may be referred to as such.

The term "nucleic acid" means any compound comprising, or consisting of, DNA or RNA. The term may be used for a polynucleotide and/or oligonucleotide. Wherever herein reference is made to a nucleic acid or nucleic acid sequence encoding a particular protein and/or peptide, said nucleic acid or nucleic acid sequence, respectively, preferably also comprises regulatory sequences allowing in a suitable host, e.g. a human being, its expression, i.e. transcription and/or translation of the nucleic acid sequence encoding the particular protein or peptide.

In the context of the present invention, the term "nucleoside modification" refers to nucleic acids such as mRNA compounds or molecules comprising nucleosides which do not normally occur in native mRNA, preferably non-natural nucleosides. In particular, the term preferably refers to mRNA nucleosides other than adenine, guanine, cytosine, uracil and thymine.

The term "nucleoside" generally refers to compounds consisting of a sugar, usually ribose or deoxyribose, and a purine or pyrimidine base. The term "nucleotide" generally refers to a nucleoside comprising a phosphate group attached to the sugar.

A "peptide" means an oligomer or polymer of at least two amino acid monomers linked by peptide bonds. The term does not limit the length of the polymer chain of amino acids. A peptide may, for example, contain less than 50 monomer units. Longer peptides are also called polypeptides, typically having 50 to 600 monomeric units, more specifically 50 to 300 monomeric units.

A "protein" comprises or consists of one or more polypeptides folded into a 3-dimensional form, facilitating a biological function.

An "influenza pandemic" or "pandemic flu" can occur when a non-human (novel) influenza virus gains the ability for efficient and sustained human-to-human transmission and then spreads globally. Influenza viruses that have the potential to cause a pandemic are referred to as "influenza viruses with pandemic potential" or "pandemic influenza virus".

Examples of influenza viruses with pandemic potential include avian influenza A (H5N1) and avian influenza A (H7N9), which are two different "bird flu" viruses. These are non-human viruses (i.e., they are novel among humans and circulate in birds in parts of the world) so there is little to no immunity against these viruses among people.

Human infections with these viruses have occurred rarely, but if either of these viruses was to change in such a way that it was able to infect humans easily and spread easily from person to person, an influenza pandemic could result.

Vaccine for pandemic influenza/flu or pandemic influenza/flu vaccine: A vaccine directed against a pandemic influenza virus is called herein as a vaccine for pandemic influenza/flu or pandemic influenza/flu vaccine.

Flu/influenza season: Flu season is an annually recurring time period characterized by the prevalence of outbreaks of influenza (flu). The season occurs during the cold half of the year in each hemisphere. Influenza activity can sometimes be predicted and even tracked geographically. While the beginning of major flu activity in each season varies by location, in any specific location these minor epidemics usually take about 3 weeks to peak and another 3 weeks to significantly diminish. Flu vaccinations have been used to diminish the effects of the flu season; pneumonia vaccinations additionally diminishes the effects and complications of flu season. Since the Northern and Southern Hemisphere have winter at different times of the year, there are actually two flu seasons each year.

Vaccine for seasonal influenza/flu or seasonal influenza/flu vaccine: A vaccine directed against the seasonal occurring influenza viruses in a flu season is termed herein "vaccine for seasonal influenza/flu or seasonal influenza/flu vaccine".

Immune system: The immune system may protect organisms from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

Immune response: An immune response may typically either be a specific reaction of the adaptive immune system to a particular antigen (so called specific or adaptive immune response) or an unspecific reaction of the innate immune system (so called unspecific or innate immune response). The invention relates to the core to specific reactions (adaptive immune responses) of the adaptive immune system. Particularly, it relates to adaptive immune responses to infections by viruses like e.g. Influenza viruses. However, this specific response can be supported by an additional unspecific reaction (innate immune response). Therefore, the invention also relates to a compound for simultaneous stimulation of the innate and the adaptive immune system to evoke an efficient adaptive immune response.

Adaptive immune system: The adaptive immune system is composed of highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered. The system is highly adaptable because of somatic hypermutation (a process of increased frequency of somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions.

Adaptive immune response: The adaptive immune response is typically understood to be antigen-specific. Antigen specificity allows for the generation of responses that are tailored to specific antigens, pathogens or pathogen-infected cells. The ability to mount these tailored responses is maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. Cell types that can serve as antigen-presenting cells are inter alia dendritic cells, macrophages, and B cells. Each of these cells has a distinct function in eliciting immune responses. Dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

Cellular immunity/cellular immune response: Cellular immunity relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g. by activating antigen-specific cytotoxic T-lymphocytes that are able to induce apoptosis in body cells displaying epitopes of an antigen on their surface, such as virus-infected cells, cells with intracellular bacteria, and cancer cells displaying tumour antigens; activating macrophages and natural killer cells, enabling them to destroy pathogens; and stimulating cells to secrete a variety of cytokines that influence the function of other cells involved in adaptive immune responses and innate immune responses.

Humoral immunity/humoral immune response: Humoral immunity refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Innate immune system: The innate immune system, also known as non-specific immune system, comprises the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins orchemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-1 like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

Adjuvant/adjuvant component: An adjuvant or an adjuvant component in the broadest sense is typically a (e.g. pharmacological or immunological) agent or composition that may modify, e.g. enhance, the efficacy of other agents, such as a drug or vaccine. Conventionally the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the present invention an adjuvant will preferably enhance the specific immunogenic effect of the active agents of the present invention. Typically, "adjuvant" or "adjuvant component" has the same meaning and can be used mutually. Adjuvants may be divided, e.g., into immunopotentiators, antigenic delivery systems or even combinations thereof.

The term "adjuvant" is typically understood not to comprise agents which confer immunity by themselves. An adjuvant assists the immune system unspecifically to enhance the antigen-specific immune response by e.g. promoting presentation of an antigen to the immune system or induction of an unspecific innate immune response. Furthermore, an adjuvant may preferably e.g. modulate the antigen-specific immune response by e.g. shifting the dominating Th2-based antigen specific response to a more Th1-based antigen specific response or vice versa. Accordingly, an adjuvant may favorably modulate cytokine expression/secretion, antigen presentation, type of immune response etc.

Immunostimulatory RNA: An immunostimulatory RNA (isRNA) in the context of the invention may typically be an RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

The term "antibody" as used herein, includes both an intact antibody and an antibody fragment. Typically, an intact "antibody" is an immunoglobulin that specifically binds to a particular antigen. An antibody may be a member of any immunoglobulin class, including any of the human classes: IgG, IgM, IgE, IgA and IgD. Typically, an intact antibody is a tetramer. Each tetramer consists of two identical pairs of polypeptide chains, each pair having a "light" chain and a "heavy" chain. An "antibody fragment" includes a portion of an intact antibody, such as the antigen-binding or variable region of an antibody. Examples of antibody fragments include Fab, Fab', F(ab') 2 and Fv fragments; the tribes; Tetra; linear antibodies; single-chain antibody molecules; and multi specific antibodies formed from antibody fragments. E.g., the antibody fragments comprise isolated fragments, "Fv" fragments consisting of heavy and light chain variable regions, recombinant single chain polypeptide molecules in which the light and heavy chain variable regions are linked together by a peptide linker ("ScFv Proteins") and minimal recognition units consisting of amino acid residues that mimic the hypervariable region. Examples of antigen-binding fragments of an antibody include, but are not limited to, Fab fragment, Fab'fragment, F (ab') 2 fragment, scFv fragment, Fv fragment, dsFv diabody, dAb fragment, fragment Fd', Fd fragment and an isolated complementarity determining region (CDR). Suitable antibodies that may be encoded by the therapeutic RNA of the invention include monoclonal antibodies, polyclonal antibodies, antibody mixtures or cocktails, human or humanized antibodies, chimeric antibodies, Fab fragments, or bispecific antibodies. In the context of the invention, an antibody may be provided by the at least one therapeutic RNA of the inventive combination/composition.

The term "antigen" in the context of the present invention refers typically to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells. In the sense of the present invention an antigen may be the product of translation of a provided nucleic acid molecule, preferably an mRNA as defined herein. In this context, also fragments, variants and derivatives of peptides and proteins comprising at least one epitope are understood as antigen. Accordingly, the term "antigen" as used herein will be recognized and understood by the person of ordinary skill in the art, and is e.g. intended to refer to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells. Also fragments, variants and derivatives of peptides or proteins derived from e.g. cancer antigens comprising at least one epitope may be understood as antigens. In the context of the present invention, an antigen may be the product of translation of a provided therapeutic RNA (e.g. coding RNA, replicon RNA, mRNA). The term "antigenic peptide or protein" will be recognized and understood by the person of ordinary skill in the art, and is e.g. intended to refer to a peptide or protein derived from a (antigenic) protein which may stimulate the body's adaptive immune system to provide an adaptive immune response. Therefore an "antigenic peptide or protein" comprises at least one epitope or antigen of the protein it is derived from (e.g. a tumour antigen, a viral antigen, a bacterial antigen, a protozoan antigen). In the context of the invention, an antigen may be provided by the at least one therapeutic RNA of the inventive combination/composition.

The term "derived from" as used throughout the present specification in the context of a nucleic acid, i.e. for a nucleic acid "derived from" (another) nucleic acid, means that the nucleic acid, which is derived from (another) nucleic acid, shares e.g. at least about 50%, 60%, 70%, 80%, 90%, 91%, 92%, 93%, 94%, 95%, 96%, 97%, 98%, or about 99% sequence identity with the nucleic acid from which it is derived. The skilled person is aware that sequence identity is typically calculated for the same types of nucleic acids, i.e. for DNA sequences or for RNA sequences. Thus, it is understood, if a DNA is "derived from" an RNA or if an RNA is "derived from" a DNA, in a first step the RNA sequence is converted into the corresponding DNA sequence (in particular by replacing U by T throughout the sequence) or, vice versa, the DNA sequence is converted into the corresponding RNA sequence (in particular by replacing the T by U throughout the sequence). Thereafter, the sequence identity of the DNA sequences or the sequence identity of the RNA sequences is determined. Preferably, a nucleic acid "derived from" a nucleic acid also refers to nucleic acid, which is modified in comparison to the nucleic acid from which it is derived, e.g. in order to increase RNA stability even further and/or to prolong and/or increase protein production. In the context of amino acid sequences, the term "derived from" means that the amino acid sequence, which is derived from (another) amino acid sequence, shares e.g. at least about 70%, 80%, 90%, 91%, 92%, 93%, 94%, 95%, 96%, 97%, 98%, or about 99% sequence identity with the amino acid sequence from which it is derived.

Epitope (also called "antigen determinant"): T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule.

B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

The term "vaccine" is typically understood to be a prophylactic or therapeutic material providing at least one antigen or antigenic function. The antigen or antigenic function may stimulate the body's adaptive immune system to provide an adaptive immune response.

The term "antigen-providing mRNA" in the context of the invention may typically be an mRNA, having at least one open reading frame that can be translated by a cell or an organism provided with that mRNA. The product of this translation is a peptide or protein that may act as an antigen, preferably as an immunogen. The product may also be a fusion protein composed of more than one immunogen, e.g. a fusion protein that consist of two or more epitopes, peptides or proteins derived from the same or different virus-proteins, wherein the epitopes, peptides or proteins may be linked by linker sequences.

The term "artificial mRNA" (sequence) may typically be understood to be an mRNA molecule, that does not occur naturally. In other words, an artificial mRNA molecule may be understood as a non-natural mRNA molecule. Such mRNA molecule may be non-natural due to its individual sequence (which does not occur naturally) and/or due to other modifications, e.g. structural modifications of nucleotides which do not occur naturally. Typically, artificial mRNA molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide. The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

The terms "heterologous" or "heterologous sequence" as used throughout the present specification in the context of a nucleic acid sequence or an amino acid sequence refers to a sequence (e.g. DNA, RNA, amino acid) will be recognized and understood by the person of ordinary skill in the art, and is intended to refer to a sequence that is derived from another gene, from another allele, from another species. Two sequences are typically understood to be "heterologous" if they are not derivable from the same gene or in the same allele. I.e., although heterologous sequences may be derivable from the same organism, they naturally (in nature) do not occur in the same nucleic acid molecule, such as e.g. in the same RNA or protein.

Bi-/multicistronic mRNA: mRNA, that typically may have two (bicistronic) or more (multicistronic) open reading frames (ORF) (coding regions or coding sequences). An open reading frame in this context is a sequence of several nucleotide triplets (codons) that can be translated into a peptide or protein. Translation of such an mRNA yields two (bicistronic) or more (multicistronic) distinct translation products (provided the ORFs are not identical). For expression in eukaryotes such mRNAs may for example comprise an internal ribosomal entry site (IRES) sequence.

Monocistronic mRNA: A monocistronic mRNA may typically be an mRNA, that comprises only one open reading frame (coding sequence or coding region). An open reading frame in this context is a sequence of several nucleotide triplets (codons) that can be translated into a peptide or protein.

3-untranslated region (3'-UTR): A 3'-UTR is typically the part of an mRNA which is located between the protein coding region (i.e. the open reading frame) and the poly(A) sequence of the mRNA. A 3'-UTR of the mRNA is not translated into an amino acid sequence. The 3'-UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'-Capping, splicing the pre-mature mRNA to excise optional introns and modifications of the 3'-end, such as polyadenylation of the 3-end of the pre-mature mRNA and optional endo- or exonuclease cleavages etc. In the context of the present invention, a 3'-UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'-UTR sequence may be an RNA sequence, such as in the mRNA sequence used for defining the 3'-UTR sequence, or a DNA sequence which corresponds to such RNA sequence. In the context of the present invention, the term "a 3'-UTR of a gene", such as "a 3'-UTR of an albumin gene", is the sequence which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence of the 3'-UTR.

5'-untranslated region (5'-UTR): A 5'-UTR is typically understood to be a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'-UTR may be post-transcriptionally modified, for example by addition of a 5'-CAP. In the context of the present invention, a 5'-UTR corresponds to the sequence of a mature mRNA which is located between the 5'-CAP and the start codon. Preferably, the 5'-UTR corresponds to the sequence which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence which corresponds to such RNA sequence. In the context of the present invention, the term "a 5'-UTR of a gene", such as "a 5'-UTR of a TOP gene", is the sequence which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR.

5'-Terminal Oligopyrimidine Tract (TOP): The 5'-terminal oligopyrimidine tract (TOP) is typically a stretch of pyrimidine nucleotides located at the 5'-terminal region of a nucleic acid molecule, such as the 5'-terminal region of certain mRNA molecules or the 5'-terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5'-TOP ends one nucleotide 5' to the first purine nucleotide located downstream of the TOP. Messenger RNA that contains a 5'-terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence which corresponds to a 5'-TOP as defined above. Thus, a TOP motif in the context of the present invention is preferably a stretch of pyrimidine nucleotides having a length of 3-30 nucleotides. Preferably, the TOP motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'-end with a cytosine nucleotide. In TOP genes and TOP mRNAs, the TOP motif preferably starts at its 5'-end with the transcriptional start site and ends one nucleotide 5' to the first purine residue in said gene or mRNA. A TOP motif in the sense of the present invention is preferably located at the 5'-end of a sequence which represents a 5'-UTR or at the 5'-end of a sequence which codes for a 5'-UTR. Thus, preferably, a stretch of 3 or more pyrimidine nucleotides is called "TOP motif" in the sense of the present invention if this stretch is located at the 5'end of a respective sequence, such as the inventive mRNA, the 5'-UTR element of the inventive mRNA, or the nucleic acid sequence which is derived from the 5'-UTR of a TOP gene as described herein. In other words, a stretch of 3 or more pyrimidine nucleotides which is not located at the 5'-end of a 5'-UTR or a 5'-UTR element but anywhere within a 5'-UTR or a 5'-UTR element is preferably not referred to as "TOP motif".

TOP gene: TOP genes are typically characterized by the presence of a 5'-terminal oligopyrimidine tract. Furthermore, most TOP genes are characterized by a growth-associated translational regulation. However, also TOP genes with a tissue specific translational regulation are known. As defined above, the 5'-UTR of a TOP gene corresponds to the sequence of a 5'-UTR of a mature mRNA derived from a TOP gene, which preferably extends from the nucleotide located 3' to the 5'-CAP to the nucleotide located 5' to the start codon. A 5'-UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'-UTRs of TOP genes are generally rather short. The lengths of 5'-UTRs of TOP genes may vary between 20 nucleotides up to 500 nucleotides, and are typically less than about 200 nucleotides, preferably less than about 150 nucleotides, more preferably less than about 100 nucleotides. Exemplary 5'-UTRs of TOP genes in the sense of the present invention are the nucleic acid sequences extending from the nucleotide at position 5 to the nucleotide located immediately 5' to the start codon (e.g. the ATG) in the sequences according to SEQ ID NO:1-1363, SEQ ID NO:1395, SEQ ID NO:1421 and SEQ ID NO:1422 of the international patent application WO2013/143700 or homologs or variants thereof, whose disclosure is incorporated herewith by reference. In this context a particularly preferred fragment of a 5'-UTR of a TOP gene is a 5'-UTR of a TOP gene lacking the 5'-TOP motif. The term "5'-UTR of a TOP gene" preferably refers to the 5'-UTR of a naturally occurring TOP gene.

Fragment of a nucleic acid sequence, particularly an mRNA: A fragment of a nucleic acid sequence consists of a continuous stretch of nucleotides corresponding to a continuous stretch of nucleotides in the full-length nucleic acid sequence which is the basis for the nucleic acid sequence of the fragment, which represents at least 20%, preferably at least 30%, more preferably at least 40%, more preferably at least 50%, even more preferably at least 60%, even more preferably at least 70%, even more preferably at least 80%, and most preferably at least 90% of the full-length nucleic acid sequence. Such a fragment, in the sense of the present invention, is preferably a functional fragment of the full-length nucleic acid sequence.

In the context of the present invention, a "fragment" or a "variant" of a protein or peptide may have at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 722%, 733%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity over a stretch of at least 10, at least 20, at least 30, at least 50, at least 75 or at least 100 amino acids of such protein or peptide. More preferably, a "fragment" or a "variant" of a protein or peptide as used herein is at least 40%, preferably at least 50%, more preferably at least 60%, more preferably at least 70%, even more preferably at least 80%, even more preferably at least 90%, most preferably at least 95% identical to the protein or peptide, from which the variant is derived.

Variant of a nucleic acid sequence, particularly an mRNA: A variant of a nucleic acid sequence refers to a variant of nucleic acid sequences which forms the basis of a nucleic acid sequence. For example, a variant nucleic acid sequence may exhibit one or more nucleotide deletions, insertions, additions and/or substitutions compared to the nucleic acid sequence from which the variant is derived. Preferably, a variant of a nucleic acid sequence is at least 40%, preferably at least 50%, more preferably at least 60%, more preferably at least 70%, even more preferably at least 80%, even more preferably at least 90%, most preferably at least 95% identical to the nucleic acid sequence the variant is derived from. Preferably, the variant is a functional variant. A "variant" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence.

Stabilized nucleic acid, preferably mRNA: A stabilized nucleic acid, preferably mRNA typically, exhibits a modification increasing resistance to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of RNA can, e.g., be achieved by providing a 5'-CAP-Structure, a polyA-Tail, or any other UTR-modification. It can also be achieved by chemical modification or modification of the G/C content of the nucleic acid. Various other methods are known in the art and conceivable in the context of the invention.

RNA In vitro transcription: The terms "RNA in vitro transcription" or "in vitro transcription" relate to a process wherein RNA is synthesized in a cell-free system (in vitro). DNA, particularly plasmid DNA, is used as template for the generation of RNA transcripts. RNA may be obtained by DNA-dependent in vitro transcription of an appropriate DNA template, which according to the present invention is preferably a linearized plasmid DNA template. The promoter for controlling in vitro transcription can be any promoter for any DNA-dependent RNA polymerase.

Particular examples of DNA-dependent RNA polymerases are the T7, T3, and SP6 RNA polymerases. A DNA template for in vitro RNA transcription may be obtained by cloning of a nucleic acid, in particular cDNA corresponding to the respective RNA to be in vitro transcribed, and introducing it into an appropriate vector for in vitro transcription, for example into plasmid DNA. In a preferred embodiment of the present invention the DNA template is linearized with a suitable restriction enzyme, before it is transcribed in vitro. The cDNA may be obtained by reverse transcription of mRNA or chemical synthesis. Moreover, the DNA template for in vitro RNA synthesis may also be obtained by gene synthesis.

Methods for in vitro transcription are known in the art (see, e.g., Geall et al. (2013) Semin. Immunol. 25(2): 152-159; Brunelle et al. (2013) Methods Enzymol. 530:101-14). Reagents used in said method typically include:

1) a linearized DNA template with a promoter sequence that has a high binding affinity for its respective RNA polymerase such as bacteriophage-encoded RNA polymerases;
2) ribonucleoside triphosphates (NTPs) for the four bases (adenine, cytosine, guanine and uracil);
3) optionally, a CAP analogue as defined above (e.g. m7G(5')ppp(5')G (m7G));
4) a DNA-dependent RNA polymerase capable of binding to the promoter sequence within the linearized DNA template (e.g. T7, T3 or SP6 RNA polymerase);
5) optionally, a ribonuclease (RNase) inhibitor to inactivate any contaminating RNase;
6) optionally, a pyrophosphatase to degrade pyrophosphate, which may inhibit transcription;
7) MgCl2, which supplies Mg2+ ions as a co-factor for the polymerase;
8) a buffer to maintain a suitable pH value, which can also contain antioxidants (e.g. DTT), and/or polyamines such as spermidine at optimal concentrations.

Full-length protein: The term "full-length protein" as used herein typically refers to a protein that substantially comprises the entire amino acid sequence of the naturally occurring protein. Nevertheless, substitutions of amino acids e.g. due to mutation in the protein are also encompassed in the term full-length protein.

Fragments of proteins: "Fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide.

The term "variant" in the context of nucleic acid sequences of genes refers to nucleic acid sequence variants, i.e. nucleic acid sequences or genes comprising a nucleic acid sequence that differs in at least one nucleic acid from a reference (or "parent") nucleic acid sequence of a reference (or "parent") nucleic acid or gene. Variant nucleic acids or genes may thus preferably comprise, in their nucleic acid sequence, at least one mutation, substitution, insertion or deletion as compared to their respective reference sequence. Preferably, the term "variant" as used herein includes naturally occurring variants, and engineered variants of nucleic acid sequences or genes. Therefore, a "variant" as defined herein can be derived from, isolated from, related to, based on or homologous to the reference nucleic acid sequence. "Variants" may preferably have a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, to a nucleic acid sequence of the respective naturally occurring (wild-type) nucleic acid sequence or gene, or a homolog, fragment or derivative thereof.

Also, the term "variant" as used throughout the present specification in the context of proteins or peptides will be recognized and understood by the person of ordinary skill in the art, and is e.g. intended to refer to a proteins or peptide variant having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. "Variants" of proteins or peptides as defined herein may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, e.g., an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra). A "variant" of a protein or peptide may have at least 70%, 75%, 80%, 85%, 90%, 95%, 98% or 99% amino acid identity over a stretch of at least 10, 20, 30, 50, 75 or 100 amino acids of such protein or peptide. Preferably, a variant of a protein comprises a functional variant of the protein, which means that the variant exerts the same effect or functionality or at least 40%, 50%, 60%, 70%, 80%, 90%, or 95% of the effect or functionality as the protein it is derived from.

Also, the term "fragment" in the context of nucleic acid sequences or genes refers to a continuous subsequence of the full-length reference (or "parent") nucleic acid sequence or gene. In other words, a "fragment" may typically be a shorter portion of a full-length nucleic acid sequence or gene. Accordingly, a fragment, typically, consists of a sequence that is identical to the corresponding stretch within the full-length nucleic acid sequence or gene. The term includes naturally occurring fragments as well as engineered fragments. A preferred fragment of a sequence in the context of the present invention, consists of a continuous stretch of nucleic acids corresponding to a continuous stretch of entities in the nucleic acid or gene the fragment is derived from, which represents at least 20%, preferably at least 30%, more preferably at least 40%, more preferably at least 50%, even more preferably at least 60%, even more preferably at least 70%, and most preferably at least 80% of the total (i.e. full-length) nucleic acid sequence or gene from which the fragment is derived. A sequence identity indicated with respect to such a fragment preferably refers to the entire nucleic acid sequence or gene. Preferably, a "fragment" may comprise a nucleic acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, to a reference nucleic acid sequence or gene that it is derived from.

Also, in this context a fragment of a protein may typically comprise an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with an amino acid sequence of the respective naturally occurring full-length protein.

The term "identity" as used throughout the present specification in the context of a nucleic acid sequence or an amino acid sequence will be recognized and understood by the person of ordinary skill in the art, and is e.g. intended to refer to the percentage to which two sequences are identical. To determine the percentage to which two sequences are identical, e.g. nucleic acid sequences or amino acid (aa) sequences as defined herein, preferably the aa sequences encoded by the nucleic acid sequence as defined herein or the aa sequences themselves, the sequences can be aligned in order to be subsequently compared to one another. Therefore, e.g. a position of a first sequence may be compared with the corresponding position of the second sequence. If a position in the first sequence is occupied by the same residue as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using an algorithm, e.g. an algorithm integrated in the BLAST program.

Fragments of proteins or peptides in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore also domains of a protein, like the extracellular domain, the intracellular domain or the transmembrane domain and shortened or truncated versions of a protein may be understood to comprise a fragment of a protein.

Variants of proteins: “Variants” of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. “Variants” of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

A “variant” of a protein or peptide may have at least 70%, 75%, 80%, 85%, 90%, 95%, 98% or 99% amino acid identity over a stretch of 10, 20, 30, 50, 75 or 100 amino acids of such protein or peptide.

Furthermore, variants of proteins or peptides as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

Identity of a sequence: In order to determine the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

Derivative of a protein or peptide: A derivative of a peptide or protein is typically understood to be a molecule that is derived from another molecule, such as said peptide or protein. A “derivative” of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

Pharmaceutically effective amount: A pharmaceutically effective amount in the context of the invention is typically understood to be an amount that is sufficient to induce an immune response.

Carrier: A carrier in the context of the invention may typically be a compound that facilitates transport and/or complexation of another compound. Said carrier may form a complex with said other compound. A polymeric carrier is a carrier that is formed of a polymer.

Vehicle: An agent, e.g. a carrier that may typically be used within a pharmaceutical composition or vaccine for facilitating administering of the components of the pharmaceutical composition or vaccine to an individual.

BRIEF DESCRIPTION OF THE DRAWINGS

FIG. 9 (Tolerability of HEXA lipids—Liver enzymes)—shows that none of the tested animals showed significant elevated AST and ALT liver enzyme activity when compared to the buffer control—for analysis of the tolerability of HEXA lipids the ALT and AST levels were measured 24 h post intravenously transfection of respective LNPs into Balb/C mice. A ALT and AST levels of HEXA lipid 1 to 9-containing LNPs and GN01 compared to buffer. B ALT and AST levels of Lipid 2 m/m ratios (m/m 20, m/m 30, m/m 40) and GN01 compared to buffer (full details can be seen in Example 4.1.2).

FIG. 12.1 (Tolerability of HEAD lipids-Liver enzymes)—shows that none of the tested animals showed significant elevated AST and ALT liver enzyme activity when compared to the buffer control—for analysis of the tolerability of HEAD lipids the ALT and AST levels were measured 24 h post intravenously transfection into Balb/C mice. ALT and AST levels of HEAD lipids ESTER (m/m 40) and CPZE (m/m 20) was measured and compared to levels of CISE/lipid 2 (m/m 30), lipid 2 (m/m 30) and GN01 and buffer. Different molar/mass (m/m) ratios (m/m 20, m/m 30, m/m 40) were used (full details can be seen in Example 4.2.2).

FIG. 12.2 (Tolerability of HEAD lipids-Immunostimulation)—shows that none of the lipid compounds tested induced significantly elevated cytokine levels—for analysis of the immunostimulatory properties of HEAD lipids (CPZE, ESTER) compared to HEXA lipids (Lipid 2), GN01 and a mixture of both (CISE/Lipid 2) a CBA assay with serum samples drawn from mice 6 h after injection of HEXA lipids into Balb/C mice was performed. Levels of IFN-α in the serum were determined by ELISA. A MCP-1. B IL-6. C MP1-B. D INF-α (full details can be seen in Example 4.2.2).

FIG. 14.1 (Biological activity of GN01 after −80 storage for 10 weeks)—shows the analysis of GN01 formulated mRNA after 10 weeks of storage which resulted in even higher expression efficiency after 6h and 24h post injection when compared to 1 week of storage—i.e. the biological activity of formulated GN01 was evaluated by ELISA. GN01 LNPs were formulated with hEPO mRNA and frozen for 1 week and 10 weeks, respectively. Balb/C mice (5 mice/group) were intravenously injected. Plasma samples were taken and analyzed 6 h and 24 h after injection (full details can be seen in Example 5.2).

FIG. 14.2 (Biological activity of GN01 LNP after different F/T cycles)—shows a second evaluation in which plasma samples were analyzed after one freeze/thaw cycle (1 F/T) compared to plasma samples after 2 F/T cycle (both after 1 week storage at −80° C.)—the results were that biological activity of HsEpo could be shown for all tested approaches—i.e. the biological activity of formulated GN01 was evaluated by ELISA. GN01 LNPs were formulated with hEPO mRNA and frozen for 1 week and intravenously injected into Balb/C mice (5 mice/group). Elisa plasma levels were analyzed after 1 F/T cycle (A) and 2 F/T cycles (B) (full details can be seen in Example 5.2).

FIGS. 15.1A and 15.1B (Variations of the phospholipid component and influence on compositions of the invention)—shows that the incorporation of DPhyPE resulted in higher expression when compared to standard neutral lipid DSPC—i.e. LNPs were generated using different phospholipids (DPhyPE, DSPC, DPhyPE+DSPC (1+1)). A Lipid 1 (lipid compound C1) and GN01 LNPs were formulated in PpLuc mRNA and transfected into HeLa cells. Transfection efficiency was analysed 24 h after transfection by measuring RLU intensity. B Measurement of degree of protonation via TNS (dye 2-p-toluidinylnaphthalene-6-sulphonate) fluorescence of GN01 and lipid compound C1-comprising LNPs comprising different phospholipids dotted line=GN01; dashed line=DPhyPE; normal line=DSPC, stair-step-like line right from dashed line with=DSPC/DPhyPE (full details can be seen in Example 6).

FIG. 15.2 (Variations of the PEG component and influence on compositions of the invention)—shows that compositions comprising polymer conjugated lipids with shorter alkyl chains ($C_8$ tails, $C_8$-ceramide-PEG, indicated in the figure as Cer8) were more efficient than compositions comprising polymer conjugated lipids comprising longer alkyl chains ($C_{14}$=$C_{14}$ DMG-PEG=1,2-dimyristoyl-rac-glycero-3-methoxypolyethylene glycol 2000 (DMG-PEG 2000)) =expression of PpLuc in HepG2 cells—filled bars shows results after 1 h, open bars show results after 4h (full details can be seen in Example 7).

—FIG. 17A shows that already a single i.m. immunization with 5 μg GN01—and GNO2-LNP-formulated RABV-G-mRNA induced very robust VNTs well above the protective titer of 0.5 IU/ml in all animals at day 35 after prime vaccination. FIGS. 17B and 17C show that the inventive GN01 and GNO2-LNP-formulated RABV-G mRNA vaccine induced specific cellular responses after vaccination, effects that were not observed in control LNP-vaccinated animals. RABV-G-specific CD4+ T cells (FIG. 17B) were observed for both mRNA-formulations GN01 and GNO2. This was also true for RABV-G-specific CD8+ T (FIG. 17C) (full details can be seen in Example 9).

FIG. 21.1 (GN01 for in vivo Malaria vaccination—Endpoint titers)—shows that GN01 formulated mRNA Malaria vaccine encoding CSP induced very strong humoral immune responses in mice, using an ELISA assay (FIG. 21.1A—coating: $[NANP]_7$ peptide, IgG1 and IgG2a endpoint titers at day 21 and day 35 post prime; FIG. 21.1B—coating C-terminal peptide, IgG1 and IgG2a endpoint titers at day 21 and day 35 post prime; Group 1: GN01-LNP with CSP vaccine; Group 2: GN01-LNP with irrelevant mRNA) (full details can be seen in Example 13).

FIG. 21.2 (GN01 for in vivo Malaria vaccination—ICS) shows that GN01 formulated mRNA Malaria vaccine encoding CSP induced cellular immune responses in mice (CD8+ and/or CD4+ T-cell responses), using an intracellular cytokine staining assay (day 35 post vaccination). Groups 1: GN01-LNP with CSP vaccine; Group 2: GN01-LNP with irrelevant mRNA (full details can be seen in Example 13).

FIG. 24 (Chemical structures of HEXA lipids)—shows the structures of inventive HEXA lipid compounds as described herein, i.e. lipid compound C24 (FIG. 24A) HEXA-C5DE-inverted PipSS, and lipid compound C25 (FIG. 24B) HEXA-C5DE-Pip-C3 thioether (full details can be seen in in Example 20.1).

FIG. 25 (Structures of HEAD lipids)—shows the structures of inventive HEAD lipid compounds as described herein (full details can be seen in Example 20.2), i.e. lipid compound THIOETHER (FIG. 25A), and lipid compound C3SS (FIG. 25B).

FIG. 27 (Immunogenicity of different cationic lipids-comprising LNPs in in vivo-T cell response-VNT analysis) FIGS. 27B and 27C show that the inventive LNP-formulated RABV-G mRNA vaccine induced specific cellular responses after vaccination in re-stimulated splenocytes vs. unstimulated splenocytes. RABV-G-specific CD4+ T cells (FIG. 27B) and RABV-G-specific CD8+ T cells (FIG. 27C) are shown for the (i) re-stimulated and the (ii) unstimulated setup. The full details can be found in Example 21.

FIG. 29 (GNO2-like LNPs for in vivo Malaria vaccination—ICS) shows that GNO2-like formulated mRNA Malaria vaccine encoding CSP induced cellular immune responses in mice (CD4+ T-cell responses), using an intracellular cytokine staining assay (day 35 post vaccination). RABV-G-specific CD4+ T cells are shown for the (i) re-stimulated and the (ii) unstimulated setup. The full details can be found in Example 22.

FIG. 30 (GNO2-like LNPs for in vivo Malaria vaccination—ICS) shows that GNO2-like formulated mRNA Malaria vaccine encoding CSP induced cellular immune responses in mice (CD8+ T-cell responses), using an intracellular cytokine staining assay (day 35 post vaccination). RABV-G-specific CD8+ T cells are shown for the (i) re-stimulated and the (ii) unstimulated setup. The full details can be found in Example 22.

FIG. 32 (LNPs with different cationic lipids of the invention for in vivo Malaria vaccination—ICS) shows that LNP formulated mRNA Malaria vaccine encoding CSP induced cellular immune responses in mice (CD4+ T-cell responses shown for the (i) re-stimulated and the (ii) unstimulated setup), using an intracellular cytokine staining assay (day 35 post vaccination). The full details can be found in Example 22.

FIG. 33 (LNPs with different cationic lipids of the invention for in vivo Malaria vaccination—ICS) shows that LNP formulated mRNA Malaria vaccine encoding CSP induced cellular immune responses in mice (CD8+ T-cell responses shown for the (i) re-stimulated and the (ii) unstimulated setup), using an intracellular cytokine staining assay (day 35 post vaccination). The full details can be found in Example 22.

DETAILED DESCRIPTION OF THE INVENTION

Figure 1:
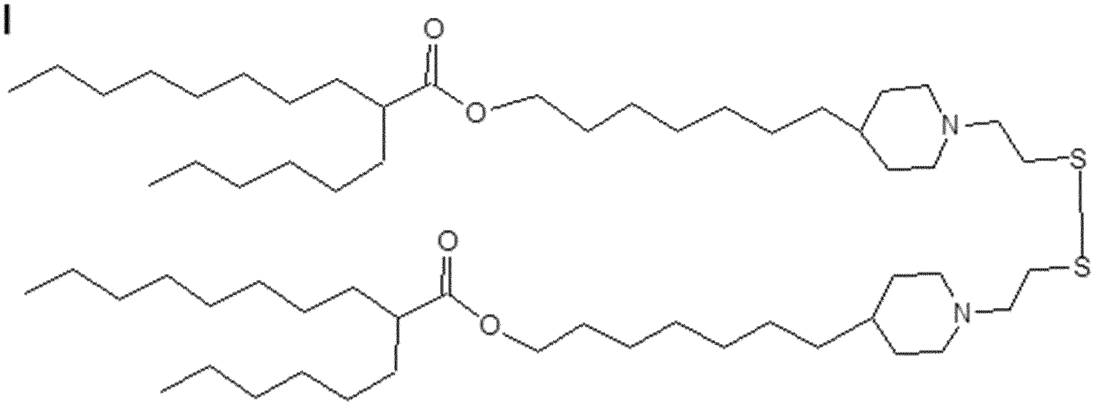
FIG. 1 (Chemical structures of HEXA lipids)—shows the structures of inventive HEXA lipid compounds as described herein, i.e. lipid compound C1 (FIG. 1A) HEXA-C4DE-PipSS, lipid compound C2 (FIG. 1B) HEXA-C5DE-PipSS, lipid compound C3 (FIG. 1C) HEXA-C6DE-PipSS, lipid compound C4 (FIG. 1D) HEXA-C7DE-PipSS, lipid compound C5 (FIG. 1E) HEXA-C8DE-PipSS, lipid compound C6 (FIG. 1F) HEXACA-C3ME-PipSS, lipid compound C7 (FIG. 1G) HEXACA-C4ME-PipSS, lipid compound C8 (FIG. 1H) HEXACA-C6ME-PipSS, lipid compound C9 (FIG. 1I) HEXACA-C8ME-PipSS (full details can be seen in in Example 2.1).

The present invention is based on the inventors' surprising finding that the use of the novel cationic lipids and/or lipid nanoparticles (LNPs) highly effective in delivering nucleic acids such as mRNA to a living organism such as a human individual. In particular, the intracellular delivery of such nucleic acids is enhanced. This has enabled the inventors to create, for example, improved vaccines that deliver mRNA compounds encoding antigenic peptides or proteins and very efficiently induce antigen-specific immune responses at very low dosages. Further advantages achieved by the present invention are that quite surprisingly, the inventors have discovered, according to aspects and embodiments of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Usually, self-replicating RNA vaccines rely on viral replication pathways to deliver enough RNA to a cell to produce an immunogenic response—the formulations of the present invention do not require viral replication to produce enough protein to result in a strong immune response. Thus, preferably, the mRNA of the invention are not self-replicating RNA and do not include components necessary for viral replication.

Lipid Compositions

In a first aspect, the invention is directed to a composition comprising a cationic lipid as described herein below. All options and preferences that are disclosed for the cationic lipid as such are also applicable to the composition to this aspect of the invention. In other words, the specifically disclosed embodiments of cationic lipids, and in particular the preferred cationic lipids, should be understood as also defining specific preferred embodiments of the composition according to the invention, i.e. compositions that are characterized in that they comprise a cationic lipid according to one of the specific selections described herein. The composition may comprise further active and/or inactive excipients which are described further below. In one specific embodiment, in addition to the cationic lipid, the composition comprises one or more lipids selected from the group consisting of: (a) a steroid; (b) a neutral lipid; and (c) a polymer conjugated lipid, preferably a pegylated lipid.

Cationic Lipids

The cationic lipid is preferably cationisable, i.e. it becomes protonated as the pH is lowered below the $pK_a$ of the ionizable group of the lipid, but is progressively more neutral at higher pH values. When positively charged, the lipid is then able to associate with negatively charged nucleic acids. In certain embodiments, the cationic lipid comprises a zwitterionic lipid that assumes a positive charge on pH decrease.

In one aspect, the invention provides a novel cationic lipid that is defined as a compound according to formula (I):

$R^a$-A-$R^b$ formula (I)

wherein is $R^a$ is selected from:

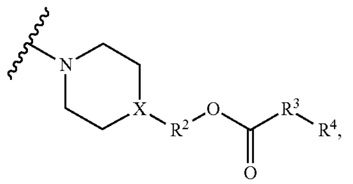

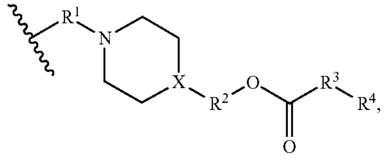

or

—$R^1$—N(H)—C(O)—$R^3$—$R^4$;

$R^b$ is selected from:

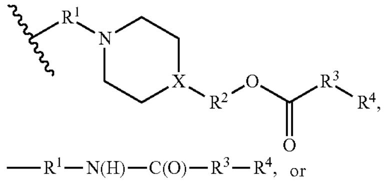

—$R^1$—N(H)—C(O)—$R^3$—$R^4$, or

—$R^1$—N($CH_3$)$_2$;

A is —S—, —S—S—, —NH—C(O)—, —NH—C(O)O—, —NH—C(O)—NH—, —S—C(O)—N(H)—, —C(O)O—, or —O—P(O)(OH)—O—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is —$R^5$—C(O)—O—, —$R^5$—O—C(O)—, —$R^5$—C(O)—NH—, —$R^5$—OC(O)—NH—, or $R^5$—NH—C(O)O—;

$R^4$ is a lipophilic substituent with 12 to 36 carbon atoms;

$R^5$ is an alkanediyl having 1 to 6 carbon atoms;

X is a carbon or nitrogen atom;

wherein all selections are independent of one another, optionally provided that if $R^1$, $R^2$ and $R^5$ are all linear unsubstituted ethanediyl, A is —S—S—, and $R^a$ and $R^b$ are identical, then $R^4$ is not

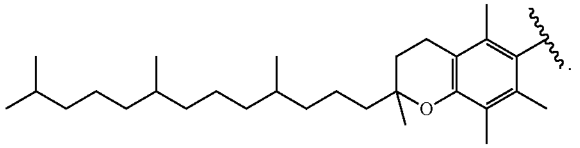 [SMILES: *c1c(C)c(C)c2c(c1C)CCC(C)(CCCC(C)CCCC(C)CCCC(C)C)O2]

In another aspect, the present invention relates to novel cationic lipids which are useful for the delivery of nucleic acids into living cells. The cationic lipids are compounds according to formula (I):

$R^a$-A-$R^b$ formula (I)

wherein $R^a$ is selected from:

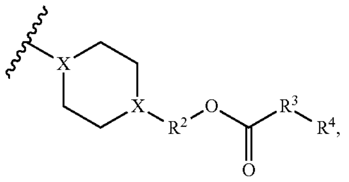

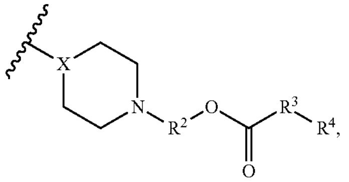

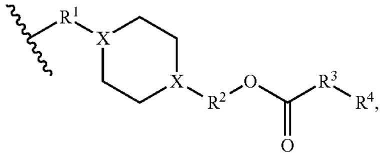

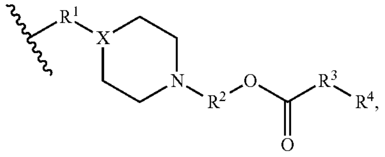

or $—R^1—N(H)—C(O)—R^3—R^4$;

$R^b$ is selected from:

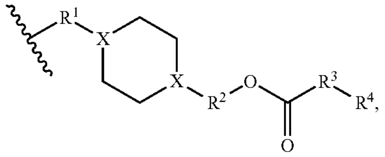

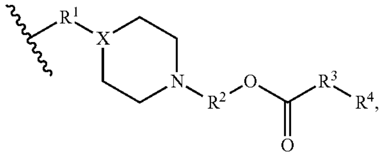

$—R^1—N(H)—C(O)—R^3—R^4$, or $—R^1—N(CH_3)_2$;

A is —S—, —S—S—, —S—C(O)— —NH—C(O)—, —NH—C(O)O—, —NH—C(O)—NH—, —S—C(O)—N(H)—, —C(O)O—, or —O—P(O)(OH)—O—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is $—R^5—C(O)—O—$, or $—R^5—O—C(O)—$, $—R^5—C(O)—NH—$, $—R^5—OC(O)—NH—$, or $R^5—NH—C(O)O—$;

$R^4$ is a lipophilic substituent with 12 to 36 carbon atoms;

$R^5$ is an alkanediyl having 1 to 6 carbon atoms;

X is a carbon or nitrogen atom;

wherein all selections are independent of one another, optionally provided that if $R^1$, $R^2$ and $R^5$ are all ethanediyl, A is —S—S—, and $R^a$ and $R^b$ are identical, then $R^4$ is not

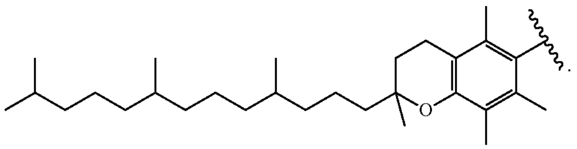 [SMILES: *c1c(C)c(C)c2c(c1C)CCC(C)(CCCC(C)CCCC(C)CCCC(C)C)O2]

In yet another aspect, aspect A, the invention provides a novel cationic lipid that is defined as a compound according to formula (I):

$R^a$-A-$R^b$ formula (I)

or a pharmaceutically acceptable salt, prodrug or stereoisomer thereof, wherein $R^a$ is selected from:

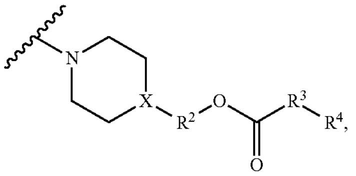

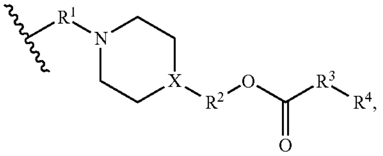

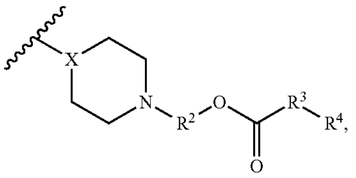

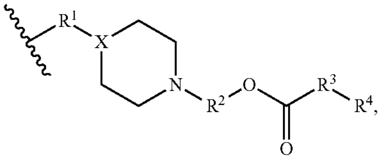

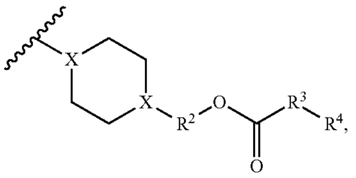

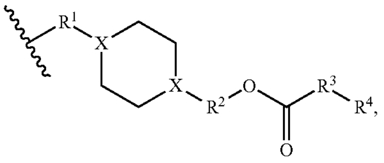

or $—R^1—N(H)—C(O)—R^3—R^4$;

$R^b$ is selected from:

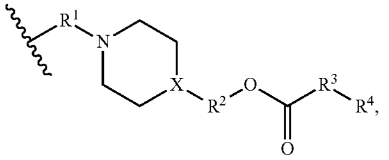

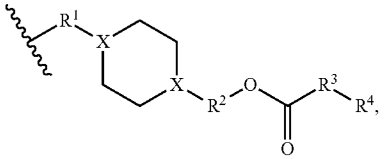

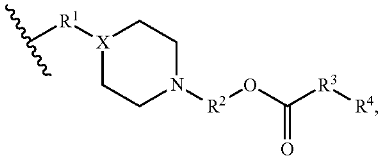

—$R^1$—N(H)—C(O)—$R^3$—$R^4$, or —$R^1$—$N(CH_3)_2$;

A is —S—, —S—S—, —NH—C(O)—, —NH—C(O)O—, —NH—C(O)—NH—, —S—C(O)—N(H)—, —C(O)O—, or —O—P(O)(OH)—O—;

$R^1$ is an ethanediyl, propanediyl, butanediyl, or linear or unbranched alkanediyl having 2 to 8 carbon atoms, wherein each substitutable carbon atom is unsubstituted or substituted with one or more $C_1$-$C_4$ alkyl, $C_1$-$C_4$ alkenylene, $C_3$-$C_8$ cycloalkylene, or $C_3$-$C_8$ cycloalkenylene;

$R^2$ is an alkanediyl having 2 to 8 carbon atoms;

$R^3$ is optional, and if present, is —$R^5$—C(O)—O—, —$R^5$—O—C(O)—, —$R^5$—C(O)—NH—, —$R^5$—OC(O)—NH—, or $R^5$—NH—C(O)O—;

$R^4$ is a lipophilic substituent with 12 to 36 carbon atoms, wherein the lipophilic substituent with 12 to 36 carbon atoms is either a linear or branched alkyl or alkenyl having 12 to 25 carbon atoms or derived from alpha-tocopherol;

$R^5$ is an alkanediyl having 1 to 6 carbon atoms;

X is a carbon atom bonded to a hydrogen atom (CH) or a nitrogen atom;

wherein all selections are independent of one another; optionally provided that that if (i) $R^3$ is present as —$R^5$—C(O)—O—, (ii) $R^1$ and $R^2$ are linear unsubstituted ethanediyl, (iii) $R^5$ is either linear unsubstituted ethanediyl, linear unsubstituted propanediyl or linear unsubstituted butanediyl, (iv) A is —S—S—, and (v) $R^a$ and $R^b$ are identical, then $R^4$ is not

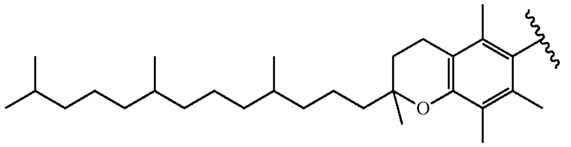 [SMILES: *c1c(C)c(C)c2c(c1C)CCC(C)(CCCC(C)CCCC(C)CCCC(C)C)O2]

and further provided that if (i) $R^3$ is absent, (ii) $R^1$ and $R^2$ are linear unsubstituted ethanediyl, (iii) A is —S—S—, and (iv) $R^a$ and $R^b$ are identical, then $R^4$ is not

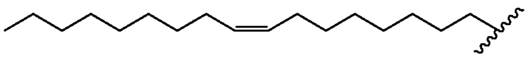

and not

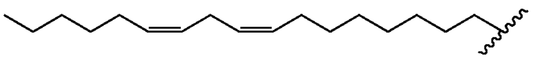

;

or, as an alternative to the above proviso, optionally provided that the cationic lipid is not a lipid selected from the group consisting of

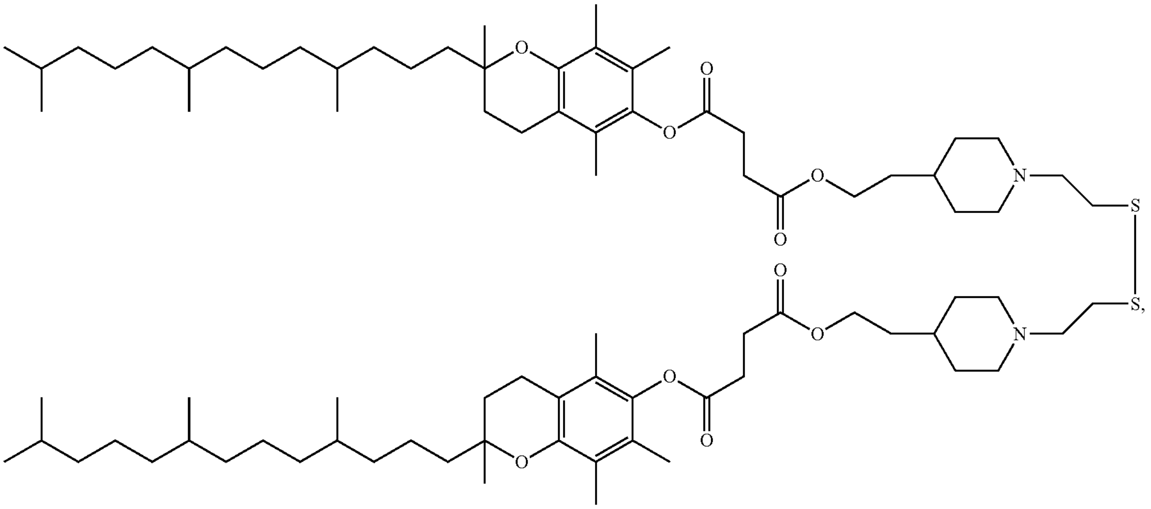

-continued
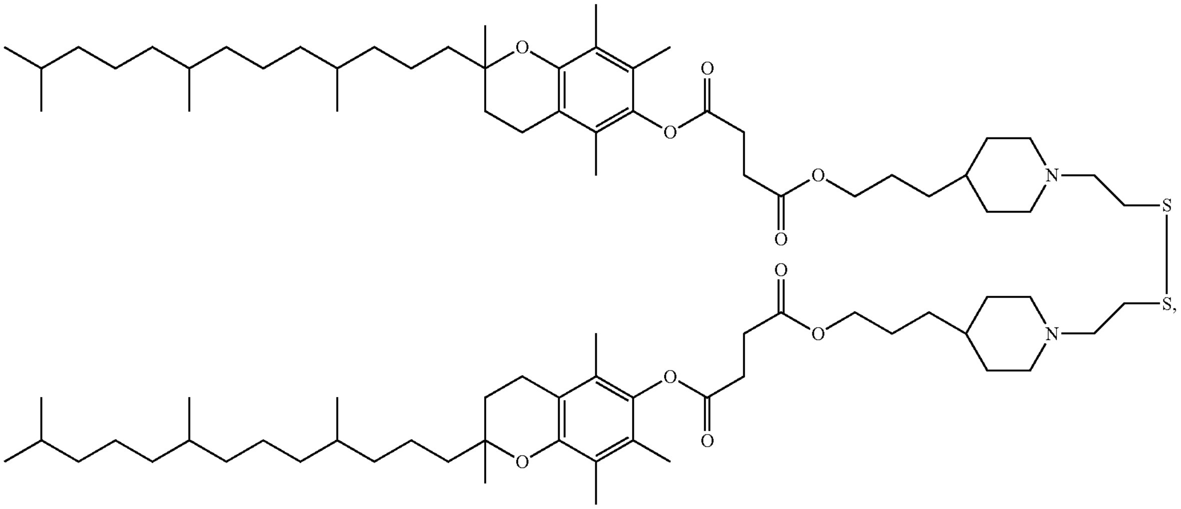
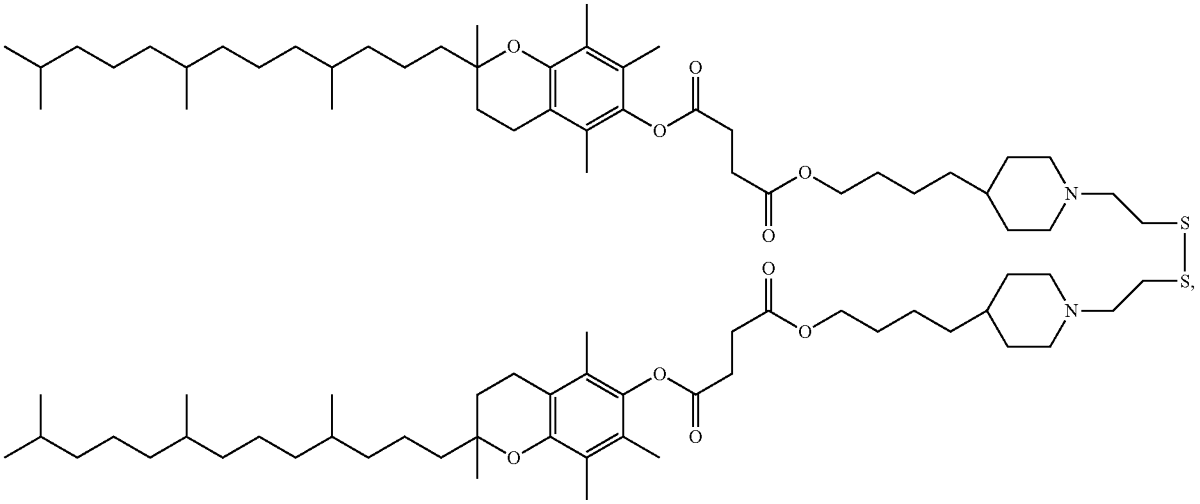
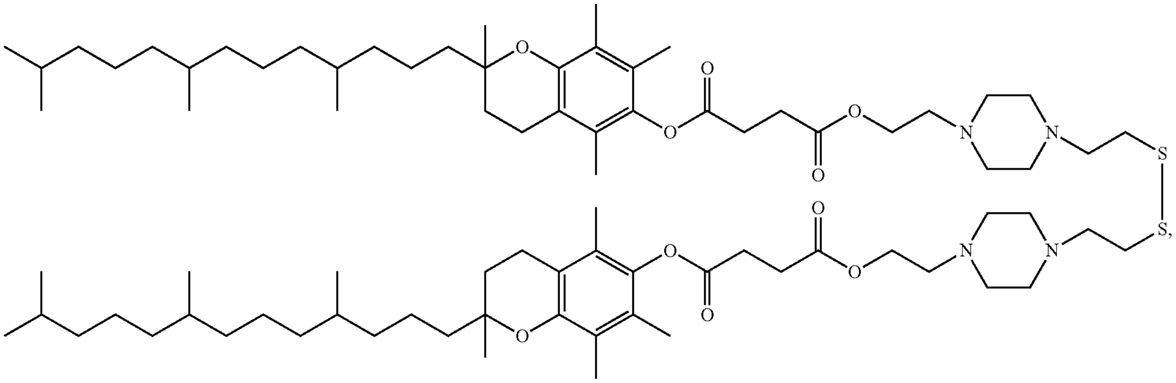
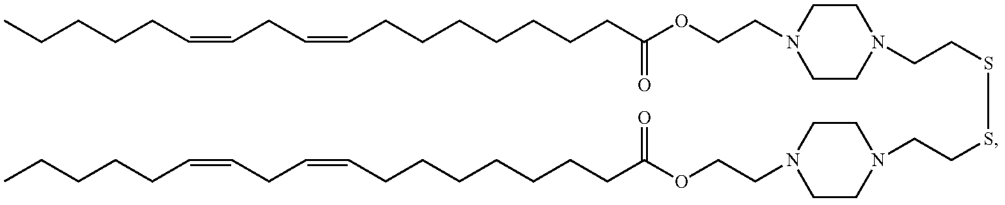

-continued

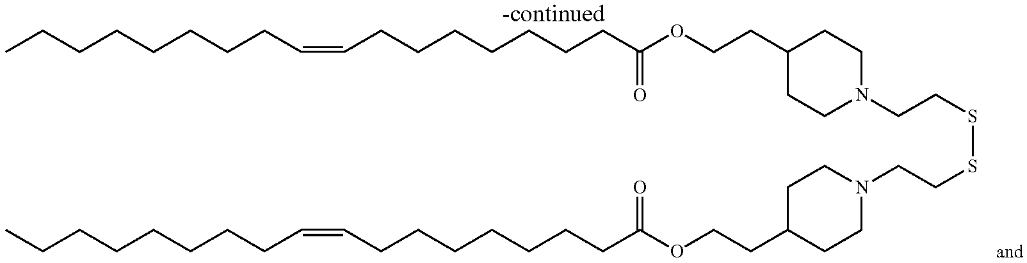

and

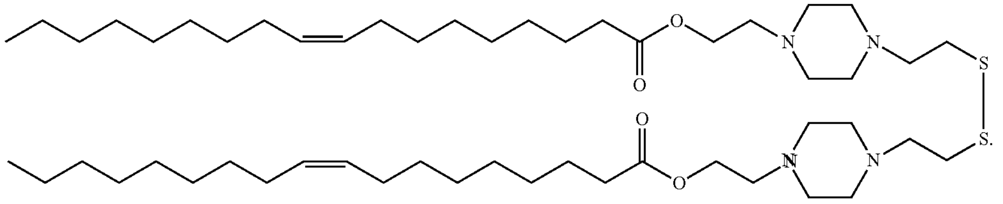

In the novel cationic lipid, the degradable/biodegradable moiety A connects the two structures $R^a$ and $R^b$ which may be the same or different. Each of $R^a$ and $R^b$ includes at least one basic, i.e. cationic, moiety that includes a tertiary nitrogen atom. At least one of $R^a$ and $R^b$ has a substantially lipophilic tail structure and at least one ester group.

The degradable/biodegradable moiety A may be selected from the following functional groups: —S—, —S—S—, —NH—C(O)—, —NH—C(O)O—, —NH—C(O)—NH—, —S—C(O)—N(H)—, —C(O)O—, or —O—P(O)(OH)—O—. In one of the preferred embodiments, A is a moiety or group containing one or more sulfur atoms, such as —S—, —S—S—, or —S—C(O)—N(H)—. In another preferred embodiment, A is a disulfide group (—S—S—), in which the cationic lipid may be represented as $R^a$—S—S—$R^b$, wherein $R^a$ and $R^b$ may be selected as defined above. In yet another preferred embodiment, in particular of aspect A above, A is —S—, in which the cationic lipid may be represented as $R^a$—S—$R^b$, wherein $R^a$ and $R^b$ may be selected as defined above.

Without wishing to be bound by theory, the inventors currently believe that the degradability of moiety A may play a key role in the pronounced biological effectiveness of the new lipids. For example, if A is a disulfide moiety, and if the lipid is used along with other excipients as described in further detail below to form a liposome or a lipid nanoparticles (LNP) loaded with a nucleic acid compound as a cargo, such liposome or LNP would effectively be taken up by a cell through endocytosis. Within an endocytotic vesicle, the disulfide group of the cationic lipid may become reduced (possibly in the presence of glutathione) into two thiol moieties, which at the same time leads to the cleavage of the cationic lipid molecule into two smaller cationic species. Potentially, the high concentration of thiols in the cell may also lead to further degradation of the lipid, such as through thioesterification.

Since $R^a$ and $R^b$ may optionally be different from one another, they may be independently selected. As mentioned, $R^a$ may be selected from

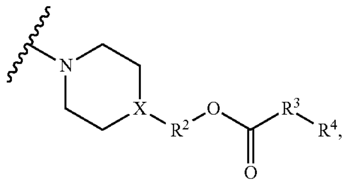

-continued

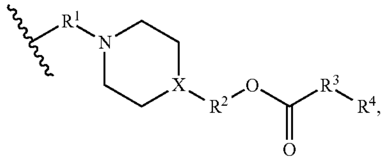

preferably with X being CH, or —$R^1$—N(H)—C(O)—$R^3$-$R^4$; and $R^b$ may be selected from

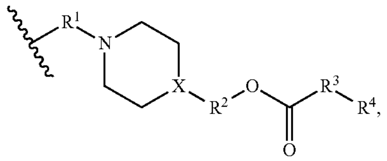

preferably with X being CH, —$R^1$—N(H)—C(O)—$R^3$—$R^4$, or —$R^1$—$N(CH_3)_2$.

Further, as mentioned, $R^a$ may be selected from

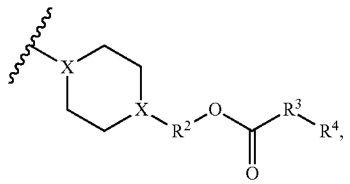

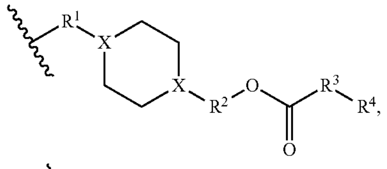

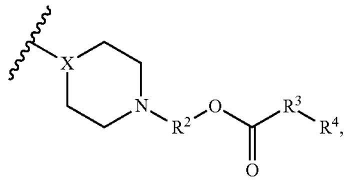

-continued

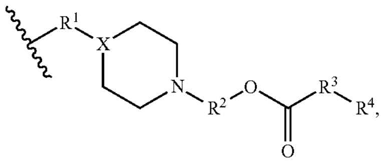

preferably with X being CH, and $R^b$ may be selected from

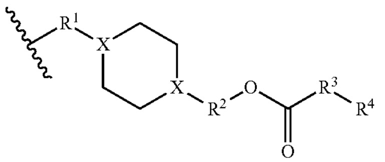

or

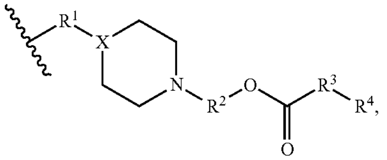

preferably with X being CH.

In one of the preferred embodiments, at least one of $R^a$ and $R^b$ comprises a piperidine- or piperazine-derived six-membered ring structure between $R^2$ and A or $R^1$, respectively. This means that at least one tertiary nitrogen atom which is present and located in vicinity to moiety A and separated from the lipophilic tail structure $R^4$ by at least one spacer ($R^2$) any an ester group. A potential advantage of the ester group (or groups, if $R^3$ is present) relates to the further enhanced degradability of the lipid in a physiological environment, for example, in an intracellular environment, which is provided by the hydrolytically labile ester bond(s).

In a further embodiment, both $R^a$ and $R^b$ comprises a piperidine- or piperazine-derived six-membered ring structure. Also preferred is a cationic lipid in which both $R^a$ and $R^b$ are

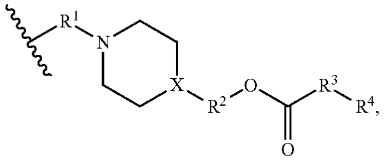

preferably with X being CH, either independently selected or, alternatively, with $R^a$ and $R^b$ being identical.

As mentioned, $R^1$ is an optionally substituted ethanediyl, propanediyl, butanediyl, or linear or unbranched alkanediyl having 2 to 8 carbon atoms. Propanediyl is preferably n-propanediyl, i.e. $—CH_2—CH_2—CH_2—$in which one or more hydrogen atoms are optionally substituted. Butanediyl is preferably n-butanediyl, i.e. $—CH_2—CH_2—CH_2—CH_2—$in which one or more hydrogen atoms are optionally substituted. Preferably, however, not more than one hydrogen atom of the ethanediyl, propanediyl or butanediyl is substituted. In some embodiments, the $R^1$ substituent in $R^a$ and the $R^1$ substituent in $R^b$ are the same or different. In some embodiments, the $R^1$ substituent in $R^a$ and the $R^1$ substituent in $R^b$ are both ethanediyl. In other embodiments, the $R^1$ substituent in $R^a$ and the $R^1$ substituent in $R^b$ are both propanediyl. In other embodiments, the $R^1$ substituent in $R^a$ and the $R^1$ substituent in $R^b$ are both butanediyl. In some embodiments, the $R^1$ substituent in $R^a$ is ethanediyl and the $R^1$ substituent in $R^b$ is propanediyl. In other embodiments, the $R^1$ substituent in $R^a$ is propanediyl and the $R^1$ substituent in $R^b$ is ethanediyl. In some embodiments, the $R^1$ substituent in $R^a$ is butanediyl and the $R^1$ substituent in $R^b$ is propanediyl. In other embodiments, the $R^1$ substituent in $R^a$ is butanediyl and the $R^1$ substituent in $R^b$ is ethanediyl. In certain other embodiments, in particular when it comes to $R^1$, the term "optionally substituted" indicates that each substitutable carbon atom may independently be substituted with one or more $C_1$-$C_4$ alkyl, $C_1$-$C_4$ alkenylene, $C_3$-$C_8$ cycloalkylene, or $C_3$-$C_8$ cycloalkenylene.

Similarly, in some embodiments, the $R^2$ substituent in $R^a$ and the $R^2$ substituent in $R^b$ are the same or different. In some embodiments, the $R^2$ substituent in $R^a$ and the $R^2$ substituent in $R^b$ are both ethanediyl, propanediyl, butanediyl, pentanediyl, hexanediyl, heptanediyl, or octanediyl. In other embodiments, the $R^2$ substituent in $R^a$ is propanediyl and the $R^2$ substituent in $R^b$ is heptanediyl. In other embodiments, the $R^2$ substituent in $R^a$ is heptanediyl and the $R^2$ substituent in $R^b$ is propanediyl. In some embodiments, in particular of aspect A above, the $R^2$ substituent in $R^a$ and the $R^2$ substituent in $R^b$ are both ethanediyl.

Further, in some embodiments where $R^3$ is present in both $R^a$ and $R^b$, the $R^5$ substituent in $R^a$ and the $R^5$ substituent in $R^b$ are the same or different. In some embodiments, the $R^5$ substituent in $R^a$ and the $R^5$ substituent in $R^b$ are both methanediyl, ethanediyl, propanediyl, butanediyl, pentanediyl, or hexanediyl. In other embodiments, the $R^5$ substituent in $R^a$ is ethanediyl and the $R^5$ substituent in $R^b$ is hexanediyl. In other embodiments, the $R^5$ substituent in $R^a$ is hexanediyl and the $R^5$ substituent in $R^b$ is ethanediyl. In some embodiments, in particular of aspect A above, where $R^3$ is present in both $R^a$ and $R^b$, the $R^5$ substituent in $R^a$ and the $R^5$ substituent in $R^b$ are both ethanediyl.

The substituent may be any suitable substituent, i.e. any linear or branched alkyl, aryl, heteroalkyl, heteroaromatic structure which may optionally include further functional groups such as ester or amide groups.

In particular if-$R^1—N(H)—C(O)—R^3$-$R^4$ is selected for $R^a$ and/or $R^b$, it is preferred that $R^1$ is a substituted ethanediyl, propanediyl, butanediyl, or linear or unbranched alkanediyl having 2 to 8 carbon atoms, such as a substituted propanediyl. In the event that an $—R^1—N(H)—C(O)—R^3$-$R^4$ is used which itself does not include a cationic moiety such as an amino group, it is preferred that the substituent of $R^1$ comprises such amino group; optionally, such amino group may be part of a cyclic structure, such as a six-membered ring structure derived from piperidine or piperazine. Optionally, the ring structure featuring the cationic nitrogen atom is linked to the ethanediyl or propanediyl via a degradable group, such as an ester group.

In one embodiment, where $R^a$ is

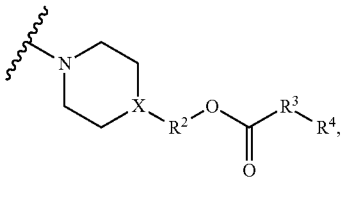

-continued or

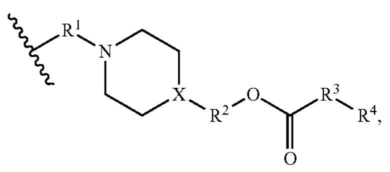

preferably with X being CH, and/or where $R^b$ is

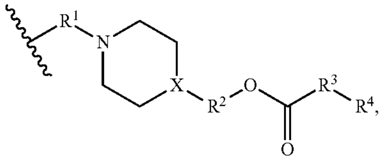

preferably with X being CH, $R^2$ serves as a linker or spacer between the respective basic piperidine- or piperazine-derived ring structure and an ester group. As mentioned, $R^2$ is defined as an alkanediyl having 2 to 8 carbon atoms. $R^2$ may be linear or branched, and otherwise (i.e. except for any branchings) it is preferably unsubstituted. In one embodiment, $R^2$ is a linear unsubstituted alkanediyl having 2, 3, 4, 5, 6, 7 or 8 carbon atoms. In another embodiment, $R^2$ is a linear unsubstituted alkanediyl having 2 to 6 carbon atoms. In a further preferred embodiment, $R^2$ is a linear unsubstituted ethanediyl or propanediyl. For example, both $R^a$ and $R^b$ may be

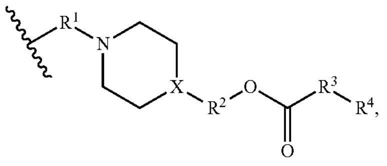

preferably with X being CH, with an $R^2$ selected from linear unsubstituted alkanediyls having 2 to 6 carbon atoms, such as ethanediyl or propanediyl.

In a further embodiment, where $R^a$ is

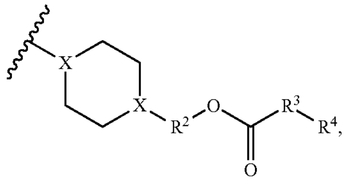

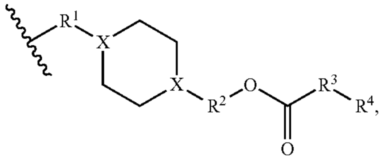

-continued

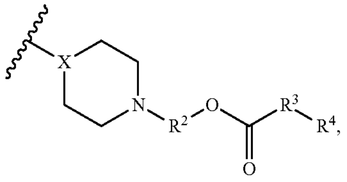

or

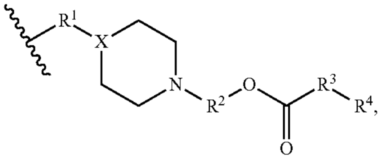

preferably with X being CH, and/or where $R^b$ is

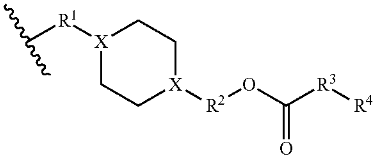

or

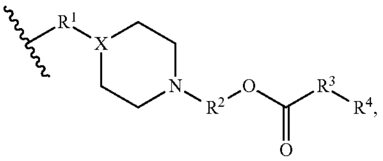

preferably with X being CH, $R^2$ serves as a linker or spacer between the respective basic piperidine- or piperazine-derived ring structure and an ester group. As mentioned, $R^2$ is defined as an alkanediyl having 2 to 8 carbon atoms. $R^2$ may be linear or branched, and otherwise (i.e. except for any branchings) it is preferably unsubstituted. In one embodiment, $R^2$ is a linear unsubstituted alkanediyl having 2, 3, 4, 5, 6, 7 or 8 carbon atoms. In another embodiment, $R^2$ is a linear unsubstituted alkanediyl having 2 to 6 carbon atoms. In a further preferred embodiment, $R^2$ is a linear unsubstituted ethanediyl or propanediyl. For example, both $R^a$ and $R^b$ may be

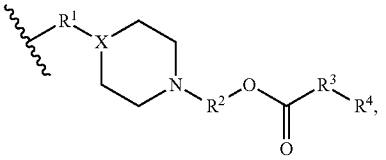

preferably with X being CH, with an $R^2$ selected from linear unsubstituted alkanediyls having 2 to 6 carbon atoms, such as ethanediyl or propanediyl.

The optional structure $R^3$ includes an ester group which may further enhance the degradability of the cationic lipid into smaller molecular species under physiological, e.g. intracellular, conditions. As defined above, $R^3$, if present, is defined inter alia as —$R^5$—C(O)—O— or —$R^5$—O—C(O)—, wherein $R^5$ can be a spacer consisting of an alkanediyl with 1 to 6 carbon atoms. In other words, the ester group may have either orientation. Preferably, $R^5$ is an unsubstituted linear alkanediyl with 1, 2, 3, 4, 5 or 6 carbon atoms. In another preferred embodiment, $R^3$ is present and $R^5$ is an unsubstituted linear alkanediyl with 2 or 3 carbon atoms, or with 3 to 6 carbon atoms.

$R^4$ is defined as a lipophilic substituent with 12 to 36 carbon atoms. This "tail" end of $R^a$ and optionally also of $R^b$(unless $R^b$ is —$R^1$—$N(CH_3)_2$) is believed to provide the degree of lipophilicity which is typically required for molecules to be able to cross biological membranes. Therefore, $R^4$ may in principle be of any structure that is substantially lipophilic. For example, a hydrocarbon structure is lipophilic. In one embodiment, $R^4$, in at least one of its occurrences, may consist of only carbon and hydrogen atoms. In one preferred embodiment, $R^4$ represents a linear or branched alkyl or alkenyl, preferably having 12 to 25 carbon atoms. The branched alkyl or alkenyl may optionally have a plurality of side chains, such as 2, 3, 4 or more methyl side chains. In another embodiment, $R^4$ may be an alkyl or alkenyl comprising a single alkyl or alkenyl side chain with e.g. 2 to 10 carbon atoms. For example, $R^4$ may be 1-n-hexyl-n-nonyl (or 7-n-pentadecyl), or 2-n-hexyl-n-decyl. In other embodiments, the lipophilic substituent may optionally include one or more heteroatoms such as O, S, or N. In other embodiments, the lipophilic substituent may optionally include one or more saturated, unsaturated, or aromatic ring structures that may optionally include one or more heteroatoms such as O, S, or N.

$R^4$ may also include a small number of hetero atoms such as oxygen atoms, as long as the predominantly lipophilic character is maintained. In one embodiment, $R^4$ comprises one or more oxygen atoms and no other hetero atoms. $R^4$ may also comprise a cyclic structure, such as an aromatic or aliphatic ring structure optionally including one or more oxygen atoms. If present, it is preferred that the hetero atoms and/or the cyclic structure are located towards the optional $R^3$ structure rather than towards the end of the "tail". In one embodiment, $R^4$ is a lipophilic group derived from tocopherol or tocotreinol. In one embodiment, $R^4$ is a lipophilic group derived from alpha-tocopherol, in particular

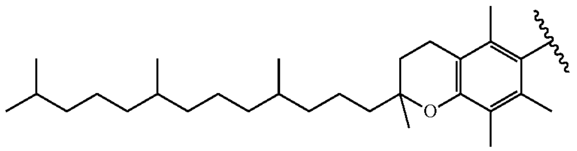 [SMILES: *c1c(C)c(C)c2c(c1C)CCC(C)(CCCC(C)CCCC(C)CCCC(C)C)O2]

in particular if not all of $R^1$, $R^2$ and $R^5$ are linear unsubstituted ethanediyl, A is —S—S—, and $R^a$ and $R^b$ are identical.

A "lipophilic group derived from tocopherol or tocotreinol" as referred to herein includes derivatives of tocopherol and tocotreinol, in particular the derivatives with the structures shown in Scheme 1 below, i.e. the derivatives derived from alpha-tocopherol, beta-tocopherol, gamma-tocopherol, delta-tocopherol, alpha-tocotreinol, beta-tocotreinol, gamma-tocotreinol and delta-tocotreinol.

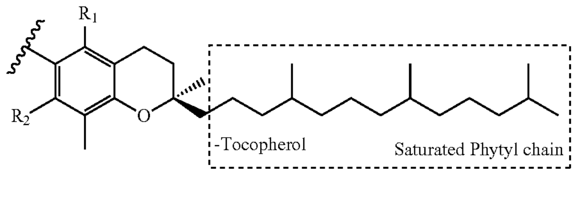

-continued

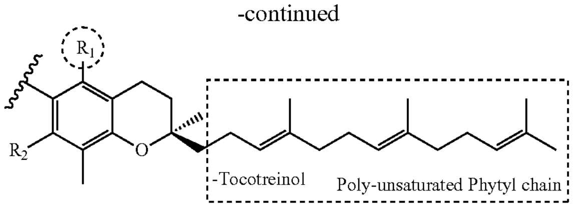

| Isoform | $R_1$ | $R_2$ |
|---|---|---|
| Alpha (α) | CH3 | CH3 |
| Beta (β) | CH3 | H |
| Gamma (γ) | H | CH3 |
| Delta (δ) | H | H |

Scheme 1: Derivatives of tocopherol have a saturated phytyl chain, whereas derivatives of tocotreinol have a poly-unsaturated phytyl chain. For both, derivatives of tocopherol and tocotreinol, the isoforms are defined by $R_1$ and $R_2$, which are selected from $CH_3$ and H. Thus, as shown, if e.g. $R_1$ is $CH_3$ and $R_2$ is $CH_3$, the resulting derivative is the alpha isoform of tocopherol and tocotreinol, respectively (referred to as derivative of alpha-tocopherol and alpha-tocotreinol, respectively). The OH-group is of course not present in the derivatives since this is the point of attachment, as shown in the two structures on the left.

In a preferred embodiment, in particular of aspect A above, $R^4$ is either a linear or branched alkyl or alkenyl having 12 to 25 carbon atoms or is a lipophilic group selected from the group consisting of the derivatives of alpha-tocopherol, beta-tocopherol, gamma-tocopherol, delta-tocopherol, alpha-tocotreinol, beta-tocotreinol, gamma-tocotreinol and delta-tocotreinol as shown herein in Scheme 1.

In yet another preferred embodiment, in particular of aspect A above, $R^4$ is either a linear or branched alkyl or alkenyl having 12 to 25 carbon atoms or

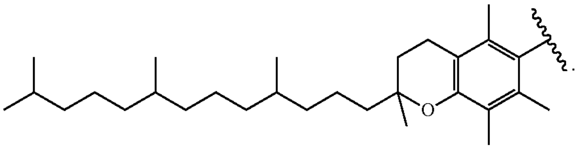 [SMILES: *c1c(C)c(C)c2c(c1C)CCC(C)(CCCC(C)CCCC(C)CCCC(C)C)O2]

In yet another preferred embodiment, in particular of aspect A above, $R^4$ is selected from the group consisting of

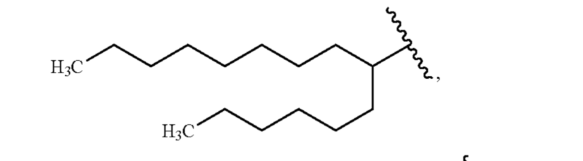

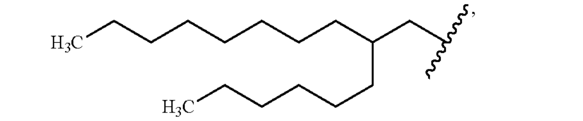

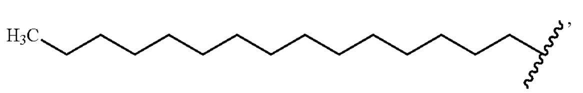

-continued

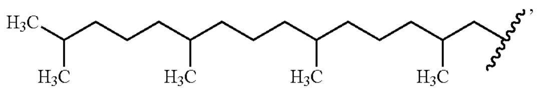

, and

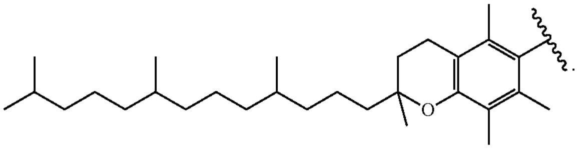 [SMILES: *c1c(C)c(C)c2c(c1C)CCC(C)(CCCC(C)CCCC(C)CCCC(C)C)O2]

.

As mentioned, X is either a carbon atom or a nitrogen atom, independently selected at each occurrence. In one embodiment, X is a carbon atom. In another embodiment, both $R^a$ and $R^b$ are structures comprising X, wherein preferably X is a carbon atom at each occurrence. Alternatively, X is a nitrogen atom; for example, both $R^a$ and $R^b$ are structures comprising X, and at each occurrence, a nitrogen atom is selected for X. Whenever reference is made herein to X being a carbon atom, this is understood to refer to a carbon atom being bonded to a hydrogen atom, i.e. CH. At some instances herein, reference is already made to X being CH.

According to a further specific embodiment, a cationic lipid having formula (I) is provided wherein $R^a$ is selected from

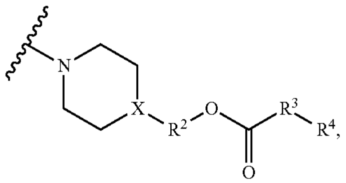

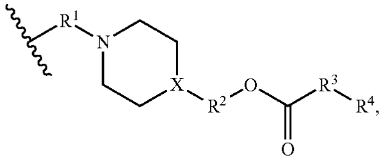

preferably with X being CH, or $—R^1—N(H)—C(O)—R^3-R^4$;

wherein $R^b$ is selected from

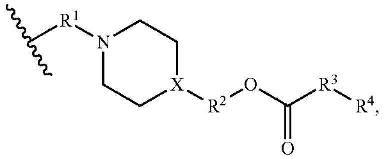

preferably with X being CH, $—R^1—N(H)—C(O)—R^3-R^4$, or $—R^1—N(CH_3)_2$;

wherein A is —S—, —S—S—, —NH—C(O)—, —NH—C(O)O—, —NH—C(O)—NH—, —S—C(O)—N(H)—, —C(O)O—, or —O—P(O)(OH)—O—;

wherein $R^1$ is an optionally substituted ethanediyl, propanediyl, butanediyl, or linear or unbranched alkanediyl having 2 to 8 carbon atoms;

wherein $R^2$ is an alkanediyl having 2 to 8 carbon atoms;

wherein $R^3$ is optional, and if present, is $—R^5—C(O)—O—$, $—R^5—O—C(O)—$, $—R^5—C(O)—NH—$, $—R^5—OC(O)—NH—$, or $R^5—NH—C(O)O—$;

wherein $R^4$ is a lipophilic substituent with 12 to 36 carbon atoms;

wherein $R^5$ is an alkanediyl having 3 to 6 carbon atoms;

wherein X is a carbon or nitrogen atom;

and wherein all selections are independent of one another. Optionally, the alkanediyls represented by $R^2$ and/or $R^5$ are linear and unsubstituted.

According to a further specific embodiment, a cationic lipid of formula (I) is provided wherein $R^a$ is selected from

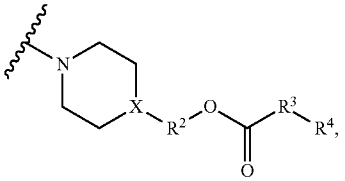

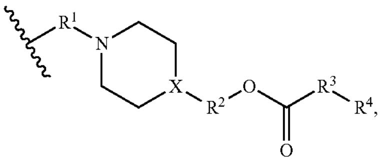

preferably with X being CH, or $—R^1—N(H)—C(O)—R^3-R^4$;

wherein $R^b$ is selected from

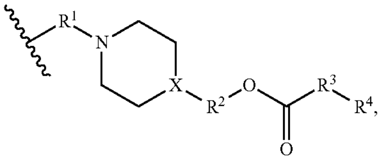

preferably with X being CH, $—R^1—N(H)—C(O)—R^3-R^4$, or $—R^1—N(CH_3)_2$;

wherein A is —S—, —S—S—, —NH—C(O)—, —NH—C(O)O—, —NH—C(O)—NH—, —S—C(O)—N(H)—, —C(O)O—, or —O—P(O)(OH)—O—;

wherein $R^1$ is an optionally substituted ethanediyl, propanediyl, butanediyl, or linear or unbranched alkanediyl having 2 to 8 carbon atoms;

wherein $R^2$ is an alkanediyl having 2 to 8 carbon atoms;

wherein $R^3$ is optional, and if present, is $—R^5—C(O)—O—$, $—R^5—O—C(O)—$, $—R^5—C(O)—NH—$, $—R^5—OC(O)—NH—$, or $R^5—NH—C(O)O—$;

wherein $R^4$ is an alkyl or alkenyl having 12 to 25 carbon atoms;

wherein $R^5$ is an alkanediyl having 1 to 6 carbon atoms;

wherein X is a carbon or nitrogen atom;

and wherein all selections are independent of one another. Optionally, the alkanediyls represented by $R^2$ and/or $R^5$ are linear and unsubstituted.

Furthermore, in another embodiment, a cationic lipid according to formula (I) is provided wherein $R^a$ and $R^b$ are selected from:

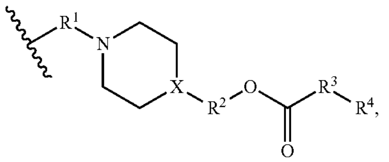

preferably with X being CH, or —$R^1$—N(H)—C(O)—$R^3$-$R^4$; A is —S—, —S—S—, —NH—C(O)—, —NH—C(O)O—, —NH—C(O)—NH—, —S—C(O)—N(H)—, —C(O)O—, or —O—P(O)(OH)—O—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is —$R^5$—C(O)—O—, —$R^5$—O—C(O)—, —$R^5$—C(O)—NH—, —$R^5$—OC(O)—NH—, or $R^5$—NH—C(O)O—;

$R^4$ is a lipophilic substituent with 12 to 36 carbon atoms;

$R^5$ is an alkanediyl having 1 to 6 carbon atoms;

X is a carbon or nitrogen atom;

wherein all selections are independent of one another, optionally provided that if $R^1$, $R^2$ and $R^5$ are all linear unsubstituted ethanediyl, A is —S—S—, and $R^a$ and $R^b$ are identical, then $R^4$ is not

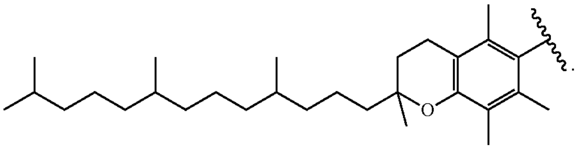 [SMILES: *c1c(C)c(C)c2c(c1C)CCC(C)(CCCC(C)CCCC(C)CCCC(C)C)O2]

In this embodiment, the alkanediyls represented by $R^2$ and/or $R^5$ may be linear and unsubstituted; optionally, $R^5$ comprises 2 to 6 carbon atoms, and each of $R^a$ and $R^b$ are

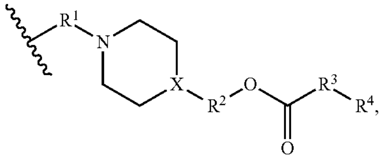

preferably with X being CH.

In a further specific embodiment, a cationic lipid according to formula (I) is provided wherein each of $R^a$ and $R^b$ is:

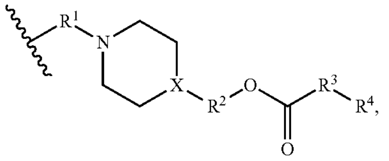

preferably with X being CH;

A is —S—S—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is —$R^5$—C(O)—O— or —$R^5$—O—C(O)—;

$R^4$ is a lipophilic substituent with 12 to 36 carbon atoms;

$R^5$ is an alkanediyl having 2 to 6 carbon atoms;

X is a carbon or nitrogen atom;

wherein all selections are independent of one another, optionally provided that if $R^1$, $R^2$ and $R^5$ are all linear unsubstituted ethanediyl, A is —S—S—, and $R^a$ and $R^b$ are identical, then $R^4$ is not

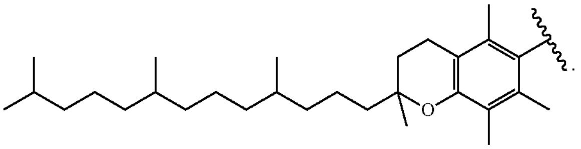

Again, the alkanediyls represented by $R^2$ and/or $R^5$ may be linear and unsubstituted.

A further embodiment provides a cationic lipid according to formula (I) wherein each of $R^a$ and $R^b$ is:

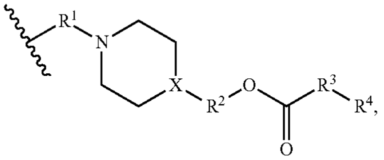

preferably with X being CH;

A is —S—S—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is —$R^5$—C(O)—O— or —$R^5$—O—C(O)—;

$R^4$ is an alkyl or alkenyl having 12 to 25 carbon atoms;

$R^5$ is an alkanediyl having 2 to 6 carbon atoms;

X is a carbon or nitrogen atom;

and wherein all selections are independent of one another, and wherein the alkanediyls represented by $R^2$ and/or $R^5$ may be linear and unsubstituted.

In another embodiment, a cationic lipid according to formula (I) is provided, wherein each of $R^a$ and $R^b$ is:

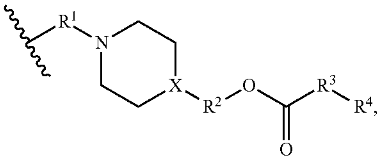

preferably with X being CH;

A is —S—S—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is —$R^5$—C(O)—O— or —$R^5$—O—C(O)—;

$R^4$ is an alkyl selected from:

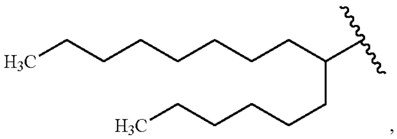

,

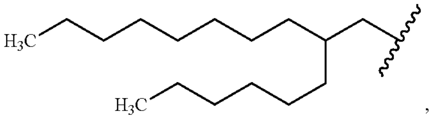

,

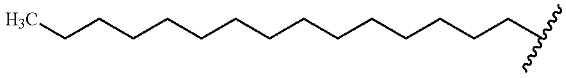

,

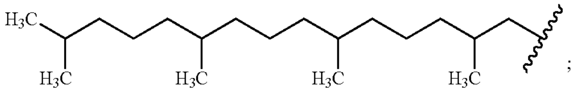

;

$R^5$ is an alkanediyl having 2 to 6 carbon atoms;

X is a carbon or nitrogen atom;

wherein all selections are independent of one another, and wherein the alkanediyls represented by $R^2$ and/or $R^5$ may be linear and unsubstituted.

A further embodiment relates to a cationic lipid according to formula (I) wherein each of $R^a$ and $R^b$ is:

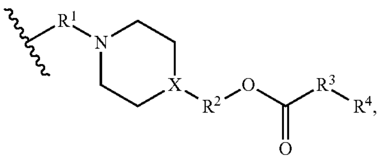

preferably with X being CH;

A is —S—S—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is —$R^5$—C(O)—O— or —$R^5$—O—C(O)—;

$R^4$ is:

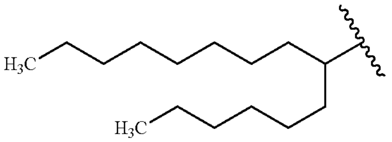

or

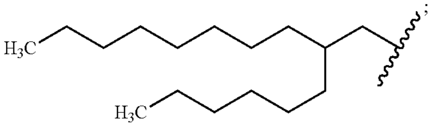

;

$R^5$ is an alkanediyl having 2 to 6 carbon atoms;

X is a carbon or nitrogen atom;

wherein $R^a$ and $R^b$ are identical and all other selections are independent of one another, and wherein the alkanediyls represented by $R^2$ and/or $R^5$ may be linear and unsubstituted.

In a further embodiment, the invention provides a cationic lipid according to formula (I) wherein each of $R^a$ and $R^b$ is:

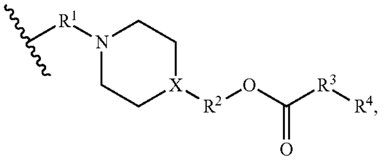

preferably with X being CH;

A is —S—S—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is-$R^5$—C(O)—O—;

$R^4$ is:

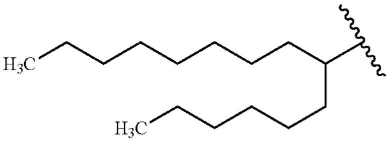

or

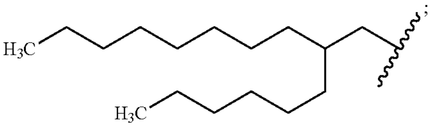

;

$R^5$ is an alkanediyl having 2 to 6 carbon atoms;

X is a carbon or nitrogen atom;

wherein $R^a$ and $R^b$ are identical and all other selections are independent of one another, and wherein the alkanediyls represented by $R^2$ and/or $R^5$ may be linear and unsubstituted.

According to a further embodiment, the cationic lipid provided by the present invention is a compound of formula (I), wherein each of $R^a$ and $R^b$ is:

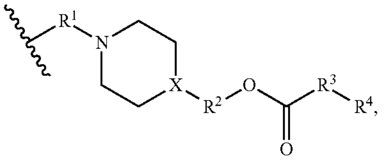

preferably with X being CH;

A is —S—S—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is-$R^5$—C(O)—O—;

$R^4$ is:

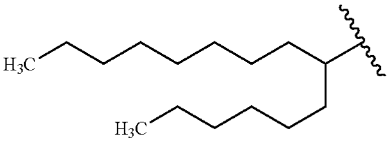

or

-continued

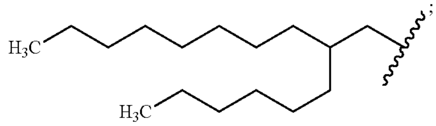

;

$R^5$ is an alkanediyl having 2 to 6 carbon atoms;

X is a carbon atom;

wherein $R^a$ and $R^b$ are identical and all other selections are independent of one another, and wherein the alkanediyls represented by $R^2$ and/or $R^5$ may be linear and unsubstituted.

In another specific embodiment, the cationic lipid provided by the invention is a compound according to formula (I), wherein each of $R^a$ and $R^b$ is:

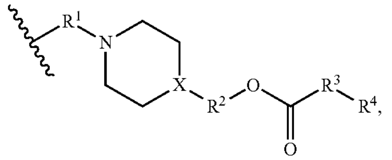

preferably with X being CH;

A is —S—S—;

$R^1$ is ethanediyl;

$R^2$ is an alkanediyl having 2 to 8 carbon atoms;

$R^3$ is-$R^5$—C(O)—O—;

$R^4$ is:

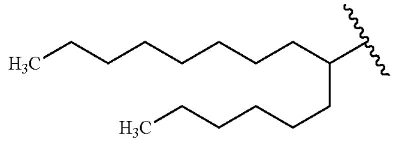

or

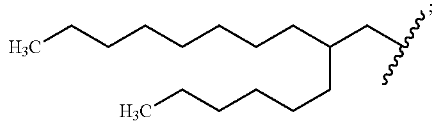

;

$R^5$ is an alkanediyl having 2 to 6 carbon atoms;

X is a carbon atom;

wherein $R^a$ and $R^b$ are identical and all other selections are independent of one another, and wherein the alkanediyls represented by $R^2$ and/or $R^5$ may be linear and unsubstituted; preferably, also the ethanediyl of $R^1$ is linear and unsubstituted.

In another one of the preferred embodiments, the cationic lipid has one or more of the following features, independently selected at each occurrence:

(i) $R^1$ is an unsubstituted ethanediyl, propanediyl, or butanediyl;

(ii) $R^2$ is an linear, unbranched alkanediyl having 2 to 8 carbon atoms;

(iii) $R^3$ is —R5—C(O)—O— or —R5-O—C(O)—;

(iv) $R^4$ is an alkyl or alkenyl having 12 to 25 carbon atoms;

(v) $R^5$ is an alkanediyl having 2 to 6 carbon atoms; and/or (vi) X is a carbon atom.

In another preferred embodiment, in particular of above aspect A, $R^3$ is present and selected from the group consisting of —R—C(O)—O—, —$R^5$—O—C(O)—, —$R^5$—C(O)—NH—, —$R^5$—OC(O)—NH—, and $R^5$—NH—C(O)O—; and $R^4$ is a linear or branched alkyl or alkenyl having 12 to 25 carbon atoms. In this embodiment, it can be particularly preferred that $R^3$ is —$R^5$—C(O)—O— or —$R^5$—O—C(O)—. In this embodiment, it can further be preferred that R4 is selected from the group consisting of

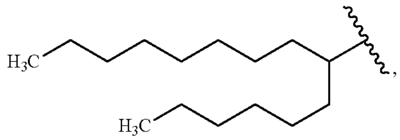

,

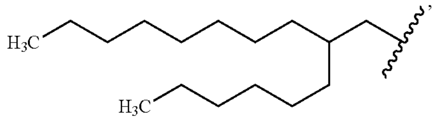

,

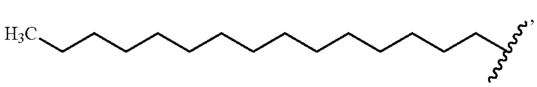

, and

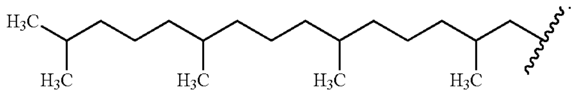

.

In yet another preferred embodiment, in particular of above aspect A, A is —S—. In this embodiment, it can be preferred that $R^a$ and $R^b$ are identical and are

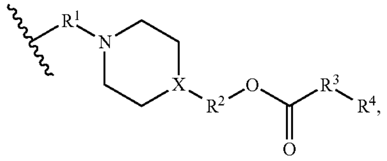

with X being preferably CH. It can further be preferred in this embodiment that $R^3$ is present and selected from —$R^5$—C(O)—O— or —$R^5$—O—C(O)—. It can also be preferred in this embodiment that $R^4$ is

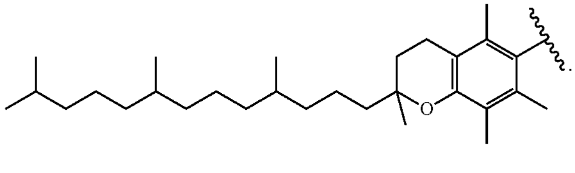 [SMILES: *c1c(C)c(C)c2c(c1C)CCC(C)(CCCC(C)CCCC(C)CCCC(C)C)O2]

.

It can further be preferred in this embodiment that $R^4$ of $R^a$ and $R^4$ of $R^b$ are identical. Finally, it is also preferred in this embodiment that one of or all of $R^1$, $R^2$ and $R^3$ are an alkanediyl having 1 to 6 carbon atoms, in particular having 2, 3 or 3 carbon atoms.

In yet a further embodiment, the cationic lipid preferably is selected from the cationic lipids as listed in Table 1.

TABLE 1
Preferred cationic lipids according to formula (I) - when it is referred to specific lipids from this table, reference is made f.e. to Lipid C1, Lipid Compound 1 or C1
| Cationic Lipid Compound No. | Structure | Ref. in FIGS./ Name |
| --- | --- | --- |
| C1 | 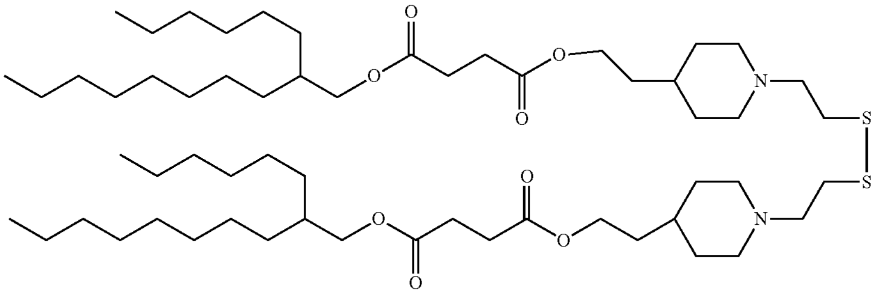 [SMILES: CCCCCCCCC(CCCCCC)COC(=O)CCC(=O)OCCC1CCN(CCSSCCN2CCC(CCOC(=O)CCC(=O)OCC(CCCCCC)CCCCCCCC)CC2)CC1] | FIG. 1A/ HEXA-C4DE-PipSS |
| C2 | 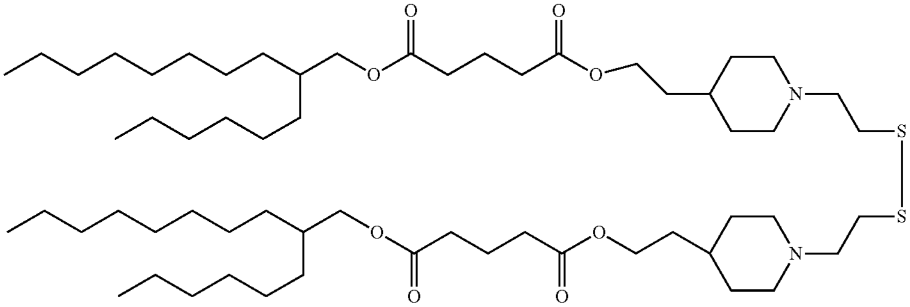 [SMILES: CCCCCCCCC(CCCCCC)COC(=O)CCCC(=O)OCCC1CCN(CCSSCCN2CCC(CCOC(=O)CCCC(=O)OCC(CCCCCC)CCCCCCCC)CC2)CC1] | FIG. 1B/ HEXA-C5DE-PipSS (GN02-lipid) |
| C3 | 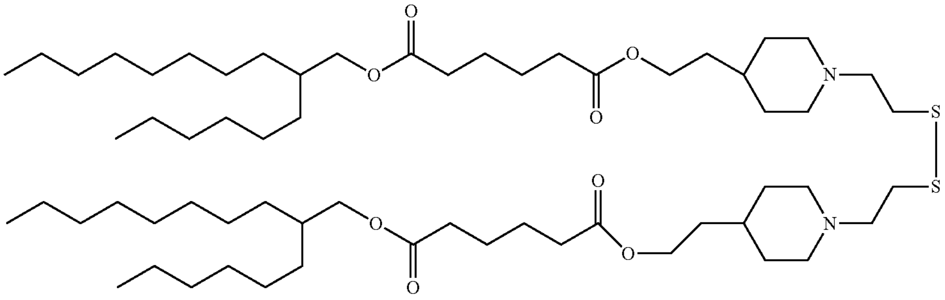 [SMILES: CCCCCCCCC(CCCCCC)COC(=O)CCCCC(=O)OCCC1CCN(CCSSCCN2CCC(CCOC(=O)CCCCC(=O)OCC(CCCCCC)CCCCCCCC)CC2)CC1] | FIG. 1C/ HEXA-C6DE-PipSS |
| C4 | 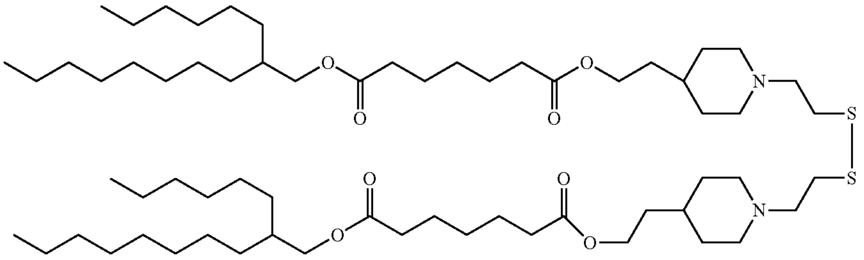 [SMILES: CCCCCCCCC(CCCCCC)COC(=O)CCCCCC(=O)OCCC1CCN(CCSSCCN2CCC(CCOC(=O)CCCCCC(=O)OCC(CCCCCC)CCCCCCCC)CC2)CC1] | FIG. 1D/ HEXA-C7DE-PipSS |
| C5 | 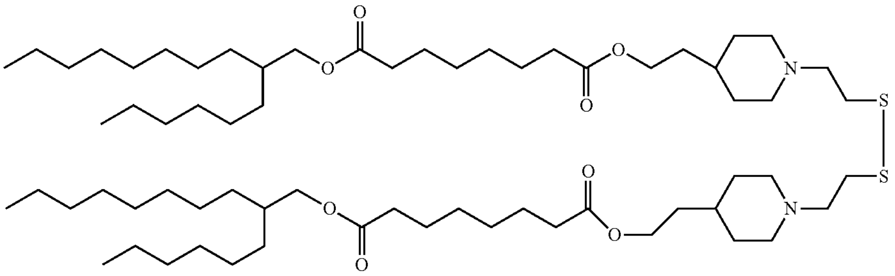 [SMILES: CCCCCCCCC(CCCCCC)COC(=O)CCCCCCC(=O)OCCC1CCN(CCSSCCN2CCC(CCOC(=O)CCCCCCC(=O)OCC(CCCCCC)CCCCCCCC)CC2)CC1] | FIG. 1E/ HEXA-C8DE-PipSS |

TABLE 1-continued
Preferred cationic lipids according to formula (I) - when it is referred to specific lipids from this table, reference is made f.e. to Lipid C1, Lipid Compound 1 or C1
| Cationic Lipid Compound No. | Structure | Ref. in FIGS./ Name |
| --- | --- | --- |
| C6 | 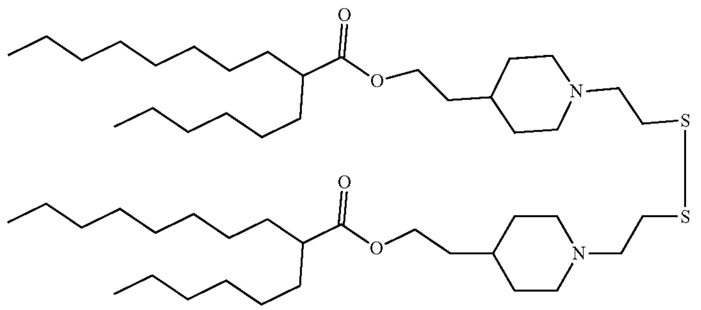 [SMILES: CCCCCCCCC(CCCCCC)C(=O)OCCC1CCN(CCSSCCN2CCC(CCOC(=O)C(CCCCCC)CCCCCCCC)CC2)CC1] | FIG. 1F/ HEXACA-C3ME-PipSS |
| C7 | 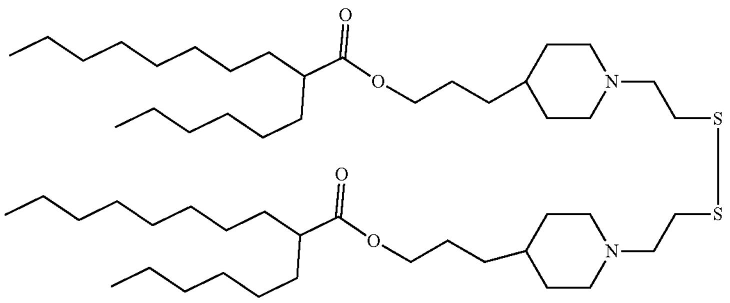 [SMILES: CCCCCCCCC(CCCCCC)C(=O)OCCCC1CCN(CCSSCCN2CCC(CCCOC(=O)C(CCCCCC)CCCCCCCC)CC2)CC1] | FIG. 1G/ HEXACA-C4ME-PipSS |
| C8 | 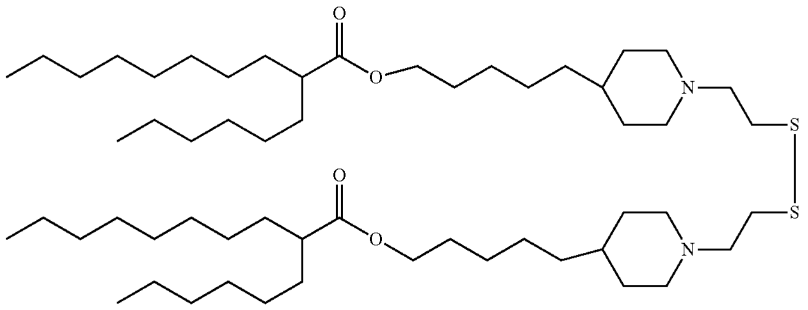 [SMILES: CCCCCCCCC(CCCCCC)C(=O)OCCCCCC1CCN(CCSSCCN2CCC(CCCCCOC(=O)C(CCCCCC)CCCCCCCC)CC2)CC1] | FIG. 1H/ HEXACA-C6ME-PipSS |
| C9 | 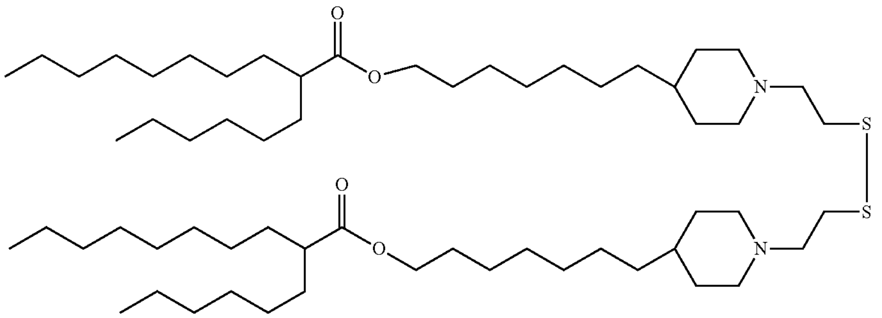 [SMILES: CCCCCCCCC(CCCCCC)C(=O)OCCCCCCCC1CCN(CCSSCCN2CCC(CCCCCCCOC(=O)C(CCCCCC)CCCCCCCC)CC2)CC1] | FIG. 1I/ HEXACA-C8ME-PipSS |

TABLE 1-continued
| Preferred cationic lipids according to formula (I) - when it is referred to specific lipids from this table, reference is made f.e. to Lipid C1, Lipid Compound 1 or C1 | | |
|---|---|---|
| Cationic Lipid Compound No. | Structure | Ref. in FIGS./ Name |
| C10 | 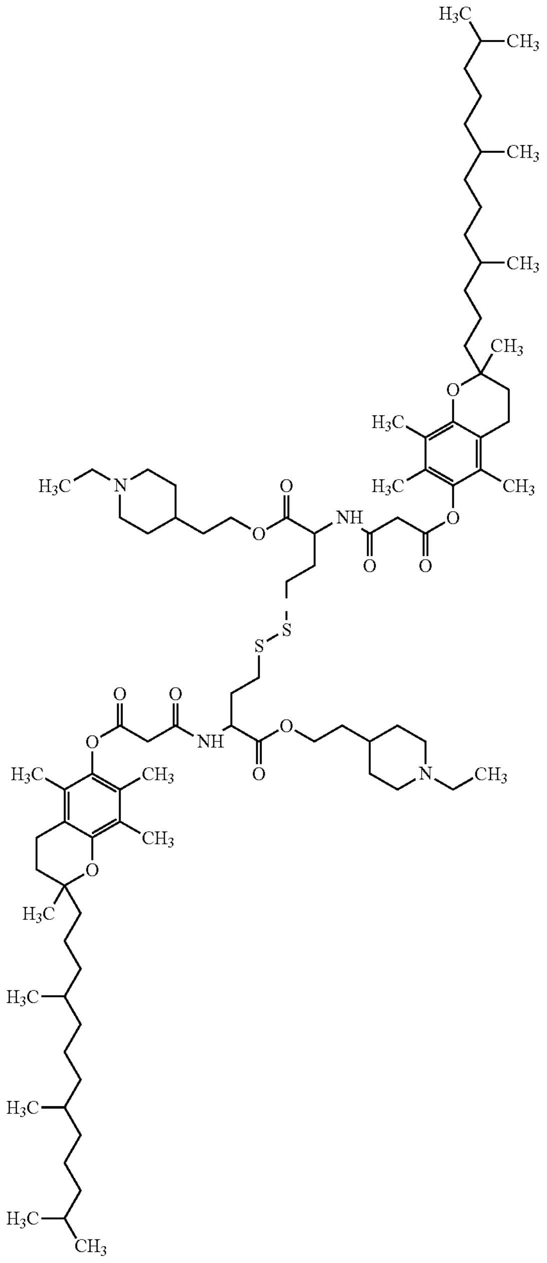 [SMILES: CCN1CCC(CCOC(=O)C(CCSSCCC(NC(=O)CC(=O)Oc2c(C)c(C)c3c(c2C)CCC(C)(CCCC(C)CCCC(C)CCCC(C)C)O3)C(=O)OCCC2CCN(CC)CC2)NC(=O)CC(=O)Oc2c(C)c(C)c3c(c2C)CCC(C)(CCCC(C)CCCC(C)CCCC(C)C)O3)CC1] | FIG. 3A |

TABLE 1-continued
| Preferred cationic lipids according to formula (I) - when it is referred to specific lipids from this table, reference is made f.e. to Lipid C1, Lipid Compound 1 or C1 | | |
|---|---|---|
| Cationic Lipid Compound No. | Structure | Ref. in FIGS./ Name |
| C11 | 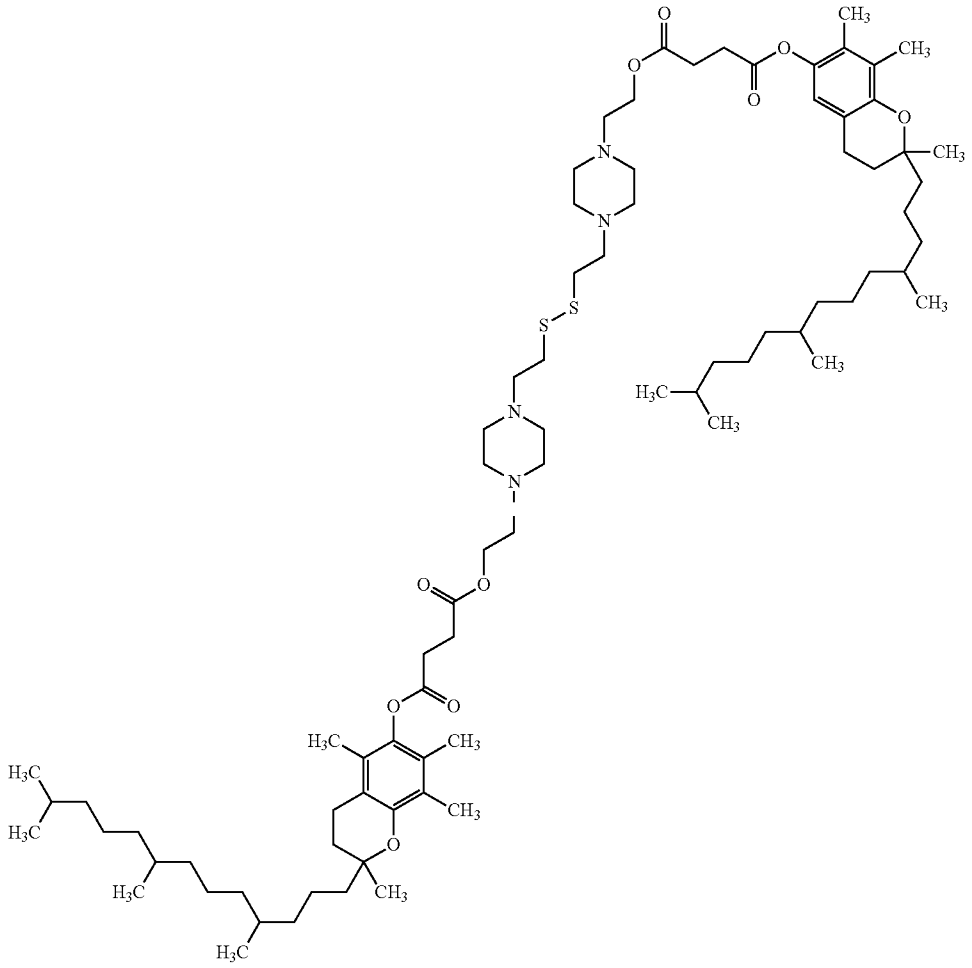 | FIG. 3B |

TABLE 1-continued
| Preferred cationic lipids according to formula (I) - when it is referred to specific lipids from this table, reference is made f.e. to Lipid C1, Lipid Compound 1 or C1 | | |
|---|---|---|
| Cationic Lipid Compound No. | Structure | Ref. in FIGS./ Name |
| C12 | 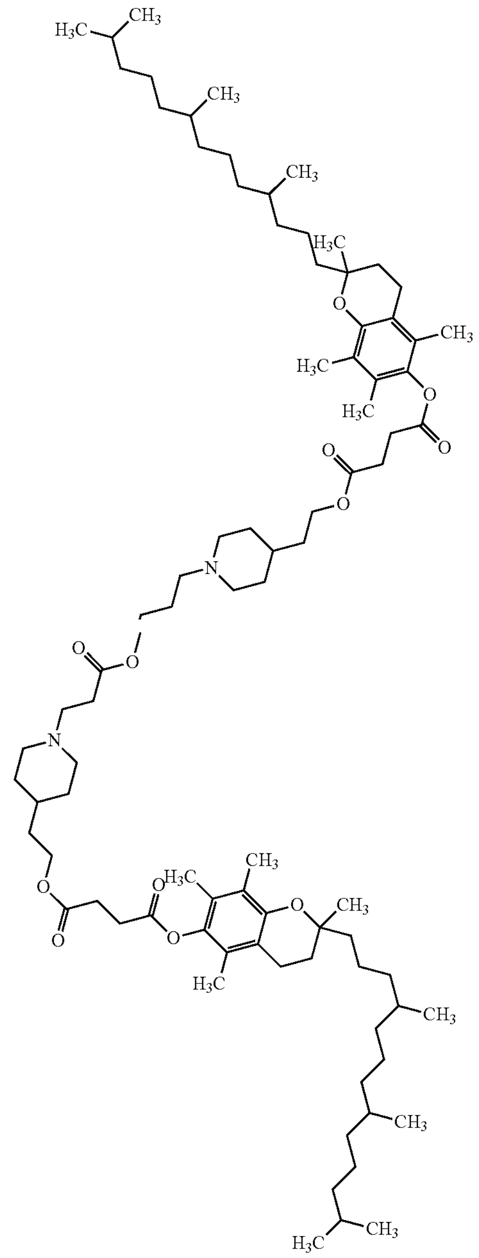 [SMILES: Cc1c(C)c2c(c(C)c1OC(=O)CCC(=O)OCCC1CCN(CCCOC(=O)CCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] | FIG. 3C |

TABLE 1-continued
| Cationic Lipid Compound No. | Structure | Ref. in FIGS./ Name |
| --- | --- | --- |
| Preferred cationic lipids according to formula (I) - when it is referred to specific lipids from this table, reference is made f.e. to Lipid C1, Lipid Compound 1 or C1 | | |
| C13 | 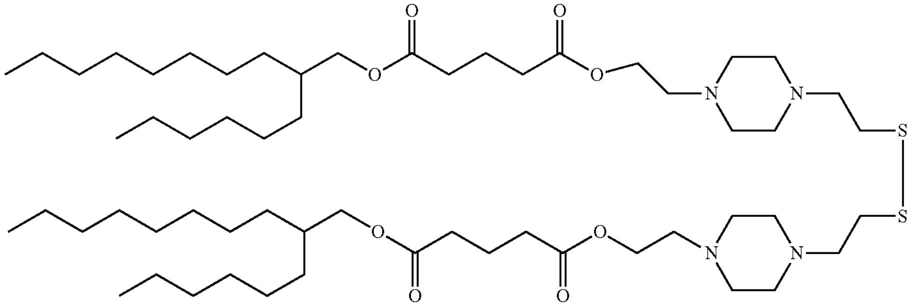 | HEXA-C5DE-PipAZSS |
| C14 | 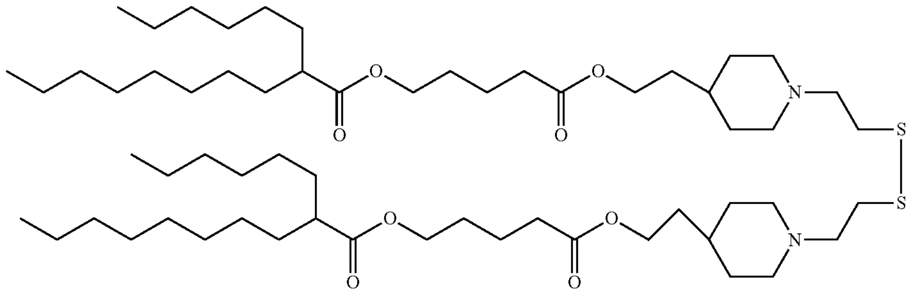 [SMILES: CCCCCCCCC(CCCCCC)C(=O)OCCCCC(=O)OCCC1CCN(CCSSCCN2CCC(CCOC(=O)CCCCOC(=O)C(CCCCCC)CCCCCCCC)CC2)CC1] | HEXACA-C5DE-PipSS |
| C15 | 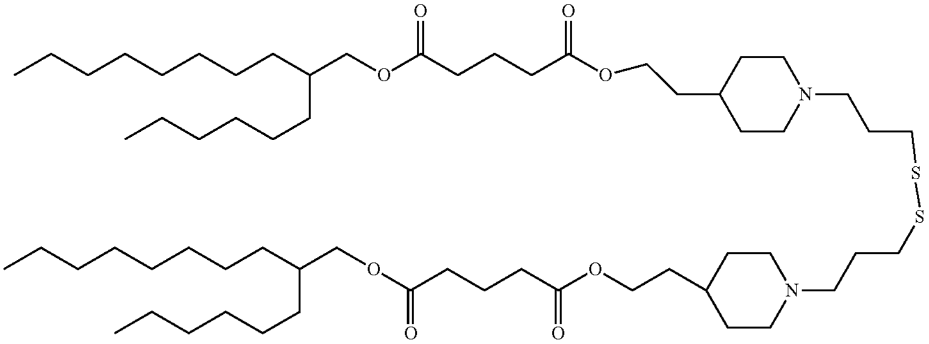 [SMILES: CCCCCCCCC(CCCCCC)COC(=O)CCCC(=O)OCCC1CCN(CCCSSCCCN2CCC(CCOC(=O)CCCC(=O)OCC(CCCCCC)CCCCCCCC)CC2)CC1] | HEXA-C5DE-PipC3SS |
| C16 | 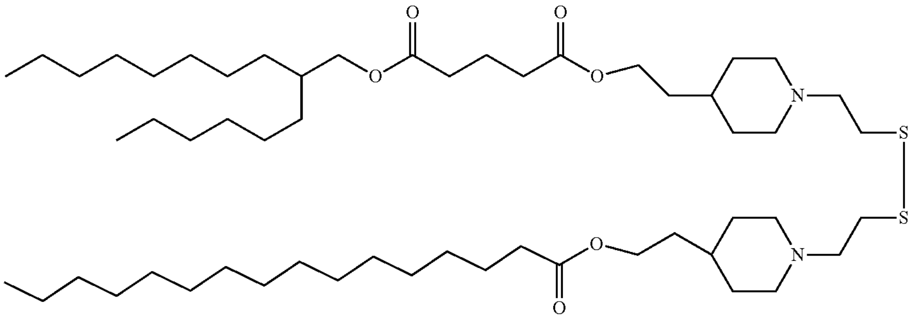 [SMILES: CCCCCCCCCCCCCCCC(=O)OCCC1CCN(CCSSCCN2CCC(CCOC(=O)CCCC(=O)OCC(CCCCCC)CCCCCCCC)CC2)CC1] | C16-HEXA-C5DE-PipSS |

TABLE 1-continued
| Preferred cationic lipids according to formula (I) - when it is referred to specific lipids from this table, reference is made f.e. to Lipid C1, Lipid Compound 1 or C1 | | |
|---|---|---|
| Cationic Lipid Compound No. | Structure | Ref. in FIGS./ Name |
| C17 | 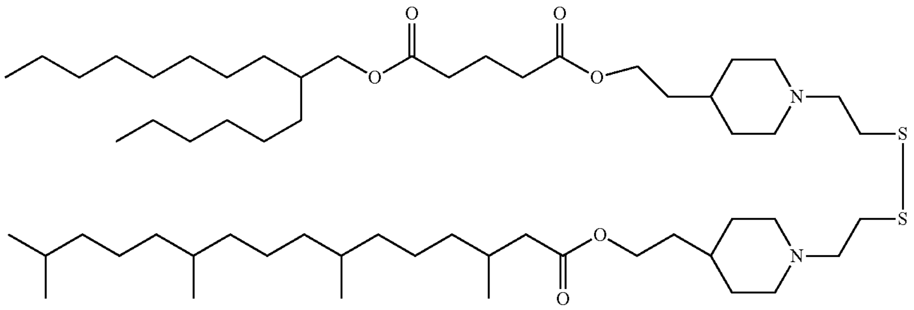 [SMILES: CCCCCCCCC(CCCCCC)COC(=O)CCCC(=O)OCCC1CCN(CCSSCCN2CCC(CCOC(=O)CC(C)CCCC(C)CCCC(C)CCCC(C)C)CC2)CC1] | DPhy-HEXA-C5DE-PipSS |
| C18 | 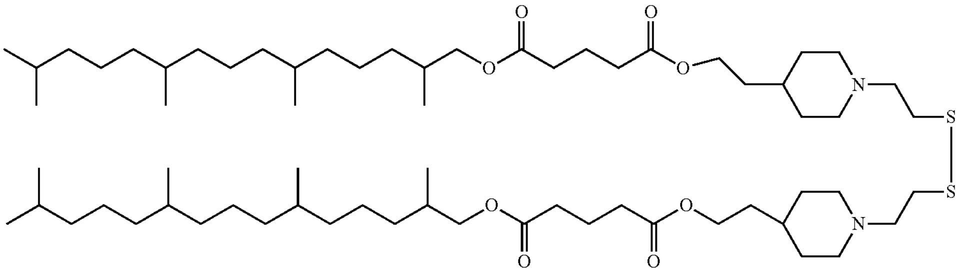 [SMILES: CC(C)CCCC(C)CCCC(C)CCCC(C)COC(=O)CCCC(=O)OCCC1CCN(CCSSCCN2CCC(CCOC(=O)CCCC(=O)OCC(C)CCCC(C)CCCC(C)CCCC(C)C)CC2)CC1] | 2DPhy-C5DE-PipSS |
| C19 | 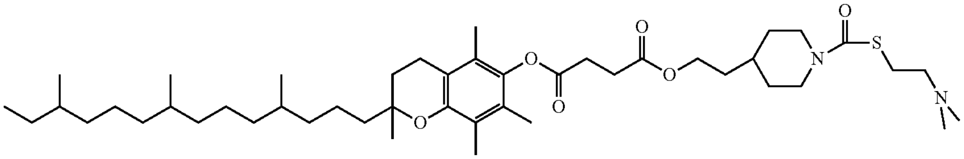 [SMILES: CCC(C)CCCC(C)CCCC(C)CCCC1(C)CCc2c(C)c(OC(=O)CCC(=O)OCCC3CCN(C(=O)SCCN(C)C)CC3)c(C)c(C)c2O1] | Vit E-C5DE-Pip-TEN |
| C20 | 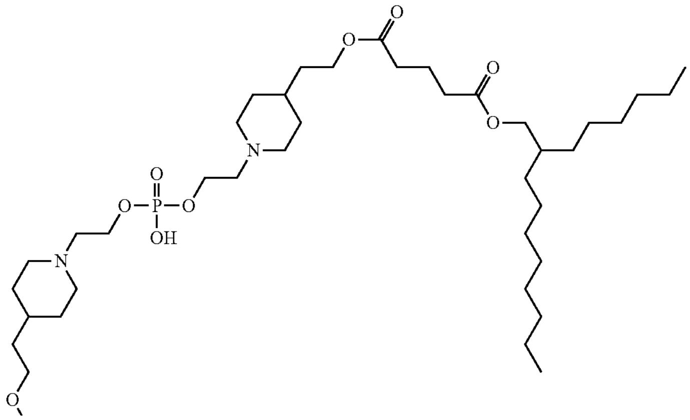 | HEXA-C5DE-Pip-Phosphate |

TABLE 1-continued
| Preferred cationic lipids according to formula (I) - when it is referred to specific lipids from this table, reference is made f.e. to Lipid C1, Lipid Compound 1 or C1 | | |
|---|---|---|
| Cationic Lipid Compound No. | Structure | Ref. in FIGS./ Name |
| | 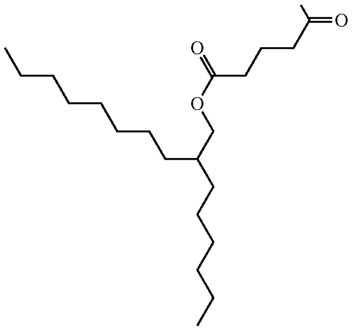 | |
| C21 | 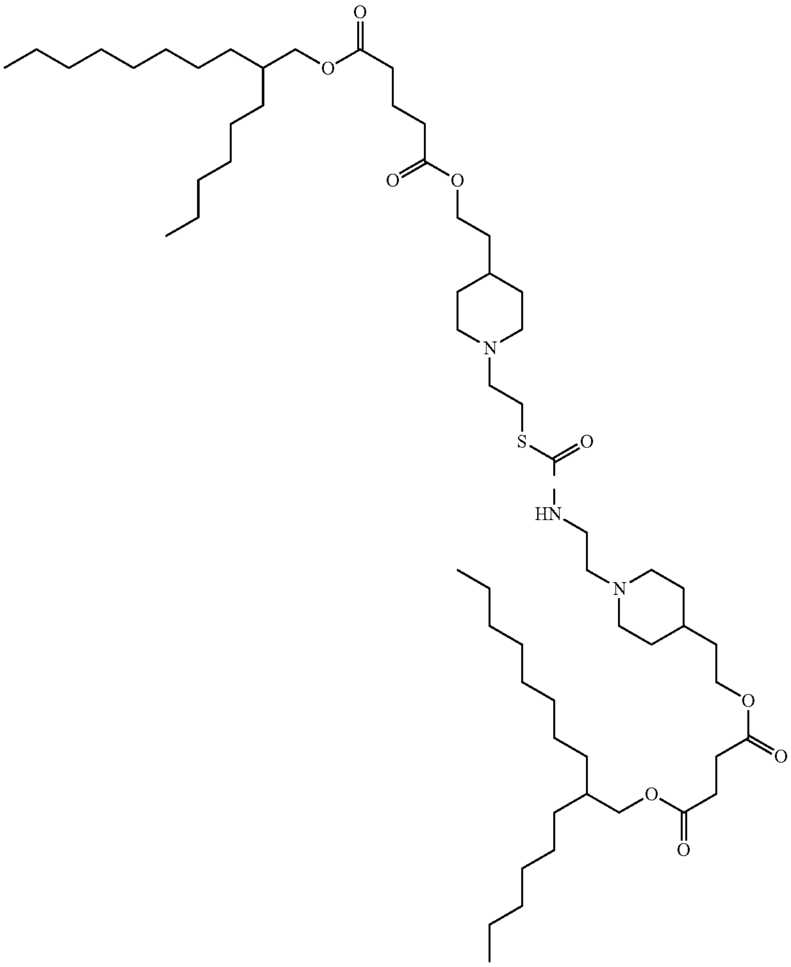 [SMILES: CCCCCCCCC(CCCCCC)COC(=O)CCCC(=O)OCCC1CCN(CCSC(=O)NCCN2CCC(CCOC(=O)CCC(=O)OCC(CCCCCC)CCCCCCCC)CC2)CC1] | HEXA-C5DE-Pip-Thiocarbamate |

TABLE 1-continued
| Cationic Lipid Compound No. | Structure | Ref. in FIGS./ Name |
|---|---|---|
| Preferred cationic lipids according to formula (I) - when it is referred to specific lipids from this table, reference is made f.e. to Lipid C1, Lipid Compound 1 or C1 | | |
| C22 | 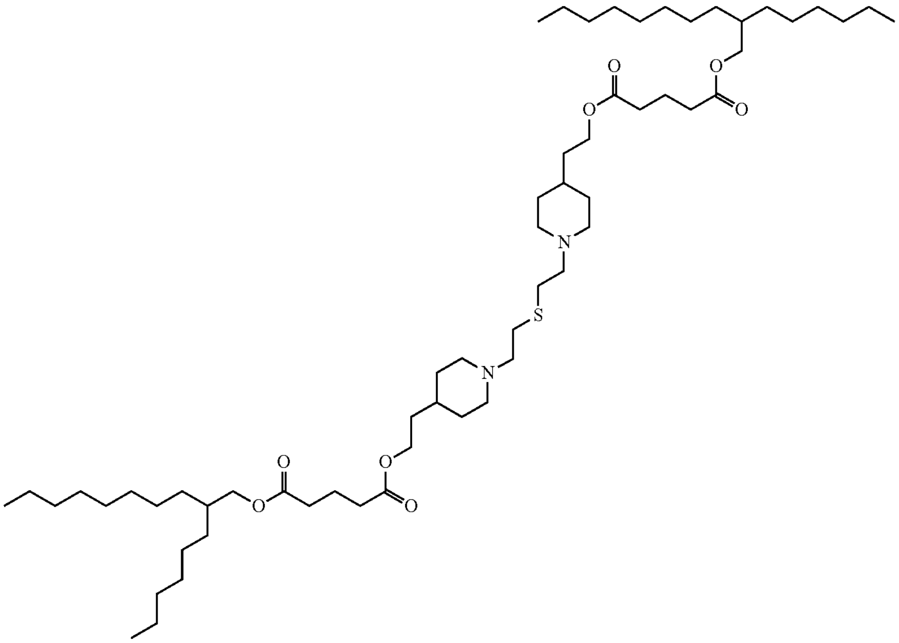 [SMILES: CCCCCCCCC(CCCCCC)COC(=O)CCCC(=O)OCCC1CCN(CCSCCN2CCC(CCOC(=O)CCCC(=O)OCC(CCCCCC)CCCCCCCC)CC2)CC1] | HEXA-C5DE-Pip-Thioether |
| C23 | 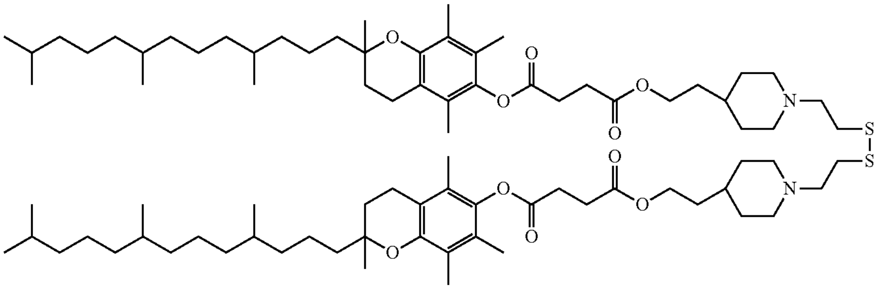 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] | COATSOME ® SS-EC |
| C24 | 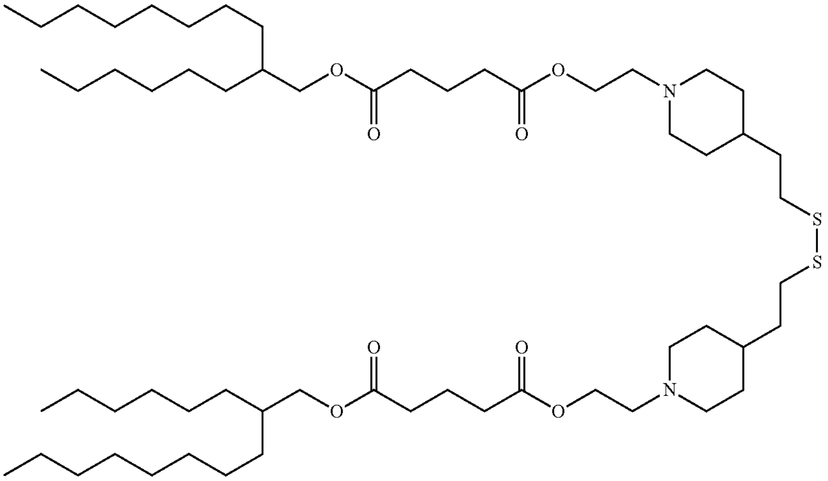 [SMILES: CCCCCCCCC(CCCCCC)COC(=O)CCCC(=O)OCCN1CCC(CCSSCCC2CCN(CCOC(=O)CCCC(=O)OCC(CCCCCC)CCCCCCCC)CC2)CC1] | HEXA-C5DE-inverted-PipSS |

TABLE 1-continued
| Preferred cationic lipids according to formula (I) - when it is referred to specific lipids from this table, reference is made f.e. to Lipid C1, Lipid Compound 1 or C1 | | |
|---|---|---|
| Cationic Lipid Compound No. | Structure | Ref. in FIGS./ Name |
| C25 | 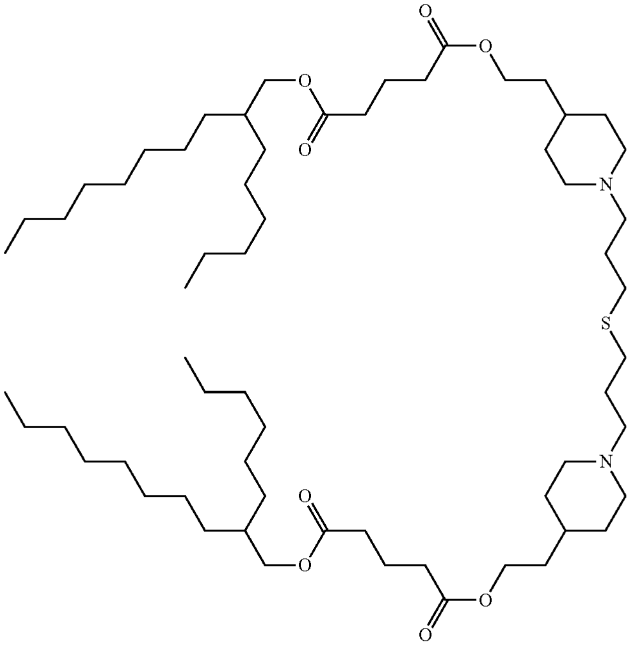 [SMILES: CCCCCCCCC(CCCCCC)COC(=O)CCCC(=O)OCCC1CCN(CCCSCCCN2CCC(CCOC(=O)CCCC(=O)OCC(CCCCCC)CCCCCCCC)CC2)CC1] | HEXA-C5DE-Pip-C3 thioether or HEXA-C5DE-piperidine-C3 thioether |
| C26 | 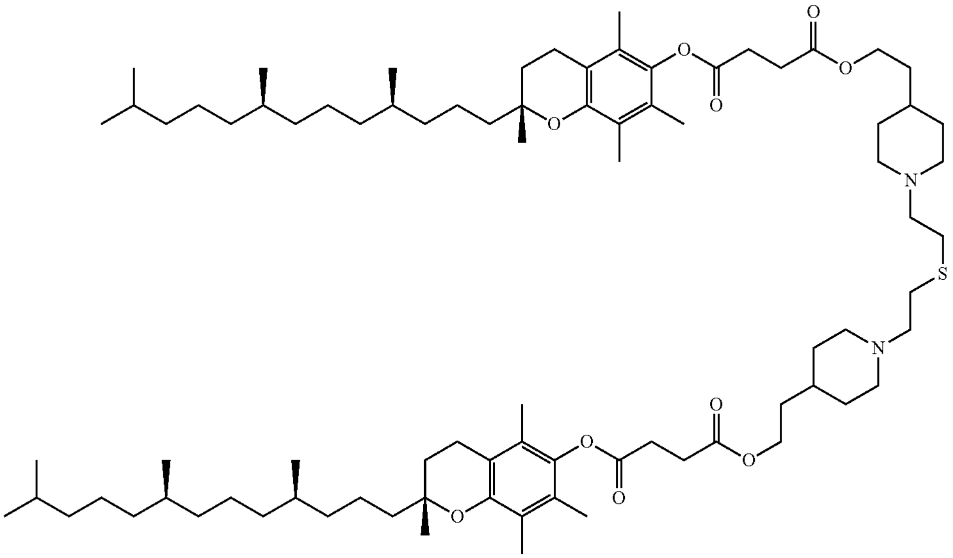 [SMILES: Cc1c(C)c2c(c(C)c1OC(=O)CCC(=O)OCCC1CCN(CCSCCN3CCC(CCOC(=O)CCC(=O)Oc4c(C)c(C)c5c(c4C)CC[C@@](C)(CCC[C@H](C)CCC[C@H](C)CCCC(C)C)O5)CC3)CC1)CC[C@@](C)(CCC[C@H](C)CCC[C@H](C)CCCC(C)C)O2] | THIOETHER or VitE-C4DE-Piperidine-Thioether |

TABLE 1-continued

| Preferred cationic lipids according to formula (I) - when it is referred to specific lipids from this table, reference is made f.e. to Lipid C1, Lipid Compound 1 or C1 | | |
|---|---|---|
| Cationic Lipid Compound No. | Structure | Ref. in FIGS./ Name |
| C27 | 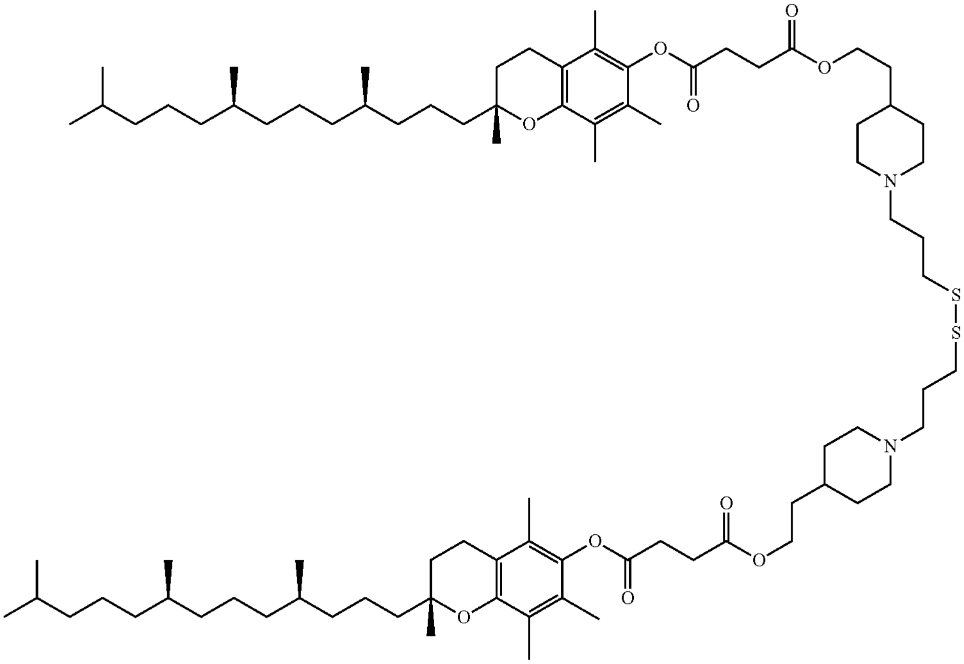 [SMILES: Cc1c(C)c2c(c(C)c1OC(=O)CCC(=O)OCCC1CCN(CCCSSCCCN3CCC(CCOC(=O)CCC(=O)Oc4c(C)c(C)c5c(c4C)CC[C@@](C)(CCC[C@H](C)CCC[C@H](C)CCCC(C)C)O5)CC3)CC1)CC[C@@](C)(CCC[C@H](C)CCC[C@H](C)CCCC(C)C)O2] | C3SS or VitE-C4DE-Piperidine-C3SS |

Accordingly, the invention is directed to a composition comprising the cationic lipid as described above. For example, the composition may comprise a cationic lipid selected from compounds C1 to C27 of Table 1.

In further certain embodiments, the cationic or cationisable lipid may be any of a number of lipid species which comprise a tertiary or quaternary nitrogen/amino group or which carry a net positive charge at a selective pH, such as physiological pH. Accordingly, in one embodiment, a cationic lipid comprising a tertiary or quaternary nitrogen/amino group or a cationic lipid carrying a net positive charge at physiological pH is selected from, but not limited to, the group consisting of N,N-dioleyl-N,N-dimethylammonium chloride (DODAC); N-(2,3-dioleyloxy)propyl)—N,N,N-trimethylammonium chloride (DOTMA); N,N-distearyl-N,N-dimethylammonium bromide (DDAB); N-(2,3dioleoyloxy)propyl)—N,N,N-trimethylammonium chloride (DOTAP); 3-(N—(N',N'dimethylaminoethane)-carbamoyl) cholesterol (DC-Chol); N-(1-(2,3-dioleoyloxy)propyl)N-2-(sperminecarboxamido)ethyl)—N,N-dimethylammonium trifluoracetate (DOSPA); dioctadecylamidoglycyl carboxyspermine (DOGS); 1,2-dioleoyl-3-dimethylammonium propane (DODAP); N,N-dimethyl-2,3-dioleoyloxy)propylamine (DODMA); and N-(1,2dimyristyloxyprop-3-yl)—N,N-dimethyl-N-hydroxyethyl ammonium bromide (DMRIE).

In a further embodiment, a cationic lipid comprising a tertiary or quaternary nitrogen/amino group or a cationic lipid carrying a net positive charge at physiological pH is selected from, but not limited to, the group consisting of amino lipids. In another embodiment, suitable amino lipids include those described in WO 2012/016184 A2, incorporated herein by reference in its entirety. [0320] Other suitable additional cationic lipids for use in the compositions include cholesterol-based cationic lipids.

Further representative amino lipids include, but are not limited to (i) those having the formula:

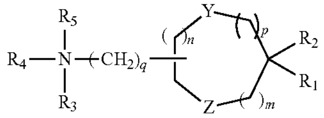

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl; $R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen; $R_5$ is either absent or present and when present is hydrogen or C1-$C_6$ alkyl; m, n, and p are either the same or different and independently either 0 or 1 with the proviso that m, n, and p are not simultaneously 0;

q is 0, 1, 2, 3, or 4; and Y and Z are either the same or different and independently O, S, or NH. In one embodiment, R, and $R_2$ are each linoleyl, and the amino lipid is a dilinoleyl amino lipid; or (ii) those selected from the group consisting of dilinoleyl amino lipid; 1,2-dilinoleyoxy-3-(dimethylamino)acetoxypropane (DLin-DAC); 1,2-dilinoleyoxy-3morpholinopropane (DLin-MA); 1,2-dilinoleoyl-3-dimethylaminopropane (DLinDAP); 1,2-dilinoleylthio-3-dimethylaminopropane (DLin-S-DMA); 1-linoleoyl-2-linoleyloxy-3dimethylaminopropane (DLin-2-DMAP); 1,2-dilinoleyloxy-3-trimethylaminopropane chloride salt (DLin-TMA.Cl); 1,2-dilinoleoyl-3-trimethylaminopropane chloride salt (DLin-TAP.Cl); 1,2-dilinoleyloxy-3-(N-methylpiperazino)propane (DLin-MPZ); 3-(N,Ndilinoleylamino)-1,2-propanediol (DLinAP); 3-(N,N-dioleylamino)-1,2-propanediol (DOAP); 1,2-dilinoleyloxo-3-(2—N,N-dimethylamino)ethoxypropane (DLin-EG-DMA); 2,2-dilinoleyl-4-dimethylaminomethyl-[1,3]-dioxolane (DLin-K-DMA); and DLin-KC2-DMA (DLin-K-DMA above, wherein n is 2).

The cationic lipids described herein can exist in the form of salts, for example acid addition salts or, in certain cases salts of organic and inorganic bases such as carboxylate, sulfonate and phosphate salts. All such salts are within the scope of this invention, and references to cationic lipids and compounds of formula (I) and sub-groups thereof include the salt forms of the compounds.

In a further embodiment, commercial preparations of cationic lipids may be used in the present invention. These include, for example, LIPOFECTIN® (commercially available cationic liposomes comprising DOTMA and 1,2-dioleoyl-sn-glycero-3-phosphoethanolamine (DOPE), from GIBCO/BRL, Grand Island, N.Y.); LIPOFECTAMINE® (commercially available cationic liposomes comprising N-(1-(2,3dioleyloxy)propyl)—N-(2-(sperminecarboxamido)ethyl)—N,N-dimethylammonium trifluoroacetate (DOSPA) and DOPE, from GIBCO/BRL); and TRANSFECTAM® (commercially available cationic lipids comprising dioctadecylamidoglycyl carboxyspermine (DOGS) in ethanol from Promega Corp., Madison, Wis.).

In a further embodiment, the compositions include an imidazole cholesterol ester or "ICE" as disclosed in paragraphs [0320] and [0339]-[0340] of WO 2019226925 A1, which is herein incorporated by reference in its entirety. Other suitable (cationic) lipids are disclosed in WO2009/086558, WO2009/127060, WO2010/048536, WO2010/054406, WO2010/088537, WO2010/129709, WO2011/153493, US2011/0256175, US2012/0128760, US2012/0027803, U.S. Pat. No. 8,158,601, WO2016118724, WO2016118725, WO2017070613, WO2017070620, WO2017099823, and WO2017112865; all of which are incorporated herewith by reference in their entirety. In some embodiments, the cationic lipid is selected from the group consisting of 98N12-5, C12-200, and ckk-E12 as disclosed in WO2017049074, U.S. Pat. No. 9,512,073B2, WO2015200465, US20150376144; all of which are incorporated herewith by reference in their entirety.

The cationic lipid can comprise from about 20 mol % to about 70 or 75 mol % or from about 45 to about 65 mol % or about 20, 25, 30, 35, 40, 45, 50, 55, 60, 65, or about 70 mol % of the total lipid present in the composition or lipid nanoparticle of the invention. In another embodiment, the lipid nanoparticles include from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle).

In general, the composition according to the invention may comprise other excipients, such as one or more further lipids. In one embodiment, a composition may comprise a further cationic lipid, i.e. a second, third and so forth cationic lipid. Such further cationic lipid may optionally be a cationic lipid as disclosed herein. Alternatively, it may be any other cationic lipid suitable for pharmaceutical compositions, in particular for compositions comprising an active ingredient selected from nucleic acid compounds, such as mRNA.

In one specific embodiment, the further cationic lipid is a permanently cationic lipid comprising at least one quaternary nitrogen atom. In this case, the first cationic lipid is preferably a lipid that is cationisable rather than permanently cationic.

Pharmaceutically acceptable salts of the basic cationic lipid may be derived from inorganic or organic acids. For example from inorganic acids such as hydrochloric, hyrdobromic, sulfuric, sulfamic, phosphoric, nitric acid and the like, as well as, salts from organic acids such as acetic, propanoic, succinic, glycolic, stearic, lactic, malic, tartaric, citric, ascorbic, pamoic, maleic, hdroxymaleic, phenylacetic, glutamic, benzoic, salicylic, sulfanilic, 2-acetoxybenzoic, fumatic, toluenesulfonic, methanesulfonic, ethanesulfonic, naphthalenesulfonic, benzenesulfonic, trifluoroacetic and the like. Further examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 1 7th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-1 9 (1977), each of which is incorporated herein by reference in its entirety.

Polymer Conjugated Lipid, Pegylated Lipid

In some embodiments, the LNPs comprise a lipid-conjugate, preferably a polymer conjugated lipid. The term "polymer conjugated lipid" refers to a molecule comprising both a lipid portion and a polymer portion. Preferably, the polymer conjugated lipid is a pegylated lipid or PEG-lipid. The terms "pegylated lipid" or "PEG-lipid" refer to a molecule comprising both a lipid portion and a polyethylene glycol portion. Pegylated lipids are known in the art and include PEG-DMG and the like.

In a specific embodiment, the polymer conjugated lipid is defined as a compound according to formula (II):

P-A-L formula (II)

wherein P is a hydrophilic polymer moiety, A is an optional linker or spacer, and L is a lipid moiety.

Hydrophilic Polymer Moiety P

The hydrophilic polymer moiety P in the polymer conjugated lipid according to formula (II) may be a polyethylene glycol ("PEG") moiety. In a specific embodiment, the PEG moiety has an average molecular mass of between 1 kDa and 3 kDa, e.g. between 1.5-2.5 kDa, between 1.7-2.3 kDa, between 1.8-2.2 kDa, between 1.9-2.1 kDa, or 2 kDa. Thus the PEG can be a PEG which is commonly known as "PEG 2000" or "PEG 2k", although the shorter "PEG 1000" and longer "PEG 3000" can also be used. The PEG moiety usually comprises linear polymer chains but, in some embodiments, the PEG moiety may comprise branched polymer chains. Alternatively, contemplated PEG-modified lipids include, but are not limited to, a polyethylene glycol chain of up to 2 kDa, up to 3 kDa, up to 4 kDa or up to 5 kDa in length covalently attached to a lipid.

In another embodiment, the hydrophilic polymer moiety P in the polymer conjugated lipid may also be a substantially hydrophilic polymer which is different from the above describes hydrophilic polymer moieties, i.e. the hydrophilic polymer moiety P in the polymer conjugated lipid may be based on poly(propylene oxide), poly(vinyl pyrrolidone), poly(vinyl alcohol), Poly-N-(2-Hydroxypropyl) methacrylamide, a hesylation-process (in accordance with PMID 24681396), a PASylation-approach (i.e. proline-alanine-serine), an XTEN-approach as known in the art (i.e. peptide based PEG), polysarcosin or poly(vinyl acetate).

Optional Linker or Spacer A

The optional linker or spacer A in the polymer conjugated lipid according to formula (II) may be any useful spacer structure, such as a spacer selected from those that have generally been found useful in pegylated lipids, for example, but not limited to, succinimide, amine, ether, ester, anhydride, aldehyde, ketone, amide, carbamate linkers or combinations thereof.

Lipid Moiety L

The lipid moiety L in the polymer conjugated lipid according to formula (II) may be derived from a phospholipid, a sphingolipid or a ceramide. As used herein, the expression "derived from a phospholipid or a ceramide" includes radicals of phospholipids and ceramides. Examples are polymer conjugated lipids comprising a phosphatidylethanolamine or phosphatidylglycerol moiety.

In a specific embodiment, the polymer conjugated lipid is a pegylated lipid. In a more specific embodiment, the polymer conjugated lipid comprised in the composition of the invention is a polymer conjugated lipid selected from the group consisting of a pegylated diacylglycerol lipid (PEG-DAG); a pegylated ceramide lipid (PEG-Cer); a pegylated phosphatidylethanoloamine lipid (PEG-PE); a pegylated succinate diacylglycerol lipid (PEG-S-DAG); a pegylated dialkoxypropylcarbamate lipid; 1,2-dimyristoyl-rac-glycero-3-methoxypolyethylene glycol ("PEG-DMG" or "DMG-PEG"); 1,2-dicapryl-rac-glycero-3-methylpolyoxyethylene glycol ($C_{10}$ diacylglycerol PEG); N-octanoyl-sphingosine-1-{succinyl[methoxy(polyethylene glycol) 2000]} (comprising N-octanoyl-D-erythro-sphingosine (d18:1/8:0), also named PEG-Ceramide8, $C_3$-ceramide-PEG, PEG-Cer8, $C_8$ PEG2000 Ceramide or Ceramide 8 PEG); 4-O-(2',3'-di(tetradecanoyloxy)propyl-1-O-(ω-methoxy(polyethoxy)ethyl)butanedioate (PEG-S-DMG); 2-mPEG2000-n,n ditetradecylacetamide; N-[(methoxy poly (ethylene glycol)2000)carbamyl]-1,2-dimyristyloxlpropyl-3-amine (PEG-c-DMA); w-methoxy(polyethoxy)ethyl-N-(2,3-di(tetradecanoxy)propyl)carbamate; a PEG-lipid as disclosed in WO2018126084, WO2020093061, or WO2020219941 (all three references are incorporated by reference herein), PEGylated cholesterol or a PEGylated cholesterol-derivate as disclosed herein, and 2,3-di(tetradecanoxy)propyl-N-(ω-methoxy(polyethoxy)ethyl)carbamate.

In a further preferred embodiment, the lipid moiety L comprises 1, 2, 3, 4, or more hydrophobic fatty acids ("tails", corresponding to aliphatic chains comprising an even number of carbon atoms). In a more preferred embodiment, the lipid moiety L comprises 2 hydrophobic fatty acids ("tails") having the same or different numbers of carbon atoms.

Preferably, lipid moiety L comprises a fatty acid ("tail") comprising, 6, 7, 8, 9, 10, 11, 12, 13, 14, 15, 16, 17, 18, 19, 20, 21, 22, 23, 24, 25 or 26 carbon atoms or combinations thereof. More preferably, lipid moiety L comprises a fatty acid ("tail") comprising, 8, 9, 10, 11, 12, 13, 14, 15, 16, 17 or 18 carbon atoms or combinations thereof. In a more specific embodiment, lipid moiety L comprises a fatty acid ("tail") selected from the group consisting of caprylic acid or octanoic acid (8:0); capric acid (10:0); lauric acid (12:0); myristic acid (14:0); palmitic acid (16:0); stearic acid (18:0); arachidic acid (20:0); behenic acid (22:0); lignoceric acid (24:0); and cerotic acid (26:0).

In an even more preferred embodiment, lipid moiety L comprises at least one fatty acid ("tail") comprising 8, 10 or 12 carbon atoms, preferably 8 or 10 carbon atoms.

In a further preferred embodiment, the composition comprises the polymer conjugated lipid 1,2-dimyristoyl-rac-glycero-3-methoxypolyethylene glycol 2000 (DMG-PEG 2000)

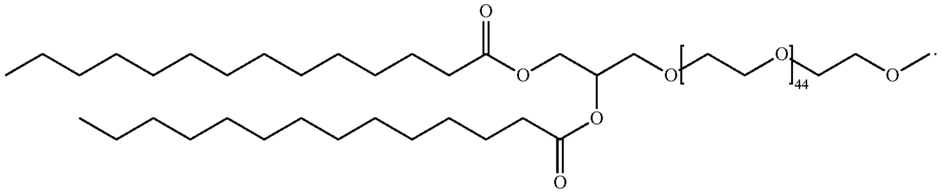

Preferably, and as used in the art, "DMG-PEG 2000" is considered a mixture of 1,2-DMG PEG2000 and 1,3-DMG PEG2000 in ~97:3 ratio.

In a further specific embodiment, the composition comprises a polymer conjugated lipid selected from the group consisting of 1,2-dicapryl-rac-glycero-3-methylpolyoxyethylene glycol 2000 ($C_{10}$-PEG 2000)

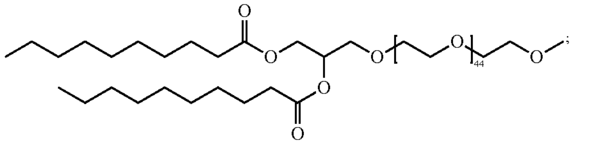

and

N-octanoyl-sphingosine-1-{succinyl[methoxy(polyethylene glycol)2000]} (Cer8-PEG 2000)

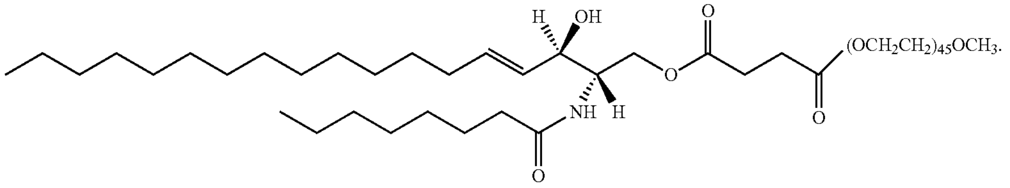

In a further embodiment, the composition comprises a polymer conjugated lipid selected from the group consisting of the following structure resembling "$C_8$-PEG 2000" having the following chemical structure:

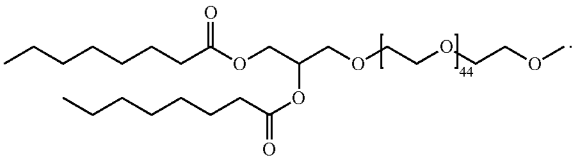

In specific embodiments of the invention, each composition as disclosed herein within the specification comprising "$C_{10}$-PEG 2000" can also be formulated with "Ca-PEG 2000" instead of "$C_{10}$-PEG 2000".

Accordingly, as an example, a polymer conjugated lipid, or respectively lipid moiety L, may have two fatty acid tails, comprising saturated fatty acids, unsaturated fatty acids or a combination thereof ("tails"), f.e. like Cer8-PEG 2000 comprising one saturated fatty acid chain (8:0; caprylic acid or respectively octanoic acid) and one unsaturated fatty acid chain of a different length with more than 8 carbon atoms.

Specifically the advantageous use of polymer conjugated lipids with shorter alkyl chains (f.e. Cer8) as disclosed herein, preferably in combination with the inventive lipids as disclosed herein f.e. in Table 1 and/or DPhyPE as neutral lipid instead of DSPC, for delivering mRNA vaccines in vivo, resulting in significantly enhanced immune responses is a further very surprising finding made by the inventors and resembles specific aspects and embodiments of the present invention.

Steroid

A "steroid" is an organic compound with four rings arranged in a specific molecular configuration. It comprises the following carbon skeleton:

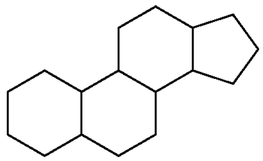 [SMILES: C1CCC2C(C1)CCC1C3CCCC3CCC21]

Steroids and neutral steroids include both naturally occurring steroids and analogues thereof (f.e. being amphipathic lipid cholesteryl hemisuccinate (CHEMS) which consists of succinic acid esterified to the beta-hydroxyl group of cholesterol as cholesterol derivate). Using the definition for "neutral" as provided herein, the neutral steroid may be a steroid either having no atoms or groups that are ionizable under physiological conditions, or it may be a zwitterionic steroid. In one of the preferred embodiments, the neutral steroid is free of atoms or groups that are ionizable under physiological conditions. In some preferred embodiments, the steroid or steroid analogue is cholesterol. The term "steroid" and "neutral steroid" is used herein interchangeably.

In a further embodiment, the steroid is an imidazole cholesterol ester or "ICE" as disclosed in paragraphs [0320] and [0339]-[0340] of WO 2019226925 A1; which is herein incorporated by reference in its entirety.

Neutral Lipid, Neutral Phospholipid

A “neutral lipid”, also termed “helper lipid” according to the invention preferably is a phospholipid or neutral phospholipid. As used herein, a “neutral phospholipid” is an amphiphilic compound consisting of molecules that typically have two hydrophobic fatty acid “tails” and a hydrophilic “head” comprising a phosphate group. The phosphate group can be modified with simple organic molecules such as choline, ethanolamine or serine. Phospholipids occur abundantly in nature. For example, they represent a significant fraction of the excipients of biological membranes. As used herein, the expression “phospholipid” or “neutral phospholipid” covers both natural and synthetic phospholipids.

The terms “neutral lipid”, “neutral phospholipid” or “zwitterionic compound”, as used herein interchangeably, refer to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydro sphingomyelins, cephalins, and cerebrosides as further described herein below.

According to one of the preferred embodiments, the composition comprises a neutral lipid that is zwitterionic, such as a phosphatidylcholine or a phosphatidylethanolamine. Examples of suitable phosphatidylcholines include native or purified mixtures, sometimes referred to as “lecithin” or “phosphatidylcholine”, often derived from egg yolk or soy beans; or highly purified or semisynthetic compounds such as phosphatidylcholines having two fatty acyl moieties selected from myristoyl, palmitoyl, stearoyl, oleoyl and the like.

In another preferred embodiment, the neutral lipid or neutral phospholipid is a zwitterionic compound selected from, but not limited to the group of 1,2-diphytanoyl-sn-glycero-3-phosphoethanolamine (DPhyPE; also referred to as 1,2-di-(3,7,11,15-tetramethylhexadecanoyl)-sn-glycero-3-phosphoethanolamine), 1,2-diphytanoyl-sn-glycero-3-phosphocholine (DPhyPC), 1,2-dioleoyl-sn-glycero-3-phosphocholine (DOPC; also referred to as dioleoylphosphatidylcholine), 1,2-Dipalmitoyl-sn-glycero-3-phosphocholine (DPPC, also referred to as dipalmitoylphosphatidylcholine), 1,2-dioleoyl-sn-glycero-3-phosphoethanolamine (DOPE), phosphatidylethanolamines, distearoylphosphatidylcholines, dioleoyl-phosphatidylethanolamine (DOPEA), 1,2-distearoyl-sn-glycero-3-phosphoethanolamine (DSPE), palmitoyloleoylphosphatidylcholine (POPC), palmitoyl-oleoyl-phosphatidylethanolamine (POPE), 1,2-Dipalmitoyl-sn-glycero-3-phosphoethanolamine (DPPE), dioleoyl-phosphatidylethanolamine 4-(N-maleimidomethyl)-cyclohexane-1-carboxylate (DOPE-mal), 1,2-Dimyristoyl-sn-glycero-3-phosphoethanolamine (DMPE), 1,2-Dilinoleoyl-sn-glycero-3-phosphoethanolamine (DLoPE), distearoyl-phosphatidylethanolamine (DSPE), 1-Palmitoyl-2-oleoyl-sn-glycero-3-phosphoethanolamine (POPE), 1,2-Di-lauroyl-sn-glycero-3-phosphoethanolamine (DLPE), 16-O-monomethylphosphoethanolamine, 16-O-dimethyl phosphatidylethanolamine, 1,2-Dierucoyl-sn-glycero-3-phosphoethanolamine (DEPE), 18-1-trans phosphatidylethanolamine, 1-stearoyl-2-oleoylphosphatidyethanolamine (SOPE), 1,2-Disqualeoyl-sn-glycero-3-phosphoethanolamine (DSQPE), 1,2-dielaidoyl-sn-glycero-3-phosphoethanolamine (transDOPE), 1—Stearoyl-2-linoleoyl-sn-glycero-3-phosphoethanolamine (SLPE), 1-tridecanoyl-sn-glycero-3-phospho-L-serine (sodium salt), 1-oleoyl-2-hydroxy-sn-glycero-3-phospho-L-serine (sodium salt), 1-palmitoyl-2-oleoyl-sn-glycero-3-phospho-L-serine (sodium salt) (POPS), 1-1-stearoyl-2-oleoyl-sn-glycero-3-phospho-L-serine (sodium salt), 1,2-dioleoyl-sn-glycero-3-phospho-L-serine (sodium salt) (DOPS), 1,2-distearoyl-sn-glycero-3-phospho-L-serine (sodium salt), 1,2-diphytanoyl-sn-glycero-3-phospho-L-serine (sodium salt), 1-O-hexadecanyl-2-O-(9Z-octadecenyl)-sn-glycero-3-phosphoethanolamine, 1,2-distearoyl-sn-glycero-3-phosphatidylcholine or 1,2-distearoyl-sn-glycero-3-phosphocholine (DSPC), 1,2-di-O-phytanyl-sn-glycero-3-phosphoethanolamine, 1-palmitoyl-2-cholesteryl-hemisuccinoyl-sn-glycero-3-phosphocholine (PChemsPC), 1,2-dicholesterylhemisuccinoyl-sn-glycero-3-phosphocholine (DChemsPC), 2-((2,3-bis(oleoyloxy)propyl)dimethylammonio)ethyl hydrogen phosphate (DOCP), 2-((2,3-bis(oleoyloxy)propyl)dimtheylammonio)ethyl ethyl phosphate (DOCPe), and 1-O-octadecyl-2-O-methyl-sn-glycero-3-phosphocholine (Edelfosine).

In a preferred embodiment, the neutral lipid according to the invention is 1,2-Dipalmitoyl-sn-glycero-3-phosphocholine (DPPC), 1,2-dioleoyl-sn-glycero-3-phosphocholine (DOPC) or 1,2-dioleoyl-sn-glycero-3-phosphoethanolamine (DOPE). In a more preferred embodiment, the neutral lipid according to the invention is 1,2-diphytanoyl-sn-glycero-3-phosphocholine (DPhyPC). In an even more preferred particularly preferred embodiment, the neutral lipid according to the invention is 1,2-diphytanoyl-sn-glycero-3-phosphoethanolamine (DPhyPE). The inventive advantage connected with the use of DPhyPE is the high capacity for fusogenicity due to its bulky tails, whereby it is able to fuse at a high level with endosomal lipids.

Specifically the advantageous use of 1,2-diphytanoyl-sn-glycero-3-phosphoethanolamine (DPhyPE) as disclosed herein, preferably in combination with the inventive lipids as disclosed herein f.e. in Table 1, specifically for delivering mRNA vaccines in vivo resulting in significantly enhanced immune responses, is a surprising finding by the inventors resembling specific aspects and embodiments of the present invention. In other words, the inventors surprisingly found that the use of DPhyPE gave a clear advantage over DSPC which to date is used in the art as standard neutral lipid in nearly all state of the art LNP-compositions for mRNA and also siRNA, specifically, but not limited to, vaccination settings. In other words, the compositions of the invention have a highly advantageous and unexpected behaviour in vivo resulting in highly enhanced immune responses.

Interestingly, the inventors found that compositions comprising DPhyPE instead of DSPC showed superior expression profiles in vitro and in vivo, even when compared to the GN01 composition. Accordingly, it was surprisingly found that the use of DPhyPE gave a clear advantage over DSPC which to date is used in the art as standard neutral lipid in nearly all state of the art LNP-compositions.

Importantly, the inventors found that one of the advantageous features of the inventive compositions and lipid nanoparticles, f.e. the GN01 formulation, is that it is capable to induce strong CD8+ T cells responses. This is due to the fact, that f.e. for malaria, as CD8+ T cells are a major protective immune mechanism against intracellular infections caused by Malaria parasites, an effective Malaria vaccine should induce strong CD8+ T cells responses.

Further, the data presented in the Examples demonstrate significant enhanced immune responses using the compositions of the invention, i.e. all inventive RNA vaccines are useful according to the invention. Surprisingly, in contrast to prior art knowledge which shows that DSPC is the most common and unquestioned neutral lipid for lipid nanoparticles, it was found by the inventors that it is preferable to use DPhyPE for mRNA formulations in compositions for the production of vaccines.

The inventors further surprisingly found that the addition of at least one further neutral lipid to the above neutral lipid, in particular a second neutral lipid, can also enhance the immune responses (see FIGS. 28 to 31 and the corresponding examples). As noted above, it is preferred for the (first) neutral lipid of the invention that it has two fatty acyl moieties selected from myristoyl, palmitoyl, stearoyl, oleoyl and the like, which in particular means that the fatty acyl moieties are rather long moieties starting from moieties with 14 carbon atoms. The inventors found that the addition of a neutral lipid with shorter fatty acyl moieties provides for beneficial effects, in particular if the additional neutral lipid has two fatty acid moieties selected from pentanoyl, hexanoyl, heptanoyl, octanoyl, nonaoyl and decanoyl, i.e. moieties with at most 10 carbon atoms. A particularly preferred additional neutral lipid is 1,2-diheptanoyl-sn-glycero-3-phosphocholine (DHPC), but related neutral lipids, such as e.g. 05:0 PC (1,2-dipentanoyl-sn-glycero-3-phosphocholine), 06:0 PC (1,2-dihexanoyl-sn-glycero-3-phosphocholine), 08:0 PC (1,2-dioctanoyl-sn-glycero-3-phosphocholine), 09:0 PC (1,2-dinonanoyl-sn-glycero-3-phosphocholine), and 10:0 PC (1,2-dihexanoyl-sn-glycero-3-phosphocholine) may be used as well.

Therefore, in one aspect of the invention, the lipid nanoparticles of the invention comprise a neutral lipid or phospholipid having at least one alkyl chain with a length of $C_5$, $C_6$, $C_7$, $C_8$, $C_9$, $C_{10}$, $C_{11}$, $C_{12}$, $C_{13}$ or $C_{14}$, preferably with a length of $C_6$, $C_7$, $C_8$, $C_9$, or $C_{10}$, more preferably with a length of $C_6$, $C_7$, $C_8$, most preferably with a length of $C_7$. In another embodiment of the invention, the lipid nanoparticles of the invention comprise a neutral lipid or phospholipid having at least two alkyl chains, whereby each alkyl chain independently has a length of $C_5$, $C_6$, $C_7$, $C_8$, $C_9$, $C_{10}$, $C_{11}$, $C_{12}$, $C_{13}$ or $C_{14}$, preferably with a length of $C_6$, $C_7$, $C_8$, $C_9$, or $C_{10}$, more preferably with a length of $C_6$, $C_7$, $C_8$, most preferably with a length of $C_7$. In a preferred embodiment, the lipid nanoparticles of the invention comprise additionally DHPC. In a further embodiment, one or more alkyl chains may comprise carbon double-bonds. In other embodiments, the lipid nanoparticles comprise an additional phospholipid selected from the group consisting of 05:0 PC (1,2-dipentanoyl-sn-glycero-3-phosphocholine), 04:0 PC (1,2-dibutyryl-sn-glycero-3-phosphocholine), 06:0 PC (DHPC, 1,2-dihexanoyl-sn-glycero-3-phosphocholine), 08:0 PC (1,2-dioctanoyl-sn-glycero-3-phosphocholine), and 09:0 PC (1,2-dinonanoyl-sn-glycero-3-phosphocholine).

Lipid Nanoparticle Compositions

The terms "lipid nanoparticle composition" and "composition" are used herein interchangeably. In the context of the present invention, lipid nanoparticles are not restricted to any particular morphology, and should be interpreted as to include any morphology generated when a cationic lipid and optionally one or more further lipids are combined, e.g. in an aqueous environment and/or in the presence of a nucleic acid compound. For example, a liposome, a lipid complex, a lipoplex and the like are within the scope of a lipid nanoparticle.

In the context of the invention, a "composition" refers to any type of composition in which the specified ingredients may be incorporated, optionally along with any further excipients, usually with at least one pharmaceutically acceptable carrier or excipient. Thus, the composition may be a dry composition such as a powder or granules, or a solid unit such as a lyophilised form or a tablet. Alternatively, the composition may be in liquid form, and each excipient may be independently incorporated in dissolved or dispersed (e.g. suspended or emulsified) form. In one of the preferred embodiments, the composition is formulated as a sterile solid composition, such as a powder or lyophilised form for reconstitution with an aqueous liquid carrier. Such formulation is also preferred for those versions of the composition which comprise a nucleic acid cargo as described in further detail below.

In the composition of the invention, the cationic lipid may be present within, or as part of, lipid nanoparticles (LNPs). In other words, such composition comprises lipid nanoparticles, and the cationic lipid is present in the lipid nanoparticles.

A "nanoparticle", as used herein, is a submicron particle having any structure or morphology. Submicron particles may also be referred to as colloids, or colloidal. With respect to the material on which the nanoparticle is based, and to the structure or morphology, a nanoparticle may be classified, for example, as a nanocapsule, a vesicle, a liposome, a lipid nanoparticle, a micelle, a crosslinked micelle, a lipoplex, a polyplex, a mixed or hybrid complex, to mention only a few of the possible designations of specific types of nanoparticles. A "lipid nanoparticle" (LNP) is a nanoparticle formed by lipids, typically including at least one amphiphilic, membrane-forming lipid, and optionally other lipids, further optionally including a cargo material such as a nucleic acid compound. As used herein, the expression "lipid nanoparticles" or "LNP" includes any sub-types and morphologies of nanoparticles formed or co-formed by lipids, such as liposomes and lipoplexes.

As defined above, lipid nanoparticles include any type of nanoparticles formed or co-formed by lipids. In particular, lipid nanoparticles may co-formed by combinations of lipids comprising at least one amphiphilic, vesicle-forming lipid. Liposomes and lipoplexes are examples of lipid nanoparticles.

In some embodiments, such lipid nanoparticles comprise a cationic lipid (e.g., a lipid of formula (I)) and one or more excipients selected from neutral lipids, charged lipids, steroids and polymer conjugated lipids (e.g., a pegylated lipid such as a pegylated lipid of formula (II)). It is currently believed by the inventors that a composition comprising the cationic lipid as defined herein, a steroid, a neutral lipid, and a polymer conjugated lipid according to formula (II) will, at least in an aqueous environment, typically exist as a composition comprising lipid nanoparticles that are formed by these excipients.

An LNP may comprise any lipid capable of forming a particle to which the one or more nucleic acid molecules are attached, or in which the one or more nucleic acid molecules are encapsulated. In some embodiments, the mRNA, or a portion thereof, is encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response. In some embodiments, the mRNA or a portion thereof is associated with the lipid nanoparticles.

As mentioned, a composition comprising the lipidic excipients as described herein will normally form lipid nanoparticles, at least in an aqueous environment. As defined herein, the nanoparticles have a predominantly submicron size. In certain embodiments, the mRNA, when present in the lipid nanoparticles, is resistant in aqueous solution to degradation with a nuclease. As used herein, the mean diameter may be represented by the z-average as determined by dynamic light scattering. In one embodiment, the composition is a sterile liquid composition comprising lipid nanoparticles having a mean hydrodynamic diameter (or mean size) as determined by dynamic laser scattering from about 30 nm to about 800 nm. In various embodiments, the lipid nanoparticles have a mean diameter of from about 30 nm to about 150 nm, from about 50 nm to about 200 nm, from about 60 nm to about 200 nm, from about 70 nm to about 200 nm, from about 80 nm to about 200 nm, from about 90 nm to about 200 nm, from about 90 nm to about 190 nm, from about 90 nm to about 180 nm, from about 90 nm to about 170 nm, from about 90 nm to about 160 nm, from about 90 nm to about 150 nm, from about 90 nm to about 140 nm, from about 90 nm to about 130 nm, from about 90 nm to about 120 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 160 nm, 170 nm, 180 nm, 190 nm, or 200 nm, and are substantially non-toxic. In another preferred embodiment of the invention the lipid nanoparticles have a hydrodynamic diameter in the range from about 50 nm to about 300 nm, or from about 60 nm to about 250 nm, from about 60 nm to about 150 nm, or from about 60 nm to about 120 nm, or from about 80 nm to about 160, or from about 90 nm to about 140 nm, 50 nm to about 300 nm, or from about 60 nm to about 250 nm, or from about 60 nm to about 200 nm, or from about 70 to 200 nm, or from about 75 nm to about 160, or from about 100 nm to about 140 nm, or from about 90 nm to about 140 nm.

Compositions comprising the lipidic excipients as described herein yielding lipid nanoparticles of the invention may be relatively homogenous. A polydispersity index (PDI) may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition of the invention may have a polydispersity index from about 0 to about 0.35, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34 or 0.35. In some embodiments, the polydispersity index (PDI) of a nanoparticle composition may be from about 0.1 to about 0.2.

Various optional features, selections and preferences relating to the composition of the invention in general have been described herein: all of these also apply to the lipid nanoparticles, as will be clearly understood by a person skilled in the art. Similarly, the options and preferences apply to compositions comprising such lipid nanoparticles.

For example, the lipid nanoparticles according to one of the preferred embodiments comprise a cationic lipid as defined above, a neutral lipid which may be DphyPE, optionally in combination with a second neutral lipid which may be DHPC, a steroid which may be cholesterol, and a polymer conjugated lipid that may be 1,2-dimyristoyl-rac-glycero-3-methoxypolyethylene glycol (PEG-DMG); wherein the cationic lipid may optionally be selected from the compounds listed in Table 1.

In the context of the present invention, the mRNA is thus preferably comprised in a liquid or semi-liquid composition, wherein the mRNA is complexed with or associated with a lipid nanoparticle according to one of the preferred embodiments. I.e. in a preferred embodiment, said liquid or semi-liquid composition comprises a complex, wherein the complex comprises the mRNA, wherein the complex is preferably present as a lipid nanoparticle as defined herein.

With respect to the amounts of the respective excipients, it is preferred that the cationic lipid is incorporated in the lipid nanoparticles, or in the composition according to the invention, at a relatively high molar amount compared to the molar amount at which the polymer conjugated lipid is present. Moreover, the molar amount of the cationic lipid is also preferably higher than the molar of amount of the neutral lipid in the composition or in the nanoparticles, respectively. Furthermore, the molar amount of the steroid is optionally higher than the molar amount of the polymer conjugated lipid.

In certain embodiments, the polymer conjugated lipid is present in the LNP in an amount from about 1 mol % to about 10 mol %, relative to the total lipid content of the nanoparticle. In one embodiment, the polymer conjugated lipid is present in the LNP in an amount from about 1 mol % to about 5 mol % percent. In one embodiment, the polymer conjugated lipid is present in the LNP in about 1 mol % or about 1.5 mol %.

In various embodiments, the molar ratio of the cationic lipid (e.g., lipid of formula (I)) to the polymer conjugated lipid ranges from about 100:1 to about 25:1, from about 50:1 to about 25:1, or from about 40:1 to about 25:1.

In certain embodiments, the LNP comprises one or more additional lipids which stabilize the formation of particles during their formation. Suitable stabilizing lipids include neutral lipids and anionic lipids. In various embodiments, the molar ratio of the cationic lipid (e.g., lipid of formula (I)) to the neutral lipid ranges from about 2:1 to about 8:1, from about 3:1 to about 7:1, or from about 4:1 to about 6:1.

As used herein, references to molar amounts of lipidic excipients in the composition of the invention should be understood as also describing the molar amounts of the respective excipients in the lipid nanoparticles comprised in the composition, as the lipid nanoparticles are typically formed by these excipients and reflect the same quantitative ratios of excipients as the overall composition containing the nanoparticles.

In general, the amount of the cationic lipid in the composition (and thus in the lipid nanoparticles) is typically at least about 20 mol %, relative to the total molar amount of all lipidic excipients in the composition (or nanoparticles). In another embodiment, the amount of the cationic lipid is at least about 25 mol %, or at least 30 mol %, respectively.

In other preferred embodiments, the amount of the cationic lipid in the composition is from about 30 mol % to about 70 mol %, or from about 40 mol % to about 70 mol %, or from about 45 mol % to about 65 mol %, respectively; such as about 30, 35, 40, 45, 50, 55, 60, 65, or 70 mol %, or from about 40 mol % to about 60 mol %, respectively; such as about 40, 41, 42, 43, 44, 45, 46, 47, 48, 49, 50, 51, 52, 53, 54, 55, 56, 57, 58, 59 or 60 mol %, respectively.

The amount of the steroid in the composition may optionally at least about 10 mol %, or it may be in the range from about 10 mol % to about 60 mol %, or from about 20 mol % to about 50 mol %, or from about 25 mol % to about 45 mol %, respectively; such as about 10, 15, 20, 25, 30, 35, 40, 45, 50, 55, or 60 mol %, respectively. Again, for the avoidance of doubt, the molar percentages are relative the total molar amount of all lipidic excipients in the composition.

The neutral lipid may optionally be present at an amount of at least about 5 mol %. In some embodiments, the amount of the neutral lipid in the composition is in the range from about 5 mol % to about 25 mol %, or from about 5 mol % to about 15 mol %, or from about 8 mol % to about 12 mol %, respectively; such as about 5 mol %, 6 mol %, 7 mol %, 8 mol %, 9 mol %, 10 mol %, 11 mol %, 12 mol %, 13 mol %, 14 mol %, 15 mol %, 16 mol %, 17 mol %, 18 mol %, 19 mol %, 20 mol %, 21 mol %, 22 mol %, 23 mol %, 24 mol % or 25 mol %, respectively, using the same basis for the molar percentages. This amount is the amount of total neutral lipid, i.e. it can be the total amount resulting from the amounts of two neutral lipids, such as e.g. DPhyPE and DHPC.

The amount of the polymer conjugated lipid in the composition or in the lipid nanoparticles may, for example, be selected to be about 0.1 mol % and higher. In certain embodiments, the amount of the polymer conjugated lipid is in the range from about 0.5 mol % to about 5 mol %, or from about 1 mol % to about 3 mol %, such as about 0.1, 0.3, 0.5, 1, 2, 3, 4 or 5 mol %, respectively, using again the total molar amount of all lipidic excipients as basis for the molar percentages. In other certain embodiments, the composition or the lipid nanoparticles may comprise 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7 mol % or more than 7 mol % polymer conjugated lipid. In a preferred embodiment, the content of the polymer conjugated lipid or pegylated lipid is about 1 to 5 mol % of the overall lipid content of the formulation. As a non-limiting example, the lipid nanoparticle comprises 1.5% polymer conjugated lipid. As another non-limiting example, the lipid nanoparticle comprises 1.7% polymer conjugated lipid. As another non-limiting example, the lipid nanoparticle comprises 3% polymer conjugated lipid. As yet another example, the lipid nanoparticle comprises 5% polymer conjugated lipid.

In one embodiment, the composition comprises lipid nanoparticles which comprise:

(a) the cationic lipid according to formula (I) or as described herein at an amount of 30-70 mol %;
(b) the steroid at an amount of 20-50 mol %;
(c) the neutral lipid at an amount of 5-25 mol %; and
(d) the polymer conjugated lipid at an amount of 0.5-5 mol %;

each amount being relative to the total molar amount of all lipidic excipients of the lipid nanoparticles.

In another embodiment, the composition comprises lipid nanoparticles comprising:

(a) the cationic lipid according to formula (I) or as described herein at an amount of 40-70 mol %;
(b) the steroid at an amount of 20-50 mol %;
(c) the neutral lipid at an amount of 5-15 mol %; and
(d) the polymer conjugated lipid at an amount of 0.5-5 mol %;

each amount being relative to the total molar amount of all lipidic excipients of the lipid nanoparticles.

In one embodiment, the composition comprises lipid nanoparticles which comprise:

(a) the cationic lipid according to formula (I) or as described herein at an amount of 20-60 mol %;
(b) the steroid at an amount of 25-55 mol %;
(c) the neutral lipid at an amount of 5-25 mol %; and
(d) the polymer conjugated lipid at an amount of 0.5-15 mol %;

each amount being relative to the total molar amount of all lipidic excipients of the lipid nanoparticles.

In a further embodiment, the composition comprises lipid nanoparticles which comprise:

(a) the cationic lipid according to formula (I) or as described herein at an amount of 45-65 mol %;
(b) the steroid at an amount of 25-45 mol %;
(c) the neutral lipid at an amount of 8-12 mol %; and
(d) the polymer conjugated lipid at an amount of 1-3 mol %;

each amount being relative to the total molar amount of all lipidic excipients of the lipid nanoparticles.

In a further preferred embodiment, the composition comprises lipid nanoparticles which comprise:

(a) a cationic lipid according to formula (I) or as described herein at an amount of 45-65 mol %;
(b) cholesterol at an amount of 25-45 mol %;
(c) the neutral lipid at an amount of 8-12 mol %; and
(d) polymer conjugated lipid at an amount of 1-3 mol %;

each amount being relative to the total molar amount of all lipidic excipients of the lipid nanoparticles.

In a further preferred embodiment, the composition comprises lipid nanoparticles that contain:

(a) a cationic lipid according to formula (I) or as described herein at an amount of 45-65 mol %;
(b) cholesterol at an amount of 25-45 mol %;
(c) DPhyPE at an amount of 8-12 mol % and optionally DHPC at an amount of 1 to 10 mol %; and
(d) polymer conjugated lipid at an amount of 1-3 mol %;

each amount being relative to the total molar amount of all lipidic excipients of the lipid nanoparticles.

In a further preferred embodiment, the composition comprises lipid nanoparticles that contain:

(a) a cationic lipid according to formula (I) or as described herein at an amount of 45-65 mol %;
(b) cholesterol at an amount of 25-45 mol %;
(c) DPhyPE at an amount of 8-12 mol % and optionally DHPC at an amount of 1 to 10 mol %; and
(d) PEG-DMG 2000 at an amount of 1-3 mol %;

each amount being relative to the total molar amount of all lipidic excipients of the lipid nanoparticles.

In these embodiments, the cationic lipid is preferably a compound selected according to any one of the preferences disclosed herein. For example, the cationic lipid may be selected from the compounds listed in Table 1. Moreover, these embodiments may also comprise a steroid, a neutral lipid, and/or a polymer conjugated lipid selected according to any one of the preferences disclosed herein. In all embodiments which recite compositions or lipid nanoparticles as described herein and where mol %-values are given for each excipient, each amount should be seen being relative to the total molar amount of all lipidic excipients of the lipid nanoparticles.

In a further preferred embodiment, the composition or the lipid nanoparticle as described herein comprises 59 mol % cationic lipid according to formula (I) of the invention, 10 mol % neutral lipid, 29.3 mol % steroid and 1.7 mol % polymer conjugated lipid.

In one embodiment, the composition or the lipid nanoparticles described herein comprise 59 mol % cationic lipid according to formula (I) of the invention, 10 mol % DPhyPE, 29.3 mol % cholesterol and 1.7 mol % DMG-PEG 2000.

In one embodiment, composition or the lipid nanoparticles described herein comprise 59 mol % cationic lipid according to formula (I) of the invention, 10 mol % DPhyPE, 29.3 mol % cholesterol and 1.7 mol % C10-PEG 2000.

In one embodiment, the composition or the lipid nanoparticles described herein comprise 59 mol % cationic lipid according to formula (I) of the invention, 10 mol % DPhyPE, 29.3 mol % cholesterol and 1.7 mol % Cer8-PEG 2000.

In another embodiment, the composition or the lipid nanoparticle as described herein comprises 47.4 mol % cationic lipid according to formula (I) of the invention, 10 mol % neutral lipid, 40.9 mol % steroid and 1.7 mol % polymer conjugated lipid.

In a further embodiment, the composition or the lipid nanoparticles described herein comprise 47.4 mol % cationic lipid according to formula (I) of the invention, 10 mol % DPhyPE, 40.9 mol % cholesterol and 1.7 mol % DMG-PEG 2000. In one embodiment, the composition or the lipid nanoparticles described herein comprise 47.4 mol % cationic lipid according to formula (I) of the invention, 10 mol % DPhyPE, 40.9 mol % cholesterol and 1.7 mol % $C_{10}$-PEG 2000. In one embodiment, the composition or the lipid nanoparticles described herein comprise 47.4 mol % cationic lipid according to formula (I) of the invention, 10 mol % DPhyPE, 40.9 mol % cholesterol and 1.7 mol % Cer8-PEG 2000.

In another embodiment, the composition or the lipid nanoparticle as described herein comprises 59 mol % cationic lipid according to formula (I) of the invention, 11 mol % neutral lipid, 28.3 mol % steroid and 1.7 mol % polymer conjugated lipid.

In one embodiment, the composition or the lipid nanoparticles described herein comprise 59 mol % cationic lipid according to formula (I) of the invention, 10 mol % DphyPE and 1 mol % DHPC, 28.3 mol % cholesterol and 1.7 mol % DMG-PEG 2000. In one embodiment, the composition or the lipid nanoparticles described herein comprise 59 mol % cationic lipid according to formula (I) of the invention, 10 mol % DphyPE and 1 mol % DHPC, 28.3 mol % cholesterol and 1.7 mol % $C_{10}$-PEG 2000. In one embodiment, the composition or the lipid nanoparticles described herein comprise 59 mol % cationic lipid according to formula (I) of the invention, 10 mol % DphyPE and 1 mol % DHPC, 29.3 mol % cholesterol and 1.7 mol % Cer8-PEG 2000.

In another embodiment, the composition or the lipid nanoparticle as described herein comprises 49 mol % cationic lipid according to formula (I) of the invention, 20 mol % neutral lipid, 29.3 mol % steroid and 1.7 mol % polymer conjugated lipid.

In one embodiment, the composition or the lipid nanoparticles described herein comprise 49 mol % cationic lipid according to formula (I) of the invention, 10 mol % DphyPE and 10 mol % DHPC, 29.3 mol % cholesterol and 1.7 mol % DMG-PEG 2000. In one embodiment, the composition or the lipid nanoparticles described herein comprise 49 mol % cationic lipid according to formula (I) of the invention, 10 mol % DphyPE and 10 mol % DHPC, 29.3 mol % cholesterol and 1.7 mol % $C_{10}$-PEG 2000. In one embodiment, the composition or the lipid nanoparticles described herein comprise 49 mol % cationic lipid according to formula (I) of the invention, 10 mol % DphyPE and 10 mol % DHPC, 29.3 mol % cholesterol and 1.7 mol % Cer8-PEG 2000.

In any of the above embodiments in this section disclosing specific compositions or lipid nanoparticles having distinct %-values for excipients, if 1,2-diphytanoyl-sn-glycero-3-phosphoethanolamine (DPhyPE) is mentioned as neutral lipid, in further embodiments DPhyPE may be exchanged with another neutral lipid, preferably 1,2-diphytanoyl-sn-glycero-3-phosphocholine (DPhyPC). Furthermore, In any of the above embodiments in this section disclosing specific compositions or lipid nanoparticles having distinct %-values for excipients, if 1,2-diphytanoyl-sn-glycero-3-phosphoethanolamine (DPhyPE) is mentioned as neutral lipid, in even further embodiments DPhyPE may be exchanged with another neutral lipid, preferably 1,2-dioleoyl-sn-glycero-3-phosphocholine (DOPC; also referred to as dioleoylphosphatidylcholine) or alternatively 1,2-dioleoyl-sn-glycero-3-phosphoethanolamine (DOPE).

Further preferred lipid compositions according to further specific embodiments of the present invention comprise at least four lipid excipients as disclosed herein in Table E. For example, a preferred lipid composition comprises the excipients as disclosed in line "E1" which are "C1" as cationic lipid (as disclosed herein in Table 1), DPhyPE as neutral lipid, cholesterol as sterol and DMG-PEG 2000 as polymer conjugated lipid excipient. As another example a preferred lipid composition comprises the excipients as disclosed in line "E35" which are "C12" as cationic lipid (as disclosed herein in Table 1), DPhyPE as neutral lipid, cholesterol as sterol and $C_{10}$-PEG 2000 as polymer conjugated lipid excipient.

TABLE E

Lipid excipient combinations for preferred compositions of the invention (Chol = Cholesterol; DMG-PEG2K = DMG-PEG 2000; $C_{10}$-PEG2K = $C_{10}$-PEG 2000; Cer8-PEG2K = Cer8-PEG 2000; table split into two tabulars)

| Excipient combination [designation] | cationic lipid | sterol | neutral lipid | polymer conjugated lipid |
|---|---|---|---|---|
| E1 | C1 | Chol | DPhyPE | DMG-PEG2K |
| E2 | C2 | Chol | DPhyPE | DMG-PEG2K |
| E3 | C3 | Chol | DPhyPE | DMG-PEG2K |
| E4 | C4 | Chol | DPhyPE | DMG-PEG2K |
| E5 | C5 | Chol | DPhyPE | DMG-PEG2K |
| E6 | C6 | Chol | DPhyPE | DMG-PEG2K |
| E7 | C7 | Chol | DPhyPE | DMG-PEG2K |
| E8 | C8 | Chol | DPhyPE | DMG-PEG2K |
| E9 | C9 | Chol | DPhyPE | DMG-PEG2K |
| E10 | C10 | Chol | DPhyPE | DMG-PEG2K |
| E11 | C11 | Chol | DPhyPE | DMG-PEG2K |
| E12 | C12 | Chol | DPhyPE | DMG-PEG2K |
| E13 | C13 | Chol | DPhyPE | DMG-PEG2K |
| E14 | C14 | Chol | DPhyPE | DMG-PEG2K |
| E15 | C15 | Chol | DPhyPE | DMG-PEG2K |
| E16 | C16 | Chol | DPhyPE | DMG-PEG2K |

TABLE E-continued

Lipid excipient combinations for preferred compositions of the invention (Chol = Cholesterol; DMG-PEG2K = DMG-PEG 2000; $C_{10}$-PEG2K = $C_{10}$-PEG 2000; Cer8-PEG2K = Cer8-PEG 2000; table split into two tabulars)

| | | | | |
|---|---|---|---|---|
| E17 | C17 | Chol | DPhyPE | DMG-PEG2K |
| E18 | C18 | Chol | DPhyPE | DMG-PEG2K |
| E19 | C19 | Chol | DPhyPE | DMG-PEG2K |
| E20 | C20 | Chol | DPhyPE | DMG-PEG2K |
| E21 | C21 | Chol | DPhyPE | DMG-PEG2K |
| E22 | C22 | Chol | DPhyPE | DMG-PEG2K |
| E23 | C23 | Chol | DPhyPE | DMG-PEG2K |
| E24 | C1 | Chol | DPhyPE | $C_{10}$-PEG2K |
| E25 | C2 | Chol | DPhyPE | $C_{10}$-PEG2K |
| E26 | C3 | Chol | DPhyPE | $C_{10}$-PEG2K |
| E27 | C4 | Chol | DPhyPE | $C_{10}$-PEG2K |
| E28 | C5 | Chol | DPhyPE | $C_{10}$-PEG2K |
| E29 | C6 | Chol | DPhyPE | $C_{10}$-PEG2K |
| E30 | C7 | Chol | DPhyPE | $C_{10}$-PEG2K |
| E31 | C8 | Chol | DPhyPE | $C_{10}$-PEG2K |
| E32 | C9 | Chol | DPhyPE | $C_{10}$-PEG2K |
| E33 | C10 | Chol | DPhyPE | $C_{10}$-PEG2K |
| E34 | C11 | Chol | DPhyPE | $C_{10}$-PEG2K |
| E35 | C12 | Chol | DPhyPE | C10-PEG2K |
| E36 | C13 | Chol | DPhyPE | $C_{10}$-PEG2K |
| E37 | C14 | Chol | DPhyPE | $C_{10}$-PEG2K |
| E38 | C15 | Chol | DPhyPE | $C_{10}$-PEG2K |
| E39 | C16 | Chol | DPhyPE | $C_{10}$-PEG2K |
| E40 | C17 | Chol | DPhyPE | $C_{10}$-PEG2K |
| E41 | C18 | Chol | DPhyPE | $C_{10}$-PEG2K |
| E42 | C19 | Chol | DPhyPE | $C_{10}$-PEG2K |
| E43 | C20 | Chol | DPhyPE | $C_{10}$-PEG2K |
| E44 | C21 | Chol | DPhyPE | $C_{10}$-PEG2K |
| E45 | C22 | Chol | DPhyPE | $C_{10}$-PEG2K |
| E46 | C23 | Chol | DPhyPE | $C_{10}$-PEG2K |
| E47 | C1 | Chol | DPhyPE | Cer8-PEG2K |
| E48 | C2 | Chol | DPhyPE | Cer8-PEG2K |
| E49 | C3 | Chol | DPhyPE | Cer8-PEG2K |
| E50 | C4 | Chol | DPhyPE | Cer8-PEG2K |
| E51 | C5 | Chol | DPhyPE | Cer8-PEG2K |
| E52 | C6 | Chol | DPhyPE | Cer8-PEG2K |
| E53 | C7 | Chol | DPhyPE | Cer8-PEG2K |
| E54 | C8 | Chol | DPhyPE | Cer8-PEG2K |
| E55 | C9 | Chol | DPhyPE | Cer8-PEG2K |
| E56 | C10 | Chol | DPhyPE | Cer8-PEG2K |
| E57 | C11 | Chol | DPhyPE | Cer8-PEG2K |
| E58 | C12 | Chol | DPhyPE | Cer8-PEG2K |
| E59 | C13 | Chol | DPhyPE | Cer8-PEG2K |
| E60 | C14 | Chol | DPhyPE | Cer8-PEG2K |
| E61 | C15 | Chol | DPhyPE | Cer8-PEG2K |
| E62 | C16 | Chol | DPhyPE | Cer8-PEG2K |
| E63 | C17 | Chol | DPhyPE | Cer8-PEG2K |
| E64 | C18 | Chol | DPhyPE | Cer8-PEG2K |
| E65 | C19 | Chol | DPhyPE | Cer8-PEG2K |
| E66 | C20 | Chol | DPhyPE | Cer8-PEG2K |
| E67 | C21 | Chol | DPhyPE | Cer8-PEG2K |
| E68 | C22 | Chol | DPhyPE | Cer8-PEG2K |
| E69 | C23 | Chol | DPhyPE | Cer8-PEG2K |

| Excipient combination [designation] | cationic lipid | sterol | neutral lipid | polymer conjugated lipid |
|---|---|---|---|---|
| E70 | C24 | Chol | DPhyPE | DMG-PEG2K |
| E71 | C25 | Chol | DPhyPE | DMG-PEG2K |
| E72 | C26 | Chol | DPhyPE | DMG-PEG2K |
| E73 | C27 | Chol | DPhyPE | DMG-PEG2K |
| E74 | C24 | Chol | DPhyPE | $C_{10}$-PEG2K |
| E75 | C25 | Chol | DPhyPE | $C_{10}$-PEG2K |
| E76 | C26 | Chol | DPhyPE | $C_{10}$-PEG2K |
| E77 | C27 | Chol | DPhyPE | $C_{10}$-PEG2K |
| E78 | C24 | Chol | DPhyPE | Cer8-PEG2K |
| E79 | C25 | Chol | DPhyPE | Cer8-PEG2K |
| E80 | C26 | Chol | DPhyPE | Cer8-PEG2K |
| E81 | C27 | Chol | DPhyPE | Cer8-PEG2K |
| E82 | C1 | Chol | DphyPE + DHPC | DMG-PEG2K or $C_{10}$-PEG2K or Cer8-PEG2K |
| E83 | C2 | Chol | DphyPE + DHPC | DMG-PEG2K or $C_{10}$-PEG2K or Cer8-PEG2K |
| E84 | C3 | Chol | DphyPE + DHPC | DMG-PEG2K or $C_{10}$-PEG2K or Cer8-PEG2K |
| E85 | C4 | Chol | DphyPE + DHPC | DMG-PEG2K or $C_{10}$-PEG2K or Cer8-PEG2K |
| E86 | C5 | Chol | DphyPE + DHPC | DMG-PEG2K or $C_{10}$-PEG2K or Cer8-PEG2K |
| E87 | C6 | Chol | DphyPE + DHPC | DMG-PEG2K or $C_{10}$-PEG2K or Cer8-PEG2K |

TABLE E-continued

Lipid excipient combinations for preferred compositions of the invention (Chol = Cholesterol; DMG-PEG2K = DMG-PEG 2000; $C_{10}$-PEG2K = $C_{10}$-PEG 2000; Cer8-PEG2K = Cer8-PEG 2000; table split into two tabulars)

| | | | | |
|---|---|---|---|---|
| E88 | C7 | Chol | DphyPE + DHPC | DMG-PEG2K or $C_{10}$-PEG2K or Cer8-PEG2K |
| E89 | C8 | Chol | DphyPE + DHPC | DMG-PEG2K or $C_{10}$-PEG2K or Cer8-PEG2K |
| E90 | C9 | Chol | DphyPE + DHPC | DMG-PEG2K or $C_{10}$-PEG2K or Cer8-PEG2K |
| E91 | C10 | Chol | DphyPE + DHPC | DMG-PEG2K or $C_{10}$-PEG2K or Cer8-PEG2K |
| E92 | C11 | Chol | DphyPE + DHPC | DMG-PEG2K or $C_{10}$-PEG2K or Cer8-PEG2K |
| E93 | C12 | Chol | DphyPE + DHPC | DMG-PEG2K or $C_{10}$-PEG2K or Cer8-PEG2K |
| E94 | C13 | Chol | DphyPE + DHPC | DMG-PEG2K or $C_{10}$-PEG2K or Cer8-PEG2K |
| E95 | C14 | Chol | DphyPE + DHPC | DMG-PEG2K or $C_{10}$-PEG2K or Cer8-PEG2K |
| E96 | C15 | Chol | DphyPE + DHPC | DMG-PEG2K or $C_{10}$-PEG2K or Cer8-PEG2K |
| E97 | C16 | Chol | DphyPE + DHPC | DMG-PEG2K or $C_{10}$-PEG2K or Cer8-PEG2K |
| E98 | C17 | Chol | DphyPE + DHPC | DMG-PEG2K or $C_{10}$-PEG2K or Cer8-PEG2K |
| E99 | C18 | Chol | DphyPE + DHPC | DMG-PEG2K or $C_{10}$-PEG2K or Cer8-PEG2K |
| E100 | C19 | Chol | DphyPE + DHPC | DMG-PEG2K or $C_{10}$-PEG2K or Cer8-PEG2K |
| E101 | C20 | Chol | DphyPE + DHPC | DMG-PEG2K or $C_{10}$-PEG2K or Cer8-PEG2K |
| E102 | C21 | Chol | DphyPE + DHPC | DMG-PEG2K or $C_{10}$-PEG2K or Cer8-PEG2K |
| E103 | C22 | Chol | DphyPE + DHPC | DMG-PEG2K or $C_{10}$-PEG2K or Cer8-PEG2K |
| E104 | C23 | Chol | DphyPE + DHPC | DMG-PEG2K or $C_{10}$-PEG2K or Cer8-PEG2K |
| E105 | C24 | Chol | DphyPE + DHPC | DMG-PEG2K or $C_{10}$-PEG2K or Cer8-PEG2K |
| E106 | C25 | Chol | DphyPE + DHPC | DMG-PEG2K or $C_{10}$-PEG2K or Cer8-PEG2K |
| E107 | C26 | Chol | DphyPE + DHPC | DMG-PEG2K or $C_{10}$-PEG2K or Cer8-PEG2K |
| E108 | C27 | Chol | DphyPE + DHPC | DMG-PEG2K or $C_{10}$-PEG2K or Cer8-PEG2K |

Furthermore, preferred lipid formulations of the invention showing distinct mol-percentages of the at least four lipid excipients of the inventive compositions are shown in Table F. For example, a preferred lipid composition comprises the mol-percentages of lipids as disclosed in line "F", i.e. 59 mol % cationic lipid, 29.3 mol % sterol, 10 mol % neutral lipid, and 1.7 mol % polymer conjugated lipid. As another example, a preferred lipid composition comprises the mol-percentages of lipids as disclosed in line "F31", i.e. 45 mol % cationic lipid, 43.5 mol % sterol, 10 mol % neutral lipid and 1.5 mol % polymer conjugated lipid.

TABLE F

Formulations incl. mol-percentages for excipients of preferred compositions of the invention (table split into two tabulars)

| Formulation [designation] | cationic lipid [mol %] | sterol [mol %] | neutral lipid [mol %] | polymer conjugated lipid [mol %] | sum [mol %] |
|---|---|---|---|---|---|
| F1 | 59 | 29.3 | 10 | 1.7 | 100 |
| F2 | 59 | 34.3 | 5 | 1.7 | 100 |
| F3 | 59 | 34.5 | 5 | 1.5 | 100 |
| F4 | 59 | 29.5 | 10 | 1.5 | 100 |
| F5 | 59 | 31 | 10 | 0 | 100 |
| F6 | 59 | 24.3 | 15 | 1.7 | 100 |
| F7 | 59 | 24.5 | 15 | 1.5 | 100 |
| F8 | 59 | 26 | 15 | 0 | 100 |
| F9 | 59 | 19.3 | 20 | 1.7 | 100 |
| F10 | 59 | 19.5 | 20 | 1.5 | 100 |
| F11 | 59 | 21 | 20 | 0 | 100 |
| F12 | 47.4 | 45.9 | 5 | 1.7 | 100 |
| F13 | 47.4 | 46.1 | 5 | 1.5 | 100 |
| F14 | 47.4 | 40.9 | 10 | 1.7 | 100 |
| F15 | 47.4 | 41.1 | 10 | 1.5 | 100 |
| F16 | 47.4 | 42.6 | 10 | 0 | 100 |
| F17 | 47.4 | 35.9 | 15 | 1.7 | 100 |
| F18 | 47.4 | 36.1 | 15 | 1.5 | 100 |
| F19 | 47.4 | 37.6 | 15 | 0 | 100 |
| F20 | 47.4 | 30.9 | 20 | 1.7 | 100 |
| F21 | 47.4 | 31.1 | 20 | 1.5 | 100 |
| F22 | 47.4 | 32.6 | 20 | 0 | 100 |
| F23 | 40 | 53.5 | 5 | 1.5 | 100 |
| F24 | 40 | 48.5 | 10 | 1.5 | 100 |
| F25 | 40 | 50 | 10 | 0 | 100 |
| F26 | 40 | 43.5 | 15 | 1.5 | 100 |
| F27 | 40 | 45 | 15 | 0 | 100 |
| F28 | 40 | 38.5 | 20 | 1.5 | 100 |

TABLE F-continued

Formulations incl. mol-percentages for excipients of preferred compositions of the invention (table split into two tabulars)

| | | | | | |
|---|---|---|---|---|---|
| F29 | 40 | 40 | 20 | 0 | 100 |
| F30 | 45 | 48.5 | 5 | 1.5 | 100 |
| F61 | 59 | 28.3 | 11 | 1.7 | 100 |

| Formulation [designation] | cationic lipid [mol %] | sterol [mol %] | neutral lipid [mol %] | polymer conjugated lipid [mol %] | sum [mol %] |
|---|---|---|---|---|---|
| F31 | 45 | 43.5 | 10 | 1.5 | 100 |
| F32 | 45 | 45 | 10 | 0 | 100 |
| F33 | 45 | 38.5 | 15 | 1.5 | 100 |
| F34 | 45 | 40 | 15 | 0 | 100 |
| F35 | 45 | 33.5 | 20 | 1.5 | 100 |
| F36 | 45 | 35 | 20 | 0 | 100 |
| F37 | 50 | 43.5 | 5 | 1.5 | 100 |
| F38 | 50 | 38.5 | 10 | 1.5 | 100 |
| F39 | 50 | 40 | 10 | 0 | 100 |
| F40 | 50 | 33.5 | 15 | 1.5 | 100 |
| F41 | 50 | 35 | 15 | 0 | 100 |
| F42 | 50 | 28.5 | 20 | 1.5 | 100 |
| F43 | 50 | 30 | 20 | 0 | 100 |
| F44 | 55 | 38.5 | 5 | 1.5 | 100 |
| F45 | 55 | 33.5 | 10 | 1.5 | 100 |
| F46 | 55 | 35 | 10 | 0 | 100 |
| F47 | 55 | 28.5 | 15 | 1.5 | 100 |
| F48 | 55 | 30 | 15 | 0 | 100 |
| F49 | 55 | 23.5 | 20 | 1.5 | 100 |
| F50 | 55 | 25 | 20 | 0 | 100 |
| F51 | 60 | 33.5 | 5 | 1.5 | 100 |
| F52 | 60 | 28.5 | 10 | 1.5 | 100 |
| F53 | 60 | 30 | 10 | 0 | 100 |
| F54 | 60 | 23.5 | 15 | 1.5 | 100 |
| F55 | 60 | 25 | 15 | 0 | 100 |
| F56 | 60 | 18.5 | 20 | 1.5 | 100 |
| F57 | 30-70 | 5-25 | 20-50 | 0.5-5 | ** |
| F58 | 40-70 | 5-15 | 20-50 | 0.5-5 | ** |
| F59 | 20-60 | 5-25 | 25-55 | 0.5-15 | ** |
| F60 | 45-65 | 8-12 | 25-45 | 1-3 | ** |
| F62 | 49 | 29.3 | 20 | 1.7 | 100 |

**self-evidently, the sum [mol %] of the last four formulations in Table F, F57, F58, F59 and F60, is defined to be at 100 mol %. I.e. a skilled artisan naturally is able to select a value from the given ranges of the four excipients, so that the mol-percentages for each excipient of preferred compositions of the invention sums up to 100%.

Accordingly, in a further preferred embodiment of the invention, a composition of the invention comprises excipients as disclosed in Table E selected from the group consisting of Excipient combination designation E1, E2, E3, E4, E5, E6, E7, E8, E9, E10, E11, E12, E13, E14, E15, E16, E17, E18, E19, E20, E21, E22, E23, E24, E25, E26, E27, E28, E29, E30, E31, E32, E33, E34, E35, E36, E37, E38, E39, E40, E41, E42, E43, E44, E45, E46, E47, E48, E49, E50, E51, E52, E53, E54, E55, E56, E57, E58, E59, E60, E61, E62, E63, E64, E65, E66, E67, E68, E69, E70, E71, E72, E73, E74, E75, E76, E77, E78, E79, E80, E81, E82, E83, E84, E85, E86, E87, E88, E89, E90, E91, E92, E93, E94, E95, E96, E97, E98, E99, E100, E101, E102, E103, E104, E105, E106, E107 and E108;

in distinct mol-percentages as disclosed in Table F selected from the group consisting of formulation designation F1, F2, F3, F4, F5, F6, F7, F8, F9, F10, F11, F12, F13, F14, F15, F16, F17, F18, F19, F20, F21, F22, F23, F24, F25, F26, F27, F28, F29, F30, F31, F32, F33, F34, F35, F36, F37, F38, F39, F40, F41, F42, F43, F44, F45, F46, F47, F48, F49, F50, F51, F52, F53, F54, F55, F56, F57, F58, F59, F60, F61 and F62.

A particularly preferred embodiment for a lipid nanoparticle of the present invention is given when the combination F1xE23 according to Table E and Table F is used for formulating a lipid nanoparticle, i.e. 59 mol % cationic lipid C23 as disclosed in Table 1, i.e. COATSOME® SS-EC (former name: SS—33/4PE-15 as apparent from the examples section; NOF Corporation, Tokyo, Japan), 29.3 mol % cholesterol as steroid, 10 mol % DPhyPE as neutral lipid/phospholipid and 1.7 mol % DMG-PEG 2000 as polymer conjugated lipid. Said LNP composition is called herein and in the working examples "GN01". SS-EC has a positive charge at pH 4 and a neutral charge at pH 7, which is advantageous for the LNPs and formulations/compositions of the present invention. For "GN01", N/P (lipid to mRNA mol ratio) preferably is 14 and total lipid/mRNA mass ratio preferably is between about 20 and about 60, more preferably between about 30 and about 50 and most preferably is 40 (m/m).

A further particularly preferred embodiment for a lipid nanoparticle of the present invention is given when the combination F1xE2 according to Table E and Table F is used for formulating a lipid nanoparticle, i.e. 59 mol % C2 lipid as disclosed in Table 1 as cationic lipid (i.e. HEXA-C5DE-PipSS as apparent from the examples section, FIG. 1B), 29.3 mol % cholesterol as steroid, 10 mol % DPhyPE as neutral lipid/phospholipid and 1.7 mol % DMG-PEG 2000 as polymer conjugated lipid. Said LNP composition is called herein and in the working examples "GNO2". For "GN02", N/P (lipid to mRNA mol ratio) preferably is 17.5 and total lipid/mRNA mass ratio preferably is between about 20 and about 60, more preferably between about 30 and about 50 and most preferably is 40 (m/m).

Another particularly preferred embodiment for a lipid nanoparticle of the present invention is given when the combination F1xE23 according to Table E and Table F is used for formulating a lipid nanoparticle, i.e. 59 mol % cationic lipid C23 as disclosed in Table 1, i.e. COATSOME® SS-EC (former name: SS—33/4PE-15 as apparent from the examples section; NOF Corporation, Tokyo, Japan), 26 mol % cholesterol as steroid, 10 mol % DPhyPE as neutral lipid/phospholipid and 5 mol % Cer8 as polymer conjugated lipid comprising shorter alkyl chains. Said LNP composition is called herein and in the working examples "GN01-C8". For "GN01-C8", N/P (lipid to mRNA mol ratio) preferably is 14 and total lipid/mRNA mass ratio preferably is between about 20 and about 60, more preferably between about 30 and about 50 and most preferably is 40 (m/m).

A further particularly preferred embodiment for a lipid nanoparticle of the present invention is given when the combination F1xE72 according to Table E and Table F is used for formulating a lipid nanoparticle, i.e. 59 mol % C26 lipid as disclosed in Table 1 as cationic lipid (i.e. THIOETHER as apparent from the examples section, FIG. 25A), 29.3 mol % cholesterol as steroid, 10 mol % DPhyPE as neutral lipid/phospholipid and 1.7 mol % DMG-PEG 2000 as polymer conjugated lipid. Said LNP composition is called herein and in the working examples "LNP28". For "LNP28", N/P (lipid to mRNA mol ratio) preferably is 14 and total lipid/mRNA mass ratio preferably is between about 20 and about 60, more preferably between about 30 and about 50 and most preferably is 40 (m/m).

Furthermore, for a preferred composition, the (i) cationic lipid may be selected from the compounds of Table 1; and/or the (ii) neutral lipid or neutral phospholipid is a zwitterionic compound selected from the group consisting of 1,2-diphytanoyl-sn-glycero-3-phosphoethanolamine (DPhyPE; also referred to as 1,2-di-(3,7,11,15-tetramethylhexadecanoyl)-sn-glycero-3-phosphoethanolamine), 1,2-diphytanoyl-sn-glycero-3-phosphocholine (DPhyPC), 1,2-dioleoyl-sn-glycero-3-phosphocholine (DOPC; also referred to as dioleoylphosphatidylcholine), 1,2-Dipalmitoyl-sn-glycero-3-phosphocholine (DPPC, also referred to as dipalmitoylphosphatidylcholine), 1,2-dioleoyl-sn-glycero-3-phosphoethanolamine (DOPE), phosphatidylethanolamines, distearoylphosphatidylcholines, dioleoylphosphatidylethanolamine (DOPEA), 1,2-distearoyl-sn-glycero-3-phosphoethanolamine (DSPE), palmitoyloleoylphosphatidylcholine (POPC), palmitoyloleoyl-phosphatidylethanolamine (POPE), 1,2-Dipalmitoyl-sn-glycero-3-phosphoethanolamine (DPPE), dioleoyl-phosphatidylethanolamine 4-(N-maleimidomethyl)-cyclohexane-1-carboxylate (DOPE-mal), 1,2-Dimyristoyl-sn-glycero-3-phosphoethanolamine (DMPE), dipalmitoyl phosphatidyl ethanolamine (DPPE), dimyristoylphosphoethanolamine (DMPE), 1,2-Dilinoleoyl-sn-glycero-3-phosphoethanolamine (DLoPE), distearoyl-phosphatidylethanolamine (DSPE), 1-Palmitoyl-2-oleoyl-sn-glycero-3-phosphoethanolamine (POPE), 1,2-Dilauroyl-sn-glycero-3-phosphoethanolamine (DLPE), 16-O-monomethylphosphoethanolamine, 16-O-dimethyl phosphatidylethanolamine, 1,2-Dierucoyl-sn-glycero-3-phosphoethanolamine (DEPE), 18-1-trans phosphatidylethanolamine, 1-stearoyl-2-oleoylphosphatidyethanolamine (SOPE), 1,2-Disqualeoyl-sn-glycero-3-phosphoethanolamine (DSQPE), 1,2-dielaidoyl-sn-glycero-3-phosphoethanolamine (transDOPE), 1—Stearoyl-2-linoleoyl-sn-glycero-3-phosphoethanolamine (SLPE), 1-tridecanoyl-sn-glycero-3-phospho-L-serine (sodium salt), 1-oleoyl-2-hydroxy-sn-glycero-3-phospho-L-serine (sodium salt), 1-palmitoyl-2-oleoyl-sn-glycero-3-phospho-L-serine (sodium salt) (POPS), 1-1-stearoyl-2-oleoyl-sn-glycero-3-phospho-L-serine (sodium salt), 1,2-dioleoyl-sn-glycero-3-phospho-L-serine (sodium salt) (DOPS), 1,2-distearoyl-sn-glycero-3-phospho-L-serine (sodium salt), 1,2-diphytanoyl-sn-glycero-3-phospho-L-serine (sodium salt), 1-O-hexadecanyl-2-O-(9Z-octadecenyl)-sn-glycero-3-phosphoethanolamine, 1,2-distearoyl-snglycero-3-phosphatidylcholine or 1,2-distearoyl-sn-glycero-3-phosphocholine (DSPC), 1,2-di-O-phytanyl-sn-glycero-3-phosphoethanolamine, 1-palmitoyl-2-cholesterylhemisuccinoyl-sn-glycero-3-phosphocholine (PChemsPC), 1,2-dicholesterylhemisuccinoyl-sn-glycero-3-phosphocholine (DChemsPC), 2-((2,3-bis(oleoyloxy)propyl)dimethylammonio)ethyl hydrogen phosphate (DOCP), 2-((2,3-bis(oleoyloxy)propyl)dimtheylammonio)ethyl ethyl phosphate (DOCPe), and 1-O-octadecyl-2-O-methyl-sn-glycero-3-phosphocholine (Edelfosine); optionally combined with 1,2-diheptanoyl-sn-glycero-3-phosphocholine (DHPC); and/or (iii) the polymer conjugated lipid may be selected from the group consisting of a pegylated diacylglycerol lipid (PEG-DAG); a pegylated ceramide lipid (PEG-Cer); a pegylated phosphatidylethanoloamine lipid (PEG-PE); a pegylated succinate diacylglycerol lipid (PEG-S-DAG); a pegylated dialkoxypropylcarbamate lipid; 1,2-dimyristoyl-rac-glycero-3-methoxypolyethylene glycol ("PEG-DMG" or "DMG-PEG"); 1,2-dicapryl-rac-glycero-3-methylpolyoxyethylene glycol ($C_{10}$ diacylglycerol PEG); N-octanoyl-sphingosine-1-succinyl [methoxy(polyethylene glycol)] (PEG-Ceramide8 or PEG-Cer8); 4-O-(2',3'-di(tetradecanoyloxy)propyl-1-O-(ω-methoxy(polyethoxy)ethyl)butanedioate (PEG-S-DMG); 2-mPEG2000-n,n ditetradecylacetamide; N-[(methoxy poly(ethylene glycol)2000)carbamyl]-1,2-dimyristyloxlpropyl-3-amine (PEG-c-DMA); w-methoxy(polyethoxy)ethyl-N-(2,3di(tetradecanoxy)propyl)carbamate; and 2,3-di(tetradecanoxy)propyl-N-(w-methoxy(polyethoxy)ethyl)carbamate.

Alternatively, the composition may be provided in solid form. In particular, it may be provided as a sterile solid composition for reconstitution with a sterile liquid carrier; the solid composition may in this case further comprise one or more inactive ingredients selected from pH-modifying agents, bulking agents, stabilizers, non-ionic surfactants and antioxidants. In this embodiment, the sterile liquid carrier is preferably an aqueous carrier.

The zeta potential of a nanoparticle composition may be used to indicate the electrokinetic potential of the composition. For example, the zeta potential may describe the surface charge of a nanoparticle composition. The lipid nanoparticles according to the invention may, due to the presence of both negatively and positively charged compounds, exhibit a relatively neutral zeta potential. The zeta potential (sometimes abbreviated as "charge") may be determined along with the particle size of the particles, for example, by dynamic light scattering and Laser Doppler Microelectrophoresis, for example using a Malvern Zetasizer Nano (Malvern Instruments Ltd.; Malvern, UK). Depending on the amount and nature of charged compounds in the lipid nanoparticles, the nanoparticles may be characterized by a zeta potential. In a preferred embodiment, the zeta potential is in the range from about −50 mV to about +50 mV. In other preferred embodiments, the zeta potential is in the range from about −25 mV to about +25 mV. In some embodiments, the zeta potential of a lipid nanoparticle of the invention may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In certain embodiments, the LNP comprises one or more targeting moieties which are capable of targeting the LNP to a cell or cell population. For example, in one embodiment, the targeting moiety is a ligand which directs the LNP to a receptor found on a cell surface.

In certain embodiments, the LNP comprises one or more internalization domains. For example, in one embodiment, the LNP comprises one or more domains which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo. In certain embodiments of the invention, ApoE may be supplemented to the medium or pharmaceutical composition used.

Preferably, in one embodiment, the compositions of the invention further comprise a biologically active ingredient.

Biologically Active Ingredients

As used herein, a biologically active ingredient means any compound or material having a biological activity due to which the compound or material is potentially useful for the prevention, management, improvement, treatment or therapy of a disease or condition in a subject, such as an animal, and in particular in a human subject.

In one of the preferred embodiments, the active ingredient is a nucleic acid compound. Examples of nucleic acid compounds that are potentially useful for carrying out the invention include nucleic acid compounds selected from the group consisting of chemically modified or unmodified messenger RNA (mRNA), chemically modified or unmodified RNA, single-stranded or double-stranded RNA, coding or non-coding RNA, viral RNA, replicon RNA, and self-replicating RNA, or any combination thereof; preferably wherein the biologically active ingredient is an mRNA.

In preferred embodiments, the nucleic acid compound is complexed or associated with one or more lipids (e.g. cationic lipids and/or neutral lipids), thereby forming liposomes, lipid nanoparticles (LNPs), lipoplexes, and/or nanoliposomes. In this context, the terms "complexed" or "associated" refer to the essentially stable combination of nucleic acid compound of the first aspect with one or more lipids into larger complexes or assemblies without covalent binding.

In specific embodiments, the active ingredient may include a CRISPR RNA (crRNA) plus a tracer RNA (tracrRNA), a guide RNA (gRNA) or a single guide RNA (sgRNA) and/or a donor DNA in conjunction with a CRISPR endonuclease. Suitably the CRISPR endonuclease may be provided as a protein or polypeptide or as an mRNA encoding said CRISPR endonuclease. A composition or formulation comprising this combination is suitable for delivering a CRISPR gene editing activity to a target cell. In one embodiment, compositions in accordance with the invention may provide the gRNA and mRNA encoding a CRISPR endonuclease, for separate, sequential or simultaneous administration. That is, the gRNA and mRNA may be provided within the same formulation or lipid nanoparticle in accordance with the invention or may be provided in separate lipid nanoparticles for separate, simultaneous or sequential administration. Suitably the ratio of gRNA to mRNA for administration is 1:1, 1:3, 1:9, 1:19, for example (i.e. 50%, 25%, 10% and 5% of guide RNA). In one embodiment, a gRNA and an mRNA encoding a CRISPR endonuclease such as cas9 are co-loaded into a formulation in accordance with the invention. Advantageously, co-loading enables a better encapsulation efficiency (EE) to be obtained. Suitably, a formulation or pharmaceutical composition in accordance with the invention into which gRNA and mRNA are co-loaded comprises LNPs with a mean diameter of between 80 and 160 nm. In one embodiment, the gRNA may be a modified gRNA sequence. Suitable modifications are described, for example in WO2016/089433 and PCT/GB2016/053312. Other suitable modifications will be familiar to those skilled in the art.

By "CRISPR endonuclease" is meant an endonuclease that can be used in a CRISPR gene editing composition. Suitable "CRISPR endonucleases" include cas9 and its mutants and modified forms. Accordingly, the mRNA for use in combination with a gRNA is one which encodes a CRISPR endonuclease, preferably cas9. Other "CRISPR endonucleases" include cpf1, for example. The skilled person will be aware that a gRNA pairs with a particular "CRISPR endonuclease". Accordingly, the invention contemplates a composition using a suitable gRNA/endonuclease pairing. Suitably, a gRNA is specific for a target gene, preferably wherein the target gene is a gene associated with liver disease.

In another embodiment, the peptide or protein expressed by the nucleic acid compound is a therapeutic protein, or a fragment or variant thereof, wherein the therapeutic protein is beneficial for the treatment or prophylaxis of any inherited or acquired disease or which improves the condition of an individual. Particularly, therapeutic proteins play a key role in the design of new therapeutic agents that could modify and repair genetic deficiencies, destroy cancer cells or pathogen infected cells, treat or prevent immune system disorders, or treat or prevent metabolic or endocrine disorders, among other functions.

In another embodiment, the peptide or protein expressed by the nucleic acid compound is an antigen. As defined in more detail herein above, an antigen is a compound or material which may be recognized by the immune system, preferably by the adaptive immune system, such as to trigger an antigen-specific immune response.

In some embodiments, the active ingredient is siRNA. siRNA are small interfering RNA as, for example, described in international patent application PCT/EP03/08666. These molecules typically consist of a double-stranded RNA structure which comprises between 15 and 25, preferably 18 to 23 nucleotide pairs which are capable of base-pairing to each other, i. e. are essentially complementary to each other, typically mediated by Watson-Crick base-pairing. One strand of this double-stranded RNA molecule is essentially complementary to a target nucleic acid, preferably an mRNA, whereas the second strand of said double-stranded RNA molecule is essentially identical to a stretch of said target nucleic acid. The siRNA molecule may be flanked on each side and each stretch, respectively, by a number of additional nucleotides which, however, do not necessarily have to base-pair to each other.

In some embodiments, the active ingredient is RNAi. RNAi has essentially the same design as siRNA, however, the molecules are significantly longer compared to siRNA. RNAi molecules typically comprise 50 or more nucleotides and base pairs, respectively.

In some embodiments, the active ingredient is an antisense nucleic acid. Antisense nucleic acids, as preferably used herein, are oligonucleotides which hybridise based on base complementarity with a target RNA, preferably mRNA, thereby activating RNaseH. RNaseH is activated by both phosphodiester and phosphothioate-coupled DNA. Phosphodiester-coupled DNA, however, is rapidly degraded by cellular nucleases although phosphothioate-coupled DNA is not. Antisense polynucleotides are thus effective only as DNA-RNA hybrid complexes. Preferred lengths of antisense nucleic acids range from 16 to 23 nucleotides. Examples for this kind of antisense oligonucleotides are described, among others, in U.S. Pat. Nos. 5,849,902 and 5,989,912.

In some embodiments, the active ingredient is a ribozyme. Ribozymes are catalytically active nucleic acids preferably consisting of RNA which basically comprises two moieties. The first moiety shows a catalytic activity, whereas the second moiety is responsible for the specific interaction with the target nucleic acid. Upon interaction between the target nucleic acid and the said moiety of the ribozyme, typically by hybridisation and Watson-Crick base-pairing of essentially complementary stretches of bases on the two hybridising strands, the catalytically active moiety may become active which means that it cleaves, either intramolecularly or intermolecularly, the target nucleic acid in case the catalytic activity of the ribozyme is a phosphodiesterase activity. Ribozymes, the use and design principles are known to the ones skilled in the art and, for example, described in Doherty and Doudna (Annu. Ref. Biophys. Biomolstruct. 2000; 30: 457-75).

In some embodiments, the active ingredient is an aptamer. Aptamers are D-nucleic acids which are either single-stranded or double-stranded and which specifically interact with a target molecule. The manufacture or selection of aptamers is, e.g., described in European patent EP 0 533 838. In contrast to RNAi, siRNA, antisense-nucleotides and ribozymes, aptamers do not degrade any target mRNA but interact specifically with the secondary and tertiary structure of a target compound such as a protein. Upon interaction with the target, the target typically shows a change in its biological activity. The length of aptamers typically ranges from as little as 15 to as much as 80 nucleotides, and preferably ranges from about 20 to about 50 nucleotides.

In some embodiments, the active ingredient is a spiegelmer. Spiegelmers are, for example, described in international patent application WO 98/08856. Spiegelmers are molecules similar to aptamers. However, spiegelmers consist either completely or mostly of L-nucleotides rather than D-nucleotides in contrast to aptamers. Otherwise, particularly with regard to possible lengths of spiegelmers, the same applies to spiegelmers as outlined in connection with aptamers.

mRNA

In one of the preferred embodiments, the nucleic acid compound is an mRNA or an mRNA compound. As has been found by the inventors, the lipids and the compositions according to the present invention are particularly suitable for the in vivo delivery of mRNA compounds expressing antigens, and thus enable highly effective, potent, versatile and safe vaccines that can be rapidly developed at moderate cost. Specific antigens of interest for carrying out the present invention are described in more detail below. The mRNA compound according to the invention in encapsulated in or associated with a lipid nanoparticle.

Advantages of the mRNA encoding at least one antigenic peptide or protein comprised in lipid nanoparticles (LNPs) are:

- Induction of a strong humoral immune response
- Induction of B-cell memory
- Faster onset of immune protection
- Longevity of the induced immune responses
- Induction of broad cellular T-cell responses
- Induction of a (local and transient) pro-inflammatory environment
- No induction of systemic cytokine or chemokine response
- Good tolerability, no side-effects, non-toxic
- Advantageous stability characteristics
- Formulation compatible with many different antigens: larger antigen cocktails feasible based on the same (production) technology
- No vector immunity, i.e. technology can be used to vaccinate the same subject multiple times against multiple (different) antigens
- Speed, adaptability, simplicity and scalability of production.

In certain embodiments, the lipid nanoparticles comprise at least:

(i) a cationic lipid and/or a polymer conjugated lipid as defined herein; and (ii) an mRNA compound comprising an mRNA sequence encoding an antigenic peptide or protein.

In other particular embodiments, the lipid nanoparticle composition comprises:

(a) a cationic lipid according to formula (I) as described herein.

(b) a steroid;

(c) a neutral lipid;

(d) a polymer conjugated lipid, wherein said polymer conjugated lipid is a compound according to formula (II) as described herein; and (e) an mRNA compound encoding a peptide or protein.

With respect to the cationic lipid, the steroid, the neutral lipid, the polymer conjugated lipid, and the mRNA compound encoding a peptide or protein, the same options, preferences and alternatives apply as have been described with respect to these features herein above. For example, in one of the preferred embodiments, the peptide or protein expressed by the mRNA compound is an antigen.

The amount of the cationic lipid relative to that of the mRNA compound in the lipid nanoparticle may also be expressed as a weight ratio (abbreviated f.e. "m/m"). For example, the lipid nanoparticles comprise the mRNA compound at an amount such as to achieve a lipid to mRNA weight ratio in the range of about 20 to about 60, or about 10 to about 50. In other embodiments, the mass ratio is in the range of about 30 and about 50. In other embodiments, the ratio of cationic lipid to nucleic acid or mRNA is from about 3 to about 15, such as from about 5 to about 13, from about 4 to about 8 or from about 7 to about 11. In a very preferred embodiment of the present invention, the total lipid/mRNA mass ratio is about 40 or 40, i.e. about 40 or 40 times mass excess to ensure mRNA encapsulation. Another preferred RNA/lipid ratio is between about 1 and about 10, about 2 and about 5, about 2 and about 4, or preferably about 3.

Further, the amount of the cationic lipid may be selected taking the amount of the nucleic acid cargo such as the mRNA compound into account. In one embodiment, the N/P ratio can be in the range of about 1 to about 50. In another embodiment, the range is about 1 to about 20, about 1 to about 10, about 1 to about 5. In one preferred embodiment, these amounts are selected such as to result in an N/P ratio of the lipid nanoparticles or of the composition in the range from about 10 to about 20. In a further very preferred embodiment, the N/P is 14 (i.e. 14 times mol excess of positive charge to ensure mRNA encapsulation). In another very preferred embodiment, the N/P is 17.5 (i.e. 17.5 times mol excess of positive charge to ensure mRNA encapsulation).

In this context, the N/P ratio is defined as the mole ratio of the nitrogen atoms ("N") of the basic nitrogen-containing groups of the cationic lipid to the phosphate groups ("P") of the nucleic acid which is incorporated within, or associated with, the lipid nanoparticle as biologically active cargo. The N/P ratio may be calculated on the basis that, for example, 1 μg RNA typically contains about 3 nmol phosphate residues, provided that the RNA exhibits a statistical distribution of bases. The "N"-value of the cationic lipid or lipidoid may be calculated on the basis of its molecular weight and the relative content of cationic groups. If more than one cationic lipid is present, the N-value should be calculated on the basis of all cationic lipids comprised in the lipid nanoparticles.

The total amount of mRNA in the lipid nanoparticles varies and may be defined depending on the mRNA to total lipid w/w ratio. In one embodiment of the invention the invention the mRNA to total lipid ratio is less than 0.06 w/w, preferably between 0.03 and 0.04 w/w.

Preferably, the mRNA compound or the coding sequence thereof has a length of about 50 to about 20000, or 100 to about 20000 nucleotides, preferably of about 250 to about 20000 nucleotides, more preferably of about 500 to about 10000, even more preferably of about 500 to about 5000.

As mentioned, the peptide or protein expressed by the mRNA compound may be an antigen. In other words, the composition comprises an mRNA compound which comprises an mRNA sequence encoding an antigenic peptide or protein, or a fragment, variant or derivative thereof. Such antigens, or antigenic peptides or proteins, may be derived from pathogenic antigens, tumour antigens, allergenic antigens or autoimmune self-antigens, or fragments or variants thereof, preferably as defined herein.

Pathogenic Antigens

Pathogenic antigens are derived from pathogenic organisms, in particular bacterial, viral or protozoological (multicellular) pathogenic organisms, which evoke an immunological reaction by subject, in particular a mammalian subject, more particularly a human. More specifically, pathogenic antigens are preferably surface antigens, e.g. proteins (or fragments of proteins, e.g. the exterior portion of a surface antigen) located at the surface of the virus or the bacterial or protozoological organism.

Accordingly, in some preferred embodiments, the artificial nucleic acid (RNA) molecule may encode in its at least one coding region at least one pathogenic antigen selected from a bacterial, viral, fungal or protozoal antigen. The encoded (poly-)peptide or protein may consist or comprise of a pathogenic antigen or a fragment, variant or derivative thereof.

Pathogenic antigens are peptide or protein antigens preferably derived from a pathogen associated with an infectious disease which are preferably selected from, but not limited to, the group of antigens derived from the pathogens disclosed on pages 21-35 in WO 2018/078053 A1; WO 2018/078053 being incorporated herein by reference in its entirety. Furthermore, pathogenic antigens are peptide or protein antigens preferably derived from a pathogen associated with an infectious disease which are preferably selected from, but not limited to, the group of antigens derived from the pathogens disclosed on page 57 paragraph 3—page 63, paragraph 2 in WO 2019/077001 A1; WO 2019/077001 being incorporated herein by reference in its entirety.

Even further pathogenic antigens are peptide or protein antigens preferably derived from a pathogen associated with infectious disease which are preferably selected from antigens derived from the pathogens selected from, but not limited to, the group of antigens derived from the pathogens disclosed on pages 32 line 26—page 34 line 27 in WO 2013120628 A1. Furthermore in this regard, the pathogenic antigen (antigen derived from a pathogen associated with infectious disease) may be preferably selected from the antigens preferably selected from antigens selected from, but not limited to, the group of antigens as disclosed on pages 34 line 29—page 59 line 5 (in brackets is the particular pathogen or the family of pathogens of which the antigen(s) is/are derived and the infectious disease with which the pathogen is associated) in WO 2013120628 A1; WO 2013120628 being incorporated herein by reference in its entirety.

Among the preferred antigens expressed by the mRNA compound incorporated in the composition of the invention are pathogens selected from, but not limited to, the group consisting of a a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory syncytial virus (RSV), Rhinovirus, Rota virus, Vaccinia virus, Yellow Fever Virus, Zika virus, *Chlamydia trachomatis* (i.e. bacterium chlamydia causing chlamydia), and Malaria parasites (e.g. *Plasmodium falciparum, Plasmodium vivax, Plasmodium malariae*, or *Plasmodium ovale*). In another one of the preferred embodiments, the pathogenic antigen is derived from a SARS coronavirus 2 (SARS-CoV-2), nCoV-2019 coronavirus, SARS coronavirus (SARS-CoV), a Malaria parasite, an Influenza virus or a Rabies virus.

Further, pathogenic antigens may further preferably be selected from antigens derived from the pathogens selected from, but not limited to, the group consisting of *Acinetobacter baumannii, Anaplasma genus, Anaplasma phagocytophilum, Ancylostoma braziliense, Ancylostoma duodenale, Arcanobacterium haemolyticum, Ascaris lumbricoides, Aspergillus* genus, Astroviridae, *Babesia* genus, *Bacillus anthracis, Bacillus cereus, Bartonella henselae*, BK virus, *Blastocystis hominis, Blastomyces dermatitidis, Bordetella pertussis, Borrelia burgdorferi, Borrelia genus, Borrelia* spp, *Brucella* genus, *Brugia malayi, Bunyaviridae family, Burkholderia cepacia* and other *Burkholderia* species, *Burkholderia mallei, Burkholderia pseudomallei, Caliciviridae family, Campylobacter genus, Candida albicans, Candida* spp, *Chlamydia trachomatis, Chlamydophila pneumoniae, Chlamydophila psittaci*, CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii*, Crimean-Congo haemorrhagic fever virus, *Cryptococcus neoformans, Cryptosporidium* genus, Cytomegalovirus (CMV), *Dientamoeba fragilis*, Ebolavirus (EBOV—for example the envelope glycoprotein), *Echinococcus* genus, *Ehrlichia chaffeensis, Ehrlichia ewingii, Ehrlichia genus, Entamoeba histolytica, Enterococcus* genus, Enterovirus genus, Enteroviruses, mainly Coxsackie A virus and Enterovirus 71 (EV71), *Epidermophyton* spp, Epstein-Barr Virus (EBV), *Escherichia coli* 01 57:H7, 01 1 1 and O1 04:H4, *Fasciola hepatica* and *Fasciola gigantica*, FFI prion, Feline immunodeficiency virus (FIV), Filarioidea superfamily, Flaviviruses, *Francisella tularensis, Fusobacterium genus, Geotrichum candidum, Giardia intestinalis, Gnathostoma* spp, GSS prion, Guanarito virus, *Haemophilus ducreyi, Haemophilus influenzae, Helicobacter pylori*, Henipavirus (Henclra virus Nipah virus), Hepatitis A Virus, Hepatitis B Virus (HBV), Hepatitis C Virus (HCV), Hepatitis D Virus, Hepatitis E Virus, *Histoplasma capsulatum, Hortaea werneckii*, Human bocavirus (HBoV), Human metapneumovirus (hMPV), Human parainfluenza viruses (HPIV), Japanese encephalitis virus, JC virus, Junin virus, Kingella kingae, *Klebsiella granulomatis*, Kuru prion, Lassa virus, *Legionella pneumophila, Leishmania* genus, Leptospira genus, *Listeria monocytogenes*, Lymphocytic choriomeningitis virus (LCMV), Machupo virus, *Malassezia* spp, Marburg virus, Measles virus, *Metagonimus yokagawai, Microsporidia phylum*, Molluscum contagiosum virus (MCV), Mumps virus, *Mycobacterium leprae* and *Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi*, Orthomyxoviridae family (Influenza), *Paracoccidioides brasiliensis, Paragonimus* spp, *Paragonimus westermani*, Parvovirus B19, *Pasteurella* genus, *Plasmodium* genus, *Pneumocystis jirovecii*, Poliovirus, Rhinovirus, rhinoviruses, *Rickettsia akari, Rickettsia genus, Rickettsia prowazekii, Rickettsia rickettsii, Rickettsia typhi*, Rift Valley fever virus, Rotavirus (preferably f.e. VP8 antigen), Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia genus, Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum*, vaccinia virus (preferably f.e. immune evasion proteins E3, K3, or B18), Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti, Yersinia enterocolitica, Yersinia pestis*, and *Yersinia pseudotuberculosis*, Zika virus, ZikaSPH2015-Brazil, Z1106033—Suriname, MR766-Uganda or Natal RGN, or an isoform, homolog, fragment, variant or derivative of any of these proteins. A particular preferred pathogenic antigen is an antigen derived from the pathogen SARS coronavirus, in particular the spike protein (S) of SARS coronavirus.

In a further embodiment, pathogenic antigens useful for treating infections may be selected from the following antigens (the related infection and related pathogen are indicated in brackets after the respective antigens—naturally, also other antigens which may be derived from the following pathogens in brackets may be derived and used according to the invention):

spike protein (S), an envelope protein (E), a membrane protein (M) or a nucleocapsid protein (N), or an immunogenic fragment or variant of any of these (infectious disease is “COVID-19 disease”; pathogen: SARS coronavirus 2 (SARS-CoV-2), nCoV-2019 coronavirus, SARS coronavirus (SARS-CoV));

spike protein (S), a spike S1 fragment (S1), an envelope protein (E), a membrane protein (M) or a nucleocapsid protein (N) (infectious disease is MERS infection; pathogen: Middle East respiratory syndrome coronavirus (MERS coronavirus/MERS-CoV));

replication protein E1, regulatory protein E2, protein E3, protein E4, protein E5, protein E6, protein E7, protein E8, major capsid protein L1, minor capsid protein L2 (infectious disease is Human papillomavirus (HPV) infection; pathogen: Human papillomavirus (HPV) or HPV16);

fusion protein F, hemagglutinin-neuramidase HN, glycoprotein G, matrix protein M, phosphoprotein P, nucleoprotein N, polymerase L, hemagglutinin-neuraminidase, Fusion (F) glycoprotein F0, F1 or F2, Recombinant PIV3/PIV1 fusion glycoprotein (F) and hemagglutinin (HN), C protein, Phosphoprotein, D protein, matrix protein (M), nucleocapsid protein (N), viral replicase (L), non-structural V protein (infectious disease is Human parainfluenza virus infection; pathogen: Human parainfluenza viruses (HPIV/PIV) hPIV-1, hPIV-2, hPIV-3, or hPIV-4 serotype, preferably hPIV-3 serotype, preferably PIV3);

fusion (F) glycoprotein, Glycoprotein G, Phosphoprotein P, Nucleoprotein N, Nucleocapsin protein (infectious disease: hMPV infection; pathogen: Human metapneumovirus (hMPV));

hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein, H10N8, H7N9, H10, H1N1, H3N2 (X31), H1, H2, H3, H4, H5, H6, H7, H8, H9, H10, H11, H12, H13, H14, H15, H16, H17, H18, antigenic subdomains of HA: HA1, HA2, neuraminidase (NA), nucleoprotein (NP), matrix protein 1 (M1), matrix protein 2 (M2), non-structural protein 1 (NS 1), nonstructural protein 2 (NS2), HA7 antigen, H7 or H10 and B, pathogen: Orthomyxoviridae family, Influenza virus (flu));

nucleoprotein N, large structural protein L, phosphoprotein P, matrix protein M, glycoprotein G, G protein (infectious disease is Rabies; pathogen: Rabies virus);

HIV p24 antigen, HIV envelope proteins (Gp120, Gp41, Gp160), polyprotein GAG, negative factor protein Nef, trans-activator of transcription Tat, Brecl (infectious disease HIV; pathogen: Human immunodeficiency virus);

major outer membrane protein MOMP, probable outer membrane protein PMPC, outer membrane complex protein B OmcB, heat shock proteins Hsp60 HSP10, protein IncA, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 (infectious disease: infection with *Chlamydia trachomatis*; pathogen: *Chlamydia trachomatis*);

pp65 antigen, membrane protein pp15, capsid-proximal tegument protein pp150, protein M45, DNA polymerase UL54, helicase UL105, glycoprotein gM, glycoprotein gN, glycoprotein H, glycoprotein B gB, protein UL83, protein UL94, protein UL99, HCMV glycoprotein selected from gH gL, gB, gO, gN, and gM, HCMV protein selected from UL83, UL123, UL128, UL130 and UL131A, Tegument protein pp150 (pp150), Tegument protein pp65/lower matrix phosphoprotein (pp65), Envelope glycoprotein M (UL100), Regulatory protein IE1 (UL123), Envelopeprotein (UL128), Envelope glycoprotein (130), Envelopeprotein (UL131A), Envelope glycoprotein B (UL55), Structural glycoprotein N gpUL73 (UL73), Structural glycoprotein O gpUL74 (UL74) (infectious disease is Cytomegalovirus infection; pathogen: Cytomegalovirus (CMV/HCMV));

capsid protein C, premembrane protein prM, membrane protein M, envelope protein E (domain I, domain II, domain II), protein NS1, protein NS2A, protein NS2B, protein NS3, protein NS4A, protein 2K, protein NS4B, protein NS5 (infectious disease Dengue fever; pathogen: Dengue viruses (DEN-1, DEN-2, DEN-3 and DEN-4));

EBOV glycoprotein (GP), surface EBOV GP, wild type EBOV pro-GP, mature EBOV GP, secreted wild type EBOV pro-GP, secreted mature EBOV GP, EBOV nucleoprotein (NP), RNA polymerase L, and EBOV matrix protein selected from VP35, VP40, VP24, and VP30 (infectious disease: Ebola; pathogen: Ebola virus);

hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 (infectious disease is Hepatitis B; pathogen: Hepatitis B Virus (HBV));

fusionprotein F, F protein, nucleoprotein N, matrix protein M, matrix protein M2-1, matrix protein M2-2, phophoprotein P, small hydrophobic protein SH, major surface glycoprotein G, polymerase L, non-structural protein 1 NS1, non-structural protein 2 NS2, RSV attachment protein (G) (glycoprotein G), Fusion (F) glycoprotein (glycoprotein F), nucleoprotein (N), phosphoprotein (P), large polymerase protein (L), matrix protein (M, M2), small hydrophobic protein (SH), nonstructural protein 1 (NS1), nonstructural protein 2 (NS2), membrane-bound RSV F protein, membrane-bound DS-Cavl (stabilized prefusion RSV F protein) (infectious disease is infection with Respiratory syncytial virus (RSV); pathogen: Respiratory syncytial virus (RSV));

secretory antigen SssA (*Staphylococcus* genus, Staphylococcal food poisoning); secretory antigen SssA (*Staphylococcus* genus e.g. *aureus*, Staphylococcal infection); molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTB8, Rpf-like proteins, protein MTB32, protein MTB39, crystallin, heat-shock protein HSP65, protein PST-S (infectious disease is Tuberculosis; pathogen: *Mycobacterium tuberculosis*);

genome polyprotein, protein E, protein M, capsid protein C, protease NS3, protein NS1, protein NS2A, protein AS2B, protein NS4A, protein NS4B, protein NS5 (infectious disease is Yellow fever; pathogen: Yellow fever virus);

circumsporozoite protein (CSP) (infectious disease is Malaria; pathogen: *P. falciparum* and *P. vivax*); and Zika virus proteins in accordance with WO 2017/140905 A1, i.e. Zika virus capsid protein (C), Zika virus premembrane protein (prM), Zika virus pr protein (pr), Zika virus membrane protein (M), Zika virus envelope protein (E), Zika virus non-structural protein, ZIKV prME antigen, ZIKV capsid protein, premembrane/membrane protein, ZIKV envelope protein, ZIKV non-structural protein 1, ZIKV non-structural protein 2A, ZIKV non-structural protein 2B, ZIKV nonstructural protein 3, ZIKV non-structural protein 4A, ZIKV non-structural protein 4B, ZIKV non-structural protein 5, or a Zika virus envelope protein (E) wherein the fusion loop in domain II is mutated in accordance with WO 2017/140905 A1; WO 2017/140905 being incorporated herein by reference in its entirety (infectious disease is Zika virus infection; pathogen: Zika virus);

In some embodiments of the present invention, disclosure is provided for methods of inducing an antigen specific immune response in a subject, comprising administering to the subject any of the RNA (e.g. mRNA) vaccine as provided herein in an amount effective to produce an antigen-specific immune response.

In some embodiments, the RNA (e.g. mRNA) vaccine is a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), and Malaria parasites (e.g. *Plasmodium falciparum, Plasmodium vivax, Plasmodium malariae*, or *Plasmodium ovale*). In another one of the preferred embodiments, the pathogenic antigen is derived from a SARS coronavirus 2 (SARS-CoV-2), nCoV-2019 coronavirus, SARS coronavirus (SARS-CoV), a Malaria parasite, an Influenza virus or a Rabies virus vaccine. In other embodiments, the RNA (e.g. mRNA) vaccine is a COVID-19, rabies, an influenza or a malaria vaccine.

In some embodiments, the RNA (e.g., mRNA) vaccine is a combination vaccine comprising a combination of influenza vaccines (a broad spectrum influenza vaccine). In some embodiments, an antigen-specific immune response comprises a T cell response or a B cell response.

In some embodiments, a method of producing an antigen-specific immune response comprises administering to a subject a single dose (i.e. no booster dose) of a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), and Malaria parasites (e.g. *Plasmodium falciparum, Plasmodium vivax, Plasmodium malariae*, or *Plasmodium ovale*). In another one of the preferred embodiments, the pathogenic antigen is derived from a SARS coronavirus 2 (SARS-CoV-2), nCoV-2019 coronavirus, SARS coronavirus (SARS-CoV), a Malaria parasite, an Influenza virus or a Rabies virus (e.g., mRNA) vaccine of the present disclosure.

In some embodiments, a method further comprises administering to the subject a second (booster) dose of a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), and Malaria parasites (e.g. *Plasmodium falciparum, Plasmodium vivax, Plasmodium malariae*, or *Plasmodium ovale*). In another one of the preferred embodiments, the pathogenic antigen is derived from a SARS coronavirus 2 (SARS-CoV-2), nCoV-2019 coronavirus, SARS coronavirus (SARS-CoV), a Malaria parasite, an Influenza virus or a Rabies virus RNA (e.g. mRNA) vaccine may be administered.

In some embodiments, the subjects exhibit a seroconversion rate of at least 80% (e.g., at least 85%, at least 90%, or at least 95%) following the first dose or the second (booster) dose of the vaccine. Seroconversion is the time period during which a specific antibody develops and becomes detectable in the blood. After seroconversion has occurred, a virus can be detected in blood tests for the antibody. During an infection or immunization, antigens enter the blood, and the immune system begins to produce antibodies in response. Before seroconversion, the antigen itself may or may not be detectable, but antibodies are considered absent. During seroconversion, antibodies are present but not yet detectable. Anytime after seroconversion, the antibodies can be detected in the blood, indicating a prior or current infection. In some embodiments, an RNA (e.g., mRNA) vaccine is administered to a subject by intradermal injection, intramuscular injection, or by intranasal administration. In some embodiments, an RNA (e.g. mRNA) vaccine is administered to a subject by intramuscular injection.

Some embodiments, of the present disclosure provide methods of inducing an antigen specific immune response in a subject, including administering to a subject a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), and Malaria parasites (e.g. *Plasmodium falciparum, Plasmodium vivax, Plasmodium malariae*, or *Plasmodium ovale*). In another one of the preferred embodiments, the pathogenic antigen is derived from a SARS coronavirus 2 (SARS-CoV-2), nCoV-2019 coronavirus, SARS coronavirus (SARS-CoV), a Malaria parasite, an Influenza virus or a Rabies virus RNA (e.g., mRNA) vaccine in an effective amount to produce an antigen specific immune response in a subject.

Antigen-specific immune responses in a subject may be determined, in some embodiments, by assaying for antibody titer (for titer of an antibody that binds to a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum, Plasmodium vivax, Plasmodium malariae*, or *Plasmodium ovale*) antigenic polypeptide) following administration to the subject of any of the SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) RNA (e.g., mRNA) vaccines of the present disclosure. In some embodiments, the anti-antigenic polypeptide antibody titer produced in the subject is increased by at least 1 log relative to a control. In some embodiments, the anti-antigenic polypeptide antibody titer produced in the subject is increased by 1-3 log relative to a control.

Tumour Antigens

In a further preferred embodiment, the mRNA compound comprising an mRNA encodes a tumour antigen, preferably as defined herein, or a fragment or variant thereof, wherein the tumour antigen is preferably selected from, but not limited to, the group consisting of tumour antigens disclosed on pages 47-51 in WO 2018/078053 A1; WO 2018/078053 A1 being incorporated herein by reference in its entirety.

Furthermore, cytokines, chemokines, suicide enzymes and gene products, apoptosis inducers, endogenous angiogenesis inhibitors, heat shock proteins, tumour antigens, innate immune activators, antibodies directed against proteins associated with tumour or cancer development, useful for the present invention f.e. for cancer treatment, are selected from, but not limited to, the group of cytokines, chemokines, suicide enzymes and gene products, apoptosis inducers, endogenous angiogenesis inhibitors, heat shock proteins, tumour antigens, innate immune activators, antibodies directed against proteins associated with tumour or cancer development as disclosed in Table 1, Table 2, Table 3, Table 4, Table 5, Table 6, Table 7, Table 8, Table 9, Table 10, Table 11 and Table 12 of WO2016/170176; WO2016/170176 and especially Tables 1-12 being specifically incorporated herein by reference in its entirety.

Therapeutic Proteins and Use for Treatment or Prophylaxis of any Inherited or Acquired Disease In a further embodiment, the active ingredient is a nucleic acid compound comprising at least one coding sequence, wherein the at least one coding sequence encodes a peptide or protein, wherein the protein is a therapeutic protein, or a fragment or variant of a therapeutic protein. In this context, a therapeutic peptide, protein or fragment thereof may be any peptidic compound useful the prevention, management, improvement, treatment or therapy of a disease or condition in a subject, such as an animal, and in particular in a human subject.

Thusly, in one embodiment, the mRNA comprising at least one coding sequence may encode (a) a peptide or protein, or a fragment or variant thereof, wherein the peptide or protein is an antigen, wherein the antigen preferably is derived from pathogenic antigens, tumour antigens, allergenic antigens or autoimmune self-antigens, or a fragment or variant thereof; or (b) a therapeutic protein or a fragment or variant thereof. The therapeutic protein may, for example, be selected from the group consisting of (i) therapeutic proteins for use in enzyme replacement therapy for the treatment of metabolic, endocrine or amino acid disorders or for use in replacing an absent, deficient or mutated protein;

(ii) therapeutic proteins for use in the treatment of blood disorders, diseases of the circulatory system, diseases of the respiratory system, infectious diseases or immune deficiencies;

(iii) therapeutic proteins for use in the treatment of cancer or tumour diseases;

(iv) therapeutic proteins for use in hormone replacement therapy;

(v) therapeutic proteins for use in reprogramming somatic cells into pluri- or omnipotent stem cells;

(vi) therapeutic proteins for use as adjuvant or immunostimulation;

(vii) therapeutic proteins being a therapeutic antibody;

(viii) therapeutic proteins being a gene editing agent; and (ix) therapeutic proteins for use in treating or preventing a liver disease selected from the group consisting of liver fibrosis, liver cirrhosis and liver cancer.

In a specific embodiment, the therapeutic protein, or fragment or variant thereof, is selected from:

therapeutic proteins for use in enzyme replacement therapy for the treatment of metabolic, endocrine or amino acid disorders or for use in replacing an absent, deficient or mutated protein, including Acid sphingomyelinase, Adipotide, Agalsidase-beta, Alglucosidase, alpha-galactosidase A, alpha-glucosidase, alpha-L-iduronidase, alpha-N-acetylglucosaminidase, Amphiregulin, Angiopoietins (Ang1, Ang2, Ang3, Ang4, ANGPTL2, ANGPTL3, ANGPTL4, ANGPTL5, ANGPTL6, ANGPTL7), ATPase, Cu(2+)-transporting beta polypeptide (ATP7B), argininosuccinate synthetase (ASS1), Betacellulin, Beta-glucuronidase, Bone morphogenetic proteins BMPs (BMP1, BMP2, BMP3, BMP4, BMP5, BMP6, BMP7, BMP8a, BMP8b, BMP10, BMP15), CLN6 protein, Epidermal growth factor (EGF), Epigen, Epiregulin, Fibroblast Growth Factor (FGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-17, FGF-18, FGF-19, FGF-20, FGF-21, FGF-22, FGF-23), Fumarylacetoacetate Hydrolase (FAH), Galsulphase, Ghrelin, Glucocerebrosidase, GM-CSF, Heparin-binding EGF-like growth factor (HB-EGF), Hepatocyte growth factor HGF, Hepcidin, Human albumin, increased loss of albumin, Idursulphase (Iduronate-2-sulphatase), Integrins aVp3, aVp5 and $\alpha 5\beta 1$, Iuduronate sulfatase, Laronidase, N-acetylgalactosamine-4-sulfatase (rhASB; galsulfase, Arylsulfatase A (ARSA), Arylsulfatase B (ARSB)), N-acetylglucosamine-6-sulfatase, Nerve growth factor (NGF, Brain-Derived Neurotrophic Factor (BDNF), Neurotrophin-3 (NT-3), and Neurotrophin 4/5 (NT-4/5), Neuregulin (NRG1, NRG2, NRG3, NRG4), Neuropilin (NRP-1, NRP-2), Obestatin, phenylalanine hydroxylase (PAH), Phenylalanine ammonia lyase (PAL), Platelet Derived Growth factor (PDGF (PDFF-A, PDGF-B, PDGF-C, PDGF-D), TGF beta receptors (endoglin, TGF-beta 1 receptor, TGF-beta 2 receptor, TGF-beta 3 receptor), Thrombopoietin (THPO) (Megakaryocyte growth and development factor (MGDF)), Transforming Growth factor (TGF (TGF-a, TGF-beta (TGFbeta1, TGFbeta2, and TGFbeta3))), VEGF (VEGF-A, VEGF-B, VEGF-C, VEGF-D, VEGF-E, VEGF-F und PIGF), Nesiritide, Trypsin, adrenocorticotrophic hormone (ACTH), Atrial-natriuretic peptide (ANP), Cholecystokinin, Gastrin, Leptin, Oxytocin, Somatostatin, Vasopressin (antidiuretic hormone), Calcitonin, Exenatide, Growth hormone (GH), somatotropin, Insulin, Insulin-like growth factor 1 IGF-1, Mecasermin rinfabate, IGF-1 analog, Mecasermin, IGF-1 analog, Pegvisomant, Pramlintide, Teriparatide (human parathyroid hormone residues 1-34), Becaplermin, Dibotermin-alpha (Bone morphogenetic protein 2), Histrelin acetate (gonadotropin releasing hormone; GnRH), Octreotide, hepatocyte nuclear factor 4 alpha (HNF4A), CCAAT/enhancer-binding protein alpha (CEBPA), fibroblast growth factor 21 (FGF21), extracellular matrix protease or human collagenase MMP1, Hepatocyte Growth Factor (HGF), TNF-related apoptosis-inducing ligand (TRAIL), opioid growth factor receptor-like 1 (OGFRL1), clostridial type II collagenase, Relaxin 1 (RLN1), Relaxin 2 (RLN2), Relaxin 3 (RLN3) and Palifermin (keratinocyte growth factor; KGF);

therapeutic proteins for use in the treatment of blood disorders, diseases of the circulatory system, diseases of the respiratory system, cancer or tumour diseases, infectious diseases or immune deficiencies, including Alteplase (tissue plasminogen activator; tPA), Anistreplase, Antithrombin III (AT-III), Bivalirudin, Darbepoetin-alpha, Drotrecogin-alpha (activated protein C, Erythropoietin, Epoetin-alpha, erythropoietin, erthropoyetin, Factor IX, Factor VIIa, Factor VIII, Lepirudin, Protein C concentrate, Reteplase (deletion mutein of tPA), Streptokinase, Tenecteplase, Urokinase, Angiostatin, Anti-CD22 immunotoxin, Denileukin diftitox, Immunocyanin, MPS (Metallopanstimulin), Aflibercept, Endostatin, Collagenase, Human deoxyribonuclease I, dornase, Hyaluronidase, Papain, L-Asparaginase, Peg-asparaginase, Rasburicase, Human chorionic gonadotropin (HCG), Human follicle-stimulating hormone (FSH), Lutropin-alpha, Prolactin, alpha-1-Proteinase inhibitor, Lactase, Pancreatic enzymes (lipase, amylase, protease), Adenosine deaminase (pegademase bovine, PEG-ADA), Abatacept, Alefacept, Anakinra, Etanercept, Interleukin-1 (IL-1) receptor antagonist, Anakinra, Thymulin, TNF-alpha antagonist, Enfuvirtide, and Thymosin $\alpha 1$;

therapeutic proteins for use in the treatment of cancer ortumour diseases, including cytokines, chemokines, suicide gene products, immunogenic proteins or peptides, apoptosis inducers, angiogenesis inhibitors, heat shock proteins, tumour antigens, beta-catenin inhibitors, activators of the STING pathway, checkpoint modulators, innate immune activators, antibodies, dominant negative receptors and decoy receptors, inhibitors of myeloid derived suppressor cells (MDSCs), IDO pathway inhibitors, and proteins or peptides that bind inhibitors of apoptosis; therapeutic proteins selected from adjuvant or immunostimulating proteins, including human adjuvant proteins, particularly pattern recognition receptors TLR1, TLR2, TLR3, TLR4, TLR5, TLR6, TLR7, TLR8, TLR9, TLR10, TLR11; NOD1, NOD2, NOD3, NOD4, NOD5, NALP1, NALP2, NALP3, NALP4, NALP5, NALP6, NALP6, NALP7, NALP7, NALP8, NALP9, NALP10, NALP11, NALP12, NALP13, NALP14, I IPAF, NAIP, CIITA, RIG-I, MDA5 and LGP2, the signal transducers of TLR signaling including adaptor proteins including e.g. Trif and Cardif; components of the Small-GTPases signalling (RhoA, Ras, Rac1, Cdc42, Rab etc.), components of the PIP signalling (PI3K, Src-Kinases, etc.), components of the MyD88-dependent signalling (MyD88, IRAK1, IRAK2, IRAK4, TIRAP, TRAF6 etc.), components of the MyD88-independent signalling (TICAM1, TICAM2, TRAF6, TBK1, IRF3, TAK1, IRAK1 etc.); the activated kinases including e.g. Akt, MEKK1, MKK1, MKK3, MKK4, MKK6, MKK7, ERK1, ERK2, GSK3, PKC kinases, PKD kinases, GSK3 kinases, JNK, $\beta$38MAPK, TAK1, IKK, and TAK1; the activated transcription factors including e.g. NF-kB, c-Fos, c-Jun, c-Myc, CREB, AP-1, Elk-1, ATF2, IRF-3, IRF-7, heat shock proteins, such as HSP10, HSP60, HSP65, HSP70, HSP75 and HSP90, gp96, Fibrinogen, TypIII repeat extra domain A of fibronectin; or components of the complement system including C1q, MBL, C1r, C1s, C2b, Bb, D, MASP-1, MASP-2, C4b, C3b, C5a, C3a, C4a, C5b, C6, C7, C8, C9, CR1, CR2, CR3, CR4, C1qR, C11NH, C4 bp, MCP, DAF, H, I, P and CD59, or induced target genes including e.g. Beta-Defensin, cell surface proteins; or human adjuvant proteins including trif, flt-3 ligand, Gp96 or fibronectin, cytokines which induce or enhance an innate immune response, including IL-1 alpha, IL1 beta, IL-2, IL-6, IL-7, IL-8, IL-9, IL-12, IL-13, IL-15, IL-16, IL-17, IL-18, IL-21, IL-23, TNFalpha, IFNalpha, IFNbeta, IFNgamma, GM-CSF, G-CSF, M-CSF; chemokines including IL-8, IP-10, MCP-1, MIP-1alpha, RANTES, Eotaxin, CCL21; cytokines which are released from macrophages, including IL-1, IL-6, IL-8, IL-12 and TNF-alpha; as well as IL-1R1 and IL-1 alpha;

bacterial (adjuvant) proteins, including bacterial heat shock proteins or chaperons, including Hsp60, Hsp70, Hsp90, Hsp100; OmpA (Outer membrane protein)

from gram-negative bacteria; OspA; bacterial porins, including OmpF; bacterial toxins, including pertussis toxin (PT) from *Bordetella pertussis*, pertussis adenylate cyclase toxin CyaA and CyaC from *Bordetella pertussis*, PT-9K/129G mutant from pertussis toxin, pertussis adenylate cyclase toxin CyaA and CyaC from *Bordetella pertussis*, tetanus toxin, cholera toxin (CT), cholera toxin B-subunit, CTK63 mutant from cholera toxin, CTE112K mutant from CT, *Escherichia coli* heat-labile enterotoxin (LT), B subunit from heat-labile enterotoxin (LTB) *Escherichia coli* heat-labile enterotoxin mutants with reduced toxicity, including LTK63, LTR72; phenol-soluble modulin; neutrophil-activating protein (HP-NAP) from *Helicobacter pylori*; Surfactant protein D; Outer surface protein A lipoprotein from *Borrelia burgdorferi*, Ag38 (38 kDa antigen) from *Mycobacterium tuberculosis*; proteins from bacterial fimbriae; Enterotoxin CT of *Vibrio cholerae*, Pilin from pili from gram negative bacteria, and Surfactant protein A and bacterial flagellins;

protozoan (adjuvant) proteins, including Tc52 from *Trypanosoma cruzi*, PFTG from *Trypanosoma gondii*, Protozoan heat shock proteins, LeIF from *Leishmania* spp., profiling-like protein from *Toxoplasma gondii;* viral (adjuvant) proteins, including Respiratory Syncytial Virus fusion glycoprotein (F-protein), envelope protein from MMT virus, mouse leukemia virus protein, Hemagglutinin protein of wild-type measles virus;

fungal (adjuvant) proteins, including fungal immunomodulatory protein (FIP; LZ-8);

animal-derived proteins, including Keyhole limpet hemocyanin (KLH);

therapeutic proteins used for hormone replacement therapy, wherein the hormones include oestrogens, progesterone or progestins, and testosterone; and therapeutic proteins used for reprogramming somatic cells into pluri- or omnipotent stem cells, including Oct-3/4, Sox gene family (Sox1, Sox2, Sox3, and Sox15), Klf family (Klf1, Klf2, Klf4, and Klf5), Myc family (c-myc, L-myc, and N-myc), Nanog, and LIN28.

This invention includes methods for preventing, ameliorating or treating a disease or condition in a subject in need comprising administering to the subject a composition as described herein. The compositions of this invention may be used in the treatment of the human or animal body.

In this context, particularly preferred therapeutic proteins which can be used inter alia in the treatment of metabolic or endocrine disorders are selected from those which are disclosed in Table A (in combination with Table C) of WO 2017/191274. Furthermore, diseases which preferably can be treated with the composition of the invention, preferably selected from infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, are disclosed in WO 2017/191274 on pages 95 line 4—page 103 line 24. Further particularly preferred therapeutic proteins which can be used inter alia in the treatment of metabolic or endocrine disorders are disclosed in Table 1 of WO 2017/191274, which also refers to specific target/disease combinations, incorporated herein by reference, and also sequences. WO 2017/191274 incl. Tables A/C and Table 1 is incorporated herein by reference in its entirety.

In preferred embodiments, artificial nucleic acid (RNA) molecules, (pharmaceutical) compositions or vaccines or kits are used for treatment or prophylaxis of infectious diseases. The term "infection" or "infectious disease" relates to the invasion and multiplication of microorganisms such as bacteria, viruses, and parasites that are not normally present within the body. An infection may cause no symptoms and be subclinical, or it may cause symptoms and be clinically apparent. An infection may remain localized, or it may spread through the blood or lymphatic system to become systemic. Infectious diseases in this context, preferably include viral, bacterial, fungal or protozoological infectious diseases. In particular, infectious diseases are selected from the group as disclosed starting on page 157, section "Infectious diseases" (ending on page 160) of WO 2019/077001 A1; WO 2019/077001 A1 being incorporated herein by reference in its entirety.

In this context, further particularly preferred examples for diseases and/or conditions for which the compositions of the invention or respectively the translatable molecules of the invention can be used for treatment are disclosed in Table 2 of US 2019/0002906; US 2019/0002906 incl. Table 2 being incorporated herein by reference in its entirety.

Liver disease or liver-related diseases in animals, more particularly humans, may include but would not be limited to congenital diseases or acquired diseases for example viral and parasite infectious diseases, oncologic pathologies such as primary tumours and metastases, metabolic, amino acid and/or endocrine disorders as well as inflammatory and immune and auto-immune conditions. Liver diseases which may preferably be treated with the inventive composition are selected from, but not limited to the group consisting of Hepatitis C, Hepatitis B, Hepatitis, Hepatitis A, Cirrhosis, Liver Cancer, Hepatocellular Carcinoma, Hepatic Encephalopathy, Autoimmune Hepatitis, Wilson Disease, Alpha-1 Antitrypsin Deficiency (AAT-deficiency), Hepatitis D, Phenylketonuria (PKU), Wilson's disease (hepatolenticular degeneration), Tyrosinemia Type I (FAH deficiency), Alagille Syndrome, Portal Hypertension, Steatohepatitis, Chronic Hepatitis and Hepatitis E.

In a further preferred embodiment, the compositions of the present invention may be used in method of treating or preventing a disorder, wherein the disorder is a liver disease, preferably selected from the group consisting of liver fibrosis, liver cirrhosis and liver cancer. Accordingly, the mRNA comprising at least one coding sequence may encode a therapeutic protein or a fragment or variant thereof for use in treating or preventing a liver disease selected from the group consisting of liver fibrosis, liver cirrhosis and liver cancer. Furthermore, preferably, the mRNA for treating or preventing liver diseases or a liver disease selected from the group consisting of liver fibrosis, liver cirrhosis and liver cancer encodes a peptide or protein selected from the group consisting of hepatocyte nuclear factor 4 alpha (HNF4A), CCAAT/enhancer-binding protein alpha (CEBPA), fibroblast growth factor 21 (FGF21), extracellular matrix protease or human collagenase MMP1, Hepatocyte Growth Factor (HGF), TNF-related apoptosis-inducing ligand (TRAIL), opioid growth factor receptor-like 1 (OGFRL1), clostridial type II collagenase, Relaxin 1 (RLN1), Relaxin 2 (RLN2) and Relaxin 3 (RLN3). In this regard, the liver disease specific disclosure of WO 2018/104538 A1 as well as the sequences which are disclosed in WO 2018/104538 A1 is incorporated herein by reference.

Other Antigens

Further antigens useful for the present invention are listed in WO 2018/078053 on pages 48-51; WO 2018/078053 being incorporated herein by reference in its entirety.

Allergenic Antigens and Autoimmune Self-Antigens

As mentioned, the mRNA compound comprised in the composition of the invention may, according to some embodiments, encode an antigen that represents an allergen, or an allergenic antigen or a self-antigen, also referred to as autoantigen or autoimmune antigen.

Such antigens and self-antigens associated with allergy or allergic disease (allergens or allergenic antigens) are derived from or preferably selected from, but not limited to, the group of antigens disclosed on pages 59-73 in WO 2018/078053 A1; WO 2018/078053 A1 being incorporated herein by reference in its entirety.

Checkpoint Modulators/Checkpoint Inhibitors

In the context of the present invention, an immune checkpoint protein, checkpoint modulator or checkpoint inhibitor is typically a molecule, such as a protein (e.g. an antibody), a dominant negative receptor, a decoy receptor, or a ligand or a fragment or variant thereof, which modulates the function of an immune checkpoint protein, e.g. it inhibits or reduces the activity of checkpoint inhibitors (or inhibitory checkpoint molecules) or it stimulates or enhances the activity of checkpoint stimulators (or stimulatory checkpoint molecules). Therefore, checkpoint modulators as defined herein, influence the activity of checkpoint molecules. In this context, inhibitory checkpoint molecules are defined as checkpoint inhibitors and can be used synonymously. In addition, stimulatory checkpoint molecules are defined as checkpoint stimulators and can be used synonymously.

In a further preferred embodiment, the mRNA compound comprising an mRNA encodes an immune checkpoint protein, checkpoint modulators or checkpoint inhibitor, preferably as defined herein, ora fragment or variant thereof, wherein the immune checkpoint protein, checkpoint modulators or checkpoint inhibitor is preferably selected from, but not limited to, the group consisting of immune checkpoint proteins, checkpoint modulators or checkpoint inhibitors disclosed on pages 51-56 in WO 2018/078053 A1; WO 2018/078053 A1 being incorporated herein by reference in its entirety.

RNA Elements, mRNA Elements

According to certain embodiments of the present invention, the mRNA sequence is mono-, bi-, or multicistronic, preferably as defined herein. The coding sequences in a bi- or multicistronic mRNA preferably encode distinct peptides or proteins as defined herein or a fragment or variant thereof. Preferably, the coding sequences encoding two or more peptides or proteins may be separated in the bi- or multicistronic mRNA by at least one IRES (internal ribosomal entry site) sequence, as defined below. Thus, the term "encoding two or more peptides or proteins" may mean, without being limited thereto, that the bi- or even multicistronic mRNA, may encode e.g. at least two, three, four, five, six or more (preferably different) peptides or proteins or their fragments or variants within the definitions provided herein. More preferably, without being limited thereto, the bi- or even multicistronic mRNA, may encode, for example, at least two, three, four, five, six or more (preferably different) peptides or proteins as defined herein or their fragments or variants as defined herein. In this context, a so-called IRES (internal ribosomal entry site) sequence as defined above can function as a sole ribosome binding site, but it can also serve to provide a bi- or even multicistronic mRNA as defined above, which encodes several peptides or proteins which are to be translated by the ribosomes independently of one another. Examples of IRES sequences, which can be used according to the invention, are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukemia virus (MLV), simian immunodeficiency viruses (SIV) or cricket paralysis viruses (CrPV).

According to a further embodiment the at least one coding region of the mRNA sequence according to the invention may encode at least two, three, four, five, six, seven, eight and more peptides or proteins (or fragments and derivatives thereof) as defined herein linked with or without an amino acid linker sequence, wherein said linker sequence can comprise rigid linkers, flexible linkers, cleavable linkers (e.g., self-cleaving peptides) or a combination thereof. Therein, the peptides or proteins may be identical or different or a combination thereof. Particular peptide or protein combinations can be encoded by said mRNA encoding at least two peptides or proteins as explained herein (also referred to herein as "multi-antigen-constructs/mRNA").

In another preferred embodiment, the mRNA compound comprised in the composition encodes a pathogenic antigen whose amino acid sequence is not modified with respect to the respective wild type amino acid sequence. In this case, the mRNA compound may also comprise a coding region with a nucleic acid sequence which is not modified with respect to the respective wild type mRNA sequence. For example, the mRNA compound may be a natural and non-modified mRNA. As used herein, natural and non-modified mRNA encompasses mRNA generated in vitro, without chemical modifications or changes in the sequence.

mRNA Modifications and Sequences

In another embodiment of the invention, the mRNA compound comprises an artificial mRNA. In this context, artificial mRNA encompasses mRNA with chemical modifications, sequence modifications or non-natural sequences.

Chemical Modifications

According to another embodiment of the invention, the mRNA compound comprised in the composition comprises at least one chemical modification. In one embodiment, the chemical modification may be selected from the group consisting of base modifications, sugar modifications, backbone modifications and lipid modifications. A backbone modification in connection with the present invention is a modification in which phosphates of the backbone of the nucleotides contained in an mRNA compound comprising an mRNA sequence as defined herein are chemically modified. A sugar modification in connection with the present invention is a chemical modification of the sugar of the nucleotides of the mRNA compound comprising an mRNA sequence as defined herein. Furthermore, a base modification in connection with the present invention is a chemical modification of the base moiety of the nucleotides of the mRNA compound comprising an mRNA sequence. In this context, nucleotide analogues or modifications are preferably selected from nucleotide analogues, which are applicable for transcription and/or translation.

Sugar Modifications

The modified nucleosides and nucleotides, which may be incorporated into a modified mRNA compound comprising an mRNA sequence as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R═H, alkyl, cycloalkyl, aryl, aralkyl, heteroaryl or sugar); polyethylene glycols (PEG), —O(CH2CH2O)nCH2CH2OR; “locked” nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

“Deoxy” modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified mRNA can include nucleotides containing, for instance, arabinose as the sugar.

Backbone Modifications

The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phospho-rodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Lipid Modifications

A lipid-modified mRNA typically comprises an mRNA as defined herein. Such a lipid-modified mRNA as defined herein typically further comprises at least one linker covalently linked with that mRNA, and at least one lipid covalently linked with the respective linker. Alternatively, the lipid-modified mRNA comprises at least one mRNA as defined herein and at least one (bifunctional) lipid covalently linked (without a linker) with that mRNA. According to a third alternative, the lipid-modified mRNA comprises an mRNA molecule as defined herein, at least one linker covalently linked with that mRNA, and at least one lipid covalently linked with the respective linker, and also at least one (bifunctional) lipid covalently linked (without a linker) with that mRNA. In this context, it is particularly preferred that the lipid modification is present at the terminal ends of a linear mRNA sequence.

In another preferred embodiment, the mRNA compound does not comprise nucleoside modifications, in particular no base modifications. In a further embodiment, the mRNA compound does not comprise 1-methylpseudouridine, pseudouridine or 5-methoxy-uridine modifications. In one preferred embodiment, the mRNA comprises only naturally existing nucleosides. In a further preferred embodiment, the mRNA compound does not comprise any chemical modification and optionally comprises sequence modifications. In a further preferred embodiment of the invention the mRNA compound only comprises the naturally existing nucleosides adenine, uracil, guanine and cytosine.

Base Modifications

In an alternative embodiment, the mRNA compound comprises at least one base modification.

Modified nucleosides and nucleotides, which may be incorporated into a modified mRNA compound comprising an mRNA sequence as described herein can further be modified in the nucleobase moiety. Examples of nucleobases found in mRNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl-inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-lodo-2'-deoxycytidine-5'-triphosphate, 5-iodouridine-5'-triphosphate, 5-lodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate. In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1- deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyl-adenosine, 2-methylthio-N6-threonyl carbamoyladenosine, N6,N6-dimethyladenosine, 7-methyladenine, 2-methyl-thio-adenine, and 2-methoxy-adenine. In other embodiments, modified nucleosides include inosine, 1-methylinosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. In some embodiments, the nucleotide can be modified on the major groove face and can include replacing hydrogen on C-5 of uracil with a methyl group or a halo group. In specific embodiments, a modified nucleoside is 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

In further specific embodiments, a modified mRNA may comprise nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-aminopurine, Pseudo-iso-cytidine, 6-Chloro-purine, N6-methyl-adenosine, α-thio-adenosine, 8-azido-adenosine, 7-deazaadenosine.

In further embodiments, the chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

In a specific embodiment, the chemical modification is selected from the group consisting of pseudouracil (LP), N1-methylpseudouracil (N1Mp), 1-ethylpseudouracil, 2-thiouracil (s2U), 4-thiouracil, 5-methylcytosine, 5-methyluracil, 5-methoxyuracil, and any combination thereof.

Sequence Modifications

According to a further embodiment, the mRNA compound comprises a modified mRNA sequence. For example, a modification of the mRNA sequence may lead to the stabilization of the mRNA sequence. In one embodiment, the mRNA compound comprises a stabilized mRNA sequence comprising at least one coding region as defined herein. In particular, the composition of the invention as described herein may comprise an mRNA compound comprising a coding region encoding a peptide or a protein, such as defined in any of the embodiments described herein, wherein said coding region exhibits a sequence modification.

According to one embodiment, the mRNA compound comprises a "stabilized mRNA sequence", that is to say as an mRNA that is essentially resistant to in vivo degradation (e.g. by an exo- or endo-nuclease). Such stabilization can be effected, for example, by a modified phosphate backbone of the mRNA of the present invention. A backbone modification in connection with the present invention is a modification in which phosphates of the backbone of the nucleotides contained in the mRNA are chemically modified. Nucleotides that may be preferably used in this connection contain e.g. a phosphorothioate-modified phosphate backbone, preferably at least one of the phosphate oxygens contained in the phosphate backbone being replaced by a sulfur atom. Stabilized mRNAs may further include, for example: non-ionic phosphate analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. Such backbone modifications typically include, without implying any limitation, modifications from the group consisting of methylphosphonates, phosphoramidates and phosphorothioates (e.g. cytidine-5'-O-(1-thiophosphate)).

In the following, specific modifications are described which are preferably capable of "stabilizing" the mRNA as defined herein.

G/C Content Modifications

According to one embodiment, the mRNA compound comprises an mRNA sequence which is modified, and thus stabilized, by a modification of its guanosine/cytosine (G/C) content. Such modification, or at least one of these modifications, is located in a coding region of the mRNA compound.

In one preferred embodiment, the G/C content of the coding region of the mRNA compound is increased compared to the G/C content of the coding region of the respective wild type mRNA, i.e. the unmodified mRNA. At the same time, the amino acid sequence encoded by the mRNA is preferably not modified as compared to the amino acid sequence encoded by the respective wild type mRNA. For example, the composition as described above may comprise an mRNA compound encoding a pathogenic antigen whose amino acid sequence is not modified with respect to the encoded amino acid sequence of the respective wild type nucleic acid.

This modification of the mRNA sequence of the present invention is based on the fact that the sequence of any mRNA region to be translated is important for efficient translation of that mRNA. Thus, the composition of the mRNA and the sequence of various nucleotides are important. In particular, sequences having an increased G (guanosine)/C (cytosine) content are more stable than sequences having an increased A (adenosine)/U (uracil) content. According to the invention, the codons of the mRNA are therefore varied compared to the respective wild type mRNA, while retaining the translated amino acid sequence, such that they include an increased amount of G/C nucleotides. In respect to the fact that several codons code for one and the same amino acid (so-called degeneration of the genetic code), the most favorable codons for the stability can be determined (so-called alternative codon usage). Depending on the amino acid to be encoded by the mRNA, there are various possibilities for modification of the mRNA sequence, compared to its wild type sequence. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present. In contrast, codons which contain A and/or U nucleotides can be modified by substitution of other codons, which code for the same amino acids but contain no A and/or U. Examples of these are: the codons for Pro can be modified from CCU or CCA to CCC or CCG; the codons for Arg can be modified from CGU or CGA or AGA or AGG to CGC or CGG; the codons for Ala can be modified from GCU or GCA to GCC or GCG; the codons for Gly can be modified from GGU or GGA to GGC or GGG. In other cases, although A or U nucleotides cannot be eliminated from the codons, it is however possible to decrease the A and U content by using codons which contain a lower content of A and/or U nucleotides. Examples of these are: the codons for Phe can be modified from UUU to UUC; the codons for Leu can be modified from UUA, UUG, CUU or CUA to CUC or CUG; the codons for Ser can be modified from UCU or UCA or AGU to UCC, UCG or AGC; the codon for Tyr can be modified from UAU to UAC; the codon for Cys can be modified from UGU to UGC; the codon for His can be modified from CAU to CAC; the codon for Gln can be modified from CAA to CAG; the codons for Ile can be modified from AUU or AUA to AUC; the codons for Thr can be modified from ACU or ACA to ACC or ACG; the codon for Asn can be modified from AAU to AAC; the codon for Lys can be modified from AAA to AAG; the codons for Val can be modified from GUU or GUA to GUC or GUG; the codon for Asp can be modified from GAU to GAC; the codon for Glu can be modified from GAA to GAG; the stop codon UAA can be modified to UAG or UGA. In the case of the codons for Met (AUG) and Trp (UGG), on the other hand, there is no possibility of sequence modification. The substitutions listed above can be used either individually or in all possible combinations to increase the G/C content of the mRNA sequence of the present invention compared to its particular wild type mRNA (i.e. the original sequence). Thus, for example, all codons for Thr occurring in the wild type sequence can be modified to ACC (or ACG). Preferably, however, for example, combinations of the above substitution possibilities are used:

- substitution of all codons coding for Thr in the original sequence (wild type mRNA) to ACC (or ACG) and
- substitution of all codons originally coding for Ser to UCC (or UCG or AGC);
- substitution of all codons coding for Ile in the original sequence to AUC and
- substitution of all codons originally coding for Lys to AAG and
- substitution of all codons originally coding for Tyr to UAC;
- substitution of all codons coding for Val in the original sequence to GUC (or GUG) and
- substitution of all codons originally coding for Glu to GAG and
- substitution of all codons originally coding for Ala to GCC (or GCG) and
- substitution of all codons originally coding for Arg to CGC (or CGG);
- substitution of all codons coding for Val in the original sequence to GUC (or GUG) and
- substitution of all codons originally coding for Glu to GAG and
- substitution of all codons originally coding for Ala to GCC (or GCG) and
- substitution of all codons originally coding for Gly to GGC (or GGG) and
- substitution of all codons originally coding for Asn to AAC;
- substitution of all codons coding for Val in the original sequence to GUC (or GUG) and
- substitution of all codons originally coding for Phe to UUC and
- substitution of all codons originally coding for Cys to UGC and
- substitution of all codons originally coding for Leu to CUG (or CUC) and
- substitution of all codons originally coding for Gln to CAG and
- substitution of all codons originally coding for Pro to CCC (or CCG); etc.

Preferably, the G/C content of the coding region of the mRNA compound comprising an mRNA sequence of the present invention is increased by at least 7%, more preferably by at least 15%, particularly preferably by at least 20%, compared to the G/C content of the coding region of the wild type RNA, which codes for an antigen as defined herein or a fragment or variant thereof. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a peptide or protein as defined herein or a fragment or variant thereof or the whole sequence of the wild type mRNA sequence are substituted, thereby increasing the G/C content of said sequence. In this context, it is particularly preferable to increase the G/C content of the mRNA sequence of the present invention, preferably of the at least one coding region of the mRNA sequence according to the invention, to the maximum (i.e. 100% of the substitutable codons) as compared to the wild type sequence. According to the invention, a further preferred modification of the mRNA sequence of the present invention is based on the finding that the translation efficiency is also determined by a different frequency in the occurrence of tRNAs in cells. Thus, if so-called “rare codons” are present in the mRNA sequence of the present invention to an increased extent, the corresponding modified mRNA sequence is translated to a significantly poorer degree than in the case where codons coding for relatively “frequent” tRNAs are present. According to the invention, in the modified mRNA sequence of the present invention, the region which codes for a peptide or protein as defined herein or a fragment or variant thereof is modified compared to the corresponding region of the wild type mRNA sequence such that at least one codon of the wild type sequence, which codes for a tRNA which is relatively rare in the cell, is exchanged for a codon, which codes for a tRNA which is relatively frequent in the cell and carries the same amino acid as the relatively rare tRNA. By this modification, the sequence of the mRNA of the present invention is modified such that codons for which frequently occurring tRNAs are available are inserted. In other words, according to the invention, by this modification all codons of the wild type sequence, which code for a tRNA which is relatively rare in the cell, can in each case be exchanged for a codon, which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons, which use for the particular amino acid the tRNA which occurs the most frequently, e.g. the Gly codon, which uses the tRNA, which occurs the most frequently in the (human) cell, are particularly preferred. According to the invention, it is particularly preferable to link the sequential G/C content which is increased, in particular maximized, in the modified mRNA sequence of the present invention, with the "frequent" codons without modifying the amino acid sequence of the protein encoded by the coding region of the mRNA sequence. This preferred embodiment allows provision of a particularly efficiently translated and stabilized (modified) mRNA sequence of the present invention. The determination of a modified mRNA sequence of the present invention as described above (increased G/C content; exchange of tRNAs) can be carried out using the computer program explained in WO02/098443—the disclosure content of which is included in its full scope in the present invention. Using this computer program, the nucleotide sequence of any desired mRNA sequence can be modified with the aid of the genetic code or the degenerative nature thereof such that a maximum G/C content results, in combination with the use of codons which code for tRNAs occurring as frequently as possible in the cell, the amino acid sequence coded by the modified mRNA sequence preferably not being modified compared to the non-modified sequence. Alternatively, it is also possible to modify only the G/C content or only the codon usage compared to the original sequence. The source code in Visual Basic 6.0 (development environment used: Microsoft Visual Studio Enterprise 6.0 with Service Pack 3) is also described in WO02/098443. In a further preferred embodiment of the present invention, the A/U content in the environment of the ribosome binding site of the mRNA sequence of the present invention is increased compared to the A/U content in the environment of the ribosome binding site of its respective wild type mRNA. This modification (an increased A/U content around the ribosome binding site) increases the efficiency of ribosome binding to the mRNA. An effective binding of the ribosomes to the ribosome binding site (Kozak sequence: SEQ ID NO:1 or SEQ ID NO:2, or a minimal Kozak sequence ACC, wherein the AUG forms the start codon) in turn has the effect of an efficient translation of the mRNA. According to a further embodiment of the present invention, the mRNA sequence of the present invention may be modified with respect to potentially destabilizing sequence elements. Particularly, the coding region and/or the 5' and/or 3' untranslated region of this mRNA sequence may be modified compared to the respective wild type mRNA such that it contains no destabilizing sequence elements, the encoded amino acid sequence of the modified mRNA sequence preferably not being modified compared to its respective wild type mRNA. It is known that, for example in sequences of eukaryotic mRNAs, destabilizing sequence elements (DSE) occur, to which signal proteins bind and regulate enzymatic degradation of mRNA in vivo. For further stabilization of the modified mRNA sequence, optionally in the region which encodes at least one peptide or protein as defined herein or a fragment or variant thereof, one or more such modifications compared to the corresponding region of the wild type mRNA can therefore be carried out, so that no or substantially no destabilizing sequence elements are contained there. According to the invention, DSE present in the untranslated regions (3'- and/or 5'-UTR) can also be eliminated from the mRNA sequence of the present invention by such modifications. Such destabilizing sequences are e.g. AU-rich sequences (AURES), which occur in 3'-UTR sections of numerous unstable mRNAs (Caput et al., Proc. Natl. Acad. Sci. USA 1986, 83: 1670-1674). The mRNA sequence of the present invention is therefore preferably modified compared to the respective wild type mRNA such that the mRNA sequence of the present invention contains no such destabilizing sequences. This also applies to those sequence motifs which are recognized by possible endonucleases, e.g. the sequence GAACAAG, which is contained in the 3'-UTR segment of the gene encoding the transferrin receptor (Binder et al., EMBO J. 1994, 13: 1969-1980). These sequence motifs are also preferably removed in the mRNA sequence of the present invention.

According to a further embodiment, the mRNA compound comprises an mRNA sequence comprising a coding region that comprises or consists of any one of the RNA sequences as disclosed in Tabs. 1-5, FIGS. 20-24 or in the sequence listing of WO 2018/078053; Tabs. 1-5 or FIGS. 20-24 of WO 2018/078053; WO 2018/078053 incorporated by reference in its entirety.

Sequences Adapted to Human Codon Usage

A further preferred modification of the mRNA compound is based on the finding that codons encoding the same amino acid typically occur at different frequencies. According to this embodiment, the frequency of the codons encoding the same amino acid in the coding region of the mRNA compound differs from the naturally occurring frequency of that codon according to the human codon usage as e.g. shown in Table 2 (Human codon usage table). For example, in the case of the amino acid alanine (Ala), the wild type coding region is preferably adapted in a way that the codon "GCC" is used with a frequency of 0.40, the codon "GCT" is used with a frequency of 0.28, the codon "GCA" is used with a frequency of 0.22 and the codon "GCG" is used with a frequency of 0.10 etc. (see Table 2).

TABLE 2

Human codon usage table, most frequent codons are marked with asterisks

| Amino acid | codon | fraction | /1000 |
|---|---|---|---|
| Ala | GCG | 0.10 | 7.4 |
| Ala | GCA | 0.22 | 15.8 |
| Ala | GCT | 0.28 | 18.5 |
| Ala | GCC* | 0.40 | 27.7 |
| Cys | TGT | 0.42 | 10.6 |
| Cys | TGC* | 0.58 | 12.6 |
| Asp | GAT | 0.44 | 21.8 |
| Asp | GAC* | 0.56 | 25.1 |
| Glu | GAG* | 0.59 | 39.6 |
| Glu | GAA | 0.41 | 29.0 |
| Phe | TTT | 0.43 | 17.6 |
| Phe | TTC* | 0.57 | 20.3 |
| Gly | GGG | 0.23 | 16.5 |
| Gly | GGA | 0.26 | 16.5 |
| Gly | GGT | 0.18 | 10.8 |
| Gly | GGC* | 0.33 | 22.2 |
| His | CAT | 0.41 | 10.9 |
| His | CAC* | 0.59 | 15.1 |
| Ile | ATA | 0.14 | 7.5 |
| Ile | ATT | 0.35 | 16.0 |
| Ile | ATC* | 0.52 | 20.8 |
| Lys | AAG* | 0.60 | 31.9 |
| Lys | AAA | 0.40 | 24.4 |
| Leu | TTG | 0.12 | 12.9 |
| Leu | TTA | 0.06 | 7.7 |
| Leu | CTG* | 0.43 | 39.6 |
| Leu | CTA | 0.07 | 7.2 |
| Leu | CTT | 0.12 | 13.2 |
| Leu | CTC | 0.20 | 19.6 |

TABLE 2-continued

| Human codon usage table, most frequent codons are marked with asterisks | | | |
|---|---|---|---|
| Amino acid | codon | fraction | /1000 |
| Met | ATG* | 1 | 22.0 |
| Asn | AAT | 0.44 | 17.0 |
| Asn | AAC* | 0.56 | 19.1 |
| Pro | CCG | 0.11 | 6.9 |
| Pro | CCA | 0.27 | 16.9 |
| Pro | CCT | 0.29 | 17.5 |
| Pro | CCC* | 0.33 | 19.8 |
| Gln | CAG* | 0.73 | 34.2 |
| Gln | CAA | 0.27 | 12.3 |
| Arg | AGG | 0.22 | 12.0 |
| Arg | AGA* | 0.21 | 12.1 |
| Arg | CGG | 0.19 | 11.4 |
| Arg | CGA | 0.10 | 6.2 |
| Arg | CGT | 0.09 | 4.5 |
| Arg | CGC | 0.19 | 10.4 |
| Ser | AGT | 0.14 | 12.1 |
| Ser | AGC* | 0.25 | 19.5 |
| Ser | TCG | 0.06 | 4.4 |
| Ser | TCA | 0.15 | 12.2 |
| Ser | TCT | 0.18 | 15.2 |
| Ser | TCC | 0.23 | 17.7 |
| Thr | ACG | 0.12 | 6.1 |
| Thr | ACA | 0.27 | 15.1 |
| Thr | ACT | 0.23 | 13.1 |
| Thr | ACC* | 0.38 | 18.9 |
| Val | GTG* | 0.48 | 28.1 |
| Val | GTA | 0.10 | 7.1 |
| Val | GTT | 0.17 | 11.0 |
| Val | GTC | 0.25 | 14.5 |
| Trp | TGG* | 1 | 13.2 |
| Tyr | TAT | 0.42 | 12.2 |
| Tyr | TAC* | 0.58 | 15.3 |
| Stop | TGA* | 0.61 | 1.6 |
| Stop | TAG | 0.17 | 0.8 |
| Stop | TAA | 0.22 | 1.0 |

*most frequent codon

Codon-Optimized Sequences

In one embodiment, all codons of the wild type sequence which code for a tRNA, which is relatively rare in the cell, are exchanged for a codon which codes for a tRNA, which is relatively frequent in the cell and which, in each case, carries the same amino acid as the relatively rare tRNA. Therefore it is particularly preferred that the most frequent codons are used for each encoded amino acid (see Table 2). Such an optimization procedure increases the codon adaptation index (CAI) and ultimately maximizes the CAI. In the context of the invention, sequences with increased or maximized CAI are typically referred to as "codon-optimized" sequences and/or CAI increased and/or maximized sequences. According to a preferred embodiment, the mRNA compound comprising an mRNA sequence of the present invention comprises at least one coding region, wherein the coding region/sequence is codon-optimized as described herein. More preferably, the codon adaptation index (CAI) of the at least one coding sequence is at least 0.5, at least 0.8, at least 0.9 or at least 0.95. Most preferably, the codon adaptation index (CAI) of the at least one coding sequence is 1.

For example, in the case of the amino acid alanine (Ala) present in the amino acid sequence encoded by the at least one coding sequence of the RNA according to the invention, the wild type coding sequence is adapted in a way that the most frequent human codon "GCC" is always used for said amino acid, or for the amino acid Cysteine (Cys), the wild type sequence is adapted in a way that the most frequent human codon "TGC" is always used for said amino acid etc.

C-Optimized Sequences

According to another embodiment, the mRNA compound comprising an mRNA sequence having a modified—in particular increased—cytosine (C) content, preferably of the coding region of the mRNA sequence, compared to the C content of the coding region of the respective wild type mRNA, i.e. the unmodified mRNA. At the same time, the amino acid sequence encoded by the at least one coding region of the mRNA sequence of the present invention is preferably not modified as compared to the amino acid sequence encoded by the respective wild type mRNA.

In a preferred embodiment of the present invention, the modified mRNA sequence is modified such that at least 10%, 20%, 30%, 40%, 50%, 60%, 70% or 80%, or at least 90% of the theoretically possible maximum cytosine-content or even a maximum cytosine-content is achieved.

In further preferred embodiments, at least 10%, 20%, 30%, 40%, 50%, 60%, 70%, 80%, 90% or even 100% of the codons of the target mRNA wild type sequence, which are "cytosine content optimizable" are replaced by codons having a higher cytosine-content than the ones present in the wild type sequence.

In a further preferred embodiment, some of the codons of the wild type coding sequence may additionally be modified such that a codon for a relatively rare tRNA in the cell is exchanged by a codon for a relatively frequent tRNA in the cell, provided that the substituted codon for a relatively frequent tRNA carries the same amino acid as the relatively rare tRNA of the original wild type codon. Preferably, all of the codons for a relatively rare tRNA are replaced by a codon for a relatively frequent tRNA in the cell, except codons encoding amino acids, which are exclusively encoded by codons not containing any cytosine, or except for glutamine (Gln), which is encoded by two codons each containing the same number of cytosines.

In a further preferred embodiment of the present invention, the modified target mRNA is modified such that at least 80%, or at least 90% of the theoretically possible maximum cytosine-content or even a maximum cytosine-content is achieved by means of codons, which code for relatively frequent tRNAs in the cell, wherein the amino acid sequence remains unchanged.

Due to the naturally occurring degeneracy of the genetic code, more than one codon may encode a particular amino acid. Accordingly, 18 out of 20 naturally occurring amino acids are encoded by more than one codon (with Tryp and Met being an exception), e.g. by 2 codons (e.g. Cys, Asp, Glu), by three codons (e.g. IIe), by 4 codons (e.g. Al, Gly, Pro) or by 6 codons (e.g. Leu, Arg, Ser). However, not all codons encoding the same amino acid are utilized with the same frequency under in vivo conditions. Depending on each single organism, a typical codon usage profile is established.

The term "cytosine content-optimizable codon" as used within the context of the present invention refers to codons, which exhibit a lower content of cytosines than other codons encoding the same amino acid. Accordingly, any wild type codon, which may be replaced by another codon encoding the same amino acid and exhibiting a higher number of cytosines within that codon, is considered to be cytosine-optimizable (C-optimizable). Any such substitution of a C-optimizable wild type codon by the specific C-optimized codon within a wild type coding region increases its overall C-content and reflects a C-enriched modified mRNA sequence. According to a preferred embodiment, the mRNA sequence of the present invention, preferably the at least one coding region of the mRNA sequence of the present invention comprises or consists of a C-maximized mRNA sequence containing C-optimized codons for all potentially C-optimizable codons. Accordingly, 100% or all of the theoretically replaceable C-optimizable codons are preferably replaced by C-optimized codons over the entire length of the coding region.

In this context, cytosine-content optimizable codons are codons, which contain a lower number of cytosines than other codons coding for the same amino acid.

Any of the codons GCG, GCA, GCU codes for the amino acid Ala, which may be exchanged by the codon GCC encoding the same amino acid, and/or

- the codon UGU that codes for Cys may be exchanged by the codon UGC encoding the same amino acid, and/or
- the codon GAU which codes for Asp may be exchanged by the codon GAC encoding the same amino acid, and/or
- the codon that UUU that codes for Phe may be exchanged for the codon UUC encoding the same amino acid, and/or
- any of the codons GGG, GGA, GGU that code Gly may be exchanged by the codon GGC encoding the same amino acid, and/or
- the codon CAU that codes for His may be exchanged by the codon CAC encoding the same amino acid, and/or
- any of the codons AUA, AUU that code for Ile may be exchanged by the codon AUC, and/or
- any of the codons UUG, UUA, CUG, CUA, CUU coding for Leu may be exchanged by the codon CUC encoding the same amino acid, and/or
- the codon AAU that codes for Asn may be exchanged by the codon AAC encoding the same amino acid, and/or
- any of the codons CCG, CCA, CCU coding for Pro may be exchanged by the codon CCC encoding the same amino acid, and/or
- any of the codons AGG, AGA, CGG, CGA, CGU coding for Arg may be exchanged by the codon CGC encoding the same amino acid, and/or
- any of the codons AGU, AGC, UCG, UCA, UCU coding for Ser may be exchanged by the codon UCC encoding the same amino acid, and/or
- any of the codons ACG, ACA, ACU coding for Thr may be exchanged by the codon ACC encoding the same amino acid, and/or
- any of the codons GUG, GUA, GUU coding for Val may be exchanged by the codon GUC encoding the same amino acid, and/or
- the codon UAU coding for Tyr may be exchanged by the codon UAC encoding the same amino acid.

In any of the above instances, the number of cytosines is increased by 1 per exchanged codon. Exchange of all non C-optimized codons (corresponding to C-optimizable codons) of the coding region results in a C-maximized coding sequence. In the context of the invention, at least 70%, preferably at least 80%, more preferably at least 90%, of the non C-optimized codons within the at least one coding region of the mRNA sequence according to the invention are replaced by C-optimized codons.

It may be preferred that for some amino acids the percentage of C-optimizable codons replaced by C-optimized codons is less than 70%, while for other amino acids the percentage of replaced codons is higher than 70% to meet the overall percentage of C-optimization of at least 70% of all C-optimizable wild type codons of the coding region.

Preferably, in a C-optimized mRNA sequence, at least 50% of the C-optimizable wild type codons for any given amino acid are replaced by C-optimized codons, e.g. any modified C-enriched mRNA sequence preferably contains at least 50% C-optimized codons at C-optimizable wild type codon positions encoding any one of the above mentioned amino acids Ala, Cys, Asp, Phe, Gly, His, Ile, Leu, Asn, Pro, Arg, Ser, Thr, Val and Tyr, preferably at least 60%.

In this context, codons encoding amino acids which are not cytosine content-optimizable and which are, however, encoded by at least two codons, may be used without any further selection process. However, the codon of the wild type sequence that codes for a relatively rare tRNA in the cell, e.g. a human cell, may be exchanged for a codon that codes for a relatively frequent tRNA in the cell, wherein both code for the same amino acid. Accordingly, the relatively rare codon GAA coding for Glu may be exchanged by the relative frequent codon GAG coding for the same amino acid, and/or

- the relatively rare codon AAA coding for Lys may be exchanged by the relative frequent codon AAG coding for the same amino acid, and/or
- the relatively rare codon CAA coding for Gln may be exchanged for the relative frequent codon CAG encoding the same amino acid.

In this context, the amino acids Met (AUG) and Trp (UGG), which are encoded by only one codon each, remain unchanged. Stop codons are not cytosine-content optimized, however, the relatively rare stop codons amber, ochre (UAA, UAG) may be exchanged by the relatively frequent stop codon opal (UGA).

The single substitutions listed above may be used individually as well as in all possible combinations in order to optimize the cytosine-content of the modified mRNA sequence compared to the wild type mRNA sequence.

Accordingly, the at least one coding sequence as defined herein may be changed compared to the coding region of the respective wild type mRNA in such a way that an amino acid encoded by at least two or more codons, of which one comprises one additional cytosine, such a codon may be exchanged by the C-optimized codon comprising one additional cytosine, wherein the amino acid is preferably unaltered compared to the wild type sequence.

According to a further preferred embodiment, the composition of the invention comprises an mRNA compound whose coding region has an increased G/C content compared to the G/C content of the corresponding coding region of the corresponding wild type mRNA, and/or an increased C content compared to the C content of the corresponding coding region of the corresponding wild type mRNA, and/or wherein the codons in the coding region are adapted to human codon usage, wherein the codon adaptation index (CAI) is preferably increased or maximised, and wherein the amino acid sequence encoded by the mRNA sequence is preferably not being modified compared to the amino acid sequence encoded by the corresponding wild type mRNA.

In one preferred embodiment of the invention, the composition comprises an mRNA compound comprising a coding region encoding a peptide or a protein, wherein the coding region exhibits a sequence modification selected from a G/C content modification, a codon modification, a codon optimization or a C-optimization of the sequence.

In another preferred embodiment, the composition or lipid nanoparticle as defined herein comprises an mRNA comprising a coding region encoding a peptide or protein as defined herein, wherein, compared with the coding region of the corresponding wild-type mRNA,

- the G/C content of the coding region is increased;
- the C content of the coding region is increased;

the codon usage in the coding region is adapted to the human codon usage; and/or the codon adaptation index (CAI) is increased or maximised in the coding region.

5'-CAP Structure

According to another preferred embodiment of the invention, the mRNA compound may have a sequence modified by the addition of a so-called "5'-CAP structure", which preferably stabilizes the mRNA as described herein. A 5'-CAP is an entity, typically a modified nucleotide entity, which generally "caps" the 5'-end of a mature mRNA. A 5-CAP may typically be formed by a modified nucleotide, particularly by a derivative of a guanine nucleotide. Preferably, the 5'-CAP is linked to the 5'-terminus via a 5'-5'-triphosphate linkage. A 5'-CAP may be methylated, e.g. m7GpppN, wherein N is the terminal 5' nucleotide of the nucleic acid carrying the 5'-CAP, typically the 5'-end of an mRNA. m7GpppN is the 5'-CAP structure, which naturally occurs in mRNA transcribed by polymerase II and is therefore preferably not considered as modification comprised in a modified mRNA in this context. Accordingly, a modified mRNA sequence of the present invention may comprise a m7GpppN as 5'-cap, but additionally the modified mRNA sequence typically comprises at least one further modification as defined herein. In one preferred embodiment, the mRNA compound of the invention comprises a 5'-CAP structure wherein said 5'-CAP structure is m7GpppN. In a most preferred embodiment, the 5'-cap structure is selected from the groups consisting of m7G(5'), m7G(5')ppp(5')(2'OMeA) and m7G(5')ppp(5')(2'OMeG) or respectively m7G(5')ppp(5')(2'OMeA)pG and m7G(5')ppp(5')(2'OMeG) pG.

In the context of the present invention, a 5'-CAP structure may also be formed in chemical RNA synthesis or RNA in vitro transcription (co-transcriptional capping) using CAP analogues, or a CAP structure may be formed in vitro using capping enzymes. Kits comprising capping enzymes are commercially available (e.g. ScriptCap™ Capping Enzyme and ScriptCap™ 2'-O-Methyltransferase (both from CellScript)). Therefore, the RNA transcript is preferably treated according to the manufacturer's instructions.

Thusly, a CAP analogue refers to a non-polymerizable di-nucleotide that has CAP functionality in that it facilitates translation or localization, and/or prevents degradation of the RNA molecule when incorporated at the 5'-end of the RNA molecule. Non-polymerizable means that the CAP analogue will be incorporated only at the 5'-terminus because it does not have a 5' triphosphate and therefore cannot be extended in the 3-direction by a template-dependent RNA polymerase.

CAP analogues include, but are not limited to, a chemical structure selected from the group consisting of m7GpppG, m7GpppA, m7GpppC; unmethylated CAP analogues (e.g., GpppG); dimethylated CAP analogue (e.g., m2,7GpppG), trimethylated CAP analogue (e.g., m2,2,7GpppG), dimethylated symmetrical CAP analogues (e.g., m7Gpppm7G), or anti reverse CAP analogues (e.g., ARCA; m7,2'OmeGpppG, m7,2'dGpppG, m7,3'OmeGpppG, m7,3'dGpppG and their tetraphosphate derivatives) (Stepinski et al., 2001. RNA 7(10):1486-95).

Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4-seco nucleotide, acyclic 3,4-dihydroxybutyl nucleotide, acyclic 3,5 dihydroxypentyl nucleotide, 3-3-inverted nucleotide moiety, 3-3-inverted abasic moiety, 3-2'-inverted nucleotide moiety, 3-2'-inverted abasic moiety, 1,4-butanediol phosphate, 3-phosphoramidate, hexylphosphate, aminohexyl phosphate, 3-phosphate, 3'phosphorothioate, phosphorodithioate, or bridging or non-bridging methylphosphonate moiety. These modified 5'-CAP structures are regarded as at least one modification in this context and may be used in the context of the present invention to modify the mRNA sequence of the inventive composition.

Particularly preferred modified 5'-CAP structures are CAP1 (methylation of the ribose of the adjacent nucleotide of m7G), cap2 (additional methylation of the ribose of the 2nd nucleotide downstream of the m7G), cap3 (additional methylation of the ribose of the 3rd nucleotide downstream of the m7G), cap4 (methylation of the ribose of the 4th nucleotide downstream of the m7G), ARCA (anti-reverse CAP analogue, modified ARCA (e.g. phosphothioate modified ARCA), CleanCap or respectively m7G(5')ppp(5')(2'OMeA)pG or m7G(5')ppp(5')(2'OMeG)pG (TriLink) and or a CAP-structure as disclosed in WO2017053297A1 (herewith incorporated by reference), inosine, N1-methyl-guanosine, 2'-fluoro-guanosine, 7-deaza-guanosine, 8-oxo-guanosine, 2-amino-guanosine, LNA-guanosine, and 2-azido-guanosine. In particular, any CAP structures derivable from the structure disclosed in claim 1-5 of WO2017/053297 may be suitably used to co-transcriptionally generate a modified CAP1 structure. Further, any CAP structures derivable from the structure defined in claim 1 or claim 21 of WO2018/075827 may be suitably used to co-transcriptionally generate a modified CAP1 structure.

Furthermore, CAP analogues have been described previously (U.S. Pat. No. 7,074,596, WO2008/016473, WO2008/157688, WO2009/149253, WO2011/015347, and WO2013/059475). The synthesis of N7-(4-chlorophenoxyethyl) substituted dinucleotide CAP analogues has been described recently (Kore et al. (2013) Bioorg. Med. Chem. 21(15): 4570-4). Further suitable CAP analogues in that context are described in WO2017/066793, WO2017/066781, WO2017/066791, WO2017/066789, WO2017/066782, WO2018075827 and WO2017/066797 wherein the specific disclosures referring to CAP analogues are incorporated herein by reference.

Poly(A) Sequence/PolyA-Tail

A polyA-tail also called "3'-poly(A) tail", "polyA sequence" or "poly(A) sequence" is typically a long sequence of adenosine nucleotides of up to about 400 adenosine nucleotides, e.g. from 10 to 200, 10 to 100, 40 to 80, 50 to 70, about 25 to about 400, preferably from about 50 to about 400, more preferably from about 50 to about 300, even more preferably from about 50 to about 250, most preferably from about 60 to about 250 adenosine nucleotides, or about 40 to about 150 adenosine nucleotides, or about 70 to 90 adenosine nucleotides, added to the 3-end of a RNA.

In a particularly preferred embodiment, the poly(A) sequence comprises about 64 adenosine nucleotides. In another particularly preferred embodiment, the poly(A) sequence comprises about 100 adenosine nucleotides. Moreover, poly(A) sequences, or poly(A) tails may be generated in vitro by enzymatic polyadenylation of the RNA, e.g. using Poly(A)polymerases derived from *E. coli* or yeast. Suitably, the poly(A) sequence of the coding RNA may be long enough to bind at least 2, 3, 4, 5 or more monomers of PolyA Binding Proteins.

Polyadenylation is typically understood to be the addition of a poly(A) sequence to a nucleic acid molecule, such as an RNA molecule, e.g. to a premature mRNA. Polyadenylation may be induced by a so called polyadenylation signal. This signal is preferably located within a stretch of nucleotides at the 3-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called pre-mature-mRNA). Typically, RNA maturation (from pre-mRNA to mature mRNA) comprises the step of polyadenylation.

Thusly, according to a further preferred embodiment, the composition comprises an mRNA compound comprising an mRNA sequence containing a polyA tail on the 3-terminus of typically about 10 to 200 adenosine nucleotides, preferably about 10 to 100 adenosine nucleotides, more preferably about 40 to 80 adenosine nucleotides, also preferably about 70 to about 90 adenosine nucleotides, or even more preferably about 50 to 70 adenosine nucleotides. Preferably, the poly(A) sequence is derived from a DNA template by RNA in vitro transcription. Alternatively, the poly(A) sequence may also be obtained in vitro by common methods of chemical-synthesis without being necessarily transcribed from a DNA-progenitor. Moreover, poly(A) sequences, or poly(A) tails may be generated by enzymatic polyadenylation of the RNA according to the present invention using commercially available polyadenylation kits and corresponding protocols known in the art.

Alternatively, the mRNA as described herein optionally comprises a polyadenylation signal, which is defined herein as a signal, which conveys polyadenylation to a (transcribed) RNA by specific protein factors (e.g. cleavage and polyadenylation specificity factor (CPSF), cleavage stimulation factor (CstF), cleavage factors I and II (CF I and CF II), poly(A) polymerase (PAP)). In this context, a consensus polyadenylation signal is preferred comprising the NN(U/T)ANA consensus sequence. In a particularly preferred aspect, the polyadenylation signal comprises one of the following sequences: AA(U/T)AAA or A(U/T)(U/T)AAA (wherein uridine is usually present in RNA and thymidine is usually present in DNA).

Poly(C) Sequence

A poly-(C)-sequence is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid.

Thusly, according to a further preferred embodiment, the composition of the invention comprises an mRNA compound comprising a poly(C) tail on the 3-terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides.

In one preferred embodiment, the mRNA compound comprises, preferably in 5'- to 3-direction:

a) a 5'-CAP structure, preferably CAP1 or m7G(5')ppp (5')(2'OMeA)pG;
b) optionally a 5'-UTR element,
c) at least one coding region encoding at least one antigenic peptide or protein,
d) optionally, a 3-UTR element,
e) optionally, a poly(A) sequence, preferably comprising 64 adenosines;
f) optionally, a poly(C) sequence, preferably comprising 30 cytosines.

UTRs

In a preferred embodiment, the composition comprises an mRNA compound comprising at least one 5'- or 3'-UTR element. In this context, an UTR element comprises or consists of a nucleic acid sequence, which is derived from the 5'- or 3'-UTR of any naturally occurring gene or which is derived from a fragment, a homolog or a variant of the 5'- or 3'-UTR of a gene. Preferably, the 5'- or 3'-UTR element used according to the present invention is heterologous to the at least one coding region of the mRNA sequence of the invention. Even if 5'- or 3'-UTR elements derived from naturally occurring genes are preferred, also synthetically engineered UTR elements may be used in the context of the present invention.

The term "3'-UTR element" typically refers to a nucleic acid sequence, which comprises or consists of a nucleic acid sequence that is derived from a 3'-UTR or from a variant of a 3'-UTR. A 3'-UTR element in the sense of the present invention may represent the 3'-UTR of an RNA, preferably an mRNA. Thus, in the sense of the present invention, preferably, a 3'-UTR element may be the 3'-UTR of an RNA, preferably of an mRNA, or it may be the transcription template for a 3'-UTR of an RNA. Thus, a 3'-UTR element preferably is a nucleic acid sequence which corresponds to the 3'-UTR of an RNA, preferably to the 3'-UTR of an mRNA, such as an mRNA obtained by transcription of a genetically engineered vector construct. Preferably, the 3'-UTR element fulfils the function of a 3'-UTR or encodes a sequence which fulfils the function of a 3'-UTR.

Preferably, the at least one 3'-UTR element comprises or consists of a nucleic acid sequence derived from the 3'-UTR of a chordate gene, preferably a vertebrate gene, more preferably a mammalian gene, most preferably a human gene, or from a variant of the 3'-UTR of a chordate gene, preferably a vertebrate gene, more preferably a mammalian gene, most preferably a human gene.

Preferably, the composition comprises an mRNA compound that comprises a 3'-UTR element, which may be derivable from a gene that relates to an mRNA with an enhanced half-life (that provides a stable mRNA), for example a 3'-UTR element as defined and described below. Preferably, the 3'-UTR element comprises or consists of a nucleic acid sequence derived from a 3'-UTR of a gene, which preferably encodes a stable mRNA, or from a homolog, a fragment or a variant of said gene.

In one preferred embodiment, the UTR-combinations which are disclosed in Table 1, claims 1 and claim 4, claims 6-8 and claim 9 of WO 2019/077001 A1 are preferred UTR-combinations for mRNA compounds of the present invention. Further, preferably, the UTR-combinations as disclosed on page 24, second full paragraph after Table 1 and page 24, last paragraph to page 29, second paragraph of WO 2019/077001 A1 are preferred UTR-combinations for mRNA compounds of the present invention. WO 2019/077001 A1 is incorporated herein by reference in its entirety.

In a further preferred embodiment, that 3'-UTR element comprises or consists of a nucleic acid sequence which is derived from a 3'-UTR of a gene selected from the group consisting of a 3'-UTR of a gene selected from PSMB3, ALB or ALB7, alpha-globin (referred to as "muag" i.e. a mutated alpha-globin 3'-UTR), CASP1, COX6B1, GNAS, NDUFA1 and RPS9, or from a homolog, a fragment or a variant of any one of these genes (for example, human albumin7/alb7 3'-UTR as disclosed in SEQ ID NO:1369 of WO2013/143700, which is incorporated herein by reference,), or from a homolog, a fragment or a variant thereof. In a further preferred embodiment, the 3'-UTR element comprises the nucleic acid sequence derived from a fragment of the human albumin gene according to SEQ ID NO:1376 of WO2013/143700 (albumin7/alb7 3'-UTR). In a further preferred embodiment, the 3'-UTR element comprises or consists of a nucleic acid sequence which is derived from a 3'-UTR of an albumin gene, preferably a vertebrate albumin gene, more preferably a mammalian albumin gene, most preferably a human albumin gene such as from the 3-UTR of the human albumin gene according to GenBank Accession number NM-000477.5 (SEQ ID NO: 13-18), or a fragment or variant thereof. In another preferred embodiment, the 3'-UTR element comprises or consists of the center, α-complex-binding portion of the 3'-UTR of an α-globin gene, such as of a human α-globin gene, or a homolog, a fragment, or a variant of an α-globin gene, preferably according to SEQ ID NO:5 or SEQ ID NO:6-8, or an α-complex-binding portion of the 3'-UTR of an α-globin gene (also named herein as "muag") GCCCGATGGGCCTCCCAACGGGCCCTCCTCCCCTCCTTGCACCG (SEQ ID NO:11 or SEQ ID NO:12, corresponding to SEQ ID NO:1393 of patent application WO2013/143700).

In another preferred embodiment, the 3'-UTR element comprises or consists of a nucleic acid sequence which is derived from a 3'-UTR of an α- or β-globin gene, preferably a vertebrate α- or β-globin gene, and preferably a mammalian α- or β-globin gene, preferably a human α- or β globin gene according to SEQ ID NOs:5, 7, 9, 11, 13, 15, 17, 19 or the corresponding RNA sequences SEQ ID NOs:6, 8, 10, 12, 14, 16, 18, 20, i.e. (SEQ ID NO:5; DNA; HBA1 3-UTR); (SEQ ID NO:7; DNA; HBA2 3-UTR); (SEQ ID NO:9; DNA; HBB 3-UTR); (SEQ ID NO:11; DNA; muag 3-UTR); (SEQ ID NO:13; DNA; albumin 3-UTR); (SEQ ID NO:15; DNA; albumin7 3-UTR); (SEQ ID NO:17; DNA; ALB7 3-UTR); (SEQ ID NO:19; DNA; PSMB3 3-UTR); (SEQ ID NO:6; RNA; HBA1 3-UTR); (SEQ ID NO:8; RNA; HBA2 3-UTR); (SEQ ID NO:10; RNA; HBB 3-UTR); (SEQ ID NO:12; RNA; muag 3-UTR); (SEQ ID NO:14; RNA; albumin 3-UTR); (SEQ ID NO:16; RNA; albumin7 3-UTR); (SEQ ID NO:18; RNA; ALB7 3-UTR); (SEQ ID NO:20; RNA; PSMB3 3-UTR).

In this context it is also preferred that the 3'-UTR element of the mRNA sequence according to the invention comprises or consists of a corresponding RNA sequence of the nucleic acid sequence according to SEQ ID NO:11 as shown in SEQ ID NO:12, or a homolog, a fragment or variant thereof.

The term "a nucleic acid sequence which is derived from the 3'-UTR of a [ . . . ] gene" preferably refers to a nucleic acid sequence which is based on the 3'-UTR sequence of a [ . . . ] gene or on a part thereof, such as on the 3'-UTR of an albumin gene, an α-globin gene, a β-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'-UTR sequence, i.e. the full length 3'-UTR sequence of a gene, and sequences corresponding to a fragment of the 3'-UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene.

The term "a nucleic acid sequence which is derived from a variant of the 3'-UTR of a [ . . . ] gene" preferably refers to a nucleic acid sequence, which is based on a variant of the 3'-UTR sequence of a gene, such as on a variant of the 3'-UTR of an albumin gene, an α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'-UTR of a gene, i.e. the full length variant 3'-UTR sequence of a gene, and sequences corresponding to a fragment of the variant 3'-UTR sequence of a gene. A fragment in this context preferably consists of a continuous stretch of nucleotides corresponding to a continuous stretch of nucleotides in the full-length variant 3'-UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'-UTR. Such a fragment of a variant, in the sense of the present invention, is preferably a functional fragment of a variant as described herein.

According to a preferred embodiment, the mRNA compound comprising an mRNA sequence according to the invention comprises a 5'-CAP structure and/or at least one 3-untranslated region element (3'-UTR element), preferably as defined herein. More preferably, the RNA further comprises a 5'-UTR element as defined herein.

In one preferred embodiment, the mRNA compound comprises, preferably in 5'- to 3-direction:

a) a 5'-CAP structure, preferably CAP1 or m7G(5')ppp (5')(2'OMeA)pG;
b) optionally, a 5'-UTR element,
c) at least one coding region encoding at least one antigenic peptide or protein,
d) optionally, a 3'-UTR element, preferably comprising or consisting of a nucleic acid sequence which is derived from an alpha globin gene, preferably comprising the corresponding RNA sequence of the nucleic acid sequence according to SEQ ID NO:11 as shown in SEQ ID NO:12, a homolog, a fragment or a variant thereof;
e) optionally, a poly(A) sequence, preferably comprising 64 adenosines or 100 adenosines;
f) optionally, a poly(C) sequence, preferably comprising 30 cytosines.

In a further preferred embodiment, the mRNA compound comprises, preferably in 5'- to 3-direction:

a) a 5'-CAP structure, preferably CAP1 or m7G(5')ppp (5')(2'OMeA)pG;
b) at least one coding region encoding at least one antigenic peptide or protein, preferably derived from a protein of an SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli*, *Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum, Plasmodium*

*vivax*, *Plasmodium malariae*, or *Plasmodium ovale*) or a fragment or variant thereof, c) optionally, a 3'-UTR element, preferably comprising or consisting of a nucleic acid sequence which is derived from an alpha globin gene, preferably comprising the corresponding RNA sequence of the nucleic acid sequence according to SEQ ID NO: 11 as shown in SEQ ID NO:12, a homolog, a fragment or a variant thereof;

d) optionally, a poly(A) sequence, preferably comprising 64 adenosines;

e) optionally, a poly(C) sequence, preferably comprising 30 cytosines.

In a further preferred embodiment, the composition comprises an mRNA compound comprising at least one 5'-untranslated region element (5'-UTR element). Preferably, the at least one 5'-UTR element comprises or consists of a nucleic acid sequence, which is derived from the 5'-UTR of a TOP gene or which is derived from a fragment, homolog or variant of the 5'-UTR of a TOP gene. It is preferred that the 5'-UTR element does not comprise a TOP motif or a 5'-TOP, as defined above.

In some embodiments, the nucleic acid sequence of the 5'-UTR element, which is derived from a 5'-UTR of a TOP gene, terminates at its 3-end with a nucleotide located at position 1, 2, 3, 4, 5, 6, 7, 8, 9 or 10 upstream of the start codon (e.g. A(U/T)G) of the gene or mRNA it is derived from. Thus, the 5'-UTR element does not comprise any part of the protein coding region. Thus, preferably, the only protein coding part of the at least one mRNA sequence is provided by the coding region.

The nucleic acid sequence derived from the 5'-UTR of a TOP gene is preferably derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'-UTR element may be selected from 5'-UTR elements comprising or consisting of a nucleic acid sequence, which is derived from a nucleic acid sequence selected from the group consisting of SEQ ID NO:1-1363, SEQ ID NO:1395, SEQ ID NO:1421 and SEQ ID NO:1422 of the patent application WO2013/143700, whose disclosure is incorporated herein by reference, from the homologs of SEQ ID NO:1-1363, SEQ ID NO:1395, SEQ ID NO:1421 and SEQ ID NO:1422 of the patent application WO2013/143700, from a variant thereof, or preferably from a corresponding RNA sequence. The term "homologs of SEQ ID NO:1-1363, SEQ ID NO:1395, SEQ ID NO:1421 and SEQ ID NO:1422 of the patent application WO2013/143700" refers to sequences of other species than *Homo sapiens*, which are homologous to the sequences according to SEQ ID NO:1-1363, SEQ ID NO:1395, SEQ ID NO:1421 and SEQ ID NO:1422 of the patent application WO2013/143700.

In a preferred embodiment, the 5'-UTR element of the mRNA compound comprises or consists of a nucleic acid sequence, which is derived from a nucleic acid sequence extending from nucleotide position 5 (i.e. the nucleotide that is located at position 5 in the sequence) to the nucleotide position immediately 5' to the start codon (located at the 3-end of the sequences), e.g. the nucleotide position immediately 5' to the ATG sequence, of a nucleic acid sequence selected from SEQ ID NO:1-1363, SEQ ID NO:1395, SEQ ID NO:1421 and SEQ ID NO:1422 of the patent application WO2013/143700, from the homologs of SEQ ID NO:1-1363, SEQ ID NO:1395, SEQ ID NO:1421 and SEQ ID NO:1422 of the patent application WO2013/143700 from a variant thereof, or a corresponding RNA sequence. It is particularly preferred that the 5'-UTR element is derived from a nucleic acid sequence extending from the nucleotide position immediately 3' to the 5'-TOP to the nucleotide position immediately 5' to the start codon (located at the 3'-end of the sequences), e.g. the nucleotide position immediately 5' to the ATG sequence, of a nucleic acid sequence selected from SEQ ID NO:1-1363, SEQ ID NO:1395, SEQ ID NO:1421 and SEQ ID NO:1422 of the patent application WO2013/143700, from the homologs of SEQ ID NO:1-1363, SEQ ID NO:1395, SEQ ID NO:1421 and SEQ ID NO:1422 of the patent application WO2013/143700, from a variant thereof, or a corresponding RNA sequence.

In a further preferred embodiment, the 5'-UTR element comprises or consists of a nucleic acid sequence, which is derived from a 5'-UTR of a TOP gene encoding a ribosomal protein or from a variant of a 5'-UTR of a TOP gene encoding a ribosomal protein. For example, the 5'-UTR element comprises or consists of a nucleic acid sequence, which is derived from a 5'-UTR of a nucleic acid sequence according to any of SEQ ID NO:67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'-TOP motif. As described above, the sequence extending from position 5 to the nucleotide immediately 5' to the ATG (which is located at the 3'-end of the sequences) corresponds to the 5'-UTR of said sequences.

Preferably, the 5'-UTR element comprises or consists of a nucleic acid sequence, which is derived from a 5'-UTR of a TOP gene encoding a ribosomal Large protein (RPL) or from a homolog or variant of a 5'-UTR of a TOP gene encoding a ribosomal Large protein (RPL). For example, the 5'-UTR element comprises or consists of a nucleic acid sequence, which is derived from a 5'-UTR of a nucleic acid sequence according to any of SEQ ID NO:67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'-TOP motif.

In a particularly preferred embodiment, the 5'-UTR element comprises or consists of a nucleic acid sequence which is derived from the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'-UTR element does not comprise the 5'-TOP of said gene.

Accordingly, in a preferred embodiment, the 5'-UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO:23 or SEQ ID NO:24 (5'-UTR of human ribosomal protein Large 32 lacking the 5'-terminal oligopyrimidine tract: GGCGCTGCCTACGGAGGTGGCAGC- CATCTCCTTCTCGGCATC; corresponding to SEQ ID NO:1368 of the patent application WO2013/143700) or preferably to a corresponding RNA sequence, or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO:23 or more preferably to a corresponding RNA sequence (SEQ ID NO:24), wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a very preferred embodiment, the 5'-UTR element of the mRNA sequence according to the invention comprises or consists of a corresponding RNA sequence of the nucleic acid sequence according to SEQ ID NO: 21 or SEQ ID NO: 22), i.e. HSD17B4. Also, in a very preferred embodiment, the 3'-UTR element of the mRNA sequence according to the invention comprises or consists of a corresponding RNA sequence of the nucleic acid sequence according to SEQ ID NO: 19 or SEQ ID NO: 20), i.e. PSMB3. In also a very preferred embodiment, the 5'-UTR element of the mRNA sequence and the 3'-UTR-element according to the invention comprises or consists of a combination of aforementioned HSD17B4 and PSMB3-UTRs.

In some embodiments, the mRNA compound comprises a 5'-UTR element, which comprises or consists of a nucleic acid sequence which is derived from the 5'-UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'-UTR element does not comprise a TOP motif or the 5'-TOP of said genes, and wherein optionally the 5'-UTR element starts at its 5'-end with a nucleotide located at position 1, 2, 3, 4, 5, 6, 7, 8, 9 or 10 downstream of the 5'-terminal oligopyrimidine tract (TOP) and wherein further optionally the 5'-UTR element which is derived from a 5'-UTR of a TOP gene terminates at its 3-end with a nucleotide located at position 1, 2, 3, 4, 5, 6, 7, 8, 9 or 10 upstream of the start codon (A(U/T)G) of the gene it is derived from.

In further preferred embodiments, the 5'-UTR element comprises or consists of a nucleic acid sequence, which is derived from the 5'-UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit Vlc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit Vlc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit Vlc gene (COX6C), or a mammalian N-acylsphingosine amidohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP synthase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit Vlc gene (COX6C), or a human N-acylsphingosine amidohydrolase (acid ceramidase) 1 gene (ASAH1) or from a variant thereof, wherein preferably the 5'-UTR element does not comprise the 5'-TOP of said gene.

Accordingly, in a preferred embodiment, the 5'-UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO:1368, or SEQ ID NO:1412-1420 of the patent application WO2013/143700, or a corresponding RNA sequence, or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO:1368, or SEQ ID NO:1412-1420 of the patent application WO2013/143700, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a preferred embodiment, the 5'-UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO:25 (5'-UTR of ATP5A1 lacking the 5'-terminal oligopyrimidine tract: GCGGCTCGGCCATTTTGTCCCAGTCAGTCCGGAGGCTGCGGCTGCAGAAGTACCGCCTGCGGAGTAACTG CAAAG; corresponding to SEQ ID NO:224289 of the patent application WO2013/143700) or preferably to a corresponding RNA sequence (SEQ ID NO:26), or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO:25 or more preferably to a corresponding RNA sequence (SEQ ID NO:26), wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In another preferred embodiment, the mRNA compound comprises a 5'-UTR element, which comprises or consists of a nucleic acid sequence which is derived from a 60S ribosomal protein L31 (RPL31) gene, wherein said 5'-UTR element comprises or consists of a DNA sequence according to SEQ ID NO:13 as disclosed in WO2019077001A1 or respectively a RNA sequence according to SEQ ID NO:14 as disclosed in WO2019077001A1. In another preferred embodiment, the mRNA compound comprises a 3'-UTR element, which comprises or consists of a nucleic acid sequence which is derived from a 40S ribosomal protein S9 (RPS9) gene, wherein said 3'-UTR element comprises or consists of a DNA sequence according to SEQ ID NO:33 as disclosed in WO2019077001A1 or respectively a RNA sequence according to SEQ ID NO:34 as disclosed in WO2019077001A1. In further preferred embodiments, the mRNA compound comprises an UTR-combination as disclosed in WO2019077001A1, i.e. both a 5'-UTR element, which comprises or consists of a nucleic acid sequence which is derived from a RPL31 gene and a 3'-UTR element, which comprises or consists of a nucleic acid sequence which is derived from a RPS9 gene.

In another preferred embodiment, the mRNA compound comprises a 5'-UTR element, which comprises or consists of a nucleic acid sequence which is derived from a cationic amino acid transporter 3 (solute carrier family 7 member 3, SLC7A3) gene, wherein said 5'-UTR element comprises or consists of a DNA sequence according to SEQ ID NO:15 as disclosed in WO2019077001A1 or respectively a RNA sequence according to SEQ ID NO:16 as disclosed in WO2019077001A1. In another preferred embodiment, the mRNA compound comprises a 3'-UTR element, which comprises or consists of a nucleic acid sequence which is derived from a proteasome subunit beta type-3 (PSMB3) gene, wherein said 3'-UTR element comprises or consists of a DNA sequence according to SEQ ID NO:23 as disclosed in WO2019077001A1 or respectively a RNA sequence according to SEQ ID NO:24 as disclosed in WO2019077001A1. In further preferred embodiments, the mRNA compound comprises an UTR-combination as disclosed in WO2019077001A1, i.e. both a 5'-UTR element, which comprises or consists of a nucleic acid sequence which is derived from a SLc7α3 gene and a 3'-UTR element, which comprises or consists of a nucleic acid sequence which is derived from a PSMB3 gene.

Preferably, the at least one 5'-UTR element and the at least one 3'-UTR element act synergistically to increase protein production from the at least one mRNA sequence as described above.

According to a preferred embodiment, the composition of the invention comprises an mRNA compound that comprises, preferably in 5'- to 3-direction:

a) a 5'-CAP structure, preferably CAP1 or m7G(5')ppp(5')(2'OMeA)pG;
b) optionally, a 5'-UTR element which preferably comprises or consists of a nucleic acid sequence which is derived from the 5'-UTR of a TOP gene, more preferably comprising or consisting of the corresponding RNA sequence of a nucleic acid sequence according to SEQ ID NO:21, 23, 25 or respectively SEQ ID NO:22, 24 or 26, a homolog, a fragment or a variant thereof;
c) at least one coding region encoding at least one antigenic peptide or protein preferably derived from a protein of a SARS coronavirus 2 (SARS-CoV-2), nCoV-2019 coronavirus, SARS coronavirus (SARS-CoV), an influenza virus or a Rabies virus, or a fragment or variant thereof, preferably comprising or consisting of any one of the nucleic acid sequences as disclosed in the sequence listing having a numeric identifier <223> which starts with "derived and/or modified CDS sequence (wt)" or "derived and/or modified CDS sequence (opt1)", "derived and/or modified CDS sequence (opt2)", "derived and/or modified CDS sequence (opt3)", "derived and/or modified CDS sequence (opt4)", or "derived and/or modified CDS sequence (opt5)", or respectively "column B" or "column C" of Tabs. 1-5 or FIGS. 20-24 or respective the sequence listing of PCT/EP2016/075843 or WO 2018/078053, incorporated by reference in their entirety; or an ORF comprised in SEQ ID NO:27-40, or 71 or of a fragment or variant of any one of these sequences; or at least one coding region encoding at least one antigenic peptide or protein preferably derived from a protein of an SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli*, *Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum*, *Plasmodium vivax*, *Plasmodium malariae*, or *Plasmodium ovale*);

d) optionally, a 3'-UTR element which preferably comprises or consists of a nucleic acid sequence which is derived from a gene providing a stable mRNA, preferably comprising or consisting of the corresponding RNA sequence of a nucleic acid sequence according to SEQ ID NO:5, 7, 9, 11, 13, 15, 17 or 19, preferably according to SEQ ID NO:11 or SEQ ID NO:17 or a homolog, a fragment or a variant thereof;

e) optionally, a poly(A) sequence preferably comprising 64 adenosines; and f) optionally, a poly(C) sequence, preferably comprising 30 cytosines.

According to one embodiment, the mRNA compound comprises an miRNA sequence. A miRNA (microRNA) is typically a small, non-coding single stranded RNA molecules of about 20 to 25 nucleotides in length which may function in gene regulation, for example, but not limited to, by mRNA degradation or translation inhibition or repression. miRNAs are typically produced from hairpin precursor RNAs (pre-miRNAs), and they may form functional complexes with proteins. Furthermore, miRNAs may bind to 3'-UTR regions of target mRNAs. Preferably, the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof.

In one embodiment, the miRNA sequence is a naturally occurring miRNA sequence. In another embodiment, the miRNA sequence may be a mimetic, or a modification of a naturally-occurring miRNA sequence.

According to one preferred embodiment, the mRNA compound comprising an mRNA sequence according to the invention may further comprise, as defined herein:

a) a 5'-CAP structure;

b) at least one miRNA sequence, preferably wherein the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof;

c) at least one 5'-UTR element;

d) at least one 3'-UTR element;

e) at least one poly(A) sequence;

f) at least one poly(C) sequence;

or any combinations of these.

Histone Stem-Loop (HSL)/Histone 3' UTR Stem-Loop

In a further preferred embodiment, the composition comprises an mRNA compound comprising a histone stem-loop sequence/structure (HSL). In said embodiment, the mRNA sequence may comprise at least one (or more) histone stem loop sequence or structure. Such histone stem-loop sequences are preferably selected from histone stem-loop sequences as disclosed in WO 2012/019780 A1, the disclosure of which is incorporated herewith by reference. A histone stem-loop sequence that may be used within the present invention may preferably be derived from formulae (I) or (II) of WO 2012/019780 A1. According to a further preferred embodiment the coding RNA may comprise at least one histone stem-loop sequence derived from at least one of the specific formulae (Ia) or (IIa) of the patent application WO 2012/019780 A1. According to a further preferred embodiment the coding RNA may comprise at least one histone stem-loop sequence derived from a Histone stem-loop as disclosed in patent application WO 2018/104538 A1 under formula (I), formula (II), formula (Ia) or on pages 49-52 under section "Histone stem-loop" and WO 2018/104538 A1—SEQ ID NOs:1451-1452 as disclosed in WO 2018/104538 A1; WO 2018/104538 A1 which is herein incorporated by reference in its entirety, also especially SEQ ID NOs:1451-1452.

In particularly preferred embodiment, the RNA of the invention comprises at least one histone stem-loop sequence, wherein said histone stem-loop sequence comprises a nucleic acid sequence being identical or at least 70%, 80%, 90%, 91%, 92%, 93%, 94%, 95%, 96%, 97%, 98%, or 99% identical to SEQ ID NOs: 3 or 4, or fragments or variants thereof.

Signal Peptides

According to another embodiment, the composition of the invention comprises an mRNA compound which may, additionally or alternatively, encode a secretory signal peptide. Such signal peptides are sequences, which typically exhibit a length of about 15 to 30 amino acids and are preferably located at the N-terminus of the encoded peptide, without being limited thereto. Signal peptides as defined herein preferably allow the transport of the antigen, antigenic protein or antigenic peptide as encoded by the at least one mRNA sequence into a defined cellular compartment, preferably the cell surface, the endoplasmic reticulum (ER) or the endosomal-lysosomal compartment. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulins as defined herein, signal sequences of the invariant chain of immunoglobulins or antibodies as defined herein, signal sequences of Lamp1, Tapasin, Erp57, Calreticulin, Calnexin, and further membrane associated proteins or of proteins associated with the endoplasmic reticulum (ER) or the endosomal-lysosomal compartment. Most preferably, signal sequences of MHC class I molecule HLA-A*0201 may be used according to the present invention. For example, a signal peptide derived from HLA-A is preferably used in order to promote secretion of the encoded antigen as defined herein or a fragment or variant thereof. More preferably, an HLA-A signal peptide is fused to an encoded antigen as defined herein or to a fragment or variant thereof.

The mRNA compound to be incorporated in the composition according to the present invention may be prepared using any method known in the art, including synthetic methods such as e.g. solid phase RNA synthesis, as well as in vitro methods, such as RNA in vitro transcription reactions, particularly as described in the examples.

Methods of Preparing Lipid Nanoparticle Compositions

The invention further relates to a method of preparing said lipid nanoparticles comprising the steps of:

(i) providing:
  a) cationic lipid of formula (I) as defined herein or a pharmaceutically acceptable salt, tautomer, prodrug or stereoisomer thereof;
  b) a polymer conjugated lipid as defined herein;
  c) at least one mRNA compound comprising an mRNA sequence encoding at least one antigenic peptide or protein;
  d) optionally, a steroid; and
  e) optionally, a neutral lipid;

(ii) solubilizing the cationic lipid and/or the polymer conjugated lipid and optionally the neutral lipid and/or the steroid or a steroid derivative in an alcohol such as ethanol;

(iii) mixing the alcoholic lipid solution with an aqueous solution comprising the mRNA polynucleotide (iv) removing the alcohol to form lipid nanoparticles encapsulating or associating with the mRNA polynucleotide; and optionally (v) separating or purifying the lipid nanoparticles.

The alcohol may be removed by any suitable method which does not negatively affect the lipids or the forming lipid nanoparticles. In one embodiment of the invention the alcohol is removed by dialysis. In an alternative embodiment the alcohol is removed by diafiltration.

Separation and optional purification of the lipid nanoparticles might also be performed by any suitable method. Preferably the lipid nanoparticles are filtrated, more preferably the lipid nanoparticles are separated or purified by filtration through a sterile filter.

In some embodiments, the solutions are mixed in a microfluidic mixer to obtain the composition. Suitably, the microfluidic mixing conditions are chosen so as to obtain encapsulation of the pharmaceutically active compound at an encapsulation efficiency (EE) of above 80%, preferably above 90%, more preferably above 94%.

Pharmaceutical Compositions and Kits

The invention further relates to a pharmaceutical composition comprising at least one lipid nanoparticle according to the present invention. The lipid nanoparticle might comprise an mRNA compound comprising a sequence encoding at least one antigenic peptide or protein as defined herein.

In one embodiment of the invention the mRNA sequence encodes one antigenic peptide or protein. In an alternative embodiment of the invention the mRNA sequence encodes more than one antigenic peptide or protein.

In one embodiment of the invention, the pharmaceutical composition comprises a lipid nanoparticle according to the invention, wherein the lipid nanoparticle comprises more than one mRNA compounds, which each comprise a different mRNA sequence encoding an antigenic peptide or protein.

In an alternative embodiment of the invention the pharmaceutical composition comprises a second lipid nanoparticle, wherein the mRNA compound comprised by the second lipid nanoparticle is different from the mRNA compound comprised by the first lipid nanoparticle.

In a further aspect, the present invention concerns a composition comprising mRNA comprising lipid nanoparticles wherein the mRNA comprises an mRNA sequence comprising at least one coding region as defined herein and a pharmaceutically acceptable carrier. The composition according to the invention is preferably provided as a pharmaceutical composition or as a vaccine.

The composition according to the invention might also comprise suitable pharmaceutically acceptable adjuvants. In preferred embodiments the adjuvant is preferably added in order to enhance the immunostimulatory properties of the composition. In this context, an adjuvant may be understood as any compound, which is suitable to support administration and delivery of the composition according to the invention. Furthermore, such an adjuvant may, without being bound thereto, initiate or increase an immune response of the innate immune system, i.e. a non-specific immune response. In other words, when administered, the composition according to the invention typically initiates an adaptive immune response due to an antigen as defined herein or a fragment or variant thereof, which is encoded by the at least one coding sequence of the inventive mRNA contained in the composition of the present invention. Additionally, the composition according to the invention may generate an (supportive) innate immune response due to addition of an adjuvant as defined herein to the composition according to the invention.

In some embodiments, the invention provides a method of inducing an immune response in a subject, the method comprising administering to the subject the vaccine of the invention in an amount effective to produce an antigen-specific immune response in the subject. In other embodiments, the invention provides a pharmaceutical composition comprising a composition or a kit or kit of parts as described herein for use in vaccination of a subject comprising an effective dose of mRNA encoding a virus antigen.

Such an adjuvant may be selected from any adjuvant known to a skilled person and suitable for the present case, i.e. supporting the induction of an immune response in a mammal. Preferably, the adjuvant may be selected from the group consisting of adjuvants, without being limited thereto, as disclosed on page 160 line 3-161 line 8 in WO 2018/078053 A1; WO 2018/078053 A1 being incorporated herein by reference in its entirety.

Particularly preferred, an adjuvant may be selected from adjuvants, which support induction of a Th1-immune response or maturation of naïve T-cells, such as GM-CSF, IL-12, IFNγ, any immunostimulatory nucleic acid as defined above, preferably an immunostimulatory RNA, CpG DNA, et cetera.

In a further preferred embodiment it is also possible that the inventive composition contains besides the antigen-providing mRNA further components which are selected from the group comprising: further antigens (e.g. in the form of a peptide or protein) or further antigen-encoding nucleic acids; a further immunotherapeutic agent; one or more auxiliary substances; or any further compound, which is known to be immunostimulating due to its binding affinity (as ligands) to human Toll-like receptors; and/or an adjuvant nucleic acid, preferably an immunostimulatory RNA (isRNA).

The composition of the present invention can additionally contain one or more auxiliary substances in order to increase its immunogenicity or immunostimulatory capacity, if desired. A synergistic action of the mRNA as defined herein and of an auxiliary substance, which may be optionally contained in the inventive composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Suitable adjuvants may furthermore be selected from nucleic acids having the formula $G_lXmG_n$ wherein: G is guanosine, uracil or an analogue of guanosine or uracil; X is guanosine, uracil, adenosine, thymidine, cytosine or an analogue of the above-mentioned nucleotides; I is an integer from 1 to 40, wherein when I=1 G is guanosine or an analogue thereof, when I>1 at least 50% of the nucleotides are guanosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 G is guanosine or an analogue thereof, when n>1 at least 50% of the nucleotides are guanosine or an analogue thereof, or formula: $(N_uG_lX_mG_nN_v)_a$, wherein: G is guanosine (guanine), uridine (uracil) or an analogue of guanosine (guanine) or uridine (uracil), preferably guanosine (guanine) or an analogue thereof; X is guanosine (guanine), uridine (uracil), adenosine (adenine), thymidine (thymine), cytidine (cytosine), or an analogue of these nucleotides (nucleosides), preferably uridine (uracil) or an analogue thereof; N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides); a is an integer from 1 to 20, preferably from 1 to 15, most preferably from 1 to 10; I is an integer from 1 to 40, wherein when I=1, G is guanosine (guanine) or an analogue thereof, when I>1, at least 50% of these nucleotides (nucleosides) are guanosine (guanine) or an analogue thereof; m is an integer and is at least 3; wherein when m=3, X is uridine (uracil) or an analogue thereof, and when m>3, at least 3 successive uridines (uracils) or analogues of uridine (uracil) occur; n is an integer from 1 to 40, wherein when n=1, G is guanosine (guanine) or an analogue thereof, when n>1, at least 50% of these nucleotides (nucleosides) are guanosine (guanine) or an analogue thereof; u, v may be independently from each other an integer from 0 to 50, preferably wherein when u=0, v>1, or when v=0, u>1; wherein the nucleic acid molecule of formula $(N_uG_lX_mG_nN_v)_a$ has a length of at least 50 nucleotides, preferably of at least 100 nucleotides, more preferably of at least 150 nucleotides, even more preferably of at least 200 nucleotides and most preferably of at least 250 nucleotides. Other suitable adjuvants may furthermore be selected from nucleic acids having the formula: $C_1X_mC_n$, wherein: C is cytosine, uracil or an analogue of cytosine or uracil; X is guanosine, uracil, adenosine, thymidine, cytosine or an analogue of the above-mentioned nucleotides; I is an integer from 1 to 40, wherein when I=1 C is cytosine or an analogue thereof, when I>1 at least 50% of the nucleotides are cytosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 C is cytosine or an analogue thereof, when n>1 at least 50% of the nucleotides are cytosine or an analogue thereof.

In this context the disclosure of WO 2008/014979 (whole disclosure, especially the subject-matter of claim 1, claim 2, claim 3, claim 4 and claim 5) and WO 2009/095226 are also incorporated herein by reference in their entirety.

In a further aspect, the present invention provides a vaccine, which is based on the mRNA comprising lipid nanoparticles according to the invention comprising at least one mRNA compound comprising a mRNA sequence comprising coding region as defined herein. The vaccine according to the invention is preferably a (pharmaceutical) composition as defined herein.

Accordingly, the vaccine according to the invention is based on the same components as the (pharmaceutical) composition described herein. Insofar, it may be referred to the description of the (pharmaceutical) composition as provided herein. Preferably, the vaccine according to the invention comprises at least one mRNA comprising lipid nanoparticles comprising at least one mRNA sequence as defined herein and a pharmaceutically acceptable carrier. In embodiments, where the vaccine comprises more than one mRNA sequence (such as a plurality of RNA sequences according to the invention, wherein each preferably encodes a distinct antigenic peptide or protein) encapsulated in mRNA comprising lipid nanoparticles, the vaccine may be provided in physically separate form and may be administered by separate administration steps. The vaccine according to the invention may correspond to the (pharmaceutical) composition as described herein, especially where the mRNA sequences are provided by one single composition. However, the inventive vaccine may also be provided physically separated. For instance, in embodiments, wherein the vaccine comprises more than one mRNA sequences/species encapsulated in mRNA comprising lipid nanoparticles as defined herein, these RNA species may be provided such that, for example, two, three, four, five or six separate compositions, which may contain at least one mRNA species/sequence each (e.g. three distinct mRNA species/sequences), each encoding distinct antigenic peptides or proteins, are provided, which may or may not be combined. Also, the inventive vaccine may be a combination of at least two distinct compositions, each composition comprising at least one mRNA encoding at least one of the antigenic peptides or proteins defined herein. Alternatively, the vaccine may be provided as a combination of at least one mRNA, preferably at least two, three, four, five, six or more mRNAs, each encoding one of the antigenic peptides or proteins defined herein. The vaccine may be combined to provide one single composition prior to its use or it may be used such that more than one administration is required to administer the distinct mRNA sequences/species encoding any of the antigenic peptides or proteins encapsulated in mRNA comprising lipid nanoparticles as defined herein. If the vaccine contains at least one mRNA comprising lipid nanoparticles, typically comprising at least two mRNA sequences, encoding the antigen combinations defined herein, it may e.g. be administered by one single administration (combining all mRNA species/sequences), by at least two separate administrations. Accordingly; any combination of mono-, bi- or multicistronic mRNAs encoding the at least one antigenic peptide or protein or any combination of antigens as defined herein (and optionally further antigens), provided as separate entities (containing one mRNA species) or as combined entity (containing more than one mRNA species), is understood as a vaccine according to the present invention. According to a particularly preferred embodiment of the inventive vaccine, the at least one antigen, preferably a combination as defined herein of at least two, three, four, five, six or more antigens encoded by the inventive composition as a whole, is provided as an individual (monocistronic) mRNA, which is administered separately.

As with the (pharmaceutical) composition according to the present invention, the entities of the vaccine may be provided in liquid and or in dry (e.g. lyophilized) form. They may contain further components, in particular further components allowing for its pharmaceutical use. The vaccine or the (pharmaceutical) composition may, e.g., additionally contain a pharmaceutically acceptable carrier and/or further auxiliary substances and additives and/or adjuvants.

The vaccine or (pharmaceutical) composition typically comprises a safe and effective amount of the mRNA compound according to the invention as defined herein, encoding an antigenic peptide or protein as defined herein or a fragment or variant thereof or a combination of antigens, encapsulate within and/or associated with the lipid nanoparticles. As used herein, "safe and effective amount" means an amount of the mRNA that is sufficient to significantly induce a positive modification of cancer or a disease or disorder related to cancer. At the same time, however, a "safe and effective amount" is small enough to avoid serious side-effects, that is to say to permit a sensible relationship between advantage and risk. The determination of these limits typically lies within the scope of sensible medical judgment. In relation to the vaccine or (pharmaceutical) composition of the present invention, the expression "safe and effective amount" preferably means an amount of the mRNA (and thus of the encoded antigen) that is suitable for stimulating the adaptive immune system in such a manner that no excessive or damaging immune reactions are achieved but, preferably, also no such immune reactions below a measurable level. Such a "safe and effective amount" of the mRNA of the (pharmaceutical) composition or vaccine as defined herein may furthermore be selected in dependence of the type of mRNA, e.g. monocistronic, bi- or even multicistronic mRNA, since a bi- or even multicistronic mRNA may lead to a significantly higher expression of the encoded antigen(s) than the use of an equal amount of a monocistronic mRNA. A "safe and effective amount" of the mRNA of the (pharmaceutical) composition or vaccine as defined above will furthermore vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The vaccine or composition according to the invention can be used according to the invention for human and also for veterinary medical purposes, as a pharmaceutical composition or as a vaccine.

In a preferred embodiment, the mRNA comprising lipid nanoparticle of the (pharmaceutical) composition, vaccine or kit of parts according to the invention is provided in lyophilized form. Preferably, the lyophilized mRNA comprising lipid nanoparticles are reconstituted in a suitable buffer, advantageously based on an aqueous carrier, prior to administration, e.g. Ringer-Lactate solution, Ringer solution, a phosphate buffer solution. In a preferred embodiment, the (pharmaceutical) composition, the vaccine or the kit of parts according to the invention contains at least one, two, three, four, five, six or more mRNA compounds, which may be provided as a single species of lipid nanoparticles, or separately for each LNP species, optionally in lyophilized form (optionally together with at least one further additive) and which are preferably reconstituted separately in a suitable buffer (such as Ringer-Lactate solution) prior to their use so as to allow individual administration of each of the (monocistronic) mRNAs.

The vaccine or (pharmaceutical) composition according to the invention may typically contain a pharmaceutically acceptable carrier or excipient. Examples of suitable carriers and excipients are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The term "pharmaceutical composition" in the context of this invention means a composition comprising an active agent and comprising additionally one or more pharmaceutically acceptable carriers. The composition may further contain ingredients selected from, for example, diluents, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The expression "pharmaceutically acceptable carrier" as used herein preferably includes the liquid or non-liquid basis of the inventive vaccine. If the inventive vaccine is provided in liquid form, the carrier will be water, typically pyrogen-free water; isotonic saline or buffered (aqueous) solutions, e.g phosphate, citrate etc. buffered solutions. Particularly for injection of the inventive vaccine, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$)) and optionally potassium chloride (KCl), wherein further anions may be present additional to the chlorides. $CaCl_2$) can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$)). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person.

However, one or more compatible solid or liquid fillers or diluents or encapsulating compounds may be used as well, which are suitable for administration to a person. The term "compatible" as used herein means that the excipients of the inventive vaccine are capable of being mixed with the mRNA according to the invention as defined herein, in such a manner that no interaction occurs, which would substantially reduce the pharmaceutical effectiveness of the inventive vaccine under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or excipients thereof are sugars, such as, for example, lactose, glucose, trehalose and sucrose; starches, such as, for example, corn starch or potato starch; dextrose; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The choice of a pharmaceutically acceptable carrier is determined, in principle, by the manner, in which the pharmaceutical composition or vaccine according to the invention is administered. The composition or vaccine can be administered, for example, systemically or locally.

Routes for systemic administration in general include, for example, transdermal, oral, parenteral routes, including subcutaneous, intravenous, intramuscular, intraarterial, intradermal and intraperitoneal injections and/or intranasal administration routes. Preferred administration routes according to the invention for the administration of vaccines are intramuscular injection and intradermal injection.

Routes for local administration in general include, for example, topical administration routes but also intradermal, transdermal, subcutaneous, or intramuscular injections or intralesional, intracranial, intrapulmonal, intracardial, and sublingual injections. More preferably, composition or vaccines according to the present invention may be administered by an intradermal, subcutaneous, orintramuscular route, preferably by injection, which may be needle-free and/or needle injection.

According to preferred embodiments, the artificial nucleic acid (RNA) molecule, (pharmaceutical) composition or vaccine or kit is administered by a parenteral route, preferably via intradermal, subcutaneous, or intramuscular routes. Preferably, said artificial nucleic acid (RNA) molecule, (pharmaceutical) composition or vaccine or kit may be administered by injection, e.g. subcutaneous, intramuscular or intradermal injection, which may be needle-free and/or needle injection. Accordingly, in preferred embodiments, the medical use and/or method of treatment according to the present invention involves administration of said artificial nucleic acid (RNA) molecule, (pharmaceutical) composition or vaccine or kit by subcutaneous, intramuscular or intradermal injection, preferably by intramuscular or intradermal injection, more preferably by intradermal injection. Such injection may be carried out by using conventional needle injection or (needle-free) jet injection, preferably by using (needle-free) jet injection.

The term "jet injection", as used herein, refers to a needle-free injection method, wherein a fluid containing at least one inventive mRNA sequence and, optionally, further suitable excipients is forced through an orifice, thus generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the mRNA sequence according to the invention. In a preferred embodiment, jet injection is used for intramuscular injection of the mRNA sequence according to the invention. In a further preferred embodiment, jet injection is used for intradermal injection of the mRNA sequence according to the invention.

Compositions/vaccines are therefore preferably formulated in liquid or solid form. The suitable amount of the vaccine or composition according to the invention to be administered can be determined by routine experiments, e.g. by using animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to a physiologically tolerable pH, such as about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive composition or vaccine is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine or composition can additionally contain one or more auxiliary substances in order to further increase the immunogenicity. A synergistic action of the mRNA contained in the inventive composition and of an auxiliary substance, which may be optionally be co-formulated (or separately formulated) with the inventive vaccine or composition as described above, is preferably achieved thereby. Depending on the various types of auxiliary substances, various mechanisms may play a role in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immune-stimulating adjuvant according to the invention to be enhanced and/or influenced in a targeted manner. Particularly preferred auxiliary substances are cytokines, such as monokines, lymphokines, interleukins orchemokines, that-additional to induction of the adaptive immune response by the encoded at least one antigen—promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH. Preferably, such immunogenicity increasing agents or compounds are provided separately (not co-formulated with the inventive vaccine or composition) and administered individually.

Further additives which may be included in the inventive vaccine or composition are emulsifiers, such as, for example, Tween; wetting agents, such as, for example, sodium lauryl sulfate; colouring agents; taste-imparting agents, pharmaceutical carriers; tablet-forming agents; stabilizers; antioxidants; preservatives.

The inventive vaccine or composition can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive vaccine or composition in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

According to another aspect of the present invention, the present invention also provides a kit, in particular a kit of parts, comprising the mRNA compound comprising mRNA sequence as defined herein and at least one lipid according to formula (I) or formula (II) as defined herein. According to another aspect of the present invention, the present invention also provides a kit, in particular a kit of parts, comprising the mRNA compound comprising mRNA sequence as defined herein and at least DPhyPE as neutral lipid/phospholipid. In a further embodiment the kit comprises a lipid nanoparticle as defined above or the (pharmaceutical) composition comprising a lipid nanoparticle as defined above, and/or the vaccine according to the invention, optionally a liquid vehicle for solubilizing and optionally technical instructions with information on the administration and dosage of the mRNA comprising lipid nanoparticles, the composition and/or the vaccine. The technical instructions may contain information about administration and dosage of the mRNA comprising lipid nanoparticles, the composition and/or the vaccine. Such kits, preferably kits of parts, may be applied e.g. for any of the above mentioned applications or uses, preferably for the use of the lipid nanoparticle according to the invention (for the preparation of an inventive medicament, preferably a vaccine) for the treatment or prophylaxis of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum, Plasmodium vivax, Plasmodium malariae*, or *Plasmodium ovale*) infections or diseases or disorders related thereto.

The kits may also be applied for the use of the lipid nanoparticle, the composition or the vaccine as defined herein (for the preparation of an inventive vaccine) for the treatment or prophylaxis of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum, Plasmodium vivax, Plasmodium malariae*, or *Plasmodium ovale*) infections or diseases or disorders related thereto, wherein the lipid nanoparticle, the composition and/or the vaccine may be capable of inducing or enhancing an immune response in a mammal as defined above.

Such kits may further be applied for the use of the lipid nanoparticle, the composition or the vaccine as defined herein (for the preparation of an inventive vaccine) for modulating, preferably for eliciting, e.g. to induce or enhance, an immune response in a mammal as defined above, and preferably for supporting treatment or prophylaxis of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum, Plasmodium vivax, Plasmodium malariae*, or *Plasmodium ovale*) infections or diseases or disorders related thereto.

Kits of parts, as a special form of kits, may contain one or more identical or different compositions and/or one or more identical or different vaccines as described herein in different parts of the kit. Kits of parts may also contain an (e.g. one) composition, an (e.g. one) vaccine and/or the mRNA comprising lipid nanoparticles according to the invention in different parts of the kit, e.g. each part of the kit containing an mRNA comprising lipid nanoparticles as defined herein, preferably encoding a distinct antigen. Preferably, the kit or the kit of parts contains as a part a vehicle for solubilizing the mRNA according to the invention, the vehicle optionally being Ringer-lactate solution. Any of the above kits may be used in a treatment or prophylaxis as defined above.

In another embodiment of this aspect, the kit according to the present invention may additionally contain at least one adjuvant. In a further embodiment, the kit according to the present invention may additionally contain at least one further pharmaceutically active component, preferably a therapeutic compound suitable for treatment and/or prophylaxis of cancer or a related disorder. Moreover, in another embodiment, the kit may additionally contain parts and/or devices necessary or suitable for the administration of the composition or the vaccine according to the invention, including needles, applicators, patches, injection-devices.

Routes of Administration

The choice of a pharmaceutically acceptable carrier is determined, in principle, by the manner, in which the pharmaceutical composition or vaccine according to the invention is administered. The composition or vaccine of the invention can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, intratumoral and sublingual injections. Administration to the respiratory system can be performed by spray administration or inhalation may in particular be performed by aerosol administration to the lungs, bronchi, bronchioli, alveoli, or paranasal sinuses.

In further preferred embodiments, the route of administration is selected from the group consisting of extravascular administration to a subject, such as by extravascular injection, infusion or implantation; topical administration to the skin or a mucosa; inhalation such as to deliver the composition to the respiratory system; or by transdermal or percutaneous administration. In even further preferred embodiments, the composition or vaccine of the invention can be administered via local or locoregional injection, infusion or implantation, in particular intradermal, subcutaneous, intramuscular, intracameral, subconjunctival, suprachoroidal injection, subretinal, subtenon, retrobulbar, topical, posterior juxtascleral administration, or intrapulmonal inhalation, interstitial, locoregional, intravitreal, intratumoral, intralymphatic, intranodal, intra-articular, intrasynovial, periarticular, intraperitoneal, intra-abdominal, intracardial, intralesional, intrapericardial, intraventricular, intrapleural, perineural, intrathoracic, epidural, intradural, peridural, intrathecal, intramedullary, intracerebral, intracavernous, intracorporus cavernosum, intraprostatic, intratesticular, intracartilaginous, intraosseous, intradiscal, intraspinal, intracaudal, intrabursal, intragingival, intraovarian, intrauterine, periocular, periodontal, retrobulbar, subarachnoid, subconjunctival or suprachoroidal injection, infusion or implantation.

Moreover, topical administration to the skin or a mucosa may be performed by dermal or cutaneous, nasal, buccal, sublingual, otic or auricular, ophthalmic, conjunctival, vaginal, rectal, intracervical, endosinusial, laryngeal, oropharyngeal, ureteral, urethral administration. Even more preferred routes of administration for a vaccine are intramuscular, intradermal, intranasal and oral administration (e.g. via a tablet comprising a polynucleotide, RNA or mRNA as disclosed herein).

Preferably, compositions or vaccines according to the present invention may be administered by an intradermal, subcutaneous, or intramuscular route, preferably by injection, which may be needle-free and/or needle injection. Compositions or vaccines according to the present invention are therefore preferably formulated in liquid or solid form. The suitable amount of the vaccine or composition according to the invention to be administered can be determined by routine experiments, e.g. by using animal models. Such models include, without implying any limitation, rabbit, sheep, mouse, rat, dog and non-human primate models.

Preferred unit dose forms for injection include sterile solutions of water, physiological saline or mixtures thereof. The pH of such solutions should be adjusted to a physiologically tolerable pH, such as about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive composition or vaccine is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

Uses of Compositions

The composition according to the invention is particularly useful as a medicament, as will be clear from the description of the active ingredient that may be incorporated within the composition and delivered to a subject, such as a human subject, by means of the composition and/or of the lipid nanoparticles contained therein. As such, a further aspect of the invention is the use of the composition as described above as a medicament. Such use may also be expressed as the use of the composition for the manufacture of a medicament. According to a related aspect, the invention provides a method of treatment, the method comprising a step of administering the composition to a subject, such as a human subject in need thereof, the composition.

In a preferred embodiment, the composition of the invention is used as a medicament, wherein the medicament is a vaccine.

In another preferred embodiment, the composition of the invention is used as a medicament, wherein the medicament is for or suitable for the prevention, prophylaxis, treatment and/or amelioration of a disease selected from infectious diseases including viral, bacterial or protozoological infectious diseases, cancer or tumour diseases, liver diseases, autoimmune diseases, allergies, monogenetic diseases including hereditary diseases, genetic diseases in general, diseases which have a genetic inherited background and which are typically caused by a defined gene defect and are inherited according to Mendel's laws; cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and diseases associated with a peptide or protein deficiency.

In another preferred embodiment, the composition of the invention is used as a medicament, wherein the medicament is for or suitable for the prevention, prophylaxis, treatment and/or amelioration of an infectious diseases including viral, bacterial or protozoological infectious diseases, wherein the medicament is a vaccine.

In another embodiment, the vaccine of the invention comprises a composition or a kit or kit of parts as described herein for prevention, prophylaxis, treatment and/or amelioration of a disease selected from infectious diseases including viral, bacterial or protozoological infectious diseases, cancer or tumour diseases.

In yet another aspect of the invention, a method of treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition is provided comprising the steps:

a) providing the mRNA, the composition, the vaccine, the kit or kit of parts as described herein; and
b) applying or administering the mRNA, the composition, the vaccine or the kit or kit of parts to a tissue or an organism.

In another embodiment, a method is provided, wherein the mRNA, the composition, the vaccine or the kit or kit of parts is administered to the tissue or to the organism by intravenous, intramuscular, subcutaneous or intradermal injection.

In yet a further embodiment, a method of inducing an immune response in a subject, the method comprising administering to the subject the vaccine of the invention in an amount effective to produce an antigen-specific immune response in the subject is provided.

In a further embodiment, a pharmaceutical composition comprising a composition or a kit or kit of parts as described herein for use or suitable for use in vaccination of a subject comprising an effective dose of mRNA encoding a virus antigen is provided.

In another preferred embodiment, use of a pharmaceutical composition comprising a composition or a kit or kit of parts as described herein for (i) inducing an immune response or for (ii) inducing CD8+ T cells responses is provided.

In a specific embodiment, a method for preventing, ameliorating or treating a disease or condition in a subject in need comprising administering to the subject a composition or a kit or kit of parts as described herein is provided.

Further, in a specific embodiment, a method is provided in which administration of the composition results in expression of the antigen encoded by mRNA in the lymphocytes of the subject. Further, a method is provided, wherein administration of the composition results in an antigen specific antibody response, preferably wherein the antigen specific antibody response is measured by the presence of antigen-specific antibodies in serum.

In a specific embodiment. the medicament is for the prevention, prophylaxis, treatment and/or amelioration of a disease selected from cancer or tumour diseases, infectious diseases including viral, bacterial or protozoological infectious diseases, autoimmune diseases, allergies, monogenetic diseases including hereditary diseases, genetic diseases in general, diseases which have a genetic inherited background and which are typically caused by a defined gene defect and are inherited according to Mendel's laws; cardiovascular diseases, neuronal diseases, diseases of the respiratory system, diseases of the digestive system, diseases of the skin, musculoskeletal disorders, disorders of the connective tissue, neoplasms, immune deficiencies, amino acid disorders, endocrine, nutritional and metabolic diseases, eye diseases, ear diseases and diseases associated with a peptide or protein deficiency. In one of the preferred embodiments, the medicament is an SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) vaccine.

In an alternative embodiment the present invention relates to the use of the pharmaceutical composition or the mRNA comprising lipid in the manufacture of a medicament. In particular said medicament is for therapeutically or prophylactically raising an immune response of a subject in need thereof.

In a preferred embodiment the medicament is for prevention or treatment of cancer or tumour diseases, infectious diseases, allergies, or autoimmune diseases or disorders related thereto.

In particular the medicament is for the treatment of a subject, preferably a vertebrate. In a preferred embodiment the subject is a mammal, preferably selected from the group comprising goat, cattle, swine, dog, cat, donkey, monkey, ape, a rodent such as a mouse, hamster, rabbit and, particularly, human.

Accordingly, in one preferred embodiment, the compositions as described herein are suitable for use as a medicament. In a in further preferred embodiment, said medicament is for the prevention, prophylaxis, treatment and/or amelioration of a disease selected from infectious diseases including viral, bacterial or protozoological infectious diseases, cancer or tumour diseases, liver diseases, autoimmune diseases, allergies, monogenetic diseases including hereditary diseases, genetic diseases in general, diseases which have a genetic inherited background and which are typically caused by a defined gene defect and are inherited according to Mendel's laws; cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and diseases associated with a peptide or protein deficiency. In a further preferred embodiment, the composition for use as a medicament preferably is a vaccine.

With respect to the administration of the composition to a subject, in particular to a human subject, any suitable route may be used. In one embodiment, the composition is adapted for administration by injection or infusion. As used herein, the expression "adapted for" means that the composition is formulated and processed such as to be suitable for the respective route of administration.

In a further preferred embodiment, the composition is adapted for extravascular administration to a subject, such as by extravascular injection, infusion or implantation; by topical administration to the skin or a mucosa; by inhalation such as to deliver the composition to the respiratory system; or by transdermal or percutaneous administration. In this context, extravascular injection, infusion or implantation may be performed by local or locoregional injection, infusion or implantation, in particular intradermal, subcutaneous, intramuscular, interstitial, locoregional, intravitreal, intratumoural, intralymphatic, intranodal, intra-articular, intrasynovial, periarticular, intraperitoneal, intra-abdominal, intracardial, intralesional, intrapericardial, intraventricular, intrapleural, perineural, intrathoracic, epidural, intradural, peridural, intrathecal, intramedullary, intracerebral, intracavernous, intracorporus cavernosum, intraprostatic, intratesticular, intracartilaginous, intraosseous, intradiscal, intraspinal, intracaudal, intrabursal, intragingival, intraovarian, intrauterine, periocular, periodontal, retrobulbar, subarachnoid, subconjunctival or suprachoroidal injection, infusion or implantation. Moreover, topical administration to the skin or a mucosa may be performed by dermal or cutaneous, nasal, buccal, sublingual, otic or auricular, ophthalmic, conjunctival, vaginal, rectal, intracervical, endosinusial, laryngeal, oropharyngeal, ureteral, or urethral administration. Administration to the respiratory system by inhalation may in particular be performed by aerosol administration to the lungs, bronchi, bronchioli, alveoli, or paranasal sinuses.

According to one aspect of the present invention, the mRNA comprising lipid nanoparticles, the (pharmaceutical) composition or the vaccine may be used according to the invention (for the preparation of a medicament) for use (i) in the treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition; and/or (ii) in enzyme replacement therapy for the treatment of metabolic, amino acid or endocrine disorders or for use in replacing an absent, deficient or mutated protein.

In this context particularly preferred is the treatment or prophylaxis of Malaria, Influenza virus or Rabies virus infections, or of a disorder related to such an infection.

Further particularly preferred is the treatment or prophylaxis of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) infections, or of a disorder related to such an infection.

Furthermore, also included in the present inventions are methods of treating or preventing cancer or tumour diseases, infectious diseases, allergies, or autoimmune diseases or disorders related thereto, preferably as defined herein, by administering to a subject in need thereof a pharmaceutically effective amount of the mRNA comprising lipid nanoparticles, the (pharmaceutical) composition or the vaccine according to the invention. Such a method typically comprises an optional first step of preparing the mRNA comprising lipid nanoparticles, the composition or the vaccine of the present invention, and a second step, comprising administering (a pharmaceutically effective amount of) said composition or vaccine to a patient/subject in need thereof. A subject in need thereof will typically be a mammal. In the context of the present invention, the mammal is preferably selected from the group comprising, without being limited thereto, e.g. goat, cattle, swine, dog, cat, donkey, monkey, ape, a rodent such as a mouse, hamster, rabbit and, particularly, human. In some embodiments of the invention, the subject is a bird, preferably a chicken.

In one embodiment, the composition, formulation or pharmaceutical composition in accordance with the invention preferentially targets cells in the liver but not in other organs (e.g. lung, kidney, heart). Liver cells include hepatocytes and hepatocyte precursors, stellate cells/pericytes, endothelial cells, Kupffer cells, macrophages and neutrophils, for example. In one embodiment, where the composition, formulation or pharmaceutical composition comprises a gRNA in combination with an mRNA encoding a CRISPR endonuclease such as cas9, the composition preferentially targets hepatocytes, pericentral hepatocytes (which act as stem cells in healthy livers) and, or, suitably hepatocyte stem cells. The preferential targeting of cells in the liver is due to the size and neutral charge of the lipid nanoparticles. In certain instances, targeting of the liver cells may have a secondary effect on, or influence other organs in the body. It will therefore be appreciated that the composition, formulations or pharmaceutical compositions of the present invention also have utility in the treatment of diseases other than those associated with the liver.

Suitably said pharmaceutical composition is for use, but not limited to in the treatment of liver disease or diseases where protein expression in the liver has an impact on vertebrate pathologies. As mentioned above, the pharmaceutical compositions described herein may also find use in the treatment of diseases not associated with the liver.

Suitably any transcript, transcript family or series of different transcripts or genomic chromosomal or mitochondrial sequences including but not limited to exons and introns of genes and regulatory elements involved in any liver disease or liver-related disorder may be targeted using a composition or formulation in accordance with the invention. Such any transcript, transcript family or series of different transcripts may be targeted by any biologically active compound as described herein. In one embodiment, the biologically active compound is a nucleic acid molecule which recognises a pathology-related transcript e.g. an mRNA, gRNA, siRNA, saRNA etc. as described herein.

Suitably any gene involved in any liver disease may be targeted using a composition or formulation in accordance with the invention. Such a gene may be targeted by any biologically active compound as described herein. In one embodiment, the biologically active compound is a nucleic acid molecule which recognises a liver disease gene e.g. an mRNA, gRNA, siRNA etc. as described herein.

The present invention furthermore comprises the use of the mRNA comprising lipid nanoparticles, the (pharmaceutical) composition or the vaccine according to the invention as defined herein for modulating, preferably for inducing or enhancing, an immune response in a mammal as defined herein, more preferably for preventing and/or treating SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum, Plasmodium vivax, Plasmodium malariae*, or *Plasmodium ovale*) infections, or of diseases or disorders related thereto.

In this context, support of the treatment or prophylaxis of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) infections may be any combination of a conventional SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) therapy method such as therapy with antivirals such as neuraminidase inhibitors (e.g. oseltamivir and zanamivir) and M2 protein inhibitors (e.g. adamantane derivatives), and a therapy using the RNA or the pharmaceutical composition as defined herein.

Support of the treatment or prophylaxis of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) infections may be also envisaged in any of the other embodiments defined herein. Accordingly, any use of the mRNA comprising lipid nanoparticles, the (pharmaceutical) composition or the vaccine according to the invention in co-therapy with any other approach, preferably one or more of the above therapeutic approaches, in particular in combination with antivirals is within the scope of the present invention.

For administration, preferably any of the administration routes may be used as defined herein. In particular, an administration route is used, which is suitable for treating or preventing an SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) infection as defined herein or diseases or disorders related thereto, by inducing or enhancing an adaptive immune response on the basis of an antigen encoded by the mRNA comprising lipid nanoparticles according to the invention.

Administration of the composition and/or the vaccine according to the invention may then occur prior, concurrent and/or subsequent to administering another composition and/or vaccine as defined herein, which may—in addition—contain another mRNA comprising lipid nanoparticle or combination of mRNA comprising lipid nanoparticles encoding a different antigen or combination of antigens, wherein each antigen encoded by the mRNA sequence according to the invention is preferably suitable for the treatment or prophylaxis of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) infections and diseases or disorders related thereto.

In this context, a treatment as defined herein may also comprise the modulation of a disease associated to SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*) infection and of diseases or disorders related thereto.

According to a preferred embodiment of this aspect of the invention, the (pharmaceutical) composition or the vaccine according to the invention is administered by injection. Any suitable injection technique known in the art may be employed. Preferably, the inventive composition is administered by injection, preferably by needle-less injection, for example by jet-injection.

In one embodiment, the inventive composition comprises at least one, two, three, four, five, six, seven, eight, nine, ten, eleven, twelve or more mRNAs as defined herein, each of which is preferably injected separately, preferably by needle-less injection. Alternatively, the inventive composition comprises at least one, two, three, four, five, six, seven, eight, nine, ten, eleven, twelve or more mRNAs, wherein the at least one, two, three, four, five, six, seven, eight, nine, ten, eleven, twelve or more mRNAs are administered, preferably by injection as defined herein, as a mixture.

In a further aspect the invention relates to a method of immunization of a subject against an antigen or a combination of antigens.

The immunization protocol for the immunization of a subject against an antigen or a combination of at least two, three, four, five, six, seven, eight, nine, ten, eleven, twelve or more antigens as defined herein typically comprises a series of single doses or dosages of the (pharmaceutical) composition or the vaccine according to the invention. A single dosage, as used herein, refers to the initial/first dose, a second dose or any further doses, respectively, which are preferably administered in order to "boost" the immune reaction. In this context, each single dosage preferably comprises the administration of the same antigen or the same combination of antigens as defined herein, wherein the interval between the administration of two single dosages can vary from at least one day, preferably 2, 3, 4, 5, 6 or 7 days, to at least one week, preferably 2, 3, 4, 5, 6, 7 or 8 weeks. The intervals between single dosages may be constant or vary over the course of the immunization protocol, e.g. the intervals may be shorter in the beginning and longer towards the end of the protocol. Depending on the total number of single dosages and the interval between single dosages, the immunization protocol may extend over a period of time, which preferably lasts at least one week, more preferably several weeks (e.g. 2, 3, 4, 5, 6, 7, 8, 9, 10, 11 or 12 weeks), even more preferably several months (e.g. 3, 4, 5, 6, 7, 8, 9, 10, 11, 12, 18 or 24 months). Each single dosage preferably encompasses the administration of an antigen, preferably of a combination of at least two, three, four, five, six, seven, eight, nine, ten, eleven, twelve or more antigens as defined herein and may therefore involve at least one, preferably 1, 2, 3, 4, 5, 6, 7, 8, 9, 10, 11 or 12 injections. In some cases, the composition or the vaccine according to the invention is administered as a single dosage typically in one injection. In the case, where the vaccine according to the invention comprises separate mRNA formulations encoding distinct antigens as defined herein, the minimum number of injections carried out during the administration of a single dosage corresponds to the number of separate components of the vaccine. In certain embodiments, the administration of a single dosage may encompass more than one injection for each component of the vaccine (e.g. a specific mRNA formulation comprising an mRNA encoding, for instance, one antigenic peptide or protein as defined herein). For example, parts of the total volume of an individual component of the vaccine may be injected into different body parts, thus involving more than one injection. In a more specific example, a single dosage of a vaccine comprising four separate mRNA formulations, each of which is administered in two different body parts, comprises eight injections. Typically, a single dosage comprises all injections required to administer all components of the vaccine, wherein a single component may be involve more than one injection as outlined above. In the case, where the administration of a single dosage of the vaccine according to the invention encompasses more than one injection, the injection are carried out essentially simultaneously or concurrently, i.e. typically in a time-staggered fashion within the time-frame that is required for the practitioner to carry out the single injection steps, one after the other. The administration of a single dosage therefore preferably extends over a time period of several minutes, e.g. 2, 3, 4, 5, 10, 15, 30 or 60 minutes.

Administration of the mRNA comprising lipid nanoparticles as defined herein, the (pharmaceutical) composition or the vaccine according to the invention may be carried out in a time staggered treatment. A time staggered treatment may be e.g. administration of the mRNA comprising lipid nanoparticles, the composition or the vaccine prior, concurrent and/or subsequent to a conventional therapy of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum, Plasmodium vivax, Plasmodium malariae*, or *Plasmodium ovale*) infections or diseases or disorders related thereto, e.g. by administration of the mRNA comprising lipid nanoparticles, the composition or the vaccine prior, concurrent and/or subsequent to a therapy or an administration of a therapeutic suitable for the treatment or prophylaxis of SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium *chlamydia* causing *chlamydia*), or Malaria parasite (e.g. *Plasmodium falciparum, Plasmodium vivax, Plasmodium malariae*, or *Plasmodium ovale*) infections or diseases or disorders related thereto. Such time staggered treatment may be carried out using e.g. a kit, preferably a kit of parts as defined herein.

Time staggered treatment may additionally or alternatively also comprise an administration of the mRNA comprising lipid nanoparticles as defined herein, the (pharmaceutical) composition or the vaccine according to the invention in a form, wherein the mRNA encoding an antigenic peptide or protein as defined herein or a fragment or variant thereof, preferably forming part of the composition or the vaccine, is administered parallel, prior or subsequent to another mRNA comprising lipid nanoparticles as defined above, preferably forming part of the same inventive composition or vaccine. Preferably, the administration (of all mRNA comprising lipid nanoparticles) occurs within an hour, more preferably within 30 minutes, even more preferably within 15, 10, 5, 4, 3, or 2 minutes or even within 1 minute. Such time staggered treatment may be carried out using e.g. a kit, preferably a kit of parts as defined herein.

In a preferred embodiment, the pharmaceutical composition or the vaccine of the present invention is administered repeatedly, wherein each administration preferably comprises individual administration of the at least one mRNA comprising lipid nanoparticles of the inventive composition or vaccine. At each time point of administration, the at least one mRNA may be administered more than once (e.g. 2 or 3 times). In a particularly preferred embodiment of the invention, at least two, three, four, five, six or more mRNA sequences (each encoding a distinct one of the antigens as defined herein) encapsulated or associated with mRNA comprising lipid nanoparticles as defined above, wherein the mRNA sequences are part of mRNA compounds of the same or different lipid nanoparticles, are administered at each time point, wherein each mRNA is administered twice by injection, distributed over the four limbs.

In another preferred embodiment, the use of a pharmaceutical composition comprising a composition of the invention or a kit or kit of parts of the invention for (i) inducing an immune response, for (ii) inducing an antigen specific T-cell response or preferably for (iii) inducing CD8+ T cells responses is provided. Said method for (i) inducing an immune response, for (ii) inducing an antigen specific T-cell response or preferably for (iii) inducing CD8+ T cells responses in a subject; comprises administering to a subject in need thereof at least once an effective amount of a composition as described herein comprises an mRNA encoding at least one immunogenic peptide or polypeptide as also described herein. In another embodiment, the use of a pharmaceutical composition comprising a composition of the invention or a kit or kit of parts of the invention for (i) inducing an immune response, for (ii) inducing an antigen specific T-cell response or preferably for (iii) inducing CD8+ T cells responses is provided when compared to a reference (lipid nanoparticle) formulation or composition. Said reference (lipid nanoparticle) formulation or composition in a preferred embodiment does not comprise DPhyPE and/or a cationic lipid according to formula (I).

First and Second/Further Medical Use:

A further aspect relates to the first medical use of the provided nucleic acid, composition, polypeptide, vaccine, or kit, wherein the composition of the invention, comprising the inventive lipid excipient(s), is used for delivering said nucleic acid. Notably, embodiments relating to the nucleic acid, the composition, the polypeptide, the vaccine, or the kit or kit of parts may likewise be read on and be understood as suitable embodiments of medical uses of the invention.

Accordingly, the invention provides at least one nucleic acid (e.g. DNA or RNA), preferably RNA as defined in the first aspect for use as a medicament, a composition for use as a medicament, a polypeptide as defined for use as a medicament, a vaccine as defined for use as a medicament, and a kit or kit of parts for use as a medicament, wherein the composition of the invention, comprising the inventive lipid excipient(s), is used for delivering said nucleic acid.

The present invention furthermore provides several applications and uses of the nucleic acid, composition, polypeptide, vaccine, or kit, i.e. in particular, nucleic acid (preferably RNA), composition, polypeptide, vaccine, or kit may be used for human medical purposes and also for veterinary medical purposes, preferably for human medical purposes, wherein the composition of the invention, comprising the inventive lipid excipient(s), is used for delivering said nucleic acid.

In particular, nucleic acid (preferably RNA), composition, polypeptide, vaccine, or kit or kit of parts is for use as a medicament for human medical purposes, wherein said nucleic acid (preferably RNA), composition, polypeptide, vaccine, or kit or kit of parts may be suitable for young infants, newborns, immunocompromised recipients, as well as pregnant and breast-feeding women and elderly people. In particular, nucleic acid (preferably RNA, most preferably mRNA), composition, polypeptide, vaccine, or kit or kit of parts is for use as a medicament for human medical purposes, wherein said nucleic acid (preferably RNA, most preferably mRNA), composition, polypeptide, vaccine, or kit or kit of parts is particularly suitable for elderly human subjects.

Said nucleic acid (preferably RNA), composition, polypeptide, vaccine, or kit is for use as a medicament for human medical purposes, wherein said RNA, composition, vaccine, or the kit or kit of parts may be particularly suitable for intramuscular injection or intradermal injection.

In yet another aspect, the invention relates to the second medical use of the provided nucleic acid, composition, polypeptide, vaccine, or kit.

Accordingly, the invention provides at least one nucleic acid, wherein the nucleic acid is comprised in a composition of the invention, comprising the inventive lipid excipient(s) used for delivering said nucleic acid, preferably RNA, most preferably mRNA, for treatment or prophylaxis of an infection with a coronavirus, preferably a betacoronavirus, more preferably a severe acute respiratory syndrome coronavirus 2 (SARS-CoV-2), or a disorder or a disease related to such an infection, such as Coronavirus disease 2019 (COVID-19); a composition for treatment or prophylaxis of an infection with a coronavirus, preferably SARS-CoV-2 coronavirus, or a disorder or a disease related to such an infection, such as COVID-19; a polypeptide for treatment or prophylaxis of an infection with a coronavirus, preferably SARS-CoV-2 coronavirus, or a disorder or a disease related to such an infection, such as COVID-19; a vaccine for treatment or prophylaxis of an infection with a coronavirus, preferably SARS-CoV-2 coronavirus, or a disorder or a disease related to such an infection, such as COVID-19; a kit or kit of parts for treatment or prophylaxis of an infection with a coronavirus, preferably SARS-CoV-2 coronavirus, or a disorder or a disease related to such an infection, such as COVID-19.

In other embodiments, the nucleic acid, preferably RNA, most preferably mRNA, the composition, the polypeptide, the vaccine, or the kit or kit of parts is for use in the treatment or prophylaxis of an infection with a coronavirus, preferably with SARS-CoV-2 coronavirus, wherein the composition of the invention, comprising the inventive lipid excipient(s), is used for delivering said nucleic acid.

Particularly, the nucleic acid, preferably RNA, most preferably mRNA, the composition, the polypeptide, the vaccine, or the kit or kit of parts may be used in a method of prophylactic (pre-exposure prophylaxis or post-exposure prophylaxis) and/or therapeutic treatment of COVID-19 disease caused by a SARS-CoV-2 coronavirus infection, wherein the composition of the invention, comprising the inventive lipid excipient(s), is used for delivering said nucleic acid.

The nucleic acid, the composition, the polypeptide, or the vaccine may preferably be administered locally. In particular, composition or vaccines may be administered by an intradermal, subcutaneous, intranasal, or intramuscular route, wherein the composition of the invention, comprising the inventive lipid excipient(s), is used for delivering said nucleic acid. In other embodiments, said nucleic acid, composition, polypeptide, vaccine may be administered by conventional needle injection or needle-free jet injection. Preferred in that context is intramuscular injection.

In other embodiments, the nucleic acid as comprised in a composition of the invention, comprising the inventive lipid excipient(s), is used for delivering said nucleic acid as defined herein is provided in an amount of about 100 ng to about 500 μg, in an amount of about 1 μg to about 200 μg, in an amount of about 1 μg to about 100 μg, in an amount of about 5 μg to about 100 μg, preferably in an amount of about 10 μg to about 50 μg, specifically, in an amount of about 1 μg, 2 μg, 3 μg, 4 μg, 5 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg or 100 μg.

In one embodiment, the immunization protocol for the treatment or prophylaxis of a subject against coronavirus, preferably SARS-CoV-2 coronavirus comprises one single doses of the composition or the vaccine, wherein the composition of the invention, comprising the inventive lipid excipient(s), is used for delivering said nucleic acid.

In some embodiments, the effective amount is a dose of 1 μg, 2 μg, 3 μg, 4 μg, 5 μg, 6 μg, 7 μg, 8 μg, 9 μg, 10 μg, 11 μg, 12 μg, 13 μg, 14 μg, 15 μg, 16 μg, 20 μg, 30 μg, 40 μg, 50 μg, 75 μg, 100 μg or 200 μg administered to the subject in one vaccination, wherein the composition of the invention, comprising the inventive lipid excipient(s), is used for delivering said nucleic acid. In preferred embodiments, the immunization protocol for the treatment or prophylaxis of a coronavirus, preferably a SARS-CoV-2 coronavirus infection comprises a series of single doses or dosages, preferably a total of two doses, of the composition or the vaccine, wherein the composition of the invention, comprising the inventive lipid excipient(s), is used for delivering said nucleic acid. A single dosage, as used herein, refers to the initial/first dose, a second dose or any further doses, respectively, which are preferably administered in order to "boost" the immune reaction, wherein the composition of the invention, comprising the inventive lipid excipient(s), is used for delivering said nucleic acid.

In preferred embodiments, the vaccine/composition immunizes the subject against a coronavirus, preferably against a SARS-CoV-2 coronavirus infection (upon administration as defined herein) for at least 1 year, preferably at least 2 years, wherein for immunization the composition of the invention, comprising the inventive lipid excipient(s), is used for delivering said nucleic acid.

Standard Therapy

More preferably, the subject receiving the pharmaceutical composition or vaccine comprising RNAs of the invention, the combination thereof or the pharmaceutical composition or vaccine comprising said RNA(s) is a patient suffering from a tumour or cancer disease as described herein and who received or receives chemotherapy (e.g. first-line or second-line chemotherapy), radiotherapy, chemoradiotherapy/chemoradiation (combination of chemotherapy and radiotherapy), kinase inhibitors, antibody therapy and/or checkpoint modulators (e.g. CTLA4 inhibitors, PD1 pathway inhibitors), or a patient, who has achieved partial response or stable disease after having received one or more of the treatments specified above. More preferably, the subject is a patient suffering from a tumour or cancer disease as described herein and who received or receives a compound conventionally used in any of these diseases as described herein, more preferably a patient who receives or received a checkpoint modulator.

Compounds which preferably are used in standard therapies and which can be applied in combination with the pharmaceutical compositions or vaccines comprising RNAs of the invention include but are not limited to those disclosed on pages 56-58 in WO 2018/078053 A1; WO 2018/078053 A1 being incorporated herein by reference in its entirety.

Tumour Indications

As used herein, the terms "tumour", "cancer" or "cancer disease" refer to a malignant disease, which is preferably selected from, but not limited to, the group of malignant diseases disclosed on pages 58-59 in WO 2018/078053 A1; WO 2018/078053 A1 being incorporated herein by reference in its entirety.

Exemplary Embodiments

In the following, several sets of different embodiments of the invention are disclosed. It is intended herein, that each and every embodiment stemming from a set of embodiments can be combined with each other, i.e. embodiment 1 from the First Set of Embodiments may be combined with f.e. embodiment 3 from the Second Set of Embodiments.

First Set of Embodiments

1. A cationic lipid according to formula (I):

$R^a$-A-$R^b$ formula (I)

or a pharmaceutically acceptable salt, prodrug or stereoisomer thereof, wherein $R^a$ is selected from:

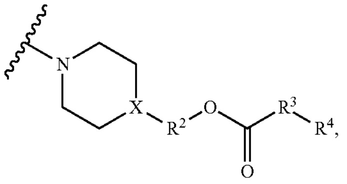

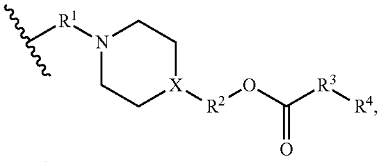

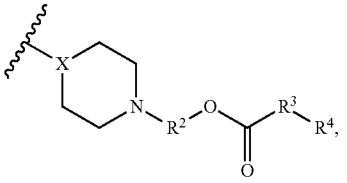

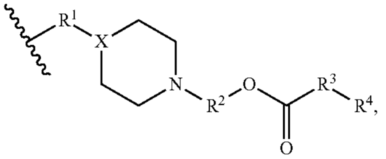

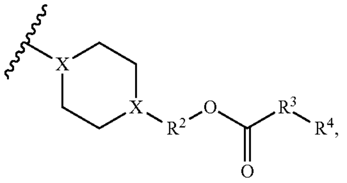

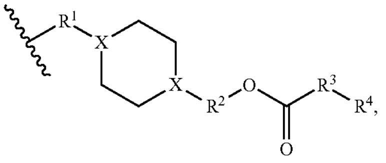

or

-continued

—$R^1$—N(H)—C(O)—$R^3$—$R^4$;

$R^b$ is selected from:

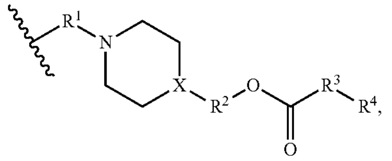

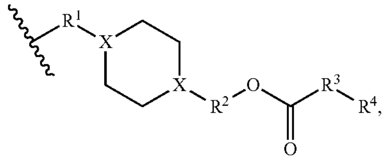

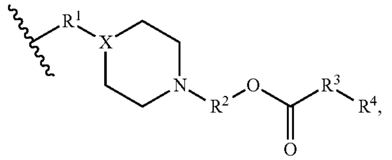

—$R^1$—N(H)—C(O)—$R^3$—$R^4$, or —$R^1$—$N(CH_3)_2$;

A is —S—, —S—S—, —NH—C(O)—, —NH—C(O)O—, —NH—C(O)—NH—, —S—C(O)—N(H)—, —C(O)O—, or —O—P(O)(OH)—O—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is —$R^5$—C(O)—O—, —$R^5$—O—C(O)—, —$R^5$—C(O)—NH—, —$R^5$—OC(O)—NH—, or $R^5$—NH—C(O)O—;

$R^4$ is a lipophilic substituent with 12 to 36 carbon atoms;

$R^5$ is an alkanediyl having 1 to 6 carbon atoms;

X is a carbon or nitrogen atom;

wherein all selections are independent of one another.

2. The cationic lipid according to embodiment 1, wherein $R^5$ is an alkanediyl having 3 to 6 carbon atoms, selected independently at each occurrence.

3. The cationic lipid according to embodiment 1 to embodiment 2, wherein $R^4$ is an alkyl or alkenyl having 12 to 25 carbon atoms, selected independently at each occurrence.

4. The cationic lipid according to embodiment 1 to embodiment 3, wherein $R^a$ and $R^b$ are independently selected from

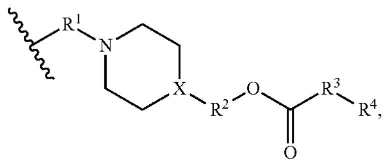

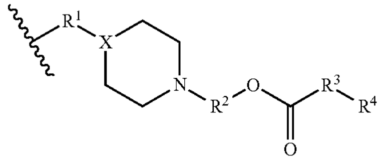

or

-continued

—$R^1$—N(H)—C(O)—$R^3$—$R^4$.

5. The cationic lipid according to embodiment 1 to embodiment 4, wherein each of $R^a$ and $R^b$ is:

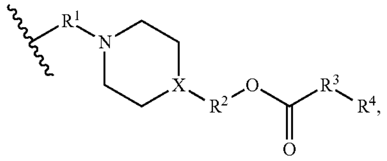

selected independently at each occurrence; and $R^5$ is an alkanediyl having 2 to 6 carbon atoms, selected independently at each occurrence.

6. The cationic lipid according to embodiment 5, wherein A is —S—S—.

7. The cationic lipid according to embodiment 6, wherein $R^4$ is an alkyl or alkenyl having 12 to 25 carbon atoms, selected independently at each occurrence.

8. The cationic lipid according to embodiment 7, wherein each $R^4$ is an alkyl selected independently at each occurrence from:

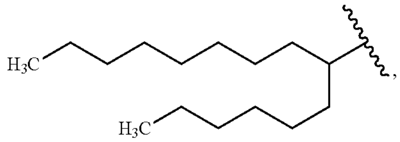

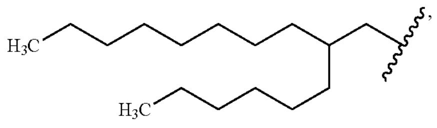

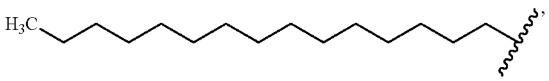

or

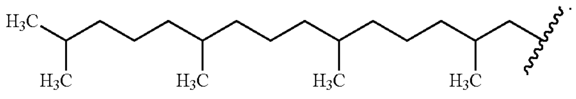

9. The cationic lipid according to embodiment 8, wherein $R^3$ is-$R^5$—C(O)—O— or —$R^5$—O—C(O)—;

$R^4$ is:

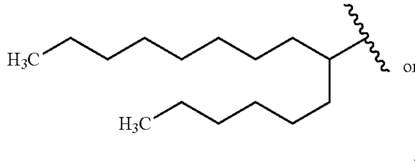

or

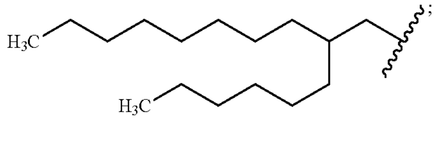

and wherein $R^a$ and $R^b$ are identical.

10. The cationic lipid according to embodiment 9, wherein $R^3$ is —$R^5$—C(O)—O—.

11. The cationic lipid according to embodiment 10, wherein X is a carbon atom.

12. The cationic lipid according to embodiment 11, wherein $R^1$ is ethanediyl.

13. The cationic lipid of any of the preceding embodiments, further exhibiting one or more of the following features, independently selected at each occurrence:

(i) $R^1$ is an unsubstituted ethanediyl, propanediyl, or butanediyl;

(ii) $R^2$ is an linear, unbranched alkanediyl having 2 to 8 carbon atoms;

(iii) $R^3$ is-$R^5$—C(O)—O— or —$R^5$—O—C(O)—;

(iv) $R^4$ is an alkyl or alkenyl having 12 to 25 carbon atoms;

(v) $R^5$ is an alkanediyl having 2 to 6 carbon atoms; and/or (vi) X is a carbon atom.

14. The cationic lipid of embodiment 1, being selected from one of the compounds as listed in Table 1.

15. A composition comprising (i) the cationic lipid of any one of embodiments 1 to 14; or (ii) the cationic lipid C15 as listed in Table 1.

16. The composition of embodiment 15, further comprising one or more of the following excipients:

(i) a steroid, preferably cholesterol;

(ii) a neutral lipid;

wherein said neutral lipid preferably is 1,2-diphytanoyl-sn-glycero-3-phosphoethanolamine (DPhyPE), optionally in combination with the neutral lipid 1,2-diheptanoyl-sn-glycero-3-phosphocholine (DHPC); or wherein said neutral lipid is a zwitterionic compound, optionally a zwitterionic compound having two fatty acid moieties selected from myristoyl, palmitoyl, stearoyl and oleyol, in combination with a zwitterionic compound having two fatty acid moieties selected from pentanoyl, hexanoyl, heptanoyl, octanoyl, nonaoyl and decanoyl;

and/or (iii) a polymer conjugated lipid;

wherein said polymer conjugated lipid is a compound according to formula (II):

P-A-L formula (II);

wherein P is a hydrophilic polymer moiety, A is an optional linker, and L is a lipid moiety;

preferably wherein the polymer conjugated lipid is a pegylated lipid.

17. A composition comprising one or more of the following excipients:

(i) a cationic lipid of any one of embodiments 1 to 14 or a cationic lipid comprising a tertiary or quaternary nitrogen/amino group or a cationic lipid carrying a net positive charge at physiological pH;

(ii) a steroid, preferably cholesterol;

(iii) a neutral lipid as described in subitem (ii) of embodiments 16; and/or (iv) a polymer conjugated lipid, wherein said polymer conjugated lipid is a compound according to formula (II):

P-A-L formula (II);

wherein P is a hydrophilic polymer moiety, A is an optional linker, and L is a lipid moiety;

preferably wherein the polymer conjugated lipid is a pegylated lipid;

more preferably, wherein the lipid moiety L comprises at least one fatty acid ("tail") comprising 8, 10 or 12 carbon atoms, preferably 8 or 10 carbon atoms;

even more preferably, wherein the pegylated lipid is selected from the group consisting of 1,2-dicapryl-rac-glycero-3-methylpolyoxyethylene glycol 2000 (C10-PEG 2000); and N-octanoyl-sphingosine-1-{succinyl[methoxy(polyethylene glycol)2000]} (Cer8-PEG 2000).

18. A composition comprising one or more of the following excipients:

(i) a cationic lipid as described in subitem (i) of embodiment 17;

(ii) a steroid, preferably cholesterol;

(iii) a neutral lipid as described in subitem (ii) of embodiment 16; and/or (iv) a polymer conjugated lipid, wherein said polymer conjugated lipid is a compound according to formula (II):

P-A-L formula (II);

wherein P is a hydrophilic polymer moiety, A is an optional linker, and L is a lipid moiety;

preferably wherein the polymer conjugated lipid is a pegylated lipid;

more preferably wherein the pegylated lipid is selected from the group consisting of 1,2-dimyristoyl-rac-glycero-3-methoxypolyethylene glycol 2000 (DMG-PEG 2000).

19. The composition of any one of embodiments 15 to 18 wherein preferably the composition comprises excipients in a ratio selected from the group consisting of (α-i) the cationic lipid at an amount of 30-70 mol %; the steroid at an amount of 20-50 mol %; the neutral lipid at an amount of 5-25 mol %; and the polymer conjugated lipid at an amount of 0.5-5 mol %;

(α-ii) the cationic lipid at an amount of 40-70 mol %; the steroid at an amount of 20-50 mol %; the neutral lipid at an amount of 5-15 mol %; and the polymer conjugated lipid at an amount of 0.5-5 mol %;

(α-iii) the cationic lipid at an amount of 20-60 mol %; the steroid at an amount of 25-55 mol %; the phospholipid at an amount of 5-25 mol %; and the polymer conjugated lipid at an amount of 0.5-15 mol %;

(α-iv) the cationic lipid at an amount of 45-65 mol %; the steroid at an amount of 25-45 mol %; the phospholipid at an amount of 8-12 mol %; and the polymer conjugated lipid at an amount of 1-3 mol %;

(α-v) the cationic lipid at an amount of 45-65 mol %; cholesterol at an amount of 25-45 mol %; the neutral lipid at an amount of 8-12 mol %; and the polymer conjugated lipid at an amount of 1-3 mol %;

(α-vi) the cationic lipid at an amount of 45-65 mol %; cholesterol at an amount of 25-45 mol %; DPhyPE at an amount of 8-12 mol % and optionally DHPC at an amount of 1 to 10 mol %; and the polymer conjugated lipid at an amount of 1-3 mol %; and (α-vi) the cationic lipid at an amount of 45-65 mol %; cholesterol at an amount of 25-45 mol %; DPhyPE at an amount of 8-12 mol % and optionally DHPC at an amount of 1 to 10 mol %; and PEG-DMG 2000 at an amount of 1-3 mol %; or more preferably the composition comprises excipients in a ratio selected from the group consisting of (b-i) the cationic lipid at an amount of 59 mol %; the steroid at an amount of 29.3 mol %; the neutral lipid at an amount of 10 mol %; and the polymer conjugated lipid at an amount of 1.7 mol %;

(b-ii) the cationic lipid at an amount of 59 mol %; cholesterol at an amount of 29.3 mol %; the neutral lipid at an amount of 10 mol %; and the polymer conjugated lipid at an amount of 1.7 mol %;

(b-iii) the cationic lipid at an amount of 59 mol %; cholesterol at an amount of 29.3 mol %; DPhyPE at an amount of 10 mol %; and the polymer conjugated lipid at an amount of 1.7 mol %;

(b-iv) the cationic lipid at an amount of 59 mol %; cholesterol at an amount of 29.3 mol %; DPhyPE at an amount of 10 mol %; and $C_{10}$-PEG 2000 at an amount of 1.7%; and (b-v) the cationic lipid at an amount of 59 mol %; cholesterol at an amount of 29.3 mol %; DPhyPE at an amount of 10 mol %; and Cer8-PEG 2000 at an amount of 1.7%;

each amount being relative to the total molar amount of all lipidic excipients of the lipid nanoparticles; more preferably the composition comprises excipients in a ratio selected from the group consisting of (c-i) a lipid excipient combination selected from the group consisting of E1 to E69 as disclosed in Table E at mol-percentages selected from the group consisting of F1 to F60 as disclosed in Table F.

20. The composition of any one of embodiments 15 to 19 wherein preferably the composition comprises excipients in a ratio of (i) 59 mol % cationic lipid C23 as disclosed in Table 1, 29.3 mol % cholesterol, 10 mol % DPhyPE and 1.7 mol % DMG-PEG 2000;

(ii) 59 mol % cationic lipid C2 as disclosed in Table 1, 29.3 mol % cholesterol, 10 mol % DPhyPE and 1.7 mol % DMG-PEG 2000; or (iii) 59 mol % cationic lipid C15 as disclosed in Table 1, 29.3 mol % cholesterol, 10 mol % DPhyPE and 1.7 mol % DMG-PEG 2000.

21. The composition any one of embodiments 15 to 20, further comprising a biologically active ingredient.

22. The composition of embodiment 21, wherein the biologically active ingredient is a nucleic acid compound selected from the group consisting of an artificial mRNA, chemically modified or unmodified messenger RNA (mRNA) comprising at least one coding sequence, self-replicating RNA, circular RNA, viral RNA, and replicon RNA; or any combination thereof, preferably wherein the biologically active ingredient is an mRNA or an mRNA compound.

23. The composition of any one of embodiments 15 to 22, wherein the lipid nanoparticles comprise the mRNA (i) at an amount such as to achieve an N/P ratio in the range of 10 to 20; or (ii) at an amount such as to achieve a lipid:mRNA weight ratio in the range of 20 to 60, preferably from about 3 to about 15, 5 to about 13, about 4 to about 8 or from about 7 to about 11.

24. The composition of any one of embodiments 15 to 23, wherein the composition is a sterile solid composition for reconstitution with a sterile liquid carrier, and wherein the composition further comprises one or more inactive ingredients selected from pH-modifying agents, bulking agents, stabilizers, non-ionic surfactants and antioxidants, and wherein the sterile liquid carrier is an aqueous carrier.

25. The composition of any one of embodiments 15 to 24, wherein the composition is a sterile liquid composition, and wherein the lipid nanoparticles have a mean hydrodynamic diameter as determined by dynamic laser scattering from about 50 nm to about 300 nm, or from about 60 nm to about 250 nm, or from about 60 nm to about 200 nm, or from about 70 to 200 nm, or from about 75 nm to about 160, or from about 90 nm to about 140 nm, or from about 100 nm to about 140 nm.

26. The composition of any one of embodiments 15 to 25, wherein the lipid nanoparticles exhibit a zeta potential in the range of −50 mV to +50 mV.

27. The composition of any one of embodiments 22 to 26, wherein the mRNA compound is a mono-, bi-, or multicistronic mRNA.

28. The composition of any one embodiments 22 to 26, wherein the mRNA compound comprises at least one chemical modification.

29. The composition of embodiment 28, wherein the chemical modification is selected from the group consisting of base modifications, sugar modifications, backbone modifications and lipid modifications, preferably wherein the chemical modification is a base modification, more preferably wherein the base modification preferably is selected from the group consisting of pseudouracil (Lp), N1-methylpseudouracil (N1Mp), 1-ethylpseudouracil, 2-thiouracil (s2U), 4-thiouracil, 5-methylcytosine, 5-methyluracil, 5-methoxyuracil, and any combination thereof.

30. The composition of any one of embodiments 22 to 29, wherein the mRNA compound comprises a coding region encoding a peptide or protein, wherein the coding region exhibits a sequence modification.

31. The composition of embodiment 30, wherein the sequence modification is selected from a G/C content modification, a codon modification, a codon optimization or a C-optimization of the sequence; preferably wherein the G/C content of the coding region is increased;

the C content of the coding region is increased;

the codon usage in the coding region is adapted to the human codon usage; and/or the codon adaptation index (CAI) is increased or maximised in the coding region compared with the coding region of the corresponding wild-type mRNA.

32. The composition of any one of embodiments 22 to 31, wherein the mRNA compound further comprises a) a 5'-CAP structure;

b) at least one miRNA sequence, preferably wherein the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof;

c) at least one 5'-UTR element;

d) at least one poly(A) sequence;

e) at least one poly(C) sequence;

f) at least one 3'-UTR element;

or any combinations of these.

33. The composition any one of embodiments 22 to 32, wherein the least one coding RNA comprises a 5'-CAP structure, preferably m7G, CAP0, CAP1, CAP2, a modified CAP0 or a modified CAP1 structure.

34. The composition of any one of embodiments 22 to 33, wherein the at least one coding RNA comprises at least one heterologous 5'-UTR and/or at least one heterologous 3'-UTR, preferably wherein the at least one heterologous 5'-UTR comprises a nucleic acid sequence derived from a 5'-UTR of a gene selected from HSD17B4, RPL32, ASAH1, ATP5A1, MP68, NDUFA4, NOSIP, RPL31, SLC7A3, TUBB4B and UBQLN2, or from a homolog, a fragment or variant of any one of these genes; and/or preferably wherein the at least one heterologous 3'-UTR comprises a nucleic acid sequence derived from a 3'-UTR of a gene selected from PSMB3, ALB7, alpha-globin, CASP1, COX6B1, GNAS, NDUFA1 and RPS9, or from a homolog, a fragment or a variant of any one of these genes.

35. The composition of any one of embodiments 22 to 34, wherein the at least one coding RNA comprises a (i) HSD17B4 5'-UTR and a PSMB3 3'-UTR or (ii) a RPL32 5'-UTR and an ALB7 3'-UTR.

36. The composition of any one of embodiments 22 to 35, comprising the following elements in the 5' to 3' direction:

a) a 5'-CAP structure, preferably selected from the group consisting of m7G(5'), m7G(5')ppp(5')(2'OMeA) and m7G(5')ppp(5')(2'OMeG);

b) a 5'-UTR element comprising a nucleic acid sequence derived from the 5'-UTR of a TOP gene, said nucleic acid sequence preferably comprising an RNA sequence that corresponds to the nucleic acid sequence according to SEQ ID NO:22, 24, 26, or a homolog, a fragment or a variant thereof;

c) at least one coding sequence;

d) a 3-UTR element comprising a nucleic acid sequence derived from an α-globin gene, said nucleic acid sequence preferably comprising an RNA sequence that corresponds to the nucleic acid sequence according to SEQ ID NO:6, 8, 10, 12, 14, 16, 18, 20, or a homolog, a fragment or a variant thereof; and/or a 3-UTR element comprising a nucleic acid sequence derived from an albumin gene, said nucleic acid sequence preferably comprising an RNA sequence that corresponds to the nucleic acid sequence according to SEQ ID NO:18, or a homolog, a fragment or a variant thereof;

e) optionally, at least one poly(A) sequence, preferably consisting of 10 to 200, 10 to 100, 40 to 80, 50 to 70, or 70 to 90 adenosine nucleotides;

f) optionally, at least one poly(C) sequence, preferably consisting of 10 to 200, 10 to 100, 20 to 70, 20 to 60 or 10 to 40 cytosine nucleotides; and g) optionally, at least one histone stem-loop, preferably comprising the RNA sequence according to SEQ ID NO:4.

37. The composition of any one of embodiments 21 to 36, wherein the biologically active ingredient is (a) an mRNA comprising at least one coding sequence encoding a peptide or protein, or a fragment or variant thereof, wherein the peptide or protein is an antigen, wherein the antigen preferably is derived from pathogenic antigens, tumour antigens, allergenic antigens or autoimmune self-antigens, or a fragment or variant thereof; or (b) an mRNA comprising at least one coding sequence encoding a therapeutic protein, or a fragment or variant thereof, wherein the therapeutic protein is selected from the group consisting of (i) therapeutic proteins for use in enzyme replacement therapy for the treatment of metabolic, endocrine or amino acid disorders or for use in replacing an absent, deficient or mutated protein;

(ii) therapeutic proteins for use in the treatment of blood disorders, diseases of the circulatory system, diseases of the respiratory system, infectious diseases or immune deficiencies;

(iii) therapeutic proteins for use in the treatment of cancer or tumour diseases;

(iv) therapeutic proteins for use in hormone replacement therapy;

(v) therapeutic proteins for use in reprogramming somatic cells into pluri- or omnipotent stem cells;

(vi) therapeutic proteins for use as adjuvant or immunostimulation;

(vii) therapeutic proteins being a therapeutic antibody;

(viii) therapeutic proteins being a gene editing agent; and (ix) therapeutic proteins for use in treating or preventing a liver disease selected from the group consisting of liver fibrosis, liver cirrhosis and liver cancer.

38. The composition of embodiment 37 subitem (a), wherein the antigen encodes a pathogenic antigen selected from the group consisting of a bacterial, viral, fungal and protozoal antigen.

39. The composition of embodiment 38, wherein the pathogenic antigen is derived from a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*).

40. The composition of any one of embodiments 15 to 39 for use (i) in the treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition; and/or (ii) for use in enzyme replacement therapy for the treatment of metabolic or endocrine disorders or for use in replacing an absent, deficient or mutated protein.

41. The composition of any one of embodiments 15 to 39 for use in the treatment or prophylaxis of infectious diseases.

42. The composition of embodiments 40 or 41 comprising at least one coding RNA, wherein said at least one coding RNA comprises at least one coding sequence encoding at least one peptide or protein for use in treatment or prevention of a disease, disorder or condition, wherein said composition is administered via intramuscular or intradermal injection a subject in need thereof.

43. A kit or kit of parts, comprising any one of the compositions of embodiments 21 to 42, optionally comprising a liquid vehicle for solubilizing, and, optionally, technical instructions providing information on administration and dosage of the components.

44. The composition of any one of embodiments 21 to 42 or the kit or kit of parts of embodiment 43 for use as a medicament.

45. The composition for use as a medicament according to embodiment 44, wherein the medicament is for the prevention, prophylaxis, treatment and/or amelioration of a disease selected from infectious diseases including viral, bacterial or protozoological infectious diseases, cancer or tumour diseases, liver diseases, autoimmune diseases, allergies, monogenetic diseases including hereditary diseases, genetic diseases in general, diseases which have a genetic inherited background and which are typically caused by a defined gene defect and are inherited according to Mendel's laws; cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and diseases associated with a peptide or protein deficiency.

46. The composition for use as a medicament according to embodiments 44 or 45, wherein the medicament is a vaccine.

47. A vaccine comprising a composition of any one of embodiments 15 to 42 or a kit or kit of parts of embodiment 43 for prevention, prophylaxis, treatment and/or amelioration of a disease selected from infectious diseases including viral, bacterial or protozoological infectious diseases, cancer or tumour diseases.

48. A method of treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition comprising the steps:

a) providing the mRNA as described in any one of the above embodiments, the composition as described in any one of the above embodiments, the vaccine of embodiment 47, the kit or kit of parts of embodiment 43; and b) applying or administering the mRNA, the composition, the vaccine or the kit or kit of parts to a tissue or an organism.

49. The method according to embodiment 48, wherein the mRNA, the composition any one of embodiments 15 to 42, the vaccine of embodiment 47 or the kit or kit of parts of embodiment 43 is administered to the tissue or to the organism by intravenous, intramuscular, subcutaneous or intradermal injection.

50. A method of inducing an immune response in a subject, the method comprising administering to the subject the vaccine of embodiment 47 in an amount effective to produce an antigen-specific immune response in the subject.

51. A pharmaceutical composition comprising a composition of any one of embodiments 15 to 42 or a kit or kit of parts of embodiment 43 for use in vaccination of a subject comprising an effective dose of mRNA encoding a virus antigen.

52. Use of a pharmaceutical composition comprising a composition of any one of embodiments 15 to 42 or a kit or kit of parts of embodiment 43 for (i) inducing an immune response, for (ii) inducing an antigen specific T-cell response or preferably for (iii) inducing CD8+ T cells responses.

53. Use of the pharmaceutical composition of embodiment 52 for the prophylaxis of an infectious disease or in the manufacture of a medicament for the prophylaxis of an infectious disease, wherein said medicament preferably is a vaccine.

54. A method for preventing, ameliorating or treating a disease or condition in a subject in need comprising administering to the subject a composition of any one of embodiments 15 to 42 or a kit or kit of parts of embodiment 43.

55. The method of any one of the preceding method embodiments, wherein administration of the composition results in expression of the antigen encoded by mRNA in the lymphocytes of the subject.

56. The method of any one of the preceding method embodiments, wherein the administration of the composition results in an antigen specific antibody response, preferably wherein the antigen specific antibody response is measured by the presence of antigen-specific antibodies in serum.

Second Set of Embodiments

1. A composition comprising a cationic lipid according to formula (I):

$$R^a\text{-}A\text{-}R^b \quad \text{formula (I)}$$

or a pharmaceutically acceptable salt, prodrug or stereoisomer thereof, wherein $R^a$ is selected from:

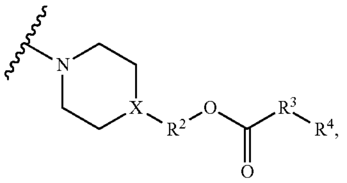

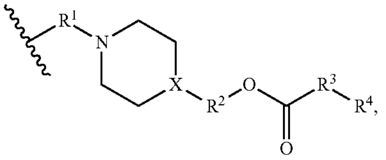

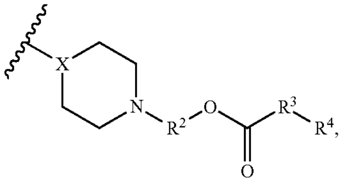

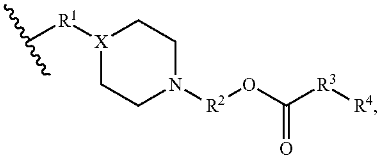

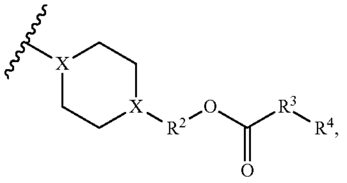

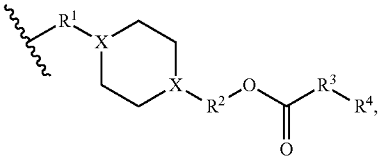

or $—R^1—N(H)—C(O)—R^3—R^4$;

$R^b$ is selected from:

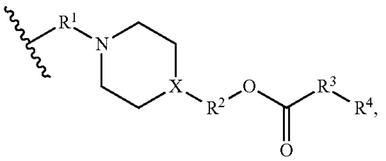

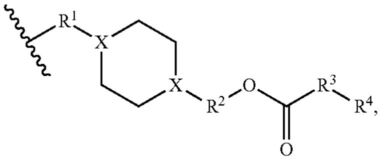

-continued

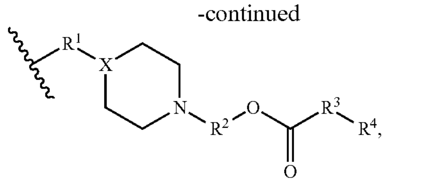

$—R^1—N(H)—C(O)—R^3—R^4$, or $—R^1—N(CH_3)_2$;

A is —S—, —S—S—, —NH—C(O)—, —NH—C(O)O—, —NH—C(O)—NH—, —S—C(O)—N(H)—, —C(O)O—, or —O—P(O)(OH)—O—;

$R^1$ is an optionally substituted ethanediyl, propanediyl, butanediyl, or linear or unbranched alkanediyl having 2 to 8 carbon atoms;

$R^2$ is an alkanediyl having 2 to 8 carbon atoms;

$R^3$ is optional, and if present, is $—R^5—C(O)—O—$, $—R^5—O—C(O)—$, $—R^5—C(O)—NH—$, $—R^5—OC(O)—NH—$, or $R^5—NH—C(O)O—$;

$R^4$ is a lipophilic substituent with 12 to 36 carbon atoms;

$R^5$ is an alkanediyl having 1 to 6 carbon atoms;

X is a carbon or nitrogen atom;

wherein all selections are independent of one another further comprising one or more of the following excipients:

(i) cholesterol;

(ii) 1,2-diphytanoyl-sn-glycero-3-phosphoethanolamine (DPhyPE);

and/or (iii) a pegylated lipid selected from the group consisting of 1,2-dimyristoyl-rac-glycero-3-methoxypolyethylene glycol 2000 (DMG-PEG 2000), 1,2-dicapryl-rac-glycero-3-methylpolyoxyethylene glycol 2000 ($C_{10}$-PEG 2000); and N-octanoyl-sphingosine-1-{succinyl [methoxy(polyethylene glycol)2000]} (Cer8-PEG 2000).

2. The composition of embodiment 1 wherein preferably the composition comprises excipients in a ratio selected from the group consisting of (α-i) the cationic lipid at an amount of 30-70 mol %; the steroid at an amount of 20-50 mol %; the neutral lipid at an amount of 5-25 mol %; and the polymer conjugated lipid at an amount of 0.5-5 mol %;

(α-ii) the cationic lipid at an amount of 40-70 mol %; the steroid at an amount of 20-50 mol %; the neutral lipid at an amount of 5-15 mol %; and the polymer conjugated lipid at an amount of 0.5-5 mol %;

(α-iii) the cationic lipid at an amount of 20-60 mol %; the steroid at an amount of 25-55 mol %; the phospholipid at an amount of 5-25 mol %; and the polymer conjugated lipid at an amount of 0.5-15 mol %;

(α-iv) the cationic lipid at an amount of 45-65 mol %; the steroid at an amount of 25-45 mol %; the phospholipid at an amount of 8-12 mol %; and the polymer conjugated lipid at an amount of 1-3 mol %;

(α-v) the cationic lipid at an amount of 45-65 mol %; cholesterol at an amount of 25-45 mol %; the neutral lipid at an amount of 8-12 mol %; and the polymer conjugated lipid at an amount of 1-3 mol %;

(α-vi) the cationic lipid at an amount of 45-65 mol %; cholesterol at an amount of 25-45 mol %; DPhyPE at an amount of 8-12 mol % and optionally DHPC at an amount of 1 to 10 mol %; and the polymer conjugated lipid at an amount of 1-3 mol %; and (α-vi) the cationic lipid at an amount of 45-65 mol %; cholesterol at an amount of 25-45 mol %; DPhyPE at an amount of 8-12 mol % and optionally DHPC at an amount of 1 to 10 mol %; and PEG-DMG 2000 at an amount of 1-3 mol %; or more preferably the composition comprises excipients in a ratio selected from the group consisting of (b-i) the cationic lipid at an amount of 59 mol %; the steroid at an amount of 29.3 mol %; the neutral lipid at an amount of 10 mol %; and the polymer conjugated lipid at an amount of 1.7 mol %;

(b-ii) the cationic lipid at an amount of 59 mol %; cholesterol at an amount of 29.3 mol %; the neutral lipid at an amount of 10 mol %; and the polymer conjugated lipid at an amount of 1.7 mol %;

(b-iii) the cationic lipid at an amount of 59 mol %; cholesterol at an amount of 29.3 mol %; DPhyPE at an amount of 10 mol %; and the polymer conjugated lipid at an amount of 1.7 mol %;

(b-iv) the cationic lipid at an amount of 59 mol %; cholesterol at an amount of 29.3 mol %; DPhyPE at an amount of 10 mol %; and $C_{10}$-PEG 2000 at an amount of 1.7%; and (b-v) the cationic lipid at an amount of 59 mol %; cholesterol at an amount of 29.3 mol %; DPhyPE at an amount of 10 mol %; and Cer8-PEG 2000 at an amount of 1.7%;

each amount being relative to the total molar amount of all lipidic excipients of the lipid nanoparticles; more preferably the composition comprises excipients in a ratio selected from the group consisting of (c-i) a lipid excipient combination selected from the group consisting of E1 to E69 as disclosed in Table E at mol-percentages selected from the group consisting of F1 to F60 as disclosed in Table F.

3. The composition of any one of embodiments 1 to 2 wherein preferably the composition comprises excipients in a ratio of (i) 59 mol % cationic lipid C23 as disclosed in Table 1, 29.3 mol % cholesterol, 10 mol % DPhyPE and 1.7 mol % DMG-PEG 2000;

(ii) 59 mol % cationic lipid C2 as disclosed in Table 1, 29.3 mol % cholesterol, 10 mol % DPhyPE and 1.7 mol % DMG-PEG 2000; or (iii) 59 mol % cationic lipid C15 as disclosed in Table 1, 29.3 mol % cholesterol, 10 mol % DPhyPE and 1.7 mol % DMG-PEG 2000.

4. The composition any one of embodiments 1 to 3, further comprising a biologically active ingredient.

5. The composition of embodiment 4, wherein the biologically active ingredient is a nucleic acid compound selected from the group consisting of an artificial mRNA, chemically modified or unmodified messenger RNA (mRNA) comprising at least one coding sequence, self-replicating RNA, circular RNA, viral RNA, and replicon RNA; or any combination thereof, preferably wherein the biologically active ingredient is an mRNA or an mRNA compound.

6. The composition of any one of embodiments 1 to 5, wherein the lipid nanoparticles comprise the mRNA (i) at an amount such as to achieve an N/P ratio in the range of 10 to 20; or (ii) at an amount such as to achieve a lipid:mRNA weight ratio in the range of 20 to 60, preferably from about 3 to about 15, 5 to about 13, about 4 to about 8 or from about 7 to about 11.

7. The composition of any one of embodiments 1 to 6, wherein the composition is a sterile solid composition for reconstitution with a sterile liquid carrier, and wherein the composition further comprises one or more inactive ingredients selected from pH-modifying agents, bulking agents, stabilizers, non-ionic surfactants and antioxidants, and wherein the sterile liquid carrier is an aqueous carrier.

8. The composition of any one of embodiments 1 to 7, wherein the composition is a sterile liquid composition, and wherein the lipid nanoparticles have a mean hydrodynamic diameter as determined by dynamic laser scattering from about 50 nm to about 300 nm, or from about 60 nm to about 250 nm, or from about 60 nm to about 200 nm, or from about 70 to 200 nm, or from about 75 nm to about 160, or from about 90 nm to about 140 nm, or from about 100 nm to about 140 nm.

9. The composition of any one of embodiments 1 to 8, wherein the lipid nanoparticles exhibit a zeta potential in the range of −50 mV to +50 mV.

10. The composition of any one of embodiments 5 to 9, wherein the mRNA compound is a mono-, bi-, or multicistronic mRNA.

11. The composition of any one embodiments 5 to 10, wherein the mRNA compound comprises at least one chemical modification.

12. The composition of embodiment 11, wherein the chemical modification is selected from the group consisting of base modifications, sugar modifications, backbone modifications and lipid modifications, preferably wherein the chemical modification is a base modification, more preferably wherein the base modification preferably is selected from the group consisting of pseudouracil (Lp), N1-methylpseudouracil (N1Mp), 1-ethylpseudouracil, 2-thiouracil (s2U), 4-thiouracil, 5-methylcytosine, 5-methyluracil, 5-methoxyuracil, and any combination thereof.

13. The composition of any one of embodiments 5 to 12, wherein the mRNA compound comprises a coding region encoding a peptide or protein, wherein the coding region exhibits a sequence modification.

14. The composition of embodiment 13, wherein the sequence modification is selected from a G/C content modification, a codon modification, a codon optimization or a C-optimization of the sequence; preferably wherein the G/C content of the coding region is increased;

the C content of the coding region is increased;

the codon usage in the coding region is adapted to the human codon usage; and/or the codon adaptation index (CAI) is increased or maximised in the coding region compared with the coding region of the corresponding wild-type mRNA.

15. The composition of any one of embodiments 5 to 14, wherein the mRNA compound further comprises a) a 5'-CAP structure;

b) at least one miRNA sequence, preferably wherein the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof;

c) at least one 5'-UTR element;

d) at least one poly(A) sequence;

e) at least one poly(C) sequence;

f) at least one 3'-UTR element;

or any combinations of these.

16. The composition any one of embodiments 5 to 15, wherein the least one coding RNA comprises a 5'-CAP structure, preferably m7G, CAP0, CAP1, CAP2, a modified CAP0 or a modified CAP1 structure.

17. The composition of any one of embodiments 5 to 16, wherein the at least one coding RNA comprises at least one heterologous 5'-UTR and/or at least one heterologous 3'-UTR, preferably wherein the at least one heterologous 5'-UTR comprises a nucleic acid sequence derived from a 5'-UTR of a gene selected from HSD17B4, RPL32, ASAH1, ATP5A1, MP68, NDUFA4, NOSIP, RPL31, SLC7A3, TUBB4B and UBQLN2, or from a homolog, a fragment or variant of any one of these genes; and/or preferably wherein the at least one heterologous 3'-UTR comprises a nucleic acid sequence derived from a 3'-UTR of a gene selected from PSMB3, ALB7, alpha-globin, CASP1, COX6B1, GNAS, NDUFA1 and RPS9, or from a homolog, a fragment or a variant of any one of these genes.

18. The composition of any one of embodiments 5 to 17, wherein the at least one coding RNA comprises a (i) HSD17B4 5'-UTR and a PSMB3 3'-UTR or (ii) a RPL32 5'-UTR and an ALB7 3'-UTR.

19. The composition of any one of embodiments 5 to 18, comprising the following elements in the 5' to 3' direction:

a) a 5'-CAP structure, preferably selected from the group consisting of m7G(5'), m7G(5')ppp(5')(2'OMeA) and m7G(5')ppp(5')(2'OMeG);

b) a 5'-UTR element comprising a nucleic acid sequence derived from the 5'-UTR of a TOP gene, said nucleic acid sequence preferably comprising an RNA sequence that corresponds to the nucleic acid sequence according to SEQ ID NO:22, 24, 26, or a homolog, a fragment or a variant thereof;

c) at least one coding sequence;

d) a 3-UTR element comprising a nucleic acid sequence derived from an α-globin gene, said nucleic acid sequence preferably comprising an RNA sequence that corresponds to the nucleic acid sequence according to SEQ ID NO:6, 8, 10, 12, 14, 16, 18, 20, or a homolog, a fragment or a variant thereof; and/or a 3-UTR element comprising a nucleic acid sequence derived from an albumin gene, said nucleic acid sequence preferably comprising an RNA sequence that corresponds to the nucleic acid sequence according to SEQ ID NO:18, or a homolog, a fragment or a variant thereof;

e) optionally, at least one poly(A) sequence, preferably consisting of 10 to 200, 10 to 100, 40 to 80, or 50 to 70 adenosine nucleotides;

f) optionally, at least one poly(C) sequence, preferably consisting of 10 to 200, 10 to 100, 20 to 70, 20 to 60 or 10 to 40 cytosine nucleotides; and g) optionally, at least one histone stem-loop, preferably comprising the RNA sequence according to SEQ ID NO:4.

20. The composition of any one of embodiments 4 to 19, wherein the biologically active ingredient is (a) an mRNA comprising at least one coding sequence encoding a peptide or protein, or a fragment or variant thereof, wherein the peptide or protein is an antigen, wherein the antigen preferably is derived from pathogenic antigens, tumour antigens, allergenic antigens or autoimmune self-antigens, or a fragment or variant thereof; or (b) an mRNA comprising at least one coding sequence encoding a therapeutic protein, or a fragment or variant thereof, wherein the therapeutic protein is selected from the group consisting of (i) therapeutic proteins for use in enzyme replacement therapy for the treatment of metabolic, endocrine or amino acid disorders or for use in replacing an absent, deficient or mutated protein;

(ii) therapeutic proteins for use in the treatment of blood disorders, diseases of the circulatory system, diseases of the respiratory system, infectious diseases or immune deficiencies;
(iii) therapeutic proteins for use in the treatment of cancer or tumour diseases;
(iv) therapeutic proteins for use in hormone replacement therapy;
(v) therapeutic proteins for use in reprogramming somatic cells into pluri- or omnipotent stem cells;
(vi) therapeutic proteins for use as adjuvant or immunostimulation;
(vii) therapeutic proteins being a therapeutic antibody;
(viii) therapeutic proteins being a gene editing agent; and
(ix) therapeutic proteins for use in treating or preventing a liver disease selected from the group consisting of liver fibrosis, liver cirrhosis and liver cancer.

21. The composition of embodiment 20 subitem (a), wherein the antigen encodes a pathogenic antigen selected from the group consisting of a bacterial, viral, fungal and protozoal antigen.

22. The composition of embodiment 21, wherein the pathogenic antigen is derived from a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli*, *Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*).

23. The composition of any one of embodiments 5 to 22 for use
(i) in the treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition; and/or
(ii) for use in enzyme replacement therapy for the treatment of metabolic or endocrine disorders or for use in replacing an absent, deficient or mutated protein.

24. The composition of any one of embodiments 5 to 23 for use in the treatment or prophylaxis of infectious diseases.

25. The composition of embodiments 5 to 24 comprising at least one coding RNA, wherein said at least one coding RNA comprises at least one coding sequence encoding at least one peptide or protein for use in treatment or prevention of a disease, disorder or condition, wherein said composition is administered via intramuscular or intradermal injection a subject in need thereof.

26. A kit or kit of parts, comprising any one of the compositions of embodiments 4 to 26, optionally comprising a liquid vehicle for solubilizing, and, optionally, technical instructions providing information on administration and dosage of the components.

27. The composition of any one of embodiments 4 to 25 or the kit or kit of parts of embodiment 26 for use as a medicament.

28. The composition for use as a medicament according to embodiment 27, wherein the medicament is for the prevention, prophylaxis, treatment and/or amelioration of a disease selected from infectious diseases including viral, bacterial or protozoological infectious diseases, cancer or tumour diseases, liver diseases, autoimmune diseases, allergies, monogenetic diseases including hereditary diseases, genetic diseases in general, diseases which have a genetic inherited background and which are typically caused by a defined gene defect and are inherited according to Mendel's laws; cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and diseases associated with a peptide or protein deficiency.

29. The composition of any of the previous embodiments for use as a medicament according to embodiments 27 or 28, wherein the medicament is a vaccine.

30. A vaccine comprising a composition of any one of embodiments 5 to 25 or a kit or kit of parts of embodiment 26 for prevention, prophylaxis, treatment and/or amelioration of a disease selected from infectious diseases including viral, bacterial or protozoological infectious diseases, cancer or tumour diseases.

31. A method of treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition comprising the steps:
a) providing the mRNA as described in any one of the above embodiments, the composition as described in any one of the above embodiments, the vaccine of embodiment 30, the kit or kit of parts of embodiment 26; and
b) applying or administering the mRNA, the composition, the vaccine or the kit or kit of parts to a tissue or an organism.

32. The method according to embodiment 31, wherein the mRNA, the composition any one of embodiments 5 to 29, the vaccine of embodiment 30 or the kit or kit of parts of embodiment 26 is administered to the tissue or to the organism by intravenous, intramuscular, subcutaneous or intradermal injection.

33. A method of inducing an immune response in a subject, the method comprising administering to the subject the vaccine of embodiment 30 in an amount effective to produce an antigen-specific immune response in the subject.

34. A pharmaceutical composition comprising a composition of any one of embodiments 4 to 29 or a kit or kit of parts of embodiment 26 for use in vaccination of a subject comprising an effective dose of mRNA encoding a virus antigen.

35. Use of a pharmaceutical composition comprising a composition of any one of embodiments 4 to 29 or a kit or kit of parts of embodiment 26 for (i) inducing an immune response, for (ii) inducing an antigen specific T-cell response or preferably for (iii) inducing CD8+ T cells responses.

36. Use of the pharmaceutical composition of embodiment 34 for the prophylaxis of an infectious disease or in the manufacture of a medicament for the prophylaxis of an infectious disease, wherein said medicament preferably is a vaccine.

37. A method for preventing, ameliorating or treating a disease or condition in a subject in need comprising administering to the subject a composition of any one of embodiments 4 to 29 or a kit or kit of parts of embodiment 26.

38. The method of any one of the preceding method embodiments, wherein administration of the composition results in expression of the antigen encoded by mRNA in the lymphocytes of the subject.

39. The method of any one of the preceding method embodiments, wherein the administration of the composition results in an antigen specific antibody response, preferably wherein the antigen specific antibody response is measured by the presence of antigen-specific antibodies in serum.

Third Set of Embodiments

1. A composition comprising a cationic lipid according to formula (I) and 1,2-diphytanoyl-sn-glycero-3-phosphoethanolamine (DPhyPE), optionally in combination with 1,2-diheptanoyl-sn-glycero-3-phosphocholine (DHPC), further comprising a biologically active ingredient, preferably the biologically active ingredient is mRNA, wherein (a) the mRNA comprises at least one coding sequence encoding a peptide or protein, or a fragment or variant thereof, wherein the peptide or protein is an antigen, wherein the antigen preferably is derived from pathogenic antigens, tumour antigens, allergenic antigens or autoimmune self-antigens, or a fragment or variant thereof; or (b) the mRNA comprises at least one coding sequence encoding a therapeutic protein, or a fragment or variant thereof, wherein the therapeutic protein is selected from the group consisting of (i) therapeutic proteins for use in enzyme replacement therapy for the treatment of metabolic, endocrine or amino acid disorders or for use in replacing an absent, deficient or mutated protein;

(ii) therapeutic proteins for use in the treatment of blood disorders, diseases of the circulatory system, diseases of the respiratory system, infectious diseases or immune deficiencies;

(iii) therapeutic proteins for use in the treatment of cancer or tumour diseases;

(iv) therapeutic proteins for use in hormone replacement therapy;

(v) therapeutic proteins for use in reprogramming somatic cells into pluri- or omnipotent stem cells;

(vi) therapeutic proteins for use as adjuvant or immunostimulation;

(vii) therapeutic proteins being a therapeutic antibody;

(viii) therapeutic proteins being a gene editing agent; and (ix) therapeutic proteins for use in treating or preventing a liver disease selected from the group consisting of liver fibrosis, liver cirrhosis and liver cancer.

2. The composition of embodiment 1 subitem (a), wherein the antigen encodes a pathogenic antigen selected from the group consisting of a bacterial, viral, fungal and protozoal antigen.

3. The composition of embodiment 2, wherein the pathogenic antigen is derived from a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*).

4. The composition of any one of the previous embodiments for use (i) in the treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition; and/or (ii) for use in enzyme replacement therapy for the treatment of metabolic or endocrine disorders or for use in replacing an absent, deficient or mutated protein.

5. The composition of any one of the previous embodiments for use in the treatment or prophylaxis of infectious diseases.

6. The composition of any one of the previous embodiments comprising at least one coding RNA, wherein said at least one coding RNA comprises at least one coding sequence encoding at least one peptide or protein for use in treatment or prevention of a disease, disorder or condition, wherein said composition is administered via intramuscular or intradermal injection a subject in need thereof.

7. A kit or kit of parts, comprising any one of the compositions of any one of the previous embodiments, optionally comprising a liquid vehicle for solubilizing, and, optionally, technical instructions providing information on administration and dosage of the components.

8. The composition of any one of the previous embodiments or the kit or kit of parts of embodiment 7 for use as a medicament.

9. The composition for use as a medicament according to any one of the previous embodiments, wherein the medicament is for the prevention, prophylaxis, treatment and/or amelioration of a disease selected from infectious diseases including viral, bacterial or protozoological infectious diseases, cancer ortumour diseases, liver diseases, autoimmune diseases, allergies, monogenetic diseases including hereditary diseases, genetic diseases in general, diseases which have a genetic inherited background and which are typically caused by a defined gene defect and are inherited according to Mendel's laws; cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and diseases associated with a peptide or protein deficiency.

10. The composition for use as a medicament according to any one of the previous embodiments, wherein the medicament is a vaccine.

11. A vaccine comprising a composition of any one of the previous embodiments or a kit or kit of parts of embodiment 7 for prevention, prophylaxis, treatment and/or amelioration of a disease selected from infectious diseases including viral, bacterial or protozoological infectious diseases, cancer ortumour diseases.

12. A method of treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition comprising the steps:

a) providing the mRNA as described in any one of the above embodiments, the composition as described in any one of the above embodiments, the vaccine of embodiment 11, the kit or kit of parts of embodiment 7; and b) applying or administering the mRNA, the composition, the vaccine or the kit or kit of parts to a tissue or an organism.

13. The method according to embodiment 12, wherein the mRNA, the composition any one of the previous embodiments, the vaccine of embodiment 11 or the kit or kit of parts of embodiment 7 is administered to the tissue or to the organism by intravenous, intramuscular, subcutaneous or intradermal injection.

14. A method of inducing an immune response in a subject, the method comprising administering to the subject the vaccine of embodiment 11 in an amount effective to produce an antigen-specific immune response in the subject.

15. A pharmaceutical composition comprising a composition of any one of the previous embodiments or a kit or kit of parts of embodiment 7 for use in vaccination of a subject comprising an effective dose of mRNA encoding a virus antigen.

16. Use of a pharmaceutical composition comprising a composition of any one of the previous embodiments or a kit or kit of parts of embodiment 7 for (i) inducing an immune response, for (ii) inducing an antigen specific T-cell response or preferably for (iii) inducing CD8+ T cells responses.

17. Use of the pharmaceutical composition of embodiment 15 for the prophylaxis of an infectious disease or in the manufacture of a medicament for the prophylaxis of an infectious disease, wherein said medicament preferably is a vaccine.

18. A method for preventing, ameliorating or treating a disease or condition in a subject in need comprising administering to the subject a composition of any one of the previous embodiments or a kit or kit of parts of embodiment 7.

19. The method of any one of the preceding method embodiments, wherein administration of the composition results in expression of the antigen encoded by mRNA in the lymphocytes of the subject.

20. The method of any one of the preceding method embodiments, wherein the administration of the composition results in an antigen specific antibody response, preferably wherein the antigen specific antibody response is measured by the presence of antigen-specific antibodies in serum.

Fourth Set of Embodiments

1. A composition comprising a cationic lipid according to formula (I) and 1,2-diphytanoyl-sn-glycero-3-phosphoethanolamine (DPhyPE), optionally in combination with 1,2-diheptanoyl-sn-glycero-3-phosphocholine (DHPC), further an mRNA which comprises at least one coding sequence encoding a peptide or protein, or a fragment or variant thereof, wherein the peptide or protein is an antigen, wherein the antigen preferably is derived from pathogenic antigens, tumour antigens, allergenic antigens or autoimmune self-antigens, or a fragment or variant thereof, wherein preferably the antigen encodes a pathogenic antigen selected from the group consisting of a bacterial, viral, fungal and protozoal antigen.

2. The composition of embodiment 1, wherein the pathogenic antigen is derived from a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*).

3. The composition of any one of the previous embodiments for use in the treatment or prophylaxis of infectious diseases.

4. The composition of any one of the previous embodiments comprising at least one coding RNA, wherein said at least one coding RNA comprises at least one coding sequence encoding at least one peptide or protein for use in treatment or prevention of a disease, disorder or condition, wherein said composition is administered via intramuscular or intradermal injection a subject in need thereof.

5. A kit or kit of parts, comprising any one of the compositions of any one of the previous embodiments, optionally comprising a liquid vehicle for solubilizing, and, optionally, technical instructions providing information on administration and dosage of the components.

6. The composition of any one of the previous embodiments or the kit or kit of parts of embodiment 5 for use as a medicament.

7. The composition for use as a medicament according to any one of the previous embodiments, wherein the medicament is for the prevention, prophylaxis, treatment and/or amelioration of a disease selected from infectious diseases including viral, bacterial or protozoological infectious diseases, cancer ortumour diseases, liver diseases, autoimmune diseases, allergies, monogenetic diseases including hereditary diseases, genetic diseases in general, diseases which have a genetic inherited background and which are typically caused by a defined gene defect and are inherited according to Mendel's laws; cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and diseases associated with a peptide or protein deficiency.

8. The composition for use as a medicament according to any one of the previous embodiments, wherein the medicament is a vaccine.

9. A vaccine comprising a composition of any one of the previous embodiments or a kit or kit of parts of embodiment 5 for prevention, prophylaxis, treatment and/or amelioration of a disease selected from infectious diseases including viral, bacterial or protozoological infectious diseases, cancer ortumour diseases.

10. A method of treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition comprising the steps:

a) providing the mRNA as described in any one of the above embodiments, the composition as described in any one of the above embodiments, the vaccine of embodiment 9, the kit or kit of parts of embodiment 5; and b) applying or administering the mRNA, the composition, the vaccine or the kit or kit of parts to a tissue or an organism.

11. The method according to embodiment 10, wherein the mRNA, the composition any one of the previous embodiments, the vaccine of embodiment 9 or the kit or kit of parts of embodiment 5 is administered to the tissue or to the organism by intravenous, intramuscular, subcutaneous or intradermal injection.

12. A method of inducing an immune response in a subject, the method comprising administering to the subject the vaccine of embodiment 9 in an amount effective to produce an antigen-specific immune response in the subject.

13. A pharmaceutical composition comprising a composition of any one of the previous embodiments or a kit or kit of parts of embodiment 5 for use in vaccination of a subject comprising an effective dose of mRNA encoding a virus antigen.

14. Use of a pharmaceutical composition comprising a composition of any one of the previous embodiments or a kit or kit of parts of embodiment 5 for (i) inducing an immune response, for (ii) inducing an antigen specific T-cell response or preferably for (iii) inducing CD8+ T cells responses.

15. Use of the pharmaceutical composition of embodiment 13 for the prophylaxis of an infectious disease or in the manufacture of a medicament for the prophylaxis of an infectious disease, wherein said medicament preferably is a vaccine.

16. A method for preventing, ameliorating or treating a disease or condition in a subject in need comprising administering to the subject a composition of any one of the previous embodiments or a kit or kit of parts of embodiment 5.

17. The method of any one of the preceding method embodiments, wherein administration of the composition results in expression of the antigen encoded by mRNA in the lymphocytes of the subject.

18. The method of any one of the preceding method embodiments, wherein the administration of the composition results in an antigen specific antibody response, preferably wherein the antigen specific antibody response is measured by the presence of antigen-specific antibodies in serum.

Fifth Set of Embodiments

1. A cationic lipid according to formula (I):

$R^a$-A-$R^b$ formula (I)

or a pharmaceutically acceptable salt, prodrug or stereoisomer thereof, wherein $R^a$ is selected from:

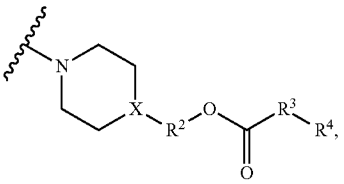

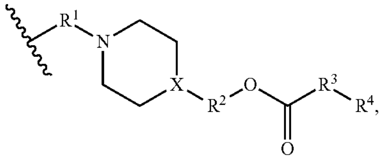

-continued

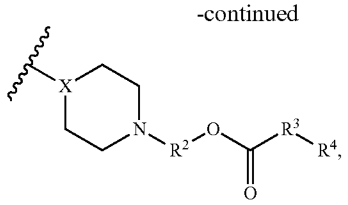

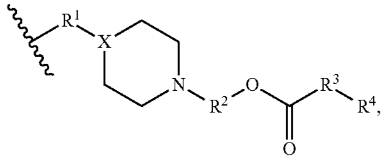

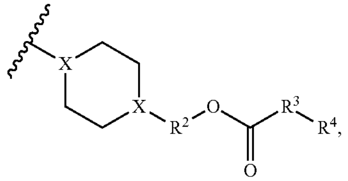

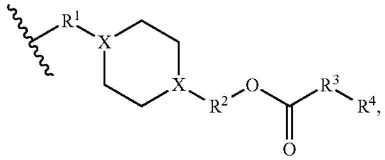

or

—$R^1$—N(H)—C(O)—$R^3$—$R^4$;

$R^b$ is selected from:

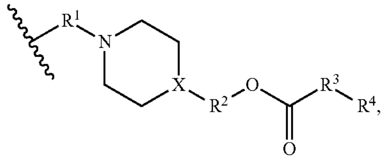

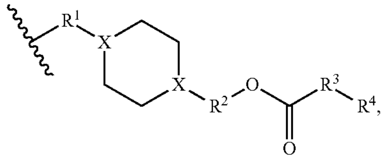

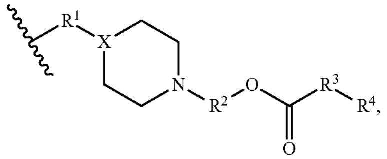

—$R^1$—N(H)—C(O)—$R^3$—$R^4$, or —$R^1$—$N(CH_3)_2$;

A is —S—, —S—S—, —NH—C(O)—, —NH—C(O)O—, —NH—C(O)—NH—, —S—C(O)—N(H)—, —C(O)O—, or —O—P(O)(OH)—O—;

$R^1$ is an ethanediyl, propanediyl, butanediyl, or linear or unbranched alkanediyl having 2 to 8 carbon atoms, wherein each substitutable carbon atom is unsubstituted or substituted with one or more C1-$C_4$ alkyl, $C_1$-$C_4$ alkenylene, $C_3$-$C_8$ cycloalkylene, or $C_3$-$C_8$ cycloalkenylene;

$R^2$ is an alkanediyl having 2 to 8 carbon atoms;

$R^3$ is optional, and if present, is —$R^5$—C(O)—O—, —$R^5$—O—C(O)—, —$R^5$—C(O)—NH—, —$R^5$—OC(O)—NH—, or $R^5$—NH—C(O)O—;

$R^4$ is a lipophilic substituent with 12 to 36 carbon atoms, wherein the lipophilic substituent with 12 to 36 carbon atoms is either (i) a linear or branched alkyl or alkenyl having 12 to 25 carbon atoms or (ii) derived from tocopherol or tocotreinol;

$R^5$ is an alkanediyl having 1 to 6 carbon atoms;

X is a carbon atom bonded to a hydrogen atom (CH) or a nitrogen atom;

wherein all selections are independent of one another.

2. The cationic lipid according to embodiment 1, wherein $R^4$ is either (i) a linear or branched alkyl or alkenyl having 12 to 25 carbon atoms or (ii) selected from the group of derivatives of tocopherol and tocotreinol shown in Scheme 1.

3. The cationic lipid according to embodiment 1 or embodiment 2, wherein $R^4$ is independently selected at each occurrence from the group consisting of

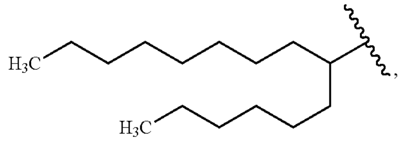
,

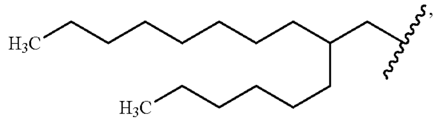
,

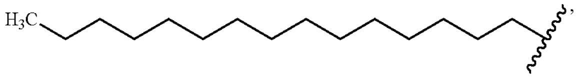
,

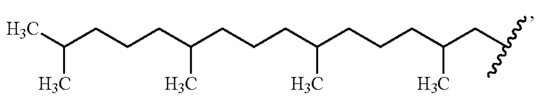
, and

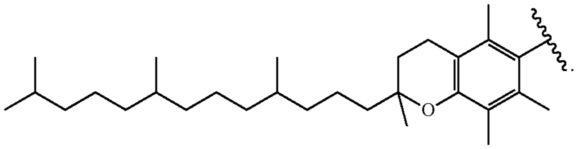
.

4. The cationic lipid according to any one of embodiments 1 to 3, with the proviso that if (i) $R^3$ is present as —$R^5$—C(O)—O—, (ii) $R^1$ and $R^2$ are linear unsubstituted ethanediyl, (iii) $R^5$ is either linear unsubstituted ethanediyl, linear unsubstituted propanediyl or linear unsubstituted butanediyl, (iv) A is —S—S—, and (v) $R^a$ and $R^b$ are identical, then $R^4$ is not

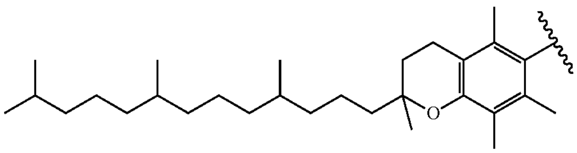 [SMILES: *c1c(C)c(C)c2c(c1C)CCC(C)(CCCC(C)CCCC(C)CCCC(C)C)O2]

and with the further proviso that if (i) $R^3$ is absent, (ii) $R^1$ and $R^2$ are linear unsubstituted ethanediyl, (iii) A is —S—S—, and (iv) $R^a$ and $R^b$ are identical, then $R^4$ is not

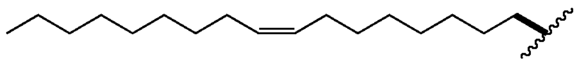

and not

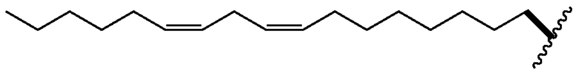

5. The cationic lipid according to any one of embodiments 1 to 3, wherein A is —S—.

6. The cationic lipid according to embodiment 1 or embodiment 2, wherein $R^3$ is present and selected from the group consisting of —$R^5$—C(O)—O—, —$R^5$—O—C(O)—, —$R^5$—C(O)—NH—, —$R^5$—OC(O)—NH—, and $R^5$—NH—C(O)O—; and $R^4$ is a linear or branched alkyl or alkenyl having 12 to 25 carbon atoms.

7. The cationic lipid according to any one of embodiments 1 to 6, wherein $R^a$ and $R^b$ are independently selected from

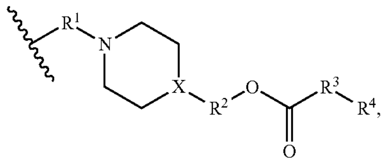

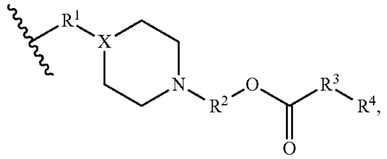

with X being CH or —$R^1$—N(H)—C(O)—$R^3$—$R^4$.

8. The cationic lipid according to any one of embodiments 1 to 7, wherein each of $R^a$ and $R^b$ is:

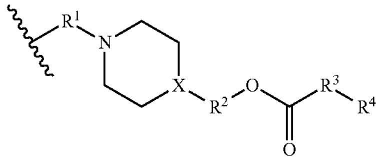

with X being CH; and $R^3$ is present and $R^5$ is an alkanediyl having 2 to 6 carbon atoms, selected independently at each occurrence.

9. The cationic lipid according to any one of embodiments 1 to 8, wherein $R^3$ is present and is —$R^5$—C(O)—O— or —$R^5$—O—C(O)—;

$R^4$ is:

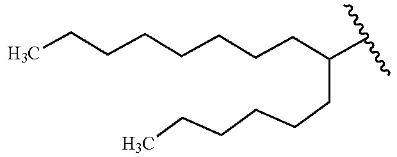
or

-continued

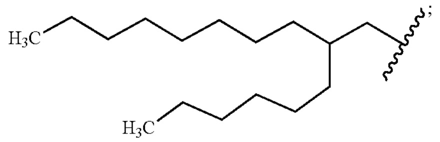

and wherein $R^a$ and $R^b$ are identical.

10. The cationic lipid according to any one of embodiments 1 to 8, wherein $R^3$ is present and is —$R^5$—C(O)—O— or —$R^5$—O—C(O)—;

$R^4$ is:

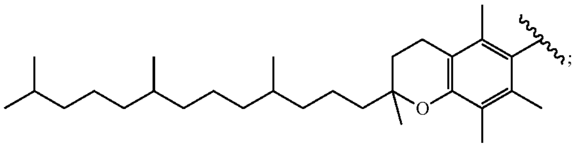 [SMILES: *c1c(C)c(C)c2c(c1C)CCC(C)(CCCC(C)CCCC(C)CCCC(C)C)O2]

and wherein $R^a$ and $R^b$ are identical.

11. The cationic lipid according to embodiment 9 or embodiment 10, wherein $R^3$ is —$R^5$—C(O)—O—.

12. The cationic lipid according to embodiment 7 or 8, wherein $R^1$ is ethanediyl.

13. The cationic lipid of any of the preceding embodiments, further exhibiting one or more of the following features, independently selected at each occurrence:

(i) $R^1$ is an unsubstituted ethanediyl, propanediyl, or butanediyl;

(ii) $R^2$ is an linear, unbranched alkanediyl having 2 to 8 carbon atoms;

(iii) $R^3$ is-$R^5$—C(O)—O— or —$R^5$—O—C(O)—;

(iv) $R^5$ is an alkanediyl having 2 to 6 carbon atoms; and/or (vi) X is CH.

14. The cationic lipid of embodiment 1, being selected from one of the compounds as listed in Table 1.

15. A composition comprising (i) the cationic lipid of any one of embodiments 1 to 14;

(ii) the cationic lipid C15 as listed in Table 1;

(iii) the cationic lipid C2 as listed in Table 1; or (iv) the cationic lipid C26 as listed in Table 1.

16. The composition of embodiment 15, further comprising one or more of the following excipients:

(i) a steroid, preferably cholesterol;

(ii) a neutral lipid;

wherein said neutral lipid preferably is 1,2-diphytanoyl-sn-glycero-3-phosphoethanolamine (DPhyPE), optionally in combination with the neutral lipid 1,2-diheptanoyl-sn-glycero-3-phosphocholine (DHPC); or wherein said neutral lipid is a zwitterionic compound, optionally a zwitterionic compound having two fatty acid moieties selected from myristoyl, palmitoyl, stearoyl and oleyol, in combination with a zwitterionic compound having two fatty acid moieties selected from pentanoyl, hexanoyl, heptanoyl, octanoyl, nonaoyl and decanoyl;

and/or (iii) a polymer conjugated lipid;

wherein said polymer conjugated lipid is a compound according to formula (II):

P-A-L formula (II);

wherein P is a hydrophilic polymer moiety, A is an optional linker, and L is a lipid moiety;

preferably wherein the polymer conjugated lipid is a pegylated lipid.

17. A composition comprising one or more of the following excipients:

(i) a cationic lipid of any one of embodiments 1 to 14 or a cationic lipid comprising a tertiary or quaternary nitrogen/amino group or a cationic lipid carrying a net positive charge at physiological pH;

(ii) a steroid, preferably cholesterol;

(iii) a neutral lipid as described in subitem (ii) of embodiments 16; and/or (iv) a polymer conjugated lipid, wherein said polymer conjugated lipid is a compound according to formula (II):

P-A-L formula (II);

wherein P is a hydrophilic polymer moiety, A is an optional linker, and L is a lipid moiety;

preferably wherein the polymer conjugated lipid is a pegylated lipid;

more preferably, wherein the lipid moiety L comprises at least one fatty acid ("tail") comprising 8, 10 or 12 carbon atoms, preferably 8 or 10 carbon atoms;

even more preferably, wherein the pegylated lipid is selected from the group consisting of 1,2-dicapryl-rac-glycero-3-methylpolyoxyethylene glycol 2000 ($C_{10}$-PEG 2000); and N-octanoyl-sphingosine-1-{succinyl[methoxy(polyethylene glycol)2000]} (Cer8-PEG 2000).

18. A composition comprising one or more of the following excipients:

(i) a cationic lipid as described in subitem (i) of embodiment 17;

(ii) a steroid, preferably cholesterol;

(iii) a neutral lipid as described in subitem (ii) of embodiment 16, or preferably a combination of two neutral lipids wherein the combination comprises a neutral lipid or phospholipid having at least two alkyl chains, whereby each alkyl chain independently has a length of preferably $C_6$, $C_7$, $C_8$, $C_9$, or $C_{10}$, more preferably with a length of $C_6$, $C_7$, $C_8$, most preferably with a length of $C_7$, further most preferably a phospholipid selected from the group consisting of 05:0 PC (1,2-dipentanoyl-sn-glycero-3-phosphocholine), 04:0 PC (1,2-dibutyryl-sn-glycero-3-phosphocholine), 06:0 PC (DHPC, 1,2-dihexanoyl-sn-glycero-3-phosphocholine), 08:0 PC (1,2-dioctanoyl-sn-glycero-3-phosphocholine), and 09:0 PC (1,2-dinonanoyl-sn-glycero-3-phosphocholine); and/or (iv) a polymer conjugated lipid, wherein said polymer conjugated lipid is a compound according to formula (II):

P-A-L formula (II);

wherein P is a hydrophilic polymer moiety, A is an optional linker, and L is a lipid moiety;

preferably wherein the polymer conjugated lipid is a pegylated lipid;

more preferably wherein the pegylated lipid is 1,2-dimyristoyl-rac-glycero-3-methoxypolyethylene glycol 2000 (DMG-PEG 2000).

19. The composition of any one of embodiments 15 to 18 wherein preferably the composition comprises excipients in a ratio selected from the group consisting of (α-i) the cationic lipid at an amount of 30-70 mol %; the steroid at an amount of 20-50 mol %; the neutral lipid at an amount of 5-25 mol %; and the polymer conjugated lipid at an amount of 0.5-5 mol %;

(α-ii) the cationic lipid at an amount of 40-70 mol %; the steroid at an amount of 20-50 mol %; the neutral lipid at an amount of 5-15 mol %; and the polymer conjugated lipid at an amount of 0.5-5 mol %;

(α-iii) the cationic lipid at an amount of 20-60 mol %; the steroid at an amount of 25-55 mol %; the phospholipid at an amount of 5-25 mol %; and the polymer conjugated lipid at an amount of 0.5-15 mol %;

(α-iv) the cationic lipid at an amount of 45-65 mol %; the steroid at an amount of 25-45 mol %; the phospholipid at an amount of 8-12 mol %; and the polymer conjugated lipid at an amount of 1-3 mol %;

(α-v) the cationic lipid at an amount of 45-65 mol %; cholesterol at an amount of 25-45 mol %; the neutral lipid at an amount of 8-12 mol %; and the polymer conjugated lipid at an amount of 1-3 mol %;

(α-vi) the cationic lipid at an amount of 45-65 mol %; cholesterol at an amount of 25-45 mol %; DPhyPE at an amount of 8-12 mol % and optionally DHPC at an amount of 1 to 10 mol %; and the polymer conjugated lipid at an amount of 1-3 mol %; and (α-vi) the cationic lipid at an amount of 45-65 mol %; cholesterol at an amount of 25-45 mol %; DPhyPE at an amount of 8-12 mol % and optionally DHPC at an amount of 1 to 10 mol %; and PEG-DMG 2000 at an amount of 1-3 mol %; or more preferably the composition comprises excipients in a ratio selected from the group consisting of (b-i) the cationic lipid at an amount of 59 mol %; the steroid at an amount of 29.3 mol %; the neutral lipid at an amount of 10 mol %; and the polymer conjugated lipid at an amount of 1.7 mol %;

(b-ii) the cationic lipid at an amount of 59 mol %; cholesterol at an amount of 29.3 mol %; the neutral lipid at an amount of 10 mol %; and the polymer conjugated lipid at an amount of 1.7 mol %;

(b-iii) the cationic lipid at an amount of 59 mol %; cholesterol at an amount of 29.3 mol %; DPhyPE at an amount of 10 mol %; and the polymer conjugated lipid at an amount of 1.7 mol %;

(b-iv) the cationic lipid at an amount of 59 mol %; cholesterol at an amount of 29.3 mol %; DPhyPE at an amount of 10 mol %; and $C_{10}$-PEG 2000 at an amount of 1.7%;

(b-v) the cationic lipid at an amount of 59 mol %; cholesterol at an amount of 29.3 mol %; DPhyPE at an amount of 10 mol %; and Cer8-PEG 2000 at an amount of 1.7%;

(b-vi) the cationic lipid at an amount of 59 mol %; the steroid at an amount of 28.3 mol %; the neutral lipid at an amount of 11 mol %; and the polymer conjugated lipid at an amount of 1.7 mol %;

(b-vii) the cationic lipid at an amount of 59 mol %; cholesterol at an amount of 28.3 mol %; the neutral lipid at an amount of 11 mol %; and the polymer conjugated lipid at an amount of 1.7 mol %;

(b-viii) the cationic lipid at an amount of 59 mol %; cholesterol at an amount of 28.3 mol %; DPhyPE at an amount of 10 mol % and DHPC at an amount of 1 mol %; and the polymer conjugated lipid at an amount of 1.7 mol %;

(b-ix) the cationic lipid at an amount of 59 mol %; cholesterol at an amount of 28.3 mol %; DPhyPE at an amount of 10 mol % and DHPC at an amount of 1 mol %; and $C_{10}$-PEG 2000 at an amount of 1.7%; and (b-x) the cationic lipid at an amount of 59 mol %; cholesterol at an amount of 28.3 mol %; DPhyPE at an amount of 10 mol % and DHPC at an amount of 1 mol %; and Cer8-PEG 2000 at an amount of 1.7%;

(b-xi) the cationic lipid at an amount of 49 mol %; the steroid at an amount of 29.3 mol %; the neutral lipid at an amount of 20 mol %; and the polymer conjugated lipid at an amount of 1.7 mol %;

(b-xii) the cationic lipid at an amount of 49 mol %; cholesterol at an amount of 29.3 mol %; the neutral lipid at an amount of 20 mol %; and the polymer conjugated lipid at an amount of 1.7 mol %;

(b-xiii) the cationic lipid at an amount of 49 mol %; cholesterol at an amount of 29.3 mol %; DPhyPE at an amount of 10 mol % and DHPC at an amount of 10 mol %; and the polymer conjugated lipid at an amount of 1.7 mol %;

(b-xiv) the cationic lipid at an amount of 49 mol %; cholesterol at an amount of 29.3 mol %; DPhyPE at an amount of 10 mol % and DHPC at an amount of 10 mol %; and $C_{10}$-PEG 2000 at an amount of 1.7%; and (b-xv) the cationic lipid at an amount of 49 mol %; cholesterol at an amount of 29.3 mol %; DPhyPE at an amount of 10 mol % and DHPC at an amount of 10 mol %; and Cer8-PEG 2000 at an amount of 1.7%;

each amount being relative to the total molar amount of all lipidic excipients of the lipid nanoparticles;

more preferably the composition comprises excipients in a ratio selected from the group consisting of (c-i) a lipid excipient combination selected from the group consisting of E1 to E108 as disclosed in Table E at mol-percentages selected from the group consisting of F1 to F62 as disclosed in Table F.

20. The composition of any one of embodiments 15 to 19 wherein preferably the composition comprises excipients in a ratio of (i) 59 mol % cationic lipid C23 (COATSOME® SS-EC) as disclosed in Table 1, 29.3 mol % cholesterol, 10 mol % DPhyPE and 1.7 mol % DMG-PEG 2000;

(ii) 59 mol % cationic lipid C2 as disclosed in Table 1, 29.3 mol % cholesterol, 10 mol % DPhyPE and 1.7 mol % DMG-PEG 2000;

(iii) 59 mol % cationic lipid C15 as disclosed in Table 1, 29.3 mol % cholesterol, 10 mol % DPhyPE and 1.7 mol % DMG-PEG 2000;

(iv) 59 mol % cationic lipid C26 as disclosed in Table 1, 29.3 mol % cholesterol, 10 mol % DPhyPE and 1.7 mol % DMG-PEG 2000;

(v) 59 mol % cationic lipid C23 (COATSOME® SS-EC) as disclosed in Table 1, 28.3 mol % cholesterol, 10 mol % DPhyPE, 1 mol % DHPC and 1.7 mol % DMG-PEG 2000;

(vi) 59 mol % cationic lipid C2 as disclosed in Table 1, 28.3 mol % cholesterol, 10 mol % DPhyPE, 1 mol % DHPC and 1.7 mol % DMG-PEG 2000;

(vii) 59 mol % cationic lipid C15 as disclosed in Table 1, 28.3 mol % cholesterol, 10 mol % DPhyPE, 1 mol % DHPC and 1.7 mol % DMG-PEG 2000;

(viii) 59 mol % cationic lipid C26 as disclosed in Table 1, 28.3 mol % cholesterol, 10 mol % DPhyPE, 1 mol % DHPC and 1.7 mol % DMG-PEG 2000;

(ix) 49 mol % cationic lipid C23 (COATSOME® SS-EC) as disclosed in Table 1, 29.3 mol % cholesterol, 10 mol % DphyPE, 10 mol % DHPC and 1.7 mol % DMG-PEG 2000;

(x) 49 mol % cationic lipid C2 as disclosed in Table 1, 29.3 mol % cholesterol, 10 mol % DPhyPE, 10 mol % DHPC and 1.7 mol % DMG-PEG 2000;

(xi) 49 mol % cationic lipid C15 as disclosed in Table 1, 29.3 mol % cholesterol, 10 mol % DPhyPE, 10 mol % DHPC and 1.7 mol % DMG-PEG 2000; or (xii) 49 mol % cationic lipid C26 as disclosed in Table 1, 29.3 mol % cholesterol, 10 mol % DPhyPE, 10 mol % DHPC and 1.7 mol % DMG-PEG 2000.

21. The composition any one of embodiments 15 to 20, further comprising a biologically active ingredient.

22. The composition of embodiment 21, wherein the biologically active ingredient is a nucleic acid compound selected from the group consisting of an artificial mRNA, chemically modified or unmodified messenger RNA (mRNA) comprising at least one coding sequence, self-replicating RNA, circular RNA, viral RNA, and replicon RNA; or any combination thereof, preferably wherein the biologically active ingredient is an mRNA or an mRNA compound.

23. The composition of any one of embodiments 15 to 22, wherein the lipid nanoparticles comprise the mRNA (i) at an amount such as to achieve an N/P ratio in the range of 10 to 20; or (ii) at an amount such as to achieve a lipid:mRNA weight ratio in the range of 20 to 60, preferably from about 3 to about 15, 5 to about 13, about 4 to about 8 or from about 7 to about 11.

24. The composition of any one of embodiments 15 to 23, wherein the composition is a sterile solid composition for reconstitution with a sterile liquid carrier, and wherein the composition further comprises one or more inactive ingredients selected from pH-modifying agents, bulking agents, stabilizers, non-ionic surfactants and antioxidants, and wherein the sterile liquid carrier is an aqueous carrier.

25. The composition of any one of embodiments 15 to 24, wherein the composition is a sterile liquid composition, and wherein the lipid nanoparticles have a mean hydrodynamic diameter as determined by dynamic laser scattering from about 50 nm to about 300 nm, or from about 60 nm to about 250 nm, or from about 60 nm to about 200 nm, or from about 70 to 200 nm, or from about 75 nm to about 160, or from about 90 nm to about 140 nm, or from about 100 nm to about 140 nm.

26. The composition of any one of embodiments 15 to 25, wherein the lipid nanoparticles exhibit a zeta potential in the range of −50 mV to +50 mV.

27. The composition of any one of embodiments 22 to 26, wherein the mRNA compound is a mono-, bi-, or multicistronic mRNA.

28. The composition of any one embodiments 22 to 26, wherein the mRNA compound comprises at least one chemical modification.

29. The composition of embodiment 28, wherein the chemical modification is selected from the group consisting of base modifications, sugar modifications, backbone modifications and lipid modifications, preferably wherein the chemical modification is a base modification, more preferably wherein the base modification preferably is selected from the group consisting of pseudouracil (Lp), N1-methylpseudouracil (N1 ML), 1-ethylpseudouracil, 2-thiouracil (s2U), 4-thiouracil, 5-methylcytosine, 5-methyluracil, 5-methoxyuracil, and any combination thereof.

30. The composition of any one of embodiments 22 to 29, wherein the mRNA compound comprises a coding region encoding a peptide or protein, wherein the coding region exhibits a sequence modification.

31. The composition of embodiment 30, wherein the sequence modification is selected from a G/C content modification, a codon modification, a codon optimization or a C-optimization of the sequence; preferably wherein the G/C content of the coding region is increased;

the C content of the coding region is increased;

the codon usage in the coding region is adapted to the human codon usage; and/or the codon adaptation index (CAI) is increased or maximised in the coding region compared with the coding region of the corresponding wild-type mRNA.

32. The composition of any one of embodiments 22 to 31, wherein the mRNA compound further comprises a) a 5'-CAP structure;

b) at least one miRNA sequence, preferably wherein the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof;

c) at least one 5'-UTR element;

d) at least one poly(A) sequence;

e) at least one poly(C) sequence;

f) at least one 3'-UTR element;

or any combinations of these.

33. The composition any one of embodiments 22 to 32, wherein the least one coding RNA comprises a 5'-CAP structure, preferably m7G, CAP0, CAP1, CAP2, a modified CAP0 or a modified CAP1 structure.

34. The composition of any one of embodiments 22 to 33, wherein the at least one coding RNA comprises at least one heterologous 5'-UTR and/or at least one heterologous 3'-UTR, preferably wherein the at least one heterologous 5'-UTR comprises a nucleic acid sequence derived from a 5'-UTR of a gene selected from HSD17B4, RPL32, ASAH1, ATP5A1, MP68, NDUFA4, NOSIP, RPL31, SLC7A3, TUBB4B and UBQLN2, or from a homolog, a fragment or variant of any one of these genes; and/or preferably wherein the at least one heterologous 3'-UTR comprises a nucleic acid sequence derived from a 3'-UTR of a gene selected from PSMB3, ALB7, alpha-globin, CASP1, COX6B1, GNAS, NDUFA1 and RPS9, or from a homolog, a fragment or a variant of any one of these genes.

35. The composition of any one of embodiments 22 to 34, wherein the at least one coding RNA comprises a (i) HSD17B4 5'-UTR and a PSMB3 3'-UTR or (ii) a RPL32 5'-UTR and an ALB7 3'-UTR.

36. The composition of any one of embodiments 22 to 35, comprising the following elements in the 5' to 3' direction:

a) a 5'-CAP structure, preferably selected from the group consisting of m7G(5'), m7G(5')ppp(5')(2'OMeA) and m7G(5')ppp(5')(2'OMeG);

b) a 5'-UTR element comprising a nucleic acid sequence derived from the 5'-UTR of a TOP gene, said nucleic acid sequence preferably comprising an RNA sequence that corresponds to the nucleic acid sequence according to SEQ ID NO:22, 24, 26, or a homolog, a fragment or a variant thereof;

c) at least one coding sequence;

d) a 3-UTR element comprising a nucleic acid sequence derived from an α-globin gene, said nucleic acid sequence preferably comprising an RNA sequence that corresponds to the nucleic acid sequence according to SEQ ID NO:6, 8, 10, 12, 14, 16, 18, 20, or a homolog, a fragment or a variant thereof; and/or a 3-UTR element comprising a nucleic acid sequence derived from an albumin gene, said nucleic acid sequence preferably comprising an RNA sequence that corresponds to the nucleic acid sequence according to SEQ ID NO:18, or a homolog, a fragment or a variant thereof;

e) optionally, at least one poly(A) sequence, preferably consisting of 10 to 200, 10 to 100, 40 to 80, or 50 to 70 adenosine nucleotides;

f) optionally, at least one poly(C) sequence, preferably consisting of 10 to 200, 10 to 100, 20 to 70, 20 to 60 or 10 to 40 cytosine nucleotides; and g) optionally, at least one histone stem-loop, preferably comprising the RNA sequence according to SEQ ID NO:4.

37. The composition of any one of embodiments 21 to 36, wherein the biologically active ingredient is (a) an mRNA comprising at least one coding sequence encoding a peptide or protein, or a fragment or variant thereof, wherein the peptide or protein is an antigen, wherein the antigen preferably is derived from pathogenic antigens, tumour antigens, allergenic antigens or autoimmune self-antigens, or a fragment or variant thereof; or (b) an mRNA comprising at least one coding sequence encoding a therapeutic protein, or a fragment or variant thereof, wherein the therapeutic protein is selected from the group consisting of (i) therapeutic proteins for use in enzyme replacement therapy for the treatment of metabolic, endocrine or amino acid disorders or for use in replacing an absent, deficient or mutated protein;

(ii) therapeutic proteins for use in the treatment of blood disorders, diseases of the circulatory system, diseases of the respiratory system, infectious diseases or immune deficiencies;

(iii) therapeutic proteins for use in the treatment of cancer or tumour diseases;

(iv) therapeutic proteins for use in hormone replacement therapy;

(v) therapeutic proteins for use in reprogramming somatic cells into pluri- or omnipotent stem cells;

(vi) therapeutic proteins for use as adjuvant or immunostimulation;

(vii) therapeutic proteins being a therapeutic antibody;

(viii) therapeutic proteins being a gene editing agent; and (ix) therapeutic proteins for use in treating or preventing a liver disease selected from the group consisting of liver fibrosis, liver cirrhosis and liver cancer.

38. The composition of embodiment 37 subitem (a), wherein the antigen encodes a pathogenic antigen selected from the group consisting of a bacterial, viral, fungal and protozoal antigen.

39. The composition of embodiment 38, wherein the pathogenic antigen is derived from a SARS coronavirus 2 (SARS-CoV-2), nCoV-2019 coronavirus, SARS coronavirus (SARS-CoV), Bunyavirales virus, Cytomegalovirus (CMV), Dengue viruses (DEN-1, DEN-2, DEN-3 and DEN-4), Ebola virus, Flavivirus, Hepatitis B virus (HBV), Herpes simplex virus (HSV), Human immunodeficiency virus (HIV), Human metapneumovirus (hMPV), Human Papilloma virus (HPV), Human parainfluenza viruses (HPIV), Influenza virus, extraintestinal pathogenic *E. coli, Lassa mammarenavirus* (LASV), MERS coronavirus, *Mycobacterium tuberculosis*, Nipah virus, Norovirus, Rabies virus, Respiratory Syncytial Virus (RSV), Rhinovirus, Rota virus, Vaccinia virus, Yellow Fever Virus, Zika virus, *Chlamydia trachomatis* (i.e. bacterium chlamydia causing chlamydia), or Malaria parasite (e.g. *Plasmodium falciparum, Plasmodium vivax, Plasmodium malariae*, or *Plasmodium ovale*).

40. The composition of any one of embodiments 15 to 39 for use (i) in the treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition; and/or (ii) for use in enzyme replacement therapy for the treatment of metabolic or endocrine disorders or for use in replacing an absent, deficient or mutated protein.

41. The composition of any one of embodiments 15 to 39 for use in the treatment or prophylaxis of infectious diseases.

42. The composition for the use of embodiments 40 or 41 comprising at least one coding RNA, wherein said at least one coding RNA comprises at least one coding sequence encoding at least one peptide or protein for use in treatment or prevention of a disease, disorder or condition, wherein said composition is administered via intramuscular or intradermal injection a subject in need thereof.

43. A kit or kit of parts, comprising any one of the compositions of embodiments 21 to 42, optionally comprising a liquid vehicle for solubilizing, and, optionally, technical instructions providing information on administration and dosage of the components.

44. The composition of any one of embodiments 21 to 42 or the kit or kit of parts of embodiment 43 for use as a medicament.

45. The composition for use as a medicament according to embodiment 44, wherein the medicament is for the prevention, prophylaxis, treatment and/or amelioration of a disease selected from infectious diseases including viral, bacterial or protozoological infectious diseases, cancer or tumour diseases, liver diseases, autoimmune diseases, allergies, monogenetic diseases including hereditary diseases, genetic diseases in general, diseases which have a genetic inherited background and which are typically caused by a defined gene defect and are inherited according to Mendel's laws; cardiovascular diseases, neuronal diseases, diseases of the respiratory system, diseases of the digestive system, diseases of the skin, musculoskeletal disorders, disorders of the connective tissue, neoplasms, immune deficiencies, endocrine, nutritional and metabolic diseases, eye diseases, ear diseases and diseases associated with a peptide or protein deficiency.

46. The composition for use as a medicament according to embodiments 44 or 45, wherein the medicament is a vaccine.

47. A vaccine comprising a composition of any one of embodiments 15 to 42 or a kit or kit of parts of embodiment 43 for prevention, prophylaxis, treatment and/or amelioration of a disease selected from infectious diseases including viral, bacterial or protozoological infectious diseases, cancer ortumour diseases.

48. A method of treatment or prophylaxis of infectious diseases; cancer or tumour diseases, disorders or conditions; liver diseases selected from the group consisting of liver fibrosis, liver cirrhosis and liver cancer; allergies; or autoimmune disease; disorder or condition comprising the steps:

a) providing the mRNA as described in any one of the above embodiments, the composition as described in any one of the above embodiments, the vaccine of embodiment 47, the kit or kit of parts of embodiment 43; and b) applying or administering the mRNA, the composition, the vaccine or the kit or kit of parts to a tissue or an organism.

49. The method according to embodiment 48, wherein the mRNA, the composition any one of embodiments 15 to 42, the vaccine of embodiment 47 or the kit or kit of parts of embodiment 43 is administered to the tissue or to the organism by intravenous, intramuscular, subcutaneous or intradermal injection.

50. A method of inducing an immune response in a subject, the method comprising administering to the subject the vaccine of embodiment 47 in an amount effective to produce an antigen-specific immune response in the subject.

51. A pharmaceutical composition comprising a composition of any one of embodiments 15 to 42 or a kit or kit of parts of embodiment 43 for use in vaccination of a subject comprising an effective dose of mRNA encoding a virus antigen.

52. Use of a pharmaceutical composition comprising a composition of any one of embodiments 15 to 42 or a kit or kit of parts of embodiment 43 for (i) inducing an immune response, for (ii) inducing an antigen specific T-cell response or preferably for (iii) inducing CD8+ T cells responses.

53. Use of the pharmaceutical composition of embodiment 52 for the prophylaxis of an infectious disease or in the manufacture of a medicament for the prophylaxis of an infectious disease, wherein said medicament preferably is a vaccine.

54. A method for preventing, ameliorating or treating a disease or condition in a subject in need comprising administering to the subject a composition of any one of embodiments 15 to 42 or a kit or kit of parts of embodiment 43.

55. The method of any one of the embodiments 48 to 50 and 54, wherein administration of the composition results in expression of the antigen encoded by mRNA in the lymphocytes of the subject.

56. The method of any one of the embodiments 48 to 50, 54 and 55, wherein the administration of the composition results in an antigen specific antibody response, preferably wherein the antigen specific antibody response is measured by the presence of antigen-specific antibodies in serum.

57. The composition of any one of embodiments 15 to 39, wherein the composition comprises a neutral lipid or phospholipid having at least one alkyl chain with a length of $C_5$, $C_6$, $C_7$, $C_8$, $C_9$, $C_{10}$, $C_{11}$, $C_{12}$, $C_{13}$ or $C_{14}$, preferably with a length of $C_6$, $C_7$, $C_8$, $C_9$, or $C_{10}$, more preferably with a length of $C_6$, $C_7$, $C_8$, most preferably with a length of $C_7$, or further most preferably wherein the composition comprises a combination of two neutral lipids wherein the combination comprises a neutral lipid or phospholipid having at least two alkyl chains, whereby each alkyl chain independently has a length of preferably $C_6$, $C_7$, $C_8$, $C_9$, or $C_{10}$, more preferably with a length of $C_6$, $C_7$, $C_8$, most preferably with a length of $C_7$, further most preferably a phospholipid selected from the group consisting of DHPC (1,2-diheptanoyl-sn-glycero-3-phosphocholine), 05:0 PC (1,2-dipentanoyl-sn-glycero-3-phosphocholine), 04:0 PC (1,2-dibutyryl-sn-glycero-3-phosphocholine), 06:0 PC (DHPC, 1,2-dihexanoyl-sn-glycero-3-phosphocholine), 08:0 PC (1,2-dioctanoyl-sn-glycero-3-phosphocholine), and 09:0 PC (1,2-dinonanoyl-sn-glycero-3-phosphocholine).

58. The composition of any one of embodiments 15 to 39, wherein the composition comprise a neutral lipid or phospholipid having at least two alkyl chains, whereby each alkyl chain independently has a length of $C_5$, $C_6$, $C_7$, $C_8$, $C_9$, $C_{10}$, $C_{11}$, $C_{12}$, $C_{13}$ or $C_{14}$, preferably with a length of $C_6$, $C_7$, $C_8$, $C_9$, or $C_{10}$, more preferably with a length of $C_6$, $C_7$, $C_8$, most preferably with a length of $C_7$, or further most preferably wherein the composition comprises a combination of two neutral lipids wherein the combination comprises a neutral lipid or phospholipid having at least two alkyl chains, whereby each alkyl chain independently has a length of preferably $C_6$, $C_7$, $C_8$, $C_9$, or $C_{10}$, more preferably with a length of $C_6$, $C_7$, $C_8$, most preferably with a length of $C_7$, further most preferably a phospholipid selected from the group consisting of DHPC (1,2-diheptanoyl-sn-glycero-3-phosphocholine), 05:0 PC (1,2-dipentanoyl-sn-glycero-3-phosphocholine), 04:0 PC (1,2-dibutyryl-sn-glycero-3-phosphocholine), 06:0 PC (DHPC, 1,2-dihexanoyl-sn-glycero-3-phosphocholine), 08:0 PC (1,2-dioctanoyl-sn-glycero-3-phosphocholine), and 09:0 PC (1,2-dinonanoyl-sn-glycero-3-phosphocholine).

EXAMPLES

In the following section, particular examples illustrating various embodiments and aspects of the invention are presented. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the claims as disclosed herein.

Example 1: Generation of RNA Constructs

The present Example provides methods for obtaining the RNA of the invention.

Example 1.1: Preparation of DNA Templates

A DNA sequence encoding the desired protein, f.e. Photinus pyralis luciferase (PpLuc), was prepared and used for subsequent RNA in vitro transcription. Exemplarily, a G/C optimized mRNA sequence encoding Photinus pyralis luciferase (PpLuc) is used herein, i.e. 5'-CAP-32L-5'-UTR (RPL32)—GC-optimized Photinus pyralis luciferase ORF albumin7-3'-UTR-poly(A) sequence-poly(C) sequence-histone stem-loop sequence; 64x adenosine at the 3-terminal end (polyA-tail); 5 nucleotides, 30 x cytosine at the 3-terminal end (poly-C-tail) and 5 additional nucleotides (SEQ ID NO:27).

Said (DNA) sequence was prepared by optionally modifying the wild type CDS sequences by introducing a GC optimized CDS. Sequences were introduced into a plasmid vector comprising UTR sequences, a stretch of adenosines, optionally a histone-stem-loop structure, and, optionally, a stretch of 30 cytosines. Obtained plasmid DNA was transformed and propagated in bacteria using common protocols and plasmid DNA was extracted, purified, and used for subsequent RNA in vitro transcription as outlined below.

Example 1.2: RNA In Vitro Transcription from Plasmid DNA Templates—Preparation of mRNA DNA plasmids prepared according to Example 1.1. were enzymatically linearized using a restriction enzyme/EcoRI and used for DNA dependent RNA in vitro transcription using T7 RNA polymerase in the presence of a nucleotide mixture (ATP/GTP/CTP/UTP) and cap analogue (e.g., m7GpppG or m7G(5')ppp(5')(2'OMeA)pG or m7G(5')ppp(5')(2'OMeG)pG)) under suitable buffer conditions. The obtained RNA was purified using RP-HPLC (PureMessenger®; according to WO2008/077592) and used for further experimentation. The obtained mRNA was enzymatically polyadenylated using a commercial polyadenylation kit.

Example 2: Synthesis of HEXA and HEAD Lipids

The present Example provides methods and information to obtain the lipid compounds of the invention as well as methods of generating and analysing compositions of the invention.

Example 2.1: HEXA Lipids—Synthesis of HEXA Lipids

HEXA lipids were synthesized according to general protocols of ChiroBlock GmbH (Bitterfeld-Wolfen, Germany). Nine HEXA lipids as shown in Table Ex-1 and FIG. 1 were synthesized and further lipids are shown in Table 1 above.

TABLE EX-1

Overview of the synthesized HEXA lipids

| Lipids No./ Compound No. | Ref. in FIG. 1 | Compound name*** [Tail-Linker-Head] | Ester structure | Additional comment |
|---|---|---|---|---|
| C1 | FIG. 1A | HEXA-C4DE-PipSS | diester | ester linkage length C2-C8 |
| C2 | FIG. 1B | HEXA-C5DE-PipSS | | branched or unbranched alkyl |
| C3 | FIG. 1C | HEXA-C6DE-PipSS | | C12-C25 |
| C4 | FIG. 1D | HEXA-C7DE-PipSS | | |
| C5 | FIG. 1E | HEXA-C8DE-PipSS | | |
| C6 | FIG. 1F | HEXACA-C3ME-PipSS | monoester | |
| C7 | FIG. 1G | HEXACA-C4ME-PipSS | | |
| C8 | FIG. 1H | HEXACA-C6ME-PipSS | | |
| C9 | FIG. 1I | HEXACA-C8ME-PipSS | | |

***the name of the lipids as indicated in Table Ex-1 is derived as follows: the basic name consists of three parts: "Tail-Linker-Head". The tail can be f.e. "HEXA" which refers to a hexyldecanoic acid (Hexyl-1-decanol) or "HEXACA" which refers to 2-Hexyldecanoic acid (carboxylic acid). The linker can be f.e. C4DE = which refers to a C4 group comprising a diester linker (C4 = 4 Carbon atoms of the linker with two esters) or f.e. C3ME which refers to a C3 group comprising a monoester linker. The reference to the head "PipSS" indicates piperidine residues connected via a disulfide bridge; PipC3SS as mentioned further in this application related to a structure with 3 carbon atoms between the piperidine/piperazine ring and the disulfide bridge.

Purity and structural identity of the HEXA lipids was confirmed by nuclear magnetic resonance spectroscopy (H-NMR, 500.13 MHz) and mass spectrometry (electrospray ionization-ESI or atmospheric pressure chemical ionization-APCI, via direct injection).

Example 2.1.1: Preparation of LNPs Using the NanoAssemblr™ Microfluidic System The LNPs were prepared using the NanoAssembr™ microfluidic system (Precision NanoSystems Inc., Vancouver, BC) according to standard protocols which enables controlled, bottom-up, molecular self-assembly of nanoparticles via custom-engineered microfluidic mixing chips that enable millisecond mixing of nanoparticle components at a nanolitre scale.

GN01-LNPs comprising the cationic lipid COATSOME® SS-EC (former name: SS—33/4PE-15; NOF Corporation, Tokyo, Japan; see compound C23 in Table 1, see Table Ex-2) have been shown to efficiently activate T cells after s.c. injection (data not shown). In the context of the working examples, if only "SS-EC" is indicated, reference is made to aforementioned COATSOME® SS-EC.

In the present examples, the cationic lipids C1-C22 (ChiroBlock GmbH, Bitterfeld-Wolfen, Germany, custom synthesis) and C24-C27 (Symeres, Groningen, The Netherlands, custom synthesis) as disclosed in Table 1 or respectively HEXA lipids, or COATSOME® SS-EC (NOF Corporation, Tokyo, Japan; compound C23 in Table 1) were used for preparation of lipid nanoparticle compositions. Furthermore, cholesterol (Avanti Polar Lipids; Alabaster, AL.), neutral lipid/phospholipid DPhyPE (Avanti Polar Lipids; Alabaster,AL.) and DMG-PEG 2000 (NOF Corporation, Tokyo, Japan) were used.

In the context of the working examples and also the disclosure of the invention, if only "DMG-PEG"/"DSG-PEG" or "DMG-mPEG"/"DSG-mPEG" is indicated, reference is made herein to 1,2-dimyristoyl-rac-glycero-3-methoxypolyethylene glycol-2000 (DMG-(m)PEG2000) and distearoyl-rac-glycerol-PEG2000 (DSG-(m)PEG 2000), respectively.

The lipids were solubilized in alcoholic solution (ethanol) according to standard procedures. The corresponding lipid nanoparticle compositions are detailed in Table Ex-2 below.

In detail, LNPs were prepared by mixing appropriate volumes of lipid stock solutions in ethanol buffer with an aqueous phase (50 mM sodium acetate, pH 4.0) containing appropriate amounts of mRNA as indicated herein; cholesterol, phospholipid and polymer conjugated lipid: 20 mg/ml in EtOH, cationic lipids, except for GN01: 20 mg/ml in EtOH, GN01-lipid: 30 mg/ml in tert-butanol and lipids C24, C25, C26 and C27 were also solubilized in 30 mg/ml t-butanol and added to the ethanol premix of lipids.

Briefly, the mRNA was diluted to 0.05 to 0.2 mg/ml in 10 to 50 mM acetate buffer, pH 4. Syringe pumps were installed into inlet parts of the NanoAssembr™ (Precision NanoSystems Inc., Vancouver, BC) and used to mix the ethanolic lipid solution with the mRNA aqueous solution at a ratio of about 1:5 to 1:3 (vol/vol) with total flow rates from about 14 ml/min to about 18 ml/min.

The ethanol was then removed and the external buffer replaced with PBS/sucrose buffer (pH 7.4, 75 mM NaCl, 10 mM phosphate, 150 mM sucrose) by dialysis (Slide-A-Lyzer™ Dialysis Cassettes, ThermoFisher). Finally, the lipid nanoparticles were filtered through a 0.2 μm pore sterile filter. Lipid nanoparticle particle diameter size was from about 90 nm to about 140 nm as determined by quasi-elastic light scattering using a Malvern Zetasizer Nano (Malvern Instruments Ltd.; Malvern, UK). For other cationic lipid compounds mentioned in the present specification, the formulation process is similar. The ethanol was then removed and buffer replaced by 10 mM PBS, pH 7.4 comprising 9% Sucrose.

TABLE EX-2

Summary/overview for preparation of lipid nanoparticle compositions of the working examples - formulations comprising HEXA lipids - if reference is made herein to a specific Composition (i.e. Composition 1/2), the respective HEXA-lipid is indicated in the respective working example

| Name of LNP formulation/ composition No. | Excipients [cationic lipid:steroid:neutral lipid:polymer conjugated lipid] | mol-percentages for excipients [mol %] |
|---|---|---|
| Composition 1 | HEXA lipid as indicated in respective working example: Chol:DSPC:DMG-PEG 2000 | 59:29.3:10:1.7 |
| Composition 2 | HEXA lipid as indicated as indicated in respective working example:Chol:DPhyPE:DMG-PEG 2000 | 59:29.3:10:1.7 |
| GN01 | SS-EC:Chol:DPhyPE:DMG-PEG 2000 | 59:29.3:10:1.7 |
| GN02 | C2:Chol:DPhyPE:DMG-PEG 2000 | 59:29.3:10:1.7 |

As described above, the term "GN01" resembles a lipid nanoparticle comprising 59 mol % cationic lipid C23 as disclosed in Table 1, i.e. COATSOME® SS-EC (former name: SS—33/4PE-15 as apparent from the present examples section), 29.3 mol % cholesterol as steroid, 10 mol % DPhyPE as neutral lipid/phospholipid and 1.7 mol % DMG-PEG 2000 as polymer conjugated lipid. For "GN01", the N/P (lipid to mRNA mol ratio) preferably is 14 and the total lipid/mRNA mass ratio preferably is 40.

Further, as described above, "GN02" resembles a lipid nanoparticle comprising 59 mol % cationic lipid C2 lipid as disclosed in Table 1 (i.e. HEXA-C5DE-PipSS as apparent from the examples section, FIG. 1B), 29.3 mol % cholesterol as steroid, 10 mol % DPhyPE as neutral lipid/phospholipid and 1.7 mol % DMG-PEG 2000 as polymer conjugated lipid. For "GNO2", the N/P (lipid to mRNA mol ratio) preferably is 17.5 and the total lipid/mRNA mass ratio preferably is 40.

Example 2.1.2: Biophysical Characterization of Lipid Nanoparticle Compositions/HEXA Lipids Each LNP was characterized in terms of particle size, zeta potential, encapsulation efficiency/%-encapsulation (EE), RNA content (basically corresponding to mRNA content within the context of the present invention) and protonation profile/p$K_a$.

To measure the protonation profile/p$K_a$ of HEXA lipids, lipids 1 to 9 as disclosed in Table Ex-1 were prepared as LNPs using different lipid compositions (as shown in Table Ex-3). Hereby the HEXA lipid compounds 1-9 as apparent from Table Ex-1 were mixed with different ratios of the neutral phospholipids DPhyPE (1,2-diphytanoyl-sn-glycero-3-phosphoethanolamine), DSPC (1,2-distearoyl-sn-glycero-3-phosphocholine), the neutral steroid cholesterol (Chol) and the polymer conjugated lipid DMG-PEG 2000.

TABLE EX-3

Formulation summary of HEXA lipids - reference to the cationic lipids as disclosed in Table 1 is made herein

| Name of LNP formulation/ composition | Excipients [cationic lipid as disclosed in Table 1:steroid:neutral lipid: polymer conjugated lipid] | mol-percentages for excipients [mol %] |
|---|---|---|
| LNP1 | C1:Chol:DSPC:DMG-PEG 2000 | 59:29.3:10:1.7 |
| LNP2 | C2:Chol:DSPC:DMG-PEG 2000 | 59:29.3:10:1.7 |
| LNP3 | C3:Chol:DSPC:DMG-PEG 2000 | 59:29.3:10:1.7 |
| LNP4 | C4:Chol:DSPC:DMG-PEG 2000 | 59:29.3:10:1.7 |
| LNP5 | C5:Chol:DSPC:DMG-PEG 2000 | 59:29.3:10:1.7 |
| LNP6 | C6:Chol:DSPC:DMG-PEG 2000 | 59:29.3:10:1.7 |
| LNP7 | C7:Chol:DSPC:DMG-PEG 2000 | 59:29.3:10:1.7 |
| LNP8 | C1:Chol:DPhyPE:DMG-PEG 2000 | 59:29.3:10:1.7 |
| LNP9 | C2:Chol:DPhyPE:DMG-PEG 2000 | 59:29.3:10:1.7 |
| LNP10 | C3:Chol:DPhyPE:DMG-PEG 2000 | 59:29.3:10:1.7 |
| LNP11 | C4:Chol:DPhyPE:DMG-PEG 2000 | 59:29.3:10:1.7 |
| LNP12 | C5:Chol:DPhyPE:DMG-PEG 2000 | 59:29.3:10:1.7 |
| LNP13 | C6:Chol:DPhyPE:DMG-PEG 2000 | 59:29.3:10:1.7 |
| LNP14 | C7:Chol:DPhyPE:DMG-PEG 2000 | 59:29.3:10:1.7 |
| LNP15 | C8:Chol:DSPC:DMG-PEG 2000 | 59:29.3:10:1.7 |
| LNP16 | C8:Chol:DPhyPE:DMG-PEG 2000 | 59:29.3:10:1.7 |
| LNP17 | C9:Chol:DSPC:DMG-PEG 2000 | 59:29.3:10:1.7 |
| LNP18 | C9:Chol:DPhyPE:DMG-PEG 2000 | 59:29.3:10:1.7 |

For formulation of mRNA of interest (f.e. PpLuc as described above) into HEEA lipid LNPs, a RNA/lipid ratio of 3 and a nitrate to phosphate (N/P) ratio of 14 was used.

Figure 2:
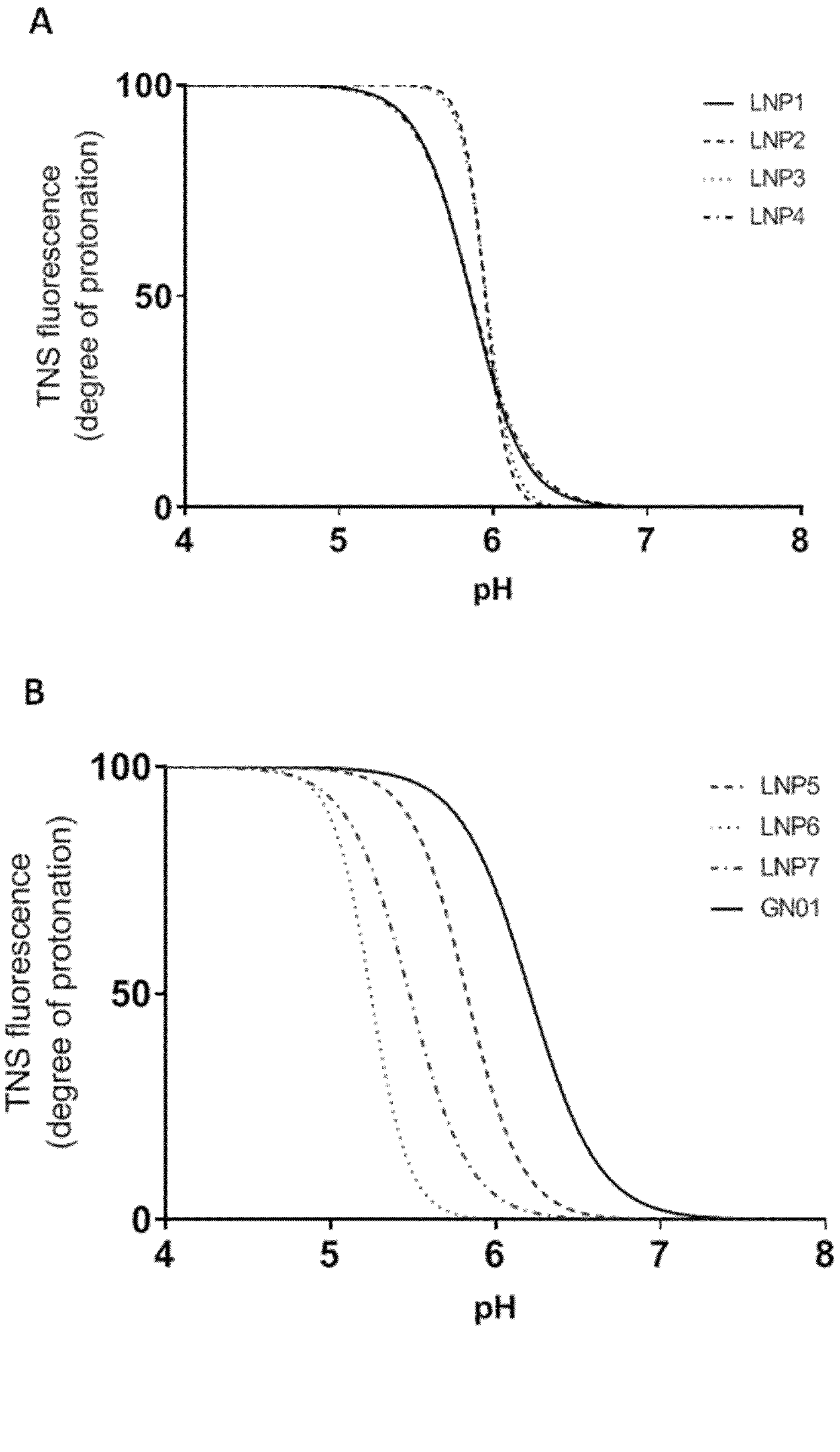
FIG. 2 (Protonation profile/pKa of HEXA lipids)—shows the protonation profile/pKa of inventive HEXA lipid compounds—Measurement of degree of protonation via TNS (dye 2-p-toluidinylnaphthalene-6-sulphonate) fluorescence. A TNS Fluorescence of LNP1, LNP2, LNP3 and LNP4 in composition 1 (DSPC). B TNS Fluorescence of LNP5, LNP6, LNP7 in composition 1 (DSPC) and GN01. C TNS Fluorescence of LNP8, LNP9, LNP10 and LNP11 in composition21 (DPhyPE or 4ME 16:0 PE). D TNS Fluorescence of LNP12, LNP13, LNP14 in composition 2 (DPhyPE) and GN01. E TNS Fluorescence of LNP15 (in composition 1-DSPC), LNP16 (in composition 2-DPhyPE), LNP17 (in composition 2-DSPC), LNP 18 (in composition 2-DPhyPE) and GN01 (full details can be seen in Example 2.1.2/Table Ex-4).
Figure 2:
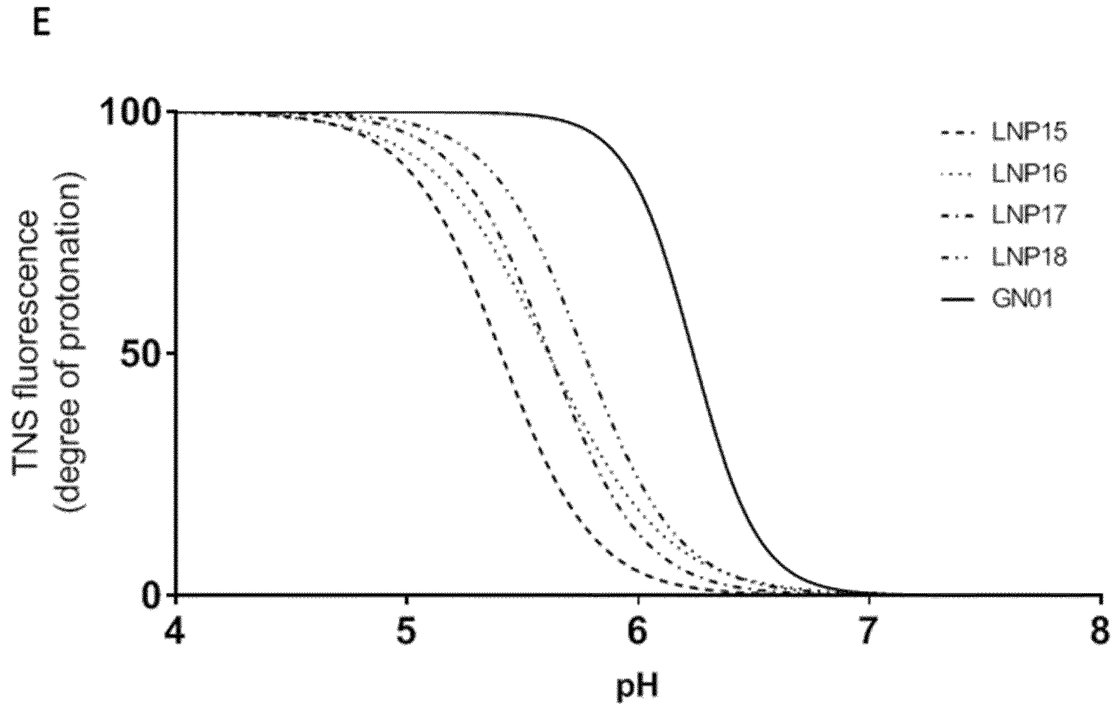

The $pK_a$ is the negative base 10 logarithm of the acid dissociation constant ($K_a$) of a solution, i.e. $pK_a=-\log(K_a)$. The $pK_a$ value was measured according to standard proceedings with fluorescent dye 2-β-toluidinylnaphthalene-6-sulphonate (TNS). The protonation profile/pKa of HEXA lipids compounds is shown in FIG. 2 or respectively in Table Ex-4.

Further, the mean diameter and zeta potential of the LNPs after dialysis was as determined by dynamic light scattering and Laser Doppler Microelectrophoresis, respectively using a Malvern Zetasizer Nano (Malvern Instruments Ltd.; Malvern, UK). Encapsulation efficiency (EE [%]) was calculated by the following equation: %-encapsulation=(Ft−Fi)/Ft×100; whereby Fi=free unencapsulated RNA as determined by addition of RiboGreen (Molecular Probes, Eugene,OR., USA) to the LNP aliquot and Ft=total content RNA content measured by adding RiboGreen (Molecular Probes, Eugene,OR., USA) to fluorescence value=Fi) to an aliquot of lysed LNP achieved by incubation with 0.25% Triton X-100.

The results ofthese analyses are shown herein below in Table Ex-4 and Table Ex-5.

TABLE EX 4

Biocharacterization of HEXA lipids

| Name of LNP formulation/composition | Composition (see Table Ex-2) | Lipid/mRNA (mass ratio) | RNA [μg/ml] | Lipid [mg/ml] | PDI | zeta potential [mV] | EE [%] | size [nm] | $pK_a$ |
|---|---|---|---|---|---|---|---|---|---|
| LNP1 | 1 | 30.9 | 75 | 2.3 | 0.14 | −14 | 95 | 131 | 5.85 |
| LNP2 | 1 | 31.5 | 75 | 2.3 | 0.11 | −12 | 96 | 107 | 5.94 |
| LNP3 | 1 | 32.1 | 75 | 2.4 | 0.12 | −12 | 96 | 94 | 5.96 |
| LNP4 | 1 | 32.7 | 75 | 2.5 | 0.11 | −9 | 94 | 93 | 5.86 |
| LNP5 | 1 | 33.3 | 75 | 2.5 | 0.09 | −10 | 94 | 91 | 5.82 |
| LNP6 | 1 | 27.2 | 75 | 2.0 | 0.12 | −10 | 73 | 95 | 5.24 |
| LNP7 | 1 | 27.8 | 75 | 2.0 | 0.09 | −13 | 46 | 92 | 5.47 |
| LNP8 | 2 | 30.9 | 75 | 2.3 | 0.18 | −8.5 | 74 | 200 | 5.91 |
| LNP9 | 2 | 31.5 | 75 | 2.3 | 0.18 | −6.8 | 81 | 177 | 6.04 |
| LNP10 | 2 | 32.2 | 75 | 2.4 | 0.18 | −7.4 | 84 | 191 | 6.03 |
| LNP11 | 2 | 32.8 | 75 | 2.4 | 0.15 | −8.5 | 89 | 193 | 5.96 |
| LNP12 | 2 | 33.4 | 75 | 2.5 | 0.09 | −7.7 | 86 | 185 | 5.96 |
| LNP13 | 2 | 27.2 | 75 | 2.0 | 0.08 | −21.9 | 54 | 125 | 5.31 |
| LNP14 | 2 | 27.8 | 75 | 2.0 | 0.09 | −17.3 | 85 | 97 | 5.71 |
| LNP15 | 1 | 29.0 | 120 | 3.5 | 0.16 | −22.00 | 38 | 78 | 5.22 |
| LNP16 | 2 | 29.0 | 120 | 3.4 | 0.20 | −17.00 | 91 | 115 | 5.38 |
| LNP17 | 1 | 30.2 | 120 | 3.6 | 0.18 | −18.00 | 40 | 88 | 5.39 |
| LNP18 | 2 | 30.2 | 120 | 3.6 | 0.30 | −13.00 | 96 | 75 | 5.55 |

TABLE EX-5

TNS fluorescence: Degree of protonation of HEXA Lipids

| Name of LNP formulation/composition | log EC50 | Composition No. (see Table Ex-2) |
|---|---|---|
| LNP1 | 5.8 | 1 |
| LNP2 | 5.9 | 1 |
| LNP3 | 5.9 | 1 |
| LNP4 | 5.8 | 1 |
| LNP5 | 8.8 | 1 |
| LNP6 | 5.2 | 1 |
| LNP7 | 5.4 | 1 |
| LNP8 | 5.9 | 2 |
| LNP9 | 6.0 | 2 |
| LNP10 | 6.0 | 2 |
| LNP11 | 5.9 | 2 |
| LNP12 | 5.9 | 2 |
| LNP13 | 5.3 | 2 |
| LNP14 | 5.7 | 2 |
| LNP15 | 5.4 | 1 |
| LNP16 | 5.6 | 2 |
| LNP17 | 5.6 | 1 |
| LNP18 | 5.7 | 2 |
| GN01 | 6.2 | / |

Example 2.2: HEAD Lipids—Synthesis of HEAD Lipids

HEAD lipids were synthesized according to general protocols of ChiroBlock GmbH (Bitterfeld-Wolfen, Germany). In this working example, three HEAD lipids were synthesized (as shown in Table Ex-6 and FIG. 3).

TABLE EX-6

Figure 3:
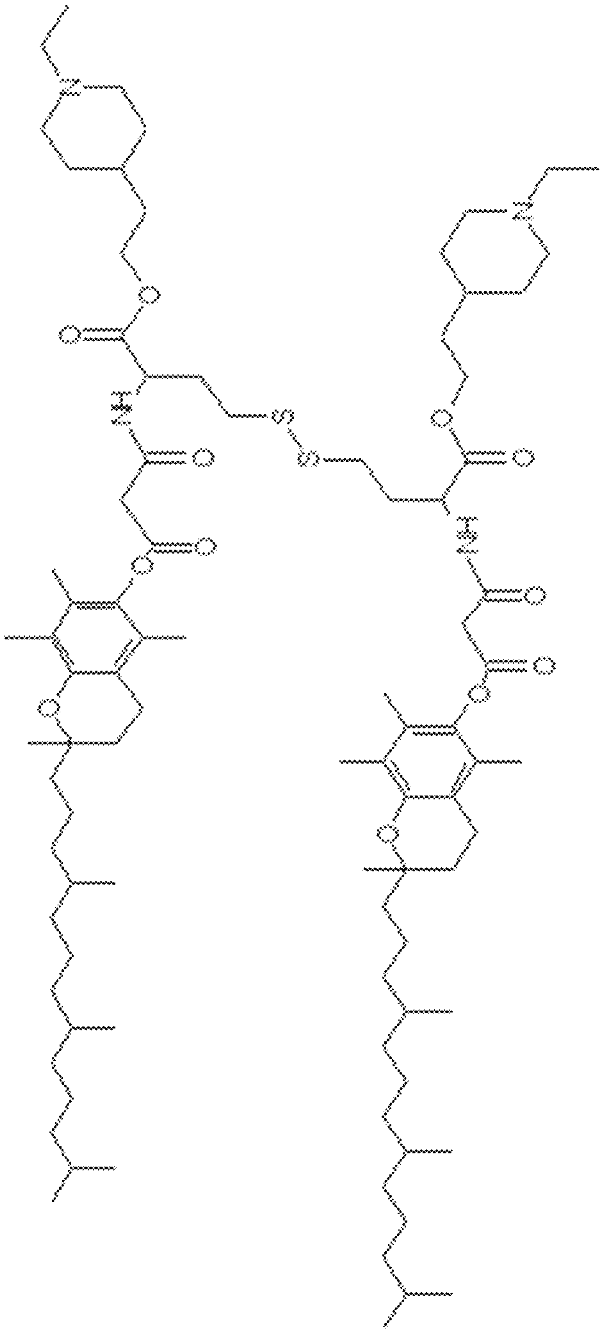
FIG. 3 (Structures of HEAD lipids)—shows the structures of inventive HEAD lipid compounds as described herein (full details can be seen in Example 2.1/Table Ex-6), i.e. lipid compound CISE (FIG. 3A), lipid compound CPZE (FIG. 3B), lipid compound ESTER (FIG. 3C).
Figure 3:
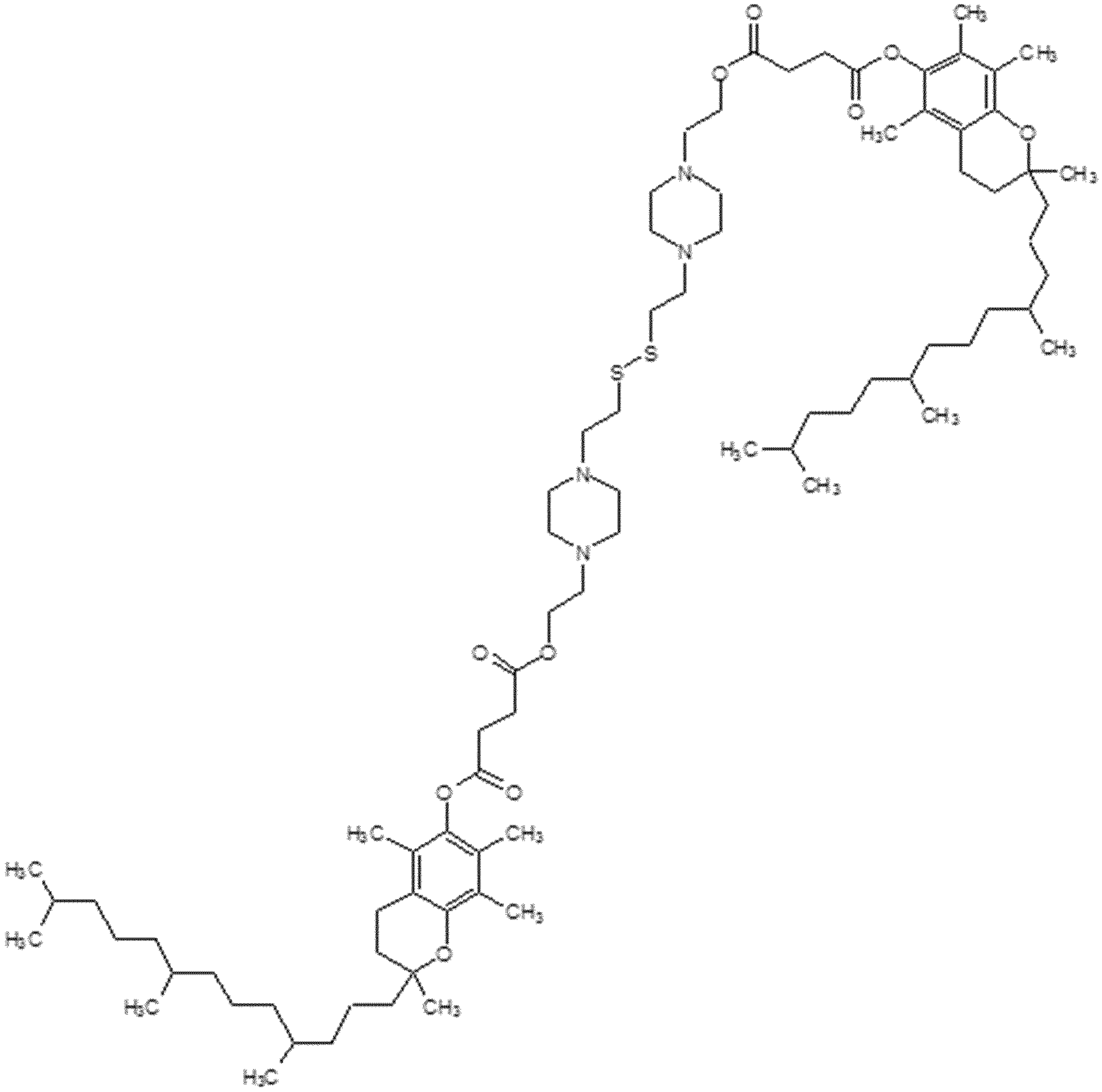
Figure 3:
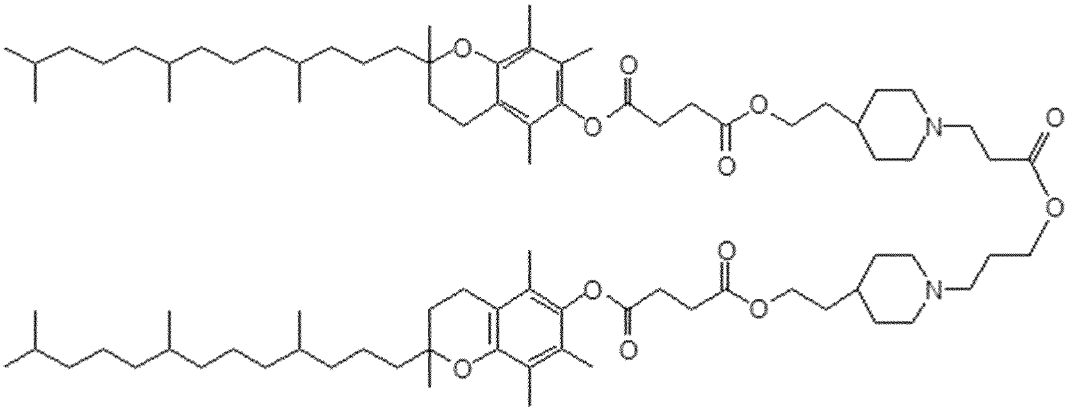

| Overview of the synthesized HEAD lipids | | | | | |
|---|---|---|---|---|---|
| | Compound name | Ref. in FIG. 3 | Chemical name | Chemical sum formula | Molecular Weight [g/mol] |
| CISE | GN-CISE-001 (CIS-Cys_Internal_Sulphur & VitE) VitE-C4DE-CysPipSS) | FIG. 3A | 2-[(1-Benzyl-6-phenyl-hexyl)amino]-5-nitro-benzoic acid | $C_{90}H_{150}N_4O_{12}S_2$ | 1544.35 |
| CPZE | GN-CPZE-001 VitE-C4DE-PipAZSS (Coatsome-like_Piperazin_VitaminE) | FIG. 3B | O1-[2-[4-[2-[2-[4-[2-[4-oxo-4-[(2R)-2,5,7,8-tetramethyl-2-[(4R,8R)-4,8,12-trimethyltridecyl]chroman-6-yl]oxy-butanoyl]oxyethyl]piperazin-1-yl]ethyldisulfanyl]ethyl]piperazin-1 -yl]ethyl] O4-[(2R)-2,5,7,8-tetra-methyl-2-[(4R,8R)-4,8,12-trimethyl-tridecyl]chroman-6-yl] butanedioate | $C_{82}H_{138}N_4O_{10}S_2$ | 1404.16 |
| ESTER | GN-E3BE-001 VitE-C4DE-PipE (E3BE- Ester bridge with 3 carbons & VitE) | FIG. 3C | O1-[2-[1-[3-[3-[4-[2-[4-oxo-4-[(2R)-2,5,7,8-tetramethyl-2-[(4R,8R)-4,8,12-trimethyltridecyl]chroman-6-yl]oxy-butanoyl]oxyethyl]-1-piperid-yl]propanoyloxy]propyl]-4-piperid-yl]ethyl] O4-[(2R)-2,5,7,8-tetra-methyl-2-[(4R,8R)-4,8,12-trimethyl-tridecyl]chroman-6-yl] butanedioate | $C_{86}H_{142}N_2O_{12}$ | 1396.10 |

Purity and structural identity of HEAD lipids was confirmed by nuclear magnetic resonance spectroscopy (H-NMR, 500.13 MHz) and mass spectrometry (electrospray ionization-ESI or atmospheric pressure chemical ionization-APCI, via direct injection).

Example 2.2.1: Preparation of LNPs Using the NanoAssemblr™ Microfluidic System 1 HEAD Lipids Similar to the HEXA lipids, HEAD lipids were formulated as LNP using the NanoAssemblr™ microfluidic system (Precision NanoSystems Inc., Vancouver, BC) according to standard protocols (see above, Example 2.1.1).

Example 2.2.2: Biophysical Characterization of Lipid Nanoparticle Compositions/HEAD Lipids Each LNP was characterized in terms of particle size, zeta potential, encapsulation efficiency (%-encapsulation; EE), RNA content and protonation profile/p$K_a$, similar to the biophysical characterization of lipid nanoparticle compositions as described before (see above, Example 2.1.2).

To measure the protonation profile/p$K_a$ of HEAD lipids, HEAD lipids were prepared as LNPs using different lipid compositions (as shown in Table Ex-7 and Table Ex-8) and measured together with GN01.

TABLE EX-7

| Summary/overview for preparation of lipid nanoparticle compositions of the working examples - formulations comprising HEAD lipids - if reference is made herein to a specific Composition (i.e. Composition A or B), the respective HEAD-lipid is indicated in the respective working example | | |
|---|---|---|
| Name of LNP formulation/ composition | Excipients [cationic lipid:steroid:neutral lipid:polymer conjugated lipid] | mol-percentages for excipients [mol %] |
| Composition A | HEAD lipid as indicated in respective working example:Chol:DSPC:DMG-PEG | 59:29.3:10:1.7 |
| Composition B | HEAD lipid as indicated in respective working example:Chol:DPhyPE:DMG-PEG | 59:29.3:10:1.7 |
| GN01 | SS-EC:Chol:DPhyPE:DMG-PEG | 59:29.3:10:1.7 |

TABLE EX-8

| Formulation summary of HEAD lipids | | |
|---|---|---|
| Name of LNP formulation/ composition designation | Excipients [cationic lipid:steroid:neutral lipid:polymer conjugated lipid] | mol-percentages for excipients [mol %] |
| Composition A | GN-CPZE-001:Chol:DSPC:DMG-PEG | 59:29.3:10:1.7 |
| Composition B | GN-CPZE-001:Chol:DPhyPE:DMG-PEG | 59:29.3:10:1.7 |
| Composition A | GN-CISE-001:Chol:DSPC:DMG-PEG | 59:29.3:10:1.7 |
| Composition B | GN-CISE-001:Chol:DPhyPE:DMG-PEG | 59:29.3:10:1.7 |

TABLE EX-8-continued

| Formulation summary of HEAD lipids | | |
|---|---|---|
| Name of LNP formulation/ composition designation | Excipients [cationic lipid:steroid:neutral lipid:polymer conjugated lipid] | mol-percentages for excipients [mol %] |
| Composition A | GN-ESTER-001:Chol:DSPC:DMG-PEG | 59:29.3:10:1.7 |
| Composition B | GN-ESTER-001:Chol:DPhyPE:DMG-PEG | 59:29.3:10:1.7 |

Figure 4:
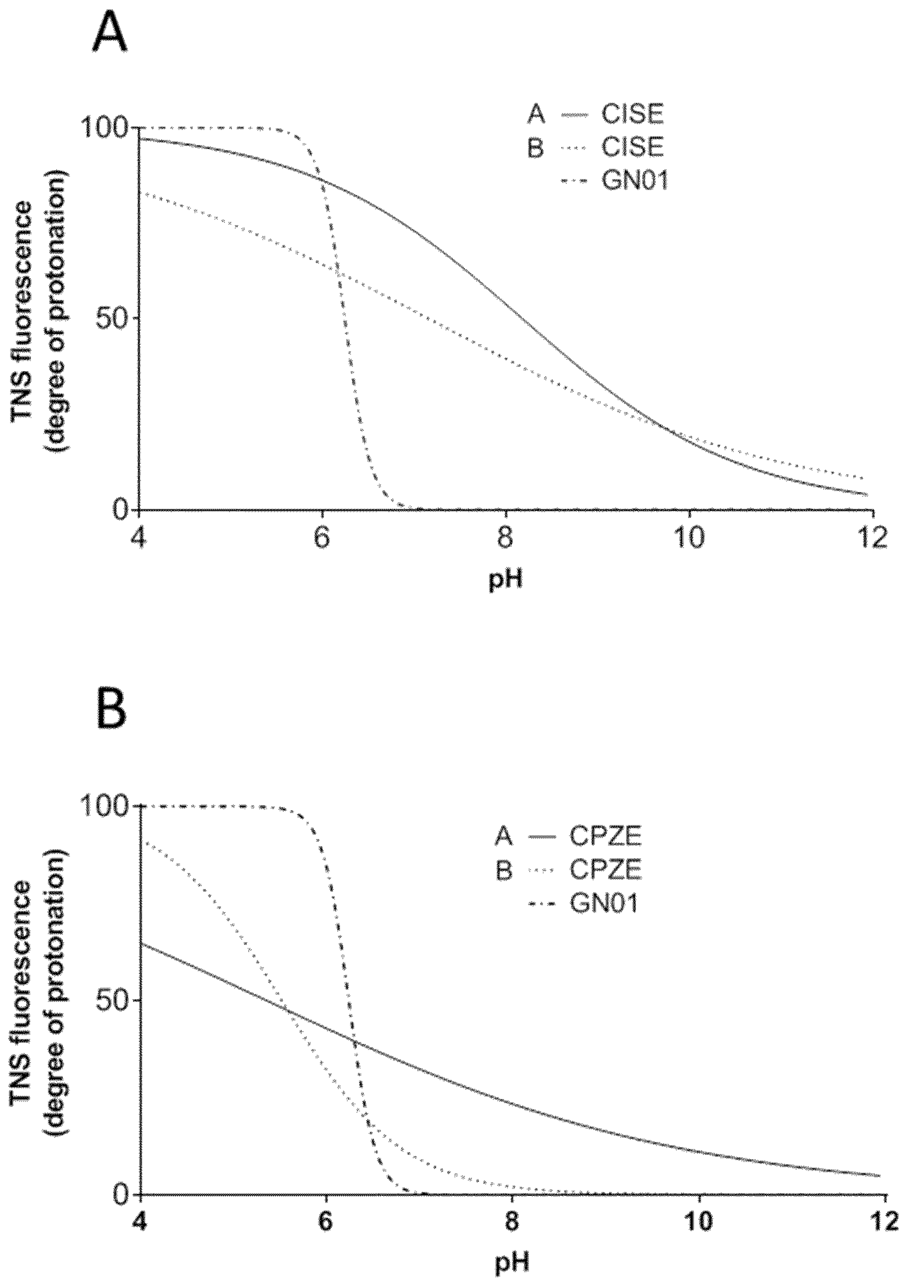
FIG. 4 (Protonation profile/pKa of HEAD lipids)—shows the protonation profile/pKa of inventive HEAD lipid compounds—Measurement of degree of protonation via TNS (dye 2-p-toluidinylnaphthalene-6-sulphonate) fluorescence. A TNS Fluorescence of HEAD lipid CISE in composition A (DSPC) and composition B (DPhyPE) compared GN01 B TNS Fluorescence of HEAD lipid CPZE in composition A (DSPC) and composition B (DPhyPE) compared GN01. C TNS Fluorescence of HEAD lipid ESTER in composition A (DSPC) and composition B (DPhyPE) compared GN01 (full details can be seen in Example 2.2.2/Table Ex-9).
Figure 4:
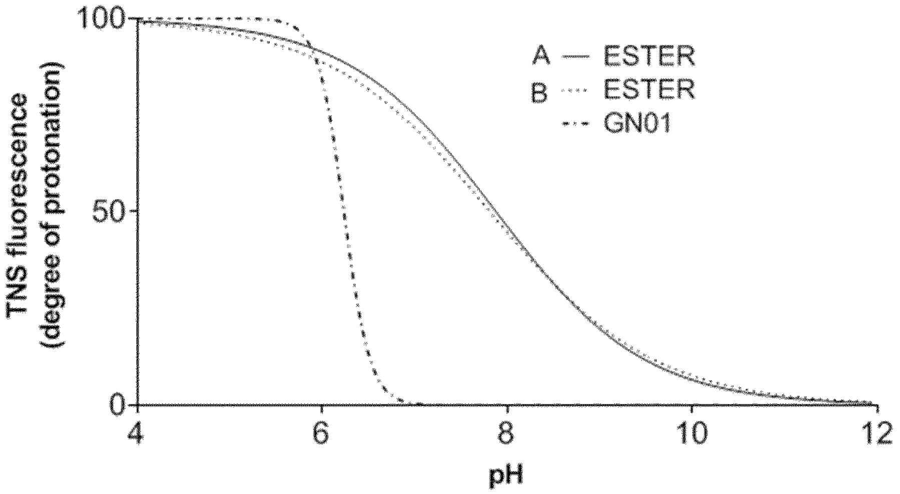

The resulting protonation profile I pKa of HEAD lipids compounds is shown in FIG. 4 or respectively Table Ex-9.

The mean diameter and zeta potential of the LNPs after dialysis was determined by dynamic light scattering and Laser Doppler Micro-electrophoresis as described above.

For formulation of mRNA (fe. PpLuc as described above and other mRNAs of interest) into HEAD lipid LNPs, a RNA/lipid ratio of 3 and a nitrate to phosphate (NIP) ratio of 14 was used.

The results of these analyses are shown herein below in Table Ex-9.

LNP8 to LNP13, which comprised the same lipids except for differing in the neutral lipid, i.e. DPhyPE instead of DSPC, showed very good and even superior expression in HeLa, also when compared to GN01. In HepG2 cells, LNP1 to LNP5 demonstrated decent expression when compared to GN01. However, also here, LNP8 to LNP13 showed much stronger expression, also in comparison to GN01 (LNP8 to LNP12 even superior). I.e. again the only difference between LNP1 to LNP5 and LNP8 to LNP12 was the use of DPhyPE instead of DSPC.

TABLE EX 9

| Biocharacterization of HEAD lipids | | | | | | | | | |
|---|---|---|---|---|---|---|---|---|---|
| Name of LNP formulation/ composition | Composition (see Table Ex-8) | Lipid/mRNA (mass ratio) | RNA [μg/ml] | Lipid [mg/ml] | PDI | zeta potential [mV] | EE [%] | size [nm] | $pK_a$ |
| CPZE | A | 19.5 | 120 | 2.3 | 0.50 | −6.30 | 80 | 105 | 6.48 |
| CPZE | B | 19.6 | 120 | 2.3 | 0.13 | −2.87 | 85 | 106 | 5.20 |
| CISE | A | 42.1 | 120 | 5.0 | 0.34 | 26.00 | 100 | 67 | 7.87 |
| CISE | B | 42.2 | 120 | 5.0 | 0.50 | 36.00 | 95 | 103 | 7.42 |
| ESTER | A | 38.9 | 120 | 4.6 | 0.37 | 19.00 | 97 | 92 | 7.36 |
| ESTER | B | 39.0 | 120 | 4.6 | 0.24 | 19.00 | 90 | 77 | 7.40 |

Example 3: In Vitro Analysis of HEXA Lipids and HEAD Lipids

The present Example provides details to the in vitro analysis of compositions and lipids of the invention.

Example 3.1: In Vitro Analysis of HEXA Lipids

Example 3.1.1: PpLuc Expression in HeLa and HepG2 Using HEXA Lipids

To determine in vitro expression, transfection and expression efficiency of various LNP compositions according to the invention comprising HEXA lipids, PpLuc mRNA was compared to positive and negative controls in HepG2 cells, a hepatocyte carcinoma cell line and HeLa cells, a cervical immortal cancer cell line.

Figure 5:
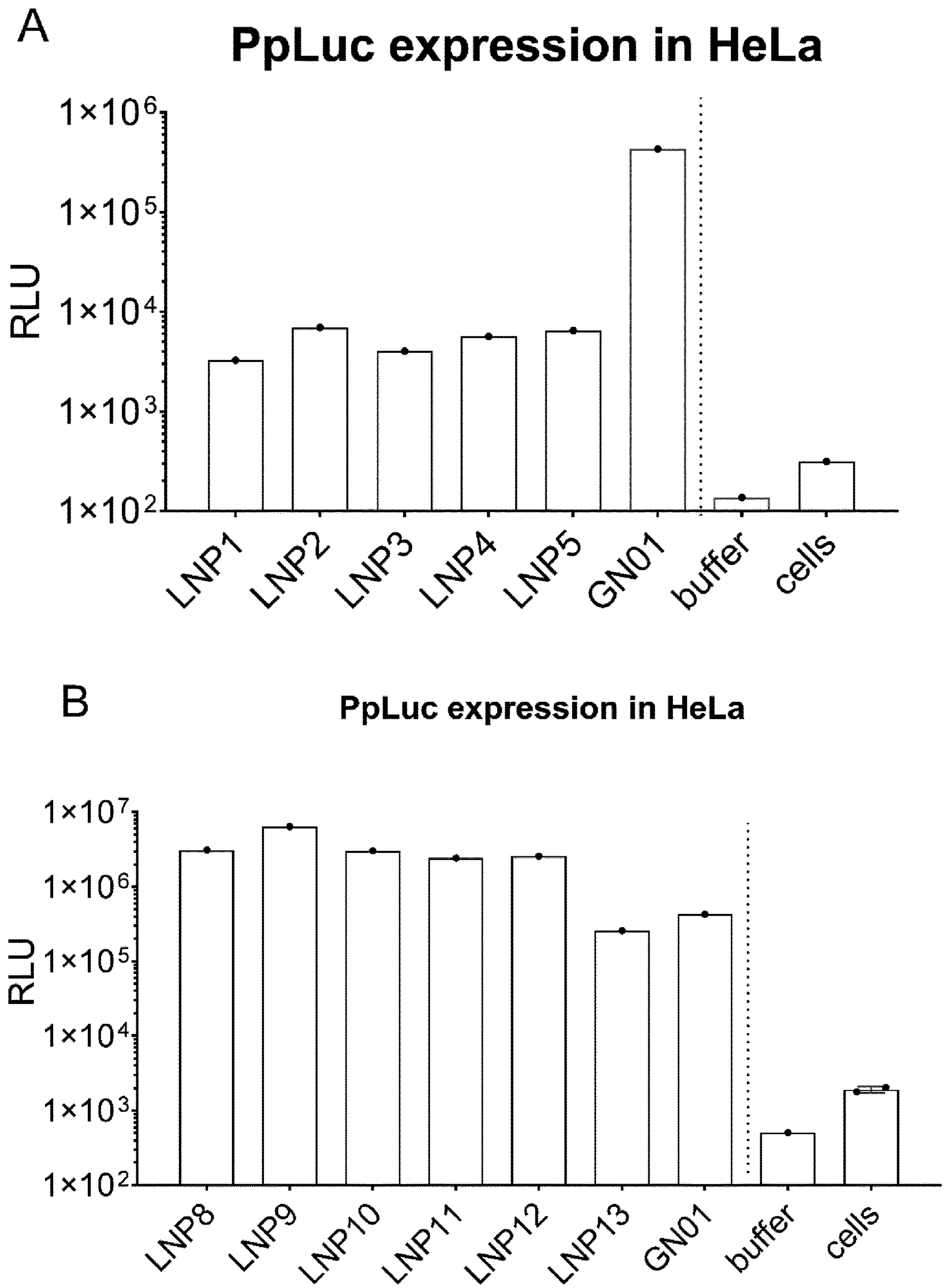
FIG. 5 (PpLuc expression in HeLa and HepG2—HEXA lipids 1 to 7)—HEXA lipids 1 to 7 were formulated as LNPs using composition 1 or 2 and transfected with PpLuc mRNA into HeLa cells or HepG2 cells. Relative light unit (RLU) was measured 24 h post transfection. A Transfection of LNP1 to LNP7 (composition 1-DSPC) and GN01 into HeLa cells. B Transfection of LNP8 to LNP14 (composition 2—DPhyPE) and GN01 into HeLa cells. C Transfection of LNP1 to LNP7 (composition 1-DSPC) and GN01 into HepG2 cells. D Transfection of LNP8 to LNP14 (composition 2—DPhyPE) and GN01 into HepG2 cells—i.e. shows that mRNA formulated with the lipids and compositions showed very good and even superior PpLuc expression in HeLa and in mice (full details can be seen in Example 3.1.1).

To analyse the expression efficiency of HEXA Lipids, different lipid compositions as described were formulated with PpLuc mRNA (sequence see Example 1.1, in acetate 50 mM pH 4). HeLa or HepG2 cells were seeded in a 12 well format with 100.000 cells/well and incubated overnight before transfection with LNPs and PpLuc 0,125 μg/ml (125 ng per well). PpLuc reading was performed 24h after transfection (see FIG. 5). Formulation details as described in Table Ex-3.

Results:

In HeLa cells, LNP1 to LNP6 demonstrated inferior PpLuc expression when compared to GN01. However, Accordingly, the use of DPhyPE again gave a clear advantage over DSPC which to date is used in the art as standard neutral lipid in nearly all state of the art LNP-compositions.

Example 3.2: In Vitro Analysis of HEAD Lipids

Example 3.2.1: PpLuc Expression of HEAD Lipids in HeLa and HepG2 Using HEAD Lipids This example shows the transfection efficiency of various LNP compositions according to the invention comprising HEAD lipids and PpLuc mRNA compared to positive and negative controls in HeLa cells.

Figure 6:
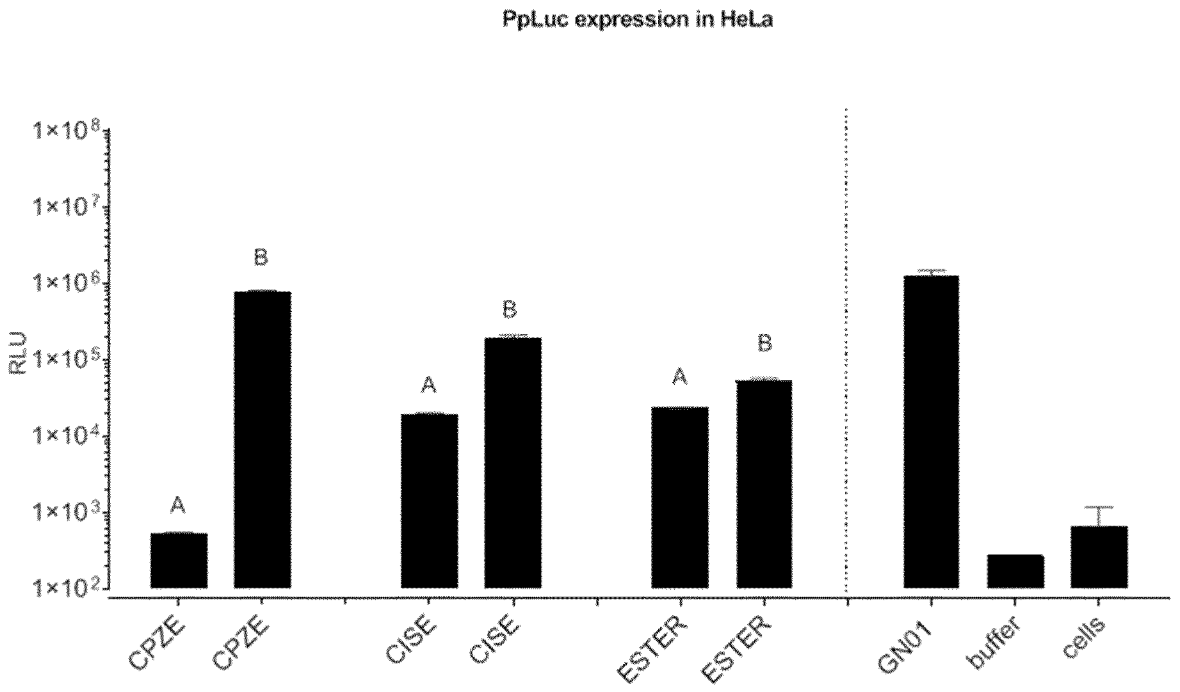
FIG. 6 (PpLuc expression in HeLa of HEAD lipids)—shows that compositions comprising DPhyPE again gave a clear advantage over DSPC which to date is used in the art as standard neutral lipid in nearly all state of the art LNP-compositions, in accordance with Example 3.1.1 and FIG. 5—HEAD lipids CISE, CPZE and ESTER were formulated as LNPs using composition A or B and transfected with PpLuc mRNA into HeLa cells. Relative light unit (RLU) was measured 24 h post transfection (full details can be seen in Example 3.2.1).

To analyse the expression efficiency of HEAD lipids, the different lipid compositions were formulated with PpLuc mRNA (sequence see Example 1.1, in acetate 50 mM pH 4). HeLa cells were seeded in a 12 well format with 100.000 cells/well and incubated overnight before transfection with LNPs and PpLuc 0,125 μg/mL (125 ng per well). PpLuc reading was performed 24h after transfection (see FIG. 6).

Results:

Hereby, composition B showed a higher expression rate for all three HEAD lipids. GN01 and CPZP with composition B showed the highest expression rate ($1\times10^6$ RLU). Accordingly, the use of DPhyPE again gave a clear advantage over DSPC which to date is used in the art as standard neutral lipid in nearly all state of the art LNP-compositions.

Example 4: In Vivo and In Vitro Analyses of HEXA Lipids and HEAD Lipids

The present Example provides details to In vivo and in vitro analyses of compositions and lipids of the invention.

Example 4.1: In Vivo and In Vitro Analysis of HEXA Lipids

Example 4.1.1: hEPO Expression in HeLa Cells and Mice Using HEXA Lipids Incl. GN01 LNPs To determine in vitro and in vivo expression, transfection and expression efficiency of various LNP compositions according to the invention comprising HEXA and HEAD lipids, different mRNA as described below was compared to certain controls as detailed below.

For in vivo analysis, human Erythropoietin encoding mRNA (hEpo) was used (SEQ ID NO:28). hEpo mRNA was enzymatically capped according to standard proceedings; a methyl-group was added in a second step to obtain CAP1, and mRNA was further enzymatically adenylated using commercially available polyadenylation kits and corresponding protocols known in the art.

LNPs were prepared as described above and as indicated in Table Ex 10. As control, LNPs comprising hEpo mRNA were transfected into HeLa cells. For in vitro transfection analysis, HeLa cells were seeded in a 12 well format with 100.000 cells/well and incubated overnight before transfection with formulated LNPs (0,125 μg/ml final concentration per well). hEpo ELISA was performed 24h after transfection.

TABLE EX-10

Overview of HEXA lipid formulations comprising HEXA lipids C1 to C5 and GN01 for analysis of hEpo expression in HeLa and mice

| LNP designation | cationic lipid/compound No. (see Table Ex-1) | Composition No. (see Table Ex-2) |
|---|---|---|
| LNP8 | C1 | 2 |
| LNP9 | C2 | 2 |
| LNP10 | C3 | 2 |
| LNP11 | C4 | 2 |
| LNP12 | C5 | 2 |
| GN01 | COATSOME ® SS-EC (SS-33/4PE-15) | GN01 |

Figure 7:
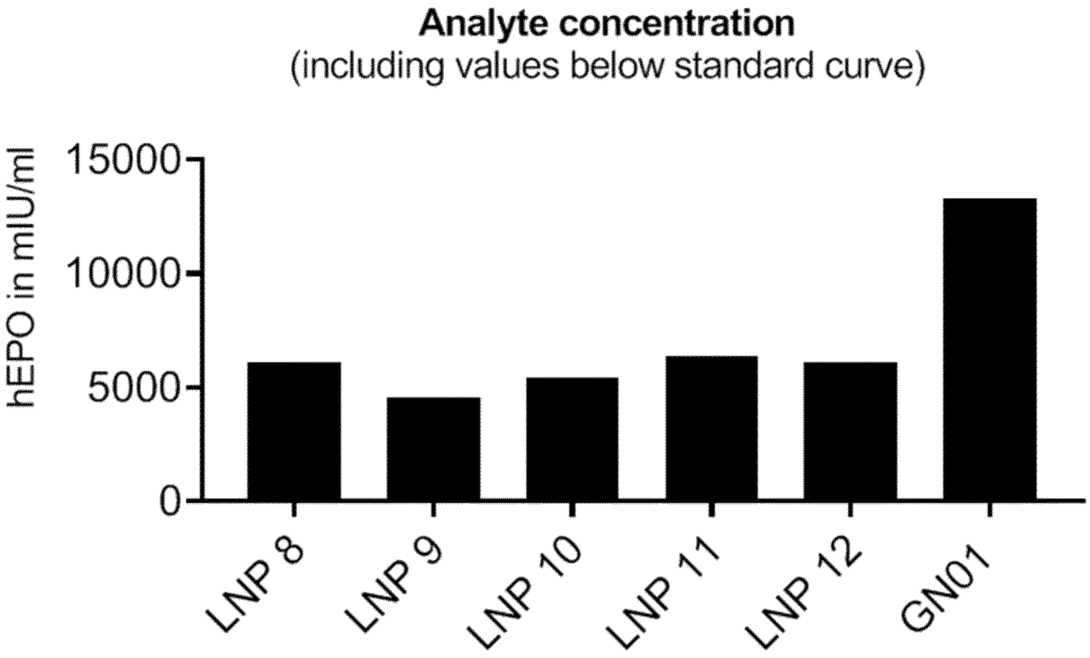
FIG. 7 (hEPO expression of HEXA lipids 1 to 7 in HeLa cells)—shows good hEpo expression in vitro in HeLa cells after treatment—GN01 and HEXA lipids prepared as LNPs using composition2—DPhyPE were formulated with mRNA coding for hEPO and transfected in HeLa cells. hEpo ELISA was performed 24 h after transfection and shows transfection efficiency (full details can be seen in Example 4.1.1).

Overall, all formulations showed a stable hEpo expression in HeLa cells (FIG. 7).

For in vivo analysis, six to eight weeks old Balb/C mice (5 mice per group) were injected with 0.5 mg/kg LNP formulated hEpo (see Table Ex-10). EDTA plasma sampling was performed 6h and 24h after injection.

Figure 8:
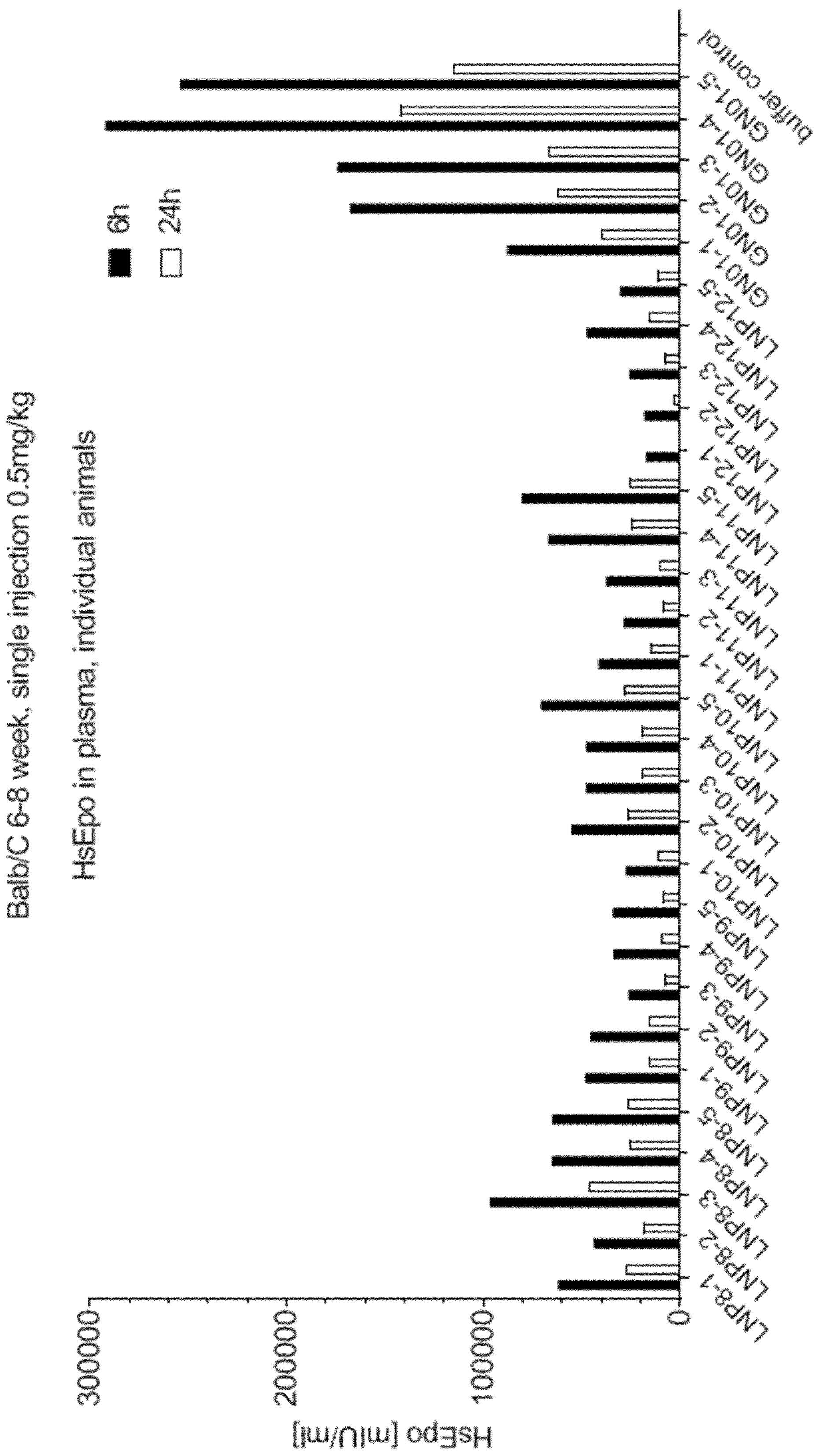
FIG. 8 (hEPO expression of HEXA lipids 1 to 7 in mice)—shows that also in vivo analysis of compositions of the invention gave distinct high hEpo expression at 6h and 24h post injection—GN01 and HEXA lipids prepared as LNPs using composition 2—DPhyPE were formulated with mRNA coding for hEPO and injected with 0.5 mg/kg in Balb/C mice (5 per group). HsEpo level was measured in 6 h and 24 h post injection in plasma using ELISA. (full details can be seen in Example 4.1.1).

Results:

In vivo analysis of LNP8 to LNP12 (HEXA lipids C1 to C5) and GN01 confirmed the results of the in vitro experiment showing a distinct high hEpo expression at 6h and 24h post injection (FIG. 8).

Figure 10:
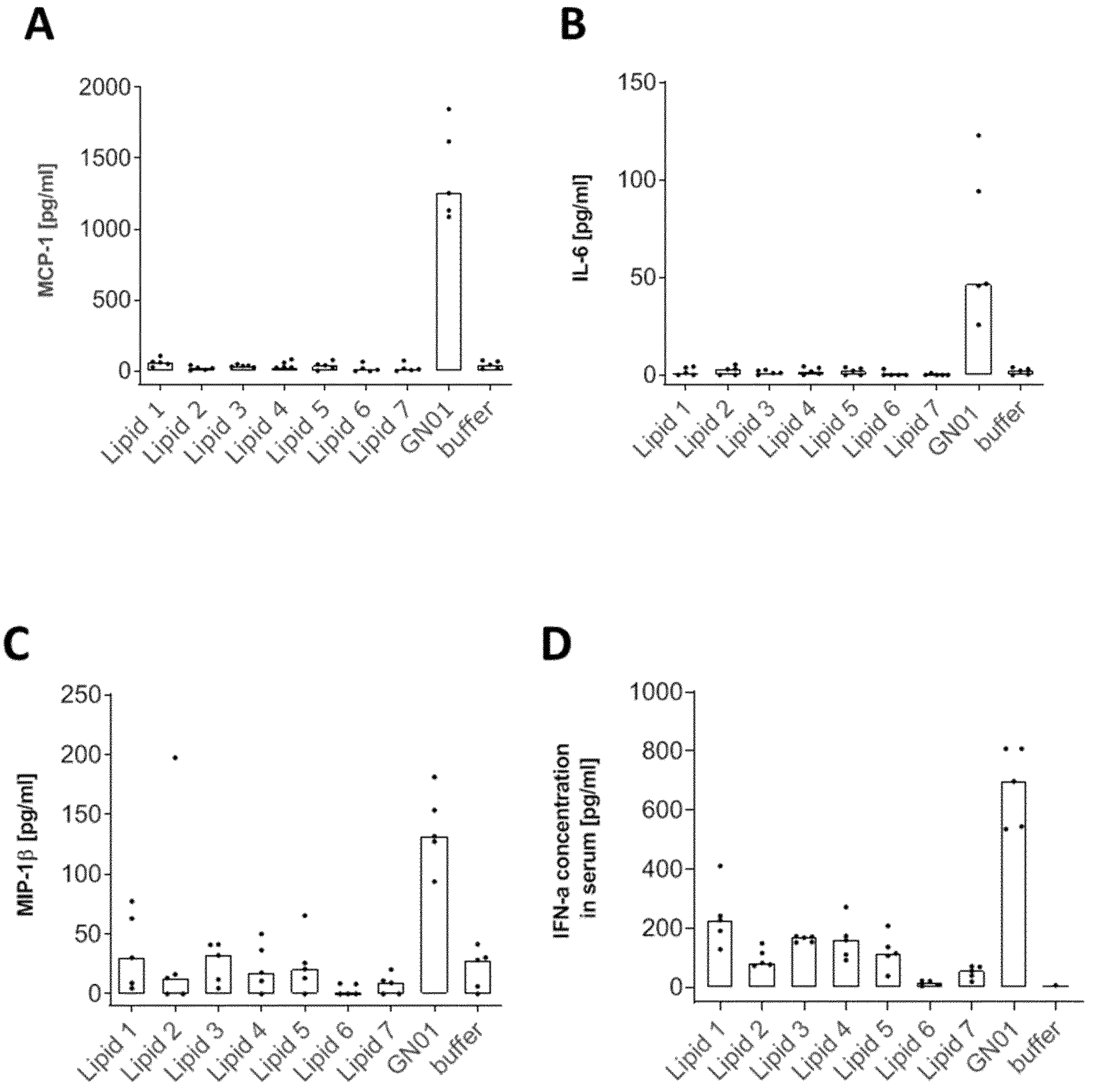
FIG. 10 (Tolerability of HEXA lipids—Immunostimulation)—shows that none of the lipid compounds tested induced significantly elevated cytokine levels—for analysis of the immunostimulatory properties of HEXA lipids a CBA assay with serum samples drawn from mice 6 h after injection of HEXA lipid-containing LNPs and GN01 LNPs into Balb/C mice was performed. Levels of IFN-α in the serum were determined by ELISA. A MCP-1 of HEXA lipids 1 to 7 and GN01. B IL-6 of HEXA lipids 1 to 7 and GN01. C MP1-B of HEXA lipids 1 to 7 and GN01. D INF-α of HEXA lipids 1 to 7 and GN01. E MCP-1 of HEXA lipids 8, 9 and Lipid 2 m/m ratios (m/m 20, m/m 30, m/m 40) and GN01. F IL-6 of HEXA lipids 8, 9 and Lipid 2 m/m ratios (m/m 20, m/m 30, m/m 40) and GN01. G MP1-B of HEXA lipids 8, 9 and Lipid 2 m/m ratios (m/m 20, m/m 30, m/m 40) and GN01. H INF-α of HEXA lipids 8, 9 and Lipid 2 m/m ratios (m/m 20, m/m 30, m/m 40) and GN01 (full details can be seen in Example 4.1.2).
Figure 10:
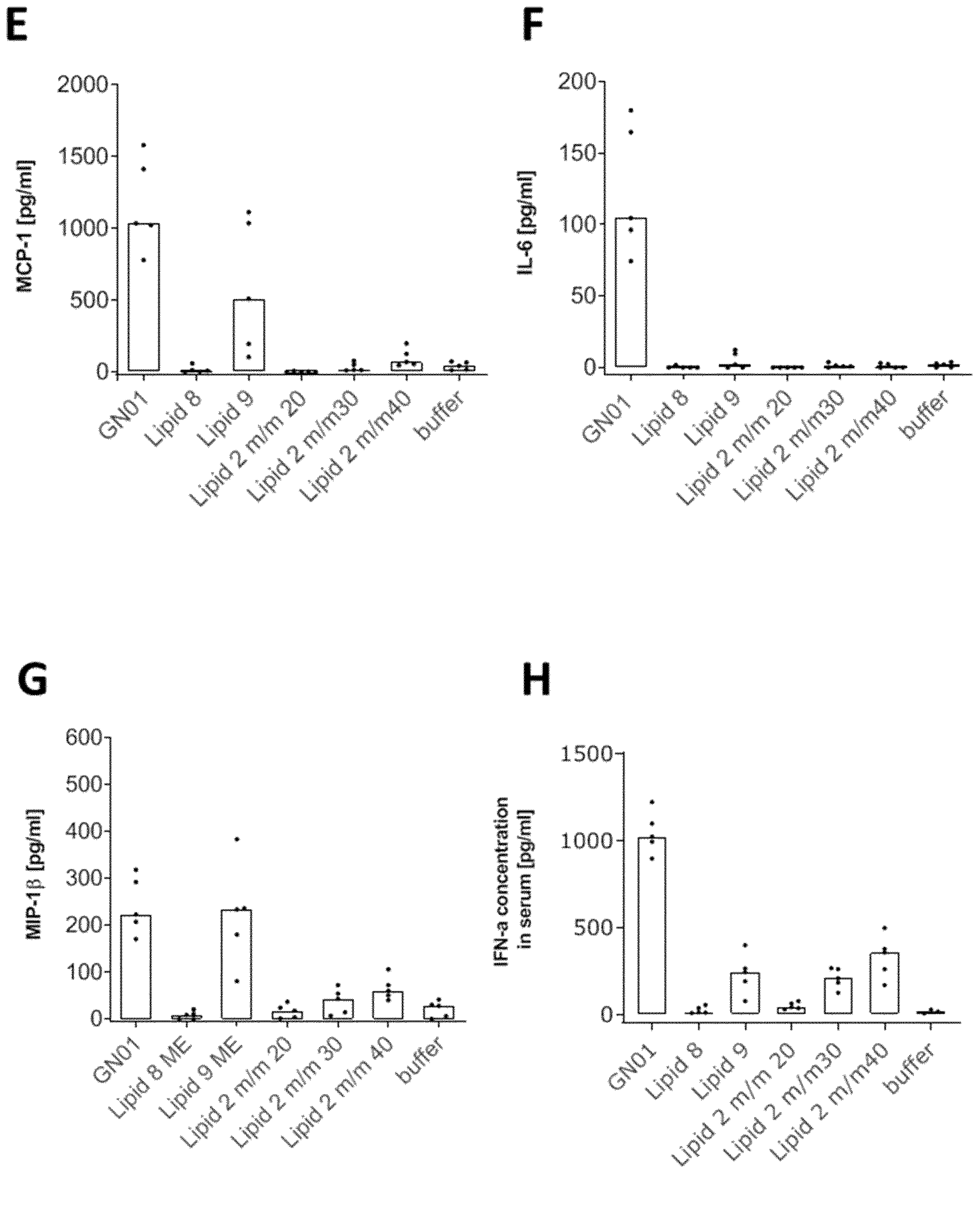

Example 4.1.2: Tolerability of HEXA Lipids—ALT/AST and Cytokine Measurements The tolerability of HEXA lipid compounds C1 to C9 and SS-EC (see Table Ex-1) was further analyzed by measuring activity of aminotransferases ALT (alanine aminotransferase) and AST (aspartate aminotransferase). For this, HEXA lipid- and SS-EC-containing LNPs (0.5 mg/kg) were injected intravenously in Balb/C and analyzed by measuring ALT and AST activity 24h post injection (FIG. 9) according to standard proceedings. For lipid compound C2, also the tolerability of different m/m ratios was also measured (FIG. 10).

Results 1:

None of the animals showed significant elevated AST and ALT liver enzyme activity when compared to the buffer control (FIG. 9). Further, body weight loss of the treated animals was less than 5% (data not shown).

For analysis of the immunostimulatory properties of HEXA lipids C1 to C9 at an early time point, an EDTA plasma cytokine analysis was performed 6h post-injection. Therefore, a CBA assay with serum samples drawn from mice 6h after treatment with HEXA lipids revealed the level of following cytokines/chemokines: MCP-1, MIP-1, MIP-1, RANTES, IL-12β70, IL-6, TNF, IL-1p, IFN-γ. Furthermore, the levels of IFN-α in the serum were determined by ELISA. Analysis of mouse IFN-α in serum was performed according to the manufacturer's instructions with 50 μl serum in reagent diluent (1:20) (FIG. 10 A-D). The immunostimulatory properties of different m/m ratios measured for lipid compound 2 was also measured (FIG. 10 E-H).

Results 2:

As apparent from the indicated figures, none of the lipid compounds tested induced significantly elevated cytokine levels.

Example 4.2: In Vivo Analysis of HEXA and HEAD Lipids

Example 4.2.1: Prophylactic and Therapeutic Vaccine Approach—Tumor Antigen Trp2 in Mice Using HEXA Lipids, HEAD Lipids, GN01 and GNO2 LNPs For testing the prophylactic and therapeutic capacities of HEXA and HEAD lipid-comprising LNPs, incl. GN01 and GNO2 LNPs, in vivo analyses were performed. For this, trp2 mRNA (encoding tumour antigen Trp2) was produced according to the procedures described above, yielding a trp2 mRNA comprising CleanCap AG, a 32L4-5'-UTR ribosomal 5TOP UTR (32L4); 64x adenosine at the 3-terminal end (polyA-tail); 5 nucleotides, 30 x cytosine at the 3-terminal end (poly-C-tail) and 5 additional nucleotides (SEQ ID NO:29).

Composition and formulation procedures for LNPs are described above f.e. under Example 2.1.1, Example 2.2.2, Table Ex-2, and Table Ex-6.

For immunization, 7-8 weeks female C57/1BL6 mice (5 mice per group) were injected intradermally (i.d) in the back with formulated mRNA coding for tumor antigen Trp2 as indicated above according to the composition details as shown in Table Ex-11.

TABLE EX-11

Composition and formulation details. Further reference is made to descriptions under Example 2.1.1, Example 2.2.2, Table Ex-2, and Table Ex-6 where designations i.e. GN01, GN02, CISE and mol %-ratios of compositions are described

| Group name in figure | cationic lipid | mRNA Dose [μg] |
|---|---|---|
| GN01 1 μg | SS-EC | 1 |
| GN01 5 μg | SS-EC | 5 |
| GN02 1 μg | HEXA-C5DE-PipSS | 1 |

TABLE EX-11-continued

Composition and formulation details. Further reference is made to descriptions under Example 2.1.1, Example 2.2.2, Table Ex-2, and Table Ex-6 where designations i.e. GN01, GN02, CISE and mol %-ratios of compositions are described

| Group name in figure | cationic lipid | mRNA Dose [µg] |
|---|---|---|
| GN02 5 µg | HEXA-C5DE-PipSS | 5 |
| CISE 1 µg | CISE [HEAD lipid] | 1 |
| CISE 5 µg | CISE [HEAD lipid] | 5 |
| trp2 5 µg | none (unformulated) | 5 |
| Buffer | none | 0 |

Immunization took place at day 0, day 7 and day 14. Blood samples were taken at 14h and blood and 21 days; organ samples were taken 21 days after first vaccination. T-cell response and humoral immune responses were measured using ELISA (results are shown in FIGS. 11A, 11B, 11C and 11D).

Figure 11:
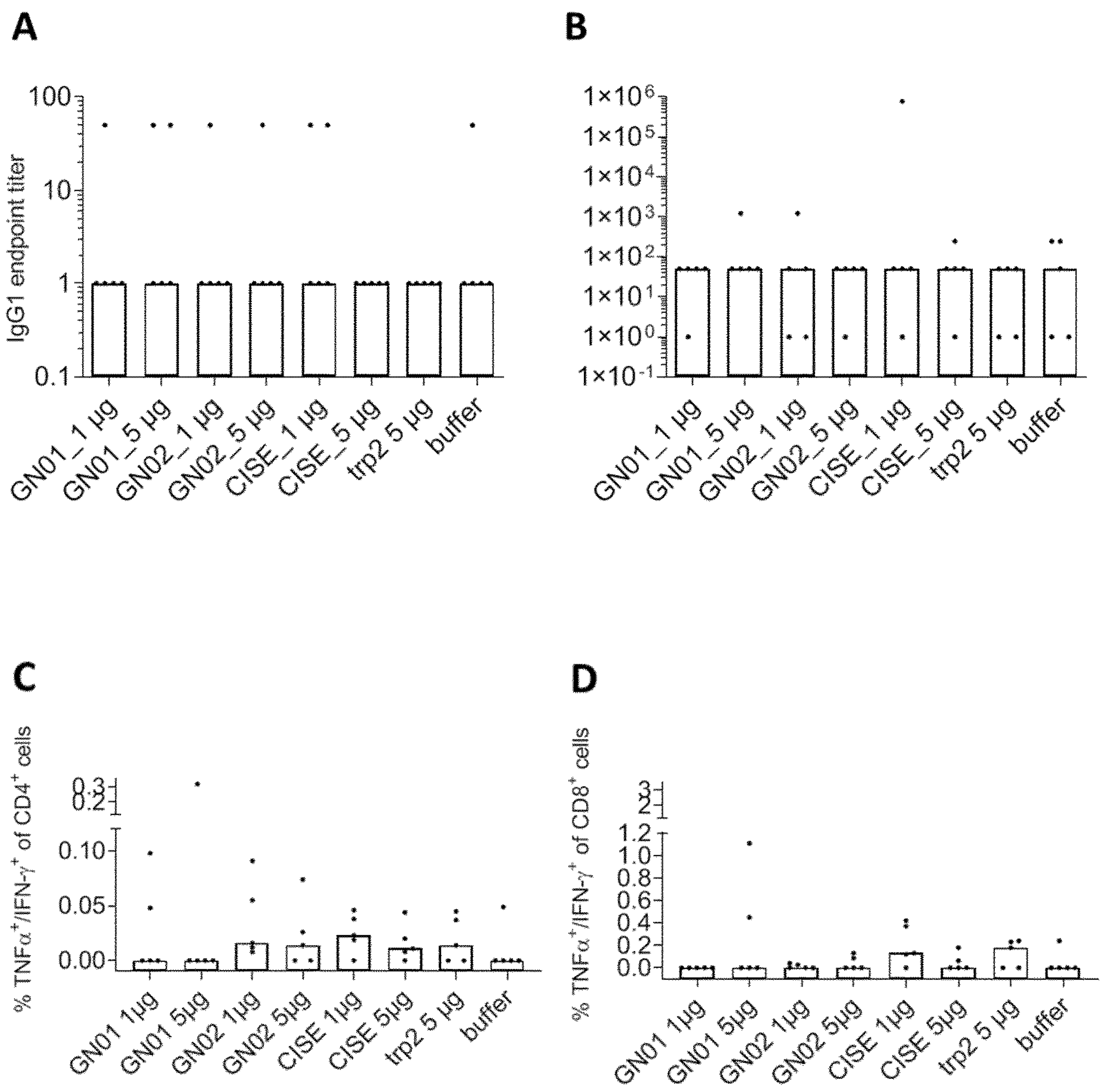
FIG. 11 (LNP for prophylactic and therapeutic vaccine approach—tumor antigen Trp2 i.d. injection)—shows that vaccination (full details can be seen in Example 4.2.1) using GN01, GNO2 and CISE LNPs comprising trp2 mRNA showed stable IgG1 and IgG2 titers (FIGS. 11A and 11B) and that GN01, GNO2 and CISE LNPs showed low T-cell responses (FIGS. 11C and 11D)—i.e. C57/BL6 mice were injected intradermal (i.d) in the back with formulated mRNA coding for tumor antigen Trp2 and GN01, GNO2 or CISE. Immunization took place at day 0, day 7 and day 14. Blood samples were taken at 14 h and blood and organ samples were taken 21 days after first vaccination. T-cell response and humoral immune responses were measured using ELISA. A IgG1 endpoint titer. B IgG2a[b] endpoint titer C % TNFα+/IFNγ+ of CD4+ cells. D % TNFα+/IFNγ+ of CD8+ cells (full details can be seen in Example 4.2.1).

Results:

According to FIGS. 11A and 11B, vaccination using GN01, GNO2 and CISE LNPs comprising trp2 mRNA showed stable IgG1 and IgG2 titers. Furthermore, according to FIGS. 11C and 11D, GN01, GNO2 and CISE LNPs showed low T-cell responses.

Example 4.2.2: Tolerability of HEAD Lipids—ALT/AST and Cytokine Measurements The tolerability of HEAD lipids CISE, CPZE and ESTER (see Table Ex-6) was further analyzed by measuring activity of aminotransferases ALT (alanine aminotransferase) and AST (aspartate aminotransferase). For this, HEAD lipid-containing LNPs and SS-EC-containing LNPs (0.5 mg/kg) were injected intravenously in Balb/C and analyzed by measuring ALT and AST 24h post injection. The tolerability of different m/m ratios was also measured for lipid compound 2.

Results:

None of the animals showed significant elevated AST and ALT when compared to the buffer control (FIG. 12.1). Further, body weight loss of the treated animals was less than 2% (data not shown).

Analogously to the cytokine measurement for HEXA lipids as described herein above, cytokine analyses for HEAD lipids were performed. As apparent, none of the lipid compounds tested induced significantly elevated cytokine levels (FIG. 12.2A-D).

Example 5: Stability Data of Compositions/LNPs of the Invention (GN01)

To analyse the stability of compositions/LNPs of the invention, different properties and biological activity were measured as described below upon f.e. storage over a prolonged period of time.

Example 5.1: Analysis of Integrity and Biophysical Properties of GN01 Formulated hEPO mRNA GN01 LNPs were formulated with hEPO mRNA as described above in Example 4.1.1 (hEPO expression in HeLa cells and mice using HEXA lipids incl. GN01 LNPs) and stored at 4° C. and −80° C. for 1.5 months and 6 months. For analysis of mRNA comprised within the LNP via gel electrophoresis, LNPs were deformulated/destroyed so that the incorporated mRNA could be displayed on the gel according to routine proceedings known in the art.

Results:

Particle size, polydispersity index (PDI), charge/zeta potential and EE % as well as RNA content have been measured. GN01 LNPs showed stable particle size, zeta potential and EE % values upon 1.5 month and to 6 months storage. Integrity of mRNA was preserved as shown by agarose gel electrophoresis up to 6 months. Activity of mRNA in LNP after storage at −80° C. for 1.5 months was tested and compared to freshly prepared LNPs.

Figure 13:
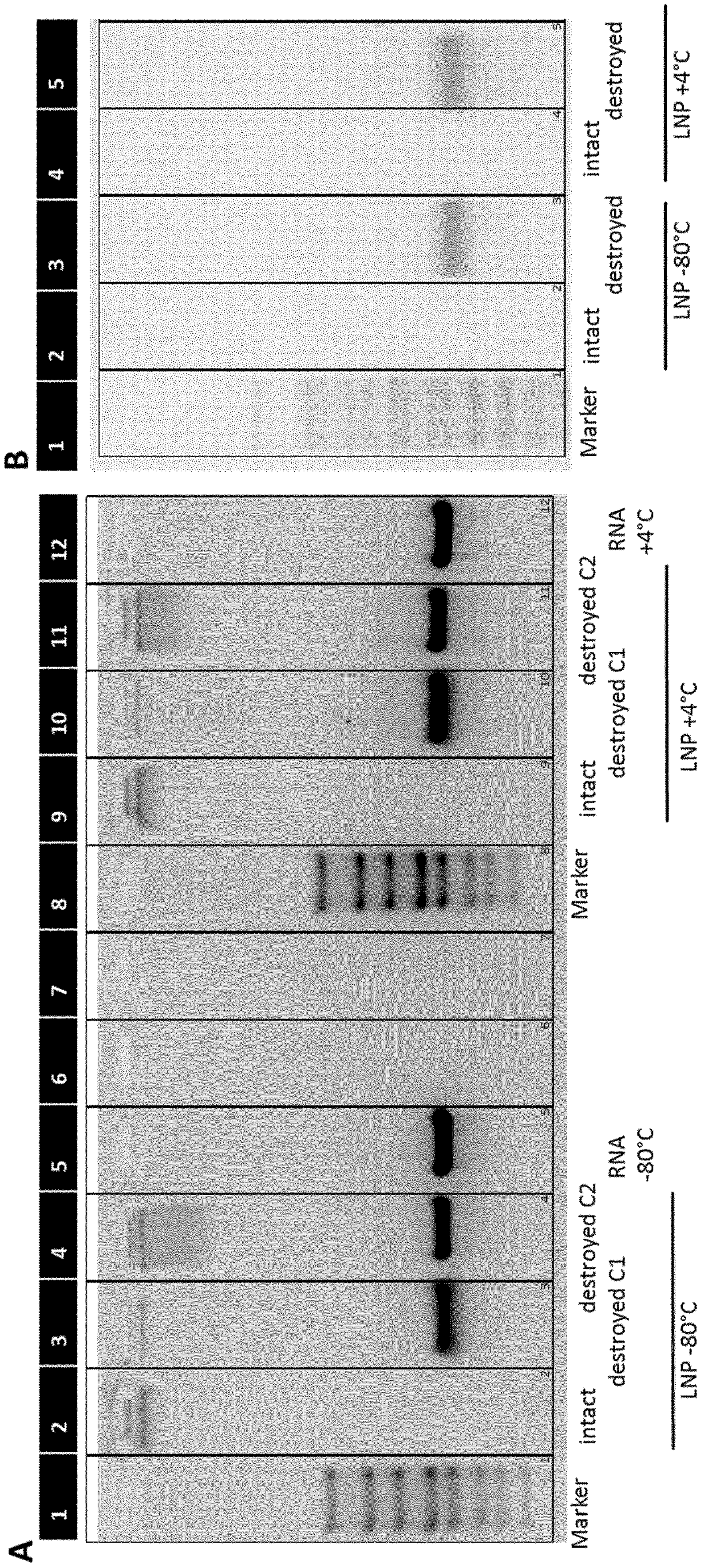
FIG. 13 (stability of inventive LNPs after long-time storage)—shows the analysis of integrity and biophysical properties of GN01 LNPs which were stored at 4° C. and −80° C. for a prolonged time period. As apparent, particles and RNA was stable and no significant differences were observed—i.e. changes in biophysical properties and mRNA integrity of LNPs could be shown on agarose gels after gel electrophoresis. GN01 LNPs were formulated with hEPO mRNA were stored at 4° C. and −80° C. for 1.5 or 6 months. For analysis on gel electrophoresis, the LNPs were destroyed so the incorporated mRNA could be displayed on the gel. After 1.5 months (A), 6 months (B)—decomposition condition 1 (heparin and triton combination was used to decompose LNPs; C1 in figure), decomposition condition 2 (heparin and Pluronic® combination and heating to 45° C. for 15 min was used to decompose LNPs; C2 in figure) (full details can be seen in Example 5.1).

Results are shown for storage at 4° C. and −80° C. for 1.5 months (FIG. 13A) and 6 months (FIG. 13B). For decomposition of LNPs, two conditions were used: decomposition condition 1 (heparin and triton combination was used to decompose LNPs; C1 in figure) or decomposition condition 2 (heparin and Pluronic® combination and heating to 45° C. for 15 min was used to decompose LNPs; C2 in figure). For analysis of 6 months condition C1 was applied.

Results:

No significant differences were observed (for detailed results see Table Ex-12 and Example 5.2 herein below).

TABLE EX 12

Biophysical properties and GN01 LNP mRNA integrity

| Months | Storing temperature | particle size average [nm] | PDI | zeta potential [mV] | EE [%] | RNA content [µg/mL] |
|---|---|---|---|---|---|---|
| 1.5 | −80° C. | 122 | 0.142 | 1.04 | 93 | 174 |
| | 4° C. | 128 | 0.155 | 1.79 | 92 | 169 |
| 6 | −80° C. | 118 | 0.149 | −1.08 | 87 | 175 |
| | 4° C. | 129 | 0.166 | 0.13 | 89 | 180 |

Example 5.2: Biological Activity of GN01 LNPs after −80° C. Storage for Up to 10 Weeks For evaluation of the biological activity after storage of formulated mRNA in GN01 LNPs, said GN01 LNPs were formulated with hEpo mRNA and frozen for 1 week before intravenously injection into Balb/C mice (10 µg mRNA, 5 mice/group). After administration of said LNPs, blood samples were taken and processed for EDTA plasma (6h and 24h after administration). Remaining GN01 LNPs were frozen and stored at −80° C. for up to 10 weeks. After this period the LNPs were injected in a new set of animals.

Results:

After 10 weeks of storage, GN01 LNPs showed similar levels indicating that storage did not impair the biological activity of LNPs (6h and 24h post injection when compared to 1 week of storage; see FIG. 14.1).

In a second evaluation, plasma samples were analysed after one freeze/thaw cycle (1 F/T) compared to plasma samples after 2 F/T cycle; both after 1 week storage at −80° C. A good reproducibility for HsEpo biological activity could be shown for all tested approaches (see FIGS. 14.2A and 14.2B).

Example 6: Effect of Phospholipids on LNP Transfection

To analyse the effect of different phospholipids on LNP transfection, DPhyPE, DSPC, and a 1:1 mixture of DPhyPE+DSPC were formulated with lipid compound No. 1 (see Table Ex-1) and GN01 as indicated in Table Ex-13. PpLuc as described above was used as cargo for LNPs (0,125 µg/ml, 125 ng per well)). The resulting compositions were transfected into HeLa cells. Hereby, 100.000 HeLa cells/well were seeded in a 12 well format.

TABLE EX 13

Effect of phospholipids DPhyPE, DSPC, DPhyPE + DSPC (1:1 mixture) on LNP transfection. Lipid compound No. C1 (see Table Ex-1). N/P ratio for GN01-based LNPs was set to 14 and for the C1-containing LNPs to 17.; Lipid/mRNA mass ratio for all compositions was set to 40 (m/m).

| Name of LNP formulation/ composition No. | Excipients [cationic lipid:steroid:neutral lipid:polymer conjugated lipid] | | | | mol-percentages for excipients [mol %] | | | | pKa |
|---|---|---|---|---|---|---|---|---|---|
| Lipid 1 DPhyPE | C1 | Chol | DPhyPE | DMG-PEG 2000 | 59 | 29.3 | 10 | 1.7 | 5,844 |
| Lipid 1 DSPC | C1 | Chol | DSPC | DMG-PEG 2000 | 59 | 29.3 | 10 | 1.7 | 5,779 |
| Lipid 1 DSPC/DPhyPE | C1 | Chol | DSPC/DPhyPE (1:1 mixture) | DMG-PEG 2000 | 59 | 29.3 | 5/5 | 1.7 | 5,891 |
| GN01 DPhyPE | SS-EC | Chol | DPhyPE | DMG-PEG 2000 | 59 | 29.3 | 10 | 1.7 | 6,265 |
| GN01 DSPC | SS-EC | Chol | DSPC | DMG-PEG 2000 | 59 | 29.3 | 10 | 1.7 | not measured |
| GN01 DSPC/DPhyPE | SS-EC | Chol | DSPC/DPhyPE (1:1 mixture) | DMG-PEG 2000 | 59 | 29.3 | 5/5 | 1.7 | not measured |

PpLuc activity was measured after 24h according to standard proceedings as described before. The results are shown in FIG. 15.1A. The influence of the neutral phospholipid on the pKa of LNPs was measured according to standard proceedings with fluorescent dye 2-β-toluidinylnaphthalene-6-sulphonate (TNS). The protonation profile/pKa of HEXA lipids compounds is shown in FIG. 15.1B or respectively pKa in Table Ex-13.

Results:

The incorporation of DPhyPE, or the 1:1 combination of DPhyPE and DSPC showed a higher expression than for neutral lipid DSPC for both cationic lipid C1 and GN01. As shown herein above, the inventors surprisingly found that fusogenic phospholipids performed much better when compared to DSPC; DSPC being is a phospholipid which is used in the majority of lipid nanoparticles in the art. Furthermore, the great effect of the phospholipid on pKa was shown (Table Ex-13).

Example 7: Effect of Polymer Conjugated Lipid Component

To analyse the effect PEG components and their alkyl tails on LNP transfection, Ceramide 8 PEG (i.e. comprising a $C_8$ tail; Cer8-PEG; comprising N-octanoyl-D-erythro-sphingosine) and $C_{14}$-DMG-PEG (i.e. comprising a $C_{14}$ tail, DMG-PEG 2000) in different amounts as well as their combination (1% Cer8 and 0.7% $C_{14}$-DMG-PEG) were formulated with SS-EC, Cholesterol and DPhyPE (basically with the above described GN01 formulation, while varying the polymer conjugated lipid excipient) and consequently transfected into HepG2 cells; compositions were as indicated in Table Ex-14. N/P ratio for all compositions was set to 14; Lipid/mRNA mass ratio for all compositions was set to 40.

TABLE EX 14

Variations on the PEG component (basis: GN01 formulation); LNP prepared with Cer8 (Ceramide 8 PEG), $C_{14}$-DMG-PEG ($C_{14}$ in Table Ex-14) and mixtures.

| Designation of LNP formulation in Figure of the working example | Excipients [cationic lipid:steroid:neutral lipid:polymer conjugated lipid] | | | | mol-percentages for excipients [mol %] | | | |
|---|---|---|---|---|---|---|---|---|
| 1.7% Cer8 | SS-EC | Chol | DPhyPE | Cer8 PEG | 59 | 29.3 | 10 | 1.7 |
| 1.7% $C_{14}$ | SS-EC | Chol | DPhyPE | $C_{14}$-DMG-PEG | 59 | 29.3 | 10 | 1.7 |
| 1% Cer8 + 0.7% $C_{14}$ | SS-EC | Chol | DPhyPE | Cer8/$C_{14}$-DMG-PEG | 59 | 29.3 | 10 | 1/0.7 |
| 5% Cer8 | SS-EC | Chol | DPhyPE | Cer8 PEG | 59 | 26 | 10 | 5 |

For this, 10.000 HepG2 cells/well were seeded in a 96 well format. PpLuc mRNA (0,125 μg/ml; 25 ng per well) as described above, was formulated in LNPs and incubated with HepG2 cells 1h or 4h in OptiMEM or complete medium.

PpLuc activity for HepG2 cells was measured after 1h or 4h (results are shown in FIG. 15.2).

Results:

As apparent, the inventors of the present invention surprisingly found that compositions comprising polymer conjugated lipids with shorter alkyl chains (f.e. Cer8) were more efficient than compositions comprising polymer conjugated lipids comprising longer alkyl chains (f.e. $C_{14}$-DMG-PEG). Use of 5% Cer8 polymer conjugated lipid surprisingly even enhanced PpLuc activity.

Example 8: Anti-Rabies Monoclonal Antibody Expression Formulated in GN01 LNP after Single i.v. Injection To further analyze the expression efficiency of mRNA formulated in GN01 LNP, NIH swiss albino (n=6) mice were injected with mRNA (1 mg/kg) encoding an anti-rabies monoclonal antibody (mAb; S057, Thran et al., EMBO Mol Med (2017)9:1434-1447). Anti-rabies mAb mRNA comprised a 5'-UTR from HSD17B4, a 3'-UTR from PSMB3, 64× adenosine at the 3-terminal end (polyA-tail); 5 nucleotides, 30x cytosine at the 3-terminal end (poly-C-tail) and 5 additional nucleotides. The mRNA was further enzymatically capped using ScriptCap™ m7G Capping System (CellScript, Madison,WI., USA) according to the manufacturer's instructions and enzymatically polyadenylated using a commercial polyadenylation kit (SEQ ID NO:30=heavy chain, SEQ ID NO:31=light chain).

Formulation of mRNA into GN01 LNPs was performed as described above.

Mice were injected intravenously (i.v.) with 20 μg LNP-formulated anti-rabies mAb encoding mRNA and bled at 6h and 24h. Analysis of antibody titer based on 1:5000 dilution was performed using an IgG serum ELISA (results are shown in FIG. 16).

Figure 16:
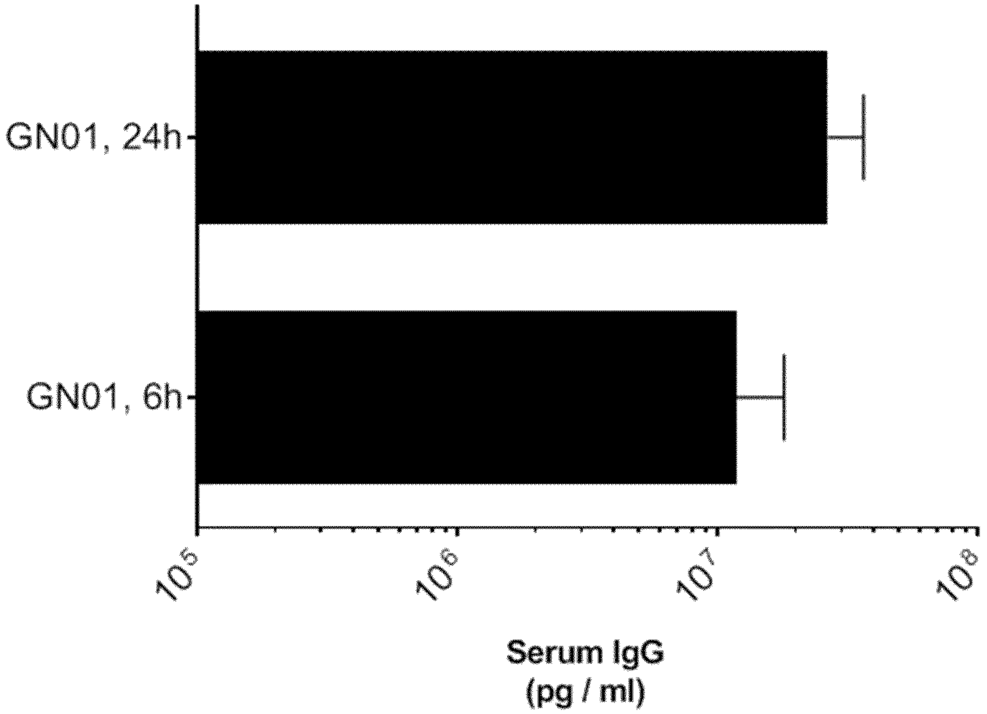
FIG. 16 (Anti-Rabies mAb expression GN01 after single i.v.)—shows expression of an anti-rabies monoclonal antibody formulated in GN01 LNP after single i.v. injection—as apparent, a very strong anti-rabies mAb expression could be detected following i.v. injection after 6h and 24h (full details can be seen in Example 8).

Results:

As apparent from FIG. 16, a very strong anti-rabies mAb expression could be detected following i.v. injection after 6h and 24h.

Example 9: GN01—and GNO2-Formulated LNPs for RABV-G Vaccination Using Intramuscular Administration To analyse the immunogenicity of GN01 and GNO2-formulated LNPs, RABV-G (or RAV-G, Rabies Virus Glycoprotein) mRNA was produced according to the procedures described above, yielding a RABV-G mRNA comprising mCap, a muag-3'-UTR; 64x adenosine at the 3-terminal end (polyA-tail); 5 nucleotides, 30x cytosine at the 3-terminal end (polyC-tail) and 5 additional nucleotides (SEQ ID NO:32):

7 weeks old female Balb/C mice (n=6) were injected intramuscularly at day 0 and day 21 with the formulations according to Table Ex-15 comprising above described RABV-G mRNA. For comparison purposes, KC2-lipid containing LNPs were formulated as well. KC2-control-LNPs comprised 57.1 mol % DLin KC2-DMA as cationic lipid, 7.1 mol % DPPC (1,2-Dipalmitoyl-sn-glycero-3-phosphocholine; Avanti Polar Lipids; Alabaster,AL.), 34.4 mol % cholesterol (Sigma-Aldrich; Merck KGaA, Darmstadt, Germany) and 1.4 mol % PEG-C-DMA.

TABLE EX 15

Composition and formulation details; further reference is made to descriptions under Example 2.1.1, Example 2.2.2, Table Ex-2, and Table Ex-6 where designations i.e. GN01, GN02, and mol %-ratios of compositions are described

| Group | cationic lipid (Formulation designation) | mRNA Dose [μg] | Particle size [nm] | PDI | Zeta potential [mV] | Route/volume | Dosing [day] |
|---|---|---|---|---|---|---|---|
| 1 | DLin KC2-DMA (Control LNP) | 5 | 54 | 0.24 | −22 | i.m./1 × 25 μl | 0, 21 |
| 2 | SS-EC (GN01) | 5 | 147 | 0.19 | 0.9 | i.m./1 × 25 μl | 0, 21 |
| 3 | HEXA-C5DE-PipSS (GN02) | 5 | 162 | 0.14 | 2.46 | i.m./1 × 25 μl | 0, 21 |
| PBS | / | / | / | / | / | i.m./1 × 25 μl | 0, 21 |

For determining the levels of antibody against the rabies virus in serum, a classical virus neutralization test was performed (Fluorescent Antibody Virus Neutralization (FAVN) assay).

Accordingly, 35 days after the first mRNA administration, mice were sacrificed and blood and organ samples (liver) were collected for further analysis, i.e. for Virus neutralizing antibodies (VNA) analysis via FAVN assay. For said immunogenicity assays, the VNT was measured as described before, i.e. anti-rabies virus neutralizing titers (VNTs) in serum were analyzed by the Eurovir® Hygiene-Labor GmbH, Germany, using the FAVN assay and the Standard Challenge Virus CVS—11 according to WHO protocol.

Furthermore, liver samples were taken for analysis of T cell response (CD4 and CD8), i.e. CD4 T cell immune response (IFNγ/TNFα producing CD4 T cells) and CD8 T cell immune response (IFNγ/TNFα producing CD8 T cells and CD107+IFNγ producing CD8 T cells) was assessed; induction of antigen-specific T cells was determined using intracellular cytokine staining (ICS). Assays were performed as described before; results are shown in FIGS. 17A, 17B and 17C.

Figure 17:
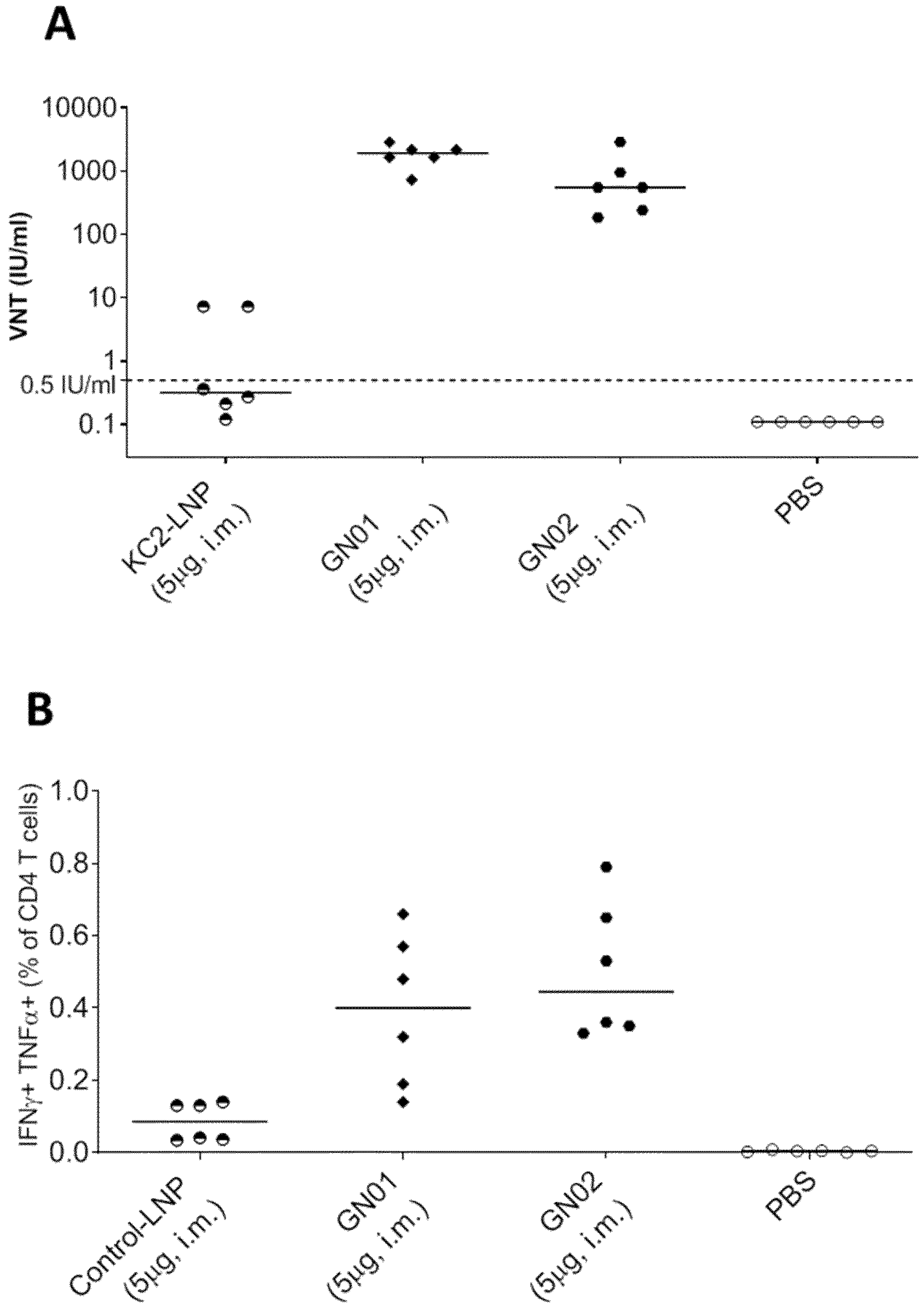
FIG. 17 (Immunogenicity of GN01 and GN02 in vivo-T cell response-VNT analysis)
Figure 17:
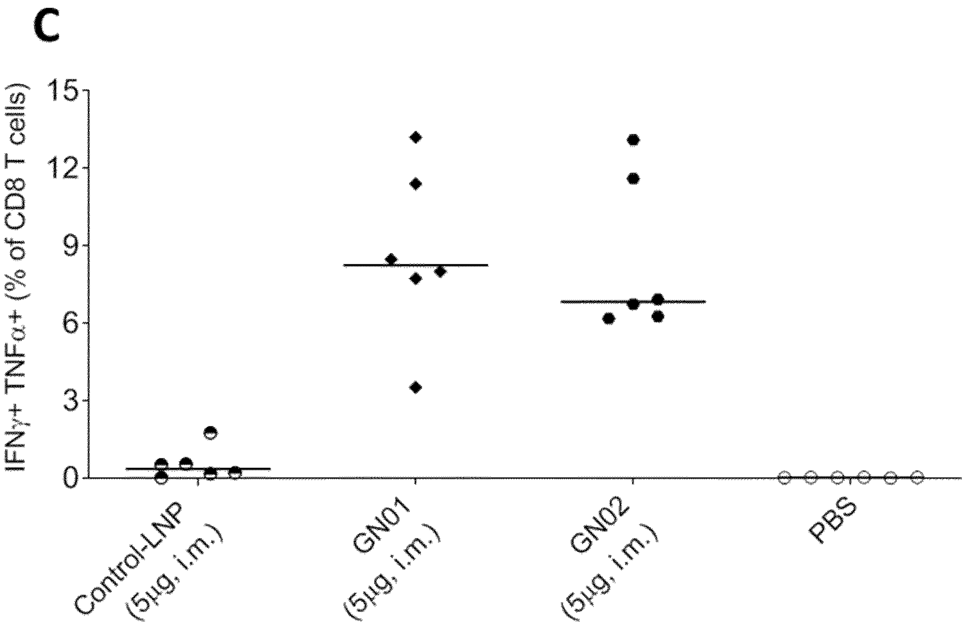

Results:

FIG. 17A shows that already a single i.m. immunization with 5 μg GN01—and GN02-LNP-formulated RABV-G-mRNA induced very robust VNTs well above the protective titer of 0.5 IU/ml in all animals at day 35 after prime vaccination.

FIGS. 17B and 17C show that the inventive GN01 and GN02-LNP-formulated RABV-G mRNA vaccine induced specific cellular responses after vaccination, effects that were not observed in control LNP-vaccinated animals. RABV-G-specific CD4+ T cells (FIG. 17B) were observed for both mRNA-formulations GN01 and GN02. This was also true for RABV-G-specific CD8+ T (FIG. 17C).

Example 10: GN01 for Monotope Approach Used as Vaccine

To further analyse GN01 in the vaccination context, an mRNA coding for the peptide huCTLA4 (1-35), the helper lipids PADRE, the linker $(G4S)_2$, were designed (details shown in Table Ex-16).

TABLE EX 16

| Group [No.] | SEQ ID NO: | Signal Peptide | Linker | Epitope | Helper Epitope | TM Domain |
|---|---|---|---|---|---|---|
| Single-Epitope RNA constructs | | | | | | |
| 1 | 34 | huCTLA4 (1-35) | (G4S)2 | Pmel (14-42; S26P) | PADRE | huCTLA4 (162-223) |
| 2 | 35 | huCTLA4 (1-35) | (G4S)2 | mTRP1 (445-473; A463M) | PADRE | huCTLA4 (162-223) |
| 3 | 36 | huCTLA4 (1-35) | (G4S)2 | mObsl1 (1750-1778; T1764M) | PADRE | huCTLA4 (162-223) |

PpLuc mRNA (SEQ ID NO:33) was used as a control. Corresponding mRNAs were formulated into GN01 LNPs as described above and injected consequently into C57B1I/6 mice (experimental details as shown in Table Ex-17).

TABLE EX-17

Experimental details with reference to groups 1-7 as shown in Table Ex-16, Control group comprising = PpLuc mRNA

| Group [No.] | RNA | RNA dose [µg] | Mice [No.] |
|---|---|---|---|
| 1 | Pmel/gp100 (PADRE) | 5 | 7 |
| 2 | Trp1 (PADRE) | 5 | 7 |
| 3 | Obsl1 (PADRE) | 5 | 7 |
| 4 | PpLuc | 5 | 7 |

For the first vaccination at day 1, C57B1I/6 mice were vaccinated intradermally with 5 µg of GN01 LNP formulated RNA. At day 7, C57B1I/6 mice were vaccinated the second time intradermally with 5 µg of GN01 LNP formulated RNA as well as serum was collected after bleeding. For the third vaccination at day 14, C57B1I/6 mice were vaccinated again. Analysis was done on day 21, wherein splenocytes were isolated from spleen and re-stimulated with all respective epitope peptides (29mers) or restimulated with all peptides in control group (ELISPOT/ICS). The frequency of cytokine secretion for a single cell was measured quantitatively using an enzyme-linked immune absorbent spot (ELISpot) assay. To identify antigen-specific, cytokine-secreting T-cells (CD107a and INFγ and TNF) on a single cell level an ICS (Intracellular Cytokine Staining) assay which is a flow cytometry-based method was used.

Figure 18:
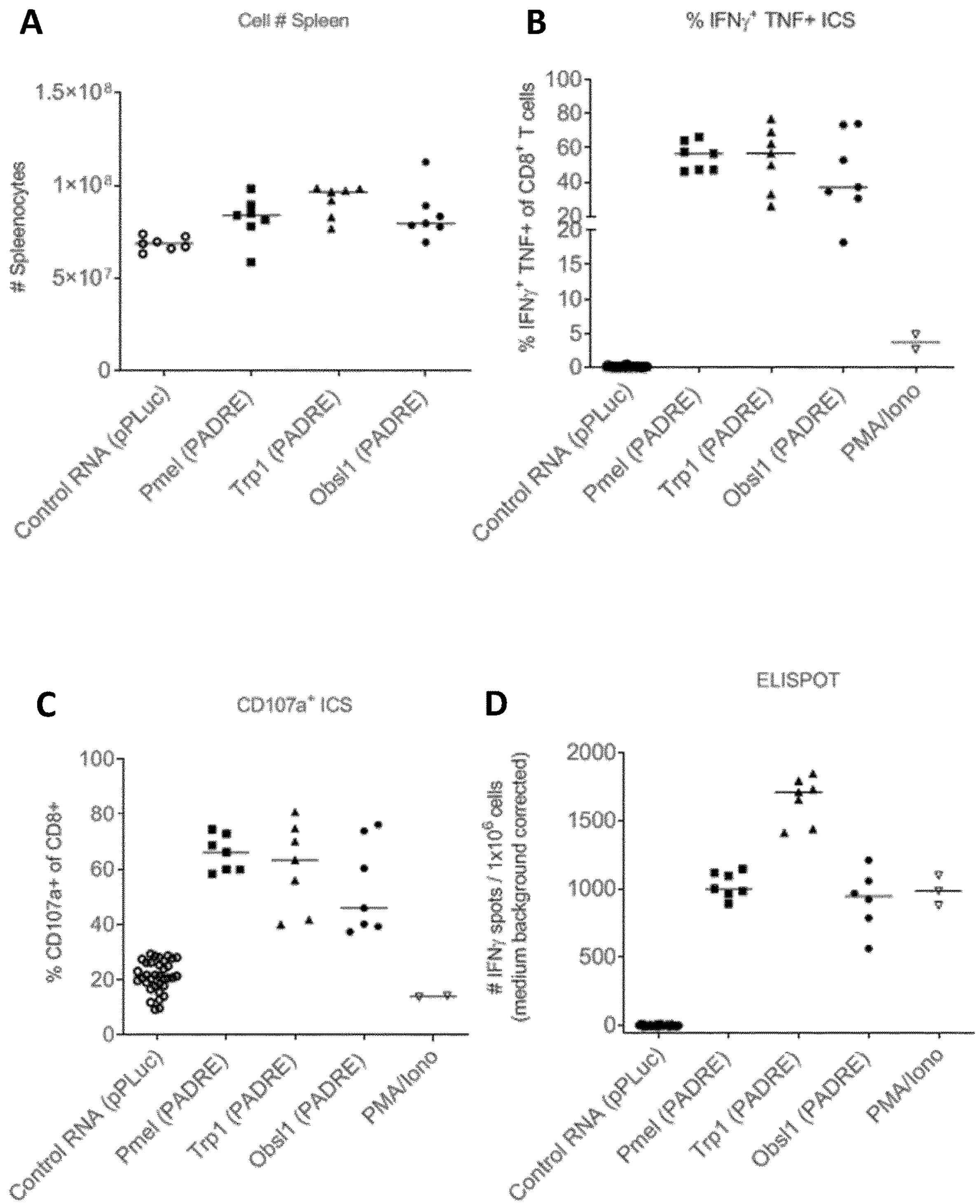
FIG. 18 (GN01 for monotope vaccine approach)—shows that a high reactogenicity of GN01 formulated RNA could be observed; the splenocyte numbers are increased by vaccination with monotope constructs containing PADRE via GN01 LNP (FIG. 18A). The monotope constructs, in combination with GN01 formulation and intradermal application, gave rise to very potent CD8 T cell responses (FIGS. 18B, 18C and 18D) (full details can be seen in Example 10).

Results:

A high reactogenicity of GN01 formulated RNA was observed. The splenocyte numbers are increased by vaccination with monotope constructs containing PADRE via GN01 LNP (see FIG. 18A). The monotope constructs, in combination with GN01 formulation and intradermal application, are in general very potent in inducing CD8 T cell responses against incorporated, strong antigens. A strong CD8 T cell response against Pmel, Trp1 and Obsl1 could be detected (see FIGS. 18B, 18C and 18D).

Example 11: GN01 for Influenza/Flu Vaccination—H3N2

To analyse the immunogenicity of GN01 formulated LNPs, HA (H3N2 A/Hongkong/4801/2014) mRNA was produced according to the procedures described above, yielding a HA mRNA comprising mCap, a muag-3'-UTR; 64× adenosine at the 3-terminal end (polyA-tail); 5 nucleotides, 30× cytosine at the 3-terminal end (polyC-tail); histone stem loop and 5 additional nucleotides (SEQ ID NO:37).

7 weeks old female Balb/C mice (n=5) were injected intramuscularly at day 0 and day 21 (prime/boost) according to the vaccination scheme shown in Table Ex-18. GN01 formulation of mRNA was achieved as described above; a control group received NaCl buffer. Serum samples were taken at day 21 and day 35 for determination of humoral immune responses.

TABLE EX-18

| Group | No. of mice | Treatment | dose | Route | Volume |
|---|---|---|---|---|---|
| Vaccination scheme of Example 11 | | | | | |
| GN01 | 5 | H3N2 (A/Hongkong/4801/2014)-HA | 10 µg | i.m. | 1 × 25 µl |
| buffer | 5 | NaCl buffer | | i.m. | 1 × 25 µl |

For immunogenicity assays, Hemagglutination inhibition (HI) titers were analyzed in the sera 3 weeks after prime and 2 weeks after boost.

Hemagglutination Inhibition Assay:

Hemagglutination inhibition (HI) assays were used for analyzing functional anti-HA antibody titers. Mouse sera were heat inactivated (56° C., 30 min), incubated with kaolin (Carl Roth, Germany) and pre-adsorbed to chicken red blood cells (CRBC; Lohmann Tierzucht, Germany). 50 µl of 2-fold dilutions of pre-treated sera were incubated for 45 min with 4 hemagglutination units (HAU) of inactivated Influenza A/Hongkong/4801/2014 (H3N2) virus (NIBSC, UK) and 50 µl 0.5% CRBC was added. HI titers were determined by the reciprocal of the highest dilution of the serum able to inhibit hemagglutination. Results of the HI assay are shown in FIG. 19.

Figure 19:
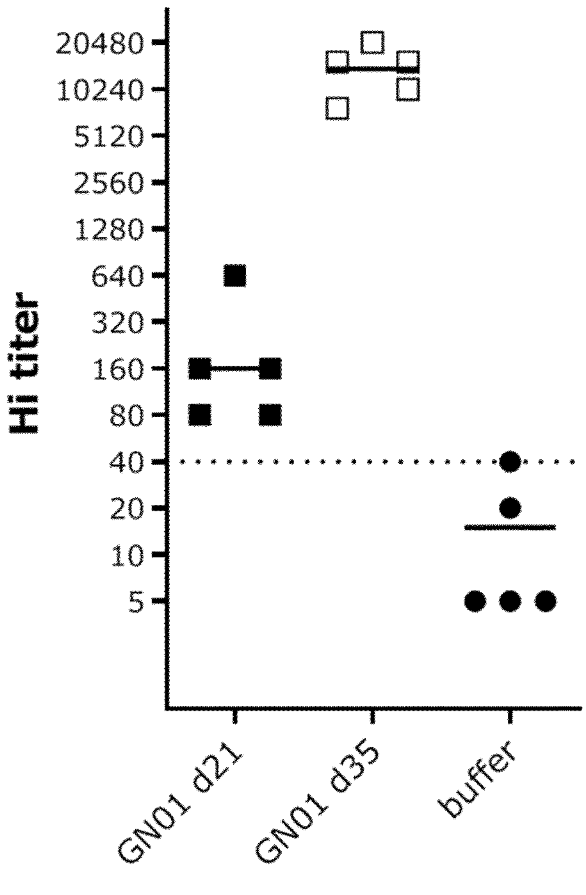
FIG. 19 (GN01 for Influenza/Flu vaccination—$H_3N2$)—shows that already a single i.m. immunization with 10 μg GN01 LNP-formulated HA-mRNA induced protective HI titer well above the protective titer of 40 in all animals at day 21 after prime vaccination and boost with 10 μg GN01 LNP-formulated HA-mRNA induced multiple increase of the humoral immune response (full details can be seen in Example 11).

Results:

FIG. 19 shows that already a single i.m. immunization with 10 µg GN01 LNP-formulated HA-mRNA induced protective HI titer well above the protective titer of 40 in all animals at day 21 after prime vaccination and boost with 10 µg GN01 LNP-formulated HA-mRNA induced multiple increase of the humoral immune response.

Example 12: GN01 for In Vivo Rabies Vaccination of Larger Animals (Calves)

For analysis of GN01 LNPs in the context of a rabies vaccine in larger animals, a study was performed in calves weighting around 100 kg using RABV-G mRNA. To analyse the immunogenicity of GN01 formulated LNPs, RABV-G mRNA was produced according to the procedures described above, yielding a RABV-G mRNA comprising mCap, a muag-3'-UTR; 64× adenosine at the 3-terminal end (polyA-tail); 5 nucleotides, 30× cytosine at the 3-terminal end (polyC-tail); histone stem loop and 5 additional nucleotides (SEQ ID NO:32).

Figure 20:
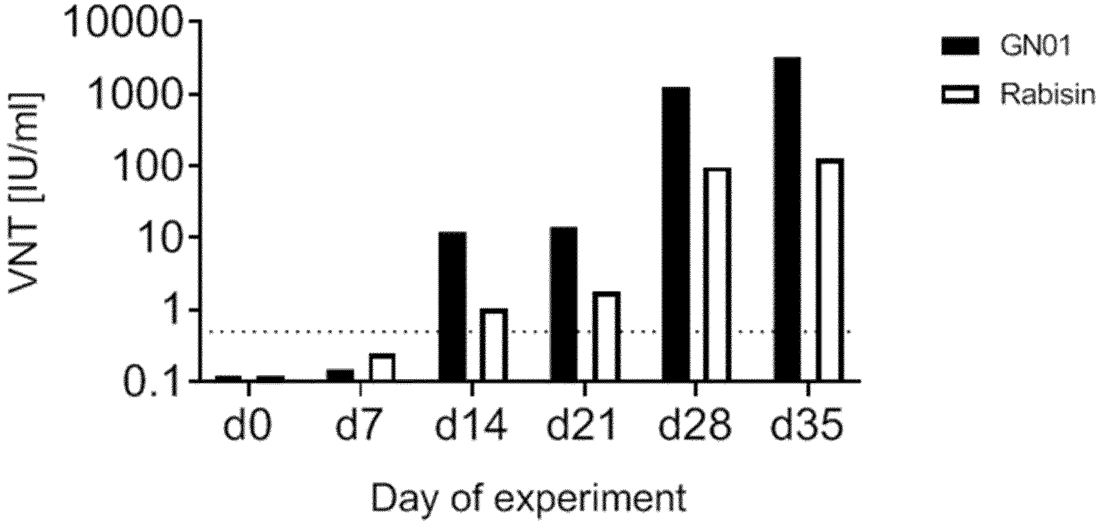
FIG. 20 (GN01 for Rabies tested in calves animal model)—shows that intramuscular vaccination of calves with GN01-formulated RABV-G-encoding mRNA led to a very strong induction of neutralizing antibodies already after prime vaccination after 14 days and already with a dose of only 30 μg mRNA (WHO standard of 0.5 IU/ml is indicated by a dashed line; open bars=Rabisin control, closed bars=GN01 formulated mRNA) (full details can be seen in Example 12).

Resulting mRNA was formulated into GN01 LNPs as described previously and injected intramuscularly into calves at day 0 and day 21 (detailed scheme shown in Table Ex-19). As positive control, Rabisin® (inactivated Rabies virus, Merial GmbH) was used. Blood samples were taken on days 0, 7, 14, 21, 28 and 35. VNT was analysed each time point. Experimental results are shown in FIG. 20.

TABLE EX 19

Vaccination/Treatment scheme and experimental design of Example 12

| Group | Number of animals | Vaccine | Dose/ animal | Dose | Route | Volume | Vaccination |
|---|---|---|---|---|---|---|---|
| 1 | 3 | R7004-GN01 | 30 μg | 0.3 μg/kg | i.m. (needle) | 1 × 1000 μl | Days 0 and 21 |
| 2 | 3 | Positive control: Rabisin ® | 1 ml | 10 μl/kg | i.m. (needle) | 1 × 1000 μl | Days 0 and 21 |

Results:

As proven in FIG. 20, intramuscular vaccination of calves with GN01-formulated RABV-G-encoding mRNA led to a very strong induction of neutralizing antibodies, surprisingly already after prime vaccination after 14 days and already with a dose of only 30 μg mRNA. WHO standard of 0.5 IU/ml is indicated by a dashed line in the graphs. Accordingly, doses of 0.3 μg/kg GN01-formulated RABV-G mRNA induced responses that were significantly higher compared to previous experiments with unformulated mRNA after prime vaccination (data not shown). The VNTs even increased after boost vaccination (FIG. 20); data displays median—tested with Mann-Whitney.

Example 13: GN01 for In Vivo Malaria Vaccination

The present example shows that Malaria mRNA vaccine encoding CSP induce strong humoral and cellular immune responses in mice.

CSP mRNA comprised a 5'-UTR from HSD17B4, a 3'-UTR from PSMB3, 64× adenosine at the 3-terminal end (polyA-tail); 5 nucleotides, 30× cytosine at the 3-terminal end (poly-C-tail), a histone-stem loop, and 5 additional nucleotides. The mRNA was further enzymatically capped using ScriptCap™ m7G Capping System (CellScript, Madison,WI., USA) according to the manufacturer's instructions and enzymatically polyadenylated using a commercial polyadenylation kit, resulting in SEQ ID NO:38.

Resulting mRNA constructs were formulated in GN01 lipid nanoparticles as described before.

The GN01-LNP formulations were applied on days 0 and 21 intramuscularly (i.m.; musculus tibialis) with doses of RNA, formulations, and control groups as shown in Table Ex-20. A negative control group received vaccinations with an irrelevant RNA, formulated in GN01-LNPs. Serum samples were taken at day 21 and day 35 for ELISA.

TABLE EX 20

Vaccination scheme of Example 13

| Group | No. of mice | RNA Treatment | Formulation | mRNA | dose | Route | Volume |
|---|---|---|---|---|---|---|---|
| 1 | 9 | mRNA encoding CSP | GN01 | CSP | 1 μg | i.m. | 1 × 25 μl |
| 2 | 5 | irrelevant RNA | GN01 | Irrelevant RNA | 1 μg | i.m. | 1 × 25 μl |

Determination of Specific Humoral Immune Responses by ELISA:

ELISA was performed using malaria $[NANP]_7$ peptide or C-terminus peptides for coating. Coated plates were incubated using respective serum dilutions, and binding of specific antibodies to the respective malaria $[NANP]_7$ or C-terminus peptide were detected using biotinylated isotype specific anti-mouse antibodies followed by streptavidin-HRP (horse radish peroxidase) with Amplex™ Red Reagent as substrate. Endpoint titers of antibodies (IgG1, IgG2a) directed against the malaria $[NANP]_7$ or C-terminus peptide were measured by ELISA on day 21 and day 35 post prime. Results are shown in FIGS. 21.1A and 21.1B.

Intracellular Cytokine Staining:

Splenocytes from vaccinated mice were isolated on day 35 according to a standard protocol known in the art. Briefly, isolated spleens were grinded through a cell strainer and washed in PBS/1% FBS followed by red blood cell lysis. After an extensive washing step with PBS/1% FBS, splenocytes were seeded into 96-well plates ($2\times10^6$ cells per well). Cells were stimulated with a mixture of CSP peptides (1 μg/ml) in the presence of 2.5 μg/ml of an anti-CD28 antibody (BD Biosciences) and a protein transport inhibitor for 6h at 37° C. After stimulation, cells were washed and stained for intracellular cytokines using the Cytofix/Cytoperm™ reagent (BD Biosciences) according to the manufacturer's instructions. The following antibodies were used for staining: Thy1.2-FITC (1:100), CD8-PE-Cy7 (1:200), TNF-PE (1:100), IFNγ-APC (1:100) (eBioscience), CD4-BD Horizon V450 (1:200) (BD Biosciences) and incubated with Fcγ-block diluted 1:100. Aqua Dye was used to distinguish live/dead cells (Invitrogen). Cells were acquired using a BD FACS Canto II flow cytometer (Becton Dickinson). Flow cytometry data was analyzed using FlowJo software (Tree Star, Inc.). Results are shown in FIG. 21.2.

Results:

As shown in FIG. 21.2, the LNP formulated CSP mRNA vaccine induced strong, humoral immune responses in mice. Under the tested conditions, the LNP formulated vaccine applied to group A (1 ug dose) induced very strong immune responses.

As shown in FIG. 21.2, the LNP formulated CSP mRNA vaccine induced cellular immune responses in mice (CD8+ and/or CD4+ T-cell responses).

As CD8+ T cells are a major protective immune mechanism against intracellular infections caused by Malaria parasites, an effective Malaria vaccine should induce strong CD8+ T cells responses. Accordingly, these findings highlight one of the advantageous features of the inventive GN01 formulation.

Example 14: In Vivo FGF21 Expression after i.v Injection of LNP-Formulated mRNA To determine transfection, in vivo expression and expression efficiency of various LNP compositions with different HEXA lipids (shown in Table Ex-21), an mRNA encoding Fibroblast growth factor 21 (FGF21) was formulated and injected intravenously (i.v.) into CD-1 mice. Additionally toxicity, cytokine release and correlation of expression and cytokine release was determined.

For this, several amino acid exchanges for higher stability and less protein degradation were introduced into human FGF21 (L126R, P199G, A208E; similar as disclosed in WO 2018/104538 A1, incorporated herein by reference). The corresponding mRNA sequence comprised a 5'UTR from HSD17B4 and a 3'-UTR from PSMB3 (SEQ ID NO:39).

Further the mRNA was enzymatically capped according to standard proceedings; a methyl-group was added in a second step to obtain CAP1, and the mRNA was further enzymatically adenylated using commercially available polyadenylation kits and corresponding protocols known in the art. Additionally the mRNA was chemically modified (i.e. full replacement of uridine with pseudouridine (ψ)). Formulation of mRNA into LNPs was performed as described above and as shown in Table Ex-21.

Figure 22:
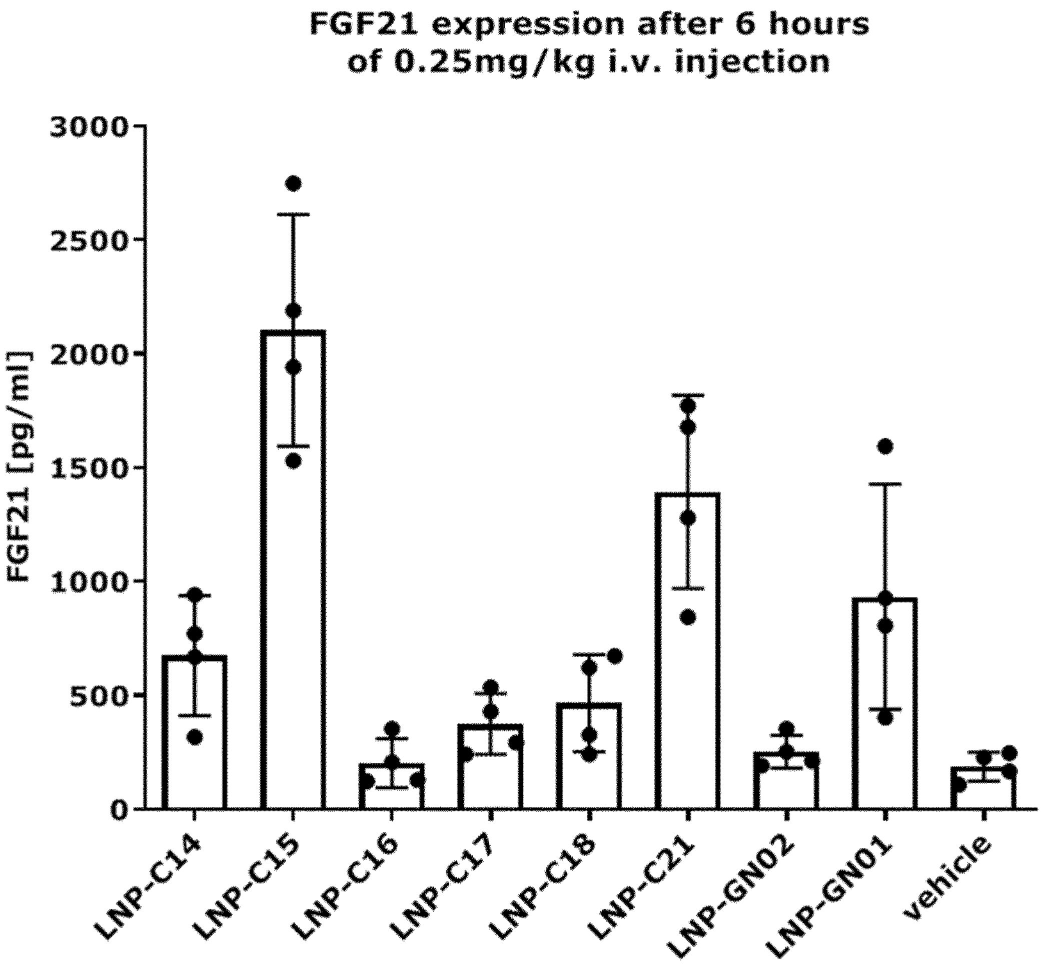
FIG. 22 (GN01 for in vivo expression of FGF21) shows that FGF21 mRNA formulated in the inventive LNPs gave rise to high FGF21 concentrations after administering a low dose of 0.25 mg/kg in mice via i.v. injection (full details can be seen in Example 14).
Figure 23:
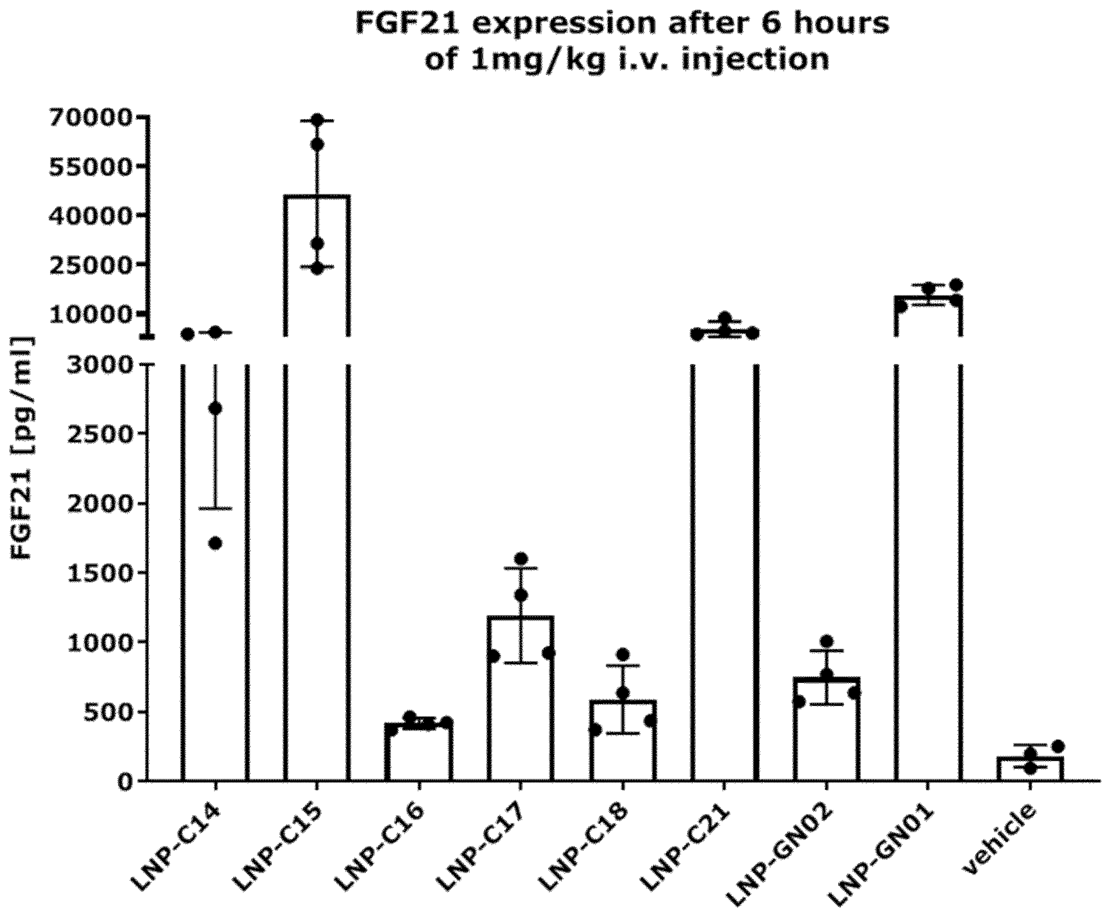
FIG. 23 (GN01 for in vivo expression of FGF21) shows that FGF21 mRNA formulated in the inventive LNPs gave rise to very high FGF21 concentrations after administering a high dose of 1 mg/kg in mice via i.v. injection (full details can be seen in Example 14).

CD-1 mice (4 individuals per group) were injected with a single iv. low or high mRNA dose (0.25 mg/kg and 1 mg/kg) and bled at 6 hours after injection. Analysis of FGF21 protein expression was performed using an anti-FGF21 protein ELISA (results are shown in FIGS. 22 and 23).

The tolerability of the various LNP compositions (see Table Ex-21) is further analyzed by measuring activity of aminotransferases ALT (alanine aminotransferase) and AST (aspartate aminotransferase). ALT and AST levels were measured 6h and 24h post injection.

For analysis of the cytokine releases EDTA plasma cytokine analysis was performed 6h post-injection. Therefore, a CBA assay with serum samples drawn from mice 6h after-treatment with various LNP formulations (see Table Ex-21) revealed the level of following cytokines/chemokines: MCP-1, MIP-1, MIP-1, RANTES, IL-12β70, IL-6, TNF, IL-1p, IFN-γ. Furthermore, the levels of IFN-α in the serum are determined by ELISA. Analysis of mouse IFN-α in serum is performed according to the manufacturer's instructions with 50 μl serum in reagent diluent (1:20).

TABLE EX-21

Formulation summary of HEXA lipids

| Name of LNP formulation/ composition | Excipients [cationic lipid:steroid:neutral lipid:polymer conjugated lipid] | mol-percentages for excipients [mol %] |
|---|---|---|
| LNP-C14 | C14:Chol:DSPC:DMG-PEG 2000 | 59:29.3:10:1.7 |
| LNP-C15 | C15:Chol:DSPC:DMG-PEG 2000 | 59:29.3:10:1.7 |
| LNP-C16 | C16:Chol:DSPC:DMG-PEG 2000 | 59:29.3:10:1.7 |
| LNP-C17 | C17:Chol:DSPC:DMG-PEG 2000 | 59:29.3:10:1.7 |
| LNP-C18 | C18:Chol:DSPC:DMG-PEG 2000 | 59:29.3:10:1.7 |
| LNP-C21 | C21:Chol:DPhyPE:DMG-PEG 2000 | 59:29.3:10:1.7 |
| LNP-GN02 | GN02:Chol:DPhyPE:DMG-PEG 2000 | 59:29.3:10:1.7 |
| LNP-GN01 | GN01:Chol:DPhyPE:DMG-PEG 2000 | 59:29.3:10:1.7 |
| Vehicle | | |

Results:

After 6 hours of low dose i.v. injection (0.25 mg/kg) of LNP formulated mRNA an expression of FGF21 protein levels were detectable for all formulations (FIG. 22). LNP-C14, LNP-C15, LNP-21 and LNP-GN01 were shown a superior expression level of the FGF12 protein after the low i.v. injection of mRNA encoding FGF21. After the treatment with 1 mg/kg very strong protein expression were detected for the formulations LNP-C14, LNP-C15, LNP-21 and LNP-GN01 (FIG. 23). All LNP formulations were shown higher protein levels compared to the vehicle. The highest protein level was measured with the LNP-C15. Surprisingly the protein level was approximately 35× higher compared to the low dose treatment.

Example 15: Synthesis of HEXA-C4DE-PipSS

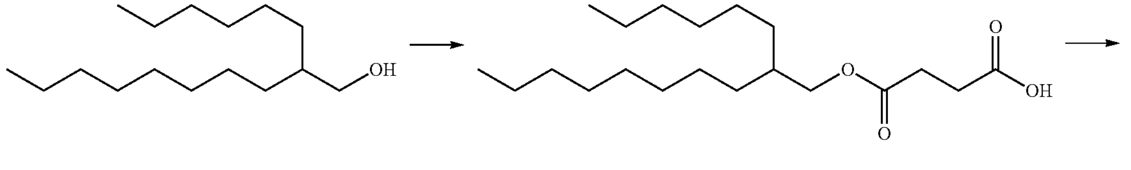

-continued

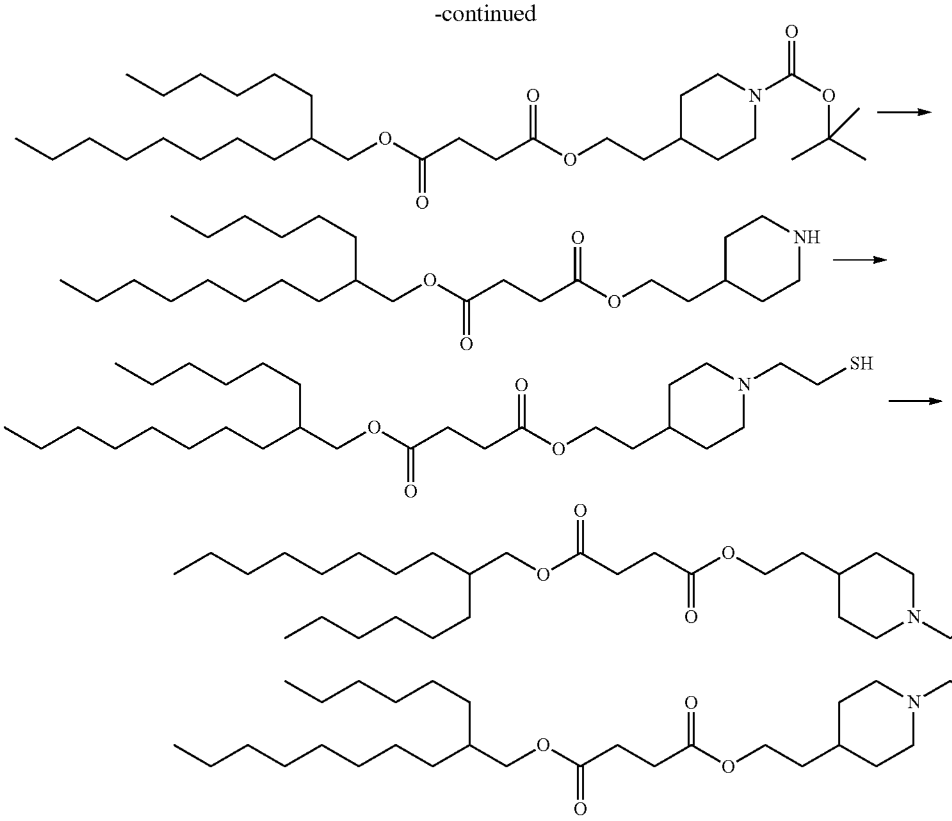

Example 15.1

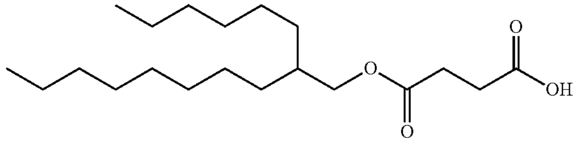 [SMILES: CCCCCCCCC(CCCCCC)COC(=O)CCC(=O)O]

Synthesis of 4-(2-hexyldecoxy)-4-oxo-butanoic acid

2-Hexyl-1-decanol (10 g) is dissolved in 100 ml of dry dichloromethane at room temperature. Succinic anhydride (4.99 g) and dimethylaminopyridine (6.1 g) is added and the reaction mixture is stirred under nitrogen overnight at room temperature. The solvent is evaporated and the crude residue purified by flash chromatography on silica eluting with a gradient dichloromethane→dichloromethane:methanol 95:5. Fractions containing the product are combined and concentrated to give the target compound as a yellowish oil (9.32 g, 65.8% yield).

Example 15.2

Synthesis of O1-[2-(1-tert-butoxycarbonyl-4-piperidyl)ethyl] 04-(2-hexyldecyl) butanedioate The product from Example 15.1 (2.5 g) and tert-Butyl 4-(2-hydroxyethyl)piperidine-1-carboxylate (1.852 g) are dissolved in 30 ml of dry dichloromethane at room temperature giving a clear solution. N,N'-Dicyclohexylcarbodiimid (1.666 g) is added and the reaction mixture is stirred at room temperature overnight. The white precipitate that has formed is filtered off and washed with a small volume of petrol ether. The combined filtrates are concentrated in vacuum and the residue purified by flash chromatography on silica with a solvent gradient from pure petrol ether to petrol ether:ethylacetate 80:20. The pure fractions of the product are combined and concentrated to give the target compound as a slightly yellow oil (3.31 g, 81.4% yield).

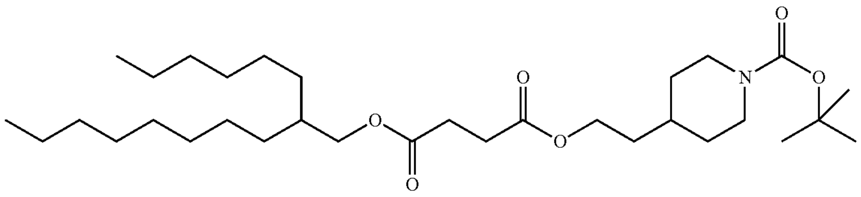 [SMILES: CCCCCCCCC(CCCCCC)COC(=O)CCC(=O)OCCC1CCN(C(=O)OC(C)(C)C)CC1]

Example 15.3

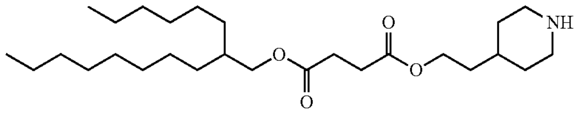 [SMILES: CCCCCCCCC(CCCCCC)COC(=O)CCC(=O)OCCC1CCNCC1]

Synthesis of O4-(2-hexyldecyl) 01-[2-(4-piperidyl) ethyl] butanedioate

The product from Example 15.2 (3.3 g) is dissolved in 10 ml of dry dichloromethane at room temperature. Trifluoroacetic acid (4 ml) is added and the mixture is stirred for 2 hours at room temperature. The mixture is washed two times with saturated sodium hydrogen carbonate solution and the aqueous phases are back-extracted with dichloromethane. The combined organic solutions are washed with brine, dried over anhydrous sodium sulphate, filtered and concentrated to give the target compound as the trifluoroacetic acid salt (yellow oil 3.08 g, 91% yield). The product was used without further purification in the next step.

Example 15.4

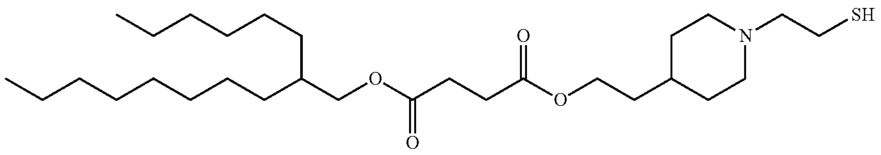 [SMILES: CCCCCCCCC(CCCCCC)COC(=O)CCC(=O)OCCC1CCN(CCS)CC1]

Synthesis of O4-(2-hexyldecyl) 01-[2-[1-(2-sulfanylethyl)-4-piperidyl]ethyl] butanedioate The crude product from Example 15.3 (1.3 g) is dissolved in 10 ml of dry toluene. N,N-diisopropylethylamine (0.526 ml) is added at room temperature resulting in a clear solution. The mixture is transferred to a pressure vial and 0.7 ml of ethylene sulphide is added. The vial is sealed and heated in an oil bath at 65° C. overnight. After cooling to room temperature, the complex reaction mixture is concentrated and used as obtained in the subsequent step.

Example 15.5

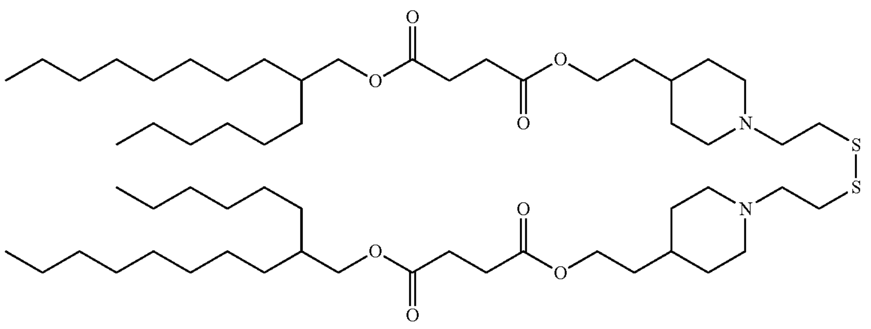 [SMILES: CCCCCCCCC(CCCCCC)COC(=O)CCC(=O)OCCC1CCN(CCSSCCN2CCC(CCOC(=O)CCC(=O)OCC(CCCCCC)CCCCCCCC)CC2)CC1]

Synthesis of O1-[2-[1-[2-[2-[4-[2-[4-(2-hexyldecoxy)-4-oxo-butanoyl]oxyethyl]-1-piperidyl]ethyldisulfanyl]ethyl]-4-piperidyl]ethyl]O4-(2-hexyldecyl) butanedioate The crude product mixture from Example 15.4 is dissolved in 15 ml acetonitrile. A solution of iodine in acetonitrile:water 9:1 is added drop wise at room temperature while stirring until a brown colour remains. The reaction mixture is concentrated and taken up in ethylacetate. This solution is washed subsequently with sodium hydrogen carbonate solution, sodium thiosulphate solution and brine. The organic phase is dried over anhydrous sodium sulphate, filtered and concentrated in vacuum. The target compound is isolated by flash chromatography on silica, eluting with a gradient chloroform 4 chloroform:methanol 80:20. The respective fractions are combined and the solvents are evaporated to provide the pure target compound as a yellow oil (272 mg, 11% yield over two steps).

1H-NMR (500 MHz, CDC13): 4.15 ppm (4H), 4.01 ppm (4H), 3.2-2.5 ppm (20H), 2.2-1.9 ppm (4H), 1.8-1.5 ppm (10H), 1.5-1.1 ppm (54H), 0.91 (12H)

Example 16: Synthesis of HEXA-C5DE-PipSS

Example 16.1

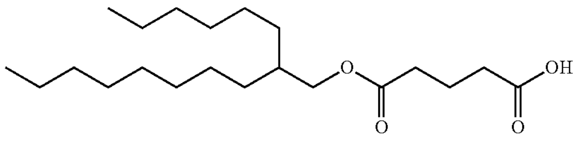 [SMILES: CCCCCCCCC(CCCCCC)COC(=O)CCCC(=O)O]

Synthesis of 5-(2-hexyldecoxy)-5-oxo-pentanoic acid

To a solution of 2-Hexyl-1-decanol (150 g) and glutaric anhydride (74.13 g) 1000 ml of dry dichloromethane dimethylaminopyridine (90.71 g) is added and the reaction mixture is stirred for 65 hours under nitrogen at room temperature. The white precipitate that has formed is filtered off and discharged. The filtrate is concentrated in vacuum and mixed with 200 ml of petrol ether for 40 minutes resulting in a white suspension. The precipitate is filtered off and the filtrate concentrated. The crude is partitioned between 300 ml 1N hydrochloric acid and 500 ml of ethyl

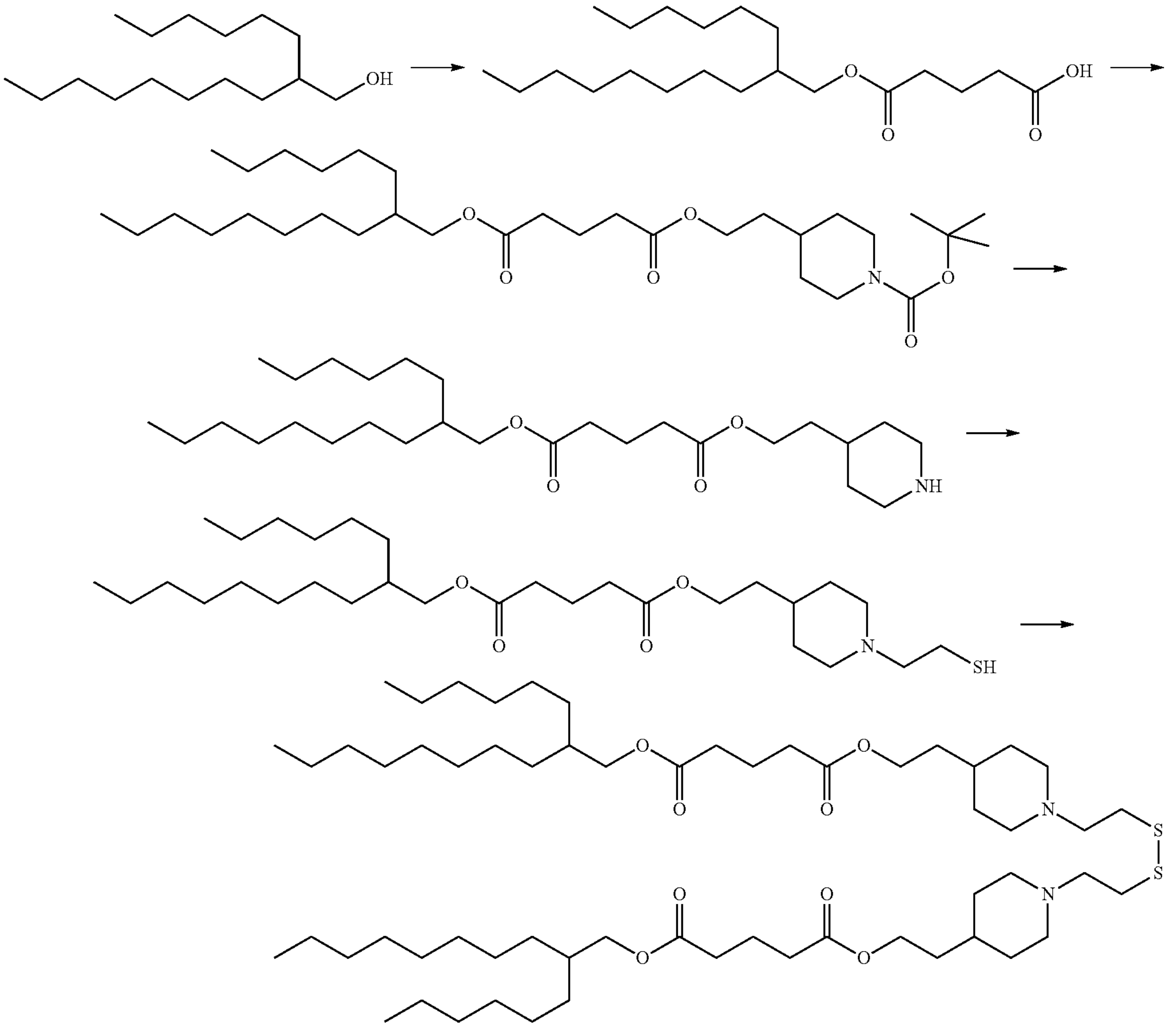

acetate. The organic phase is separated, washed with 500 ml of water and dried over anhydrous sodium sulphate. The sodium sulphate is filtered off and the solvent evaporated in vacuum. The crude residue is purified by flash chromatography on silica eluting with a gradient dichloromethane→dichloromethane:methanol 90:10. Fractions containing the product are combined and concentrated to give the pure target compound as a yellow oil (123.9 g, 56.1% yield).

Example 16.2

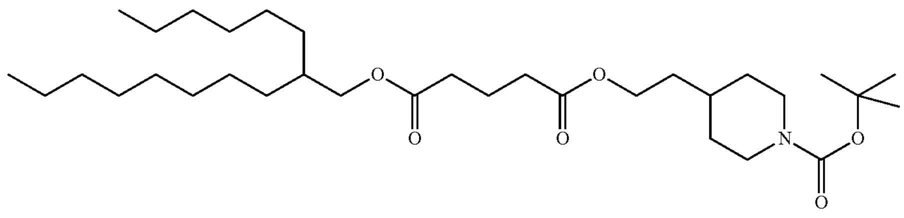 [SMILES: CCCCCCCCC(CCCCCC)COC(=O)CCCC(=O)OCCC1CCN(C(=O)OC(C)(C)C)CC1]

Synthesis of O1-[2-(1-tert-butoxycarbonyl-4-piperidyl)ethyl] 05-(2-hexyldecyl) pentanedioate The product from Example 16.1 (52.6 g) and tert-Butyl 4-(2-hydroxyethyl)piperidine-1-carboxylate (37.2 g) are dissolved in 600 ml of dichloromethane at room temperature giving a clear yellow solution. N,N'-Dicyclohexylcarbodiimid (33,48.6 g) is added and the reaction mixture is stirred at room temperature for 22 hours. More N,N'-Dicyclohexylcarbodiimid (15.2 g) is added and the mixture stirred at room temperature for another 42 hours. The white precipitate that has formed is filtered off and washed with a small volume of petrol ether. The combined filtrates are concentrated in vacuum and the residue purified by flash chromatography on silica with a solvent gradient from pure petrol ether to petrol ether:ethylacetate 90:10. The pure fractions of the product are combined and concentrated to give the target compound as an oil (32.8 g, 39.2% yield).

Example 16.3

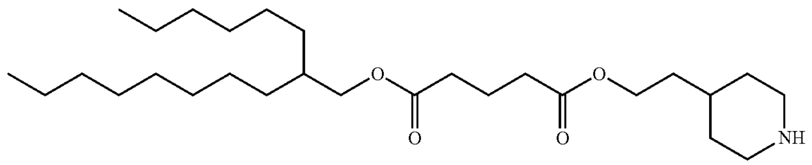 [SMILES: CCCCCCCCC(CCCCCC)COC(=O)CCCC(=O)OCCC1CCNCC1]

Synthesis of O5-(2-hexyldecyl) 01-[2-(4-piperidyl) ethyl] pentanedioate

The product from Example 16.2 (32.8 g) is dissolved in 1000 ml of dichloromethane at room temperature. The solution is cooled in an ice bath and trifluoroacetic acid (35.6 ml) is added slowly at −0° C. The mixture is allowed to warm up to room temperature and stirred overnight. The mixture is washed with saturated sodium hydrogen carbonate solution and the aqueous phase is back-extracted with dichloromethane. The combined organic solutions are washed with brine, dried over anhydrous sodium sulphate, filtered and concentrated to give the target compound as a yellow oil (27.15 g, quantitative yield). The product was used without further purification in the next step.

Example 16.4

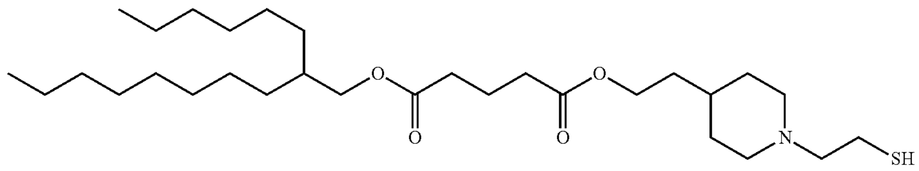 [SMILES: CCCCCCCCC(CCCCCC)COC(=O)CCCC(=O)OCCC1CCN(CCS)CC1]

Synthesis of O5-(2-hexyldecyl) 01-[2-[1-(2-sulfanylethyl)-4-piperidyl]ethyl] pentanedioate The crude product from Example 16.3 (1.37 g) is dissolved in 10 ml of dry toluene. N,N-diisopropylethylamine (0.533 ml) is added at room temperature resulting in a clear solution. The mixture is transferred to a pressure vial and 0.7 ml of ethylene sulphide is added. The vial is sealed and heated in an oil bath at 65° C. overnight. After cooling to room temperature, the complex reaction mixture is concentrated and used as obtained in the subsequent step.

Example 16.5

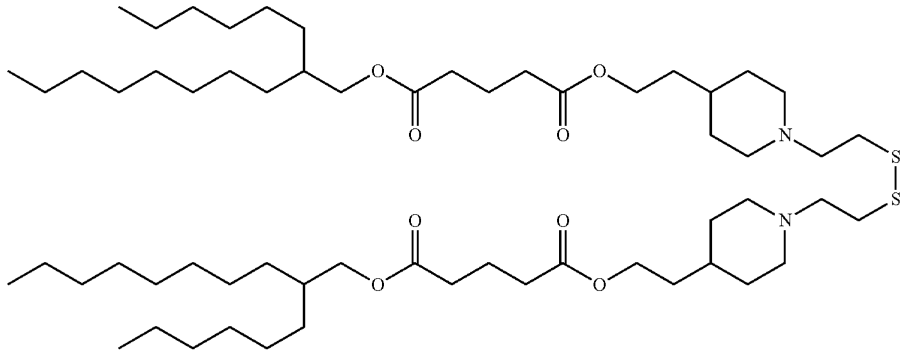 [SMILES: CCCCCCCCC(CCCCCC)COC(=O)CCCC(=O)OCCC1CCN(CCSSCCN2CCC(CCOC(=O)CCCC(=O)OCC(CCCCCC)CCCCCCCC)CC2)CC1]

Synthesis of O1-[2-[1-[2-[2-[4-[2-[5-(2-hexyldecoxy)-5-oxo-pentanoyl]oxyethyl]-1-piperidyl]ethyldisulfanyl]ethyl]-4-piperidyl]ethyl] 05-(2-hexyldecyl) pentanedioate The crude product mixture from Example 16.4 is dissolved in 15 ml acetonitrile. A solution of iodine in acetonitrile:water 9:1 is added drop wise at room temperature while stirring until a brown colour remains. The reaction mixture is concentrated and taken up in ethylacetate. This solution is washed subsequently with sodium hydrogen carbonate solution and sodium thiosulphate solution. The organic phase is dried over anhydrous sodium sulphate, filtered and concentrated in vacuum. The target compound is isolated by flash chromatography on silica, eluting with a gradient chloroform 4 chloroform:methanol 80:20. The respective fractions are combined and the solvents are evaporated to provide the pure target compound as a yellow oil (562 mg, 22% yield over two steps).

1H-NMR (500 MHz, CDCl3): 4.11 ppm (4H), 3.98 ppm (4H), 3.15-2.5 ppm (12H), 2.37 (8H), 2.17-1.84 ppm (8H), 1.81-1.5 ppm (10H), 1.49-1.08 ppm (54H), 0.88 (12H)

Example 17: Synthesis of HEXA-C5DE-PipC3SS

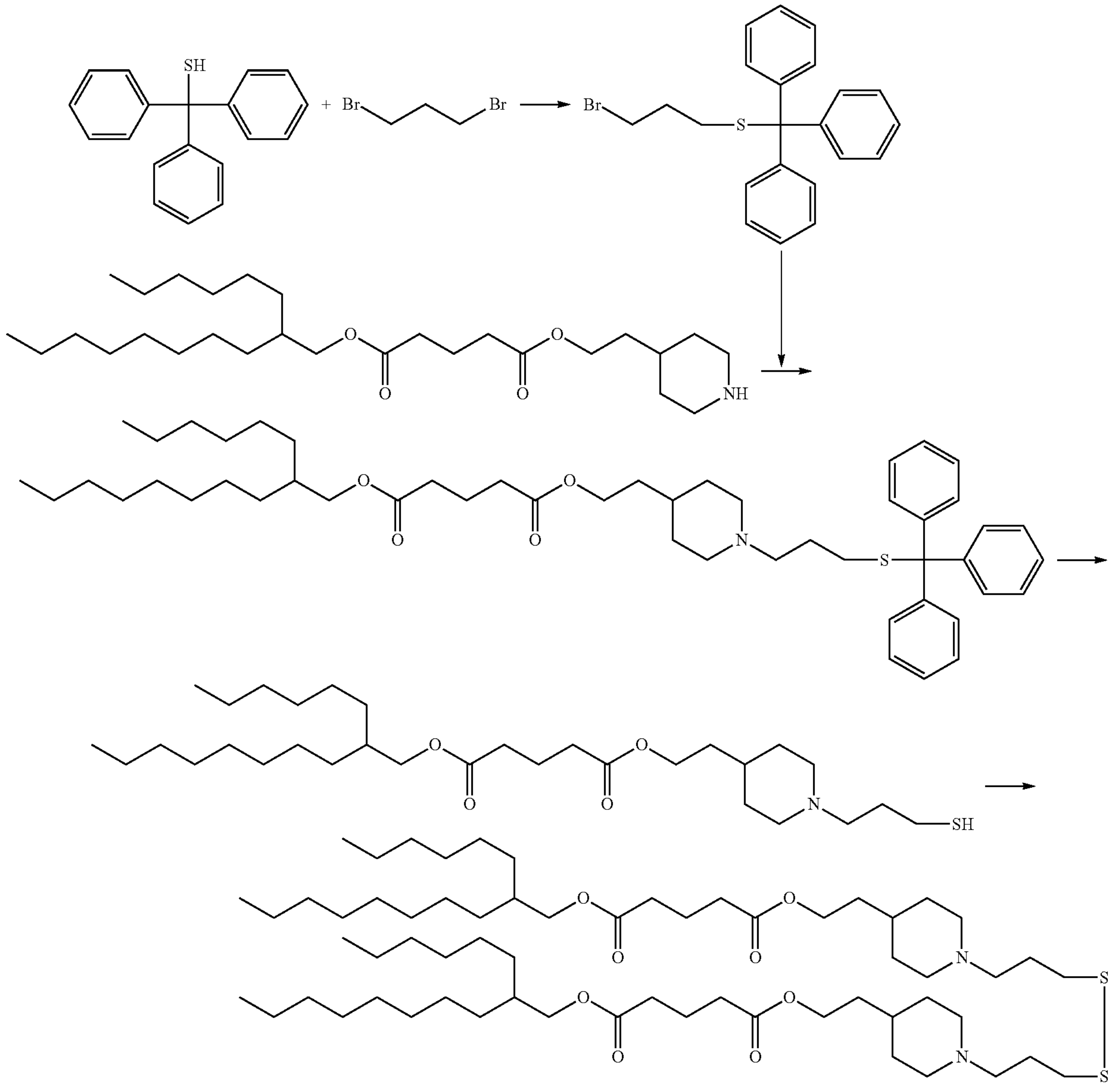

Example 17.1

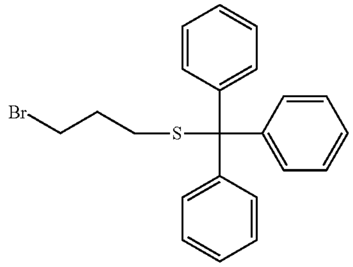 [SMILES: BrCCCSC(c1ccccc1)(c1ccccc1)c1ccccc1]

Synthesis of [3-bromopropylsulfanyl(diphenyl)methyl]benzene

To a solution of triphenylmethanethiole (12 g) and 1,3-dibromopropane (22 ml) in 225 ml of dry tetrahydrofurane was added potassium carbonate (6.6 g). The reaction mixture is stirred at 50° C. for two days and at 60° C. for another 4 days under nitrogen. The insoluble salts are filtered off and the filtrate is concentrated in vacuum. The solution of the residue in 150 ml of dichloromethane is washed with 500 ml water and dried over anhydrous sodium sulphate, filtered and concentrated. The residue is purified by flash chromatography on silica eluting with petrol ether:dichloromethane 4:1. Relevant fractions are combined and the solvents evaporated in vacuum to give the pure target compound as a solid (4.2 g, 24.3% yield).

Example 17.2

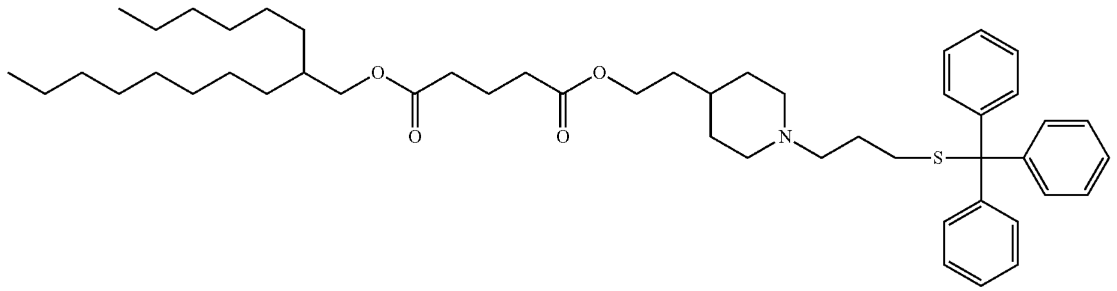 [SMILES: CCCCCCCCC(CCCCCC)COC(=O)CCCC(=O)OCCC1CCN(CCCSC(c2ccccc2)(c2ccccc2)c2ccccc2)CC1]

Synthesis of O5-(2-hexyldecyl) 01-[2-[1-(3-tritylsulfanylpropyl)-4-piperidyl]ethyl] pentanedioate The product from Example 16.3 (4 g) and the product from Example 17.1 (3.4 g) is mixed with 85 ml acetonitrile at room temperature to give a suspension. Dimethyl formamide (2 ml) is added and the mixture is stirred at 55° C. for 16 hours and additionally 24 hours at 65° C. Potassium carbonate (600 mg) is added and the mixture stirred for another 3 hours. The reaction mixture is filtered, concentrated and purified by flash chromatography (silica, dichloromethane:methanol 90:10 as eluent) to provide the essentially pure target compound (3.55 g, 52.9% yield) containing some residual dimethyl formamide.

Example 17.3

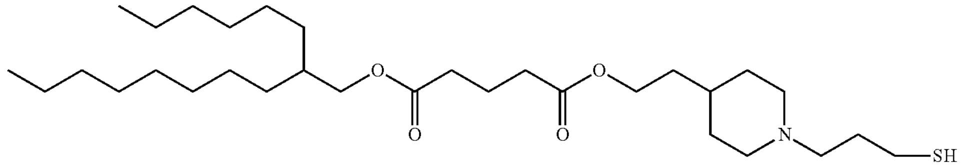 [SMILES: CCCCCCCCC(CCCCCC)COC(=O)CCCC(=O)OCCC1CCN(CCCS)CC1]

Synthesis of O5-(2-hexyldecyl) 01-[2-[1-(3-sulfanylpropyl)-4-piperidyl]ethyl] pentanedioate The product from Example 17.2 (1 g) is dissolved in 5 ml of dry dichloromethane and the solution is cooled to 0° C. in an ice bath. Subsequently trifluoro acetic acid (1.965 ml) and triethyl silane (0.206 ml) is added to give a slightly brownish solution. The reaction mixture is stirred at 0° C. for 30 minutes, diluted with 50 ml dichloromethane and washed with 100 ml of saturated sodium hydrogen carbonate solution. The organic phase is separated, dried over anhydrous sodium sulphate and concentrated. The residue is purified by flash chromatography on silica eluting with a gradient dichloromethane 4 dichloromethane:methanol 95:5 to give the target compound (0.47 g, 68% yield).

Example 17.4

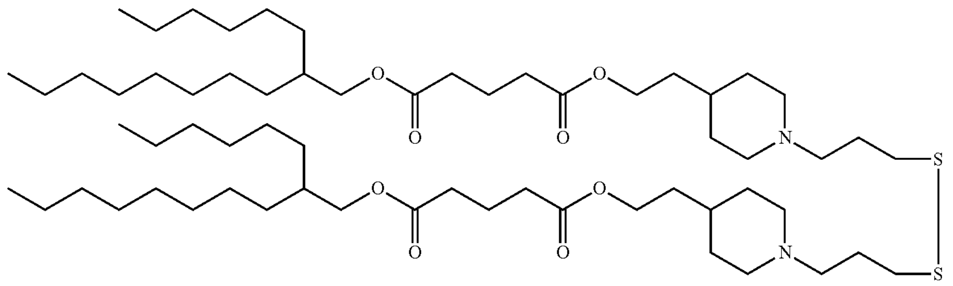 [SMILES: CCCCCCCCC(CCCCCC)COC(=O)CCCC(=O)OCCC1CCN(CCCSSCCCN2CCC(CCOC(=O)CCCC(=O)OCC(CCCCCC)CCCCCCCC)CC2)CC1]

Synthesis of O1-[2-[1-[3-[3-[4-[2-[5-(2-hexyl-decoxy)-5-oxo-pentanoyl]oxyethyl]-1-piperidyl]propyldisulfanyl]propyl]-4-piperidyl]ethyl] 05-(2-hexyldecyl) pentanedioate The product from Example 17.3 (0.47 g) is dissolved in 10 ml acetonitrile. A solution of iodine in acetonitrile:water 9:1 is added drop wise at room temperature until a brown colour remains. The reaction mixture is stirred for 58 hours at room temperature, concentrated and purified by flash chromatography (silica, dichloromethane 4 dichloromethane:methanol 95:5) to give the target compound as the hydroiodic acid salt (240 mg, 45.8% yield).

1H-NMR (500 MHz, CDCl3): 10.01 ppm (2H), 4.15 ppm (4H), 3.99 ppm (4H), 3.83 ppm (4H), 3.28 ppm (4H), 2.94-2.80 ppm (8H), 2.53-2.44 ppm (4H), 2.43-2.36 ppm (8H), 2.21-2.09 ppm (4H), 2.04-1.91 ppm (8H), 1.84-1.67 ppm (6H), 1.36-1.2 ppm (50H), 0.90 ppm (12H)

Example 18: Synthesis of HEXACA-C5DE-PipSS

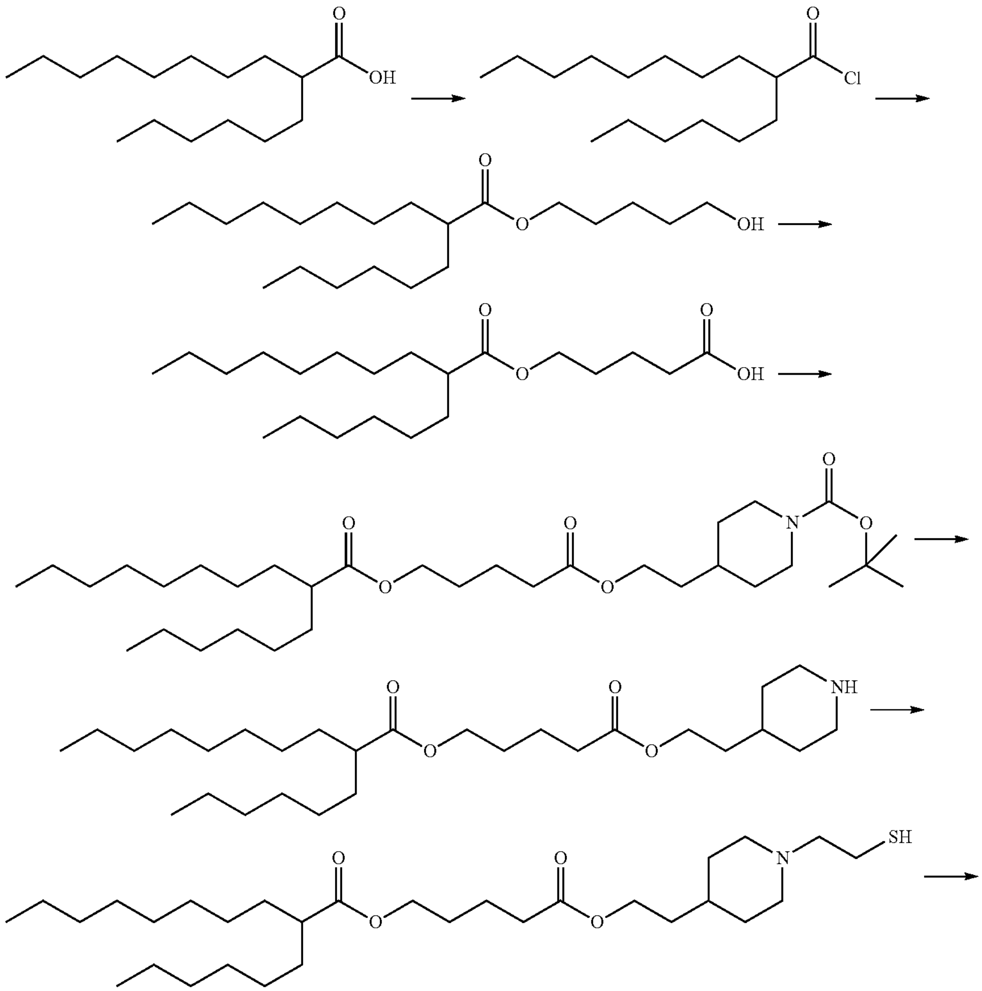

-continued

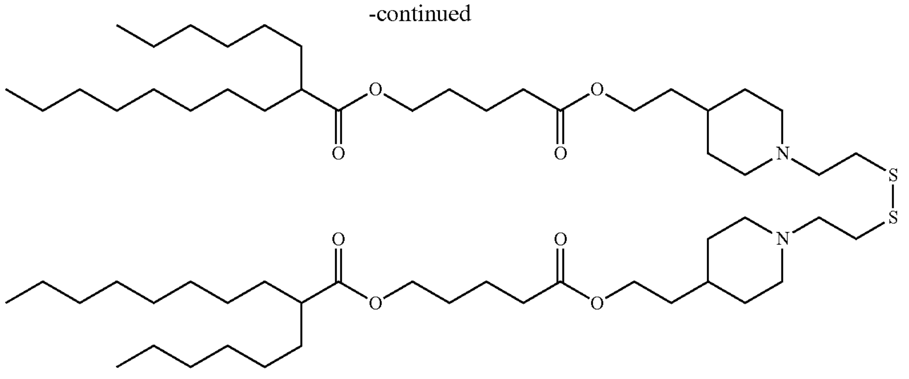

Example 18.1

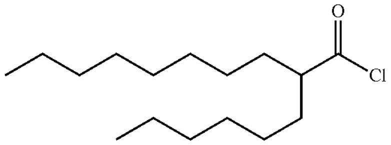 [SMILES: CCCCCCCCC(CCCCCC)C(=O)Cl]

Synthesis of 2-hexyldecanoyl chloride

A solution of 2-Hexyldecanoic acid (25 g) in 250 ml dry dichloromethane+0.1 ml dimethyl formamide is cooled in an ice bath to 0° C. and oxalyl chloride (12.54 ml) is added drop wise at this temperature. The mixture is warmed to room temperature and stirred for 3 hours. The solvents are removed in vacuum to give a yellow oil (26.5 g) which is used in the next step without further purification.

Example 18.2

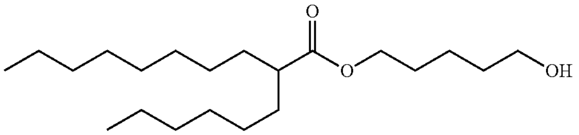 [SMILES: CCCCCCCCC(CCCCCC)C(=O)OCCCCCO]

Synthesis of 5-hydroxypentyl 2-hexyldecanoate

A solution of 1,5-pentanediol (51.07 g) and triethyl amine in 250 ml dry tetrahydrofuran is stirred at 0° C. in an ice bath. A solution of the product from Example 18.1 (26.5 g) in 250 ml dry tetrahydrofuran is added slowly over 80 minutes at this temperature. The reaction mixture is warmed to room temperature and stirred overnight. The solvent is evaporated in vacuum and the resulting brown oil is dissolved in 300 ml dichloromethane and washed two times with 500 ml water. The organic phase is dried over anhydrous sodium sulphate, filtered and concentrated. The crude product is purified by flash chromatography on silica eluting with dichloromethane:methanol 95:5. Relevant fractions are pooled and the solvents are evaporated to give the target compound as a slightly brownish oil (27.36 g, 81.9% yield).

Example 18.3

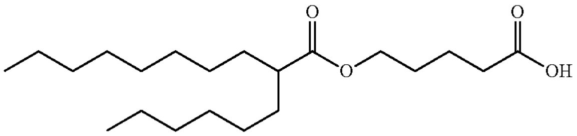 [SMILES: CCCCCCCCC(CCCCCC)C(=O)OCCCCC(=O)O]

Synthesis of 5-(2-hexyldecanoyloxy)pentanoic acid

A solution of Jones reagent is freshly prepared by adding concentrated sulphuric acid (158.36 g) drop wise to a cooled solution (5° C.) of chromium(VI)oxide (86.06 g) in 258 ml water to give a deep orange solution. This solution is added slowly over 70 minutes to a solution of the compound from Example 18.2 (19.75 g) in 258 ml acetone at 0° C. The mixture is stirred for one hour and the reaction is quenched by adding 120 ml isopropanol cautiously (exothermic), forming a sticky precipitate. The solution is decanted and partitioned between 400 ml dichloromethane and 300 ml water. The dichloromethane solution is separated. The sticky precipitate is stirred with 500 ml dichloromethane and 500 ml water. The organic phase is separated, combined with the previously obtained dichloromethane solution, dried over anhydrous sodium sulphate and concentrated. The residue is purified by flash chromatography on silica (eluent dichloromethane:methanol 96:4) to give after evaporation of the solvents the target compound as a yellowish oil (16.38 g, 79.7% yield).

Example 18.4

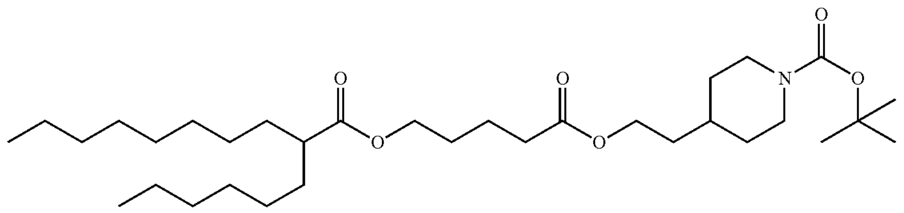 [SMILES: CCCCCCCCC(CCCCCC)C(=O)OCCCCC(=O)OCCC1CCN(C(=O)OC(C)(C)C)CC1]

Synthesis of tert-butyl 4-[2-[5-(2-hexyldecanoyloxy)pentanoyloxy]ethyl]piperidine-1-carboxylate A solution of the compound from Example 18.3 (10 g) in dry 200 ml dichloromethane is treated with 20 mg dry dimethylformamide and oxalyl chloride (3.6 ml). The mixture is stirred at 20° C. for 1 hour, concentrated in vacuum and re-dissolved in 100 ml dry dichloromethane. This solution is added drop wise to a solution of tert-butyl 4-(2-hydroxyethyl)piperidine-1-carboxylate (7.08 g) and triethyl amine (5.67 g) in 100 ml dichloromethane at room temperature. The reaction mixture is stirred overnight and then concentrated in vacuum. The residue is purified by flash chromatography on silica, eluting with ethylacetate:petrol ether 1:5. The relevant fractions are combined and the solvents evaporated to give the pure target compound (13.05 g, 81.9% yield) as a slightly yellow oil.

Example 18.5

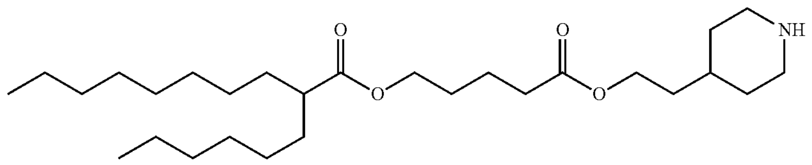 [SMILES: CCCCCCCCC(CCCCCC)C(=O)OCCCCC(=O)OCCC1CCNCC1]

Synthesis of [5-oxo-5-[2-(4-piperidyl)ethoxy]pentyl] 2-hexyldecanoate

The product from Example 18.4 (5 g) is dissolved in 120 ml of dichloromethane at room temperature. Trifluoroacetic acid (10.04 g) is added and the mixture is stirred overnight. All volatiles are removed in vacuum and the residue (6.28 g, quantitative yield) is used in the subsequent step without further purification.

Example 18.6

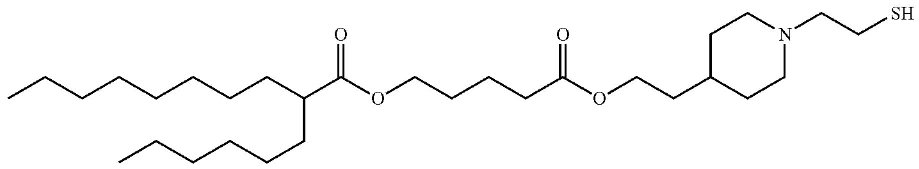 [SMILES: CCCCCCCCC(CCCCCC)C(=O)OCCCCC(=O)OCCC1CCN(CCS)CC1]

Synthesis of [5-oxo-5-[2-[1-(2-sulfanylethyl)-4-piperidyl]ethoxy]pentyl] 2-hexyldecanoate The crude product from Example 18.5 (3 g) is dissolved in 35 ml of dry toluene. N,N-diisopropylethylamine (5.6 ml) is added at room temperature resulting in a clear solution. The mixture is transferred to a pressure vial and 1.91 ml of ethylene sulphide is added. The vial is sealed and heated in an oil bath at 65° C. overnight. After cooling to room temperature, the reaction mixture is concentrated and used as obtained in the next step.

Example 18.7

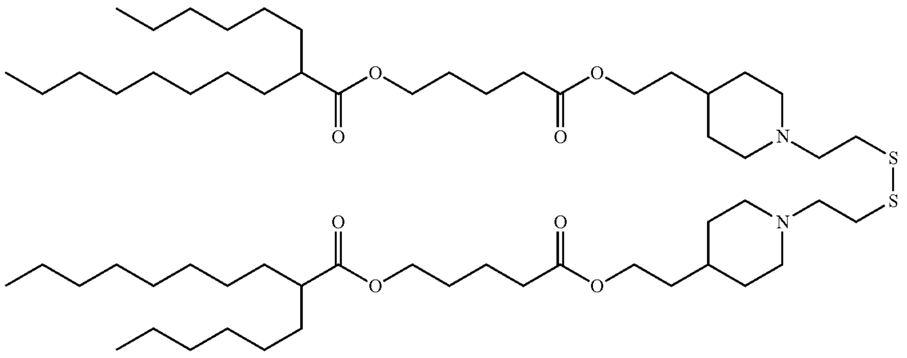 [SMILES: CCCCCCCCC(CCCCCC)C(=O)OCCCCC(=O)OCCC1CCN(CCSSCCN2CCC(CCOC(=O)CCCCOC(=O)C(CCCCCC)CCCCCCCC)CC2)CC1]

Synthesis of [5-[2-[1-[2-[2-[4-[2-[5-(2-hexyldecanoyloxy)pentanoyloxy]ethyl]-1-piperidyl]ethyldisulfanyl]ethyl]-4-piperidyl]ethoxy]-5-oxo-pentyl] 2-hexyldecanoate The crude product mixture from Example 18.6 is dissolved in 30 ml acetonitrile. A solution of iodine (814 mg) in 20 ml acetonitrile is added drop wise at room temperature until a brown colour remains. The reaction mixture is stirred for 90 minutes at room temperature and then concentrated in vacuum. The residue is dissolved in 50 ml chloroform and the solution is washed subsequently with 50 ml saturated sodium hydrogen carbonate solution and sodium thiosulphate solution. The organic phase is separated, dried over anhydrous sodium sulphate, filtered and concentrated in vacuum. The target compound is isolated by flash chromatography on silica (eluent dichloromethane:methanol 20:1+1% aqueous ammonia). Fractions containing pure product are combined and the solvents are evaporated to provide the target compound as a yellow oil (680 mg, 10% yield over two steps).

1H-NMR (500 MHz, CDCl3): 4.15-4.02 ppm (8H), 2.92 ppm (4H), 2.83 ppm (4H), 2.66 ppm (4H), 2.36-2.26 ppm (6H), 2.0 ppm (4H), 1.74-1.62 (12H), 1.61-1.52 ppm (8H), 1.46-1.17 ppm (50H), 0.86 ppm (12H)

Example 19: Synthesis of HEXA-C5DE-Pip-Thioether

Example 19.1

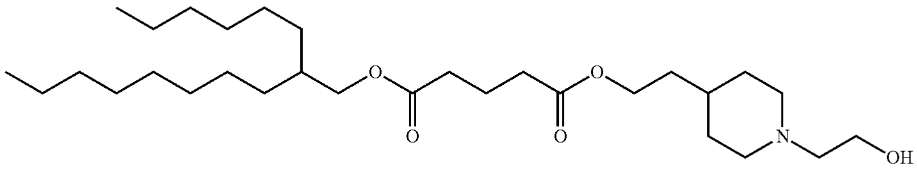 [SMILES: CCCCCCCCC(CCCCCC)COC(=O)CCCC(=O)OCCC1CCN(CCO)CC1]

Synthesis of O5-(2-hexyldecyl) 01-[2-[1-(2-hydroxyethyl)-4-piperidyl]ethyl] pentanedioate A mixture of the product from Example 16.3 (4 g), 2-bromoethanol (2.14 g) and potassium carbonate (2.37 g) in 65.8 ml dimethyl formamide is stirred at 50° C. overnight. The reaction mixture is cooled to room temperature, diluted with 500 ml water and extracted 3 times with 250 ml dichloromethane each. The combined organic extracts are dried over anhydrous sodium sulphate, filtered and concentrated. The crude target compound obtained (3.3 g) is used in the subsequent step without further purification.

Example 19.2

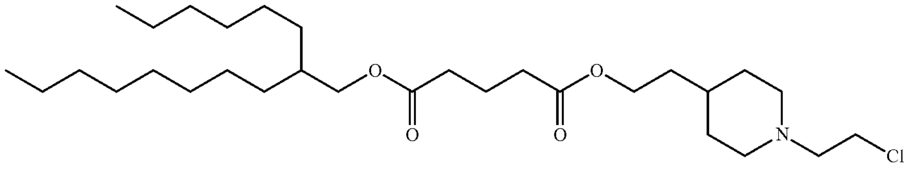 [SMILES: CCCCCCCCC(CCCCCC)COC(=O)CCCC(=O)OCCC1CCN(CCCl)CC1]

Synthesis of O1-[2-[1-(2-chloroethyl)-4-piperidyl] ethyl] 05-(2-hexyldecyl) pentanedioate To a solution of the crude product from Example 19.1 (3.3 g) in 60 ml toluene is added thionyl chloride (1.58 g) drop wise at room temperature. The reaction mixture is stirred for 90 minutes and then concentrated. The product is pre-purified by flash chromatography on silica eluting with a gradient dichloromethane→dichloromethane:methanol 90:10. Fractions containing the target compound (as the hydrochloric acid salt) are combined and solvents are evaporated. The final purification is accomplished by a second flash chromatography on silica using ethylacetate→ethylacetate:methanol 98:2 as the eluent. The solvents are removed in vacuum the residue is taken up in 100 ml dichloromethane. This solution is washed intensively with 100 ml saturated sodium hydrogencarbonate solution and brine. The organic phase is separated, dried over anhydrous sodium sulphate, filtered and concentrated to provide the target compound as the free base (1.95 g, 57% yield).

Example 19.3

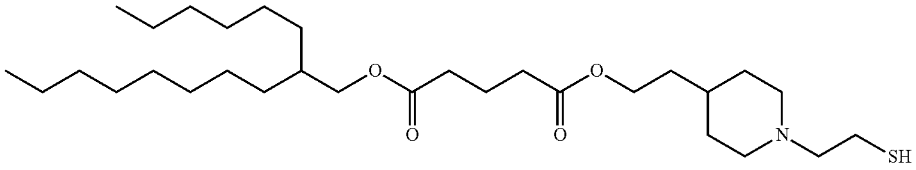

Synthesis of O5-(2-hexyldecyl) 01-[2-[1-(2-sulfanylethyl)-4-piperidyl]ethyl] pentanedioate The crude product from Example 16.3 (12.5 g) is dissolved in 75 ml of dry toluene. N,N-diisopropylethylamine (14 ml) is added at room temperature resulting in a clear solution. Ethylene sulphide (7.96 ml) is added and the mixture is stirred under argon atmosphere for 8 hours at 55° C. and at room temperature overnight. The mixture is concentrated and purified by flash chromatography on silica eluting with a gradient dichloromethane 4 dichloromethane: methanol 95:5. Fractions containing mainly the target compound are combined and solvents evaporated. The product (1.95 g, 12.4% yield) contains some respective disulfide (resulting from oxidation by air).

Example 19.4

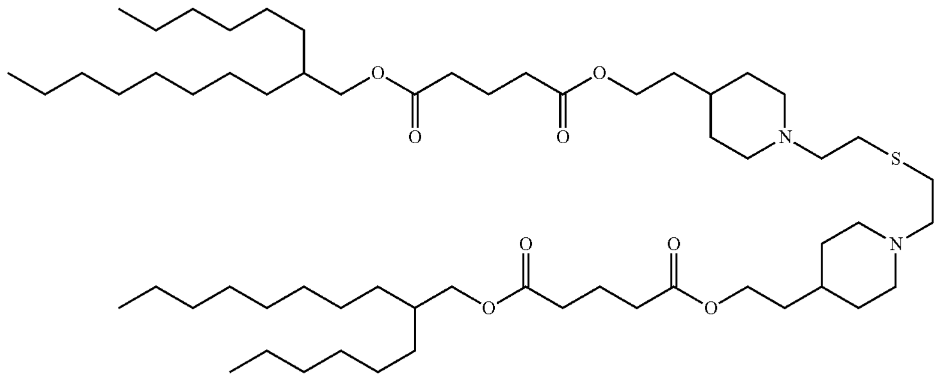 [SMILES: CCCCCCCCC(CCCCCC)COC(=O)CCCC(=O)OCCC1CCN(CCSCCN2CCC(CCOC(=O)CCCC(=O)OCC(CCCCCC)CCCCCCCC)CC2)CC1]

Synthesis of O1-[2-[1-[2-[2-[4-[2-[5-(2-hexyldecoxy)-5-oxo-pentanoyl]oxyethyl]-1-piperidyl] ethylsulfanyl]ethyl]-4-piperidyl]ethyl]O5-(2-hexyldecyl) pentanedioate The product from Example 19.3 (1 g) is dissolved in 10 ml dimethylformamide+two drops of water. The solution is degassed in three cycles alternately applying vacuum/purging with argon. Tris(2-carboxyethyl)phosphine hydrochloride (0.543 g) is added and the mixture stirred for 3 days at room temperature. The reaction mixture is diluted with 250 ml degassed dichloromethane and washed with degassed sodium hydrogen carbonate solution and degassed brine (200 ml each). The organic layer is separated, dried over anhydrous sodium sulphate, filtered and concentrated.

The residue is taken up in 10 ml degassed dimethyl formamide and a solution of the product from Example 19.2 (1.005 g) in 5 ml degassed dimethylformamide and triethylamine (0.72 ml) is added. The reaction mixture is stirred under argon at room temperature for 18 hours. Most of the dimethylformamide is distilled off under reduced pressure at 55° C. The residue is purified by flash chromatography in multiple runs to work up mixed fractions. The silica used is pre conditioned with the eluent (dichloromethane:methanol: aqueous ammonia 97:2.85:0.15). Pure fractions are combined and solvents are removed in vacuum to give the clean target compound (120 mg, 5.9% yield).

1H-NMR (500 MHz, CDC13): 4.11 ppm (4H), 3.98 ppm (4H), 3.07-2.84 ppm (4H), 2.75-2.51 ppm (8H), 2.37 (8H), 2.10-1.88 ppm (8H), 1.69-1.54 ppm (10H), 1.44-1.15 ppm (54H), 0.88 (12H)

Example 20: Synthesis of HEXA and HEAD Lipids

The present Example provides methods and information to obtain lipid compounds of the invention as well as methods of generating and analysing compositions of the invention.

Example 20.1: HEXA Lipids—Synthesis of HEXA Lipids

HEXA lipids were synthesized according to general protocols of ChiroBlock GmbH (Bitterfeld-Wolfen, Germany). Two HEXA lipids as shown in Table Ex-22 and FIG. 24 were synthesized, see Examples 23 and 24.

TABLE EX-22

| Overview of the synthesized HEXA lipids | | | |
|---|---|---|---|
| Lipids No./ Compound No. | Ref. in FIG. 24 | Compound name*** [Tail-Linker-Head] | Ester structure |
| C24 | FIG. 24A | HEXA-C5DE-inverted-PipSS | Diester |
| C25 | FIG. 24B | HEXA-C5DE-Pip-C3 thioether | diester |

***see comments to Table Ex-1

Purity and structural identity of the HEXA lipids was confirmed by nuclear magnetic resonance spectroscopy (H-NMR, 500.13 MHz) and mass spectrometry (electrospray ionization-ESI or atmospheric pressure chemical ionization-APCI, via direct injection).

The NMR data for C24 were as follows:

$^1$H NMR (400 MHz, $C_6D_6$) δ 4.28-4.14 (8H), 2.83 (4H), 2.70-2.61 (4H), 2.48 (4H), 2.31 (8H), 2.03 (4H), 1.88 (4H), 1.76-1.61 (6H), 1.57-1.20 (58H), 1.03 (12H)

The NMR data for C25 were as follows:

$^1$H NMR (400 MHz, $C_6D_6$) δ 4.21-4.08 (8H), 2.84 (4H), 2.62 (4H), 2.41 (4H), 2.31 (8H), 2.04 (4H), 1.84 (8H), 1.71 (2H), 1.59-1.21 (62H), 1.03 (12H)

Example 20.1.1: Preparation of LNPs Using the NanoAssembr™ Microfluidic System

The LNPs were prepared as set out in Example 2.1.1 with the general formulation entitled “Composition 2” in Table Ex-2 for LNP19 to LNP24 shown below in Table Ex-23.

LNP25 to LNP27 were also prepared as set out in Example 2.1.1. Thus, the cationic lipids were formulated as LNP using the NanoAssembr™ microfluidic system (Precision NanoSystems Inc., Vancouver, BC) according to standard protocols.

The structure of (07:0) PC (DHPC—1,2-diheptanoyl-sn-glycero-3-phosphocholine) from Avanti Polar Lipids (Alabaster,AL.) is as follows:

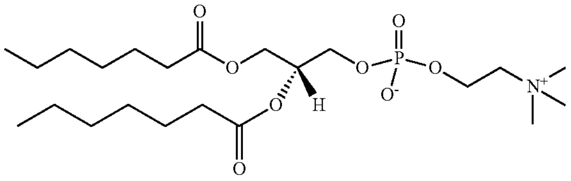 [SMILES: CCCCCCC(=O)OC[C@H](COP(=O)([O-])OCC[N+](C)(C)C)OC(=O)CCCCCC]

Example 20.1.2: Biophysical Characterization of Lipid Nanoparticle Compositions/HEXA Lipids The LNPs shown in Table Ex-23 were formulated and characterized along the lines as discussed in Example 2.1.2. The characterization showed that the LNPs of Table Ex-23 exhibited similar characteristics to the LNPs of Example 2.1.2, i.e. the obtained results of the characterization were basically inside the ranges of the LNPs of Example 2.1.2.

TABLE EX-23

Formulation of HEXA lipids - reference to the cationic lipids as disclosed in Table Ex-22 and Table 1 is made herein

| Name of LNP formulation/ composition | Excipients [cationic lipid as disclosed in Table Ex-22/Table 1:steroid:neutral lipid (optionally two as indicated):polymer conjugated lipid] | mol-percentages for excipients [mol %] |
|---|---|---|
| LNP19 | C24:Chol:DPhyPE:DMG-PEG 2000 | 59:29.3:10:1.7 |
| LNP20 | C25:Chol:DPhyPE:DMG-PEG 2000 | 59:29.3:10:1.7 |
| LNP21 | C13:Chol:DPhyPE:DMG-PEG 2000 | 59:29.3:10:1.7 |
| LNP22 | C16:Chol:DPhyPE:DMG-PEG 2000 | 59:29.3:10:1.7 |
| LNP23 | C17:Chol:DPhyPE:DMG-PEG 2000 | 59:29.3:10:1.7 |
| LNP24 | C18:Chol:DPhyPE:DMG-PEG 2000 | 59:29.3:10:1.7 |
| LNP25 | C2:Chol:DPhyPE:PCL*** | 59:29.3:10:1.7 |
| LNP26 | C2:Chol:DPhyPE + (0:7) PC (DHPC):PCL*** | 59:28.3:10 + 1:1.7 |
| LNP27 | C2:Chol:DPhyPE + (0:7) PC (DHPC):PCL*** | 49:29.3:10 + 10:1.7 |

***The term "PCL" indicates a lipid of the class "polymer conjugated lipid"

Example 20.2: HEAD Lipids—Synthesis of HEAD Lipids

HEAD lipids were synthesized according to general protocols of ChiroBlock GmbH (Bitterfeld-Wolfen, Germany). In this working example, two HEAD lipids were synthesized (as shown in Table Ex-24 and FIG. 25), see Examples 25 and 26.

TABLE EX-24

Overview of the synthesized HEAD lipids

| Compound name | | Ref. in FIG. 25 | Chemical sum formula | Molecular Weight [g/mol] |
|---|---|---|---|---|
| THIOETHER | VitE-C4DE-Pip-Thioether | FIG. 25A | $C_{84}H_{140}N_2O_{10}S$ | 1370.11 |
| C3SS | VitE-C4DE-Pip-C3SS | FIG. 25B | $C_{86}H_{144}N_2O_{10}S_2$ | 1430.22 |

Purity and structural identity of HEAD lipids was confirmed by nuclear magnetic resonance spectroscopy (H-NMR, 500.13 MHz) and mass spectrometry (electrospray ionization-ESI or atmospheric pressure chemical ionization-APCI, via direct injection).

The NMR data for THIOETHER were as follows:

$^1$H NMR (400 MHz, $C_6D_6$) δ 4.16 (4H), 2.85-2.67 (12H), 2.64-2.52 (8H), 2.44 (4H), 2.35 (6H), 2.23 (12H), 1.84 (4H), 1.64 (16H), 1.55-1.17 (50H), 1.04 (24H)

The NMR data for C3SS were as follows:

$^1$H NMR (400 MHz, $C_6D_6$) δ 4.17 (4H), 2.85-2.71 (12H), 2.63-2.52 (4H), 2.45 (4H), 2.34 (10H), 2.23 (12H), 1.92 (4H), 1.79 (4H), 1.73-1.15 (68H), 1.01 (24H)

Example 20.2.1: Preparation of LNPs Using the NanoAssembr™ Microfluidic System/HEAD Lipids LNP28 to LNP32 were prepared as set out in Example 2.1.1 with the general formulation entitled "Composition B" in Table Ex-7. LNP-C was prepared as set out in Example 2.1.1 with the general formulation entitled "Composition A" in Table Ex-7. Thus, the cationic lipids were formulated as LNP using the NanoAssembr™ microfluidic system (Precision NanoSystems Inc., Vancouver, BC) according to standard protocols.

Example 20.2.2: Biophysical Characterization of Lipid Nanoparticle Compositions/HEAD Lipids The LNPs shown in Table Ex-25 were formulated and characterized along the lines as discussed in Example 2.2.2. The characterization showed that the LNPs of Table Ex-25 exhibited similar characteristics to the LNPs of Example 2.2.2, i.e. the obtained results of the characterization were basically inside the ranges of the LNPs of Example 2.2.2.

TABLE EX-25

Formulation summary of HEAD lipids and a control (LNP-C)

| Name of LNP formulation/ composition designation | Excipients [cationic lipid as disclosed in Table Ex-24:steroid:neutral lipid (optionally two as indicated):polymer conjugated lipid] | mol-percentages for excipients [mol %] |
|---|---|---|
| LNP28 | THIOETHER:Chol:DPhyPE:DMG-PEG 2000 | 59:29.3:10:1.7 |
| LNP29 | C3SS:Chol:DPhyPE:DMG-PEG 2000 | 59:29.3:10:1.7 |
| LNP30 | THIOETHER:Chol:DPhyPE + (0:7) PC (DHPC):DMG-PEG 2000 | 58:29.3:10 + 1:1.7 |
| LNP31 | THIOETHER:Chol:DPhyPE + (0:7) PC (DHPC):DMG-PEG 2000 | 49:29.3:10 + 10:1.7 |
| LNP32 | THIOETHER:Chol:DPhyPE:DMG-PEG 2000 | 49:39.3:10:1.7 |
| LNP-C | CL***:Chol:DSPC:PL*** | 47.4:40.9:10:1.7 |

***The term "CL" indicates a state of the art cationic lipid

***The term "PL" indicates a state of the art polymer conjugated lipid comprising mPEG 2000

TABLE EX-26

Composition and formulation details; further reference is made to descriptions under Example 20.1.1, Example 20.2.2, Table Ex-23, and Table Ex-25 where the mol %-ratios of the compositions are described

| Group | Name of LNP formulation/ composition | mRNA Dose [μg] | Route/ volume | Dosing [day] |
|---|---|---|---|---|
| 1 | LNP28 | 5 | i.m./1 × 25 μl | 0, 21 |
| 2 | LNP29 | 5 | i.m./1 × 25 μl | 0, 21 |
| 3 | LNP19 | 5 | i.m./1 × 25 μl | 0, 21 |
| 4 | LNP20 | 5 | i.m./1 × 25 μl | 0, 21 |
| 5 | LNP21 | 5 | i.m./1 × 25 μl | 0, 21 |
| 6 | LNP24 | 5 | i.m./1 × 25 μl | 0, 21 |
| 7 | LNP23 | 5 | i.m./1 × 25 μl | 0, 21 |
| 8 | LNP22 | 5 | i.m./1 × 25 μl | 0, 21 |
| 9 | PBS only | / | i.m./1 × 25 μl | 0, 21 |

TABLE EX-27

Composition and formulation details; further reference is made to descriptions under Example 20.1.1 and Table Ex-23 where the mol %-ratios of the compositions are described

| Group | Name of LNP formulation/ composition | mRNA Dose [μg] | Route/ volume | Dosing [day] |
|---|---|---|---|---|
| 1 | LNP26 | 5 | i.m./1 × 25 μl | 0, 21 |
| 2 | LNP27 | 5 | i.m./1 × 25 μl | 0, 21 |
| 3 | LNP25 | 5 | i.m./1 × 25 μl | 0, 21 |
| 4 | PBS only | / | i.m./1 × 25 μl | 0, 21 |

Example 21: LNPs of Example 20 for RABV-G Vaccination Using Intramuscular Administration To analyse the immunogenicity of LNPs according to example 20, RABV-G (Rabies Virus Glycoprotein) mRNA was produced according to the procedures described above, yielding a RABV-G mRNA comprising mCap, a muag-3'-UTR; 64× adenosine at the 3-terminal end (polyA-tail); 5 nucleotides, 30× cytosine at the 3-terminal end (polyC-tail) and 5 additional nucleotides (SEQ ID NO:32): 7 weeks old female Balb/C mice (n=8 for each group of Tables Ex-26 and Ex-27; n=6 for each group of Table Ex-28) were injected intramuscularly at day 0 and day 21 with the formulations according to Table Ex-26, Table Ex-27 and Table Ex-28 comprising above described RABV-G mRNA.

TABLE EX-28

Composition and formulation details; further reference is made to descriptions under Example 20.2.2 and Table Ex-25 where the mol %-ratios of the compositions are described

| Group | Name of LNP formulation/ composition | mRNA Dose [μg] | Route/ volume | Dosing [day] |
|---|---|---|---|---|
| 1 | LNP30 | 1 | i.m./1 × 25 μl | 0, 21 |
| 2 | LNP31 | 1 | i.m./1 × 25 μl | 0, 21 |
| 3 | LNP28 | 1 | i.m./1 × 25 μl | 0, 21 |
| 4 | LNP32 | 1 | i.m./1 × 25 μl | 0, 21 |
| 5 | LNP-C | 1 | i.m./1 × 25 μl | 0, 21 |
| 6 | PBS only | / | i.m./1 × 25 μl | 0, 21 |

For determining the levels of antibody against the rabies virus in serum, a classical virus neutralization test was performed (Fluorescent Antibody Virus Neutralization (FAVN) assay) for the groups of Tables Ex-26, Ex-27 and Ex-28.

28 days after the first mRNA administration, mice were sacrificed and blood and organ samples (spleen) were collected for further analysis. In this regard, rabies virus glycoprotein (RABV-G)-specific cellular responses in splenocyte samples obtained in this step were measured as RABV-G-specific T cell activation. This was analyzed by intracellular cytokine staining and subsequent analysis by flow cytometry according to standard protocols as follows: splenocytes were stimulated with a RABV-G peptide cocktail in the presence of anti-CD1O7a (Biolegend, San Diego, USA) and anti-CD28 (BD Biosciences, San Jose, USA). Unstimulated splenocytes were treated the same way but were not supplemented with the peptide cocktail. Additional controls were splenocytes stimulated with PMA/ionomycin (no anti-CD28; PMA and ionomycin from Sigma-Aldrich; Merck KGaA, Darmstadt, Germany) (positive control) and splenocytes which were left unstained by fluorophore-conjugated antibodies (negative control). After the stimulation procedure, splenocytes were stained with surface and intracellular, fluorophore-conjugated antibodies and analysed by flow cytometry.

Serum samples were also taken on day 21 prior to the boost, wherein the serum samples at day 21 were analyzed for Virus neutralizing antibodies (VNA) analysis via FAVN assay. Further, serum samples were taken 18h after first application of the formulation for an early analysis of cytokine levels in the serum of mice immunized with RABV-G-encoding mRNA formulated with LNPs.

For said immunogenicity assays, the VNT was measured as described before, i.e. anti-rabies virus neutralizing titers (VNTs) in serum were analyzed by the Eurovir® Hygiene-Labor GmbH, Germany, using the FAVN assay and the Standard Challenge Virus CVS—11 according to WHO protocol.

A CBA assay was performed with serum samples drawn from mice 18 h after immunization with LNP-formulated antigen-encoding mRNA with the following cytokines/chemokines included in the array: MIG, MCP-1, MIP-1a, MIP-1P, RANTES, IL-12β70, IL-6, TNF, IL-1P, IFN-γ. Furthermore, the level of IFN-α in the serum was determined by ELISA according to standard protocols.

Furthermore, for the groups of Table Ex-26, the spleen samples taken at day 28 were re-stimulated with a RABV-G peptide library and assayed for the T cell response (CD4 and CD8), i.e. CD4 T cell immune response (IFNγ/TNFα producing CD4 T cells) and CD8 T cell immune response (IFNγ/TNFα producing CD8 T cells and CD107+IFNγ producing CD8 T cells); induction of antigen-specific T cells was determined using intracellular cytokine staining (ICS). Assays were performed as described before.

Figure 26:
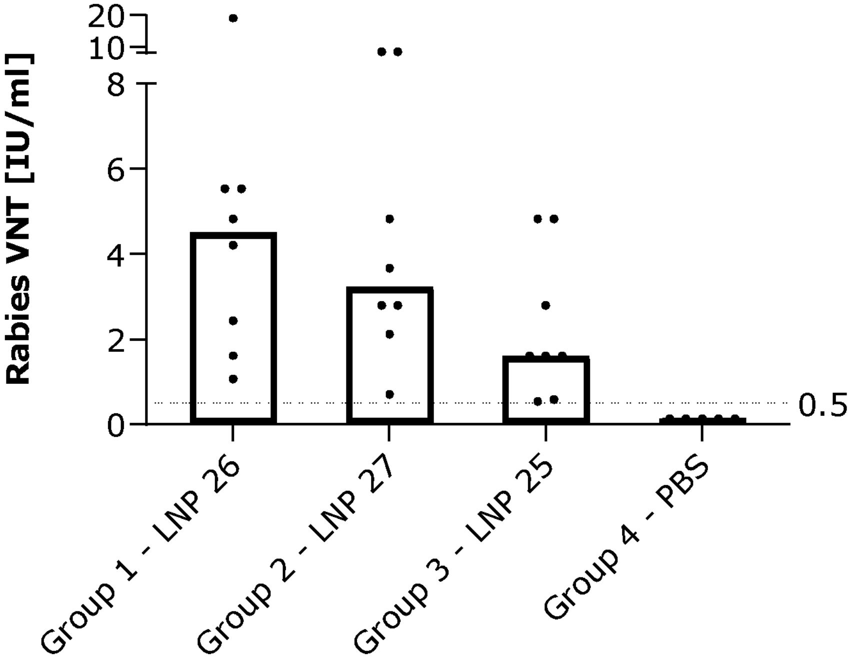
FIG. 26 (Immunogenicity of C2-comprising LNPs in in vivo-T cell response-VNT analysis)—the figure shows that already a single i.m. immunization with 5 μg LNP (comprising C2)-formulated RABV-G-mRNA induced very robust VNTs well above the protective titer of 0.5 IU/ml in all animals at day 21 after prime vaccination. The full details can be found in Example 21.
Figure 27A:
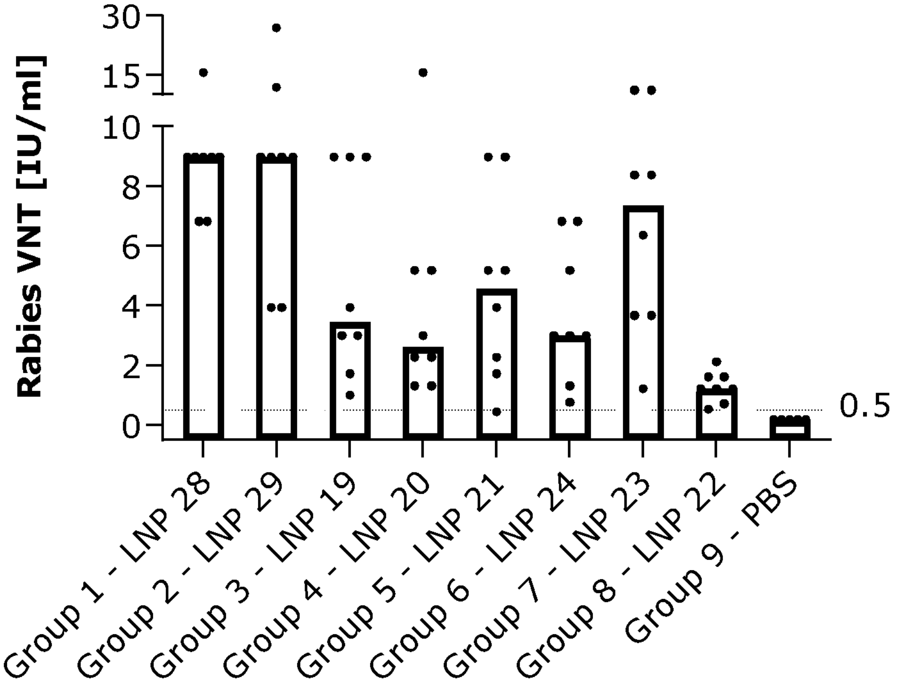
—FIG. 27A shows that already a single i.m. immunization with 5 μg LNP-formulated RABV-G-mRNA induced very robust VNTs well above the protective titer of 0.5 IU/ml in all animals at day 21 after prime vaccination. The LNPs were formulated with different cationic lipids according to the invention as indicated in Example 21.
Figure 27C:
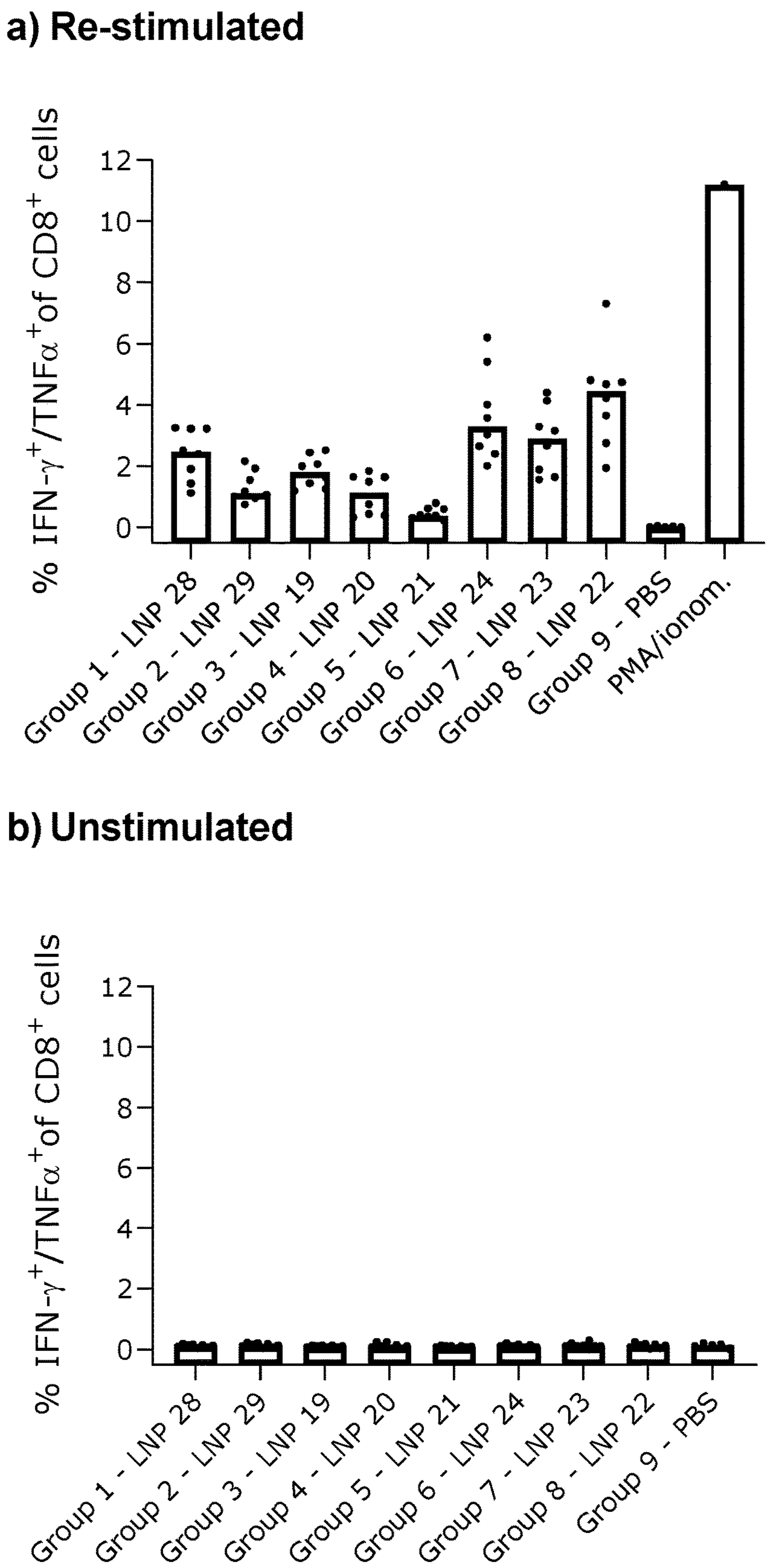
Figure 28:
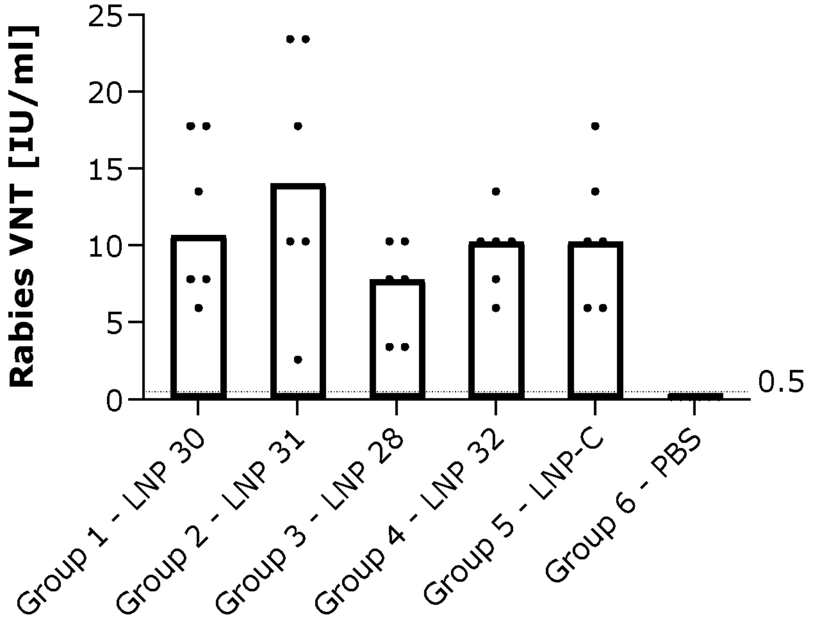
FIG. 28 (Immunogenicity of THIOETHER-comprising LNPs in in vivo-T cell response-VNT analysis)—the figure shows that already a single i.m. immunization with 1 μg LNP (comprising THIOETHER)-formulated RABV-G-mRNA induced very robust VNTs well above the protective titer of 0.5 IU/ml in all animals at day 21 after prime vaccination. The full details can be found in Example 21.

The results are shown in FIG. 26 (relating to the groups of Table Ex-27), in FIGS. 27A, 27B and 27C (relating to the groups of Table Ex-26) as well as in FIG. 28 (relating to the groups of Table Ex-28).

Results:

FIG. 26, FIG. 27A and FIG. 28 show that already a single i.m. immunization with 5 μg RABV-G-mRNA and 1 μg RABV-G-mRNA, respectively, formulated in the LNPs as set out in Table Ex-27 (FIG. 26), Table Ex-26 (FIG. 27A) and Table Ex-28 (FIG. 28) induced very robust VNTs well above the protective titer of 0.5 IU/ml in all animals at day 21 after prime vaccination.

FIGS. 27B and 27C show that the LNP-RABV-G mRNA vaccines of Table Ex-26 induced specific cellular responses after vaccination, namely in spleen cells re-stimulated with a RABV-G peptide library (controls with unstimulated spleen cells are also shown). The effects were not observed in control animals where buffer was injected i.m. RABV-G-specific CD4+ T cells (FIG. 27B) and RABV-G-specific CD8+ T (FIG. 27C) were observed for all formulations.

Example 22: Different LNPs Comprising Lipids of the Present Invention for In Vivo Malaria Vaccination CSP mRNA comprised a 5'-UTR from HSD17B4, a 3'-UTR from PSMB3, 64× adenosine at the 3-terminal end (polyA-tail); 5 nucleotides, 30× cytosine at the 3-terminal end (poly-C-tail)-, a histone-stem loop, and 5 additional nucleotides. The mRNA was further enzymatically capped using ScriptCap™ m7G Capping System (CellScript, Madison,WI., USA) according to the manufacturer's instructions and enzymatically polyadenylated using a commercial polyadenylation kit, resulting in SEQ ID NO:38.

Resulting mRNA constructs were formulated in the lipid nanoparticles as shown in Tables Ex-29 to Ex-31, with the following structures of lipids (all commercially available) referred to therein (see example 20.1.1 for the structure of (07:0) PC (DHPC):

$C_8$-PEG 2000 (N-octanoyl-sphingosine-1-{succinyl [methoxy(polyethylene glycol)2000]}, Avanti Polar Lipids; AlabasterAL.):

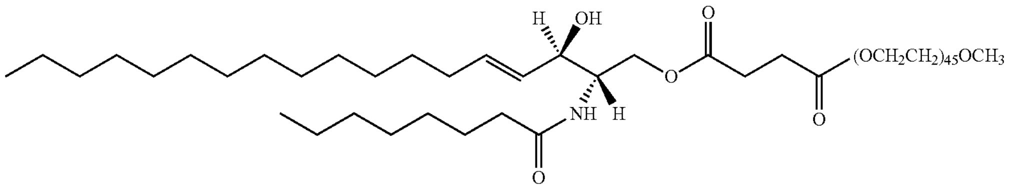

$C_{10}$-PEG 2000 (NOF Corporation, Tokyo, Japan):

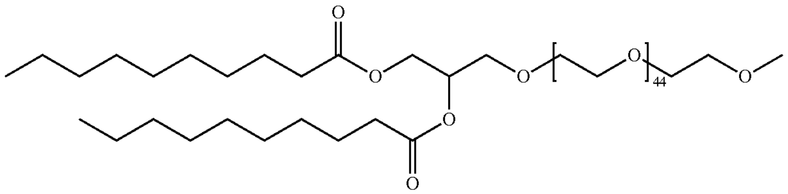

TABLE EX-29

| Formulation of HEXA lipids - reference to the cationic lipids as disclosed in Table 1 is made herein | | |
|---|---|---|
| Name of LNP formulation/ composition | Excipients [cationic lipid as disclosed in Table 1:steroid:neutral lipid (optionally two as indicated):polymer conjugated lipid] | mol-percentages for excipients [mol %] |
| LNP33 | C2:Chol:DPhyPE:$C_8$-PEG 2000 | 59:29.3:10:1.7 |
| LNP34 | C2:Chol:DPhyPE:$C_8$-PEG 2000 | 59:26:10:5 |
| LNP35 | C2:Chol:DPhyPE:$C_{10}$-PEG 2000 | 59:29.3:10:1.7 |
| LNP36 | C2:Chol:DPhyPE:$C_{10}$-PEG 2000 | 59:28:10:3 |
| LNP37 | C2:Chol:DPhyPE + (07:0) PC (DHPC):DMG-PEG 2000 | 59:28.3:10 + 1:1.7 |
| LNP38 | C2:Chol:DPhyPE + (07:0) PC (DHPC):DMG-PEG 2000 | 49:29.3:10 + 10:1.7 |

TABLE EX-30

| Formulation of HEXA lipids - reference to the cationic lipids as disclosed in Table 1 is made herein | | |
|---|---|---|
| Name of LNP formulation/ composition | Excipients [cationic lipid as disclosed in Table 1 or Table Ex-23:steroid:neutral lipid:polymer conjugated lipid] | mol-percentages for excipients [mol %] |
| LNP39 | C15:Chol:DPhyPE:DMG-PEG 2000 | 59:29.3:10:1.7 |
| LNP40 | C16:Chol:DPhyPE:DMG-PEG 2000 | 59:29.3:10:1.7 |
| LNP41 | C17:Chol:DPhyPE:DMG-PEG 2000 | 59:29.3:10:1.7 |
| LNP42 | C18:Chol:DPhyPE:DMG-PEG 2000 | 59:29.3:10:1.7 |
| LNP43 | C22:Chol:DPhyPE:DMG-PEG 2000 | 59:29.3:10:1.7 |

TABLE EX-31

| Formulation of HEAD lipids - reference to the cationic lipids as disclosed in Table Ex-25 is made herein | | |
|---|---|---|
| Name of LNP formulation/ composition | Excipients [cationic lipid as disclosed in Table Ex-25:steroid:neutral lipid (optionally two as indicated):polymer conjugated lipid] | mol-percentages for excipients [mol %] |
| LNP44 | THIOETHER:Chol:DPhyPE + (07:0) PC (DHPC):PLC*** | 58:28.5:10 + 1:2.5 |
| LNP45 | THIOETHER:Chol:DPhyPE + (07:0) PC (DHPC):PLC*** | 49:28.5:10 + 10:2.5 |
| LNP46 | THIOETHER:Chol:DPhyPE:PLC*** | 59:28.5:10:2.5 |
| LNP47 | THIOETHER:Chol:DPhyPE:PLC*** | 49:38.5:10:2.5 |

***PCL indicates a "polymer conjugated lipid"

The LNP formulations according to Tables Ex-29 and Ex-30 and some of Ex-25 were applied on days 0 and 21 intramuscularly (im.; musculus tibialis) with doses of RNA, formulations, and control groups as shown in Tables Ex-32 to Ex-34. A negative control group received buffer only. Serum samples were taken at day 21 and day 35 for ELISA.

TABLE EX 32

Vaccination scheme for LNPs according to Table Ex-29

| Group | No. of mice | RNA Treatment | Formulation | mRNA | Dose | Route | Volume |
|---|---|---|---|---|---|---|---|
| 1 | 6 | mRNA encoding CSP | LNP33 | CSP | 1 μg | i.m. | 1 × 25 μl |
| 2 | 6 | mRNA encoding CSP | LNP34 | CSP | 1 μg | i.m. | 1 × 25 μl |
| 3 | 6 | mRNA encoding CSP | LNP35 | CSP | 1 μg | i.m. | 1 × 25 μl |
| 4 | 6 | mRNA encoding CSP | LNP36 | CSP | 1 μg | i.m. | 1 × 25 μl |
| 5 | 6 | mRNA encoding CSP | LNP37 | CSP | 1 μg | i.m. | 1 × 25 μl |
| 6 | 6 | mRNA encoding CSP | LNP38 | CSP | 1 μg | i.m. | 1 × 25 μl |
| 7 | 6 | mRNA encoding CSP | GN02 | CSP | 1 μg | i.m. | 1 × 25 μl |
| 8 | 6 | n.a.: buffer only | n.a. | n.a. | | i.m. | 1 × 25 μl |

TABLE EX 33

Vaccination scheme for LNPs according to Table Ex-30

| Group | No. of mice | RNA Treatment | Formulation | mRNA | Dose | Route | Volume |
|---|---|---|---|---|---|---|---|
| 1 | 6 | mRNA encoding CSP | LNP39 | CSP | 1 μg | i.m. | 1 × 25 μl |
| 2 | 6 | mRNA encoding CSP | LNP40 | CSP | 1 μg | i.m. | 1 × 25 μl |
| 3 | 6 | mRNA encoding CSP | LNP41 | CSP | 1 μg | i.m. | 1 × 25 μl |
| 4 | 6 | mRNA encoding CSP | LNP42 | CSP | 1 μg | i.m. | 1 × 25 μl |
| 5 | 6 | mRNA encoding CSP | LNP43 | CSP | 1 μg | i.m. | 1 × 25 μl |
| 6 | 6 | mRNA encoding CSP | GN02 | CSP | 1 μg | i.m. | 1 × 25 μl |
| 7 | 6 | n.a.: buffer only | n.a. | n.a. | | i.m. | 1 × 25 μl |

TABLE EX 34

Vaccination scheme for some of the LNPs according to Table Ex-25

| Group | No. of mice | RNA Treatment | Formulation | mRNA | Dose | Route | Volume |
|---|---|---|---|---|---|---|---|
| 1 | 6 | mRNA encoding CSP | LNP28 | CSP | 1 μg | i.m. | 1 × 25 μl |
| 2 | 6 | mRNA encoding CSP | LNP32 | CSP | 1 μg | i.m. | 1 × 25 μl |
| 3 | 6 | mRNA encoding CSP | LNP-C | CSP | 1 μg | i.m. | 1 × 25 μl |
| 4 | 6 | n.a.: buffer only | n.a. | n.a. | | i.m. | 1 × 25 μl |

TABLE EX 35

Vaccination scheme for some of the LNPs according to Table Ex-25

| Group | No. of mice | RNA Treatment | Formulation | mRNA | Dose | Route | Volume |
|---|---|---|---|---|---|---|---|
| 1 | 6 | mRNA encoding CSP | LNP30 | CSP | 1 μg | i.m. | 1 × 25 μl |
| 2 | 6 | mRNA encoding CSP | LNP31 | CSP | 1 μg | i.m. | 1 × 25 μl |
| 3 | 6 | mRNA encoding CSP | LNP28 | CSP | 1 μg | i.m. | 1 × 25 μl |
| 4 | 6 | mRNA encoding CSP | LNP32 | CSP | 1 μg | i.m. | 1 × 25 μl |
| 5 | 6 | mRNA encoding CSP | LNP-C | CSP | 1 μg | i.m. | 1 × 25 μl |
| 6 | 6 | n.a.: buffer only | n.a. | n.a. | | i.m. | 1 × 25 μl |

Figure 31:
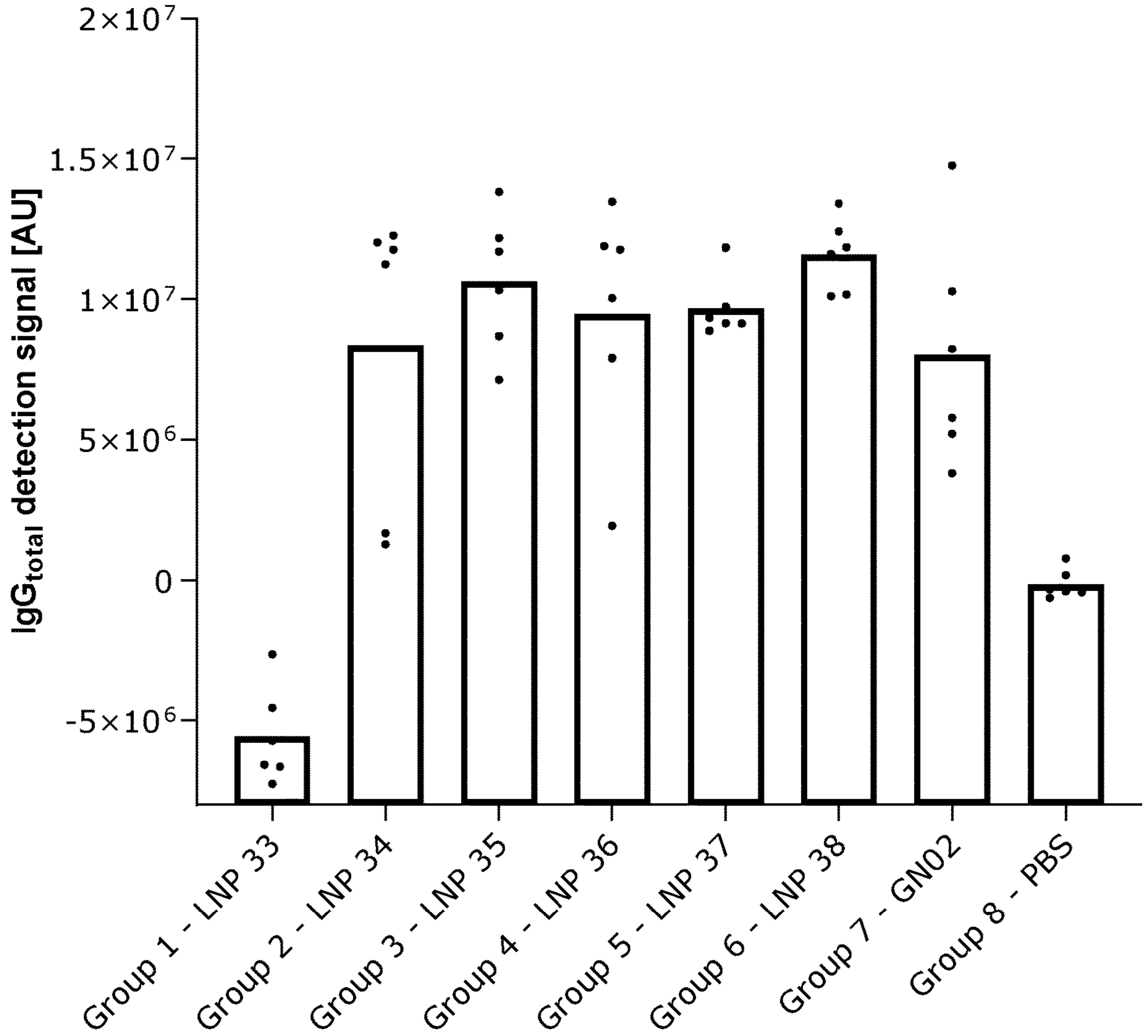
FIG. 31 (GNO2-like LNPs for in vivo Malaria vaccination—$IgG_{total}$ titer)—shows that GNO2-like formulated mRNA Malaria vaccine encoding CSP induced very strong humoral immune responses in mice, using an ELISA assay (coating: $[NANP]_7$ peptide, $IgG_{total}$ endpoint titers at day 35 post prime (full details can be found in Example 22).
Figure 34:
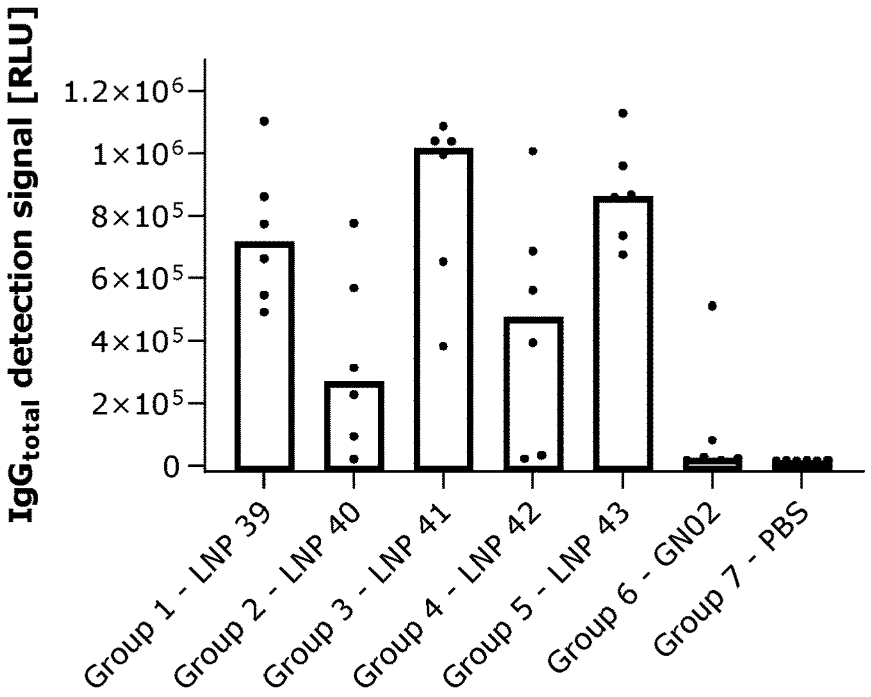
FIG. 34 (LNPs with different cationic lipids of the invention for in vivo Malaria vaccination—$IgG_{total}$ titer)—shows that LNP formulated mRNA Malaria vaccine encoding CSP induced very strong humoral immune responses in mice, using an ELISA assay (coating: $[NANP]_7$ peptide, $IgG_{total}$ endpoint titers at day 35 post prime (full details can be found in Example 22).
Figure 35:
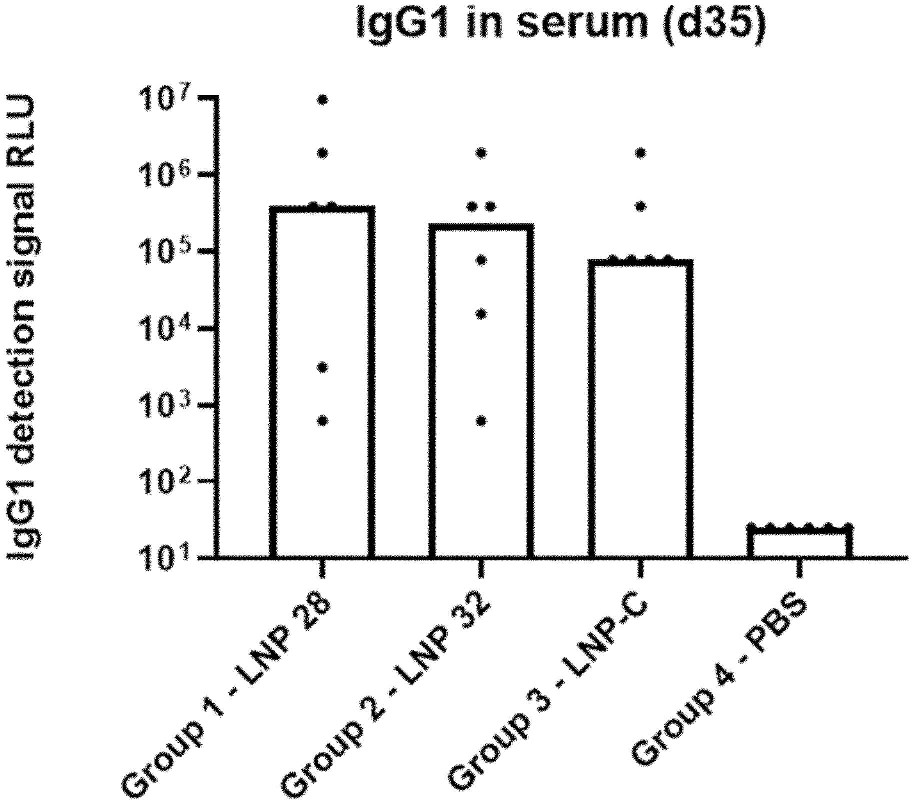
FIG. 35 (LNPs with the C26-lipid of the invention for in vivo Malaria vaccination—IgG1 titer)—shows that LNP formulated mRNA Malaria vaccine encoding CSP induced very strong humoral immune responses in mice, using an ELISA assay (coating: $[NANP]_7$ peptide, IgG1 endpoint titers at day 35 post prime (full details can be found in Example 22).

Determination of Specific Humoral Immune Responses by ELISA:

ELISA was performed using malaria $[NANP]_7$ peptide for coating. Coated plates were incubated using respective serum dilutions, and binding of specific antibodies to the respective malaria $[NANP]_7$ peptide were detected using biotinylated isotype specific anti-mouse antibodies followed by streptavidin-HRP (horse radish peroxidase) with Amplex™ Red Reagent as substrate. Endpoint titers of antibodies (total IgG or IgG as indicated in the respective Figures) directed against the malaria $[NANP]_7$ peptide were measured by ELISA on day 35 post prime. Results are shown in FIGS. 31, 34 and 35.

Intracellular Cytokine Staining:

Splenocytes from vaccinated mice were isolated on day 35 according to a standard protocol known in the art. Briefly, isolated spleens were grinded through a cell strainer and washed in PBS/1% FBS followed by red blood cell lysis. After an extensive washing step with PBS/1% FBS, splenocytes were seeded into 96-well plates ($2\times10^6$ cells per well). Cells were stimulated with a mixture of CSP peptides (1 μg/ml) in the presence of 2.5 μg/ml of an anti-CD28 antibody (BD Biosciences) and a protein transport inhibitor for 6h at 37° C. After stimulation, cells were washed and stained for intracellular cytokines using the Cytofix/Cytoperm™ reagent (BD Biosciences) according to the manufacturer's instructions. The following antibodies were used for staining: Thy1.2-FITC (1:100), CD8-PE-Cy7 (1:200), TNF-PE (1:100), IFNγ-APC (1:100) (eBioscience), CD4-BD Horizon V450 (1:200) (BD Biosciences) and incubated with Fcγ-block diluted 1:100. Aqua Dye was used to distinguish live/dead cells (Invitrogen). Cells were acquired using a BD FACS Canto II flow cytometer (Becton Dickinson). Flow cytometry data was analyzed using FlowJo software (Tree Star, Inc.). Results are shown in FIGS. 29, 30, 32 and 33.

Results:

As shown in FIGS. 31, 34 and 35, the LNP formulated CSP mRNA vaccine induced strong, humoral immune responses in mice (except for the LNP33-formulation, see FIG. 31). It is noted that the IgG1-concentrations for the C26-lipid comprising LNPs (LNP28 and LNP32) were higher compared to a state of the art LNP formulation (LNP-C), see FIG. 35.

As shown in FIGS. 29, 30, 32 and 33, the LNP formulated CSP mRNA vaccine induced cellular immune responses in mice (CD4+[FIGS. 29 and 32] and CD8+[FIGS. 30 and 33] T-cell responses).

As CD8+ T cells are a major protective immune mechanism against intracellular infections caused by Malaria parasites, an effective Malaria vaccine should induce strong CD8+ T cells responses. Accordingly, these findings highlight one of the advantageous features of the inventive GN01 formulation.

Example 23: Synthesis of HEXA-C5DE-Inverted-PipSS

For the synthesis of HEXA-C5DE-inverted-PipSS, alkylation of potassium thioacetate with tosylate 11 afforded thioacetate derivative 12 in a quantitative yield. Formation of disulfide derivative 13 was achieved with aqueous NaOH in MeOH and after purification 13 was obtained in 80%. Boc-deprotection with HCl gave 14 in quantitative yield. Direct alkylation with 2-bromoethanol to compound 16 failed. Therefore reductive alkylation of 14 with aldehyde 19 was carried out and afforded TBDMS-protected diol 16' in 37-45%. Subsequent deprotection with TBAF gave clean conversion to 16. Because the product could not be separated completely from residual TBA-salts, it was used in the final coupling with carboxylic acid 21 as such. This carboxylic acid was prepared by treatment of alcohol 20 with glutaric anhydride and afforded 21 in 34-40%. The final coupling of 21 and 16 was successfully tested and gave HEXA-C5DE-inverted-PiPSS, although it was isolated in low yield (23%) and insufficient purity. Scale-up initially gave HEXA-C5DE-inverted-PiPSS in only 9%. But from the extraction step on large scale, material was isolated from the MeCN-layer that contained the intermediate in which only one acid moiety was coupled to 16. This material was successfully re-used in the coupling towards final product using the same conditions and purification of this material together with the impure batches afforded HEXA-C5DE-inverted-PiPSS in 43% and desired purity.

Reaction scheme

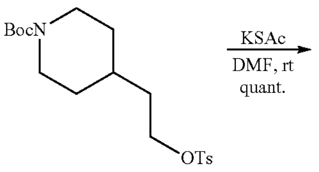

11

-continued

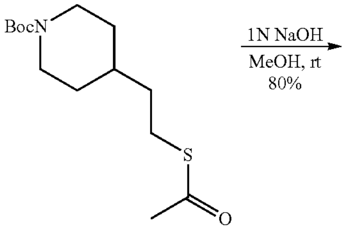

12

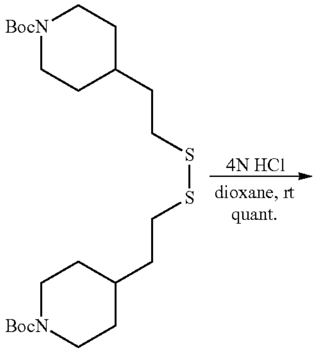

13

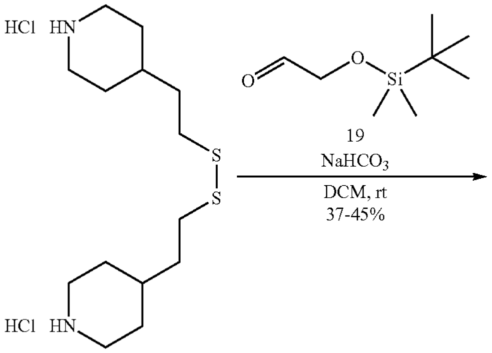

14

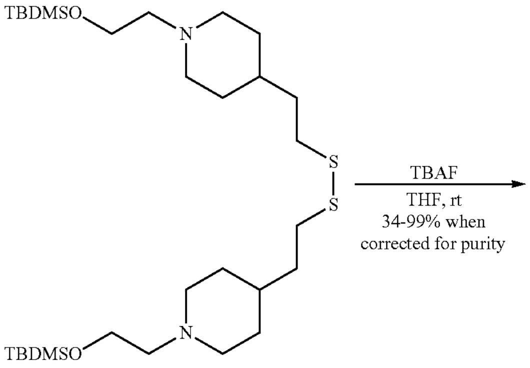

16'

-continued

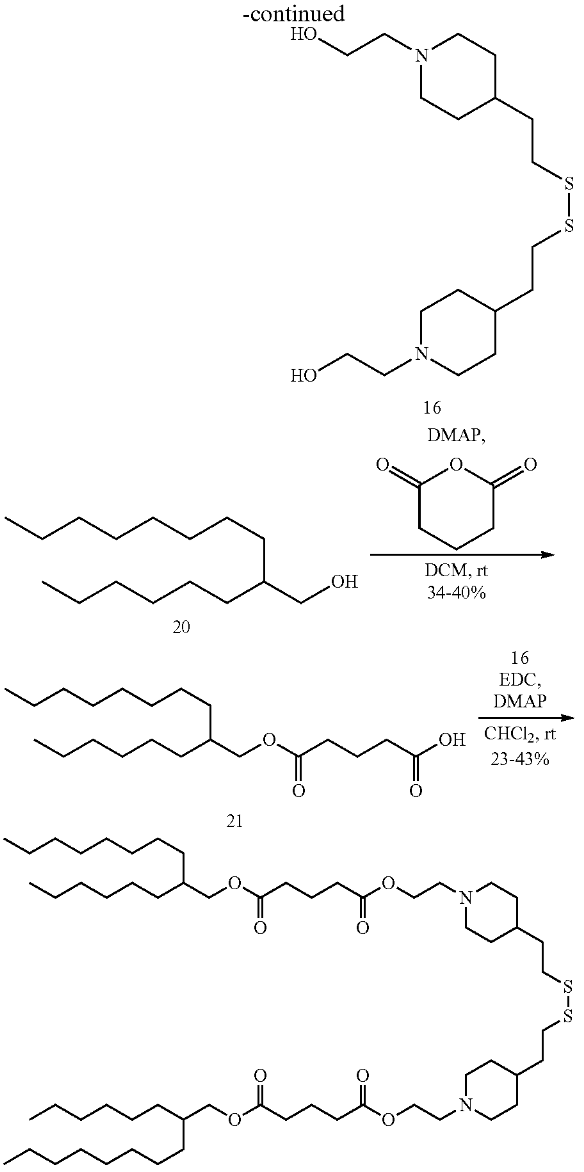

Example 24: Synthesis of HEXA-C5DE-Pip-C3 Thioether

The route towards HEXA-C5DE-Pip-C3 thioether started with mesylation of diol 22, which provided bismesylated derivative 23 in 99%. Subsequent substitution gave bisamine 24 in 68%. The final esterification with carboxylic acid 21 gave HEXA-C5DE-Pip-C3 thioether in 23% after extraction and flash chromatography.

Reaction scheme

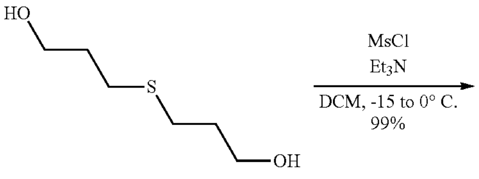

22

-continued

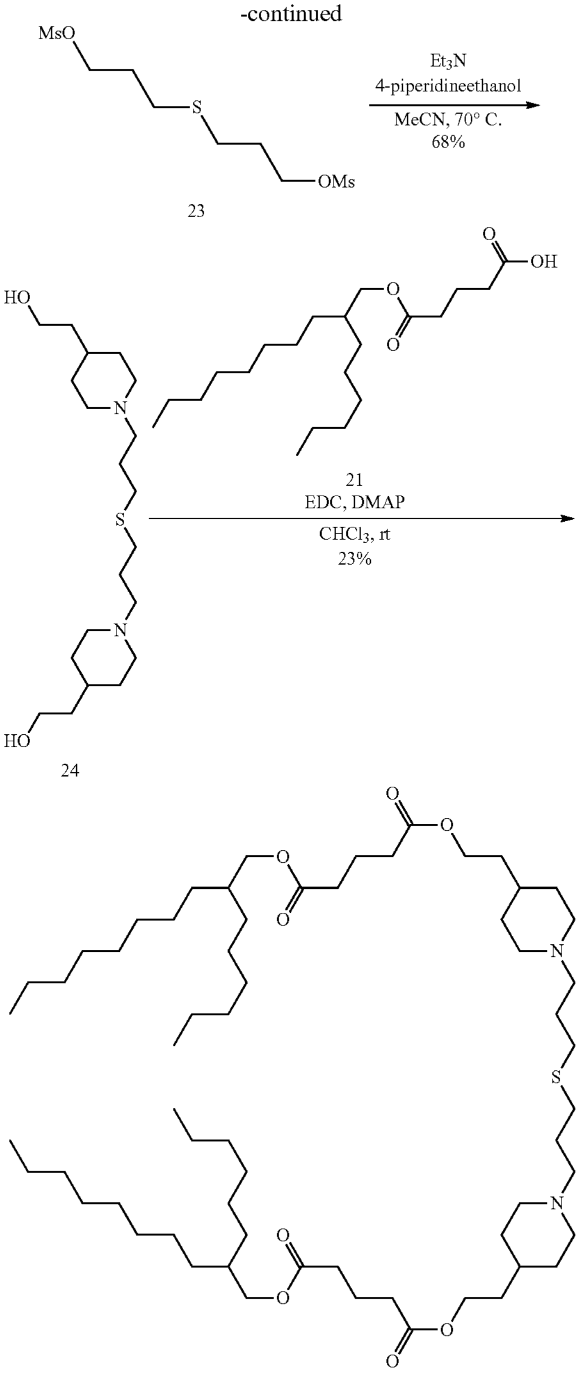

Example 25: Synthesis of THIOETHER

For the synthesis of THIOETHER, coupling of dicarboxylic acid derivative 3 and 4-piperidineethanol gave bisamide 4 in 86%. Subsequent reduction with $LiAlH_4$ afforded 5 in 24% after purification by flash chromatography. Final coupling with commercially available Vitamin E derivative 6 gave THIOETHER in 52%, which was purified by extraction between heptane and MeCN, followed by flash chromatography.

Reaction scheme
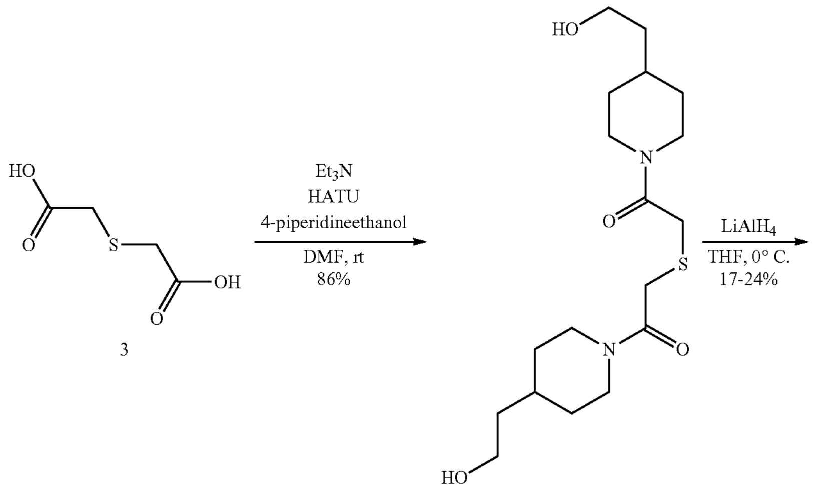
3
4
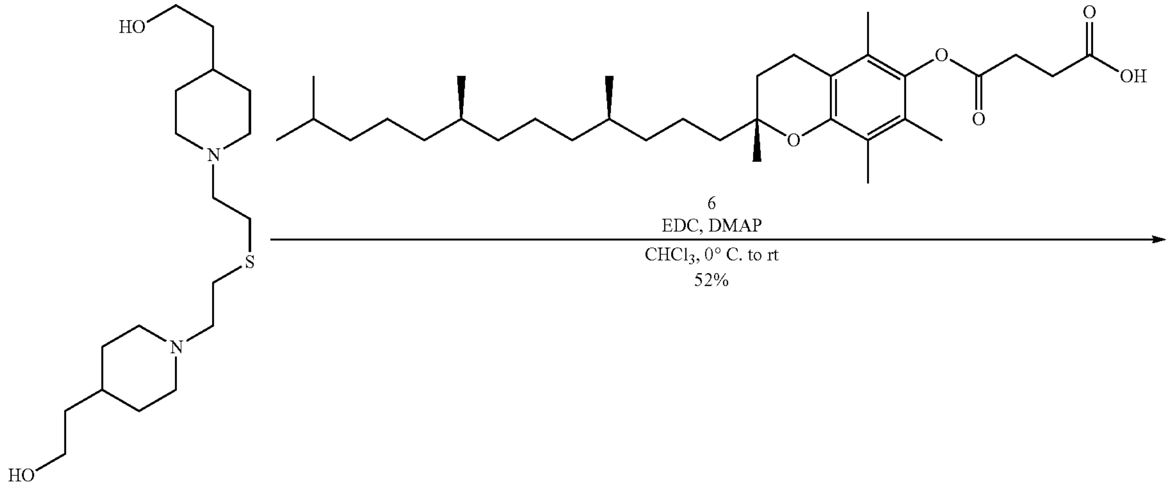
5

-continued
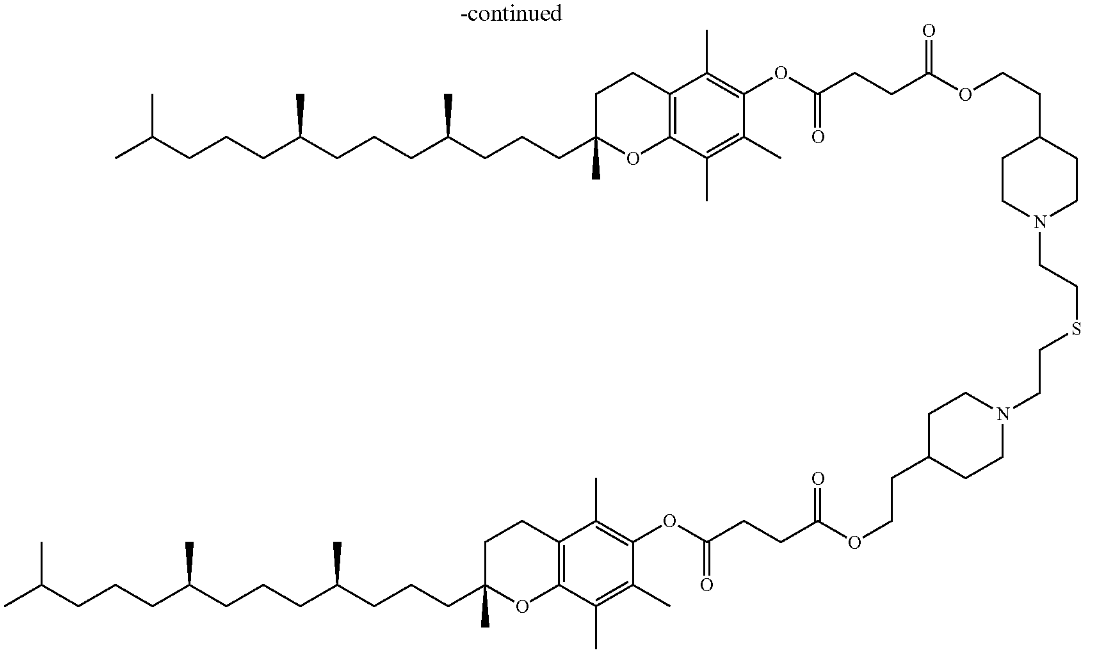
Example 26: Synthesis of C3SS
The route towards C3SS started with dimerization of 7, which afforded 8 in quantitative yield. Mesylation gave 9 in 70% after purification by flash chromatography. Coupling with 4-piperdineethanol yielded 10 in 33%. Subsequent coupling with 6 afforded C3SS in 51% after extraction and flash purification.
Reaction scheme
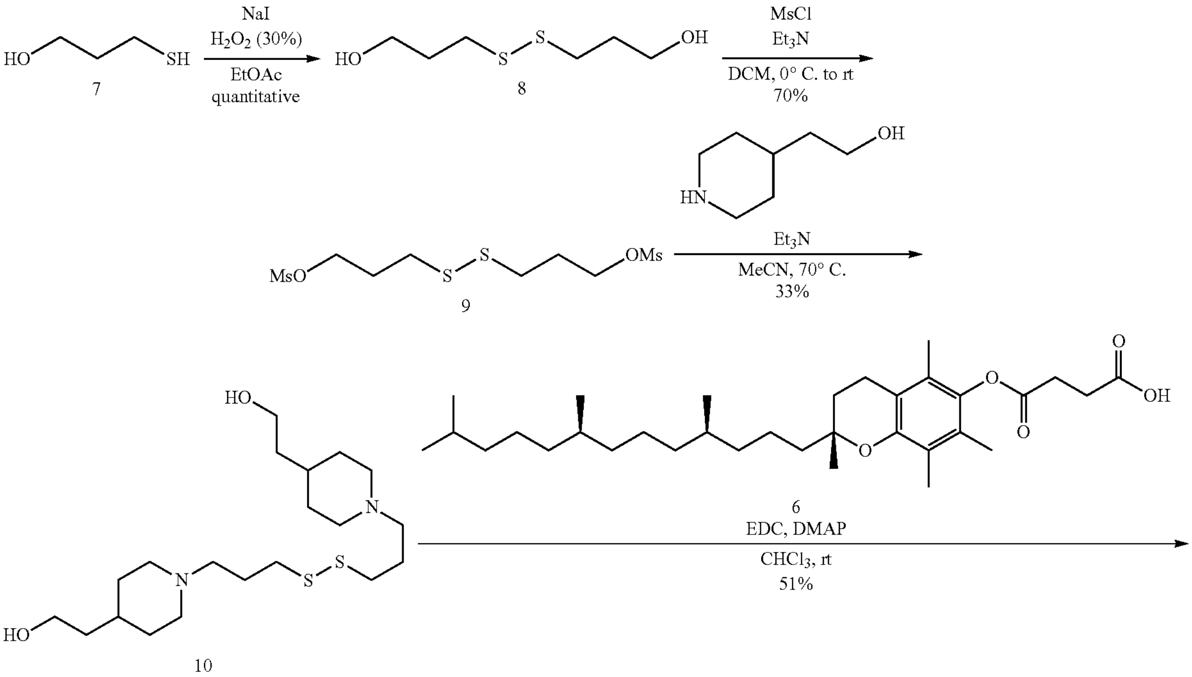

-continued

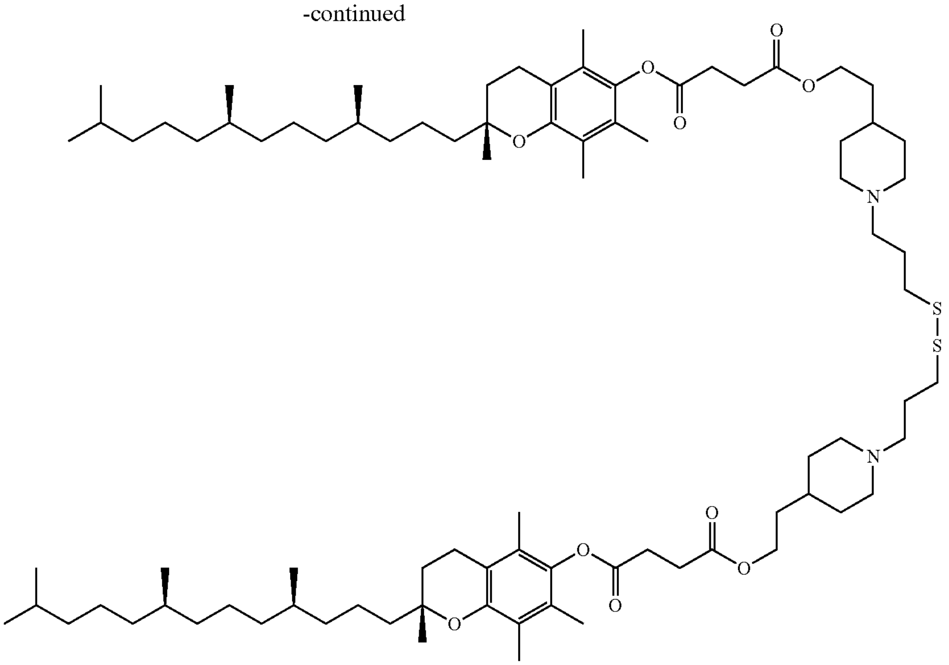

Example P1: Intramuscular Injections in Rabbits Yield High Antibody Levels HEXA JET Injection Rabbits are injected i.m. with different mRNA encoded antibodies formulated in GN01 LNPs and LNPs based on above described HEXA and HEAD lipids. For injection, conventional needle injection or needle-free injection are applied; needle-free injection is performed by using jet injection (PharmaJet i.m. device).

Each Group consists of 10 animals. Rabbits are bled at 10 time points: day 0 (before injection), day 1, day 3, day 5, day 7, day 9, day 11, day 14, day 21, day 28. To assess IgG concentration in serum, a human Fc-specific ELISA serves as readout of produced antibodies (IgG ELISA).

Example P2: In Vivo Effect of Polymer Conjugated Lipid Component after Intradermal and Intramuscular Injections in Mice To analyse the effect of PEG components in vivo, the LNPs from Example 7 are used analogously in an in vivo setting. Instead of PpLuc, hEpo mRNA as described above is used as cargo. For in vivo analysis, six to eight weeks old Balb/C mice (5 mice per group) are injected with 0.5 mg/kg LNP formulated hEpo. EDTA plasma sampling is performed 6h and 24h after injection; one group is administered with hEpo via intradermal route and another group is administered with hEpo via intramuscular route.

Results:

In vivo analysis confirms the results of the in vitro experiments shown in Example 7, i.e. a distinct effect of polymer conjugated lipids having shorter alkyl chains (Ca) i.e. higher hEpo expression at 6h and 24h post injection is shown.

Example P3

The following vaccines are formulated with a standard mRNA used in in vivo vaccination assays and tested for in vivo vaccination in mice.

TABLE P-1

Vaccination scheme for LNPs according to Table Ex-2, Table Ex-8 and Table Ex-25

| Group | No. of mice | RNA Treatment | Formulation | mRNA | Dose | Route | Volume |
|---|---|---|---|---|---|---|---|
| 1 | 6 | Standard mRNA | GN01** | Vaccine | 1 μg | i.m. | 1 × 25 μl |
| 2 | 6 | Standard mRNA | GN02** | Vaccine | 1 μg | i.m. | 1 × 25 μl |
| 3 | 6 | Standard mRNA | CISE*** | Vaccine | 1 μg | i.m. | 1 × 25 μl |
| 4 | 6 | Standard mRNA | LNP-C**** | Vaccine | 1 μg | i.m. | 1 × 25 μl |
| 5 | 6 | n.a.: buffer only | n.a. | n.a. | | i.m. | 1 × 25 μl |

**See Table Ex-2

***See Table Ex-8: "composition B", GN-CISE-001:Chol:DPhyPE:DMG-PEG 2000

****See Table Ex-25

The invention claimed is:

1. A composition comprising the cationic lipid of:

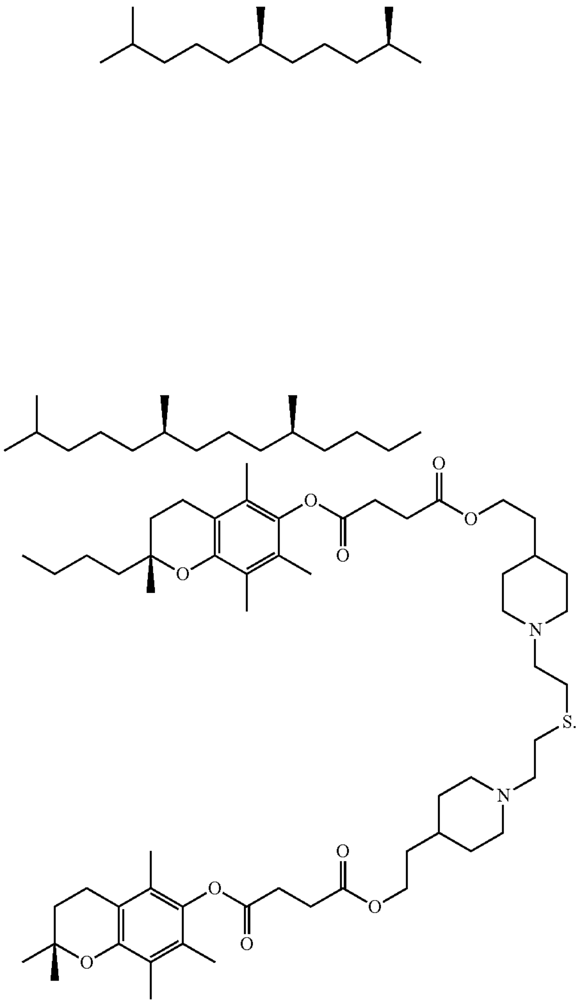

2. The composition of claim 1, further comprising one or more of the following excipients:

(i) a steroid;

(ii) a neutral lipid; and/or (iii) a polymer conjugated lipid.

3. The composition of claim 2, further comprising a RNA.

4. A kit or kit of parts, comprising the composition of claim 3, and technical instructions providing information on administration and dosage of the components.

5. The composition of claim 2, wherein the composition comprises:

(i) a steroid;

(ii) a neutral lipid; and (iii) a polymer conjugated lipid.

6. The composition of claim 5, wherein the composition comprises lipid nanoparticles (LNPs).

7. The composition of claim 6, wherein the steroid is cholesterol.

8. The composition of claim 7, wherein the neutral lipid is a zwitterionic compound.

9. The composition of claim 6, wherein the neutral lipid comprises 1,2-diphytanoyl-sn-glycero-3-phosphoethanolamine (DPhyPE).

10. The composition of claim 6, wherein the composition further comprises 1,2-diheptanoyl-sn-glycero-3-phosphocholine (DHPC).

11. The composition of claim 6, wherein the polymer conjugated lipid is a compound according to formula (II):

P-A-L formula (II);

wherein P is a hydrophilic polymer moiety, A is an optional linker, and L is a lipid moiety.

12. The composition of claim 6, wherein the polymer conjugated lipid is a pegylated lipid.

13. The composition of claim 6, wherein the cationic lipid, the steroid, the neutral lipid and the polymer conjugated lipid are present in the composition in the following molar ratio: the cationic lipid at an amount of 30-70 mol %; the steroid at an amount of 20-50 mol %; the neutral lipid at an amount of 5-25 mol %; and the polymer conjugated lipid at an amount of 0.5-5 mol %.

14. The composition of claim 6, further comprising RNA in association with the LNPs.

15. The composition of claim 14, wherein the RNA is mRNA.

16. The composition of claim 14, wherein the RNA is self-replicating RNA.

17. The composition of claim 14, wherein the LNPs comprise the RNA in an amount such as to achieve an N/P ratio in the range of 10 to 20.

18. The composition of claim 14, wherein the LNPs comprise the RNA in an amount such as to achieve a lipid: RNA weight ratio in the range of 20 to 60.

19. The composition of claim 14, wherein the LNPs have a mean hydrodynamic diameter as determined by dynamic laser scattering from about 50 nm to about 300 nm.

20. The composition of claim 14, wherein the LNPs wherein the lipid nanoparticles exhibit a zeta potential in the range of −50 mV to +50 mV.

* * * * *

SEQUENCE LISTING

<160> NUMBER OF SEQ ID NOS: 71

<210> SEQ ID NO 1
<211> LENGTH: 13
<212> TYPE: DNA
<213> ORGANISM: Artificial Sequence
<220> FEATURE:
<223> OTHER INFORMATION: Kozak sequence

<400> SEQUENCE: 1
gccgccacca tgg 13

<210> SEQ ID NO 2
<211> LENGTH: 13
<212> TYPE: RNA
<213> ORGANISM: Artificial Sequence
<220> FEATURE:
<223> OTHER INFORMATION: Kozak sequence

<400> SEQUENCE: 2
gccgccacca ugg 13

<210> SEQ ID NO 3
<211> LENGTH: 24
<212> TYPE: DNA
<213> ORGANISM: Artificial Sequence
<220> FEATURE:
<223> OTHER INFORMATION: histone stem-loop

<400> SEQUENCE: 3
caaaggctct tttcagagcc acca 24

<210> SEQ ID NO 4
<211> LENGTH: 24
<212> TYPE: RNA
<213> ORGANISM: Artificial Sequence
<220> FEATURE:
<223> OTHER INFORMATION: histone stem-loop

<400> SEQUENCE: 4
caaaggcucu uuucagagcc acca 24

<210> SEQ ID NO 5
<211> LENGTH: 110
<212> TYPE: DNA
<213> ORGANISM: Artificial Sequence
<220> FEATURE:
<223> OTHER INFORMATION: HBA1 3'-UTR

<400> SEQUENCE: 5
gctggagcct cggtggccat gcttcttgcc ccttgggcct ccccccagcc cctcctcccc 60
ttcctgcacc cgtacccccg tggtctttga ataaagtctg agtgggcggc 110

<210> SEQ ID NO 6
<211> LENGTH: 110
<212> TYPE: RNA
<213> ORGANISM: Artificial Sequence
<220> FEATURE:
<223> OTHER INFORMATION: HBA1 3'-UTR

<400> SEQUENCE: 6
gcuggagccu cgguggccau gcuucuugcc ccuugggccu ccccccagcc ccuccucccc 60
uuccugcacc cguacccccg uggucuuuga auaaagucug agugggcggc 110

<210> SEQ ID NO 7
<211> LENGTH: 108
<212> TYPE: DNA
<213> ORGANISM: Artificial Sequence
<220> FEATURE:
<223> OTHER INFORMATION: HBA2 3'-UTR

<400> SEQUENCE: 7
gctggagcct cggtagccgt tcctcctgcc cgctgggcct cccaacgggc cctcctcccc 60
tccttgcacc ggcccttcct ggtctttgaa taaagtctga gtgggcag 108

<210> SEQ ID NO 8
<211> LENGTH: 108
<212> TYPE: RNA
<213> ORGANISM: Artificial Sequence
<220> FEATURE:
<223> OTHER INFORMATION: HBA2 3'-UTR

<400> SEQUENCE: 8
gcuggagccu cgguagccgu uccuccugcc cgcugggccu cccaacgggc ccuccucccc 60
uccuugcacc ggcccuuccu ggucuuugaa uaaagucuga gugggcag 108

<210> SEQ ID NO 9
<211> LENGTH: 132
<212> TYPE: DNA
<213> ORGANISM: Artificial Sequence
<220> FEATURE:
<223> OTHER INFORMATION: HBB 3'-UTR

<400> SEQUENCE: 9
gctcgctttc ttgctgtcca atttctatta aaggttcctt tgttccctaa gtccaactac 60
taaactgggg gatattatga agggccttga gcatctggat tctgcctaat aaaaaacatt 120
tattttcatt gc 132

<210> SEQ ID NO 10
<211> LENGTH: 132
<212> TYPE: RNA
<213> ORGANISM: Artificial Sequence
<220> FEATURE:
<223> OTHER INFORMATION: HBB 3'-UTR

<400> SEQUENCE: 10
gcucgcuuuc uugcugucca auuucuauua aagguuccuu uguucccuaa guccaacuac 60
uaaacugggg gauauuauga agggccuuga gcaucuggau ucugccuaau aaaaaacauu 120
uauuuucauu gc 132

<210> SEQ ID NO 11
<211> LENGTH: 44
<212> TYPE: DNA
<213> ORGANISM: Artificial Sequence
<220> FEATURE:
<223> OTHER INFORMATION: muag 3'-UTR

<400> SEQUENCE: 11
gcccgatggg cctcccaacg ggccctcctc ccctccttgc accg 44

<210> SEQ ID NO 12
<211> LENGTH: 44
<212> TYPE: RNA
<213> ORGANISM: Artificial Sequence
<220> FEATURE:
<223> OTHER INFORMATION: muag 3'-UTR

<400> SEQUENCE: 12
gcccgauggg ccucccaacg ggcccuccuc cccuccuugc accg 44

<210> SEQ ID NO 13
<211> LENGTH: 186
<212> TYPE: DNA
<213> ORGANISM: Artificial Sequence
<220> FEATURE:
<223> OTHER INFORMATION: albumin 3'-UTR

<400> SEQUENCE: 13
catcacattt aaaagcatct cagcctacca tgagaataag agaaagaaaa tgaagatcaa 60
aagcttattc atctgttttt ctttttcgtt ggtgtaaagc caacaccctg tctaaaaaac 120
ataaatttct ttaatcattt tgcctctttt ctctgtgctt caattaataa aaaatggaaa 180
gaatct 186

<210> SEQ ID NO 14
<211> LENGTH: 186
<212> TYPE: RNA
<213> ORGANISM: Artificial Sequence
<220> FEATURE:
<223> OTHER INFORMATION: albumin 3'-UTR

<400> SEQUENCE: 14
caucacauuu aaaagcaucu cagccuacca ugagaauaag agaaagaaaa ugaagaucaa 60
aagcuuauuc aucuguuuuu cuuuuucguu gguguaaagc caacacccug ucuaaaaaac 120
auaaauuucu uuaaucauuu ugccucuuuu cucugugcuu caauuaauaa aaaauggaaa 180
gaaucu 186

<210> SEQ ID NO 15
<211> LENGTH: 186
<212> TYPE: DNA
<213> ORGANISM: Artificial Sequence
<220> FEATURE:
<223> OTHER INFORMATION: albumin7 3'-UTR

<400> SEQUENCE: 15
catcacattt aaaagcatct cagcctacca tgagaataag agaaagaaaa tgaagatcaa 60
tagcttattc atctcttttt ctttttcgtt ggtgtaaagc caacaccctg tctaaaaaac 120
ataaatttct ttaatcattt tgcctctttt ctctgtgctt caattaataa aaaatggaaa 180
gaacct 186

<210> SEQ ID NO 16
<211> LENGTH: 186
<212> TYPE: RNA
<213> ORGANISM: Artificial Sequence
<220> FEATURE:
<223> OTHER INFORMATION: albumin7 3'-UTR

<400> SEQUENCE: 16
caucacauuu aaaagcaucu cagccuacca ugagaauaag agaaagaaaa ugaagaucaa 60
uagcuuauuc aucucuuuuu cuuuuucguu gguguaaagc caacacccug ucuaaaaaac 120
auaaauuucu uuaaucauuu ugccucuuuu cucugugcuu caauuaauaa aaaauggaaa 180
gaaccu 186

<210> SEQ ID NO 17
<211> LENGTH: 187

<212> TYPE: DNA
<213> ORGANISM: Artificial Sequence
<220> FEATURE:
<223> OTHER INFORMATION: ALB7 3'-UTR

<400> SEQUENCE: 17
gcatcacatt taaaagcatc tcagcctacc atgagaataa gagaaagaaa atgaagatca 60
atagcttatt catctctttt tctttttcgt tggtgtaaag ccaacaccct gtctaaaaaa 120
cataaatttc tttaatcatt ttgcctcttt tctctgtgct tcaattaata aaaaatggaa 180
agaacct 187

<210> SEQ ID NO 18
<211> LENGTH: 187
<212> TYPE: RNA
<213> ORGANISM: Artificial Sequence
<220> FEATURE:
<223> OTHER INFORMATION: ALB7 3'-UTR

<400> SEQUENCE: 18
gcaucacauu uaaaagcauc ucagccuacc augagaauaa gagaaagaaa augaagauca 60
auagcuuauu caucucuuuu ucuuuuucgu ugguguaaag ccaacacccu gucuaaaaaa 120
cauaaauuuc uuuaaucauu uugccucuuu ucucugugcu ucaauuaaua aaaaauggaa 180
agaaccu 187

<210> SEQ ID NO 19
<211> LENGTH: 57
<212> TYPE: DNA
<213> ORGANISM: Artificial Sequence
<220> FEATURE:
<223> OTHER INFORMATION: PSMB3 3'-UTR

<400> SEQUENCE: 19
ccctgttccc agagcccact ttttttctt tttttgaaat aaaatagcct gtctttc 57

<210> SEQ ID NO 20
<211> LENGTH: 57
<212> TYPE: RNA
<213> ORGANISM: Artificial Sequence
<220> FEATURE:
<223> OTHER INFORMATION: PSMB3 3'-UTR

<400> SEQUENCE: 20
cccuguuccc agagcccacu uuuuuucuu uuuuugaaau aaaauagccu gucuuuc 57

<210> SEQ ID NO 21
<211> LENGTH: 62
<212> TYPE: DNA
<213> ORGANISM: Artificial Sequence
<220> FEATURE:
<223> OTHER INFORMATION: HSD17B4 5'-UTR

<400> SEQUENCE: 21
gtcccgcagt cggcgtccag cggctctgct tgttcgtgtg tgtgtcgttg caggccttat 60
tc 62

<210> SEQ ID NO 22
<211> LENGTH: 62
<212> TYPE: RNA
<213> ORGANISM: Artificial Sequence
<220> FEATURE:
<223> OTHER INFORMATION: HSD17B4 5'-UTR

<400> SEQUENCE: 22
gucccgcagu cggcguccag cggcucugcu uguucgugug ugugucguug caggccuuau 60
uc 62

<210> SEQ ID NO 23
<211> LENGTH: 42
<212> TYPE: DNA
<213> ORGANISM: Artificial Sequence
<220> FEATURE:
<223> OTHER INFORMATION: RPL32 (32L4) 5'-UTR

<400> SEQUENCE: 23
ggcgctgcct acggaggtgg cagccatctc cttctcggca tc 42

<210> SEQ ID NO 24
<211> LENGTH: 42
<212> TYPE: RNA
<213> ORGANISM: Artificial Sequence
<220> FEATURE:
<223> OTHER INFORMATION: RPL32 (32L4) 5'-UTR

<400> SEQUENCE: 24
ggcgcugccu acggaggugg cagccaucuc cuucucggca uc 42

<210> SEQ ID NO 25
<211> LENGTH: 75
<212> TYPE: DNA
<213> ORGANISM: Artificial Sequence
<220> FEATURE:
<223> OTHER INFORMATION: ATP5A1 5'-UTR

<400> SEQUENCE: 25
gcggctcggc cattttgtcc cagtcagtcc ggaggctgcg gctgcagaag taccgcctgc 60
ggagtaactg caaag 75

<210> SEQ ID NO 26
<211> LENGTH: 75
<212> TYPE: RNA
<213> ORGANISM: Artificial Sequence
<220> FEATURE:
<223> OTHER INFORMATION: ATP5A1 5'-UTR

<400> SEQUENCE: 26
gcggcucggc cauuuugucc cagucagucc ggaggcugcg gcugcagaag uaccgccugc 60
ggaguaacug caaag 75

<210> SEQ ID NO 27
<211> LENGTH: 2035
<212> TYPE: RNA
<213> ORGANISM: Artificial Sequence
<220> FEATURE:
<223> OTHER INFORMATION: PpLuc mRNA

<400> SEQUENCE: 27
ggggcgcugc cuacggaggu ggcagccauc uccuucucgg caucaagcuu gaggauggag 60
gacgccaaga acaucaagaa gggcccggcg cccuucuacc cgcuggagga cgggaccgcc 120
ggcgagcagc uccacaaggc caugaagcgg uacgcccugg ugccgggcac gaucgccuuc 180
accgacgccc acaucgaggu cgacaucacc uacgcggagu acuucgagau gagcgugcgc 240
cuggccgagg ccaugaagcg guacggccug aacaccaacc accggaucgu ggugugcucg 300
gagaacagcc ugcaguucuu caugccggug cugggcgccc ucuucaucgg cguggccguc 360
gccccggcga acgacaucua caacgagcgg gagcugcuga acagcauggg gaucagccag 420
ccgaccgugg uguucgugag caagaagggc cugcagaaga uccugaacgu gcagaagaag 480
cugcccauca uccagaagau caucaucaug gacagcaaga ccgacuacca gggcuuccag 540
ucgauguaca cguucgugac cagccaccuc ccgccgggcu ucaacgagua cgacuucguc 600
ccggagagcu ucgaccggga caagaccauc gcccugauca ugaacagcag cggcagcacc 660
ggccugccga agggggugge ccugccgcac cggaccgccu gcgugcgcuu cucgcacgcc 720
cgggacccca ucuucggcaa ccagaucauc ccggacaccg ccauccugag cguggugccg 780
uuccaccacg gcuucggcau guucacgacc cugggcuacc ucaucugcgg cuuccgggug 840
guccugaugu accgguucga ggaggagcug uuccugcgga gccugcagga cuacaagauc 900
cagagcgcgc ugcucgugcc gacccuguuc agcuucuucg ccaagagcac ccugaucgac 960
aaguacgacc ugucgaaccu gcacgagauc gccagcgggg gcgccccgcu gagcaaggag 1020
gugggcgagg ccguggccaa gcgguuccac cucccgggca uccgccaggg cuacggccug 1080
accgagacca cgagcgcgau ccugaucacc cccgaggggg acgacaagcc gggcgccgug 1140
ggcaaggugg ucccguucuu cgaggccaag gugguggacc uggacaccgg caagacccug 1200
ggcgugaacc agcggggcga gcugugcgug cgggggccga ugaucaugag cggcuacgug 1260
aacaacccgg aggccaccaa cgcccucauc gacaaggacg gcuggcugca cagcggcgac 1320
aucgccuacu gggacgagga cgagcacuuc uucaucgucg accggcugaa gucgcugauc 1380
aaguacaagg gcuaccaggu ggcgccggcc gagcuggaga gcauccugcu ccagcacccc 1440
aacaucuucg acgccggcgu ggccgggcug ccggacgacg acgccggcga gcugccggcc 1500
gcgguggugg ugcuggagca cggcaagacc augacggaga aggagaucgu cgacuacgug 1560
gccagccagg ugaccaccgc caagaagcug cggggcggcg uggugugcgu ggacgagguc 1620
ccgaagggcc ugaccgggaa gcucgacgcc cggaagaucc gcgagauccu gaucaaggcc 1680
aagaagggcg gcaagaucgc cguguaagac uagugcauca cauuuaaaag caucucagcc 1740
uaccaugaga auaagagaaa gaaaaugaag aucaauagcu uauucaucuc uuuuucuuuu 1800
ucguuggugu aaagccaaca cccugucuaa aaaacauaaa uuucuuuaau cauuuugccu 1860
cuuuucucug ugcuucaauu aauaaaaaau ggaaagaacc uagaucuaaa aaaaaaaaaa 1920
aaaaaaaaaa aaaaaaaaaa aaaaaaaaaa aaaaaaaaaa aaaaaaaaaa augcaucccc 1980
cccccccccc cccccccccc cccccccaaa ggcucuuuuc agagccacca gaauu 2035

<210> SEQ ID NO 28
<211> LENGTH: 858
<212> TYPE: RNA
<213> ORGANISM: Artificial Sequence
<220> FEATURE:
<223> OTHER INFORMATION: HsEPO mRNA

<400> SEQUENCE: 28
gggagagucc cgcagucggc guccagcggc ucugcuuguu cgugugugug ucguugcagg 60
ccuuauucaa gcuuaccaug ggcgugcacg agugccccgc cuggcugugg cuccugcuga 120
gccuccuguc ccugccgcuc gggcugcccg uccugggcgc ccccccgcgg cucaucugcg 180
acagccgcgu gcuggagcgg uaccugcucg aggcgaagga ggccgagaac aucaccaccg 240
ggugcgccga gcacugcucc cugaacgaga acaucacggu gccggacacc aaggucaacu 300
ucuacgccug gaagcgcaug gaggugggcc agcaggccgu ggaggucugg caggggcugg 360

-continued cgcuccugag cgaggccgug cugcggggcc aggcccuccu ggugaacucc agccagcccu 420
gggagccccu gcagcuccac gucgacaagg ccguguccgg ccugcgcagc cugaccaccc 480
uccugcgggc gcugggggcc cagaaggagg ccaucucccc cccggacgcc gccagcgcgg 540
ccccgcuccg cacgaucacc gccgacaccu uccggaagcu guuccgcgug uacuccaacu 600
uccugcgggg caagcucaag cuguacaccg gggaggccug ccgcacgggc gaccggugag 660
gacuaguccc uguucccaga gcccacuuuu uuuucuuuuu uugaaauaaa auagccuguc 720
uuucagaucu aaaaaaaaaa aaaaaaaaaa aaaaaaaaaa aaaaaaaaaa aaaaaaaaaa 780
aaaaaaaaaa aaaaugcauc cccccccccc cccccccccc cccccccccc aaaggcucuu 840
uucagagcca ccagaauu 858

<210> SEQ ID NO 29
<211> LENGTH: 1975
<212> TYPE: RNA
<213> ORGANISM: Artificial Sequence
<220> FEATURE:
<223> OTHER INFORMATION: MmDCT mRNA

<400> SEQUENCE: 29
agggcgcugc cuacggaggu ggcagccauc uccuucucgg caucaagcuu accaugggcc 60
ugguggggug gggccuccug cuggggugcc ucggcugcgg gauccugcug cgggcccgcg 120
cccaguuccc ccgggucugc augacccucg acggcgugcu gaacaaggag ugcugcccgc 180
cccugggccc cgaggcgacc aacaucugcg gguuccucga gggccgcggg cagugcgccg 240
aggugcagac ggacacccgg cccuggagcg gcccguacau ccugcgcaac caggacgacc 300
gggagcagug gccccgcaag uucuucaacc ggaccugcaa gugcaccggg aacuucgccg 360
gcuacaacug cggcgggugc aaguucggcu ggacggggcc cgacugcaac cgcaagaagc 420
ccgccauccu gcggcgcaac auccacuccc ucaccgccca ggagcgggag caguuccugg 480
gcgcgcugga ccucgccaag aagagcaucc acccggacua cgucaucacc acccagcacu 540
ggcugggccu gcucgggccc aacggcacgc agccccagau cgccaacugc uccguguacg 600
acuucuucgu guggcugcac uacuacagcg uccgcgacac ccugcucggg cccggccggc 660
cguacaaggc caucgacuuc ucccaccagg ggcccgcguu cgugaccugg caccgcuacc 720
accugcugug gcucgagcgg gagcugcagc gccugaccgg caacgagagc uucgcccucc 780
ccuacuggaa cuucgccacg ggcaagaacg agugcgacgu gugcaccgac gagcugcugg 840
gggccgcccg gcaggacgac ccccacccuga ucucccgcaa cagccgguuc uccaccuggg 900
agaucgucug cgacagccuc gacgacuaca accgccgggu gacgcugugc aacggcaccu 960
acgaggggcu gcuccggcgc aacaaggugg gccggaacaa cgagaagcug ccgacccuga 1020
agaacgucca ggacugccuc ucccugcaga aguucgacag ccccccccuuc uuccagaacu 1080 ccaccuucag cuuccgcaac gcgcuggagg gguucgacaa ggccgacggc acgcucgacu 1140
cccaggugau gaaccugcac aaccuggccc acagcuuccu caacggcacc aacgcccugc 1200
cccacuccgc cgcgaacgac ccggguguucg ucgugcugca cagcuucacc gacgccaucu 1260
ucgacgagug gcucaagcgg aacaaccccu ccaccgacgc cuggccccag gagcuggccc 1320
ccaucgggca caaccgcaug uacaacaugg ugccguucuu cccgcccguc acgaacgagg 1380
agcuguuccu gaccgccgag cagcucggcu acaacuacgc gguggaccug agcgaggagg 1440
aggcccccgu guggagcacc acccuguccg ucgugaucgg gauccucggc gccuucgugc 1500
ugcugcucgg gcugcuggcc uuccuccagu accggcgccu gcggaagggc uacgccccgc 1560
ugauggagac gggccucagc uccaagcgcu acaccgagga ggcggccaag uucguggccg 1620
ccuggacccu gaaggcggcc gccugaggac uagugcauca cauuuaaaag caucucagcc 1680
uaccaugaga auaagagaaa gaaaaugaag aucaauagcu uauucaucuc uuuuucuuuu 1740
ucguuggugu aaagccaaca cccugucuaa aaaacauaaa uuucuuuaau cauuuugccu 1800
cuuuucucug ugcuucaauu aauaaaaaau ggaaagaacc uagaucuaaa aaaaaaaaaa 1860
aaaaaaaaaa aaaaaaaaaa aaaaaaaaaa aaaaaaaaaa aaaaaaaaaa augcaucccc 1920
cccccccccc cccccccccc cccccccaaa ggcucuuuuc agagccacca gaauu 1975

<210> SEQ ID NO 30
<211> LENGTH: 1707
<212> TYPE: RNA
<213> ORGANISM: Artificial Sequence
<220> FEATURE:
<223> OTHER INFORMATION: anti-Rabies Antibody HC mRNA

<400> SEQUENCE: 30
gggagagucc cgcagucggc guccagcggc ucugcuuguu cgugugugug ucguugcagg 60
ccuuauucaa gcuuaccaug gacuggaccu ggcgcuuccu guucguggucg gccgccgcga 120 ccggcgugca gagccaggug cagcucgucc aguccggggc cgaggugaag aagcccggca 180
gcuccgugaa ggucagcugc aaggccuccg gggcacguu caaccgguac accgugaacu 240
gggugcgcca ggcccggggg cagggccugg aguggauggg cgggaucauc cccaucuucg 300
gcaccgccaa cuacgcgcag cgguuccagg gcgccugac caucacggcc gacgagagca 360
ccuccaccgc cuacauggag cucagcuccc ugcggagcga cgacaccgcc gucuacuucu 420
gcgcgcgcga gaaccuggac aacuccggca cguacuacua cuucagcggg ugguucgacc 480
ccuggggcca gggcacccuc gugaccgugu ccagcgccuc caccaagggg cccagcgucu 540
ucccgcuggc cccuccagc aaguccacga gcggcgggac cgccgcccug ggcugccucg 600
ugaaggacua cuuccccgag cccgugaccg ucagcuggaa cuccggcgcg cugaccagcg 660 ggugcacac guucccggcc gugcugcagu ccagcggccu cuacucccug agcuccgucg 720
ugaccgugcc cagcuccagc cuggggaccc agaccuacau cugcaacguc aaccacaagc 780
ccuccaacac gaagguggac aagcgggugg agcccaagag cugcgacaag acccacaccu 840
gcccgcccug ccccgccccg gagcuccugg gcgggccguc cgucuuccug uucccuccca 900
agcccaagga cacccucaug aucagccgca cgccggaggu gaccugcguc gugguggacg 960
ugucccacga ggaccccgag gugaaguuca acugguacgu ggacggcguc gaggugcaca 1020
acgccaagac caagccccgg gaggagcagu acaacagcac cuaccgcgug gucuccgugc 1080
ugacggugcu gcaccaggac uggcucaacg gcaaggagua caagugcaag gucagcaaca 1140
aggcccugcc cgcgccgauc gagaagacca ucuccaaggc caaggggcag ccccgggagc 1200
cccaggugua cacccugccc ccgagccgcg aggagaugac caagaaccag gugagccuca 1260
cgugccuggu caagggcuuc uaccccuccg acaucgccgu ggagugggag agcaacgggc 1320
agcccgagaa caacuacaag accacccccgc ccgugcugga cuccgacggc agcuucuucc 1380
ucuacuccaa gcugaccguc gacaagagcc gguggcagca ggggaacgug uucuccugca 1440
gcgugaugca cgaggcccug cacaaccacu acacgcagaa gucccucagc cugucccccg 1500
gcaagugagg acuagucccu guucccagag cccacuuuuu uuucuuuuuu ugaaauaaaa 1560
uagccugucu uucagaucua aaaaaaaaaa aaaaaaaaaa aaaaaaaaaa aaaaaaaaaa 1620
aaaaaaaaaa aaaaaaaaaa aaaugcaucc cccccccccc cccccccccc ccccccccca 1680
aaggcucuuu ucagagccac cagaauu 1707

<210> SEQ ID NO 31
<211> LENGTH: 1005
<212> TYPE: RNA
<213> ORGANISM: Artificial Sequence
<220> FEATURE:
<223> OTHER INFORMATION: anti-Rabies Antibody LC mRNA

<400> SEQUENCE: 31
gggagagucc cgcagucggc guccagcggc ucugcuuguu cgugugugug ucguugcagg 60
ccuuauucaa gcuuaccaug agcgugccca ccauggccug ggcccugcuc cugcuguccc 120
uccugaccca gggcacgggg agcugggcgc aguccgcccu gacccagccg cgcagcgucu 180
ccggcagccc cgggcagucc gugaccauca gcugcaccgg cacguccagc gacaucgggg 240
gcuacaacuu cguguccugg uaccagcagc accccggcaa ggcccccaag cucaugaucu 300
acgacgccac caagcggccg agcggggucc ccgaccgcuu cuccggcagc aaguccggga 360
acaccgccag ccugaccauc uccggccugc aggcggagga cgaggccgac uacuacugcu 420
gcagcuacgc cggggacuac acgcccggcg ugguguucgg cgggggcacc aagcucaccg 480
uccuggggca gccgaaggcc gcgccguccg ugacccuguu cccucccagc agcgaggagc 540
uccaggccaa caaggccacg cuggugugcc ugaucuccga cuucuacccc ggcgccguca 600
ccguggccug gaaggcggac agcuccccgg ugaaggccgg cgucgagacc accacgccca 660
gcaagcaguc caacaacaag uacgccgcca gcuccuaccu cagccugacc cccgagcagu 720
ggaaguccca ccggagcuac uccugccagg ugacccacga ggggagcacc guggagaaga 780
cggucgcccc caccgagugc uccugaggac uagucccugu ucccagagcc cacuuuuuuu 840
ucuuuuuuug aaauaaaaua gccugucuuu cagaucuaaa aaaaaaaaaa aaaaaaaaaa 900
aaaaaaaaaa aaaaaaaaaa aaaaaaaaaa aaaaaaaaaa augcaucccc cccccccccc 960
cccccccccc cccccccaaa ggcucuuuuc agagccacca gaauu 1005

<210> SEQ ID NO 32
<211> LENGTH: 1792
<212> TYPE: RNA
<213> ORGANISM: Artificial Sequence
<220> FEATURE:
<223> OTHER INFORMATION: RABV-G mRNA

<400> SEQUENCE: 32
gggagaaagc uuaccauggu gccccaggcc cugcucuucg ucccgcugcu gguguucccc 60
cucugcuucg gcaaguuccc caucuacacc auccccgaca agcuggggcc guggagcccc 120
aucgacaucc accaccuguc cugccccaac aaccucgugg ucgaggacga gggcugcacc 180
aaccugagcg gguucuccua cauggagcug aaggugggcu acaucagcgc caucaagaug 240
aacggguuca cgugcaccgg cgugguca cc gaggcggaga ccuacacgaa cuucgugggc 300
uacgugacca ccaccuucaa gcggaagcac uuccgcccca cgccggacgc cugccgggcc 360
gccuacaacu ggaagauggc cggggacccc cgcuacgagg agucccucca caaccccuac 420
cccgacuacc acuggcugcg gaccgucaag accaccaagg agagccuggu gaucaucucc 480
ccgagcgugg cggaccucga ccccuacgac cgcucccugc acagccgggu cuuccccggc 540
gggaacugcu ccggcguggc cgugagcucc acguacugca gcaccaacca cgacuacacc 600
aucuggaugc ccgagaaccc gcgccugggg auguccugcg acaucuucac caacagccgg 660
ggcaagcgcg ccuccaaggg cagcgagacg ugcggguucg ucgacgagcg gggccucuac 720
aagucccuga agggggccug caagcugaag cucugcggcg ugcugggccu gcgccucaug 780
gacgggaccu ggguggcgau gcagaccagc aacgagacca aguggugccc ccccggccag 840
cuggucaacc ugcacgacuu ccggagcgac gagaucgagc accucguggu ggaggagcug 900
gucaagaagc gcgaggagug ccuggacgcc cucgagucca ucaugacgac caagagcgug 960
uccuuccggc gccugagcca ccugcggaag cucgugcccg gguucggcaa ggccuacacc 1020
aucuucaaca agacccugau ggaggccgac gcccacuaca aguccguccg cacguggaac 1080
gagaucaucc cgagcaaggg gugccugcgg gugggcggcc gcugccaccc ccacgucaac 1140 ggggguguucu ucaacggcau cauccucggg cccgacggca acgugcugau ccccgagaug 1200
caguccagcc ugcuccagca gcacauggag cugcuggucu ccagcgugau cccgcucaug 1260
cacccccugg cggaccccuc caccguguuc aagaacgggg acgaggccga ggacuucguc 1320
gaggugcacc ugcccgacgu gcacgagcgg aucagcggcg ucgaccucgg ccugccgaac 1380
ugggggaagu acgugcugcu cuccgccggc gcccugaccg cccugaugcu gaucaucuuc 1440
cucaugaccu gcuggcgccg ggugaaccgg agcgagccca cgcagcacaa ccugcgcggg 1500
accggccggg aggucuccgu gaccccgcag agcgggaaga ucaucuccag cugggagucc 1560
uacaagagcg gcggcgagac cgggcuguga ggacuaguua uaagacugac uagcccgaug 1620
ggccucccaa cgggcccucc uccccuccuu gcaccgagau uaauaaaaaa aaaaaaaaaa 1680
aaaaaaaaaa aaaaaaaaaa aaaaaaaaaa aaaaaaaaaa aaaaaaaaug caucccccc 1740 cccccccccc cccccccccc ccccaaaggc ucuuuucaga gccaccagaa uu 1792

<210> SEQ ID NO 33
<211> LENGTH: 1870
<212> TYPE: RNA
<213> ORGANISM: Artificial Sequence
<220> FEATURE:
<223> OTHER INFORMATION: PpLuc mRNA

<400> SEQUENCE: 33
aggagaaagc uuaccaugga ggacgccaag aacaucaaga agggcccggc gcccuucuac 60
ccgcuggagg acgggaccgc cggcgagcag cuccacaagg ccaugaagcg guacgcccug 120
gugccgggca cgaucgccuu caccgacgcc cacaucgagg ucgacaucac cuacgcggag 180
uacuucgaga ugagcgugcg ccuggccgag gccaugaagc gguacggccu gaacaccaac 240
caccggaucg uggugugcuc ggagaacagc cugcaguucu ucaugccggu gcugggcgcc 300
cucuucaucg gcguggccgu cgccccggcg aacgacaucu acaacgagcg ggagcugcug 360
aacagcaugg ggaucagcca gccgaccgug guguucguga gcaagaaggg ccugcagaag 420
auccugaacg ugcagaagaa gcugcccauc auccagaaga ucaucaucau ggacagcaag 480
accgacuacc agggcuucca gucgauguac acguucguga ccagccaccu cccgccgggc 540
uucaacgagu acgacuucgu cccggagagc uucgaccggg acaagaccau cgcccugauc 600
augaacagca gcggcagcac cggccugccg aagggggugg cccugccgca ccggaccgcc 660
ugcgugcgcu ucucgcacgc ccgggacccc aucuucggca accagaucau cccggacacc 720
gccauccuga gcgugggugcc guuccaccac ggcuucggca uguucacgac ccugggcuac 780
cucaucugcg gcuuccgggu gguccugaug uaccgguucg aggaggagcu guuccugcgg 840
agccugcagg acuacaagau ccagagcgcg cugcucgugc cgacccuguu cagcuucuuc 900

```
gccaagagca cccugaucga caaguacgac cugucgaacc ugcacgagau cgccagcggg    960

ggcgccccgc ugagcaagga gguggggcgag gccguggcca agcgguucca ccucccgggc   1020

auccgccagg gcuacggccu gaccgagacc acgagcgcga uccugaucac ccccgagggg   1080

gacgacaagc cgggcgccgu gggcaaggug gucccguucu ucgaggccaa gguggugggac   1140

cuggacaccg gcaagacccu gggcgugaac cagcggggcg agcugugcgu gcgggggccg   1200

augaucauga gcggcuacgu gaacaacccg gaggccacca acgcccucau cgacaaggac   1260

ggcuggcugc acagcggcga caucgccuac ugggacgagg acgagcacuu cuucaucguc   1320

gaccggcuga agucgcugau caaguacaag ggcuaccagg uggcgccggc cgagcuggag   1380

agcauccugc uccagcaccc caacaucuuc gacgccggcg uggccgggcu gccggacgac   1440

gacgccggcg agcugccggc cgcggguggug gugcuggagc acggcaagac caugacggag   1500

aaggagaucg ucgacuacgu ggccagccag gugaccaccg ccaagaagcu gcggggcggc   1560

gugguguucg uggacgaggu cccgaagggc cugaccggga agcucgacgc ccggaagauc   1620

cgcgagaucc ugaucaaggc caagaagggc ggcaagaucg ccgugugagg acuaguuaua   1680

agacugacua gcccgauggg ccucccaacg ggcccuccuc cccuccuugc accgagauua   1740

auaaaaaaaa aaaaaaaaaa aaaaaaaaaa aaaaaaaaaa aaaaaaaaaa aaaaaaaaaa   1800

aaaaaaugca ucccccccccc cccccccccc cccccccccc ccaaaggcuc uuuucagagc   1860

caccagaauu                                                          1870
```

<210> SEQ ID NO 34
<211> LENGTH: 727
<212> TYPE: RNA
<213> ORGANISM: Artificial Sequence
<220> FEATURE:
<223> OTHER INFORMATION: Monoepitope construct MmPmel(14-43) mRNA

<400> SEQUENCE: 34

```
aggagaaagc uuaccauggc cugccugggc uuccagcgcc acaaggccca gcucaaccug     60

gcgacccgga ccuggcccug cacgcuccug uucuuccugc uguucauccc gguguucugc    120

ggcgggggug gaagcggcgg ggguggaagu cugagcgccc uccuggccgu gggcgcgcug    180

gaggggcccc gcaaccagga cuggcucggc gucccgcggc agcuggugac caagaccgga    240

gguggcgggu cuggaggugg cgggucagcc aaguucgugg ccgcguggac ccugaaggcc    300

gccgccggug gcggaggguc ggguggcgga ggguccuucc ugcucuggau ccuggccgcc    360

gugagcuccg gccuguucuu cuacagcuuc cuccugaccg cggucucccu gagcaagaug    420

cucaagaagc gcuccccccu gaccacgggg guguacguga agaugccgcc caccgagccc    480

gagugcgaga agcaguucca gcccuacuuc aucccgauca acugaggacu aguuauaaga    540

cugacuagcc cgaugggccu cccaacgggc ccuccucccc uccuugcacc gagauuaaua    600

aaaaaaaaaa aaaaaaaaaa aaaaaaaaaa aaaaaaaaaa aaaaaaaaaa aaaaaaaaaa    660

aaaugcaucc cccccccccc cccccccccc ccccccccca aaggcucuuu ucagagccac    720

cagaauu                                                              727
```

<210> SEQ ID NO 35
<211> LENGTH: 727
<212> TYPE: RNA
<213> ORGANISM: Artificial Sequence
<220> FEATURE:
<223> OTHER INFORMATION: Monoepitope construct MmTrp1(455-473) mRNA

<400> SEQUENCE: 35
aggagaaagc uuaccauggc cugccugggc uuccagcgcc acaaggccca gcucaaccug 60
gcgacccgga ccuggcccug cacgcuccug uucuuccugc uguucauccc gguguucugc 120
ggcgggggug gaagcggcgg ggguggaagu cccccgguga ccaacaccga gauguucguc 180
acggcccccg acaaccuggg cuacauguac gaggugcagu ggcccgggca ggaguucgga 240
gguggcgggu cuggaggugg cgggucagcc aaguucgugg ccgcguggac ccugaaggcc 300
gccgccggug gcggagggug gggugcgga ggguccuucc ugcucuggau ccuggccgcc 360
gugagcuccg gccuguucuu cuacagcuuc cuccugaccg cggucucccu gagcaagaug 420
cucaagaagc gcuccccccu gaccacgggg guguacguga agaugccgcc caccgagccc 480
gagugcgaga agcaguucca gcccuacuuc aucccgauca acugaggacu aguuauaaga 540
cugacuagcc cgaugggccu cccaacgggc ccuccucccc uccuugcacc gagauuaaua 600
aaaaaaaaaa aaaaaaaaaa aaaaaaaaaa aaaaaaaaaa aaaaaaaaaa aaaaaaaaaa 660
aaaugcaucc cccccccccc cccccccccc ccccccccca aaggcucuuu ucagagccac 720
cagaauu 727

<210> SEQ ID NO 36
<211> LENGTH: 727
<212> TYPE: RNA
<213> ORGANISM: Artificial Sequence
<220> FEATURE:
<223> OTHER INFORMATION: Monoepitope construct MmObsl1(1750-1778) mRNA

<400> SEQUENCE: 36
aggagaaagc uuaccauggc cugccugggc uuccagcgcc acaaggccca gcucaaccug 60
gcgacccgga ccuggcccug cacgcuccug uucuuccugc uguucauccc gguguucugc 120
ggcgggggug gaagcggcgg ggguggaagu augcgcgagg gcguggagcu gugccccggg 180
aacaaguacg agaugcggcg ccacggcacc acccacagcc ucgucaucca cgacguggga 240
gguggcgggu cuggaggugg cgggucagcc aaguucgugg ccgcguggac ccugaaggcc 300
gccgccggug gcggagggug gggugcgga ggguccuucc ugcucuggau ccuggccgcc 360
gugagcuccg gccuguucuu cuacagcuuc cuccugaccg cggucucccu gagcaagaug 420
cucaagaagc gcuccccccu gaccacgggg guguacguga agaugccgcc caccgagccc 480
gagugcgaga agcaguucca gcccuacuuc aucccgauca acugaggacu aguuauaaga 540
cugacuagcc cgaugggccu cccaacgggc ccuccucccc uccuugcacc gagauuaaua 600
aaaaaaaaaa aaaaaaaaaa aaaaaaaaaa aaaaaaaaaa aaaaaaaaaa aaaaaaaaaa 660
aaaugcaucc cccccccccc cccccccccc ccccccccca aaggcucuuu ucagagccac 720
cagaauu 727

<210> SEQ ID NO 37
<211> LENGTH: 1918
<212> TYPE: RNA
<213> ORGANISM: Artificial Sequence
<220> FEATURE:
<223> OTHER INFORMATION: H3N2-HA mRNA

<400> SEQUENCE: 37
gggagaaagc uuaccaugaa gaccaucauc gcccugagcu acauccucug ccugguguuc 60
gcccagaaga uccccggcaa cgacaacucc accgcgacgc ugugccucgg gcaccacgcc 120
gucccgaacg gcaccaucgu gaagaccauc accaacgacc gcaucgaggu gacgaacgcc 180
accgagcugg uccagaacag cuccaucggg gagaucugcg acagccccca ccagauccug 240
gacggcgaga acugcacccu caucgacgcc cugcuggggg acccccagug cgacggcuuc 300
cagaacaaga agugggaccu cuucguggag cgguccaagg ccuacagcaa cugcuacccc 360
uacgacgugc cggacuacgc gucccugcgc agccuggucg ccuccagcgg cacccucgag 420
uucaacaacg aguccuucaa cuggacgggg gugacccaga acggcaccag cuccgccugc 480
auccggcgca gcuccagcuc cuucuucagc cggcugaacu ggcugaccca ccucaacuac 540
aaguaccccg cccugaacgu gacgaugccc aacaacgagc aguucgacaa gcuguacauc 600
uggggcgucc accaccccgg gaccgacaag gaccagaucu ucccguacgc gcaguccagc 660
gggcgcauca ucgugagcac caagcggucc cagcaggccg ugauccccaa caucggcagc 720
cgcccccgga uccgcgacau cccgucccgg aucagcaucu acuggaccau cgucaagccg 780
ggcgacaucc uccugaucaa cuccacgggg aaccugaucg ccccgcgcgg cuacuucaag 840
cuccggagcg ggaaguccag caucaugcgc uccgacgccc ccaucggcaa gugcaagagc 900
gagugcauca cccccaacgg cuccaucccg aacgacaagc ccuuccagaa cgugaaccgg 960
aucaccuacg ggccugcccc ccgcuacgug aagcacagca cccugaagcu ggcgacgggc 1020
augcggaacg uccccgagaa gcagacccgc gggaucuucg gcgccaucgc cggguucauc 1080
gagaacggcu gggagggcau gguggacggg ugguacggcu uccggcacca gaacuccgag 1140
gggcgcggcc aggccgccga ccucaagagc acccaggcgg ccaucgacca gaucaacggg 1200
aagcugaacc ggcugaucgg caagaccaac gagaaguucc accagaucga gaaggaguuc 1260
uccgaggugg agggccgcau ccaggaccuc gagaaguacg ucgaggacac gaagaucgac 1320
cuguggagcu acaacgccga gcugcucgug gcccuggaga accagcacac caucgaccug 1380
accgacuccg agaugaacaa gcucuucgag aagaccaaga agcagcugcg cgagaacgcc 1440
gaggacaugg ggaacggcug cuucaagauc uaccacaagu gcgacaacgc gugcaucggg 1500
agcauccgga acggcacgua cgaccacaac guguaccgcg acgaggcccu gaacaaccgg 1560
uuccagauca agggggucga gcucaagucc ggcuacaagg acuggauccu guggaucagc 1620
uucgccauca gcugcuuccu gcucugcgug gcccugcugg gcuucaucau gugggccugc 1680
cagaagggga acauccgcug caacaucugc aucugaggac uaguuauaag acugacuagc 1740
ccgaugggcc ucccaacggg cccuccuccc cuccuugcac cgagauuaau aaaaaaaaaa 1800
aaaaaaaaaa aaaaaaaaaa aaaaaaaaaa aaaaaaaaaa aaaaaaaaaa aaaaugcauc 1860
cccccccccc cccccccccc cccccccccc aaaggcucuu uucagagcca ccagaauu 1918

<210> SEQ ID NO 38
<211> LENGTH: 1470
<212> TYPE: RNA
<213> ORGANISM: Artificial Sequence
<220> FEATURE:
<223> OTHER INFORMATION: PfCSP mRNA

<400> SEQUENCE: 38
gggagagucc cgcagucggc guccagcggc ucugcuuguu cgugugugug ucguugcagg 60
ccuuauucaa gcuuaccaug augcgcaagc uggccauccu cagcgugucc agcuuccugu 120
ucgucgaggc ccuguuccag gaguaccagu gcuacggcuc cagcuccaac acccgggugc 180
ucaacgagcu gaacuacgac aacgcgggga ccaaccugua caacgagcuc gagaugaacu 240
acuacggcaa gcaggagaac ugguacagcc ugaagaagaa cucccgcagc cuggggggaga 300 acgacgacgg caacaacgag gacaacgaga agcuccggaa gcccaagcac aagaagcuga 360
agcagccggc cgacgggaac cccgacccca acgccaaccc caacguggac ccgaacgcca 420
accccaacgu cgaccccaac gccaacccca acguggaccc gaacgcgaac cccaacgcca 480
accccaacgc caaccccaac gccaacccga acgcgaaccc caacgccaac cccaacgcca 540
accccaacgc caacccgaac gccaacccca acgcgaaccc caacgccaac cccaacgcca 600
acccgaacgc caaccccaac gccaacccca acgcgaaccc caacgccaac ccgaacgcca 660
accccaacgu ggaccccaac gccaacccca acgccaaccc gaacgcgaac cccaacgcca 720
accccaacgc caacccgaac gccaacccca acgccaaccc caacgcgaac cccaacgcca 780
acccgaacgc caaccccaac gccaacccca acgcgaaccc caacgccaac ccgaacgcca 840
accccaacgc caaccccaac gccaacccca acgcgaaccc gaacgccaac cccaacaaga 900
acaaccaggg caacggccag gggcacaaca ugcccaacga ccccaaccgc aacgucgacg 960
agaacgccaa cgccaacucc gccgugaaga acaacaacaa cgaggagccg agcgacaagc 1020
acaucaagga guaccugaac aagauccaga acucccucag cacggagugg ucccccugca 1080
gcgugaccug cggcaacggg auccaggucc ggaucaagcc cggcuccgcg aacaagccca 1140
aggacgagcu ggacuacgcc aacgacaucg agaagaagau cugcaagaug gagaagugca 1200
gcuccguguu caacgugguc aacagcucca ucgggcugau cauggugcuc agcuuccugu 1260
uccugaacug aggacuaguc ccuguuccca gagcccacuu uuuuuucuuu uuuugaaaua 1320
aaauagccug ucuuucagau cuaaaaaaaa aaaaaaaaaa aaaaaaaaaa aaaaaaaaaa 1380
aaaaaaaaaa aaaaaaaaaa aaaaaaugca uccccccccc cccccccccc cccccccccc 1440
ccaaaggcuc uuuucagagc caccagaauu 1470

<210> SEQ ID NO 39
<211> LENGTH: 847
<212> TYPE: RNA
<213> ORGANISM: Artificial Sequence
<220> FEATURE:
<223> OTHER INFORMATION: HsFGF21 mRNA

<400> SEQUENCE: 39
aggagagucc cgcagucggc guccagcggc ucugcuuguu cgugugugug ucguugcagg 60
ccuuauucaa gcuuaccaug gacucggacg agaccggguu cgagcacuca ggacuguggg 120
uuucugugcu ggcuggucuu cugcugggag ccugccaggc acaccccauc ccugacucca 180
guccucuccu gcaauucggg ggccaagucc ggcagcggua ccucuacaca gaugaugccc 240
agcagacaga agcccaccug gagaucaggg aggaugggac gguggggggc gcugcugacc 300
agagccccga aagucuccug cagcugaaag ccuugaagcc gggaguuauu caaaucuugg 360
gagucaagac auccagguuc cugugccagc ggccagaugg ggcccuguau ggaucgcucc 420
acuuugaccc ugaggccugc agcuuccggg agcggcuucu ugaggacgga uacaauguuu 480
accaguccga agcccacggc cucccgcugc accucccagg gaacaagucc ccacaccggg 540
acccugcacc ccgaggacca gcucgcuucc ugccacuacc aggccugccc cccgcacucc 600
cggagccacc cggaauccug gccccccagc cccccgaugu gggcuccucg gacccucuga 660
gcaugguggg agguucccag ggccgaagcc ccagcuacga guccugagga cuagucccug 720
uucccagagc ccacuuuuuu uucuuuuuuu gaaauaaaau agccugucuu ucagaucuaa 780
aaaaaaaaaa aaaaaaaaaa aaaaaaaaaa aaaaaaaaaa aaaaaaaaaa aaaaaaaaaa 840
aagaauu 847

<210> SEQ ID NO 40
<211> LENGTH: 1470
<212> TYPE: RNA
<213> ORGANISM: Artificial Sequence
<220> FEATURE:
<223> OTHER INFORMATION: PfCSP mRNA

<400> SEQUENCE: 40
aggagagucc cgcagucggc guccagcggc ucugcuuguu cgugugugug ucguugcagg 60
ccuuauucaa gcuuaccaug augcgcaagc uggccauccu cagcgugucc agcuuccugu 120
ucgucgaggc ccuguuccag gaguaccagu gcuacggcuc cagcuccaac acccgggugc 180
ucaacgagcu gaacuacgac aacgcgggga ccaaccugua caacgagcuc gagaugaacu 240
acuacggcaa gcaggagaac ugguacagcc ugaagaagaa cucccgcagc cugggggaga 300
acgacgacgg caacaacgag gacaacgaga agcuccggaa gcccaagcac aagaagcuga 360
agcagccggc cgacgggaac cccgacccca acgccaaccc caacguggac ccgaacgcca 420
accccaacgu cgaccccaac gccaacccca acguggaccc gaacgcgaac cccaacgcca 480
accccaacgc caaccccaac gccaaccccga acgcgaaccc caacgccaac cccaacgcca 540
accccaacgc caacccgaac gccaacccca acgcgaaccc caacgccaac cccaacgcca 600
acccgaacgc caaccccaac gccaacccca acgcgaaccc caacgccaac ccgaacgcca 660
accccaacgu ggaccccaac gccaacccca acgccaaccc gaacgcgaac cccaacgcca 720
accccaacgc caacccgaac gccaacccca acgccaaccc caacgcgaac cccaacgcca 780
acccgaacgc caaccccaac gccaacccca acgcgaaccc caacgccaac ccgaacgcca 840
accccaacgc caaccccaac gccaacccca acgcgaaccc gaacgccaac cccaacaaga 900
acaaccaggg caacggccag ggcacaaca ugcccaacga ccccaaccgc aacgucgacg 960
agaacgccaa cgccaacucc gccgugaaga acaacaacaa cgaggagccg agcgacaagc 1020
acaucaagga guaccugaac aagauccaga acucccucag cacggagugg ucccccugca 1080
gcgugaccug cggcaacggg auccagguce ggaucaagcc cggcuccgcg aacaagccca 1140
aggacgagcu ggacuacgcc aacgacaucg agaagaagau cugcaagaug gagaagugca 1200
gcuccguguu caacgugguc aacagcucca ucgggcugau cauggugcuc agcuuccugu 1260
uccugaacug aggacuaguc ccuguuccca gagcccacuu uuuuuucuuu uuuugaaaua 1320
aaauagccug ucuuucagau cuaaaaaaaa aaaaaaaaaa aaaaaaaaaa aaaaaaaaaa 1380
aaaaaaaaaa aaaaaaaaaa aaaaaaugca uccccccccc cccccccccc cccccccccc 1440
ccaaaggcuc uuuucagagc caccagaauu 1470

<210> SEQ ID NO 41
<211> LENGTH: 128
<212> TYPE: RNA
<213> ORGANISM: Artificial Sequence
<220> FEATURE:
<223> OTHER INFORMATION: mRNA 3'-end A64-N5-C30-histoneSL-N5

<400> SEQUENCE: 41
aaaaaaaaaa aaaaaaaaaa aaaaaaaaaa aaaaaaaaaa aaaaaaaaaa aaaaaaaaaa 60
aaaaugcauc cccccccccc cccccccccc cccccccccc aaaggcucuu uucagagcca 120
ccagaauu 128

<210> SEQ ID NO 42
<211> LENGTH: 129

<212> TYPE: RNA
<213> ORGANISM: Artificial Sequence
<220> FEATURE:
<223> OTHER INFORMATION: mRNA 3'-end histoneSL-A100-N5

<400> SEQUENCE: 42
caaaggcucu uuucagagcc accaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaagaauu 129

<210> SEQ ID NO 43
<211> LENGTH: 93
<212> TYPE: RNA
<213> ORGANISM: Artificial Sequence
<220> FEATURE:
<223> OTHER INFORMATION: mRNA 3'-end histoneSL-A64-N5

<400> SEQUENCE: 43
caaaggcucu uuucagagcc accaaaaaaa aaaaaaaaaa aaaaaaaaaa aaaaaaaaaa 60
aaaaaaaaaa aaaaaaaaaa aaaaaaaaga auu 93

<210> SEQ ID NO 44
<211> LENGTH: 105
<212> TYPE: RNA
<213> ORGANISM: Artificial Sequence
<220> FEATURE:
<223> OTHER INFORMATION: mRNA 3'-end A100-N5

<400> SEQUENCE: 44
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa gaauu 105

<210> SEQ ID NO 45
<211> LENGTH: 69
<212> TYPE: RNA
<213> ORGANISM: Artificial Sequence
<220> FEATURE:
<223> OTHER INFORMATION: mRNA 3'-end A64-N5

<400> SEQUENCE: 45
aaaaaaaaaa aaaaaaaaaa aaaaaaaaaa aaaaaaaaaa aaaaaaaaaa aaaaaaaaaa 60
aaaagaauu 69

<210> SEQ ID NO 46
<211> LENGTH: 124
<212> TYPE: RNA
<213> ORGANISM: Artificial Sequence
<220> FEATURE:
<223> OTHER INFORMATION: mRNA 3'-end histoneSL-A100

<400> SEQUENCE: 46
caaaggcucu uuucagagcc accaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaa 124

<210> SEQ ID NO 47
<211> LENGTH: 88
<212> TYPE: RNA
<213> ORGANISM: Artificial Sequence
<220> FEATURE:
<223> OTHER INFORMATION: mRNA 3'-end histoneSL-A64

```
<400> SEQUENCE: 47

caaaggcucu uuucagagcc accaaaaaaa aaaaaaaaaa aaaaaaaaaa aaaaaaaaaa     60

aaaaaaaaaa aaaaaaaaaa aaaaaaaa                                        88


<210> SEQ ID NO 48
<211> LENGTH: 100
<212> TYPE: RNA
<213> ORGANISM: Artificial Sequence
<220> FEATURE:
<223> OTHER INFORMATION: mRNA 3'-end A100

<400> SEQUENCE: 48

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa                          100


<210> SEQ ID NO 49
<211> LENGTH: 64
<212> TYPE: RNA
<213> ORGANISM: Artificial Sequence
<220> FEATURE:
<223> OTHER INFORMATION: mRNA 3'-end A64

<400> SEQUENCE: 49

aaaaaaaaaa aaaaaaaaaa aaaaaaaaaa aaaaaaaaaa aaaaaaaaaa aaaaaaaaaa     60

aaaa                                                                  64


<210> SEQ ID NO 50
<211> LENGTH: 93
<212> TYPE: RNA
<213> ORGANISM: Artificial Sequence
<220> FEATURE:
<223> OTHER INFORMATION: mRNA 3'-end A64-histoneSL-N5

<400> SEQUENCE: 50

aaaaaaaaaa aaaaaaaaaa aaaaaaaaaa aaaaaaaaaa aaaaaaaaaa aaaaaaaaaa     60

aaaacaaagg cucuuuucag agccaccaga auu                                  93


<210> SEQ ID NO 51
<211> LENGTH: 134
<212> TYPE: RNA
<213> ORGANISM: Artificial Sequence
<220> FEATURE:
<223> OTHER INFORMATION: mRNA 3'-end N6-A64-N5-C30-histoneSL-N5

<400> SEQUENCE: 51

auuaauaaaa aaaaaaaaaa aaaaaaaaaa aaaaaaaaaa aaaaaaaaaa aaaaaaaaaa     60

aaaaaaaaaa ugcaucccccc cccccccccc cccccccccc ccccccaaag gcucuuuuca    120

gagccaccag aauu                                                      134


<210> SEQ ID NO 52
<211> LENGTH: 134
<212> TYPE: RNA
<213> ORGANISM: Artificial Sequence
<220> FEATURE:
<223> OTHER INFORMATION: mRNA 3'-end N6-A64-N5-C30-histoneSL-N5

<400> SEQUENCE: 52

agaucuaaaa aaaaaaaaaa aaaaaaaaaa aaaaaaaaaa aaaaaaaaaa aaaaaaaaaa     60

aaaaaaaaaa ugcaucccccc cccccccccc cccccccccc ccccccaaag gcucuuuuca    120

gagccaccag aauu                                                      134
```

<210> SEQ ID NO 53
<211> LENGTH: 135
<212> TYPE: RNA
<213> ORGANISM: Artificial Sequence
<220> FEATURE:
<223> OTHER INFORMATION: mRNA 3'-end N6-histoneSL-A100-N5

<400> SEQUENCE: 53
auuaaucaaa ggcucuuuuc agagccacca aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa gaauu 135

<210> SEQ ID NO 54
<211> LENGTH: 135
<212> TYPE: RNA
<213> ORGANISM: Artificial Sequence
<220> FEATURE:
<223> OTHER INFORMATION: mRNA 3'-end N6-histoneSL-A100-N5

<400> SEQUENCE: 54
agaucucaaa ggcucuuuuc agagccacca aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa gaauu 135

<210> SEQ ID NO 55
<211> LENGTH: 99
<212> TYPE: RNA
<213> ORGANISM: Artificial Sequence
<220> FEATURE:
<223> OTHER INFORMATION: mRNA 3'-end N6-histoneSL-A64-N5

<400> SEQUENCE: 55
auuaaucaaa ggcucuuuuc agagccacca aaaaaaaaaa aaaaaaaaaa aaaaaaaaaa 60
aaaaaaaaaa aaaaaaaaaa aaaaaaaaaa aaaagaauu 99

<210> SEQ ID NO 56
<211> LENGTH: 99
<212> TYPE: RNA
<213> ORGANISM: Artificial Sequence
<220> FEATURE:
<223> OTHER INFORMATION: mRNA 3'-end N6-histoneSL-A64-N5

<400> SEQUENCE: 56
agaucucaaa ggcucuuuuc agagccacca aaaaaaaaaa aaaaaaaaaa aaaaaaaaaa 60
aaaaaaaaaa aaaaaaaaaa aaaaaaaaaa aaaagaauu 99

<210> SEQ ID NO 57
<211> LENGTH: 111
<212> TYPE: RNA
<213> ORGANISM: Artificial Sequence
<220> FEATURE:
<223> OTHER INFORMATION: mRNA 3'-end N6-A100-N5

<400> SEQUENCE: 57
auuaauaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaagaau u 111

<210> SEQ ID NO 58
<211> LENGTH: 111
<212> TYPE: RNA

<213> ORGANISM: Artificial Sequence
<220> FEATURE:
<223> OTHER INFORMATION: mRNA 3'-end N6-A100-N5

<400> SEQUENCE: 58
agaucuaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaagaau u 111

<210> SEQ ID NO 59
<211> LENGTH: 75
<212> TYPE: RNA
<213> ORGANISM: Artificial Sequence
<220> FEATURE:
<223> OTHER INFORMATION: mRNA 3'-end N6-A64-N5

<400> SEQUENCE: 59
auuaauaaaa aaaaaaaaaa aaaaaaaaaa aaaaaaaaaa aaaaaaaaaa aaaaaaaaaa 60
aaaaaaaaaa gaauu 75

<210> SEQ ID NO 60
<211> LENGTH: 75
<212> TYPE: RNA
<213> ORGANISM: Artificial Sequence
<220> FEATURE:
<223> OTHER INFORMATION: mRNA 3'-end N6-A64-N5

<400> SEQUENCE: 60
agaucuaaaa aaaaaaaaaa aaaaaaaaaa aaaaaaaaaa aaaaaaaaaa aaaaaaaaaa 60
aaaaaaaaaa gaauu 75

<210> SEQ ID NO 61
<211> LENGTH: 130
<212> TYPE: RNA
<213> ORGANISM: Artificial Sequence
<220> FEATURE:
<223> OTHER INFORMATION: mRNA 3'-end N6-histoneSL-A100

<400> SEQUENCE: 61
auuaaucaaa ggcucuuuuc agagccacca aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa 130

<210> SEQ ID NO 62
<211> LENGTH: 130
<212> TYPE: RNA
<213> ORGANISM: Artificial Sequence
<220> FEATURE:
<223> OTHER INFORMATION: mRNA 3'-end N6-histoneSL-A100

<400> SEQUENCE: 62
agaucucaaa ggcucuuuuc agagccacca aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa 130

<210> SEQ ID NO 63
<211> LENGTH: 94
<212> TYPE: RNA
<213> ORGANISM: Artificial Sequence
<220> FEATURE:
<223> OTHER INFORMATION: mRNA 3'-end N6-histoneSL-A64

<400> SEQUENCE: 63
auuaaucaaa ggcucuuuuc agagccacca aaaaaaaaaa aaaaaaaaaa aaaaaaaaaa 60
aaaaaaaaaa aaaaaaaaaa aaaaaaaaaa aaaa 94

<210> SEQ ID NO 64
<211> LENGTH: 94
<212> TYPE: RNA
<213> ORGANISM: Artificial Sequence
<220> FEATURE:
<223> OTHER INFORMATION: mRNA 3'-end N6-histoneSL-A64

<400> SEQUENCE: 64
agaucucaaa ggcucuuuuc agagccacca aaaaaaaaaa aaaaaaaaaa aaaaaaaaaa 60
aaaaaaaaaa aaaaaaaaaa aaaaaaaaaa aaaa 94

<210> SEQ ID NO 65
<211> LENGTH: 106
<212> TYPE: RNA
<213> ORGANISM: Artificial Sequence
<220> FEATURE:
<223> OTHER INFORMATION: mRNA 3'-end N6-A100

<400> SEQUENCE: 65
auuaauaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaa 106

<210> SEQ ID NO 66
<211> LENGTH: 106
<212> TYPE: RNA
<213> ORGANISM: Artificial Sequence
<220> FEATURE:
<223> OTHER INFORMATION: mRNA 3'-end N6-A100

<400> SEQUENCE: 66
agaucuaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaa 106

<210> SEQ ID NO 67
<211> LENGTH: 70
<212> TYPE: RNA
<213> ORGANISM: Artificial Sequence
<220> FEATURE:
<223> OTHER INFORMATION: mRNA 3'-end N6-A64

<400> SEQUENCE: 67
auuaauaaaa aaaaaaaaaa aaaaaaaaaa aaaaaaaaaa aaaaaaaaaa aaaaaaaaaa 60
aaaaaaaaaa 70

<210> SEQ ID NO 68
<211> LENGTH: 70
<212> TYPE: RNA
<213> ORGANISM: Artificial Sequence
<220> FEATURE:
<223> OTHER INFORMATION: mRNA 3'-end N6-A64

<400> SEQUENCE: 68
agaucuaaaa aaaaaaaaaa aaaaaaaaaa aaaaaaaaaa aaaaaaaaaa aaaaaaaaaa 60
aaaaaaaaaa 70

<210> SEQ ID NO 69
<211> LENGTH: 99
<212> TYPE: RNA

<213> ORGANISM: Artificial Sequence
<220> FEATURE:
<223> OTHER INFORMATION: mRNA 3'-end N6-A64-histoneSL-N5

<400> SEQUENCE: 69
auuaauaaaa aaaaaaaaaa aaaaaaaaaa aaaaaaaaaa aaaaaaaaaa aaaaaaaaaa 60
aaaaaaaaaa caaaggcucu uuucagagcc accagaauu 99

<210> SEQ ID NO 70
<211> LENGTH: 99
<212> TYPE: RNA
<213> ORGANISM: Artificial Sequence
<220> FEATURE:
<223> OTHER INFORMATION: mRNA 3'-end N6-A64-histoneSL-N5

<400> SEQUENCE: 70
agaucuaaaa aaaaaaaaaa aaaaaaaaaa aaaaaaaaaa aaaaaaaaaa aaaaaaaaaa 60
aaaaaaaaaa caaaggcucu uuucagagcc accagaauu 99

<210> SEQ ID NO 71
<211> LENGTH: 1925
<212> TYPE: RNA
<213> ORGANISM: Artificial Sequence
<220> FEATURE:
<223> OTHER INFORMATION: PpLuc mRNA

<400> SEQUENCE: 71
aggagagucc cgcagucggc guccagcggc ucugcuuguu cgugugugug ucguugcagg 60
ccuuauucaa gcuuaccaug gaggacgcca agaacaucaa gaagggcccg gcgcccuucu 120
acccgcugga ggacgggacc gccggcgagc agcuccacaa ggccaugaag cgguacgccc 180
uggugccggg cacgaucgcc uucaccgacg cccacaucga ggucgacauc accuacgcgg 240
aguacuucga gaugagcgug cgccuggccg aggccaugaa gcgguacggc cugaacacca 300
accaccggau cgugguguge ucggagaaca gccugcaguu cuucaugccg gugcugggcg 360
cccucuucau cggcguggcc gucgccccgg cgaacgacau cuacaacgag cgggagcugc 420
ugaacagcau ggggaucagc cagccgaccg ugguguucgu gagcaagaag ggccugcaga 480
agauccugaa cgugcagaag aagcugccca ucauccagaa gaucaucauc auggacagca 540
agaccgacua ccagggcuuc cagucgaugu acacguucgu gaccagccac cucccgccgg 600
gcuucaacga guacgacuuc gucccggaga gcuucgaccg ggacaagacc aucgcccuga 660
ucaugaacag cagcggcagc accggccugc cgaagggggu ggcccugccg caccggaccg 720
ccugcgugcg cuucucgcac gcccgggacc ccaucuucgg caaccagauc aucccggaca 780
ccgccauccu gagcguggug ccguuccacc acggcuucgg cauguucacg acccugggcu 840
accucaucug cggcuuccgg gugguccuga uguaccgguu cgaggaggag cuguuccugc 900
ggagccugca ggacuacaag auccagagcg cgcugcucgu gccgacccug uucagcuucu 960
ucgccaagag cacccugauc gacaaguacg accugucgaa ccugcacgag aucgccagcg 1020
ggggcgcccc gcugagcaag gaggugggcg aggccguggc caagcgguuc caccucccgg 1080
gcauccgcca gggcuacggc cugaccgaga ccacgagcgc gauccugauc acccccgagg 1140
gggacgacaa gccgggcgcc gugggcaagg uggucccguu cuucgaggcc aagguggugg 1200
accuggacac cggcaagacc cugggcguga accagcgggg cgagcugugc gugcgggggc 1260
cgaugaucau gagcggcuac gugaacaacc cggaggccac caacgcccuc aucgacaagg 1320
acggcuggcu gcacagcggc gacaucgccu acugggacga ggacgagcac uucuucaucg 1380

-continued

```
ucgaccggcu gaagucgcug aucaaguaca agggcuacca gguggcgccg gccgagcugg   1440

agagcauccu gcuccagcac cccaacaucu ucgacgccgg cguggccggg cugccggacg   1500

acgacgccgg cgagcugccg gccgcggugg uggugcugga gcacggcaag accaugacgg   1560

agaaggagau cgucgacuac guggccagcc aggugaccac cgccaagaag cugcggggcg   1620

gcgugguguu cguggacgag gucccgaagg gccugaccgg gaagcucgac gcccggaaga   1680

uccgcgagau ccugaucaag gccaagaagg gcggcaagau cgccguguga ggacuagucc   1740

cuguucccag agcccacuuu uuuuucuuuu uuugaaauaa aauagccugu cuuucagauc   1800

ucaaaggcuc uuuucagagc caccaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa aaaaaaaaaa   1920

aaaaa                                                               1925
```